US012442026B2

(12) United States Patent
Hutagalung et al.

(10) Patent No.: US 12,442,026 B2
(45) **Date of Patent: *Oct. 14, 2025**

(54) PRODUCTION OF FATTY ACYL-COA IN YEAST USING A FATTY ACID FEEDSTOCK

(71) Applicant: Pyrone Systems, Inc., San Diego, CA (US)

(72) Inventors: Alexander Hutagalung, San Diego, CA (US); Jose Miguel Laplaza, San Diego, CA (US)

(73) Assignee: Pyrone Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/421,170

(22) Filed: Jan. 24, 2024

(65) Prior Publication Data

US 2024/0384314 A1 Nov. 21, 2024

Related U.S. Application Data

(63) Continuation of application No. 17/449,847, filed on Oct. 4, 2021, now Pat. No. 11,884,948, which is a continuation of application No. 16/783,122, filed on Feb. 5, 2020, now Pat. No. 11,136,605, which is a continuation of application No. PCT/US2019/051357, filed on Sep. 16, 2019.

(60) Provisional application No. 62/731,978, filed on Sep. 17, 2018, provisional application No. 62/731,980, filed on Sep. 17, 2018.

(51) Int. Cl.
*C12P 17/06* (2006.01)
*C12N 1/16* (2006.01)
*C12P 7/42* (2006.01)

(52) U.S. Cl.
CPC ................ *C12P 17/06* (2013.01); *C12N 1/16* (2013.01); *C12P 7/42* (2013.01); *C12Y 103/03006* (2013.01); *C12Y 203/01206* (2015.07); *C12Y 404/01026* (2015.07)

(58) Field of Classification Search
None
See application file for complete search history.

(56) References Cited

U.S. PATENT DOCUMENTS

| | | | | |
|---|---|---|---|---|
| 4,683,195 | A | 7/1987 | Mullis | |
| 4,683,202 | A | 7/1987 | Mullis | |
| 4,965,188 | A | 10/1990 | Mullis | |
| 5,232,841 | A | 8/1993 | Hashimoto | |
| 5,268,273 | A | 12/1993 | Buckholz | |
| 5,389,529 | A | 2/1995 | Panayotatos | |
| 5,470,719 | A | 11/1995 | Meng | |
| 5,648,247 | A | 7/1997 | Picataggio | |
| 5,656,493 | A | 8/1997 | Mullis | |
| 5,712,114 | A | 1/1998 | Mankovich | |
| 5,766,891 | A | 6/1998 | Shuman | |
| 5,846,818 | A | 12/1998 | Robinson | |
| 5,888,732 | A | 3/1999 | Hartley | |
| 5,932,474 | A | 8/1999 | Tsien | |
| 6,008,378 | A | 12/1999 | Tsien | |
| 6,054,271 | A | 4/2000 | Tsien | |
| 6,143,557 | A | 11/2000 | Hartley | |
| 6,171,861 | B1 | 1/2001 | Hartley | |
| 6,270,969 | B1 | 8/2001 | Hartley | |
| 6,277,608 | B1 | 8/2001 | Hartley | |
| 6,288,302 | B1 | 9/2001 | Yu | |
| 6,451,569 | B1 | 9/2002 | Tsien | |
| 6,518,488 | B1 | 2/2003 | Agarwal | |
| 6,720,140 | B1 | 4/2004 | Hartley | |
| 7,851,199 | B2 | 12/2010 | Bailey et al. | |
| 8,884,100 | B2 | 11/2014 | Page et al. | |
| 9,546,362 | B2 | 1/2017 | Page et al. | |
| 9,611,460 | B2 | 4/2017 | Page et al. | |
| 9,765,308 | B2 | 9/2017 | Page et al. | |
| 9,822,384 | B2 | 11/2017 | Poulos et al. | |
| 10,059,971 | B2 | 8/2018 | Page et al. | |
| 10,287,557 | B2 | 5/2019 | Geysens et al. | |
| 11,136,605 | B2 * | 10/2021 | Hutagalung | C12N 15/52 |
| 11,884,948 | B2 * | 1/2024 | Hutagalung | C12N 9/0004 |
| 2002/0007051 | A1 | 1/2002 | Cheo | |
| 2003/0083373 | A1 | 5/2003 | Tsien | |
| 2005/0032176 | A1 | 2/2005 | Khosla | |
| 2005/0112590 | A1 | 5/2005 | Boom | |
| 2005/0287592 | A1 | 12/2005 | Kless | |
| 2006/0057689 | A1 | 3/2006 | Otto et al. | |

(Continued)

FOREIGN PATENT DOCUMENTS

| | | |
|---|---|---|
| JP | 2000-078979 | 3/2000 |
| JP | 2001-029082 | 2/2001 |

(Continued)

OTHER PUBLICATIONS

Accession Q33DR0. Dec. 6, 2005 (Year: 2005).
Agarwal et al. 2001 "Gene isolation and characterization of two acyl CoA oxidases from soybean with broad substrate specificities and enhanced expression in the growing seedling axis." Plant Mol Biol. Nov. 2001;47(4):519-31.
Aizpurua-Olaizola et al. "Identification and quantification of cannabinoids in *Cannabis sativa* L. plants by high performance liquid chromatography-mass spectrometry." Anal Bioanal Chem. Nov. 2014;406(29):7549-60.
Akbergenov et al., ARC-1, a sequence element complementary to an internal 18S rRNA segment, enhances translation efficiency in plants when present in the leader or intercistronic region of mRNAs Nucleic Acids Research 32:1, 239-247 (2004).

(Continued)

*Primary Examiner* — Christian L Fronda
(74) *Attorney, Agent, or Firm* — KNOBBE, MARTENS, OLSON & BEAR, LLP

(57) ABSTRACT

Strains of yeasts are provided containing the genes for the production of cannabinoids from fatty acids. The enzymes that mediate cannabinoid production are localized to the cytosol, peroxisome or different compartments within the secretory pathway (e.g., endoplasmic reticulum, Golgi, vacuole) to ensure efficient production. The engineered microorganisms produce cannabinoids in a controlled fermentation process.

19 Claims, 31 Drawing Sheets

Specification includes a Sequence Listing.

(56) References Cited

U.S. PATENT DOCUMENTS

| | | | |
|---|---|---|---|
| 2008/0026421 | A1 | 1/2008 | Sagt et al. |
| 2012/0077252 | A1 | 3/2012 | Picataggio |
| 2012/0122180 | A1 | 5/2012 | Austin |
| 2014/0004598 | A1 | 1/2014 | Picataggio et al. |
| 2014/0228586 | A1 | 8/2014 | Beardslee et al. |
| 2016/0010126 | A1 | 1/2016 | Poulos et al. |
| 2016/0298151 | A1 | 10/2016 | Butt et al. |
| 2017/0211049 | A1 | 7/2017 | Page et al. |
| 2017/0233779 | A1 | 8/2017 | Page et al. |
| 2018/0030486 | A1 | 2/2018 | Beardslee et al. |
| 2018/0073043 | A1 | 3/2018 | Poulos et al. |
| 2018/0155748 | A1 | 6/2018 | Butt et al. |
| 2018/0334692 | A1 | 11/2018 | Barr et al. |
| 2019/0078098 | A1 | 3/2019 | Alper |
| 2019/0169661 | A1 | 6/2019 | Page |

FOREIGN PATENT DOCUMENTS

| | | | |
|---|---|---|---|
| WO | WO 1996/019497 | A1 | 6/1996 |
| WO | WO 1998/056943 | A1 | 12/1998 |
| WO | WO 1999/021013 | A1 | 4/1999 |
| WO | WO 2017/139496 | A1 | 9/2017 |
| WO | WO 2017/160801 | A1 | 9/2017 |
| WO | WO 2018/148848 | A1 | 8/2018 |
| WO | WO 2018/148849 | A1 | 8/2018 |
| WO | WO 2018/200888 | A1 | 11/2018 |
| WO | WO 2018/219995 | A1 | 12/2018 |
| WO | WO 2019/071000 | A1 | 4/2019 |

OTHER PUBLICATIONS

Alani et al., "A method for gene disruption that allows repeated use of URA3 selection in the construction of multiply disrupted yeast strains", Genetics 116(4):541-545 Aug. 1987.

Alconado and Juarez 2006. "Acyl-CoA oxidase activity from Beauveria bassiana, an entomopathgenic fungus". J Basic Microbiol. 2006;46(6):435-43.

Arie et al., "Phylogenetic identification of n-alkane assimilating Candida yeasts based on nucleotide divergence in the 5 end of LSU rDNA gene" J. Gen. Appl. Microbiol., 46, 257-262 (2000).

Austin, M. B. and J. P. Noel., "The chalcone synthase superfamily of type III polyketide synthases", Natural Product Reports, 2002. 20(1): p. 79-110.

Backer et al. "Innovative development and validation of an HPLC/DAD method for the qualitative and quantitative determination of major cannabinoids in cannabis plant material." J Chromatogr B Analyt Technol Biomed Life Sci. Dec. 15, 2009;877(32):4115-24.

Bakke et al. "N-ethylmaleimide-resistant acyl-coenzyme A oxidase from Arthrobacter ureafaciens NBRC 12140: molecular cloning, gene expression and characterization of the recombinant enzyme." Biochim Biophys Acta. Jan. 2007;1774(1):65-71.

Barth and Gaillardin. "Physiology and genetics of the dimorphic fungus Yarrowia lipolytica." FEMS Microbiol Rev. Apr. 1997;19(4):219-37.

Beggah et al. "Intra- and intermolecular events direct the propeptide-mediated maturation of the Candida albicans secreted aspartic proteinase Sap1p." Microbiology. Nov. 2000;146 ( Pt 11):2765-73.

Brocard and Hartig. "Peroxisome targeting signal 1: is it really a simple tripeptide?" Biochim Biophys Acta. Dec. 2006;1763(12):1565-73.

Brown et al. Aspergillus has distinct fatty acid synthases for primary and secondary metabolism.: Proc Natl Acad Sci U S A. Dec. 10, 1996;93(25):14873-7.

Capone et al., "Amber, ochre and opal suppressor tRNA genes derived from a human serine tRNA gene", EMBO J. 4:213, 1985.

Carvalho et al. "Designing microorganisms for heterologous biosynthesis of cannabinoids." FEMS Yeast Res. Jun. 1, 2017;17(4).

Chica et al. Curr Opin Biotechnol. Aug. 2005; 16(4):378-84. (Year: 2005).

Current Protocols in Molecular Biology, John Wiley & Sons, N.Y., 6.3.1-6.3.6 (1989).

Deshpande, Mukund V., Appl. Biochem. Biotechnol., 36:227 (1992).

Eggertsson, et al., "Transfer ribonucleic acid-mediated suppression of termination codons in *Escherichia coli*.", (1988) Microbiological Review 52(3):354-374.

Engleerg-Kukla, et al. (1996) in *Escherichia coli* and *Salmonella* Cellular and Molecular Biology, Chapter 60, pp. 909-921, Neidhardt, et al. eds., ASM Press, Washington, D.C.

Gagne et al. "Identification of olivetolic acid cyclase from Cannabis sativa reveals a unique catalytic route to plant polyketides." Proc Natl Acad Sci U S A. Jul. 31, 2012;109(31):12811-6.

Gajewski et al. "Engineering fungal de novo fatty acid synthesis for short chain fatty acid production." Nat Commun. Mar. 10, 2017;8:14650.

Gallie et al., "The 5'-leader sequence of tobacco mosaic virus RNA enhances the expression of foreign gene transcripts in vitro and in vivo", Nucleic Acids Research 15: 3257-3273 (1987).

Gallie, The 5'-leader of tobacco mosaic virus promotes translation through enhanced recruitment of elF4F Nucleic Acids Research 30: 3401-3411 (2002).

Gao et al. "Iterative integration of multiple-copy pathway genes in Yarrowia lipolytica for heterologous β-carotene production". Metab Eng. May 2017;41:192-201.

Ghaedi et al. Journal of Sciences, Islamic Republic of Iran (2009), 20(3), 205-211. Abstract. (Year: 2009).

Gietz and Woods "Transformation of Yeast by Lithium Acetate/Single-Stranded Carrier DNA/Polyethylene Glycol Method". Methods Enzymol. 2002;350:87-96.

Hiltunen et al. (JBC, vol. 267, No. 10, Apr. 5, 1992, pp. 6646-6653).

Hong et al. "Engineering Yarrowia lipolytica to express secretory invertase with strong FBA1IN promoter". Yeast. Feb. 2012;29(2):59-72.

Hooks et al. "Long-chain acyl-CoA oxidases of *Arabidopsis*." Plant J. Oct. 1999;20(1):1-13.

Hooks et al., Biochem J., 320:607-614 (1996).

Hunkova and Fenci. "Toxic effects of fatty acids on yeast cells: dependence of inhibitory effects on fatty acid concentration." Biotechnol Bioeng. Nov. 1977;19(11):1623-41.

Kistler and Broz "Cellular compartmentalization of secondary metabolism" Front. Microbiology Feb. 2015.

Kizer et al. Appl Environ Microbial. May 2008;74(10):3229-41. (Year: 2008).

Klionsky et al. "Intracellular sorting and processing of a yeast vacuolar hydrolase: proteinase A propeptide contains vacuolar targeting information." Mol Cell Biol. May 1988;8(5):2105-16.

Krink-Koutsoubelis et al."Engineered Production of Short-Chain Acyl-Coenzyme A Esters in *Saccharomyces cerevisiae*." ACS Synth Biol. Apr. 20, 2018;7(4):1105-1115.

Lametschwandtner et al. "The difference in recognition of terminal tripeptides as peroxisomal targeting signal 1 between yeast and human is due to different affinities of their receptor Pex5p to the cognate signal and to residues adjacent to it." J Biol Chem. Dec. 11, 1998;273(50):33635-43.

Landy, Curr. Opin. Biotech. 3:699-707 (1993).

Ledesma-Amaro and Nicaud. "Yarrowia lipolytica as a biotechnological chassis to produce usual and unusual fatty acids." Prog Lipid Res. Jan. 2016;61:40-50.

Liang et al. "Structure, mechanism and function of prenyltransferase." Eur J Biochem. Jul. 2002;269(14):3339-54.

Lim et al., "Exploiting the Biosynthetic Potential of Type III Polyketide Synthases", Molecules, 2016.21(6): p. 806.

Lui et al. "Membrane stress caused by octanoic acid in *Saccharomyces cerevisiae*" Appl Microbiol Biotechnol. Apr. 2013;97(7):3239-51.

Luo et al.2019 "Complete biosynthesis of cannabinoids and their unnatural analogues in yeast." Nature. Mar. 2019;567(7746):123-126.

Luo et al.2002 "The acyl-CoA oxidases from the yeast Yarrowia lipolytica: characterization of Aox2p." Arch Biochem Biophys. Nov 1;407(1):32-8.

Marks M D, et al. (2009) Identification of candidate genes affecting Delta9-tetrahydrocannabinol biosynthesis in Cannabis sativa. J Exp Bot. 60, 3715-3726.

(56) References Cited

OTHER PUBLICATIONS

Meyers & Miller, Cabios 4: 11-17 (1988).
Mignone et al., "Untranslated regions of mRNAs", Genome Biology 3(3): reviews 0004.1-0001.10 (2002).
Mignone et al., "UTRdb and UTRsite: a collection of sequences and regulatory motifs of the untranslated regions of eukaryotic mRNAs", Nucleic Acids Research 33: D141-D146 (2005).
Morimoto et al. (1998) Purification and characterization of cannabichromenic acid synthase from Cannabis sativa. Phytochemistry. 49: 1525-1529.
Needleman & Wunsch, J. Mol. Biol. 48: 444-453 (1970).
Nelson Biochemistry Jun. 1996. 25; 35(25):8429-38.
Page and Nagel, "Biosynthesis of terpenophenolics in hop and cannabis", In J T Romeo, ed, Integrative Plant Biochemistry, vol. 40. Elsevier, Oxford, pp. 179-210, 2006.
Pamplaniyi "Identification, isolation, and functional characterization of prenyltransferases in cannabis sativa "Dissertation Dortmund 2016.
Papanikolaou S., and Aggelis G., Bioresour. Technol. 82(1):43-9 (2002).
Paulous et al., "Comparison of the capacity of different viral internal ribosome entry segments to direct translation initiation in poly(A)-dependent reticulocyte lysates", Nucleic Acids Research 31: 722-733 (2003).
Prather et al. Curr Opin Biotechnol. Oct. 2008; 19(5):468-7 4. (Year: 2008).
Reiser et al 2009 "AoxA is a major peroxisomal long chain fattyacyl-CoA oxidase required for beta-oxidation in A. nidulans". Curr Genet. Apr. 2010;56(2):139-50.
Sauer, B., Curr. Opin. Biotech. 5:521-527 (1994).
Sekiguchi and Shuman, Nucl. Acids Res. 22:5360-5365, 1994.
Setoyama et. al 1995 "Functional expression of two forms of rat acyl-CoA oxidase and their substrate specificities" Dec. 14;217(2):482-7.
Shimiu et al. Type III Polyketide Synthases: Functional Classification and Phylogenomics. Chembiochem. Jan. 3, 2017;18(1):50-65.
Shuman, "Site-specific Interaction of Vaccinia Virus Topoisomerase I with Duplex DNA", J. Biol. Chem. 266:11372-11379, 1991.
Singh et al. Curr Protein Pept Sci. 2017, 18, 1-11 (Year: 2017).
Sirikantaramas S. et al. (2005) Tetrahydrocannabinolic acid synthase, the enzyme controlling marijuana psychoactivity, is secreted into the storage cavity of the glandular trichomes. Plant Cell Physiol. 46: 1578-1582.
Stout et al. "The hexanoyl-CoA precursor for cannabinoid biosynthesis is formed by an acyl-activating enzyme in Cannabis sativa trichomes." Plant J. Aug. 2012;71(3):353-65.
Tan et al. "Synthetic Pathway for the Production of Olivetolic Acid in *Escherichia coli*," ACS Synthetic Biology, Jul. 5, 2018, vol. 7, No. 8, pp. 1886-1896.
Taura et al. "Characterization of olivetol synthase, a polyketide synthase putatively involved in cannabinoid biosynthetic pathway." FEBS Lett. Jun. 18, 2009;583(12):2061-6.
Taura F. et al. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. J Biol Chem. 271: 17411-17416.
Taura F. et al. (2007) Cannabidiolic-acid synthase, the chemotype-determining enzyme in the fiber-type Cannabis sativa. FEBS Lett. 581: 2929-2934.
Taura F. et al.(1995) First direct evidence for the mechanism of 1-tetrahydrocannabinolic acid biosynthesis. J Am Chem Soc. 117: 9766-9767.
Tjalsma et al., "Signal Peptide-Dependent Protein Transport in Bacillus subtilis: a Genome-Based Survey of the Secretome", Microbiol. Molec. Biol. Rev. 64: 515-547 (2000).
Vincent et al., "Helicase-dependent isothermal DNA amplification". EMBO reports 5 (8): 795-800 (2004).
Yang et al "Structural basis for olivetolic acid formation by a polyketide cyclase from Cannabis sativa." FEBS J. Mar. 2016;283(6):1088-106.
Yu et al. "Type III Polyketide Synthases in Natural Product Biosynthesis", IUBMB Life, 2012. 64(4): p. 285-295.
Zirpel "Recombinant Expression and Functional Characterization of Cannabinoid Producing Enzymes in Komagataella phaffii" Dissertation Dortmund 2018.
Zirpel et al. "Optimization of Δ9-tetrahydrocannabinolic acid synthase production in Komagataella phaffii via post-translational bottleneck identification." J Biotechnol. Apr. 20, 2018;272-273:40-47.
Zirpel et al. "Production of Δ9-tetrahydrocannabinolic acid from cannabigerolic acid by whole cells of Pichia (Komagataella) pastoris expressing Δ9-tetrahydrocannabinolic acid synthase from *Cannabis sativa* L." Biotechnol Lett. Sep. 2015;37(9):1869-75.

* cited by examiner

Map of pLD1

Map of pLD10

Map of pLD12

Map of pLD14

Map of pLD16

Map of pLD20

Map of pLD22

Map of pLD24

Map of pLD56

Map of pLD87

Map of pLD101

Map of pLD102

Map of pLD111

Map of pLD112

Map of pLD113

Map of pLD125

Map of pLD127

Map of pLD131

Map of pLD132

Map of pLD135

Map of pLD137

Map of pLD138

Map of pLD139

Map of pLD19

Map of pLD26

PRODUCTION OF FATTY ACYL-COA IN YEAST USING A FATTY ACID FEEDSTOCK

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. patent application Ser. No. 17/449,847, filed on Oct. 4, 2021, which is a continuation of U.S. patent application Ser. No. 16/783,122, filed Feb. 5, 2020, which issued as U.S. Pat. No. 11,136,605 on Oct. 5, 2021, which is a continuation of PCT International Application No. PCT/US2019/051357, filed Sep. 16, 2019, designating the United States and published in English, which claims the benefit of U.S. Provisional Application No. 62/731,978, filed Sep. 17, 2018, and U.S. Provisional Application No. 62/731,980, filed Sep. 17, 2018. Each of the aforementioned applications is incorporated by reference herein in its entirety, and each is hereby expressly made a part of this specification.

FIELD

Strains of yeasts are provided containing the genes for the production of cannabinoids from fatty acids. The enzymes that mediate cannabinoid production are localized to the cytosol, peroxisome, or different compartments within the secretory pathway (e.g., endoplasmic reticulum, Golgi, vacuole) to ensure efficient production. The engineered microorganisms produce cannabinoids in a controlled fermentation process.

REFERENCE TO SEQUENCE LISTING

This application is filed with an electronic sequence listing entitled SEQLISTING_PYSYS002C3.xml, created on Jan. 24, 2024, which is 421 KB in size. The information in the electronic sequence listing is hereby incorporated by reference in its entirety.

BACKGROUND

Microorganisms employ various enzyme-driven biological pathways to support their own metabolism and growth. A cell synthesizes native proteins, including enzymes, in vivo from deoxyribonucleic acid (DNA). DNA first is transcribed into a complementary ribonucleic acid (RNA) that comprises a ribonucleotide sequence encoding the protein. RNA then directs translation of the encoded protein by interaction with various cellular components, such as ribosomes. The resulting enzymes participate as biological catalysts in pathways involved in production of molecules by the organism.

SUMMARY

These pathways can be exploited for the harvesting of the naturally produced products. The pathways also can be altered to increase production or to produce different products that may be commercially valuable. Advances in recombinant molecular biology methodology allow researchers to isolate DNA from one organism and insert it into another organism, thus altering the cellular synthesis of enzymes or other proteins. Advances in recombinant molecular biology methodology also allow endogenous genes, carried in the genomic DNA of a microorganism, to be increased in copy number, thus altering the cellular synthesis of enzymes or other proteins. Such genetic engineering can change the biological pathways within the host organism, causing it to produce a desired product.

Microorganic industrial production instead of plant production can increase the availability of natural products while reducing the manufacturing and environmental cost.

DETAILED DESCRIPTION

Figure 1:
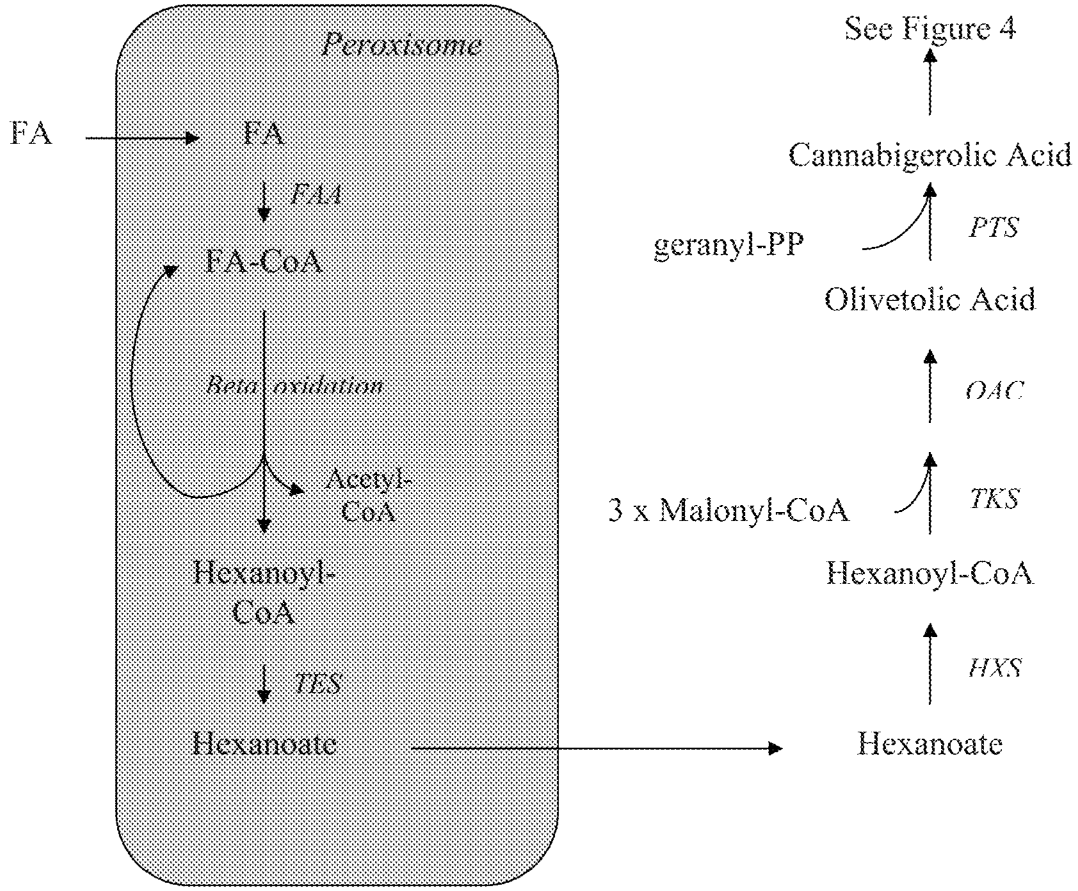
FIG. 1 depicts production of cannabinoids by producing hexanoic acid in the peroxisome. A fatty acid (FA) enters the peroxisome and is activated by a fatty acyl-CoA synthetase/fatty acyl activating enzyme (FAA) to become a fatty acyl-CoA (FA-CoA). It undergoes multiple rounds of beta oxidation, with each round producing one acetyl-CoA. Eventually, a molecule of hexanoyl-CoA is produced. An acyl-CoA thioesterase (TES) acts on the hexanoyl-CoA to produce hexanoic acid (hexanoate). The hexanoic acid leaves the peroxisome and is activated by a hexanoyl-CoA synthetase (HXS) to become hexanoyl-CoA, which is then acted upon by a polyketide synthase (TKS) and olivetolic acid cyclase (OAC) to produce olivetolic acid. A prenyltransferase (PTS) adds a geranyl moiety to olivetolic acid to produce cannabigerolic acid, which is converted to one of several cannabinoids as described in FIG. 4.

*Cannabis* is the dried preparation of the *Cannabis sativa* plant and has been widely used to treat disease or alleviate disease symptoms. The flowers of the plant are used to produce *cannabis*, but other parts of the plant can be used as well. According to some accounts, *cannabis* is composed of at least 483 known chemical compounds, which include cannabinoids, terpenoids, flavonoids, nitrogenous compounds, amino acids, proteins, glycoproteins, enzymes, sugars and related compounds, hydrocarbons, alcohols, aldehydes, ketones, acids, fatty acids, esters, lactones, steroids, terpenes, non-cannabinoid phenols, vitamins, and pigments.

The cannabinoids are believed to mediate the medical and recreational properties of the plant. Cannabinoids act by binding to cannabinoid receptors found in the brain to mediate many of the effects of *cannabis*. The efficacy of cannabinoids for treating specific ailments is the subject of ongoing research with either a purified cannabinoid, a synthetic cannabinoid or *cannabis*.

For medical applications, the use of a purified cannabinoid is preferred to a mixture of molecules extracted from *cannabis*. One option for the production of cannabinoids is synthetic biology: the construction of specific strains of bacteria, yeast or filamentous fungi that will produce cannabinoids in a fermentation process. Producing cannabinoids with a genetically modified organism in fermentation has multiple advantages.

A fermentation-based process is more controlled and economical than the current process of isolating cannabinoids from *Cannabis sativa* plants, which requires expensive indoor facilities and cloning of plant strains under sterile conditions to ensure consistent distribution of cannabinoids in the final plant material.

Usually, cannabinoids are extracted from the *cannabis* plant as part of a crude mixture, combined with other chemical compounds found in the *cannabis* plant. Most extractions of *cannabis* plant matter aim to extract cannabinoids, particularly tetrahydrocannabinol (THC). THC is useful for relieving pain, treating glaucoma, and relieving nausea. THC is also gaining immense popularity as a recreational drug substance. Other cannabinoids of interest include, Cannabigerol (CBG), Cannabigerolic Acid (CBGA), Cannabidiol (CBD), Cannabinol (CBN), Cannabichromene (CBC), Tetrahydrocannabivarin (THCV), Cannabigerovarin (CBGV), and Cannabigerovarinic Acid (CBGVA).

A variety of growing and cultivating techniques have been developed for increasing the production of secondary compounds within plants of genus *cannabis*. These techniques include outdoor cultivation, indoor cultivation, hydroponics, fertilization, atmospheric manipulation, cloning, crossbreeding, Screen of Grow (SCROG), Sea of Green (SOG), pinching, training, topping, etc.

While breeding and farming techniques yield plants with high concentrations of cannabinoids, these techniques fail to provide the level of control and production needed. In addition, the production time is measured in multiple weeks if not months.

Production of a single cannabinoid by fermentation with a microorganism, will provide the cannabinoid of interest in less complex chemical matrix facilitating the isolation of purified cannabinoid. This will result in less equipment needed and lower cost of purification. In addition, a fermentation-based process timeline will be measured in days and not weeks, allowing production to quickly adapt to changing market needs. Finally, a fermentation-based process footprint will allow production of cannabinoids in a smaller facility than those required for plant-based process where big greenhouses are required.

Microorganisms

A microorganism selected often is suitable for genetic manipulation and often can be cultured at cell densities useful for industrial production of a target fatty dicarboxylic acid product. A microorganism selected often can be maintained in a fermentation device.

The term "engineered microorganism" as used herein refers to a modified microorganism that includes one or more activities distinct from an activity present in a microorganism utilized as a starting point (hereafter a "host microorganism"). An engineered microorganism includes a heterologous polynucleotide in some embodiments, and in certain embodiments, an engineered organism has been subjected to selective conditions that alter an activity, or introduce an activity, relative to the host microorganism. Thus, an engineered microorganism has been altered directly or indirectly by a human being. A host microorganism sometimes is a native microorganism, and at times is a microorganism that has been engineered to a certain point.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is a yeast.

Any suitable yeast may be selected as a host microorganism, engineered microorganism, genetically modified organism, or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi, C. viswanathii, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and *Lipomyces* yeast (e.g., *L. starkeyii, L. lipoferus*). In some embodiments, a suitable yeast is of the genus *Arachniotus, Aspergillus, Aureobasidium, Auxarthron, Blastomyces, Candida, Chrysosporuim, Chrysosporuim Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon*, or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus* var. *diffluens, Cryptococcus laurentii, Cryptococcus neofomans, Debaryomyces hansenii, Gymnoascus dugwayensis, Hansenula anomala, Histoplasma capsulatum, Issatchenkia occidentalis, lsstachenkia orientalis, Kluyveromyces lactis, Kluyveromyces marxianus, Kluyveromyces thermotolerans, Kluyveromyces waltii, Lipomyces lipoferus, Lipomyces starkeyii, Microsporum gypseum, Myxotrichum deflexum, Oidiodendron echinulatum, Pachysolen tannophilis, Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica*, or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii* and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3-/ura3-), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases, strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et. al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental stains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), Thraustochytrium fungi, Schizochytrium fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, Norcardia bacteria, *Xanthobacter* bacteria, *Escherichia* bacteria (e.g., *E. coli* (e.g., strains DH10B, Stb12, DH5-alpha, DB3, DB3.1), DB4, DB5, JDP682 and ccdA-over (e.g., U.S. application Ser. No. 09/518,188)), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria, *Chloroflexus* bacteria (e.g., *C. aurantiacus*), *Chloronema* bacteria (e.g., *C. gigateum*)), green sulfur bacteria (e.g., *Chlorobium* bacteria (e.g., *C. limicola*)), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and *Rhodomicrobium* bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusia* (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-C6, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea avigera* var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. *mesostemon, Cuphea carthagenensis, Cuphea circaeoides, Cuphea confertiflora, Cuphea cordata, Cuphea crassiflora, Cuphea cyanea, Cuphea decandra, Cuphea denticulata, Cuphea disperma, Cuphea epilobiifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexican-heather), *Cuphea hyssopoides, Cuphea ignea, Cuphea ingrata, Cuphea jorullensis, Cuphea lanceolata, Cuphea linarioides, Cuphea Ilavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea splendida* var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii, Cuphea lanceolata*)).

Microorganisms or cells used as host organisms or source for a heterologous polynucleotide are commercially available. Microorganisms and cells described herein, and other suitable microorganisms and cells are available, for example, from Invitrogen Corporation (Carlsbad, Calif.), American Type Culture Collection (Manassas, Va.), and Agricultural Research Culture Collection (NRRL; Peoria, Ill.).

Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Important Pathways for Cannabinoid Production—Beta Oxidation

Cellular fatty acid degradation occurs via the β-oxidation pathway in all organisms. See, e.g., European Published Application No. EP2502932A1. So far it has been established that there are two different β-oxidation systems in eukaryotes: the β-oxidation located in mitochondria for mammals and some filamentous fungi and the β-oxidation system located in peroxisomes for plants, fungi, and animals.

Fatty acid beta-oxidation begins with the addition of coenzyme A to a fatty acid and occurs by successive cycles of reactions during each of which the fatty acid is shortened by a two-carbon fragment removed as acetyl coenzyme A, generating trans-2,3 hydroxyl, and 3-keto intermediates, until only two or three carbons remain (as acetyl-CoA or propionyl-CoA respectively). The proteins involved in the mitochondrial β-oxidation and in the peroxisomal 3-oxidation are however different. Multifunctional proteins (MFPs) or multifunctional enzymes (MFEs) are involved in the peroxisomal β-oxidation pathway, whereas β-oxidation consists of monofunctional enzymes.

The peroxisomal β-oxidation process begins with oxidation of the acyl-CoA substrate into trans-2-enoyl-CoA by Acyl-CoA oxidase, namely Fox1p/Pox1p. It has been demonstrated that Pox1Δ yeasts are unable to grow on fatty acids as sole carbon atoms. Then the peroxisomal β-oxidation proceeds from trans-2-enoyl-CoA to 3-ketoacyl-CoA via the (3R)-hydroxyacyl-CoA ester intermediates. In the yeast oxidation system, the second and third reactions of the β-oxidation cycle are catalyzed by the same enzymes called Mfe2p, Fox2p or again Pox2p, which contains both the 3-hydroxyacyl-CoA and 2-enoyl-CoA hydratase activities. The 2-enoyl-CoA hydratase converts the trans-2-enoyl CoA esters into (3R)-hydroxyacyl-CoA esters, whereas the hydratase 2 produces the 3-ketoacyl-CoA. This enzyme was first isolated from *Candida tropicalis* and comprise a duplicated domain organization in its N-terminal region, which contains two dehydrogenase active domains A and B. Domain A was demonstrated to have highest activity with long and medium chain substrates, whereas domain B has the highest activity with short-chain substrates. The C-terminal region of the Fox2p enzyme contains the 2-enoyl-CoA hydratase 2 activity. Hiltunen et al. (JBC, Vol. 267, No. 10, Apr. 5, 1992, pp 6646-6653) showed that fatty acid catabolism in yeast was mainly based on the activity of Fox2p and that disruption of FOX2 resulted in the inability of yeast cells to grow on fatty acids as their sole carbon source. At the next reaction of the β-oxidation cycle the ketoacyl-CoA intermediate undergoes thiolytic cleavage by a 3-ketoacyl-CoA thiolase, namely Pot1p/Fox3p. The Pot1p/Fox3p is a dimeric protein with a subunit size of 45 kDa. A single subunit comprises three domains: two core domains, and a loop domain of 120 residues. The active site of yeast thiolase is shaped by residues from the two core domains and surrounded by the loop domain. The products of this last step are acetyl-CoA and a C2-shortened acyl-CoA, which acts as substrate for Pox1 p/Fox1 p for an additional cycle. The acetyl-CoA which is produced by peroxisomal beta oxidation is then used in the glyoxylic cycle, thereby allowing the transformation of acetyl-CoA into oxaloacetate. These reactions are catalyzed by two enzymes: isocitrate lyase (Icl1p) and malate synthase (Mls1p) which permits the use of two carbon atoms such as acetate, in the neoglucogenese.

Cannabinoid Production

Acyl-CoA oxidase (EC 1.3.3.6) is the first reported enzyme of the fatty acid 3-oxidation pathway. See, e.g., U.S. Pat. No. 6,518,488. This enzyme catalyzes the desaturation of acyl-CoAs longer than eight carbons to 2-trans-enoyl-CoAs, by donating electrons directly to molecular oxygen and releasing $H_2O_2$(Lazarow et al., 1976). There are multiple isozymes of acyl-CoA oxidase and these isozymes show specificity towards short, medium, and long chain fatty acyl-CoAs (Hooks et al., Biochem J., 320:607-614 (1996); Hooks et al., Plant J., 20:1-13 (1999)). For example, *Arabidopsis thaliana* acyl-CoA oxidase isoform 1 (ACX1) has optimal activity on an acyl-CoA substrate that is fourteen carbons long and minimal activity on substrates shorter than six carbons. However, ACX2 has optimal activity on an acyl-CoA substrate that is eighteen carbons long and minimal activity on substrates shorter than ten carbons. In *Y. lipolytica*, there are five acyl-CoA oxidase isoforms that have different activities on acyl-CoA substrates of different lengths. For example, the protein encoded by POX3 has maximal activity on C6 and C8 acyl-CoA substrates.

Cannabinoids have their biosynthetic origins in both polyketide and terpenoid metabolism and are termed terpenophenolics or prenylated polyketides (See, e.g., US Patent Publication No. US20190169661; Page J., Nagel J. (2006) Biosynthesis of terpenophenolics in hop and *cannabis*. In J T Romeo, ed, Integrative Plant Biochemistry, Vol. 40. Elsevier, Oxford, pp 179-210).

Polyketides represent a large family of diverse compounds ultimately synthesized from 2-carbon units through a series of Claisen-type condensations and subsequent modifications. See, e.g., US Patent Publication No. US20050032176. Members of this group include antibiotics such as tetracyclines, anticancer agents such as daunomycin, and immunosuppressants such as FK506 and rapamycin. Polyketides occur in many types of organisms including fungi and mycelial bacteria, in particular, the actinomycetes.

The structural diversity of polyketides is achieved through the series of reactions catalyzed by polyketide synthases (PKS), with features that contribute to diversity including the selection of various starter and extender units, final chain length, cyclization, degree of reduction, and the like. See, e.g., US20120122180. Downstream reactions such as glycosylation, hydroxylation, halogenation, prenylation, acylation, and alkylation can add additional diversity to the resulting products. This group of enzymatically active proteins is considered in a different category from the fatty acid synthases which also catalyze condensation of 2-carbon units to result in, for example, fatty acids and prostaglandins. Two major types of PKS are known which are vastly different in their construction and mode of synthesis. These are commonly referred to as Type I or "modular" and Type II, "aromatic."

There is a third class of PKS enzymes, the Type III PKS synthases, which consist of a small homodimer containing one active site where both chain extension and cyclization take place (See. e.g., US20190078098; Austin, M. B. and J. P. Noel. Natural Product Reports, 2002. 20(1): p. 79-110; Lim, Y., et al. Molecules, 2016.21(6): p. 806; Yu, D., et al. IUBMB Life, 2012. 64(4): p. 285-295). Type III PKSs are able to produce a wide diversity of polyketide products by using a variety of larger, CoA-containing precursors as a starting unit. These starters range from small aliphatic molecules, such as acetyl-CoA, to larger ring-containing compounds derived from the phenylpropanoid pathway, such as 4-coumaroyl-CoA. Often, these CoA molecules are formed through the function of acid CoA ligases that convert carboxylic acids into corresponding CoA molecules.

Cannabinoid biosynthesis occurs primarily in glandular trichomes that cover female flowers at a high density. See, e.g., US20190169661. Cannabinoids are formed by a three-step biosynthetic process: polyketide formation, aromatic prenylation and cyclization (see FIG. 1).

The first enzymatic step in cannabinoid biosynthesis is the formation of olivetolic acid by a putative polyketide synthase enzyme that catalyzes the condensation of hexanoyl coenzyme A (CoA) and malonyl CoA. A Type III polyketide synthase, termed "olivetol synthase" and referred to herein as polyketide synthase/olivetol synthase (CsPKS/olivetol synthase), from *Cannabis sativa* has recently been shown to form olivetol and several pyrone products but not olivetolic acid (Taura F, Tanaka S, Taguchi C, Fukamizu T, Tanaka H, Shoyama Y, Morimoto, S. (2009) Characterization of olivetol synthase, Type III a polyketide synthase putatively involved in cannabinoid biosynthetic pathway. FEBS Lett. 583: 2061-2066). The nucleotide sequence of the gene encoding CsPKS/olivetol synthase is found in GenBank under accession number AB164375 with the polypeptide as accession BAG14339. The aforementioned products include the pyrones hexanoytriacetic lactone (HTAL) and pentyldiacetic lactone (PDAL). The reason for the inability of this enzyme to form olivetolic acid, which is clearly a pathway intermediate based on the carboxylate structure of the cannabinoids, is not known. The lack of olivetolic acid formation by this polyketide synthase from *cannabis* was confirmed by the inventors, as further described herein and also by Marks et al. (Marks M D, Tian L, Wenger J P, Omburo S N, Soto-Fuentes W, He J, Gang D R, Weiblen G D, Dixon R A. (2009) Identification of candidate genes affecting Delta9-tetrahydrocannabinol biosynthesis in *Cannabis sativa*. J Exp Bot. 60, 3715-3726).

The second enzymatic step is the prenylation of olivetolic acid to form cannabigerolic acid (CBGA) by the enzyme geranylpyrophosphate:olivetolate geranyltransferase. This enzyme is an aromatic prenyltransferase and is the subject of commonly owned U.S. Provisional patent applications U.S. Ser. No. 61/272,057 filed Aug. 12, 2009 and U.S. Ser. No. 61/272,117 filed Aug. 18, 2009. CBGA is a central branch-point intermediate for the biosynthesis of the different classes of cannabinoids. Cyclization of CBGA yields Δ9-tetrahydrocannabinolic acid (THCA) or its isomers cannabidiolic acid (CBDA) or cannabichromenic acid (CBCA) (see FIG. 1). The Shoyama group has previously published the identification and purification of the three enzymes responsible for these cyclizations (Morimoto S, Komatsu K, Taura F, Shoyama, Y. (1998) Purification and characterization of cannabichromenic acid synthase from *Cannabis sativa*. Phytochemistry. 49: 1525-1529; Taura F, Morimoto S, Shoyama Y. (1996) Purification and characterization of cannabidiolic-acid synthase from *Cannabis sativa* L. Biochemical analysis of a novel enzyme that catalyzes the oxidocyclization of cannabigerolic acid to cannabidiolic acid. J Biol Chem. 271: 17411-17416; and Taura F, Morimoto S, Shoyama Y, Mechoulam R. (1995) First direct evidence for the mechanism of 1-tetrahydrocannabinolic acid biosynthesis. J Am Chem Soc. 117: 9766-9767). Cloning of THCA and CBDA synthases has also been previously published (Sirikantaramas S, Taura F, Tanaka Y, Ishikawa Y, Morimoto S, Shoyama Y. (2005) Tetrahydrocannabinolic acid synthase, the enzyme controlling marijuana psychoactivity, is secreted into the storage cavity of the glandular trichomes. Plant Cell Physiol. 46: 1578-1582; Taura F, Sirikantaramas S, Shoyama Y, Yoshikai K, Shoyama Y, Morimoto S. (2007) Cannabidiolic-acid synthase, the chemotype-determining enzyme in the fiber-type *Cannabis sativa*. FEBS Lett. 581: 2929-2934. The genes for THCA synthase and CBDA synthase have been reported in Japan (Japanese Patent Publication 2000-078979; Japanese Patent Publication 2001-029082).

Beta-Oxidation Activities

The term "beta oxidation pathway" as used herein, refers to a series of enzymatic activities utilized to metabolize fatty alcohols, fatty acids, or dicarboxylic acids. The activities utilized to metabolize fatty alcohols, fatty acids, or dicarboxylic acids include, but are not limited to, acyl-CoA ligase activity, acyl-CoA oxidase activity, acyl-CoA hydrolase activity, acyl-CoA thioesterase activity, enoyl-CoA hydratase activity, 3-hydroxyacyl-CoA dehydrogenase activity and acetyl-CoA C-acyltransferase activity. The term "beta oxidation activity" refers to any of the activities in the beta oxidation pathway utilized to metabolize fatty alcohols, fatty acids, or dicarboxylic acids.

Beta-Oxidation—Acyl-CoA Ligase

An acyl-CoA ligase enzyme sometimes is encoded by the host organism and can be added to generate an engineered organism. In some embodiments, host acyl-CoA ligase activity can be increased by increasing the number of copies of an acyl-CoA ligase gene, by increasing the activity of a promoter that regulates transcription of an acyl-CoA ligase gene, or by increasing the number copies of the gene and by increasing the activity of a promoter that regulates transcription of the gene, thereby increasing production of target due to increased carbon flux through the pathway. In certain embodiments, the acyl-CoA ligase gene can be isolated from any suitable organism. Non-limiting examples of organisms that include, or can be used as donors for, acyl-CoA ligase enzymes include *Arxula, Candida, Saccharomyces*, or *Yarrowia.*

Beta-Oxidation-Enoyl-CoA Hydratase

An enoyl-CoA hydratase enzyme catalyzes the addition of a hydroxyl group and a proton to the unsaturated β-carbon on a fatty-acyl CoA and sometimes is encoded by the host organism and sometimes can be added to generate an engineered organism. In certain embodiments, the enoyl-CoA hydratase activity is unchanged in a host or engineered organism. In some embodiments, the host enoyl-CoA hydratase activity can be increased by increasing the number of copies of an enoyl-CoA hydratase gene, by increasing the activity of a promoter that regulates transcription of an enoyl-CoA hydratase gene, or by increasing the number copies of the gene and by increasing the activity of a promoter that regulates transcription of the gene, thereby increasing the production of target product (due to increased carbon flux through the pathway. In certain embodiments, the enoyl-CoA hydratase gene can be isolated from any suitable organism. Non-limiting examples of organisms that include, or can be used as donors for, enoyl-CoA hydratase enzymes include *Arxula, Candida, Saccharomyces*, or *Yarrowia.*

Beta-Oxidation-3-Hydroxyacyl-CoA Dehydrogenase 3-hydroxyacyl-CoA dehydrogenase enzyme catalyzes the formation of a 3-ketoacyl-CoA by removal of a hydrogen from the newly formed hydroxyl group created by the activity of enoyl-CoA hydratase. In some embodiments, the activity is encoded by the host organism and sometimes can be added or increased to generate an engineered organism. In certain embodiments, the 3-hydroxyacyl-CoA activity is unchanged in a host or engineered organism. In some embodiments, the host 3-hydroxyacyl-CoA dehydrogenase activity can be increased by increasing the number of copies of a 3-hydroxyacyl-CoA dehydrogenase gene, by increasing the activity of a promoter that regulates transcription of a 3-hydroxyacyl-CoA dehydrogenase gene, or by increasing the number copies of the gene and by increasing the activity of a promoter that regulates transcription of the gene, thereby increasing production of target product (e.g., sebacic or dodecanedioic acid) due to increased carbon flux through the pathway. In certain embodiments, the 3-hydroxyacyl-CoA dehydrogenase gene can be isolated from any suitable organism. Non-limiting examples of organisms that include, or can be used as donors for, 3-hydroxyacyl-CoA dehydrogenase enzymes include *Arxula, Candida, Saccharomyces*, or *Yarrowia.*

Beta-Oxidation-Acetyl-CoA C-Acyltransferase

An Acetyl-CoA C-acyltransferase (e.g., beta-ketothiolase) enzyme catalyzes the formation of a fatty acyl-CoA shortened by 2 carbons by cleavage of the 3-ketoacyl-CoA by the thiol group of another molecule of CoA. The thiol is inserted between C-2 and C-3, which yields an acetyl CoA molecule and an acyl CoA molecule that is two carbons shorter. An Acetyl-CoA C-acyltransferase sometimes is encoded by the host organism and sometimes can be added to generate an engineered organism. In certain embodiments, the acetyl-CoA C-acyltransferase activity is unchanged in a host or engineered organism. In some embodiments, the host acetyl-CoA C-acyltransferase activity can be increased by increasing the number of copies of an acetyl-CoA C-acyltransferase gene, or by increasing the activity of a promoter that regulates transcription of an acetyl-CoA C-acyltransferase gene, thereby increasing the production of target product due to increased carbon flux through the pathway. In certain embodiments, the acetyl-CoA C-acyltransferase gene can be isolated from any suitable organism. Non-limiting examples of organisms that include, or can be used as donors for, acetyl-CoA C-acyltransferase enzymes include *Arxula, Candida, Saccharomyces*, or *Yarrowia.*

Altered Activities and Engineering Pathways

In one embodiment, which is represented by FIG. 1, the microorganism is engineered to consume fatty acids through peroxisomal beta-oxidation by insertion of a gene encoding an acyl-CoA oxidase. The acyl-CoA oxidase is targeted to the peroxisome by the addition of a peroxisomal targeting sequence (PTS) to the carboxyl-terminus to the protein. A PTS sequence can be GRRAKL or a smaller subset of those amino acids based on the consensus sequence [S/A/H/C/E/P/Q/V]-[K/R/H/Q]-[L/F]. Alternatively, a microorganism that naturally consumes fatty acids can be used. The microorganism will be constructed to express a hexanoate-acyl activating enzyme (HXS), an olivetol synthase (TKS), an olivetol cyclase (OAC), a cannabigerolic acid synthase (PTS), and either a cannabidiolic synthase (CBDAS) to produce cannabidiolic acid, a tetrahydrocannabinolic acid synthase (THCAS) to produce tetrahydrocannabinolic acid, or a cannabichromenic acid synthase (CBCAS) to produce cannabichromenic acid. The CBDAS, THCAS or CBCAS may be localized to either the cytosol, the peroxisome, a secretory traffic compartment such as the ER or Golgi or the vacuole through the use of signal sequences as described in FIG. 4. Other genetic manipulations may be performed that are known to increase the carbon flux into the isoprenoid pathway.

Figure 2:
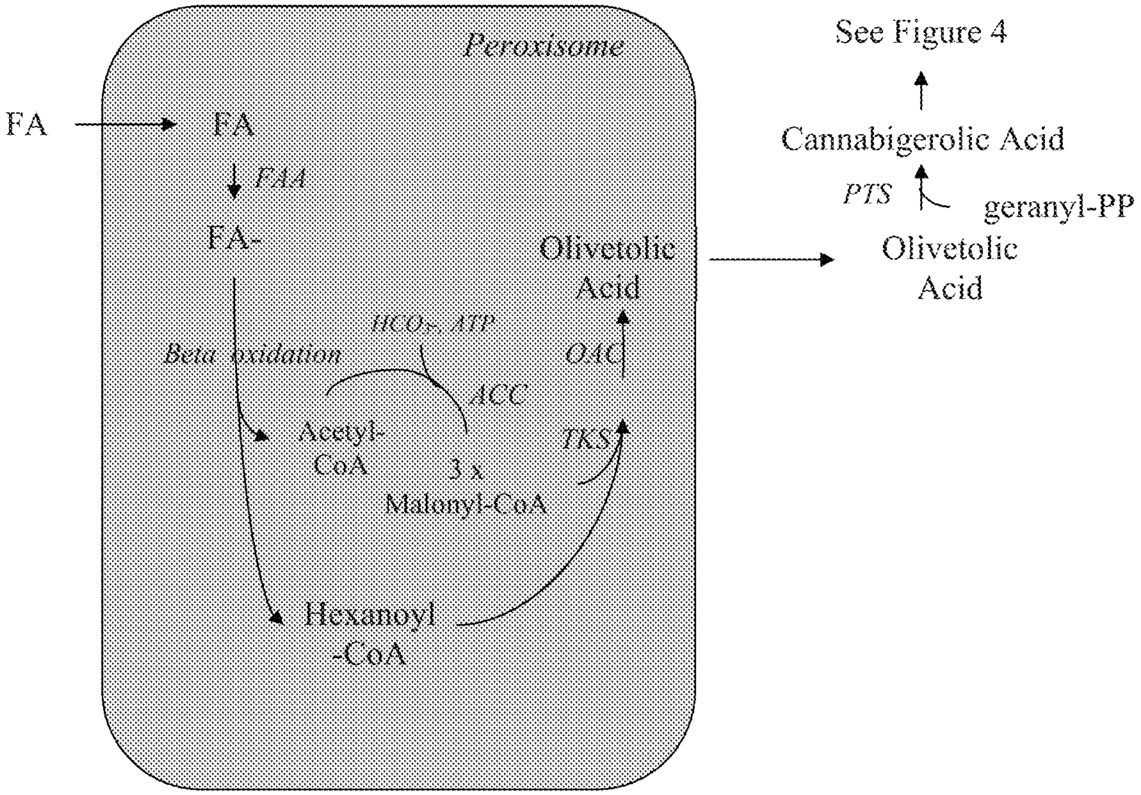
FIG. 2 depicts production of cannabinoids by producing olivetolic acid in the peroxisome. A fatty acid (FA) enters the peroxisome and is activated by a fatty acyl-CoA synthetase/fatty acyl activating enzyme (FAA) to become a fatty acyl-CoA (FA-CoA). It undergoes multiple rounds of beta oxidation, with each round producing one acetyl-CoA. Eventually, a molecule of hexanoyl-CoA is produced, which is then acted upon by a polyketide synthase (TKS) and olivetolic acid cyclase (OAC) to produce olivetolic acid. If necessary, an acetyl-CoA carboxylase (ACC) will be localized to the peroxisome to produce additional malonyl-CoA. The olivetolic acid leaves the peroxisome and enters the cytosol. A prenyltransferase (PTS) adds a geranyl moiety to olivetolic acid to produce cannabigerolic acid, which is converted to one of several cannabinoids as described in FIG. 4.

In one embodiment, which is represented by FIG. 2, the microorganism is engineered to consume fatty acids through peroxisomal beta-oxidation by insertion of a gene encoding an acyl-CoA oxidase. The acyl-CoA oxidase is targeted to the peroxisome by the addition of a peroxisomal targeting sequence (PTS) to the carboxyl-terminus of the protein. A PTS sequence can be GRRAKL or a smaller subset of those amino acids based on the consensus sequence [S/A/H/C/E/P/Q/V]-[K/R/H/Q]-[L/F]. Alternatively, a microorganism that naturally consumes fatty acids can be used. The microorganism will be constructed to express an olivetol synthase (TKS), an olivetol cyclase (OAC), a cannabigerolic acid synthase (PTS), and either a cannabidiolic synthase (CBDAS) to produce cannabidiolic acid, a tetrahydrocannabinolic acid synthase (THCAS) to produce tetrahydrocannabinolic acid, or a cannabichromenic acid synthase (CBCAS) to produce cannabichromenic acid. The TKS and OAC enzymes will be targeted to the peroxisome by the addition of a PTS sequence, such as GRRAKL or a smaller subset of those amino acids based on the consensus sequence of [S/A/H/C/E/P/Q/V]-[K/R/H/Q]-[L/F], which will be added to the carboxyl terminus of the proteins. An alternative mechanism of targeting to the peroxisome is the use of a PTS2 sequence near the N-terminus of the protein, which is defined by the consensus sequence -(R/K)(L/V/I/Q)XX(L/V/I/H/Q)(L/S/G/A/K)X(H/Q)(L/A/F)-. An example could be RRMLSSKQL as found in Pcdlp from *S. cerevisiae*. The CBDAS, THCAS or CBCAS may be localized to either the cytosol, the peroxisome, a secretory traffic compartment such as the ER or Golgi or the vacuole through the use of signal sequences as described in FIG. 4. Other genetic manipulations may be performed that are known to increase the carbon flux into the isoprenoid pathway.

Figure 3:
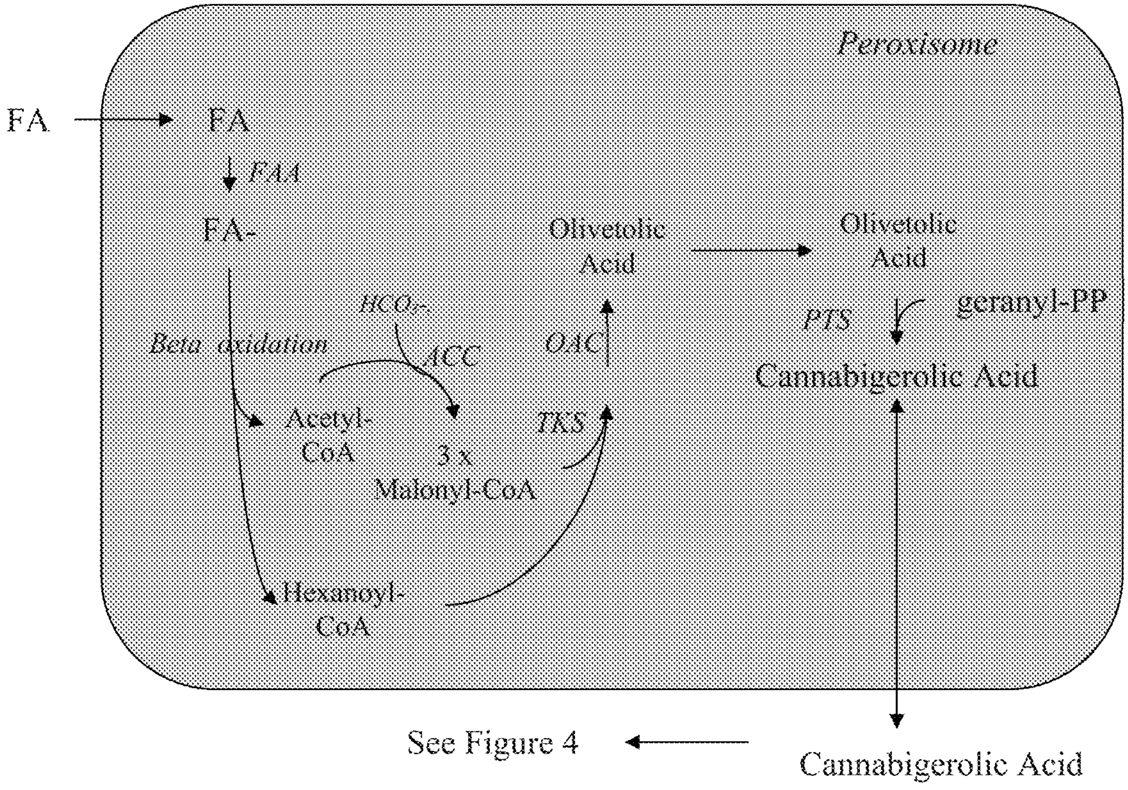
FIG. 3 depicts production of cannabinoids by producing cannabigerolic acid in the peroxisome. A fatty acid (FA) enters the peroxisome and is activated by a fatty acyl-CoA synthetase/fatty acyl activating enzyme (FAA) to become a fatty acyl-CoA (FA-CoA). It undergoes multiple rounds of beta oxidation, with each round producing one acetyl-CoA. Eventually, a molecule of hexanoyl-CoA is produced, which is then acted upon by a polyketide synthase (TKS) and olivetolic acid cyclase (OAC) to produce olivetolic acid. If necessary, an acetyl-CoA carboxylase (ACC) will be localized to the peroxisome to produce additional malonyl-CoA. A prenyltransferase (PTS) adds a geranyl moiety to olivetolic acid to produce cannabigerolic acid, which is converted to one of several cannabinoids as described in FIG. 4.

In one embodiment, which is represented by FIG. 3, the microorganism is engineered to consume fatty acids through peroxisomal beta-oxidation by insertion of a gene encoding an acyl-CoA oxidase. The acyl-CoA oxidase is targeted to the peroxisome by the addition of a peroxisomal targeting sequence (PTS) to the carboxyl-terminus of the protein. A PTS sequence can be GRRAKL or a smaller subset of those amino acids based on the consensus sequence of [S/A/H/C/E/P/Q/V]-[K/R/H/Q]-[L/F]. Alternatively, a microorganism that naturally consumes fatty acids can be used. The microorganism will be constructed to express an olivetol synthase (TKS), an olivetol cyclase (OAC), a cannabigerolic acid synthase (PTS), and either a cannabidiolic synthase (CBDAS) to produce cannabidiolic acid, a tetrahydrocannabinolic acid synthase (THCAS) to produce tetrahydrocannabinolic acid, or a cannabichromenic acid synthase (CBCAS) to produce cannabichromenic acid. The TKS, OAC and PTS enzymes will be targeted to the peroxisome by the addition of a PTS sequence, such as GRRAKL or a smaller subset of those amino acids based on the consensus sequence of [S/A/H/C/E/P/Q/V]-[K/R/H/Q]-[L/F], which will be added to the carboxyl terminus of the proteins. An alternative mechanism of targeting to the peroxisome is the use of a PTS2 sequence near the N-terminus of the protein, which is defined by the consensus sequence -(R/K)(L/V/I/Q)XX(L/V/I/H/Q)(L/S/G/A/K)X(H/Q)(L/A/F)-. An example could be RRMLSSKQL as found in Pcd1p from *S. cerevisiae*. If necessary, an acetyl-CoA carboxylase will be expressed and targeted to the peroxisome through a PTS1 or PTS2. The CBDAS, THCAS or CBCAS may be localized to either the cytosol, the peroxisome, a secretory traffic compartment such as the ER or Golgi or the vacuole through the use of signal sequences as described in FIG. 4. Other genetic manipulations may be performed that are known to increase the carbon flux into the isoprenoid pathway.

Figure 4:
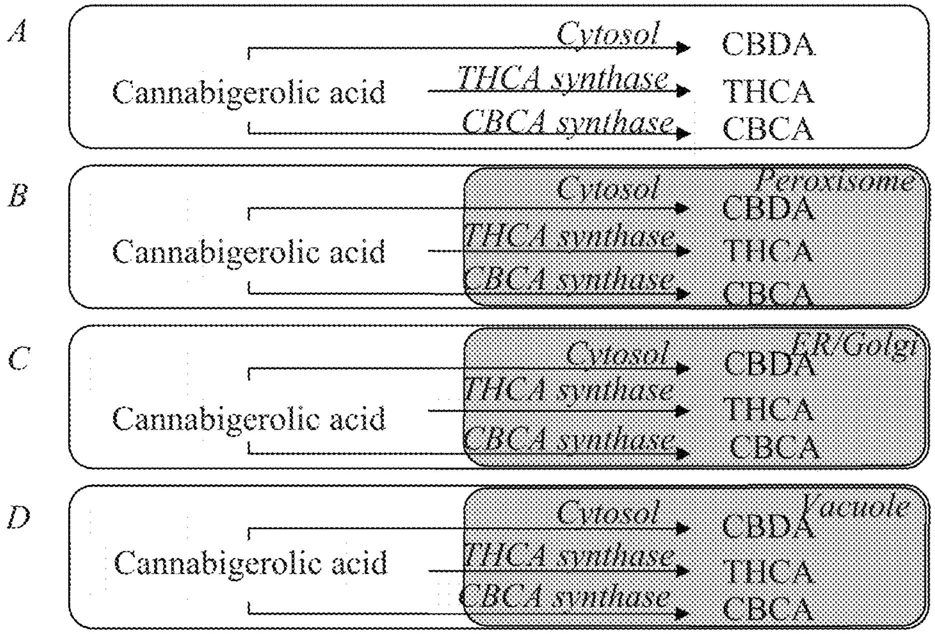
FIG. 4 depicts compartmentalization of enzymes for cannabinoid production. Cannabidiolic acid (CBDA) synthase, tetrahydrocannabidiolic acid (THCA) synthase or cannabichromenic acid (CBCA) synthase will be localized to: A) the cytoplasm, B) the peroxisome, C) compartments of the secretory pathway, such as the endoplasmic reticulum (ER) or Golgi or D) the vacuole. The enzymes will be localized to different compartments through the use of signal sequences.
Figure 5:
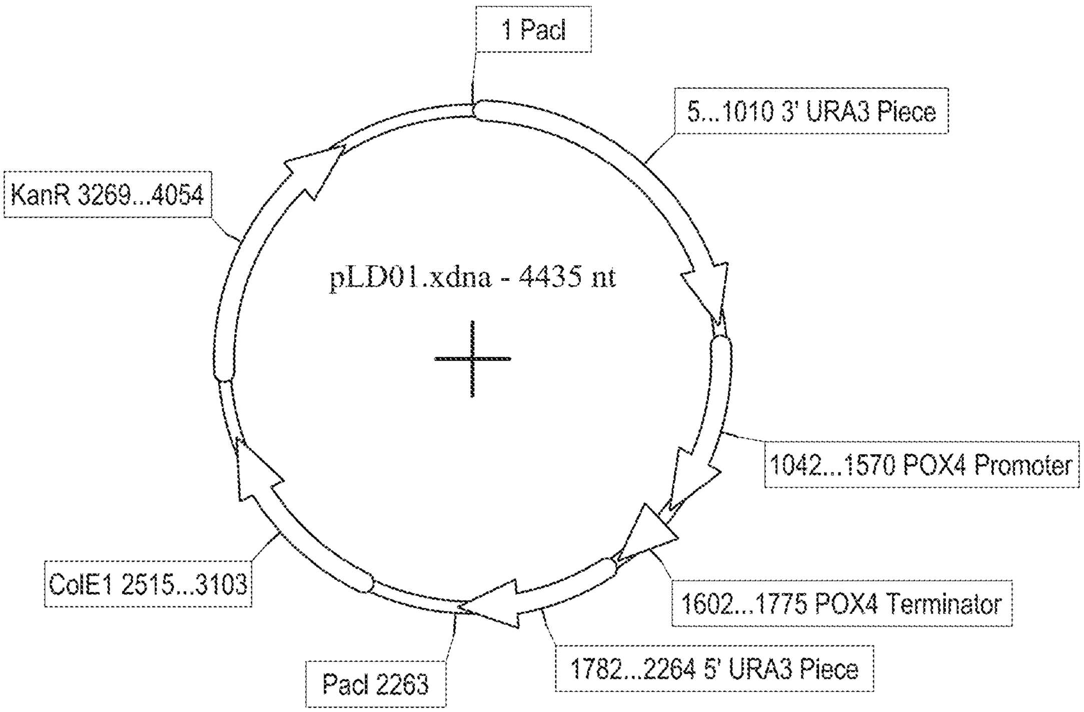
FIG. 5 provides a map of plasmid pLD1.
Figure 6:
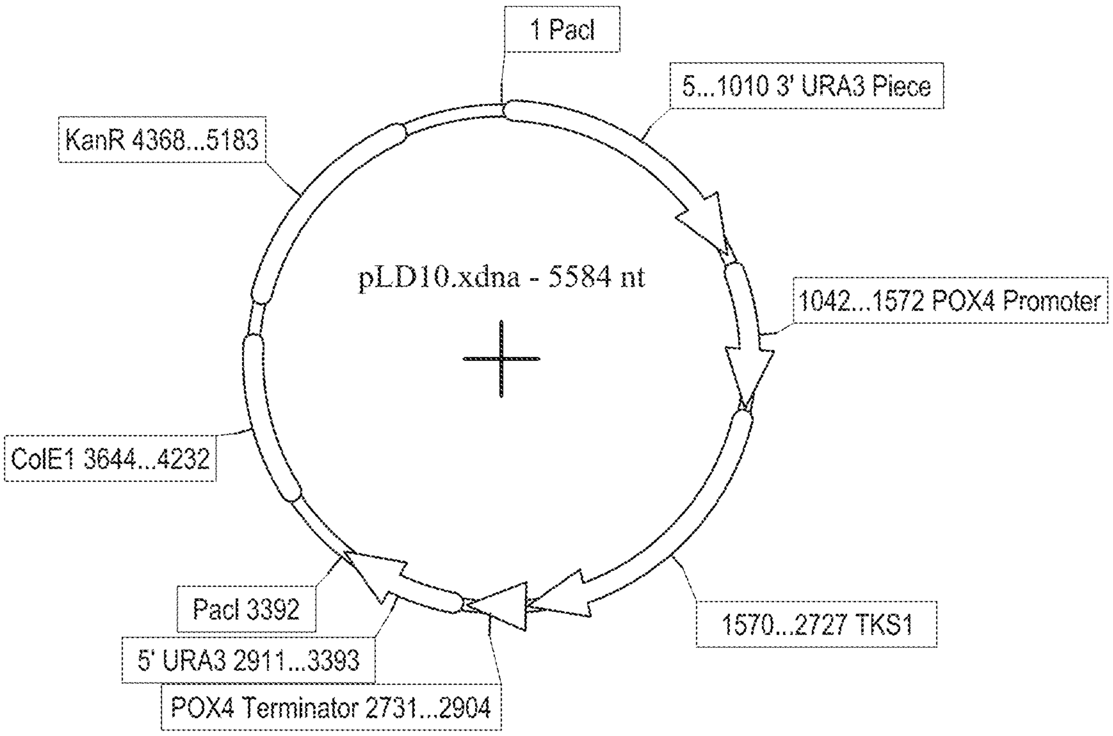
FIG. 6 provides a map of plasmid pLD10.
Figure 7:
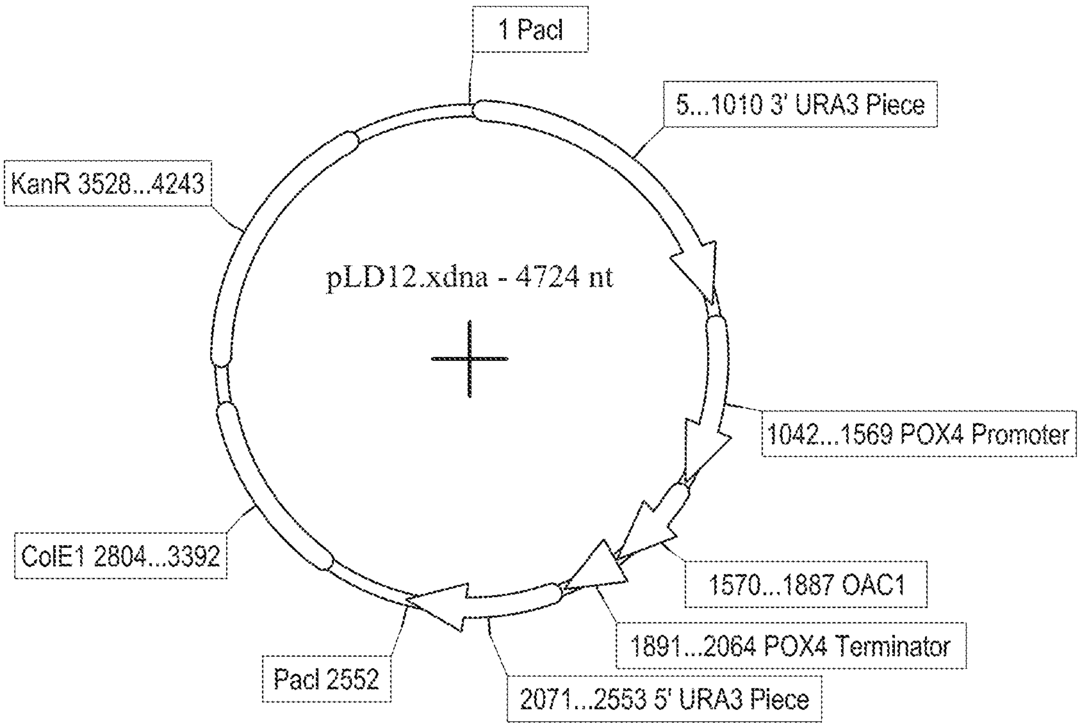
FIG. 7 provides a map of plasmid pLD12.
Figure 8:
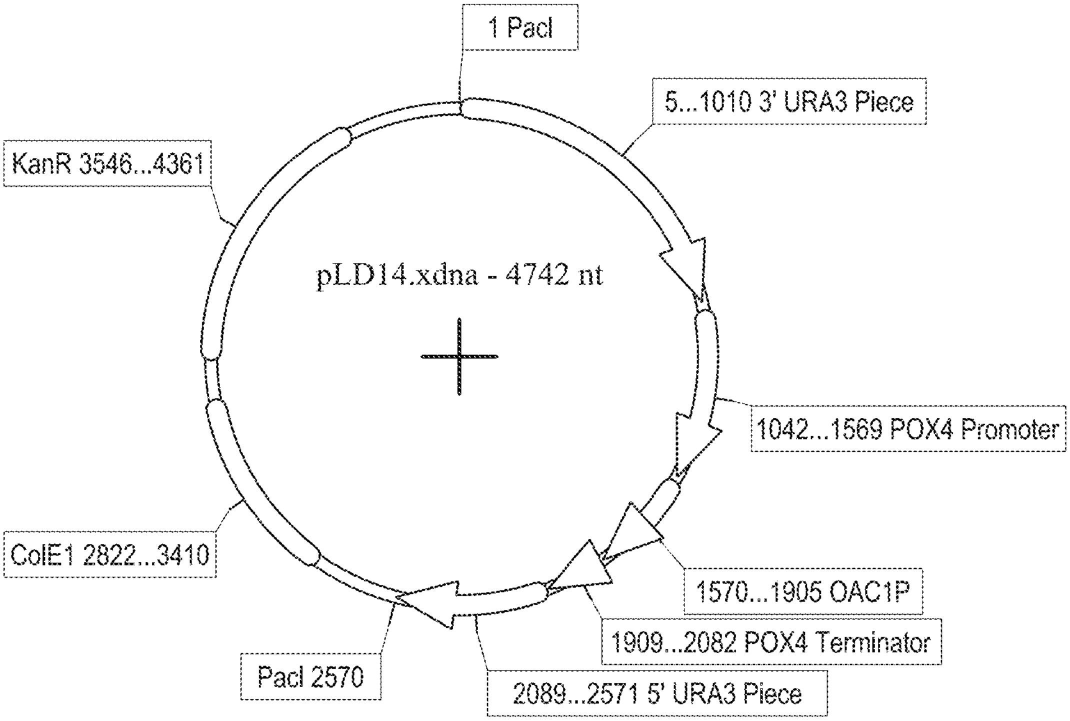
FIG. 8 provides a map of plasmid pLD14.
Figure 9:
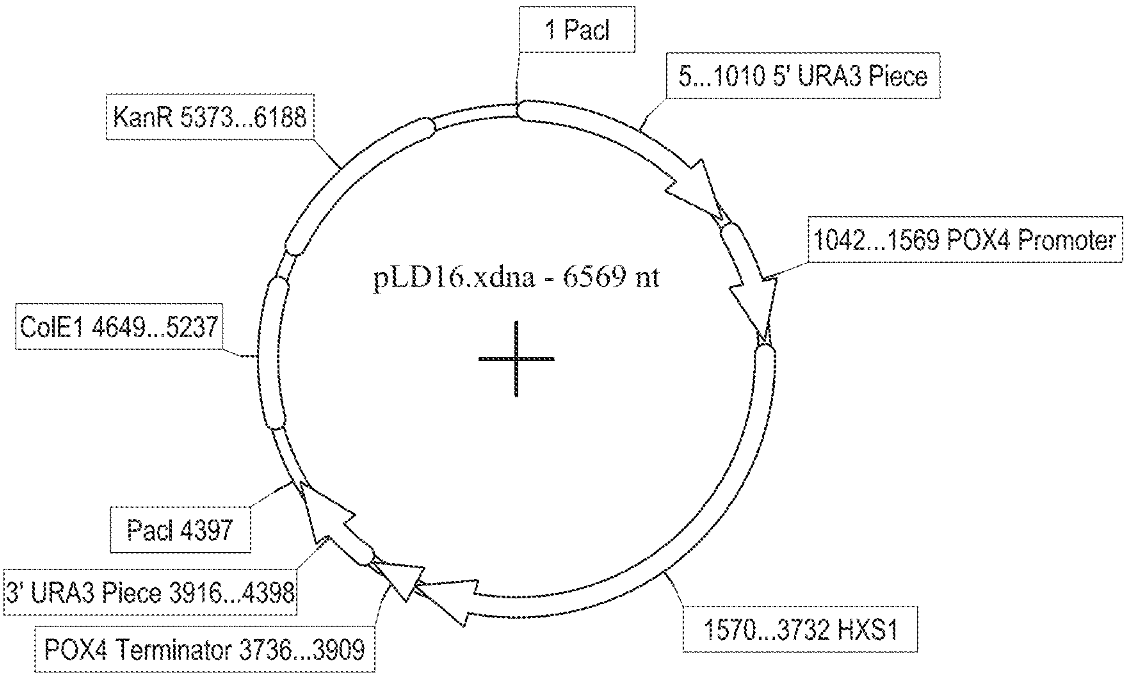
FIG. 9 provides a map of plasmid pLD16.
Figure 10:
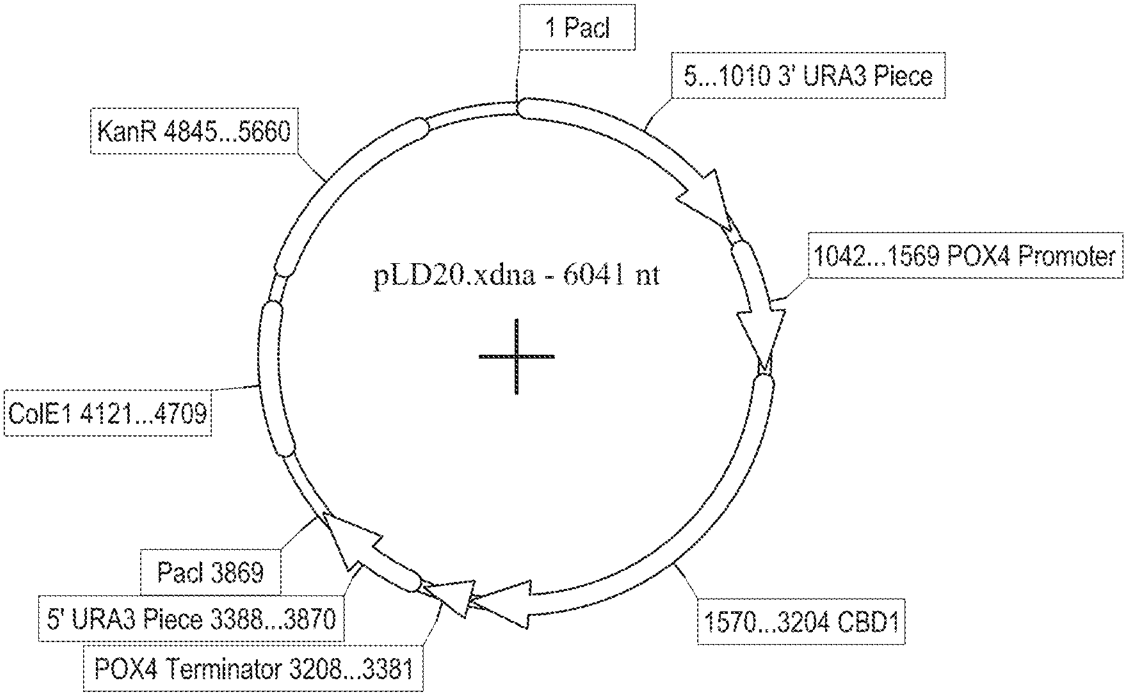
FIG. 10 provides a map of plasmid pLD20.
Figure 11:
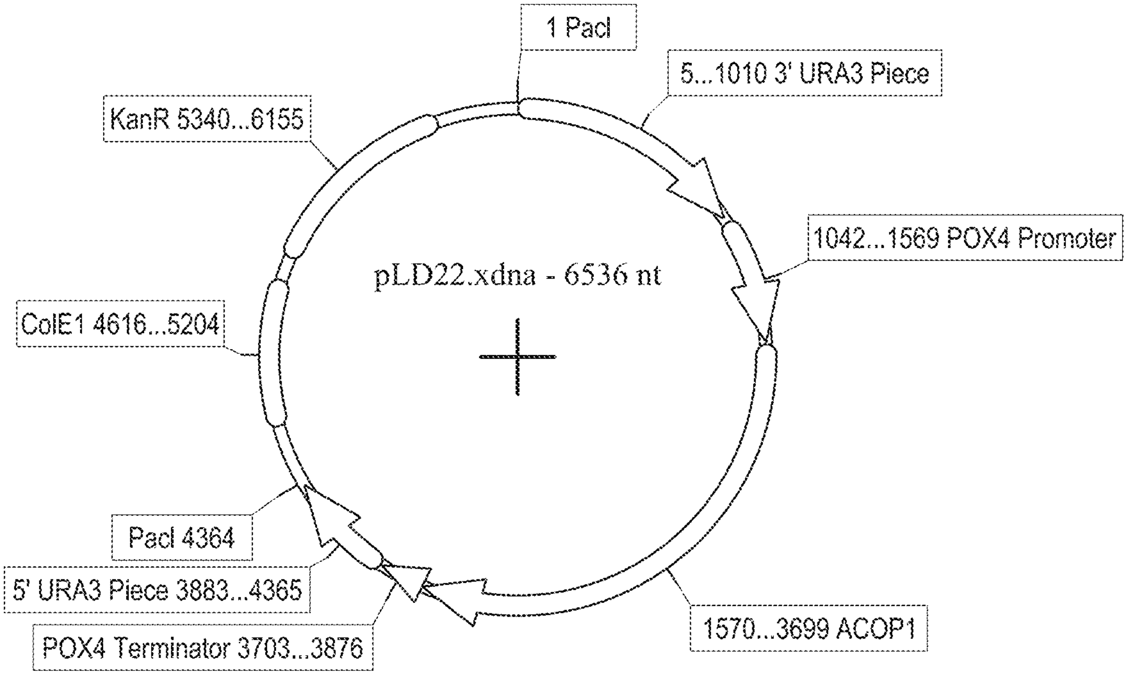
FIG. 11 provides a map of plasmid pLD22.
Figure 12:
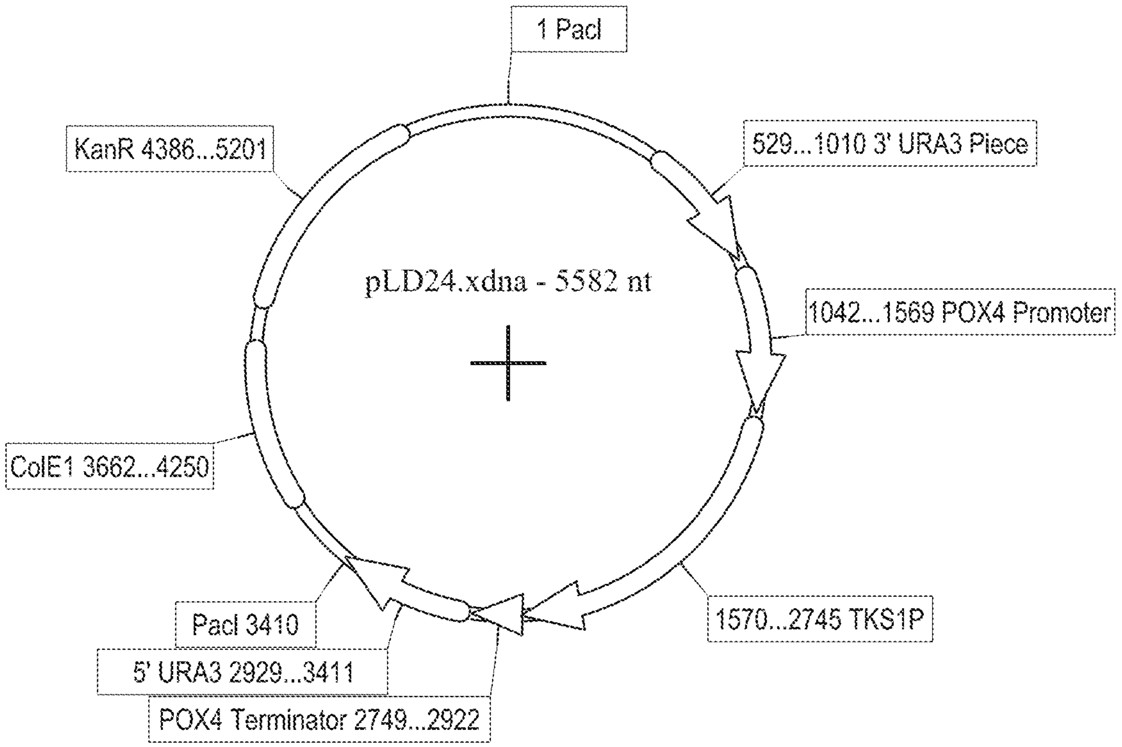
FIG. 12 provides a map of plasmid pLD24.
Figure 13:
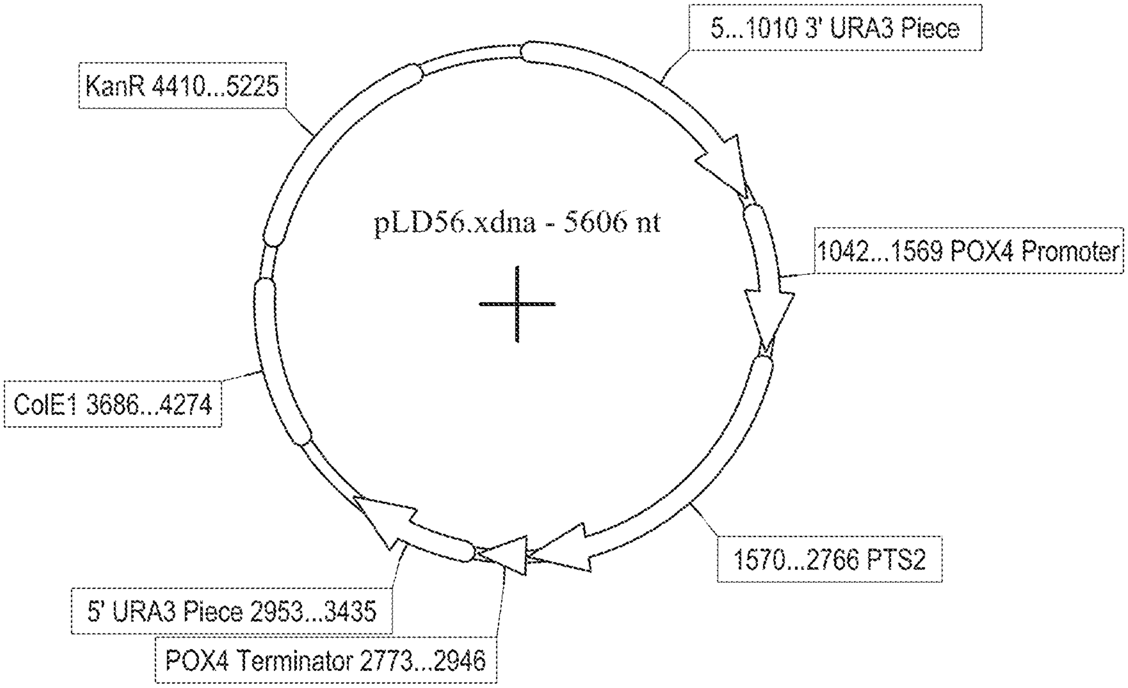
FIG. 13 provides a map of plasmid pLD56.
Figure 14:
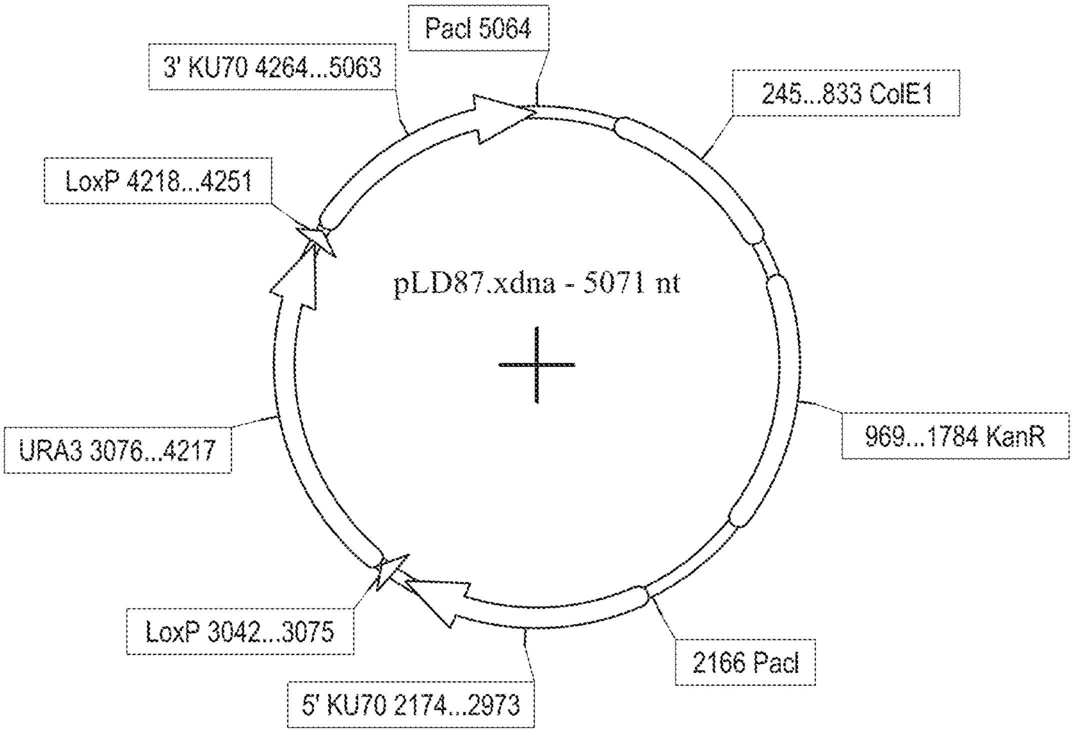
FIG. 14 provides a map of plasmid pLD87.
Figure 15:
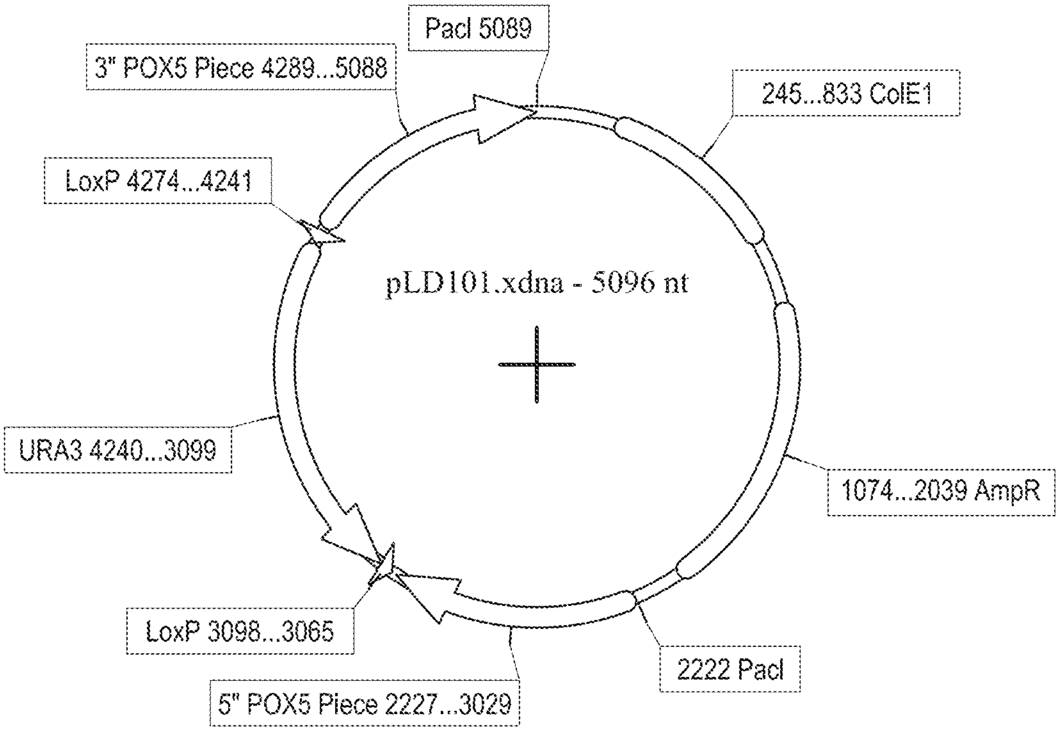
FIG. 15 provides a map of plasmid pLD101.
Figure 16:
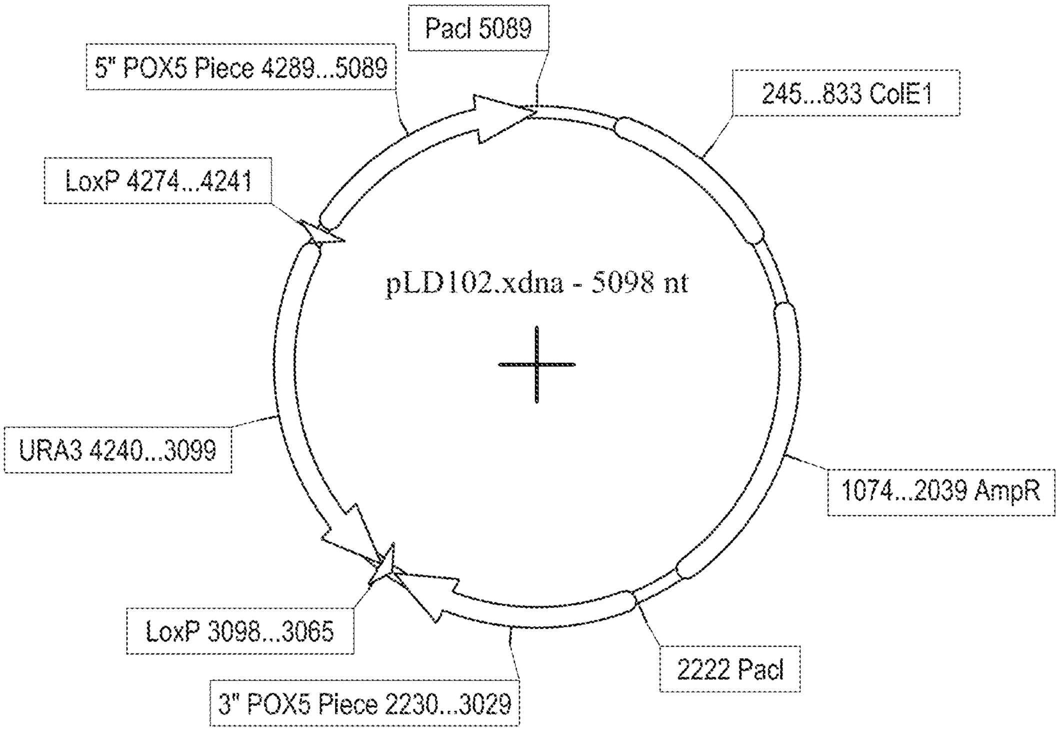
FIG. 16 provides a map of plasmid pLD102.
Figure 17:
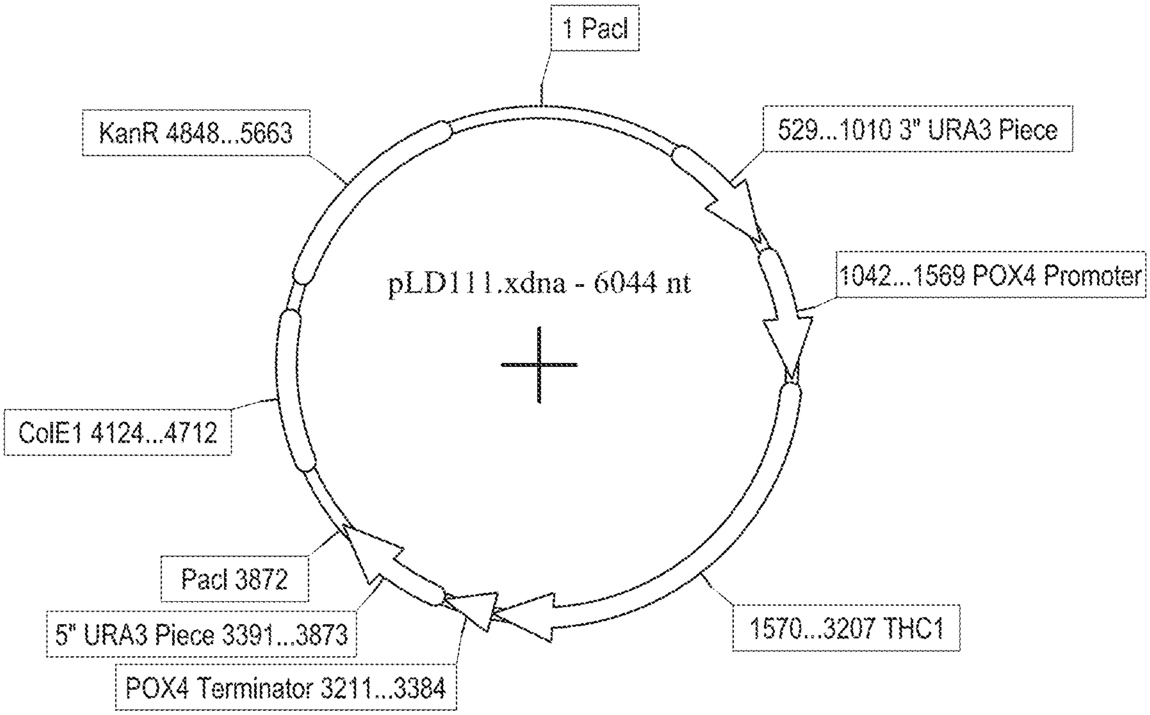
FIG. 17 provides a map of plasmid pLD111.
Figure 18:
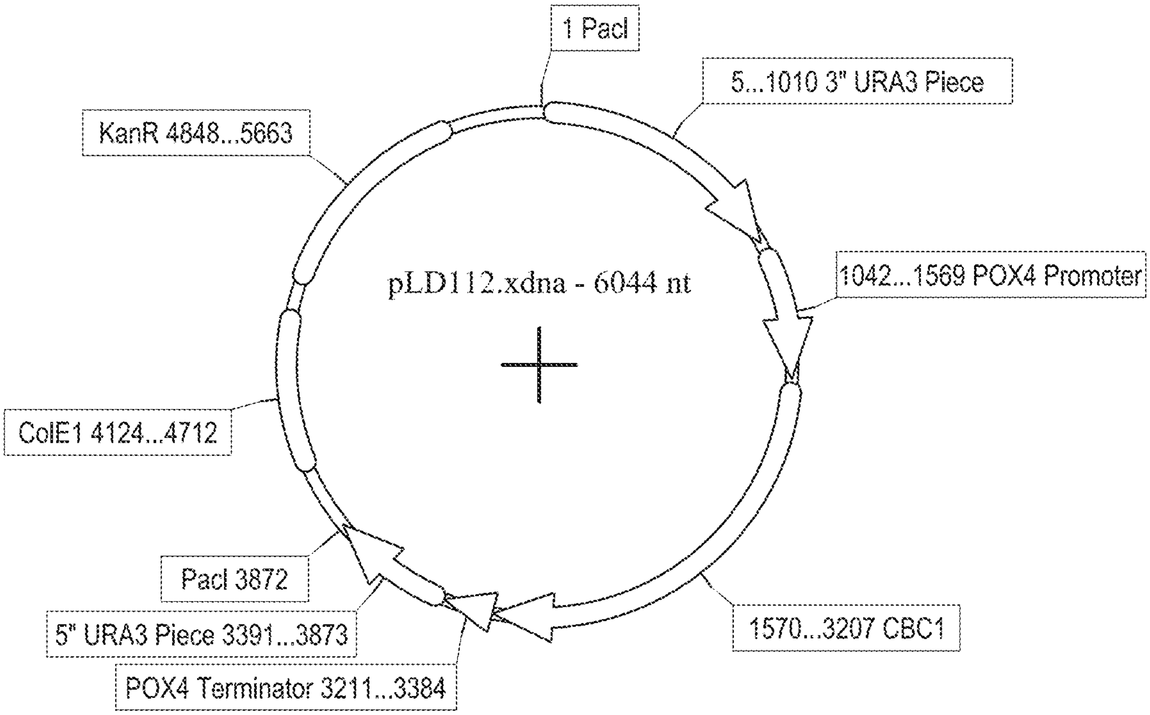
FIG. 18 provides a map of plasmid pLD112.
Figure 19:
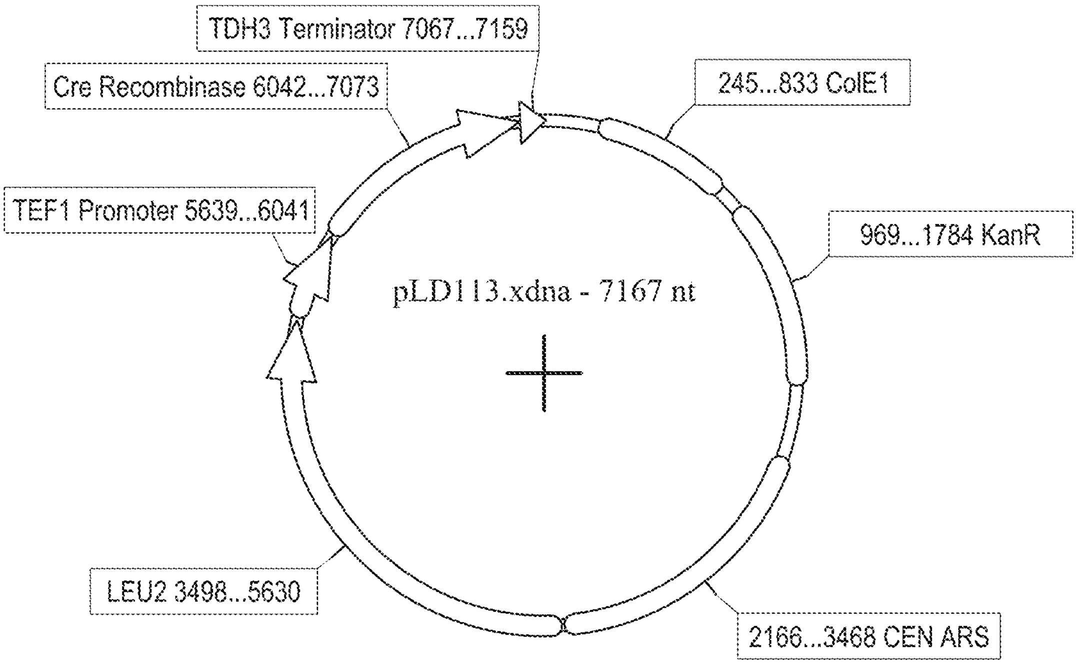
FIG. 19 provides a map of plasmid pLD113.
Figure 20:
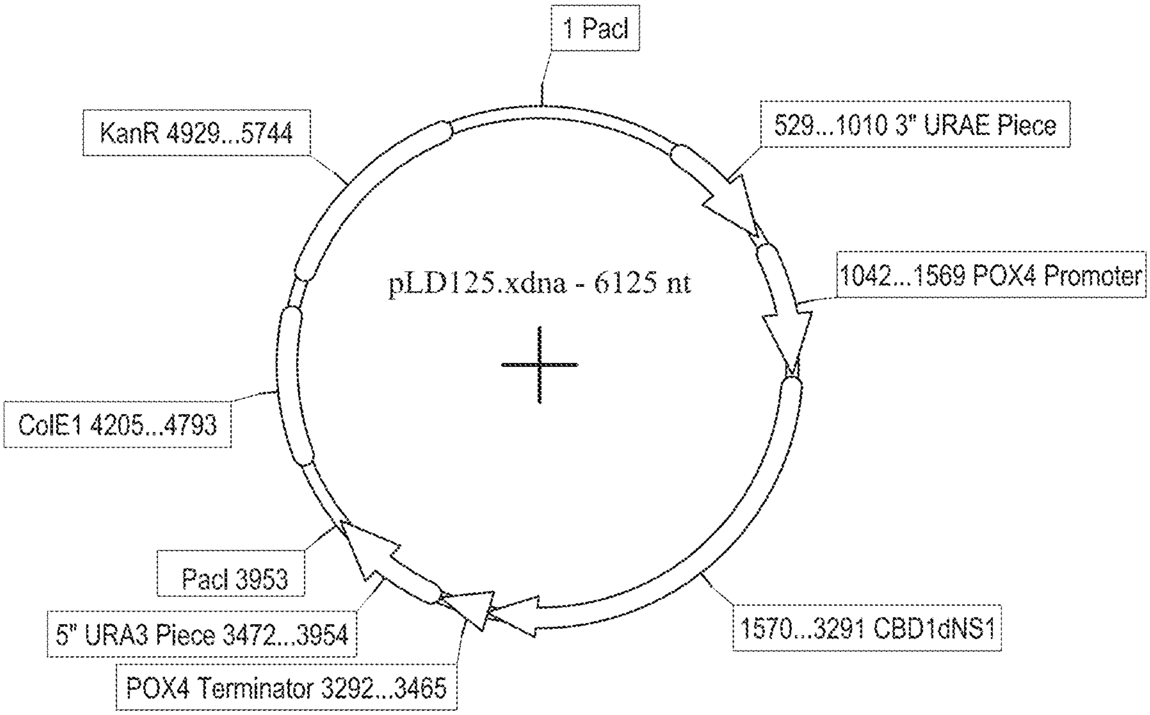
FIG. 20 provides a map of plasmid pLD125.
Figure 21:
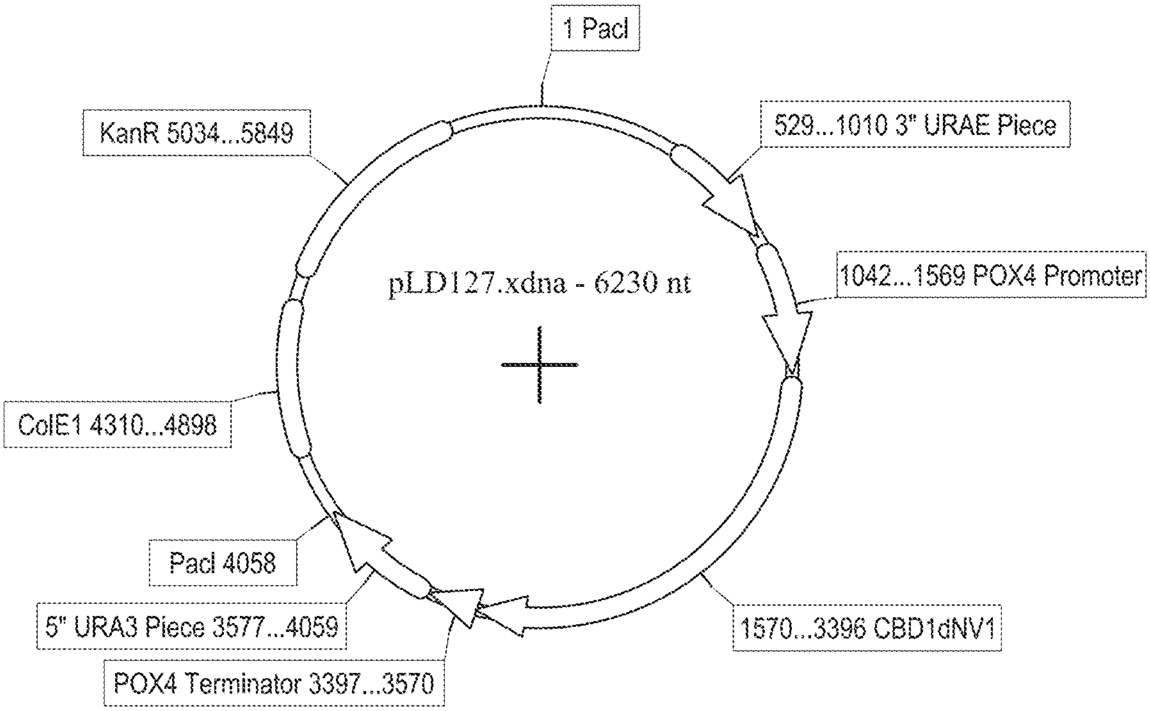
FIG. 21 provides a map of plasmid pLD127.
Figure 22:
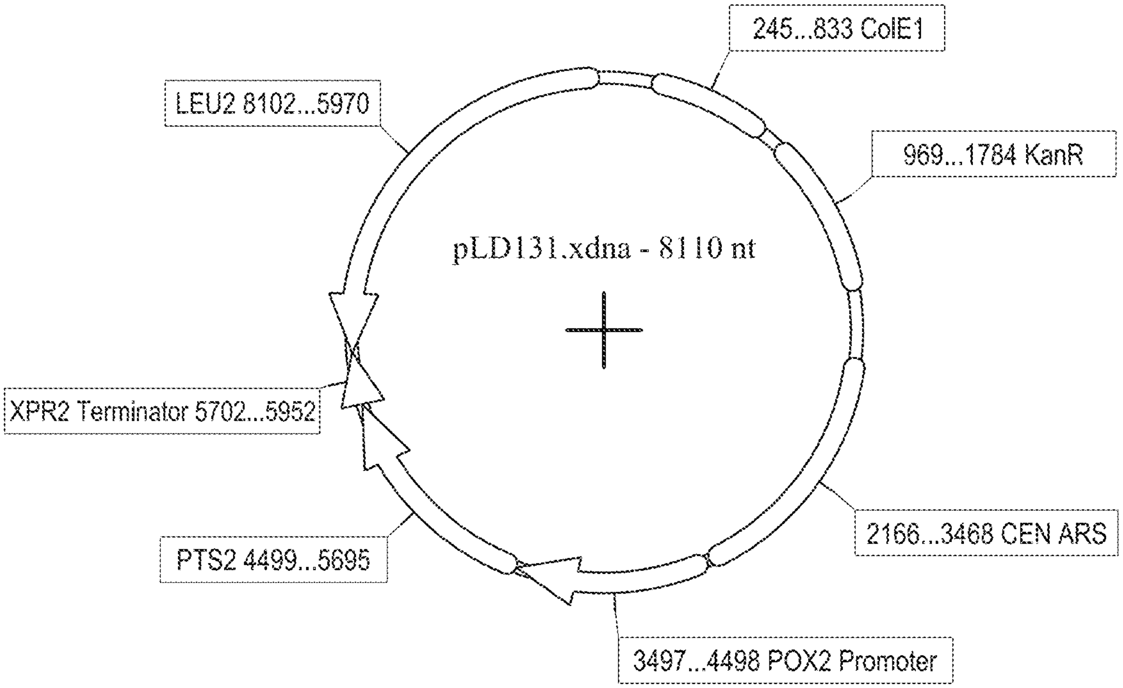
FIG. 22 provides a map of plasmid pLD131.
Figure 23:
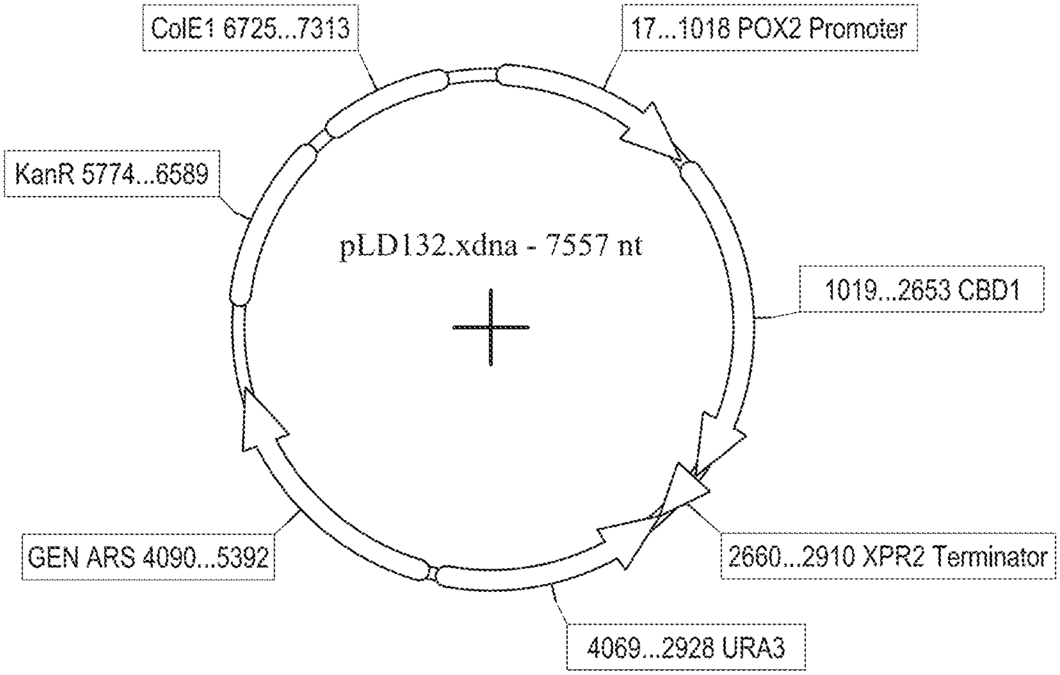
FIG. 23 provides a map of plasmid pLD132.
Figure 24:
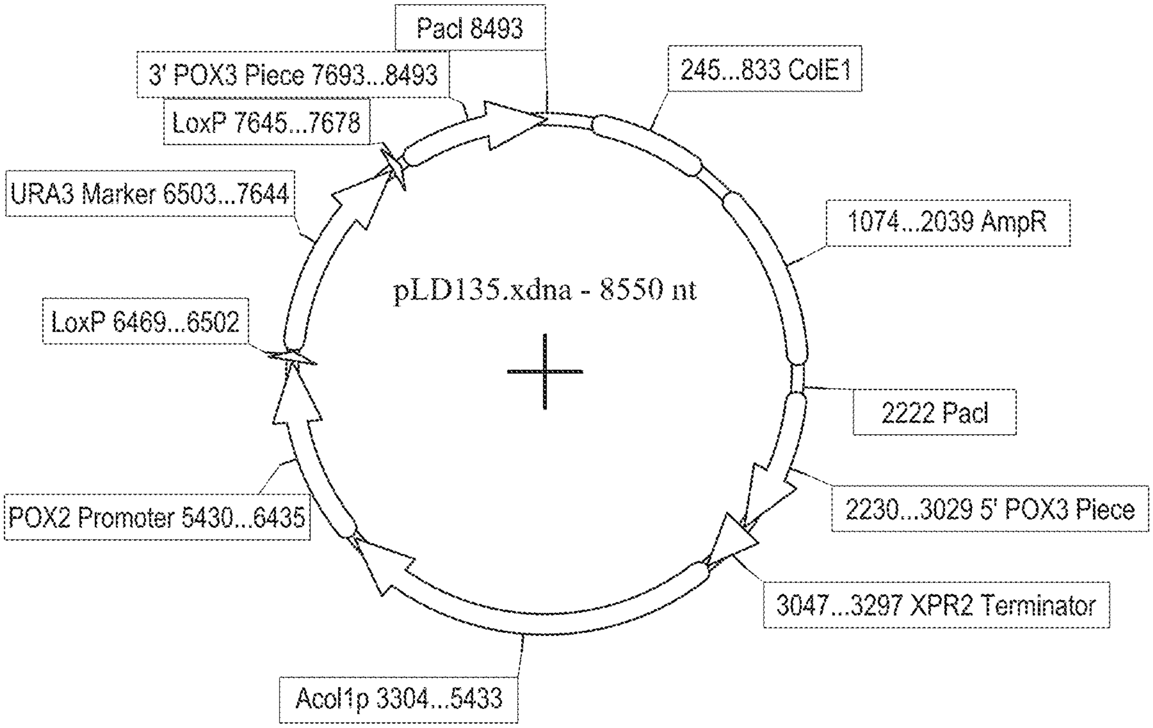
FIG. 24 provides a map of plasmid pLD135.
Figure 25:
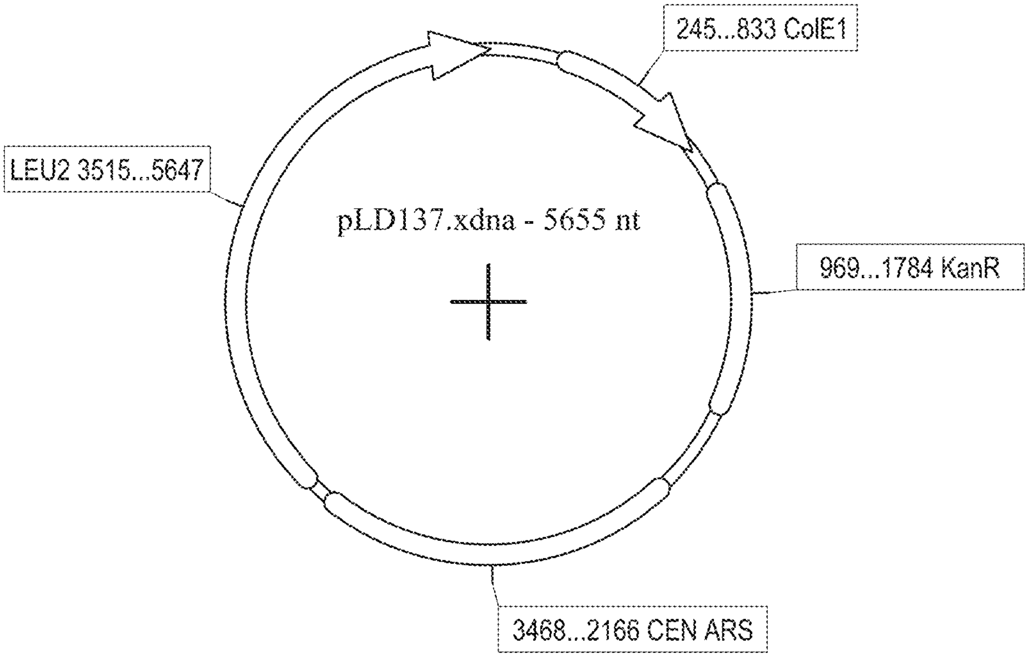
FIG. 25 provides a map of plasmid pLD137.
Figure 26:
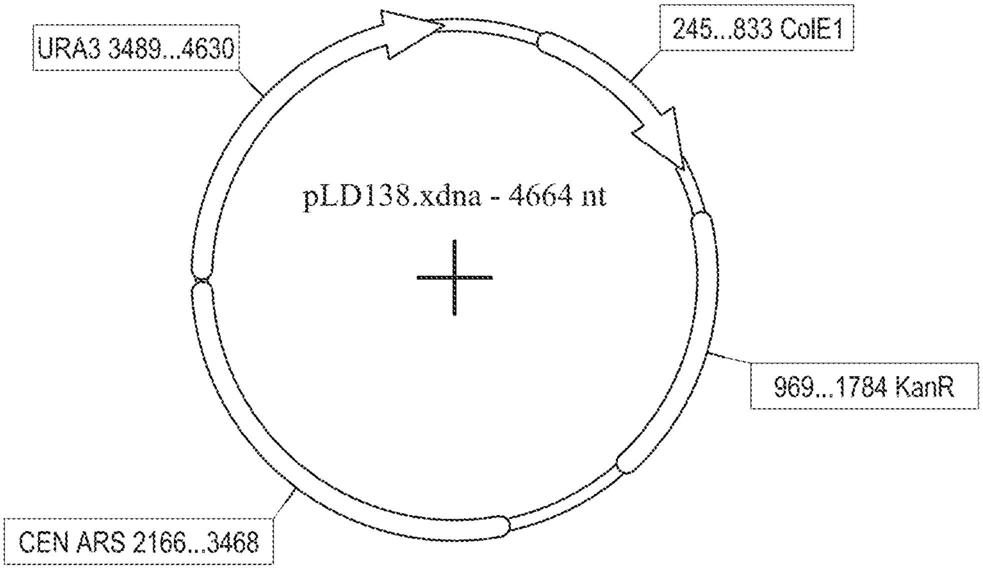
FIG. 26 provides a map of plasmid pLD138.
Figure 27:
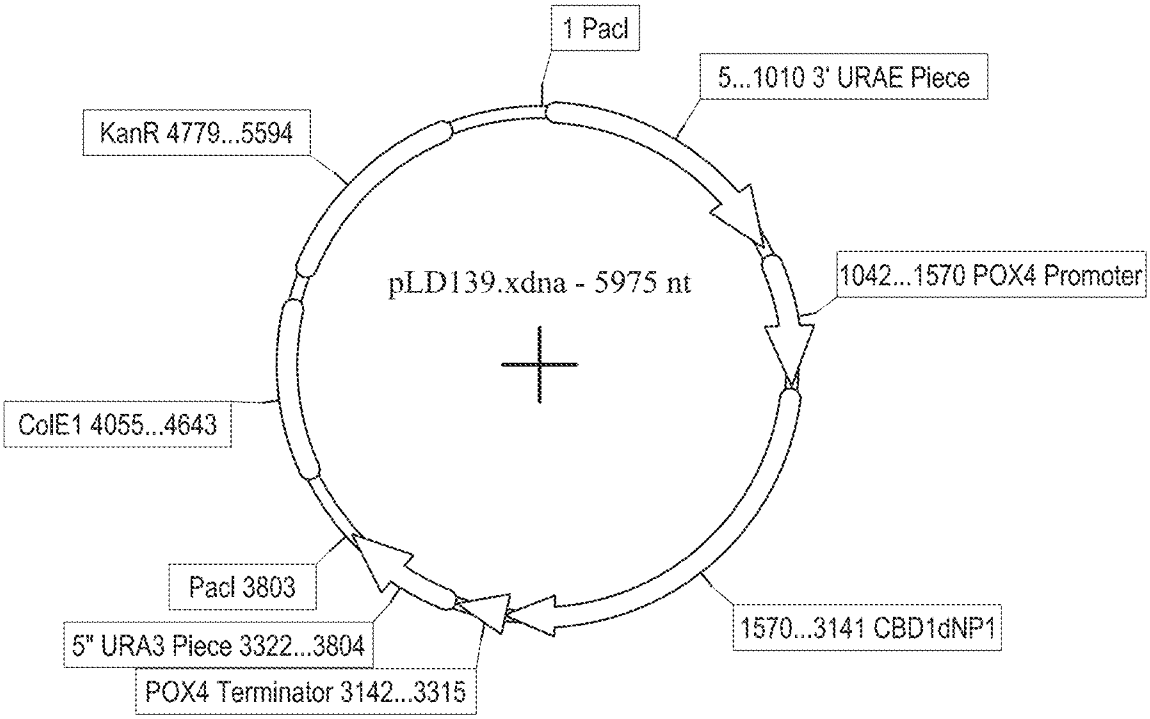
FIG. 27 provides a map of plasmid pLD139.
Figure 28:
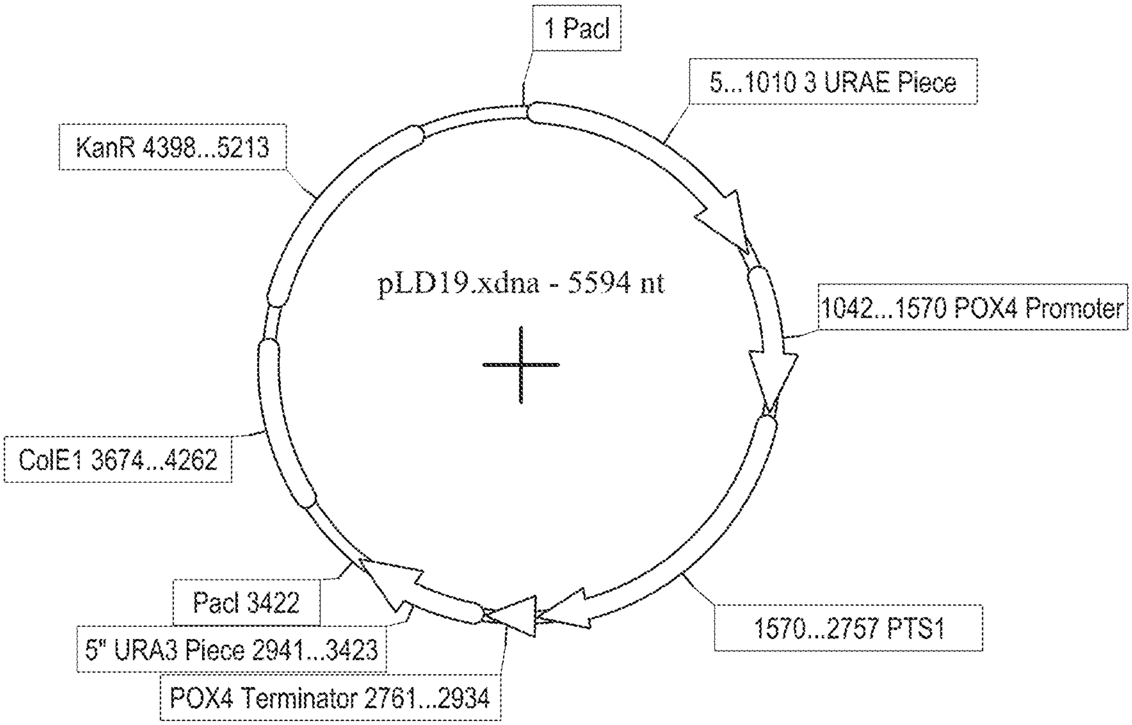
FIG. 28 provides a map of plasmid pLD19.
Figure 29:
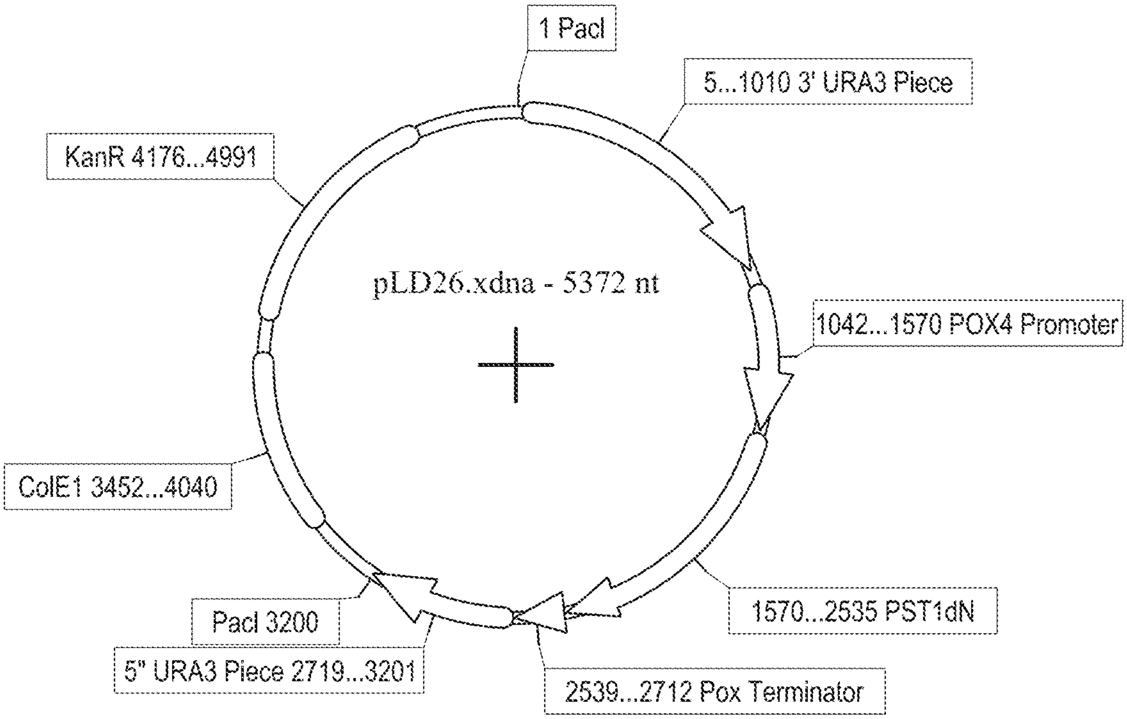
FIG. 29 provides a map of plasmid pLD26.

In one embodiment, which is represented by "A" of FIG. 4, the THCA synthase, CBDA synthase or CBCA synthase enzyme is expressed in the cytoplasm or cytosol as the native form of the enzyme.

In one embodiment, which is represented by "B" of FIG. 4, the THCA synthase, CBDA synthase or CBCA synthase enzyme is targeted to the vacuole by the addition of a KFERQ motif to the enzyme or the addition of an N-terminal QRPL motif found on carboxypeptidase Y from *Saccharomyces cerevisiae*. An alternative vacuolar targeting sequence is the hydrophobic 22 amino acid signal sequence, or pre sequence (MFSLKALLPLALLLVSANQVAA) (SEQ ID NO: 1), and 54 amino acid propeptide (KVHKAKIYKHELSDEMKEVTFEQHLAHLGQKYLTQFEKANPEVVFSREHPFFTE) (SEQ ID NO: 2) of pre-pro Proteinase A from *Saccharomyces cerevisiae* or of the particular yeast that will be engineered for cannabinoid production. Deletions in proteinases, such as PEP4, may be performed to ensure the targeted enzyme is not degraded in the vacuole.

In one embodiment, which is represented by "C" of FIG. 4, the THCA synthase, CBDA synthase or CBCA synthase enzyme is targeted to the endoplasmic reticulum (ER), Golgi or generally to the secretory pathway by the addition of some or all of the pre-pro region of alpha-factor from *Saccharomyces cerevisiae* or the Ost1p signal sequence from *Saccharomyces cerevisiae*. The alpha-factor or Ost1p secretion signal from the non-conventional yeast that will be engineered will be identified and considered as well. Other possible secretion signals include the 22 amino acid pre sequence of Proteinase A from *Saccharomyces cerevisiae*, MVRMVPVLLSLLLLLGPA (SEQ ID NO: 3) from human zinc-binding alpha-2-glycoprotein, MLFSNTLLIAAASALLAEA (SEQ ID NO: 4) from *Kluyveromyces marxianus* polygalacturonase, and MKFGVLFSVFAAIVSALPA (SEQ ID NO: 5) from Saccharomycopsis fibuligera glucoamylase. An HDEL motif can be added to the C-terminus of a protein to ensure retention in the ER.

In one embodiment, which is represented by "D" FIG. 4, the THCA synthase, CBDA synthase or CBCA synthase enzyme is targeted to the peroxisome by the addition of some or all of the PTS sequence GRRAKL (SEQ ID NO: 6) or a smaller subset of those amino acids based on the consensus sequence of [S/A/H/C/E/P/Q/V]-[K/R/H/Q]-[L/F] (SEQ ID NO: 7) to the C-terminus of each protein. An alternative mechanism of targeting to the peroxisome is the use of a PTS2 sequence near the N-terminus of the protein, which is defined by the consensus sequence -(R/K)(L/V/I/Q)XX(L/V/I/H/Q)(L/S/G/A/K)X(H/Q)(L/A/F)- (SEQ ID NO: 8). An example could be RRMLSSKQL (SEQ ID NO: 9) as found in Pcdlp from *S. cerevisiae*.

One of the intermediates for the production of some polyketides a fatty is acid. For example, an intermediate for cannabinoids is hexanoic acid. This six-carbon liner carboxylic acid is toxic to yeast at low concentration. This lipophilic weak acid crosses the plasma membrane by passive diffusion and dissociate in the neutral cytosol leading to a decrease in the intracellular pH and accumulating. This cause inhibition of growth and death. For example, at pH 5, the specific growth of *Saccharomyces cerevisiae* in minimum media drops from 0.4 hr-1 to 0.22 hr-1 at a hexanoic concentration of 2 mm (0.3 g/L). The inhibition and toxicity of hexanoic acid and some other short fatty acids makes it a challenge to run a fermentation with it. The fermentation will need to be run in a fed batch form adding hexanoic acid at a very low rate to avoid accumulating and causing toxicity. The fermentation will be needed to run at a higher pH where the toxicity of fatty acids is less. This will make the fermentation more prone to contamination. Some short fatty acids such as hexanoic acid can be corrosive to metals so special metallurgy needs to be used for the piping of the feedstock.

Herein, also disclosed is the use of fatty acid esters for the production of polyketides by fermentation. Some suitable fatty acid esters include methyl, ethyl, butyl, allyl, isobutyl, hexyl, propyl, and geranyl fatty acid esters. Of special interest are ethyl esters, as the ethyl group can be used to produce acetyl coA as a carbon source, and geraryl caproate as it will provide two intermediates for the cannabinoid pathway. In addition, this process may require the expression of an esterase to slowly cleave the fatty acid ester if there is not an endogenous esterase being produced.

Figure 30:
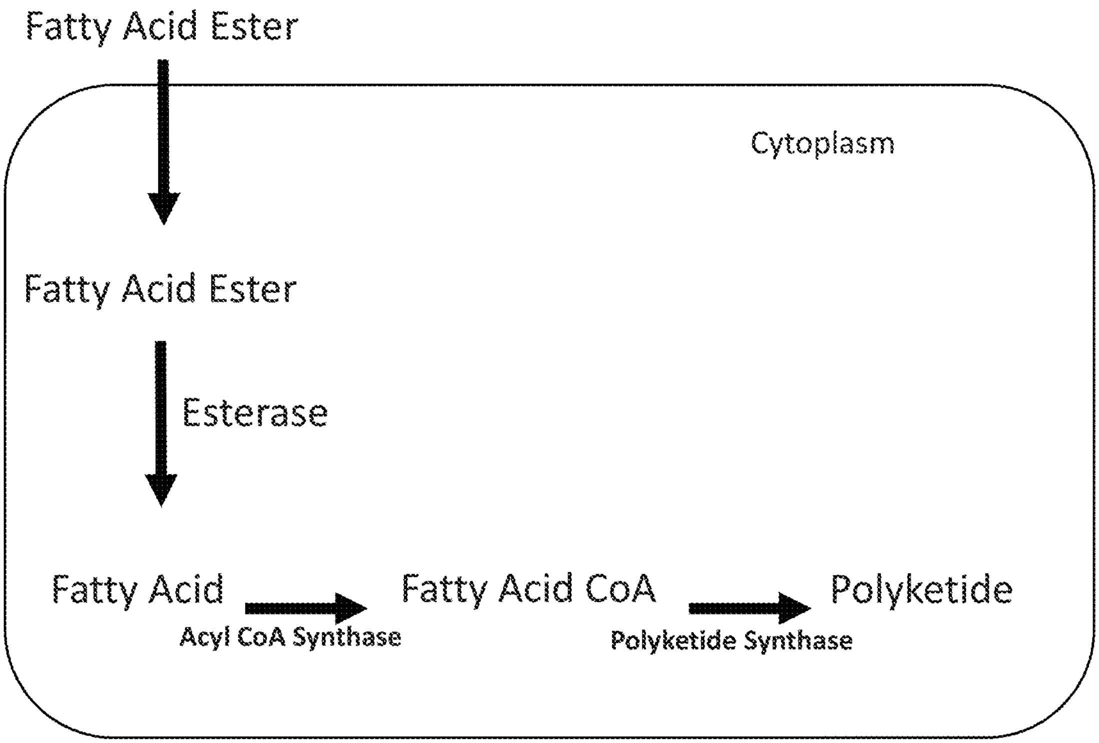
FIG. 30 depicts the use of a fatty acid ester where the fatty acid ester is transported to the cytoplasm. In the cytoplasm, a native or introduce fatty acid esterase cleaves the fatty acid ester to release the fatty acid. This fatty acid is then the substrate for an acyl-CoA synthase forming the corresponding fatty acid CoA. This fatty acid CoA is then the substrate of a polyketide synthase to crease a polyketide.

In one embodiment as illustrated in FIG. 30 for the production of the polyketides, a strain from yeast that had been modified to produce polyketides from a fatty and dextrose, is modified to express an esterase or it has an endogenous cytoplasmic fatty acid esterase.

Figure 31:
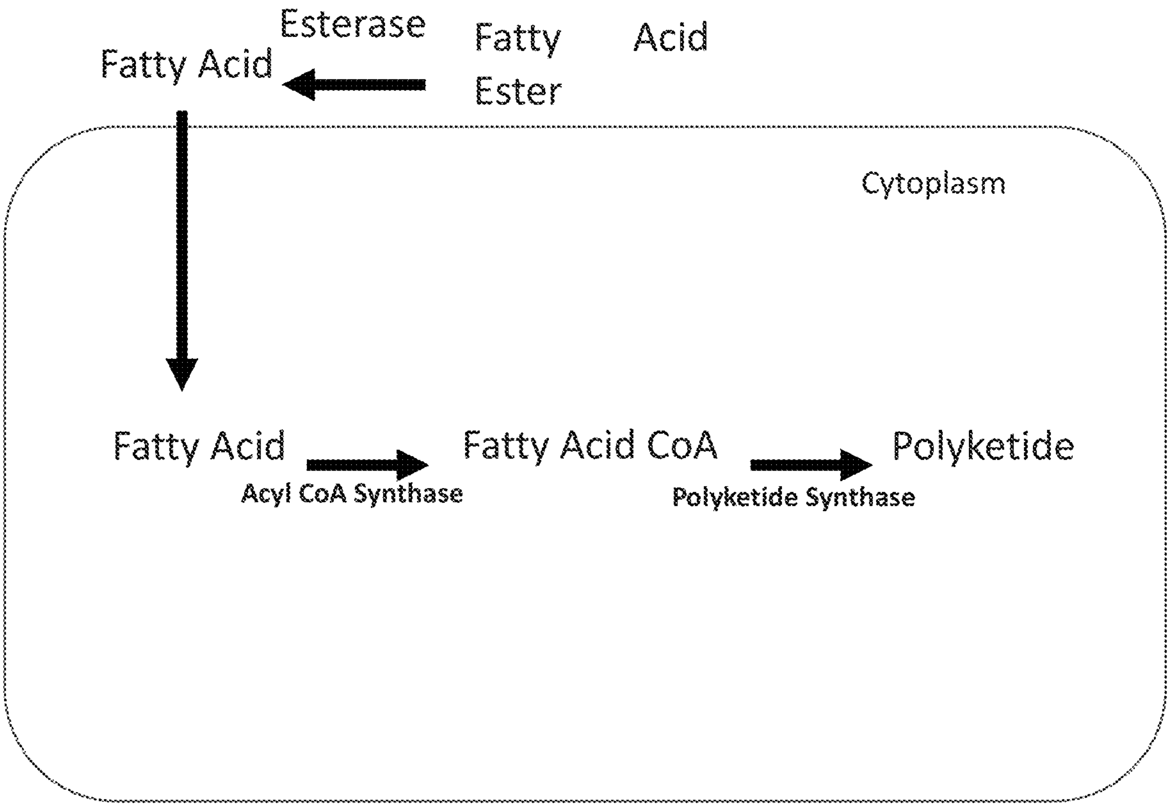
FIG. 31 depicts the use of a fatty acid ester where the fatty acid ester is cleaved outside of the cell by a native or introduced fatty acid esterase to release the fatty acid. This fatty acid is then transported into the cytoplasm where it is the substrate for an acyl-CoA synthase forming the corresponding fatty acid CoA. This fatty acid CoA is then the substrate of a polyketide synthase to crease a polyketide.

In another embodiment as illustrated in FIG. 31, a strain from a yeast that had been modified to produce cannabinoids from hexanoic acid and dextrose is modified to express a hexanoate esterase or it has an endogenous secreted hexanoate esterase. The hexanoate esterase has been targeted for secretion by a terminal fusion with a secretion motif such as the leader sequence of the yeast mating pheromone alpha-factor or invertase. In addition to the motifs mentioned here, other motifs could be used.

Some potential sources for the hexanoate ester are as follows: *Lactobacillus casei* EstB, *Lactobacillus plantarum* Lp_0796, *Acinetobacter* sp. ADP1 AreA, and *Lactococcus lactis* EstA.

The methods used to construct these strains are commonly known, have been used extensively to engineer *S. cerevisiae* and non-conventional yeasts and are described in numerous scientific publications and patents. Promoters will be used that are active during the preferred fermentation conditions. Some examples of promoters that could be used are those of the genes encoding glyceraldehyde 3-phosphate dehydrogenase and the translational elongation factor EF-1 alpha. Genes will be inserted in intergenic regions or non-essential genes.

Sources for Enzymes

Expressing one of these proteins in an acyl-CoA oxidase null mutant may result in the production of hexanoate CoA.

ACO1P Protein (Source *Anthrobacter*)
(SEQ ID NO: 10)

```
MTEVVDRASSPASPGSTTAAADGAKVAVEPRVDVA
ALGEQLLGRWADIRLHARDLAGREVVQKVEGLTHT
EHRSRVFGQLKYLVDNNAVHRAFPSRLGGSDDHGG
NIAGFEELVTADPSLQIKAGVQWGLFGSAVMHLGT
REHHDKWLPGIMSLEIPGCFAMTETGHGSDVASIA
TTATYDEETQEFVIDTPFRAAWKDYIGNAANDGLA
AVVFAQLITRKVNHGVHAFYVDLRDPATGDFLPGI
GGEDDGIKGGLNGIDNGRLHFTNVRIPRTNLLNRY
GDVAVDGTYSSTIESPGRRFFTMLGTLVQGRVSLD
GAAVAASKVALQSAIHYAAERRQFNATSPTEEEVL
LDYQRHQRRLFTRLATTYAASFAHEQLLQKFDDVF
SGARDTDADRQDLETLAAALKPLSTWHALDTLQEC
REACGGAGFLIENRFASLRADLDVYVTFEGDNTVL
LQLVAKRLLADYAKEFRGANFGVLARYVVDQAAGV
ALHRTGLRQVAQFVADSGSVQKSALALRDEEGQRT
LLTDRVQSMVAEVGAALKGAGKLPQHQAAALFNQH
QNELIEAAQAHAELLQWEAFTEALAKVDDAGTKEV
LTRLRDLFGLSLIEKHLSWYLMNGRLSMQRGRTVG
TYINRLLVKIRPHALDLVDAFGYGAEHLRAAIATG
AEATRQDEARTYFRQQRASGSAPADEKTLLAIKAG
KSRGRRAKL
```

ACO2 Protein
(Source *Yarrowia lipolytica*)
(SEQ ID NO: 11)

```
MNPNNTGTIEINGKEYNTFTEPPVAMAQERAKTSF
PVREMTYFLDGGEKNTLKNEQIMEEIERDPLFNND
```

-continued

```
NYYDLNKEQIRELTMERVAKLSLFVRDQPEDDIKK
RFALIGIADMGTYTRLGVHYGLFFGAVRGTGTAEQ
FGHWISKGAGDLRKFYGCFSMTELGHGSNLAGLET
TAIYDEETDEFIINTPHIAATKWWIGGAAHTATHT
VVFARLIVKGKDYGVKTFVVQLRNINDHSLKVGIS
IGDIGKKMGRDGIDNGWIQFTNVRIPRQNLLMKYT
KVDREGNVTQPPLAQLTYGSLITGRVSMASDSHQV
GKRFITIALRYACIRRQFSTTPGQPETKIIDYPYH
QRRLLPLLAYVYALKMTADEVGALFSRTMLKMDDL
KPDDKAGLNEVVSDVKELFSVSAGLKAFSTWACAD
VIDKTRQACGGHGYSGYNGFGQAYADWVVQCTWEG
DNNILTLSAGRALIQSAVALRKGEPVGNAVSYLKR
YKDLANAKLNGRSLTDPKVLVEAWEVAAGNIINRA
TDQYEKLIGEGLNADQAFEVLSQQRFQAAKVHTRR
HLIAAFFSRIDTEAGEAIKQPLLNLALLFALWSIE
EDSGLFLREGFLEPKDIDTVTELVNKYCTTVREEV
IGYTDAFNLSDYFINAPIGCYDGDAYRHYFQKVNE
QNPARDPRPPYYASTLKPFLFREEEDDDICELDEE
```

ACO3 Protein
(Source *Rattus norvegicus*)
(SEQ ID NO: 12)

```
MNPDLRKERASATFNPELITHILDGSPENTRRRRE
IENLILNDPDFQHEDYNFLTRSQRYEVAVKKSATM
VKKMREYGISDPEEIMWFKKLYLANFVEPVGLNYS
MFIPTLLNQGTTAQQEKWMRPSQELQIIGTYAQTE
MGHGTHLRGLETTATYDPKTQEFILNSPTVTSIKW
WPGGLGKTSNHAIVLAQLITQGECYGLHAFVVPIR
EIGTHKPLPGITVGDIGPKFGYEEMDNGYLKMDNY
RIPRENMLMKYAQVKPDGTYVKPLSNKLTYGTMVF
VRSFLVGNAAQSLSKACTIAIRYSAVRRQSEIKQS
EPEPQILDFQTQQYKLFPLLATAYAFHFVGRYMKE
TYLRINESIGQGDLSELPELHALTAGLKAFTTWTA
NAGIEECRMACGGHGYSHSSGIPNIYVTFTPACTF
EGENTVMMLQTARFLMKIYDQVRSGKLVGGMVSYL
NDLPSQRIQPQQVAVWPTMVDINSLEGLTEAYKLR
AARLVEIAAKNLQTHVSHRKSKEVAWNLTSVDLVR
ASEAHCHYVVVKVFSDKLPKIQDKAVQAVLRNLCL
LYSLYGISQKGGDFLEGSIITGAQLSQVNARILEL
LTLIRPNAVALVDAFDFKDMTLGSVLGRYDGNVYE
NLFEWAKKSPLNKTEVHESYHKHLKPLQSKL
```

-continued

ACO4 Protein
(Source *Rattus norvegicus*)

(SEQ ID NO: 13)

MNPDLRKERASATFNPELITHILDGSPENTRRRRE

IENLILNDPDFQHEDYNFLTRSQRYEVAVKKSATM

VKKMREYGISDPEEIMWFKNSVHRGHPEPLDLHLG

MFLPTLLHQATAEQQERFFMPAWNLEITGTYAQTE

MGHGTHLRGLETTATYDPKTQEFILNSPTVTSIKW

WPGGLGKTSNHAIVLAQLITQGECYGLHAFVVPIR

EIGTHKPLPGITVGDIGPKFGYEEMDNGYLKMDNY

RIPRENMLMKYAQVKPDGTYVKPLSNKLTYGTMVF

VRSFLVGNAAQSLSKACTIAIRYSAVRRQSEIKQS

EPEPQILDFQTQQYKLFPLLATAYAFHFVGRYMKE

TYLRINESIGQGDLSELPELHALTAGLKAFTTWTA

NAGIEECRMACGGHGYSHSSGIPNIYVTFTPACTF

EGENTVMMLQTARFLMKIYDQVRSGKLVGGMVSYL

NDLPSQRIQPQQVAVWPTMVDINSLEGLTEAYKLR

AARLVEIAAKNLQTHVSHRKSKEVAWNLTSVDLVR

ASEAHCHYVVVKVFSDKLPKIQDKAVQAVLRNLCL

LYSLYGISQKGGDFLEGSIITGAQLSQVNARILEL

LTLIRPNAVALVDAFDFKDMTLGSVLGRYDGNVYE

NLFEWAKKSPLNKTEVHESYHKHLKPLQSKL

ACO5 Protein
(Glycine max)

(SEQ ID NO: 14)

MEDGVDHLAFERNKAQFDVEDMKIIWAGSRQDFEL

SDRISRLVASDPAFRKDDRTRLIGRLFKNTLRKAA

YAWKRINELRLNEQEAYKLRSFVDQPAFTDLHWGM

FVPAIQGQGTDEQQQKWLPLAYGMQIIGCYAQTEL

GHGSNVQGLETTATFDPKTDEFVIHSPTLTSSKWW

PGGLGKISTHAVAYARLIIGGEDHGVHGFIVQLRS

LDDHLPLPGITIGDIGMKFGNAAYNTMDNGVLRFD

HVRIPRNQMLMRVSQVTREGRYVSSNVPRQLVYGT

MVNVRQKIVADASVALSRAVCIATRYSAVRRQFGS

HNGGLETQVIDYKTQQARLFPLLASAYAFRFVGGW

LKWLYMDVTERLQANDFSTLPEAHACTAGLKSLTT

TATADGIEECRKLCGGHGYLCSSGLPELFAVYVPA

CTYEGDNVVLLLQVARHLMKTVSQLGSGNKPVGTT

AYMARVEQLMQYHSDVEKAEDWLKPNVVLEAFEAR

ASRMSVACAQNLSKFANPEEGFQELAADLVDAAVA

HCQLIVVSKFIEKLQQDIPGKGVKKQLEVLCSIYA

LFLLHKHLGDFLSTGCINPKQGSLASEQLRNLYSQ

VRPNAIALVDAFNYTDHYLGSILGRYDGNVYPKMN

EEAWKDPLNDSVVPDGFKEYIQPMLKQQLRNARL

-continued

ACO6 Protein
(Glycine Max)

(SEQ ID NO: 15)

MEGMVDHLAFERNNSQFDVDEMKIVWAGSRHAFEV

SDKMARLVASDPAFRKDDRVVLDRKALFKNTLRKA

AYAWKRBELRLSEEEAAMLRSFVDQPAFTDLHWGM

FVPAIKGQGTEEQQKKWLPLAHKMQIIGCYAQTEL

GHGSNVQGLETTATFDPRTDEFVIHSPTLTSSKWW

PGGLGKVSTHAVVYARLITDGQDHGVHGFIVQLRS

LDDHLPLPGITVGDIGMKFGNGAYNSMDNGMLRFD

HVRIPRNQMLMRVSQVTREGKYVQSSVPRQLVYGT

MVYVRQTIVSDASVALSRAVCIATRYSAVRRQFGS

KEGGLETQVIDYKTQQARLFPLLASAYAFRFVGEW

LKWLYMDVMKRLQASDFSTLPEAHACTAGLKSLTT

SATADGIEECRKLCGGHGYLCSSGLPELFAVYIPT

CTYEGDNTVLLLQVARHLIKTISQLGSRNKPVGTT

SYIGRVEQLMQYRSDVQKVEDWLKPNAVLGAFEAR

AAKKVVACAQNLSKFTNPEEGFQELSVDLVEAAVA

HCQLIVVSKFIEKLQQDIPGKGVKQQLELLCSIYA

LFLLHKHLGDFLATGCITPKQGSLANELLRSLYSQ

VRPNAIALVDAFNYTDHYLGSVLGRYDGDVYPKLY

EEAWKDPLNDSVVPDGFQEYIRPMLKQQLRNARL

ACO7 Protein
(Source *Beuvaria bassiana*)

(SEQ ID NO: 16)

MSFPDNLKPKEPSGSSLLEKERRQSPVDVDALGKH

IFAGTSFLERQARVLRAIEQEPLFDKSRQQQLSRV

ERVKLGLARGKLMRRLQDRHGWDMDDYHMAAYLVG

EQSPYRLHVGMFRTTVEEQSSDAQRAYWMPRVNGW

EVSGAYSQTELGHGSNVRGVELEARWDPAAREFVV

HSPTLTAAKWWNGSLGRTANHAILMAQLMVPDPKR

EGQYISHGPQAFIAQIRDLKTNLPLEGVVIGDIGV

KIGFTSMDNGYMLFNQFRIPHSALLSRYVQLDPET

GVFSKSPNPALAYGTMTSIRTMLVEEAGTHLARAV

TIAIRYTAIRQQFRDKDSQDPSSAELQVLDYPTVQ

VRLFPLLAAAFALQYTGKVMRQDYAKTRGEVEKGN

LEGLAVMHSNSSGLKSLSTEITNAGIETCRRAMGG

HGYGSGSGLVEMQKDYQAKPILEGDNWMITQQTSS

FLIKRMTAAAKTRNEPPKDQIDAQLKTFLHQKDKG

RTFDILNSDSDIEESFKWRAASMTYDAYEARVIKK

KRHNDLLIQFHKLSHAHSQSIMVSSFLTTLTSSND

LAHETKEIVFDLYRLFAYTTIQAESYEFLRCGAAS

SKDLDALPERIQALLTRIRPHAVKLVDAWKIPDYL

-continued

LDSALGRYDGNVYEDLFNRAHRLNPLNDIVFNPDY

KDDEIVKGSGERKPLSPKL

ACO8 Protein
(Source *Aspergillus nidulans*)
(SEQ ID NO: 17)

MPNPPPAWVQALKPASPQGTELLTQERAQSNIDVD

TLGDLLHTKEALKKQDEILSVLKSEKVFDKSRNHV

LGRTEKIQLALARGKRLQQLKKAHNWSDEDVHVAN

DLVSEPTPYGLHASMFLVTLREQGTPEQHKLFYER

ARNYEIIGCYAQTELGHGSNVRGLETTATWDPSDQ

TFIIHSPTLTASKWWIGSLGRTANHAVVMAQLYIG

GKNYGPHPFVVQIRDMETHQPLENVYVGDIGPKFG

YNTMDNGFLLFNKLKIPHVNMLARFAQVDKATNKY

IRPASPSLMYGTMTWVRSNIVLQAGGVLARGVTIA

VRYCAVRRQFQDRDAKANAEENQVLNYKMVQIRLL

PLLAAMYALHFTGRGMMRLYEENQERMKAAAQADQ

EKRGAGPEQLRAGSDLLADLHATSCGLKALASTTA

GEGLEVCRRACGGHGYSNYSGIGPWYADYLPTLTW

EGDNYMLTQQVARYLLKSARAVLAGKGTANDTSRI

LQAYLARRDKGASFDILGNDADIVAAFAWRTAHLT

FETLKYRDVEKRSWNSLLINFWRLSTALSQYLVVK

NFYEAVNSPEIRSSLDKDTASTLRSLFRLHALHTL

DREASEFFSSAAVTVRQIGLTQTSEVPKLLDEIRP

HAVRLVDSWKIPDWQLDSALGRSDGDVYPDLFKRA

SMQNPVNDLVFDPYPWNENVLKNAGEIKSKL

ACO9 Protein
(Source *Arabidopsis thaliana*)
(SEQ ID NO: 18)

MESRREKNPMTEEESDGLIAARRIQRLSLHLSPSL

TPSPSLPLVQTETCSARSKKLDVNGEALSLYWIRG

KHIDIQEKIFDFFNSRPDLQTPIEISKDDHRELCM

NQLIGLVREAGVRPFRYVADDPEKYFAIMEAVGSV

DMSLGIKMGVQYSLWGGSVINLGTKKHRDKYFDGI

DNLDYTGCFAMTELHEGSNVQGLQTTATFDPLKDE

FVIDTPNDGAIKWWIGNAAVHGKFATVFARLILPT

HDSKGVSDMGVHAFIVPIRDMKTHQTLPGVEIQDC

GHKVGLNGVDNGALRFRSVRIPRDNLLNRFGDVSR

-continued

DGTYTSSLPTINKRFGATLGELVGGRVGLAYASVG

VLKISATIAIRYSLLRQQFGPPKQPEVSILDYQSQ

QHKLMPMLASTYAYHFATVYLVEKYSEMKKTHDEQ

LVADVHALSAGLKSYVTSYTAKALSVCREACGGHG

YAAVNRFGSLRNDHDIFQTFEGDNTVLLQQVAADL

LKRYKEKFQGGTLTVTWSYLRESMNTYLSQPNPVT

ARWEGEDHLRDPKFQLDAFRYRTSRLLQNVAARLQ

KHSKTLGGFGAWNRCLNHLLTLAESHIETVILAKF

IEAVKNCPDPSAKAALKLACDLYALDRIWKDIGTY

RNVDYVAPNKAKVCFLV

ACO10 Protein
(Source *Arabidopsis thaliana*)
(SEQ ID NO: 19)

MESRREKNPMTEEESDGLIAARRIQRLSLHLSPSL

TPSPSLPLVQTETCSARSKKLDVNGEALSLYWIRG

KHIDIQEKIFDFFNSRPDLQTPIEISKDDHRELCM

NQLIGLVREAGVRPFRYVADDPEKYFAIMEAVGSV

DMSLGIKMGVQYSLWGGSVINLGTKKHRDKYFDGI

DNLDYTGCFAMTELHHGSNVQGLQTTATFDPLKDE

FVIDTPNDGAIKWWIGNAAVHGKFATVFARLILPT

HDSKGVSDMGVHAFIVPIRDMKTHQTLPGVEIQDC

GHKVGLNGVDNGALRFRSVRIPRDNLLNRFGDVSR

DGTYTSSLPTINKRFGATLGELVGGRVGLAYASVG

VLKISATIAIRYSLLRQQFGPPKQPEVSILDYQSQ

QHKLMPMLASTYAYHFATVYLVEKYSEMKKTHDEQ

LVADVHALSAGLKSYVTSYTAKALSVCREACGGHG

YAAVNRFGSLRNDHDIFQTFEGDNTVLLQQVAADL

LKRYKEKFQGGTLTVTWSYLRESMNTYLSQPNPVT

ARWEGEDHLRDPKFQLDAFRYRTSRLLQNVAARLQ

KHSKTLGGFGAWNRCLNHLLTLAESHIETVILAKF

IEAVKNCPDPSAKAALKLACDLYALDRIWKDIGTY

RNVDYVAPNKAKAIHKLTEYLSFQVRNVAKELVDA

FELPDHVTRAPIAMQSDAYSQYTQVVGF

Proteins involved in beta-oxidation that their encoding gene may be modified, disrupted or replaced to produce a short-chain fatty acid intermediate.

POX4 Acyl-CoA Oxidase (Source *Candida viswanathii*)
(SEQ ID NO: 20)

MTFTKKNVSVSQGPDPRTSIQTERANSKFDPVTMNYFLEGSKERSELMKSLAQQIERDPI

LFTDGSYYDLTKDQQRELTVLKINRLSRYREGDSVDTFNKRLSIMGVVDPQVATRIGVNL

GLFLSCISGNGTAEQFKYWAIDKGTHNIQGLYGCFGMTELGHGSNVAGVETTATFDKETD

EFVINTPHIGATKWWIGGAAHSATHCSVYARLVVDGKDYGVKTFVVPLRDSNHDLMPGVT

-continued

VGDIGAKMGRDGIDNGWIQFSNVRIPRFFMLQKFCKVSAEGEVVLPPLEQLSYSALLGGR

VMMVLDSYRMLARVSTIALRYAIGRRQFKGDNVDQNDPNALETQLIDYPLHQKRLFPYLA

AAYVVSTGALKVEHTIQSTLATLDAAVENNDTTAIFKSIDDMKSLFIDSGSLKATTTWLA

AEAIDQCRQACGGHGYSSYNGFAKAFNDWVVQCTWEGDNNVLSLSVGKPIIKQIIGIEDN

GKTVRGSTAFLNQVKDFTGSNASKVVLNNTSDLNDINKVIKSIEVAIIRLAHEAAISVRK

ESLDFAGAELVQISKLKAHHYLLTEFVKRVGEFEHKELVPFLNTIGRLYSATVVLDKFAG

VFLTFNVASPQAITDLASTQIPKLCAEVRPNVVAYTDSFQQSDMVINSAIGKYDGDVYEN

YFDLVKQLNPPKNTKAPYTAALEGMLNRPSLEARERYEKSDETAAILSKPOX5

POX5 Acyl-CoA Oxidase (Source *Candida viswanathii*)

(SEQ ID NO: 21)

MPTELQKERELTKFNPKELNYFLEGSQERSEIISNMVEQMQKDPILKVDASYYNLTKDQQ

REVTAKKIARLSRYFEHEYPDQQAQRLSILGVFDPQVFTRIGVNLGLFVSCVRGNGTNSQ

FFYWTINKGIDKLRGIYGCFGMTELAHGSNVQGIETTATFDEDTDEFVINTPHIGATKWW

IGGAAHSATHCSVYARLKVKGKDYGVKTFVVPLRDSNHDLEPGVTVGDIGAKMGRDGIDN

GWIQFSNVRIPRFFMLQKYCKVSRSGEVTMPPSEQLSYSALIGGRVTMMMDSYRMTSRFI

TIALRYAIHRRQFKKKDTDTIETKLIDYPLHQKRLFPFLAAAYLFSQGALYLEQTMNATN

DKLDEAVSAGEKEAIDAAIVESKKLFVASGCLKSTCTWLTAEAIDEARQACGGHGYSSYN

GFGKAYSDWVVQCTWEGDNNILAMNVAKPMVRDLLKEPEQKGLVLSSVADLDDPAKLVKA

FDHALSGLARDIGAVAEDKGFDITGPSLVLVSKLNAHRFLIDGFFKRITPEWSEVLRPLG

FLYADWILTNFGATFLQYGIITPDVSRKISSEHFPALCAKVRPNVVGLTDGFNLTDMMTN

AAIGRYDGNVYEHYFETVKALNPPENTKAPYSKALEDMLNRPDLEVRERGEKSEEAAEIL

SS

POX1 Acyl-CoA Oxidase (Source *Yarrowia lipolytica*)

(SEQ ID NO: 22)

MTTNTFTDPPVEMAKERGKTQFTVRDVTNFLNGGEEETQIVEKIMSSIERDPVLSVTADY

DCNLQQARKQTMERVAALSPYLVTDTEKLSLWRAQLHGMVDMSTRTRLSIHNNLFIGSIR

GSGTPEQFKYWVKKGAVAVKQFYGCFAMTELGHGSNLKGLETTATYDQDSDQFIINTPHI

GATKWWIGGAAHTSTHCVCFAKLIVHGKDYGTRNFVVPLRNVHDHSLKVGVSIGDIGKKM

GRDGVDNGWIQFTNVRIPRQNMLMRYAKVSDTGVVTKPALDQLTYGALIRGRVSMIADSF

HVSKRFLTIALRYACVRRQFGTSGDTKETKIIDYPYHQRRLLPLLAYCYAMKMGADEAQK

TWIETTDRILALNPNDPAQKNDLEKAVTDTKELFAASAGMKAFTTWGCAKIIDECRQACG

GHGYSGYNGFGQGYADWVVQCTWEGDNNVLCLSMGRGLVQSALQILAGKHVGASIQYVGD

KSKISQNGQGTPREQLLSPEFLVEAFRTASRNNILRTTDKYQELVKTLNPDQAFEELSQQ

RFQCARIHTRQHLISSFYARIATAKDDIKPHLLKLANLFALWSIEEDTGIFLRENILTPG

DIDLINSLVDELCVAVRDQVIGLTDAFGLSDFFINAPIGSYDGNVYEKYFAKVNQQNPAT

NPRPPYYESTLKPFLFREEEDDEICDLDE

POX2 Acyl-CoA Oxidase (Source *Yarrowia lipolytica*)

(SEQ ID NO: 23)

MNPNNTGTIEINGKEYNTFTEPPVAMAQERAKTSFPVREMTYFLDGGEKNTLKNEQIMEE

IERDPLFNNDNYYDLNKEQIRELTMERVAKLSLFVRDQPEDDIKKRFALIGIADMGTYTR

LGVHYGLFFGAVRGTGTAEQFGHWISKGAGDLRKFYGCFSMTELGHGSNLAGLETTAIYD

EETDEFIINTPHIAATKWWIGGAAHTATHTVVFARLIVKGKDYGVKTFVVQLRNINDHSL

KVGISIGDIGKKMGRDGIDNGWIQFTNVRIPRQNLLMKYTKVDREGNVTQPPLAQLTYGS

LITGRVSMASDSHQVGKRFITIALRYACIRRQFSTTPGQPETKIIDYPYHQRRLLPLLAY

-continued

VYALKMTADEVGALFSRTMLKMDDLKPDDKAGLNEVVSDVKELFSVSAGLKAFSTWACAD

VIDKTRQACGGHGYSGYNGFGQAYADWVVQCTWEGDNNILTLSAGRALIQSAVALRKGEP

VGNAVSYLKRYKDLANAKLNGRSLTDPKVLVEAWEVAAGNIINRATDQYEKLIGEGLNAD

QAFEVLSQQRFQAAKVHTRRHLIAAFFSRIDTEAGEAIKQPLLNLALLFALWSIEEDSGL

FLREGFLEPKDIDTVTELVNKYCTTVREEVIGYTDAFNLSDYFINAPIGCYDGDAYRHYF

QKVNEQNPARDPRPPYYASTLKPFLFREEEDDDICELDEE

POX3 Acyl-CoA Oxidase (Source *Yarrowia lipolytica*)
(SEQ ID NO: 24)

MISPNLTANVEIDGKQYNTFTEPPKALAGERAKVKFPIKDMTEFLHGGEENVTMIERLMT

ELERDPVLNVSGDYDMPKEQLRETAVARIAALSGHWKKDTEKEALLRSQLHGIVDMGTRI

RLGVHTGLFMGAIRGSGTKEQYDYWVRKGAADVKGFYGCFAMTELGHGSNVAGLETTATY

IQDTDEFIINTPNTGATKWWIGGAAHSATHTACFARLLVDGKDYGVKIFVVQLRDVSSHS

LMPGIALGDIGKKMGRDAIDNGWIQFTNVRIPRQNMLMKYAKVSSTGKVSQPPLAQLTYG

ALIGGRVTMIADSFFVSQRFITIALRYACVRRQFGTTPGQPETKIIDYPYHQRRLLPLLA

FTYAMKMAADQSQIQYDQTTDLLQTIDPKDKGALGKAIVDLKELFASSAGLKAFTTWTCA

NIIDQCRQACGGHGYSGYNGFGQAYADWVVQCTWEGDNNVLCLSMGRGLIQSCLGHRKGK

PLGSSVGYLANKGLEQATLSGRDLKDPKVLIEAWEKVANGAIQRATDKFVELTKGGLSPD

QAFEELSQQRFQCAKIHTRKHLVTAFYERINASAKADVKPYLINLANLFTLWSIEEDSGL

FLREGFLQPKDIDQVTELVNHYCKEVRDQVAGYTDAFGLSDWFINAPIGNYDGDVYKHYF

AKVNQQNPAQNPRPPYYESTLRPFLFREDEDDDICELDEE*

POX4 Acyl-CoA Oxidase (Source *Yarrowia lipolytica*)
(SEQ ID NO: 25)

MITPNPANDIVHDGKLYDTFTEPPKLMAQERAQLDFDPRDITYFLDGSKEETELLESLML

MYERDPLFNNQNEYDESFETLRERSVKRIFQLSKSIAMDPEPMSFRKIGFLGILDMGTYA

RLGVHYALFCNSIRGQGTPDQLMYWLDQGAMVIKGFYGCFAMTEMGHGSNLSRLETIATF

DKETDEFIINTPHVGATKWWIGGAAHTATHTLAFARLQVDGKDYGVKSFVVPLRNLDDHS

LRPGIATGDIGKKMGRDAVDNGWIQFTNVRVPRNYMLMKHTKVLRDGTVKQPPLAQLTYG

SLITGRVQMTTDSHNVSKKFLTIALRYATIRRQFSSTPGEPETRLIDYLYHQRRLLPLMA

YSYAMKLAGDHVRELFFASQEKAESLKEDDKAGVESYVQDIKELFSVSAGLKAATTWACA

DIIDKARQACGGHGYSAYNGFGQAFQDWVVQCTWEGDNTVLTLSAGRALIQSALVYRKEG

KLGNATKYLSRSKELANAKRNGRSLEDPKLLVEAWEAVSAGAINAATDAYEELSKQGVSV

DECFEQVSQERFQAARIHTRRALIEAFYSRIATADEKVKPHLIPLANLFALWSTEEDSAL

FLAEGYFEPEDIIEVTSLVNKYCGIVRKNVIGYTDAFNLSDYFINAAIGRYDGDVYKNYF

EKVKQQYPPEGGKPHYYEDVMKPFLHRERIPDVPMEPEDIQ

POX5 Acyl-CoA Oxidase (Source *Yarrowia lipolytica*)
(SEQ ID NO: 26)

MNNNPTNVILGGKEYDTFTEPPAQMELERAKTQFKVRDVTNFLTGSEQETLLTERIMREI

ERDPVLNVAGDYDADLPTKRRQAVERIGALARYLPKDSEKEAILRGQLHGIVDMGTRTRI

AVHYGLFMGAIRGSGTKEQYDYWVAKGAATLHKFYGCFAMTELGHGSNVAGLETTATLDK

DTDEFIINTPNSGATKWWIGGAAHSATHTACLARLIVDGKDYGVKIFIVQLRDLNSHSLL

NGIAIGDIGKKMGRDAIDNGWIQFTDVRIPRQNMLMRYDRVSRDGEVTTSELAQLTYGAL

LSGRVTMIAESHLLSARFLTIALRYACIRRQFGAVPDKPETKLIDYPYHQRRLLPLLAYT

YAMKMGADEAQQQYNSSFGALLKLNPVKDAEKFAVATADLKALFASSAGMKAFTTWAAAK

-continued

IIDECRQACGGHGYSGYNGFGQAYADWVVQCTWEGDNNVLCLSMGRSLIQSCIAMRKKKG

HVGKSVEYLQRRDELQNARVDNKPLTDPAVLITAWEKVACEAINRATDSFIKLTQEGLSP

DQAFEELSQQRFECARIHTRKHLITSFYARISKAKARVKPHLTVLANLFAVWSIEEDSGL

FLREGCFEPAEMDEITALVDELCCEAREQVIGFTDAFNLSDFFINAPIGRFDGDAYKHYM

DEVKAANNPRNTHAPYYETKLRPFLFRPDEDEEICDLDE

POX6 Acyl-CoA Oxidase (Source *Yarrowia lipolytica*)

(SEQ ID NO: 27)

MLSQQSLNTFTEPPVEMARERNQTSFNPRLLTYFLDGGEKNTLLMDRLMQEYERDPVFRN

EGDYDITDVAQSRELAFKRIAKLIEYVHTDDEETYLYRCMLLGQIDMGAFARYAIHHGVW

GGAIRGAGTPEQYEFWVKKGSLSVKKFYGSFSMTELGHGSNLVGLETTATLDKNADEFVI

NTPNVAATKWWIGGAADTATHTAVFARLIVDGEDHGVKTFVVQLRDVETHNLMPGIAIGD

CGKKMGRQGTDNGWIQFTHVRIPRQNMLMRYCHVDSDGNVTEPMMAQMAYGALLAGRVGM

AMDSYFTSRKFLTIALRYATIRRAFAAGGGQETKLIDYPYHQRRLLPLMAQTYAIKCTAD

KVRDQFVKVTDMLLNLDVSDQEAVPKAIAEAKELFSVSAGVKATTTWACAHTIDQCRQAC

GGHGYSAYNGFGRAYSDWVIQCTWEGDNNILCLSAGRALVQSNRAVRAGKPIGGPTAYLA

APAGSPKLAGRNLYDPKVMIGAWETVSRALINRTTDEFEVLAKKGLSTAQAYEELSQQRF

LCTRIHTRLYMVKNFYERIAEEGTEFTKEPLTRLANLYAFWSVEEEAGIFLREGYITPQE

LKYISAEIRKQLLEVRKDVIGYTDAFNVPDFFLNSAIGRADGDVYKNYFKVVNTQNPPQD

PRPPYYESVIRPFLFRKDEDEEICSLEDE

FOX2 Peroxisomal hydratase-dehydrogenase-epimerase
(Source *Candida viswanathii*)

(SEQ ID NO: 28)

MSPVDFKDKVVIITGAGGGLGKYYSLEFAKLGAKVVVNDLGGALNGQGGNSKAADVVVDE

IVKNGGVAVADYNNVLDGDKIVETAVKNFGTVHVIINNAGILRDASMKKMTEKDYKLVID

VHLNGAFAVTKAAWPYFQKQKYGRIVNTSSPAGLYGNFGQANYASAKSALLGFAETLAKE

GAKYNIKANAIAPLARSRMTESILPPPMLEKLGPEKVAPLVLYLSSAENELTGQFFEVAA

GFYAQIRWERSGGVLFKPDQSFTAEVVAKRFSEILDYDDSRKPEYLKNQYPFMLNDYATL

TNEARKLPANDASGAPTVSLKDKVVLITGAGAGLGKEYAKWFAKYGAKVVVNDFKDATKT

VDEIKAAGGEAWPDQHDVAKDSEAIIKNVIDKYGTIDILVNNAGILRDRSFAKMSKQEWD

SVQQVHLIGTFNLSRLAWPYFVEKQFGRIINITSTSGIYGNFGQANYSSSKAGILGLSKT

MAIEGAKNNIKVNIVAPHAETAMTLTIFREQDKNLYHADQVAPLLVYLGTDDVPVTGETF

EIGGGWIGNTRWQRAKGAVSHDEHTTVEFIKEHLNEITDFTTDTENPKSTTESSMAILSA

VGGDDDDDDEDEEEDEGDEEEDEEDEEEDDPVWRFDDRDVILYNIALGATTKQLKYVYEN

DSDFQVIPTFGHLITFNSGKSQNSFAKLLRNFNPMLLLHGEHYLKVHSWPPPTEGEIKTT

FEPIATTPKGTNVVIVHGSKSVDNKSGELIYSNEATYFIRNCQADNKVYADRPAFATNQF

LAPKRAPDYQVDVPVSEDLAALYRLSGDRNPLHIDPNFAKGAKFPKPILHGMCTYGLSAK

ALIDKEGMENEIKARFTGIVFPGETLRVLAWKESDDTIVFQTHVVDRGTIAINNAAIKLV

GDKAKI

Proteins with motifs or regions important for cellular localization are as follows.

OST1 (Source *Candida viswanathii*)
(SEQ ID NO: 29)
MMWKFLIAIGLIFSYCCNAQLLDSLSFDNNWVNTHYIRTIDLSKGFVKETDLIQIKNIND

KPQDEYYFVVNDGFDSIDELSIFSAFVGDQALEVEVDEVVPDKVFKLKLPVPIAPNSDLE

LRINFVYIDSLVSVPSKIAMDATQQLLYKTNKFPFSPYVTQEYTLALSGMSKGQEMDLHI

DVEDTPGLPDLKPRVESQVLKYGPIAEDIPAFALKPMGLMYDHNRPLTKAVSLNRSIWLP

ASDINKVSIEEYYELTNTGAELDKGFSRVDWMKGRFESTRNHWALSHLEIPLLERGFDDY

YYTDKVGVVSTHKIFKNHLLLQPRYPVFGGWKYNFTLGWSEELSKFLHKLHDNQDEYIIK

FPILNSLRDVTYQDVYLEFYLPENAEFQNISSPIAFESISIENELSYLDVSKGHTKITVH

YTNLFDDLHKLDVFVKYQYTQVAFIYKIAKISGFVFLGLVSYYLLGLLDLSI

GlU1 Glucoamylase (Source *Saccharomyces fibuligera*)
(SEQ ID NO: 30)
MKFGVLFSVFAAIVSALPLQEGPLNKRAYPSFEAYSNYKVDRTDLETFLDKQKEVSLYYL

LQNIAYPEGQFNNGVPGTVIASPSTSNPDYYYQWTRDSAITFLTVLSELEDNNFNTTLAK

AVEYYINTSYNLQRTSNPSGSFDDENHKGLGEPKFNTDGSAYTGAWGRPQNDGPALRAYA

ISRYLNDVNSLNEGKLVLTDSGDINFSSTEDIYKNIIKPDLEYVIGYWDSTGFDLWEENQ

GRHFFTSLVQQKALAYAVDIAKSFDDGDFANTLSSTASTLESYLSGSDGGFVNTDVNHIV

ENPDLLQQNSRQGLDSATYIGPLLTHDIGESSSTPFDVDNEYVLQSYYLLLEDNKDRYSV

NSAYSAGAAIGRYPEDVYNGDGSSEGNPWFLATAYAAQVPYKLAYDAKSASNDITINKIN

YDFFNKYIVDLSTINSAYQSSDSVTIKSGSDEFNTVADNLVTFGDSFLQVILDHINDDGS

LNEQLNRYTGYSTGAYSLTWSSGALLEAIRLRNKVKALA

SIAT1_RAT alpha-2,6-sialyltransferase (Source
*Rat norvegicus*)
(SEQ ID NO: 31)
MIHTNLKKKFSLFILVFLLFAVICVWKKGSDYEALTLQAKEFQMPKSQEKVAMGSASQVV

FSNSKQDPKEDIPILSYHRVTAKVKPQPSFQVWDKDSTYSKLNPRLLKIWRNYLNMNKYK

VSYKGPGPGVKFSVEALRCHLRDHVNVSMIEATDFPFNTTEWEGYLPKENFRTKVGPWQR

CAVVSSAGSLKNSQLGREIDNHDAVLRFNGAPTDNFQQDVGSKTTIRLMNSQLVTTEKRF

LKDSLYTEGILIVWDPSVYHADIPKWYQKPDYNFFETYKSYRRLNPSQPFYILKPQMPWE

LWDIIQEISADLIQPNPPSSGMLGIIIMMTLCDQVDIYEFLPSKRKTDVCYYHQKFFDSA

CTMGAYDPLLFEKNMVKHLNEGTDEDIYLFGKATLSGFRNIRC

B4galt1 Beta-1,4-galactosyltransferase 1 (Source
*Homo sapiens*)
(SEQ ID NO: 32)
MRLREPLLSGSAAMPGASLQRACRLLVAVCALHLGVTLVYYLAGRDLSRLPQLVGVSTPL

QGGSNSAAAIGQSSGELRTGGARPPPPLGASSQPRPGGDSSPVVDSGPGPASNLTSVPVP

HTTALSLPACPEESPLLVGPMLIEFNMPVDLELVAKQNPNVKMGGRYAPRDCVSPHKVAI

IIPFRNRQEHLKYWLYYLHPVLQRQQLDYGIYVINQISF

DOA4 Ubiquitin carboxyl-terminalhydrolase4
(Source *Candida viswanathii*)
(SEQ ID NO: 33)
MTLLLKPTSELDATSRKIIERIQSNSPTFQHLFDLLLNLLPFFDKTVSLLGSIGYCDYEV

AYVTYQTCIQVVGLMKPKTNSLNQDIFKGVQLQTRKRASTFKAILSYFAEPETQEEDPLL

NRFKSLSGGGSKTKSSQDEVFHEWITSSELQRELSSKKVLLIDFRPRKDYLNNHIKYKDL

VHIEPTQLETLLDSASDQDLETLVKKSAPYDQYHIFLERHKYDLIVVYNYNYGSESTDRL

LGIIDVVSKPNPFTKLITILMNNKYISSRLKVKPLFLSGGVLNWYKTFGIEYLERTLVQN

-continued

GVAHTSDNQYLKSFNDYVSTSKETPKTQVKTQNGDYIRPSQRKVNQFDPVPVKSGPTVFA

SAKVDLPPTPGSPAVSTPSPPRAPAPPTKTTSLTHVPEKEAKSPSPVTKEVTVSSKKSQF

LELYTTGLVNLGNSCYMNCVVQCLAAAPQLTSFFFPTITESFSDHSYRQHINSNNKLGTK

GELTTSFVELILNMLNNNGKAFSPTKFKRTMGSLSPSQQFLTYDQQDCIEFLNFLLDALH

EDLNNVTITDPSERKLITDLSPEQEKSRETLPVRLASTIEWERYLKLNFSVIVDYFQGQH

LSQLKCLECGFTSTTYNAFSILSLPIPQKLNNLGKVLLKDCLEEFVTTELLDDNNKWYCP

QCKRFTRLTKKIAITRLPQVLIVNFNRFKMTNTGGFNKLETFVTYPVNEELDMTPYWPDV

GSRINENSTMSIEMEQDLLQSFPIRNQTPPFKYKLFGVANHFGNLTTGHYTSYVYKHSDS

KKTRNWCYFDDSKITYNVSPSQVVNKNAYCLFFQRV

APR1 Vacuolar aspartic protease (Source *Candida viswanathii*)

(SEQ ID NO: 34)

MQLSLSVLSTVATALLSLTTAVDAKSHNIKLSKLSNEETLDASTFQEYTSSLANKYMNLF

NAAHGNPTSFGLQHVLSNQEAEVPFVTPQKGGKYDAPLTNYLNAQYFTEIEIGTPGQPFK

VILDTGSSNLWVPSQDCTSLACFLHSKYDHDASSTYKANGSEFSIQYGSGSMEGYISQDI

LTIGDLVIPKQDFAEATSEPGLAFAFGKFDGILGLAYDSISVNHIVPPVYNAINQGLLDK

PQVSFYLGNTEKDENDGGLATFGGYDASLFQGKITWLPVRRKAYWEVSFEGIGLGDEYAE

LQKTGAAIDTGTSLITLPSSLAEIINAKIGATKSWSGQYQIDCAKRDELPDLTLTFAGHN

FTLTAHDYILEVSGSCISVFTPMDFPKPIGDLAIIGDAFLRKYYSIYDLDKNAVGLAPSK

A

PHO8 (Source *Candida viswanathii*)

(SEQ ID NO: 35)

MGITNETQALLGGDSLSCLNKKKSNTKRNLSYLLNIITVSIIAYLCFFATHNHHNDSGIP

KVDPHKKKNIIMMVTDGMGPASLSAARSFRQFRDKLAINDILTLDQYLIGSSRTRSSSSL

VTDSAAGATAFSCALKSYNGAIGVSPDKSPCGTILEALKLQGYYTGLVVTTRITDATPAA

FSAHVDYRFQEDLIAEHQLGEYPFGRAVDLILGGGRCHFLPTAQGGCRADDRNLIKESSD

TWQYVGDRQQFDQLKGGKNVSLPLLGLLANTDIPYAIDRDEKEYPSLAEQVKVALTALSD

ATKDSDQGFFLLIEGSRIDHAGHEINDPTAQVREVLAYDEAFGEVIKFIDSTDVETVATS

TSDHETGGLVVSRQVTPEYPDYIWYPEVLLNSTHSGDYLAHKIADYKNKDDTAKLTKFIK

HEILETDLGVTDYTDKDVQAILDKVNDPANLLYVLNDIVSFRAQIGWTTHGHSAVDVNIY

AHTNSPAIRAKLASAKAYHGLSGNHENIEIGAFMEEITGSNLSRVTELIKKTAHSPSLSK

KEFSVDEFHGNV

SNA4 (Source *Saccharomyces cerevisiae*)

(SEQ ID NO: 36)

MCCYCVCCTVSDFILYIVAFFFPPAAVLLRSGPCSSDFLLNVLLTLLGFLPGMLHAFYYI

TITSPLRNAEYVYYYQQGWVDSERNVPSNRPQNSQTPQNRPQQGSSARNVYPSVETPLLQ

GAAPHDNKQSLVESPPPYVP

OCH1 (Source *Candida viswanathii*)

(SEQ ID NO: 37)

MRLKDIKLILIGILTISVTYFLISSFSGPRAYTTSDPNSSKMQFLRALESHPNWKETGLN

FQPTKKLEVDDSSTPVRQQLAARFPYDPTQPFPKNIWQTWKVGIEDETFPKRYLKFQLSW

DTKNPEYKHHVIPDDQCDELVAQLFEDVPDVARAYKVMPKSILKADFFRYLILFARGGVY

TDIDTVGLKPIDTWMSNMELLWGEPNRAGLVVGIEADPDRPDWADWYARRIQFCQWTIQL

-continued

KKGHPMLRELITKITDITLTREKRNELKKVLGKDEGGDIMNWTGPGIFTDTVFSYMNAIL

QAPEVITGKYKWDNIVDWKVFTGMQMPIAIDDVLVLPITSFSPDVSQMGSKSSTDPMAYA

KHMFLGSWKDDGMPEME

Proteins for use in the cannabinoid pathway are as follows.

HXS1 Protein (Source *Cannabis sativa*)

(SEQ ID NO: 38)

MGKNYKSLDSVVASDFIALGITSEVAETLHGRLAEIVCNYGAATPQTWINIANHILSPDL

PFSLHQMLFYGCYKDFGPAPPAWIPDPEKVKSTNLGALLEKRGKEFLGVKYKDPISSFSH

FQEFSVRNPEVYWRTVLMDEMKISFSKDPECILRRDDINNPGGSEWLPGGYLNSAKNCLN

VNSNKKLNDTMIVWRDEGNDDLPLNKLTLDQLRKRVWLVGYALEEMGLEKGCAIAIDMPM

HVDAVVIYLAIVLAGYVVVSIADSFSAPEISTRLRLSKAKAIFTQDHIIRGKKRIPLYSR

VVEAKSPMAIVIPCSGSNIGAELRDGDISWDYFLERAKEFKNCEFTAREQPVDAYTNILF

SSGTTGEPKAIPWTQATPLKAAADGWSHLDIRKGDVIVWPTNLGWMMGPWLVYASLLNGA

SIALYNGSPLVSGFAKFVQDAKVTMLGVVPSIVRSWKSTNCVSGYDWSTIRCFSSSGEAS

NVDEYLWLMGRANYKPVIEMCGGTEIGGAFSAGSFLQAQSLSSFSSQCMGCTLYILDKNG

YPMPKNKPGIGELALGPVMFGASKTLLNGNHHDVYFKGMPTLNGEVLRRHGDIFELTSNG

YYHAHGRADDTMNIGGIKISSIEIERVCNEVDDRVFETTAIGVPPLGGGPEQLVIFFVLK

DSNDTTIDLNQLRLSFNLGLQKKLNPLFKVTRVVPLSSLPRTATNKIMRRVLRQQFSHFE

TKS1 Protein (Source *Cannabis sativa*)

(SEQ ID NO: 39)

MNHLRAEGPASVLAIGTANPENILIQDEFPDYYFRVTKSEHMTQLKEKFRKICDKSMIRK

RNCFLNEEHLKQNPRLVEHEMQTLDARQDMLVVEVPKLGKDACAKAIKEWGQPKSKITHL

IFTSASTTDMPGADYHCAKLLGLSPSVKRVMMYQLGCYGGGTVLRIAKDIAENNKGARVL

AVCCDIMACLFRGPSDSDLELLVGQAIFGDGAAAVIVGAEPDESVGERPIFELVSTGQTI

LPNSEGTIGGHIREAGLIFDLHKDVPMLISNNIEKCLIEAFTPIGISDWNSIFWITHPGG

KAILDKVEEKLDLKKEKFVDSRHVLSEHGNIVISSSTVLFVMDELRKRSLEEGKSTTGDG

FEWGVLFGFGPGLTVERVVVRSVPIKY

TKS1P Protein (Source *Cannabis sativa*)

(SEQ ID NO: 40)

MNHLRAEGPASVLAIGTANPENILIQDEFPDYYFRVTKSEHMTQLKEKFRKICDKSMIRK

RNCFLNEEHLKQNPRLVEHEMQTLDARQDMLVVEVPKLGKDACAKAIKEWGQPKSKITHL

IFTSASTTDMPGADYHCAKLLGLSPSVKRVMMYQLGCYGGGTVLRIAKDIAENNKGARVL

AVCCDIMACLFRGPSDSDLELLVGQAIFGDGAAAVIVGAEPDESVGERPIFELVSTGQTI

LPNSEGTIGGHIREAGLIFDLHKDVPMLISNNIEKCLIEAFTPIGISDWNSIFWITHPGG

KAILDKVEEKLDLKKEKFVDSRHVLSEHGNMSSSTVLFVMDELRKRSLEEGKSTTGDGFE

WGVLFGFGPGLTVERVVVRSVPIKYGRRAKL

OAC1 Protein (Source *Cannabis sativa*)

(SEQ ID NO: 41)

MAVKHLIVLKFKDEITEAQKEEFFKTYVNLVNIIPAMKDVYWGKDVTQKNKEEGYTHIVE

VTFESVETIQDYIIHPAHVGFGDVYRSFWEKLLIFDYTPRKLKPK

OAC1P Protein (Source *Cannabis sativa*)

(SEQ ID NO: 42)

MAVKHLIVLKFKDEITEAQKEEFFKTYVNLVNIIPAMKDVYWGKDVTQKNKEEGYTHIVE

VTFESVETIQDYIIHPAHVGFGDVYRSFWEKLLIFDYTPRKLKPKGRRAKL

-continued

PTS1 Protein (Source *Cannabis sativa*)

(SEQ ID NO: 43)

MGLSSVCTFSFQTNYHTLLNPHNNNPKTSLLCYRHPKTPIKYSYNNFPSKHTKS1FHLQN

KCSESLSIAKNSIRAATTNQTEPPESDNHSVATKILNFGKACWKLQRPYTHAFTSCACGL

FGKELLHNTNLISWSLMFKAFFFLVAILCIASFTTTINQIYDLHIDRINKPDLPLASGEI

SVNTAWIMSIIVALFGLITTIKMKGGPLYIFGYCFGIFGGIVYSVPPFRWKQNPSTAFLL

NFLAHIITNFTFYYASRAALGLPFELRPSFTFLLAFMKSMGSALALIKDASDVEGDTKFG

ISTLASKYGSRNLTLFCSGIVLLSYVAAILAGIIWPQAFNSNVMLLSHAILAFWLILQTR

DFALTNYDPEAGRRFYEFMWKLYYAEYLVYVFI

PTS1dN (Source *Cannabis sativa*)

(SEQ ID NO: 44)

MAATTNQTEPPESDNHSVATKILNFGKACWKLQRPYTIIAFTSCACGLFGKELLHNTNLI

SWSLMFKAFFFLVAILCIASFTTTINQIYDLHIDRINKPDLPLASGEISVNTAWIMSIIV

ALFGLIITIKMKGGPLYIFGYCFGIFGGIVYSVPPFRWKQNPSTAFLLNFLAHIITNFTF

YYASRAALGLPFELRPSFTFLLAFMKSMGSALALIKDASDVEGDTKFGISTLASKYGSRN

LTLFCSGIVLLSYVAAILAGIIWPQAFNSNVMLLSHAILAFWLILQTRDFALTNYDPEAG

RRFYEFMWKLYYAEYLVYVFI

PTS2 Protein (Source *Cannabis sativa*)

(SEQ ID NO: 45)

MGLSLVCTFSFQTNYHTLLNPHNKNPKNSLLSYQHPKTPIIKSSYDNFPSKYCLTKNFHL

LGLNSHNRISSQSRSIRAGSDQIEGSPHHESDNSIATKILNFGHTCWKLQRPYVVKGMIS

IACGLFGRELFNNRHLFSWGLMWKAFFALVPILSFNFFAAIMNQIYDVDIDRINKPDLPL

VSGEMSIETAWILSIIVALTGLIVTIKLKSAPLFVFIYIFGIFAGFAYSVPPIRWKQYPF

TNFLITISSHVGLAFTSYSATTSALGLPFVWRPAFSFITAFMTVMGMTIAFAKDISDIEG

DAKYGVSTVATKLGARNMTFVVSGVLLLNYLVSISIGIIWPQVFKSNIMILSHAILAFCL

IFQTRELALANYASAPSRQFFEFIWLLYYAEYFVYVFI

PTS3 Protein (Source *Cannabis sativa*)

(SEQ ID NO: 46)

MGLSSVCTFSFQTNYHTLLNPHNNNPKTSLLYRHPKTPIKYSYNNFPSKHCSTKSFHLQN

KCSESLSIAKNSIRAATTNQTEPPESDNHSVATKILNFGKACWKLQRPYTIIAFTSCACG

LFGKELLHNTNLISWSLMFKAFFFLVAVLCIASFTTTINQIYDLHIDRINKPDLPLASGE

ISVNTAWIMSIIVALFGLIITIKMKGGPLYIFGYCFGIFGGTVYSVPPFRWKQNPSTAFL

LNFLAHIITNFTFYHASRAALGLPFELRPSFTFLLAFMKSMGSALALIKDASDVEGDTKF

GISTLASKYGSRNLTLFCSGIVLLSYVAAILAGIIWPQAFNSNVMLLSHAILAFWLILQT

RDFALTNYDPEAGRRFYEFMWKLYYAEYLVYVFI

PTS4 Protein (Source *Cannabis sativa*)

(SEQ ID NO: 47)

MELSSICNFSFQTNYHTLLNPHNKNPKSSLLSHQHPKTPIITSSYNNFPSNYCSNKNFHL

QNRCSKSLLIAKNSIRTDTANQTEPPESNTKYSVVTKILSFGHTCWKLQRPYTFIGVISC

ACGLFGRELFHNTNLLSWSLMLKAFSSLMVILSVNLCTNIINQITDLDIDRINKPDLPLA

SGEMSIETAWIMSIIVALTGLILTIKLNCGPLFISLYCVSILVGALYSVPPFRWKQNPNT

AFSSYFMGLVIVNFTCYYASRAAFGLPFEMSPPFTFILAFVKSMGSALFLCKDVSDIEGD

SKHGISTLATRYGAKNITFLCSGIVLLTYVSAILAAIIWPQAFKSNVMLLSHATLAFWLI

FQTREFALTNYNPEAGRKFYEFMWKLHYAEYLVYVFI

-continued

PTS5 Protein (Source *Cannabis sativa*)

(SEQ ID NO: 48)

MVFSSVCSFPSSLGTNFKLVPRSNFKASSSHYHEINNFINNKPIKFSYFSSRLYCSAKPI
VHRENKFTKSFSLSHLQRKSSIKAHGEIEADGSNGTSEFNVMKSGNAIWRFVRPYAAKGV
LFNSAAMFAKELVGNLNLFSWPLMFKILSFTLVILCIFVSTSGINQIYDLDIDRLNKPNL
PVASGEISVELAWLLTIVCTISGLTLTIITNSGPFFPFLYSASIFFGFLYSAPPFRWKKN
PFTACFCNVMLYVGTSVGVYYACKASLGLPANWSPAFCLLFWFISLLSIPISIAKDLSDI
EGDRKFGIITFSTKFGAKPIAYICHGLMLLNYVSVMAAAIIWPQFFNSSVILLSHAFMAI
WVLYQAWILEKSNYATETCQKYYIFLWIIFSLEHAFYLFM

PTS6 Protein (Source *Cannabis sativa*)

(SEQ ID NO: 49)

MELSLSLGGPTIFPRYRASYTSTKLTTHFSNFPSKFSTKNFHQTLSFYGPTRGSKSLLNT
HQWRNSIRACAEAGAAGSNPVLNKVSDFRDACWRFLRPHTIRGTTLGSIALVARALIENP
NLIKWSLLLKAFSGLLALICGNGYIVGINQIYDIGIDKVNKPYLPIAAGDLSVQSAWYLV
ILFAVAGLLTVGFNFGPFITSLYCLGLVLGTIYSVPPFRMKRFPVAAFLIIATVRGFLLN
FGVYYATRAALGLTFEWSSAVAFITTFVTLFALVIAITKDLPDVEGDRKFQISTFATKLG
VRNIAYLGSGLLLLNYIGAIAAAIYMPQAFKRNLMLPIHTILALSLVFQAWVLEQANYTK
EAIAGFYRFIWNLFYVEYIIFPFI

PTS7 Protein (Source *Cannabis sativa*)

(SEQ ID NO: 50)

MAIALWLPRISRSTTRRFLKPSSSLTLFSVSHSHNYIVTSNRSPIPRLFTVPNQSHGREW
VSVSEVRLGYVSHISTAGKSDENRSRDAQVADVSWIDLYLPRQIHPYVRLARLDKPIGTW
LLAWPCMWSISLAANPGHLPDIKMMTLFGCGALLLRGAGCTINDLLDRDIDTMVERTKLR
PVASGIITPFQGICFLGFQLLLGLGILLQLNNYSRILGASSLLLVFSYPLMKRLTFWPQA
YLGLTFNWGALLGWAAVKGNIDPAIVLPLYASGVFWTLVYDTIYAHQDKEDDVRVGIKST
ALRFGDLTKQWNMGFGAACISSLALSGYNAEIGWPFYASLVAASGQLAWQISTVDLSSRD
DCNKKFVSNKWFGAIIFSGIVLARISS

PTS8 Protein (Source *Cannabis sativa*)

(SEQ ID NO: 51)

MSEAADVERVYAAMEEAAGLLGVACARDKIYPLLSTFQDTLVEGGSVVVFSMASGRHSTE
LDFSISVPTSHGDPYATVVEKGLFPATGHPVDDLLADTQKHLPVSMFAIDGEVTGGFKKT
YAFFPTDNMPGVAELSAIPSMPPAVAENAELFARYGLDKVQMTSMDYKKRQVNLYFSELS
AQTLEAESVLALVRELGLHVPNELGLKFCKRSFSVYPTLNWETGKIDRLCFAVISNDPTL
VPSSDEGDIEKFHNYATKAPYAYVGEKRTLVYGLTLSPKEEYYKLGAYYHITDVQRGLLK
AFDSLEDG

PTS9 Protein (ScNphB) (Source *Streptomyces*)

(SEQ ID NO: 52)

MSEAADVERVYAAMEEAAGLLGVACARDKIYPLLSTFQDTLVEGGSVVVFSMASGRHSTE
LDFSISVPTSHGDPYATVVEKGLFPATGHPVDDLLADTQKHLPVSMFAIDGEVTGGFKKT
YAFFPTDNMPGVAELSAIPSMPPAVAENAELFARYGLDKVQMTSMDYKKRQVNLYFSELS
AQTLEAESVLALVRELGLHVPNELGLKFCKRSFSVYPTLNWETGKIDRLCFAVISNDPTL
VPSSDEGDIEKFHNYATKAPYAYVGEKRTLVYGLTLSPKEEYYKLGAYYHITDVQRGLLK
AFDSLEDGMKCSTFSFWFVCKIIFFFFSFNIQTSIANPRENFLKCFSQYIPNNATNLKLV
YTQNNPLYMSVLNSTIHNLRFTSDTTPKPLVIVTPSHVSHIQGTILCSKKVGLQIRTRSG
GHDSEGMSYISQVPFVIVDLRNMRSIKIDVHSQTAWVEAGATLGEVYYWVNEKNENLSLA
AGYCPTVCAGGHFGGGGYGPLMRNYGLAADNIIDAHLVNVHGKVLDRKSMGEDLFWALRG

-continued

GGAESFGIIVAWKIRLVAVPKSTMFSVKKIMEIHELVKLVNKWQNIAYKYDKDLLLMTHF
ITRNITDNQGKNKTAIHTYFSSVFLGGVDSLVDLMNKSFPELGIKKTDCRQLSWIDTIIF
YSGVVNYDTDNFNKEILLDRSAGQNGAFKIKLDYVKKPIPESVFVQILEKLYEEDIGAGM
YALYPYGGIMDEISESAIPFPHRAGILYELWYICSWEKQEDNEKHLNWIRNIYNFMTPYV
SKNPRLAYLNYRDLDIGINDPKNPNNYTQARIWGEKYFGKNFDRLVKVKTLVDPNNFFRN
EQSIPPLPRHRH

CBD1dNS1 Protein (Source *Cannabis sativa*)

(SEQ ID NO: 53)

MFLKHIFVALAFALLADATPAQKRSPGFVALDFDIVKVQKNVTANDDAAAIVAKRQTNPR
ENFLKCFSQYIPNNATNLKLVYTQNNPLYMSVLNSTIHNLRFTSDTTPKPLVIVTPSHVS
HIQGTILCSKKVGLQIRTRSGGHDSEGMSYISQVPFVIVDLRNMRSIKIDVHSQTAWVEA
GATLGEVYYWVNEKNENLSLAAGYCPTVCAGGHFGGGGYGPLMRNYGLAADNIIDAHLVN
VHGKVLDRKSMGEDLFWALRGGGAESFGIIVAWKIRLVAVPKSTMFSVKKIMEIHELVKL
VNKWQNIAYKYDKDLLLMTHFITRNITDNQGKNKTAIHTYFSSVFLGGVDSLVDLMNKSF
PELGIKKTDCRQLSWIDTIIFYSGVVNYDTDNFNKEILLDRSAGQNGAFKIKLDYVKKPI
PESVFVQILEKLYEEDIGAGMYALYPYGGIMDEISESAIPFPHRAGILYELWYICSWEKQ
EDNEKHLNWIRNIYNFMTPYVSKNPRLAYLNYRDLDIGINDPKNPNNYTQARIWGEKYFG
KNFDRLVKVKTLVDPNNFFRNEQSIPPLPRHRH

CBD1dNS2 Protein (Source *Cannabis sativa*)

(SEQ ID NO: 54)

MQLSLSVLSTVATALLSLTTAVDAKSHNPRENFLKCFSQYIPNNATNLKLVYTQNNPLYM
SVLNSTIHNLRFTSDTTPKPLVIVTPSHVSHIQGTILCSKKVGLQIRTRSGGHDSEGMSY
ISQVPFVIVDLRNMRSIKIDVHSQTAWVEAGATLGEVYYWVNEKNENLSLAAGYCPTVCA
GGHFGGGGYGPLMRNYGLAADNIIDAHLVNVHGKVLDRKSMGEDLFWALRGGGAESFGII
VAWKIRLVAVPKSTMFSVKKIMEIHELVKLVNKWQNIAYKYDKDLLLMTHFITRNITDNQ
GKNKTAIHTYFSSVFLGGVDSLVDLMNKSFPELGIKKTDCRQLSWIDTIIFYSGVVNYDT
DNFNKEILLDRSAGQNGAFKIKLDYVKKPIPESVFVQILEKLYEEDIGAGMYALYPYGGI
MDEISESAIPFPHRAGILYELWYICSWEKQEDNEKHLNWIRNIYNFMTPYVSKNPRLAYL
NYRDLDIGINDPKNPNNYTQARIWGEKYFGKNFDRLVKVKTLVDPNNFFRNEQSIPPLPR
HRH

CBD1dNV1 Protein (Source *Cannabis sativa*)

(SEQ ID NO: 55)

MQLSLSVLSTVATALLSLTTAVDAKSHNIKLSKLSNEETLDASTFQEYTSSLANKYMNLF
NAAHGNPTSFGLQHVLSNQEAEVPFVTPQKGGNPRENFLKCFSQYIPNNATNLKLVYTQN
NPLYMSVLNSTIHNLRFTSDTTPKPLVIVTPSHVSHIQGTILCSKKVGLQIRTRSGGHDS
EGMSYISQVPFVIVDLRNMRSIKIDVHSQTAWVEAGATLGEVYYWVNEKNENLSLAAGYC
PTVCAGGHFGGGGYGPLMRNYGLAADNIIDAHLVNVHGKVLDRKSMGEDLFWALRGGGAE
SFGIIVAWKIRLVAVPKSTMFSVKKIMEIHELVKLVNKWQNIAYKYDKDLLLMTHFITRN
ITDNQGKNKTAIHTYFSSVFLGGVDSLVDLMNKSFPELGIKKTDCRQLSWIDTIIFYSGV
VNYDTDNFNKEILLDRSAGQNGAFKIKLDYVKKPIPESVFVQILEKLYEEDIGAGMYALY
PYGGIMDEISESAIPFPHRAGILYELWYICSWEKQEDNEKHLNWIRNIYNFMTPYVSKNP
RLAYLNYRDLDIGINDPKNPNNYTQARIWGEKYFGKNFDRLVKVKTLVDPNNFFRNEQSI
PPLPRHRH

-continued

CBD1dNP1 Protein (Source *Cannabis sativa*)

(SEQ ID NO: 56)

MNPRENFLKCFSQYIPNNATNLKLVYTQNNPLYMSVLNSTIHNLRFTSDTTPKPLVIVTP
SHVSHIQGTILCSKKVGLQIRTRSGGHDSEGMSYISQVPFVIVDLRNMRSIKIDVHSQTA
WVEAGATLGEVYYWVNEKNENLSLAAGYCPTVCAGGHFGGGGYGPLMRNYGLAADNBDAH
LVNVHGKVLDRKSMGEDLFWALRGGGAESFGIIVAWKIRLVAVPKSTMFSVKKIMEIHEL
VKLVNKWQNIAYKYDKDLLLMTHFITRNITDNQGKNKTAIHTYFSSVFLGGVDSLVDLMN
KSFPELGIKKTDCRQLSWIDTIIFYSGVVNYDTDNFNKEILLDRSAGQNGAFKIKLDYVK
KPIPESVFVQILEKLYEEDIGAGMYALYPYGGIMDEISESAIPFPHRAGILYELWYICSW
EKQEDNEKHLNWIRNIYNFMTPYVSKNPRLAYLNYRDLDIGINDPKNPNNYTQARIWGEK
YFGKNFDRLVKVKTLVDPNNFFRNEQSIPPLPRHRHGRRAKL

THC1 Protein (Source *Cannabis sativa*)

(SEQ ID NO: 57)

MNCSAFSFWFVCKIIFFFLSFNIQISIANPQENFLKCFSEYIPNNPANPKFIYTQHDQLY
MSVLNSTIQNLRFTSDTTPKPLVIVTPSNVSHIQASILCSKKVGLQIRTRSGGHDAEGMS
YISQVPFVVVDLRNMEISIKIDVHSQTAWVEAGATLGEVYYWINEKNENFSFPGGYCPTV
GVGGHFSGGGYGALMRNYGLAADNIIDAHLVNVDGKVLDRKSMGEDLFWAIRGGGGENFG
IIAAWKIKLVAVPSKSTIFSVKKNMEIHGLVKLFNKWQNIAYKYDKDLVLMTHFITKNIT
DNHGKNKTTVHGYFSSIFHGGVDSLVDLMNKSFPELGIKKTDCKEFSWIDTTIFYSGVVN
FNTANFKKEILLDRSAGKKTAFSIKLDYVKKPIPETAMVKILEKLYEEDVGVGMYVLYPY
GGIMEEISESAIPFPHRAGIMYELWYTASWEKQEDNEKHINWVRSVYNFTTPYVSQNPRL
AYLNYRDLDLGKTNPESPNNYTQARIWGEKYFGKNFNRLVKVKTKADPNNFFRNEQSIPP
LPPHHH

THC1dNS1 Protein (Source *Cannabis sativa*)

(SEQ ID NO: 58)

MFLKHIFVALAFALLADATPAQKRSPGFVALDFDIVKVQKNVTANDDAAAIVAKRQTNPQ
ENFLKCFSEYIPNNPANPKFIYTQHDQLYMSVLNSTIQNLRFTSDTTPKPLVIVTPSNVS
HIQASILCSKKVGLQIRTRSGGHDAEGMSYISQVPFVVVDLRNIVIHSIKIDVHSQTAWV
EAGATLGEVYYWINEKNENFSFPGGYCPTVGVGGHFSGGGYGALMRNYGLAADNIIDAHL
VNVDGKVLDRKSMGEDLFWAIRGGGGENFGIIAAWKIKLVAVPSKSTIFSVKKNMEIHGL
VKLFNKWQNIAYKYDKDLVLMTHFITKNITDNHGKNKTTVHGYFSSIFHGGVDSLVDLMN
KSFPELGIKKTDCKEFSWIDTTIFYSGVVNFNTANFKKEILLDRSAGKKTAFSIKLDYVK
KPIPETAMVKILEKLYEEDVGVGMYVLYPYGGIMEEISESAIPFPHRAGIMYELWYTASW
EKQEDNEKHINWVRSVYNFTTPYVSQNPRLAYLNYRDLDLGKTNPESPNNYTQARIWGEK
YFGKNFNRLVKVKTKADPNNFFRNEQSIPPLPPHHH

THC1dNS2 Protein (Source *Cannabis sativa*)

(SEQ ID NO: 59)

MQLSLSVLSTVATALLSLTTAVDAKSHNPQENFLKCFSEYIPNNPANPKFIYTQHDQLYM
SVLNSTIQNLRFTSDTTPKPLVIVTPSNVSHIQASILCSKKVGLQIRTRSGGHDAEGMSY
ISQVPFVVVDLRNMHSIKIDVHSQTAWVEAGATLGEVYYWINEKNENFSFPGGYCPTVGV
GGHFSGGGYGALMRNYGLAADNIIDAHLVNVDGKVLDRKSMGEDLFWAIRGGGGENFGII
AAWKIKLVAVPSKSTIFSVKKNMEIHGLVKLFNKWQNIAYKYDKDLVLMTHFITKNITDN
HGKNKTTVHGYFSSIFHGGVDSLVDLMNKSFPELGIKKTDCKEFSWIDTTIFYSGVVNFN

-continued

TANFKKEILLDRSAGKKTAFSIKLDYVKKPIPETAMVKILEKLYEEDVGVGMYVLYPYGG

IMEEISESAIPFPHRAGIMYELWYTASWEKQEDNEKHINWVRSVYNFTTPYVSQNPRLAY

LNYRDLDLGKTNPESPNNYTQARIWGEKYFGKNFNRLVKVKTKADPNNFFRNEQSIPPLP

PHHH

THC1dNV1 Protein (Source *Cannabis sativa*)

(SEQ ID NO: 60)

MQLSLSVLSTVATALLSLTTAVDAKSHNIKLSKLSNEETLDASTFQEYTSSLANKYMNLF

NAAHGNPTSFGLQHVLSNQEAEVPFVTPQKGGNPQENFLKCFSEYIPNNPANPKFIYTQH

DQLYMSVLNSTIQNLRFTSDTTPKPLVIVTPSNVSHIQASILCSKKVGLQIRTRSGGHDA

EGMSYISQVPFVVVDLRNMHSIKIDVHSQTAWVEAGATLGEVYYWINEKNENFSFPGGYC

PTVGVGGHFSGGGYGALMRNYGLAADNIIDAHLVNVDGKVLDRKSMGEDLFWAIRGGGGE

NFGIIAAWKIKLVAVPSKSTIFSVKKNMEIHGLVKLFNKWQNIAYKYDKDLVLMTHFITK

NITDNHGKNKTTVHGYFSSIFHGGVDSLVDLMNKSFPELGIKKTDCKEFSWIDTTIFYSG

VVNFNTANFKKEILLDRSAGKKTAFSIKLDYVKKPIPETAMVKILEKLYEEDVGVGMYVL

YPYGGIMEEISESAIPFPHRAGIMYELWYTASWEKQEDNEKHINWVRSVYNFTTPYVSQN

PRLAYLNYRDLDLGKTNPESPNNYTQARIWGEKYFGKNFNRLVKVKTKADPNNFFRNEQS

IPPLPPHHH

THC1dNP1 Protein (Source *Cannabis sativa*)

(SEQ ID NO: 61)

MSNPQENFLKCFSEYIPNNPANPKFIYTQHDQLYMSVLNSTIQNLRFTSDTTPKPLVIVT

PSNVSHIQASILCSKKVGLQIRTRSGGHDAEGMSYISQVPFVVVDLRNMHSIKIDVHSQT

AWVEAGATLGEVYYWINEKNENFSFPGGYCPTVGVGGHFSGGGYGALMRNYGLAADNIID

AHLVNVDGKVLDRKSMGEDLFWAIRGGGGENFGIIAAWKIKLVAVPSKSTIFSVKKNMEI

HGLVKLFNKWQNIAYKYDKDLVLMTHFITKNITDNHGKNKTTVHGYFSSIFHGGVDSLVD

LMNKSFPELGIKKTDCKEFSWIDTTIFYSGVVNFNTANFKKEILLDRSAGKKTAFSIKLD

YVKKPIPETAMVKILEKLYEEDVGVGMYVLYPYGGIMEEISESAIPFPHRAGIMYELWYT

ASWEKQEDNEKHINWVRSVYNFTTPYVSQNPRLAYLNYRDLDLGKTNPESPNNYTQARIW

GEKYFGKNFNRLVKVKTKADPNNFFRNEQSIPPLPPHHHGRRAKL

CBC1 Protein (Source *Cannabis sativa*)

(SEQ ID NO: 62)

MNCSTFSFWFVCKIIFFFLSFNIQISIANPQENFLKCFSEYIPNNPANPKFIYTQHDQLY

MSVLNSTIQNLRFTSDTTPKPLVIVTPSNVSHIQASILCSKKVGLQIRTRSGGHDAEGLS

YISQVPFAIVDLRNMHTVKVDIHSQTAWVEAGATLGEVYYWINEMNENFSFPGGYCPTVG

VGGHFSGGGYGALMRNYGLAADNIIDAHLVNVDGKVLDRKSMGEDLFWAIRGGGGENFGI

IAACKIKLVVVPSKATIFSVKKNMEIHGLVKLFNKWQNIAYKYDKDLMLTTHFRTRNITD

NHGKNKTTVHGYFSSIFLGGVDSLVDLMNKSFPELGIKKTDCKELSWIDTTIFYSGVVNY

NTANFKKEILLDRSAGKKTAFSIKLDYVKKLIPETAMVKILEKLYEEEVGVGMYVLYPYG

GIMDEISESAIPFPHRAGIIVIYELWYTATWEKQEDNEKHINWVRSVYNFTTPYVSQNPR

LAYLNYRDLDLGKTNPESPNNYTQARIWGEKYFGKNFNRLVKVKTKADPNNFFRNEQSIP

PLPPRHH

Promoters for Use in *Candida*

Multiple promoters can be used including synthetic ones. The following are some examples.

PEX11 Promoter Cv (SEQ ID NO: 63)

GAGGATGAAGAAGACGAAGACGAATTGGATGAAGATGAAGCGTATGAGTA
TTATGAGTACTGTCGGACGTTGGAAGGTGGCAGAGTTAAGCCCGAGAAAG
CAAGGAAGGAGTGGGAGATGATGAGTGATGCGGCCAAGAGGATGTGAAGG
CTGCGTATCTGTTTTTGATAGCTGGTGGTAGCCGAATAGAGGAAGGCAAG
CTTGTTCATATTGGATGATGATGGTAGATGGTGGCTGCCAAAGTGGTTGT
AAATAGAAAAAAGTGGGTTTGGGTCTGTTGATAGTTAGTGGTGGCGGCTG
TCTGTGATTACGTCAGCAAGTAGCACCTCGGCAGTTAAAACAGCAGCAAC
AGAAAAAAAATGTGTGAAAGTTTGATTCCCCCACAGTCTACCACACCCAG
AGTTCCATTTATCCATAATATCACAAGCAATAGAAAAATAAAAAATTATC
AACAAATCACAACGAAAAGATTCTGCAAAATTATTTTCACTTCTTCTTTT
GACTTCCTCTTCTTCTTGTTAGGTTCTTTCCATATTTTCCCCTTAAACCC
ATACACAACGCAGCCAT

PoX4 Promoter CV (SEQ ID NO: 64)

GAGCTCCAATTGTAATATTTCGGGAGAAATATCGTTGGGGTAAAACAACA
GAGAGAGAGAGGGAGAGATGGTTCTGGTAGAATTATAATCTGGTTGTTGC
AAATGCTACTGATCGACTCTGGCAATGTCTGTAGCTCGCTAGTTGTATGC
AACTTAGGTGTTATGCATACACACGGTTATTCGGTTGAATTGTGGAGTAA
AAATTGTCTGAGTTGTGTCTTAGCTACTGGCTGGCCCCCCGCGAAAGATA
ATCAAAATTACACTTGTGAATTTTTGCACACACACCGATTAACATTTCCC
TTTTTTGTCCACCGATACACGCTTGCCTCTTCTTATTTTCTCTGTGCTTC
CCCCTCCTGTGACTTTTTCCACCATTGATATAAAATCAACTCCATTTCCC
TAAAATCTCCCCAGATTCTAAAAACAACTTCTTCTCTTCTGCTTTTCCTT
ATTTTTGTTATATTTATTTACCATCCCTTATTTGAATAGTTATTCCCCA
CTAACATTGTTCAAATCTTCACGACATAA

POX2 Promoter CV (SEQ ID NO: 65)

GTGCCGACGGAGTAACAAAAATGTTACAGTGCGCACTACTTATCCCGCTA
AGGTGATAAACTGCAAAAACACACCGTCAAGGAGAAGTCGACGTTTTGCC
GCCACTTGTGAAGGGAAGAAGAGTCGTTGAGTTGATGTAATTAAGCTGGC
ACGTAGATACCAGAAGGTTCTAGAGTAGAGCTTGGGTGGTGTTTGGCCCT
GTTTGGACCACGGATAGAGATGGAGAATCCCTTGGTTAGAGCGGAGAGGA
AAAAATTGAAACTTTGCATATCCCACTTCATTATCCTTGATGTAACCGTT
TTATGGGGTAATTAAAGTGTGGAAAAATAATCAGGGAGACATATTCCCGA
TCAATTGGGTGGTGGTCGCTCAATTTCTGTGAGTAGTAGGCTCAGTGGTG
TGTATTGGGATTGGTAGTAGTCTGTATAAGCAGTGTTATATAACCCATTG
CTTGTTGATTCCTATTTTGCTGGCAAAAGTGACAACTGTAGTTGTGAGAT
AATCCTCGGTTATTACGCCTGGGGGGGCAGACAGCCAAAGTTGTGCCCGT
GCGACAATGGCATCAGAAGAAACAGAAAAAAAAAACACAGGCATTTTTAT

-continued

CCACATGCACACTACCCCCACTATTCCTGTCTGCAGTGTGCTTGTGTGTG
GCCCCCCGCAGAATCAACAGGGCAAACTCTGGAGCCTGAATCTTTATATA
AACTTCAGGCATTGGCCCCCCTTTTCACAATTCTTCACATCCACCATTTT
TTTTCTTCTTTCCTACCATATTAGTTTTTTTTTATTCTTTTCCTACCTAT
CTGATTATTATCAAACATCTGGTCATCCTCAAAAGAAAGAAAGAAACTAT
AACAATCAATC

FOX3 Promoter CV (SEQ ID NO: 66)

TGGATTATGTAATCACAGGCTGTTTCTCCATTCCTGCATGTAGGCTGGCC
CGCGGTATCAACCATCGTCCCGCTTCTTCTGGTTTTTTTTTTTTTTTCCGC
TATGATATTTTTGATCTCTTGGGGGATTTGGTGGGTCTGCCCCCCCCGCT
ACTACAAGCTCAAACACCCGAAACCTTACAACACACACACACACATCCCG
CTTAGTTGCGGGTTGAAGAACGTGTATTCCCGTAGGGTTAATGGTGTGTC
CCCCCCTAGTCACCCGCTTCTGCCATTCTGGGTTTGCCTTCAAAGCTGGC
ATAAATGACGAAAAAAAAGCACAGCATCCTGCACACAACCCTGCTCAGTG
TGACAGGTGGTGGTGTAATAGAAAACCTCGGCTTAAAACCTCTGGTCAGA
GCATCAACTGCAATCTTGTCTTTTTCTGCTGCCCTCACATTCTCCCCACA
CATTCCCACCCTCAAGATTTCACAGGCAAAAACTGCAAATATATATAAAT
CTACAACCAATTCTTTCCCCAGATGGAAAATCTAATTTTTGTTCACCCTT
TTTCTTTCTCCTGCTATCACTGCTACTGCACATATTCAACACCACAACC

TEF1 promoter CV (SEQ ID NO: 67)

GACTGGGAGAACAGACCAAGGATGCCCATACACCATTAATAACAAGCACA
CCTTGATAAATCTCTAGTGTTGACAAATTGGTGATTTGAACATGACTGTA
GAGAGAGAGACAAGTAACCACTGATGGATTGGTGGTGGCAAATAACCACT
TTAAATAAAGACCAACTCACACACAAAGACAGCAGGTCGTGTTCCTATTT
CCAATTTTCACAAGGAGAAGAATAAAAATTTTTCAATGAGATTAACTAAA
GAAACAGACAGGCAGCCCACAAGAAGAAGAAGAAGAAGAGGAAGAGGAAG
AAGAAGAAGAAGAAGAAGAAGAAGAGAAAAAAAATTTTTCCCTCTGCGTT
GCGTTGGGCTTGGGTTGCCAGCACCCACCATATATAACTCTCATCAAATA
CCCAGTAGAGAAAAATTTTTCCTCCCTCTTTTTCTTTCTTTCTTCTCCTT
CTTTTGCTACTCTTTCTGTTTTTCATCAAAAAGATATATATAATCAATCA
TG

TDH3 Promoter CV (SEQ ID NO: 68)

ACCAAACGTTACTTTTTTTTTGCAATCGGATGGTATGGGTCTGGGGTTCA
CCTGTTTTGTAAAGCTACAGAAGGTGGCATATTTCTCTGATCAGGTGTTT
TTTTTTTCGGCTGCTGCTGCTCGTGGTGGTGTAGTGGTAGTGGTGTGTGT
GTGTGTGTGTGCGTGCGTGTGGAAGGACGCTTTTTGCTCTCTGACTCCTC
CCAATCAGAAGTTGCTATAGTGGTGAAACAACAATGGATGATAATGCCCC
GGGCGGTGCGTGTCCGACACAAACCACTACATTTTTTAGCTGGGAGCCTA
CTGCCACTACGACCCACCCACCCATGGTCAACAAAAAAATTCTGACAAAT

-continued

TATAAAATAACCCTTGAATTCCCCCTTGGAAAAATTTTTGGTATTTCTCT

CTCTCTTTTCCTTTCCCTCTTCTTTTTCTCTCCATCAATCAATTGACGTT

CAGTAACTCAATTAATTACATCACATCCCTCAATTAAAGAATTTAAACAA

TG

Promoters for use in *Yarrowia*

Multiple promoters can be used including synthetic ones. The following are some examples.

POX2 Promoter Yl (SEQ ID NO: 69)

ACGATTCCGCCAAGTGAGACTGGCGATCGGGAGAAGGGTTGGTGGTCATG

GGGGATAGAATTTGTACAAGTGGAAAAACCACTACGAGTAGCGGATTTGA

TACCACAAGTAGCAGAGATATACAGCAATGGTGGGAGTGCAAGTATCGGA

ATGTACTGTACCTCCTGTACTCGTACTCGTACGGCACTCGTAGAAACGGG

GCAATACGGGGGAGAAGCGATCGCCCGTCTGTTCAATCGCCACAAGTCCG

AGTAATGCTTGAGTATCGAAGTCTTGTACCTCCCTGTCAATCATGGCACC

ACTGGTCTTGACTTGTCTATTCATACTGGACAAGCGCCAGAGTTAAGCTT

GTAGCGAATTTCGCCCTCGGACATCACCCCATACGACGGACACACATGCC

CGACAAACAGCCTCTCTTATTGTAGCTGAAAGTATATTGAATGTGAACGT

GTACAATATCAGGTACCAGCGGGAGGTTACGGCCAAGGTGATACCGGAAT

AACCCTGGCTTGGAGATGGTCGGTCCATTGTACTGAAGTGTCCGTGTCGT

TTCCGTCACTGCCCCAATTGGACATGTTTGTTTTTCCGATCTTTCGGGCG

CCCTCTCCTTGTCTCCTTGTCTGTCTCCTGGACTGTTGCTACCCCATTTC

TTTGGCCTCCATTGGTTCCTCCCCGTCTTTCACGTCGTCTATGGTTGCAT

GGTTTCCCTTATACTTTTCCCCACAGTCACATGTTATGGAGGGGTCTAGA

TGGAGGCCTAATTTTGACGTGCAAGGGGCGAATTGGGGCGAGAAACACGT

CGTGGACATGGTGCAAGGCCCGCAGGGTTGATTCGACGCTTTTCCGCGAA

AAAAACAAGTCCAAATACCCCCGTTTATTCTCCCTCGGCTCTCGGTATTT

CACATGAAAACTATAACCTAGACTACACGGGCAACCTTAACCCCAGAGTA

TACTTATATACCAAAGGGATGGGTCCTCAAAAATCACACAAGCAACGACG

CCATGA

LIP2 promoter Yl (SEQ ID NO: 70)

AAACTTCTCCGAGTCTGTGCCTTCAGGTGGGCATAGTTGATGGGTGTTTT

GAAGTTAATAGTGGGGAAGAACTATGGCAAACAAGCAGATGCAGGCACCT

TGTAACTGCAGACCGGTTCTTGTCTACCGACTCCGCTGCACCTGTGCCGC

GGTACATGTCGTCACAGGCTGCGGGGTTCGGAGGCCCCCTTGCAACCTCC

TTTGATAGTTGCTATGGCCCCAAAGAGTTATACGAGATAGACCCACAGAT

CTACTTGACTGTTGTCACAGAACCTGCTAGGTTTGCTTATTGTACCCGCT

TTGTAGCTACTGTACAACGACAACGTCAAAAATTGAGACGCGAACAAACT

CCAGATGCAGAACCCAAACCTCTCTCTCAGAGTTTCGAGTGCTTCTACCT

CACAGTAAAGTGGAGGTGGACCTGCAAGGGAATTCAGTCACAAGGCCCCG

AATGTCTCCGAAACTCCAATCGGACCGTTTAAACAGACTAATATCACGTC

ATTGATTGATATTAGCATCCGGCAAGAGCCGCAAGGTTATCTCCTCACCA

-continued

ATGAGCCTGTTGTACGGCTCATTCCGCATCTGCGGCTGATTCAGTTTCGA

GTGGGGATGGTAGACTTCATTGCAGCATTCCTAACCTTCTACTTGGTCCG

TGGAGATGTCATGGACATCGATTTTGGGCTGAGAAGCCTTTTGACGATGT

TGATATCACTGACCGCTAATTTACTCTGGCAGTTTCTCCGGCTCTCGAGG

CATCGTCGATCACCAAACACTATCTGCTAGTCTAAATGTCCGACACGACA

GCTTTTGATCGCCGTGAACGGCGCAGACCTCATGCACCATGCACCAGGGC

CAAATCAATTACGGGTCGCTTAGCGTTGCAGTCGGGGCATTATGGTGGAA

GTTCCGATACGGCACAGACACATTCCATAGTGGGGGGATTGGATTATAAA

AGGGCCATAGAAAGCCCTCAATTGATACCCAAGTACCAGCTCTCCTCACT

ATGA

ICL1 Promoter Yk (SEQ ID NO: 71)

GACCCCCTCCTTTTGCCAGTATATCCACCGCAACACCCACCATGAGCGAC

ATCTGATACCGTGCCGCGACCACTACCCCAAATAAGCTCCAACTAATATG

CCGAGGCAGGTGGGAAACTATGCACTCCAGACGACGCTGTAGAAGCACAT

GGAAGGTGCGGAGGCGGTGGCAACGAGGGGCATGAGCCATCAACGAGTAA

CCACAGACAAGGCAAGGGGGGAAACGCGACCGGAATCTCTCGCGGTCACG

TGACCCGCCCGGGTTCCACTCGTCCATGTTGTGTCTCTGGTGTCTTCGGC

CGACTCGCATTGGTTAAACTTCCACCACCGCAATCACGTCCCACTGGCCA

AACTTTTTCTGCTTTCTCTGACTTTTTCTGGCCAAAAGGCAACGTCGGAA

AGGGTCGGGAGGATTCGGAACCGACGAAAATCGGCCGGCTCCAGCGGGGG

TAGTTCGGCAGTCCTGGTGGGAGCTCTAGGGGAGCTGTGGTCTGTGTAGG

GCGCGGGTCCGGGTTTGTTGGGTGTCAAATCACGTGTTTTTGCCCCCCCG

CTGAGCCGGACTCCGACAACCGTGTCTCCAACGGCCTGACTAAGCTGCTC

CCAGCACTCTGCCGTAGCGTTGGTCTGTCCTGTCGCACTCTGTTCAAAGA

CAGAAGAAAGAAAAAGCTAACCTCCACGTCAGAGACAATGGTAGAAGGCT

TGTTCCTTGCAACCGAGGAGAGTGAGTGTTCTCGGCACGAGCATCATGGG

CGATCTGGAGGGTATTTTTGAGGGGAAAAAACGGGATCAGGACAAACAGA

GGCCACAGACCGGGAATCTGGGCCCCAAAACGGCCTTTTCCCGTCGCAAA

ACCGGTCTACATACACCCCTTCGGCCCGCCACAGGCCGGTGTGAAAAACC

CTAAAGCTTGCTTCAAACCAGACGGACGCACAGCAAGACACATCATGAAG

AGTCACCTGCAGTATATATAGATCTGGGGATTCCCAGTAGACTGACCAAG

CATACAAAAGTGAGTATCCAACAGCGACACGTGAGATGGCAGAGACACAG

AGACGTGTCTACATGGTTGGACAAGTCTCCACATTCGCCAGAGACGTATC

CACATACAAACACAATCTCACAGCTGATCTGCTCCTGTGACAGCACAGTA

CATGTTAGTGGATGAGGTGTTGTGTAGTGGGTTAAATGGGTGGACTGATT

CAGTGGCATCGGTGGCGACACCCTCTACTCTTCATGTCGTCACCTACCGT

TCGGAATCCCAATTATCTGATGAACTAAACGATTTCTGGCCAAAACACAA

-continued

TTTTGCCAAAGAAGTCGTTCTCACCAATGCAAGTGTCACATCAAACATCT

GTCCCGTACTAACCCAG

POT1 Promoter Yl (SEQ ID NO: 72)

CCACAATACCCCACAGTGTGCATATCAAACCTACCGGTTGTTGCTCTCTC

CAGCCTTACTAAGAAGGAGGCGACGTGGCAGTGGCTCGCGGGAGGATCGG

CGGGAAACTCCGGGATATCCGTCGAGAGTTTACACGTGAATGGGCAGCGC

AATCCGTTGACGACGATACGACTGGCAAAGTAGCGACGATACCTGCCAGA

CAGGTGACATGTGCAGGCCGCACTAACAAGGAAACGGGCGCTGGGGGGGG

CGGGCTTCTAGACTTTGCCCTTGAACAGGAATCTAGTGGGGGCTTGTCTT

TCCGCCAATGGGGGAGCGCCTGTTGAGCGACCGTGCATGCTGGAACGCCA

AGTGTATGTACAGCTGGTGTTCTCGCAGCGGTATGTGACGGGACTTACAT

CTCTCGTTTTTTCATGACCACGTTTTCACAGGCTCGGAGGTACGTTAAAG

TTTTGAAGGCTGCATCTGAACCGAGGTATGGGGGAGTTTGAGGAGCAACA

GTGTTGGGGCTGAGGGGGCCAAGATCGGGGCAAGCAGAGGTCTTAGATCA

ATTGTGGGAATCCCAAAGGGCTCGTTATCACCTTTTTCCACCCAATTCGG

GTCCCAATTGATCCACTACTGGCTTGCCCAAGTTACCCCAGAAATGCCGC

CCCGGATTTCTCCAAAAACCTAATAAGCTTCATGGAACTTGGTGGAAGTG

ACTTTCTACAGAGTGGAGAGAACCGTGGACACGTGGCAATGGCGCTGACC

GTGTCCCCGAGCCGAATCGACGTGAGGGGAGAACGGAGTATCTGCGGTCA

TGTGACCTTCCAGAGCGGCGTCGCCAGTGTGCACGCGGTGACCCCCAGTT

TGGTTCTCTGTCACACGCATACTACCTCGGCTCTCCACATGCTGAACTTT

ATCTTTCGTGGGGATCATACCGAAAGTTGCAACTACCAGGTGTATATAAA

GCCTGGTAGACTCCCCCCACTTTGGACCTCATCCAACCAAGACACACAAA

AATG

Terminators to Use in *Candida viswanathii*

Multiple terminators can be used. The following are some examples.

POX4 Terminator Cv (SEQ ID NO: 73)

GAGTGACTCTTTTGATAAGAGTCGCAAATTTGATTTCATAAGTATATATT

CATTATGTAAAGTAGTAAATGGAAAATTCATTAAAAAAAAAGCAAATTTC

CGTTGTATGCATACTCCGAACACAAAACTAGCCCCGGAAAAACCCTTAGT

TGATAGTTGCGAATTTAGGTCGAC

PEX11 Terminator CV (SEQ ID NO: 74)

AGCTCCAGGCTTGTTATGACTCTAGAGAGAAGTGTGTGTGTTTGCGTTTG

TTTTACTATACATTCAACATGTTCTTTTTCTTTTTTGATATTTATTCCAA

CTATAATTATACACAGATTCGTATATACTTTACTTTACCCTCTTTCGTAG

TTTTTTAATTTGATGATTTTTGAGTTTCATATCCAAGGTCAAAACCCGAC

Terminators to use in *Yarrowia lipolytica*

Multiple terminators can be used. The following are some examples.

XPR2 Terminato Yl (SEQ ID NO: 75)

TAGGCAATTAACAGATAGTTTGCCGGTGATAATTCTCTTAACCTCCCACA

CTCCTTTGACATAACGATTTATGTAACGAAACTGAAATTTGACCAGATAT

TGTTGTAAATAGAAAATCTGGCTTGTAGGTGGCAAAATGCGGCGTCTTTG

TTCATCAATTCCCTCTGTGACTACTCGTCATCCCTTTATGTTCGACTGTC

GTATTTCTTATTTTCCATACATATGCAAGTGAGATGCCCGTGTCCGAATT

C

TDH3 terminator YL (SEQ ID NO: 76)

CTTCCGAGTAGCTATCCGAAGATCAAGAGCGAAGCAAGTTGTAAGTCCAG

GACATGTTTCCCGCCCACGCGAGTGATTTATAACACCTCTCTTTTTTGAC

ACCCGCTCGCCTTGAAATTCATGTCACATAAATTATAGTCAACGACGTTT

GAATAACTTGTCTTGTAGTTCGATGATGATCATATGATTACATTAATAGT

AATTACTGTATTTGATATATATACTAATTACAATAGTACATATTAGAACA

TACAATAGTTAGTGCCGTGAAGTGGCTTAAAATACCGCGAGTCGATTACG

TAATATTA

Markers for Use in *Yarrowia*

LEU2 Marker Yl (SEQ ID NO: 77)

AACGTACCACTGTCCTCCACTACAAACACACCCAATCTGCTTCTTCTAGTCAAGGTT

GCTACACCGGTAAATTATAAATCATCATTTCATTAGCAGGGCTGGGCCCTTTTTATA

GAGTCTTATACACTAGCGGACCCTGCCGGTAGACCAACCCGCAGGCGCGTCAGTTTG

CTCCTTCCATCAATGCGTCGTAGAAACGACTTACTCCTTCTTGAGCAGCTCCTTGACC

TTGTTGGCAACAAAGTCTCCGACCTCGGAGGTGGAGGAGGAGCCTCCGATATCGGC

GGTAGTGATACCAGCCTCGACGGACTCCTTGACGGCAGCCTCAACAGCGTCACCGG

CGGGCTTCATGTTAAGAGAGAACTTGAGCATCATGGCGGCAGACAGAATGGTGGCA

ATGGGGTTGACCTTCTGCTTGCCGAGATCGGGGGCAGATCCGTGACAGGGCTCGTAC

AGACCGAACGCCTCGTTGGTGTCGGGCAGAGAAGCCAGAGAGGCGGAGGGCAGCA

GACCCAGAGAACCGGGGATGACGGAGGCCTCGTCGGAGATGATATCGCCAAACATG

-continued

TTGGTGGTGATGATGATACCATTCATCTTGGAGGGCTGCTTGATGAGGATCATGGCG

GCCGAGTCGATCAGCTGGTGGTTGAGCTCCAGCTGGGGGAATTCGTCCTTGAGGACT

CGGGTGACGGTCTTTCGCCAAAGTCGAGAGGAGGCCAGCACGTTGGCCTTGTCAAG

GGACCACACGGGAAGAGGGGGGTTGTGCTGAAGGGCCAGGAAGGCGGCCATTCGG

GCAATTCGCTCAACCTCAGGAACGGAGTAAGTCTCAGTGTCGGAAGCGACGCCAGA

TCCGTCATCCTCCTTTCGCTCTCCAAAGTAGATACCTCCGACGAGCTCTCGGACAAT

GATGAAGTCGGTGCCCTCAACGTTTCGGATGGGGGAGAGATCGGCGAGCTTGGGCG

ACAGCAGCTGGCAGGGTCGCAGGTTGGCGTACAGGTTCAGGTCCTTTCGCAGCTTGA

GAAGACCCTGCTCGGGTCGCACGTCGGTTCGTCCGTCGGGAGTGGTCCATACGGTGT

TGGCAGCGCCTCCGACAGCACCGAGCATAATAGAGTCAGCCTTTCGGCAGATGTCG

AGAGTAGCGTCGGTGATGGGCTCGCCCTCCTTCTCAATGGCAGCTCCTCCAATGAGT

CGGTCCTCAAACACAAACTCGGTGCCGGAGGCCTCAGCAACAGACTTGAGCACCTT

GACGGCCTCGGCAATCACCTCGGGGCCACAGAAGTCGCCGCCGAGAAGAACAATCT

TCTTGGAGTCAGTCTTGGTCTTCTTAGTTTCGGGTTCCATTGTGGATGTGTGTGGTTG

TATGTGTGATGTGGTGTGTGGAGTGAAAATCTGTGGCTGGCAAACGCTCTTGTATAT

ATACGCACTTTTGCCCGTGCTATGTGGAAGACTAAACCTCCGAAGATTGTGACTCAG

GTAGTGCGGTATCGGCTAGGGACCCAAACCTTGTCGATGCCGATAGCGCTATCGAAC

GTACCCCAGCCGGCCGGGAGTATGTCGGAGGGGACATACGAGATCGTCAAGGGTTT

GTGGCCAACTGGTAAATAAATGATGACTCAGGCGACGACGGAATTCGACAGCAACT

ACTCCTTTCACCAACCATGTGCATTTTAGCTCGAATAACATTCACAGGCTTGGTGATC

TACATCCATGGTGTCTGGCCGATTACCGTGGTGTTTTGGCAGTAACGAGAATATTGA

GTGAACTCTTCCCATCACCAATAAAGACTCATACTACAATCACGAGCGCTTCAGCTG

CCACTATAGTGTTGGTGACACAATACCCCTCGATGCTGGGCATTACTGTAGCAAGAG

ATATTATTTCATGGCGCATTTTCCAGTCTACCTGACTTTTTAGTGTGATTTCTTCTCCA

CATTTTATGCTCAGTGTGAAAAGTTGGAGTGCACACTTAATTATCGCCGGTTTTCGG

AAAGTACTATGTGCTCAAGGTTGCACCCCACGTTACGTATGCAGCACATTGAGCAGC

CTTTGGACCGTGGAGATAACGGTGTGGAGATAGCAACGGGTAGTCTTCGTATTAATT

CAATGCATTGTTAGTTTTATATGATATGGTGTCGA

URA3 Marker Yl (SEQ ID NO: 78)

TTTCTAATTTGGACCGATAGCCGTATAGTCCAGTCTATCTATAAGTTCAACTAACTCG

TAACTATTACCATAACATATACTTCACTGCCCCAGATAAGGTTCCGATAAAAAGTTG

TGCAGACTAAATTTATTTCAGTCTCCTCTTCACCACCAAAATGCCCTCCTACGAAGC

GCGAGCTAACGTCCACAAGTCCGCCTTTGCCGCCCGAGTGCTCAAGCTCGTGGCAGC

CAAGAAAACCAACCTGTGTGCTTCTCTGGATGTTACCACCACCAAGGAGCTCATTGA

GCTTGCCGATAAGGTCGGACCTTATGTGTGCATGATCAAGACCCATATCGACATCAT

TGACGACTTCACCTACGCCGGAACTGTGCTCCCCCTCAAGGAACTTGCTCTTAAGCA

CGGTTTCTTCCTGTTCGAGGACAGAAAGTTCGCAGATATTGGCAACACTGTCAAGCA

CCAGTACAAGAACGGTGTCTACCGAATCGCCGAGTGGTCCGATATCACCAACGCCC

ACGGTGTACCCGGAACCGGAATCATTGCTGGCCTGCGAGCTGGTGCCGAGGAAACT

GTCTCTGAACAGAAGAAGGAGGATGTCTCTGACTACGAGAACTCCCAGTACAAGGA

GTTCCTGGTCCCCTCTCCCAACGAGAAGCTGGCCAGAGGTCTGCTCATGCTGGCCGA

-continued

```
GCTGTCTTGCAAGGGCTCTCTGGCCACTGGCGAGTACTCCAAGCAGACCATTGAGCT

TGCCCGATCCGACCCCGAGTTTGTGGTTGGCTTCATTGCCCAGAACCGACCTAAGGG

CGACTCTGAGGACTGGCTTATTCTGACCCCCGGGGTGGGTCTTGACGACAAGGGAG

ATGCTCTCGGACAGCAGTACCGAACTGTTGAGGATGTCATGTCTACCGGAACGGATA

TCATAATTGTCGGCCGAGGTCTGTACGGCCAGAACCGAGATCCTATTGAGGAGGCC

AAGCGATACCAGAAGGCTGGCTGGGAGGCTTACCAGAAGATTAACTGTTAGAGGTT

AGACTATGGATATGTCATTTAACTGTGTATATAGAGAGCGTGCAAGTATGGAGCGCT

TGTTCAGCTTGTATGATGGTCAGACGACCTGTCTGATCGAGTATGTATGATACTGCA

CAACCTG
```

Polynucleotides and Polypeptides

A nucleic acid (e.g., also referred to herein as nucleic acid reagent, target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). A nucleic acid can also comprise DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Deoxyribonucleotides include deoxyadenosine, deoxycytidine, deoxyguanosine and deoxythymidine. For RNA, the uracil base is uridine.

A nucleic acid sometimes is a plasmid, phage, autonomously replicating sequence (ARS), centromere, artificial chromosome, yeast artificial chromosome (e.g., YAC) or other nucleic acid able to replicate or be replicated in a host cell. In certain embodiments a nucleic acid can be from a library or can be obtained from enzymatically digested, sheared, or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often will cleave specifically according to a particular nucleotide sequence at a particular site. Examples of enzymic specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afi III, Alu I, Alw44 I, Apa I, Asn I, Ava I, Ava II, BamH I, Ban II, Bcl I, Bgl I. Bgl II, Bln I, Bsa I, Bsm I, BsmBI, BssH II, BstE II, Cfo I, Cla I, Dde I, Dpn I, Dra I, EclX I, EcoR I, EcoR I, EcoR II, EcoR V, Hae II, Hae II, Hind III, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sap I, Sal I, Sau3A I, Sea I, ScrF I, Sfi I, Sma I, Spe I, Sph I, Ssp I, Stu I, Sty I, Swa I, Taq I, Xba I, Xho I); glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'—N5'-phosphoroamidate-containing nucleic acid; and osmium tetroxide and piperidine treatment of nucleic acid.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialized culture conditions and the like). The terms "amplify", "amplification", "amplification reaction", or "amplifying" as used herein, refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step. In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids). As described herein, the term "native sequence" refers to an unmodified nucleotide sequence as found in its natural setting (e.g., a nucleotide sequence as found in an organism).

A nucleic acid or nucleic acid reagent can comprise certain elements often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR, and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR.

A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments.

A promoter often interacts with an RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide, or protein. The term "operably linked" as used herein with respect to promoters refers to a nucleic acid sequence (e.g., a coding sequence) present on the same nucleic acid molecule as a promoter element and whose expression is under the control of said promoter element.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional, or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermentor, growth on solid nutrient plates and the like for example).

In some embodiments, regulation of a promoter element can be used to alter (e.g., increase, add, decrease, or substantially eliminate) the activity of a peptide, polypeptide, or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

In some embodiments the activity can be altered using recombinant DNA and genetic techniques known to the artisan. Methods for engineering microorganisms are further described herein. Tables herein provide non-limiting lists of yeast promoters that are up-regulated by oxygen, yeast promoters that are down-regulated by oxygen, yeast transcriptional repressors and their associated genes, DNA binding motifs as determined using the MEME sequence analysis software. Potential regulator binding motifs can be identified using the program MEME to search intergenic regions bound by regulators for overrepresented sequences. For each regulator, the sequences of intergenic regions bound with p-values less than 0.001 were extracted to use as input for motif discovery. The MEME software was run using the following settings: a motif width ranging from 6 to 18 bases, the "zoops" distribution model, a 6th order Markov background model, and a discovery limit of 20 motifs. The discovered sequence motifs were scored for significance by two criteria: an E-value calculated by MEME and a specificity score. The motif with the best score using each metric is shown for each regulator. All motifs presented are derived from datasets generated in rich growth conditions with the exception of a previously published dataset for epitope-tagged Gal4 grown in galactose.

In some embodiments, the altered activity can be found by screening the organism under conditions that select for the desired change in activity. For example, certain microorganisms can be adapted to increase or decrease an activity by selecting or screening the organism in question on a media containing substances that are poorly metabolized or even toxic. An increase in the ability of an organism to grow a substance that is normally poorly metabolized would result in an increase in the growth rate of that substance, for example. A decrease in the sensitivity to a toxic substance might be manifested by growth on higher concentrations of the toxic substance, for example. Genetic modifications that are identified in this manner sometimes are referred to as naturally occurring mutations or the organisms that carry them can sometimes be referred to as naturally occurring mutants. Modifications obtained in this manner are not limited to alterations in promoter sequences. That is, screening microorganisms by selective pressure, as described above, can yield genetic alterations that can occur in non-promoter sequences, and sometimes also can occur in sequences that are not in the nucleotide sequence of interest, but in a related nucleotide sequences (e.g., a gene involved in a different step of the same pathway, a transport gene, and the like). Naturally occurring mutants sometimes can be found by isolating naturally occurring variants from unique environments, in some embodiments.

In addition to the regulated promoter sequences, regulatory sequences, and coding polynucleotides provided herein, a nucleic acid reagent may include a polynucleotide sequence 70% or more identical to the foregoing (or to the complementary sequences). That is, a nucleotide sequence that is at least 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address at world wide web uniform resource locator gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address at world wide web uniform resource locator gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. As used herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used. An example of stringent hybridization conditions is hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5 M sodium phosphate, 7% SDS at 65° C., followed by one or more washes at 0.2×SSC, 1% SDS at 65° C.

As noted above, nucleic acid reagents may also comprise one or more 5' UTRs, and one or more 3'UTR's. A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA, or mRNA, for example, from any suitable organism (e.g., virus, bacterium, yeast, fungi, plant, insect, or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., http address at world wide web uniform resource locator interscience.wiley.com, DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA, or mRNA, for example, from any suitable organism (e.g., a virus, bacterium, yeast, fungi, plant, insect, or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease, or substantially eliminate) the activity of a promoter. Alteration of the promoter activity can in turn alter the activity of a peptide, polypeptide, or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

A nucleotide reagent sometimes can comprise a target nucleotide sequence. A "target nucleotide sequence" as used herein encodes a nucleic acid, peptide, polypeptide, or protein of interest, and may be a ribonucleotide sequence or a deoxyribonucleotide sequence.

A target nucleic acid sometimes can comprise a chimeric nucleic acid (or chimeric nucleotide sequence), which can encode a chimeric protein (or chimeric amino acid sequence). The term "chimeric" as used herein refers to a nucleic acid or nucleotide sequence, or encoded product thereof, containing sequences from two or more different sources. Any suitable source can be selected, including, but not limited to, a sequence from a nucleic acid, nucleotide sequence, ribosomal nucleic acid, RNA, DNA, regulatory nucleotide sequence (e.g., promoter, URL, enhancer, repressor, and the like), coding nucleic acid, gene, nucleic acid linker, nucleic acid tag, amino acid sequence, peptide, polypeptide, protein, chromosome, and organism. A chimeric molecule can include a sequence of contiguous nucleotides or amino acids from a source including, but not limited to, a virus, prokaryote, eukaryote, genus, species, homolog, ortholog, paralog and isozyme, nucleic acid linkers, nucleic acid tags, the like and combinations thereof). A chimeric molecule can be generated by placing in juxtaposition fragments of related or unrelated nucleic acids, nucleotide sequences or DNA segments, in some embodiments. In certain embodiments the nucleic acids, nucleotide sequences or DNA segments can be native or wild type sequences, mutant sequences or engineered sequences (completely engineered or engineered to a point, for example).

In some embodiments, a chimera includes about 1, 2, 3, 4 or 5 sequences (e.g., contiguous nucleotides, contiguous amino acids) from one organism and 1, 2, 3, 4 or 5 sequences (e.g., contiguous nucleotides, contiguous amino acids) from another organism. The organisms sometimes are a microbe, such as a bacterium (e.g., gram positive, gram negative), yeast or fungus (e.g., aerobic fungus, anaerobic fungus), for example. In some embodiments, the organisms are bacteria, the organisms are yeast or the organisms are fungi (e.g., different species), and sometimes one organism is a bacterium or yeast and another is a fungus. A chimeric molecule may contain up to about 99% of sequences from one organism (e.g., about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99%) and the balance percentage from one or more other organisms. In certain embodiments, a chimeric molecule includes altered codons (in the case of a chimeric nucleic acid) and one or more mutations (e.g., point mutations, nucleotide substitutions, amino acid substitutions).

A chimera sometimes is the result of recombination between two or more nucleic acids, nucleotide sequences or genes, and sometimes is the result of genetic manipulation (e.g., designed and/or generated by the hand of a human being). Any suitable nucleic acid or nucleotide sequence and method for combining nucleic acids or nucleotide sequences can be used to generate a chimeric nucleic acid or nucleotide sequence. Non-limiting examples of nucleic acid and nucleotide sequence sources and methods for generating chimeric nucleic acids and nucleotide sequences are presented herein.

In some embodiments, fragments used to generate a chimera can be juxtaposed as units (e.g., nucleic acid from the sources are combined end to end and not interspersed. In embodiments where a chimera includes one stretch of contiguous nucleotides for each organism, nucleotide sequence combinations can be noted as DNA source 1 DNA source 2 or DNA source 1/DNA source 2/DNA source 3, the like and combinations thereof, for example. In certain embodiments, fragments used to generate a chimera can be juxtaposed such that one or more fragments from one or more sources can be interspersed with other fragments used to generate the chimera (e.g., DNA source 1/DNA source 2/DNA source 1/DNA source 3/DNA source 2/DNA source 1). In some embodiments, the nucleotide sequence length of the fragments used to generate a chimera can be in the range from about 5 base pairs to about 5,000 base pairs (e.g., about 5 base pairs (bp), about 10 bp, about 15 bp, about 20 bp, about 25 bp, about 30 bp, about 35 bp, about 40 bp, about 45 bp, about 50 bp, about 55 bp, about 60 bp, about bp, about 65 bp, about 70 bp, about 75 bp, about 80 bp, about 85 bp, about 90 bp, about 95 bp, about 100 bp, about 125 bp, about 150 bp, about 175 bp, about 200 bp, about 250 bp, about 300 bp, about 350 bp, about 400 bp, about 450 bp, about 500 bp, about 550 bp, about 600 bp, about 650 bp, about 700 bp, about 750 bp, about 800 bp, about 850 bp, about 900 bp, about 950 bp, about 1000 bp, about 1500 bp, about 2000 bp, about 2500 bp, about 3000 bp, about 3500 bp, about 4000 bp, about 4500 bp, or about 5000 bp).

In certain embodiments, a chimeric nucleic acid or nucleotide sequence encodes the same activity as the activity encoded by the source nucleic acids or nucleotide sequences. In some embodiments, a chimeric nucleic acid or nucleotide sequence has a similar or the same activity, but the amount of the activity, or kinetics of the activity, are altered (e.g., increased, decreased). In certain embodiments, a chimeric nucleic acid or nucleotide sequence encodes a different activity, and in some embodiments a chimeric nucleic acid or nucleotide sequences encodes a chimeric activity (e.g., a combination of two or more activities).

A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide, or protein, which are sometimes referred to herein as "target peptides," "target polypeptides" or "target proteins."

Any peptides, polypeptides or proteins, or an activity catalyzed by one or more peptides, polypeptides or proteins may be encoded by a target nucleotide sequence and may be selected by a person of ordinary skill in the art. Representative proteins include enzymes (e.g., phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like, for example), antibodies, serum proteins (e.g., albumin), membrane bound proteins, hormones (e.g., growth hormone, erythropoietin, insulin, etc.), cytokines, etc., and include both naturally occurring and exogenously expressed polypeptides. Representative activities (e.g., enzymes or combinations of enzymes which are functionally associated to provide an activity) include phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activity and the like for example. The term "enzyme" as used herein refers to a protein which can act as a catalyst to induce a chemical change in other compounds, thereby producing one or more products from one or more substrates.

Specific polypeptides (e.g., enzymes) useful for embodiments described herein are listed hereafter. The term "protein" as used herein refers to a molecule having a sequence of amino acids linked by peptide bonds. This term includes fusion proteins, oligopeptides, peptides, cyclic peptides, polypeptides, and polypeptide derivatives, whether native or recombinant, and also includes fragments, derivatives, homologs, and variants thereof. A protein or polypeptide sometimes is of intracellular origin (e.g., located in the nucleus, cytosol, or interstitial space of host cells in vivo) and sometimes is a cell membrane protein in vivo. In some embodiments (described above, and in further detail below in Engineering and Alteration Methods), a genetic modification can result in a modification (e.g., increase, substantially increase, decrease, or substantially decrease) of a target activity.

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A nucleic acid reagent sometimes comprises one or more ORFs. An ORF may be from any suitable source, sometimes from genomic DNA, mRNA, reverse transcribed RNA, or complementary DNA (cDNA) or a nucleic acid library comprising one or more of the foregoing and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat, or mouse, for example.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG (SEQ ID NO: 79)), V5 (e.g., GKPIPNPLLGLDST (SEQ ID NO: 80)), c-MYC (e.g., EQKLISEEDL (SEQ ID NO: 81)), HSV (e.g., QPELAPEDPED (SEQ ID NO: 82)), influenza hemaglutinin, HA (e.g., YPYDVPDYA (SEQ ID NO: 83)), VSV-G (e.g., YTDIEMNRLGK (SEQ ID NO: 182)), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 84)) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 85), wherein X is any amino acid and n is 1 to 3, and the cysteine-rich sequence sometimes is CCPGCC (SEQ ID NO: 86). In certain embodiments, the tag comprises a cysteine-rich element and a polyhistidine element (e.g., CCPGCC (SEQ ID NO: 87) and His6 (SEQ ID NO: 88)).

A tag often conveniently binds to a binding partner. For example, some tags bind to an antibody (e.g., FLAG) and sometimes specifically bind to a small molecule. For example, a polyhistidine tag specifically chelates a bivalent metal, such as copper, zinc, and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FIAsH™ (EDT2[4',5'-bis(1,3,2-dithiarsolan-2-yl)fluorescein-(1,2-ethanedithiol)2]) and ReAsH reagents (e.g., U.S. Pat. No. 5,932,474 to Tsien et al., entitled "Target Sequences for Synthetic Molecules;" U.S. Pat. No. 6,054,271 to Tsien et al., entitled "Methods of Using Synthetic Molecules and Target Sequences;" U.S. Pat. Nos. 6,451,569 and 6,008,378; published U.S. Patent Application 2003/0083373, and published PCT Patent Application WO 99/21013, all to Tsien et al. and all entitled "Synthetic Molecules that Specifically React with Target Sequences"). Such antibodies and small molecules sometimes are linked to a solid phase for convenient isolation of the target protein or target peptide.

A tag sometimes comprises a sequence that localizes a translated protein or peptide to a component in a system, which is referred to as a "signal sequence" or "localization signal sequence" herein. A signal sequence often is incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273)).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS (SEQ ID NO: 89)), enterokinase (e.g., recognition site DDDDK (SEQ ID NO: 90)), TEV protease (e.g., recognition site ENLYFQG (SEQ ID NO: 91)) or PreScission™ protease (e.g., recognition site LEVLFQGP (SEQ ID NO: 92)), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine, and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583, filed Jul. 14, 2004, entitled "Production of Fusion Proteins by Cell-Free Protein Synthesis,"; Eggertsson, et al., (1988) Microbiological Review 52(3):354-374, and Engleerg-Kukla, et al. (1996) in *Escherichia coli* and *Salmonella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003, at http address at world wide web uniform resource locator invitrogen.com/content/sfs/manuals/tagondemand_supernatant_man.pdf; Tag-On-Demand™ Gateway® Vector Instruction Manual, Version B, 20 Jun. 2003 at http address at world wide web uniform resource locator invitrogen.com/content/sfs/manuals/tagondemand_vectors_man.pdf; and Capone et al., Amber, ochre and opal suppressor tRNA genes derived from a human serine tRNA gene. EMBO J. 4:213, 1985).

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described hereafter. In some embodiments, a cloning strategy can be combined with genetic manipulation such as recombination (e.g., recombination of a nucleic acid reagent with a nucleic acid sequence of interest into the genome of the organism to be modified, as described further below). In some embodiments, the cloned ORF(s) can produce (directly or indirectly) a desired product, by engineering a microorganism with one or more ORFs of interest, which microorganism comprises one or more altered activities selected from the group consisting of phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity, sugar transport activity, phosphoglucoisomerase activity, transaldolase activity, transketolase activity, glucose-6-phosphate dehydrogenase activity, 6-phosphogluconolactonase activity, 6-phosphogluconate dehydrogenase (decarboxylating) activity, and thymidylate synthase activity.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is IoxP, which is a 34 base pair sequence comprised of two 13 base pair inverted repeats (serving as the recombinase binding sites) flanking an 8 base pair core sequence (e.g., FIG. 1 of Sauer, B., Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. No. 09/517,466, filed Mar. 2, 2000, and Ser. No. 09/732,914, filed Aug. 14, 2003, and in U.S. patent publication no. 2002-0007051-A1; Landy, Curr. Opin. Biotech. 3:699-707 (1993)).

Examples of recombinase cloning nucleic acids are in Gateway® systems (Invitrogen, California), which include at least one recombination site for cloning a desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A recombination system useful for engineering yeast is outlined briefly. The system makes use of the ura3 gene (e.g., for *S. cerevisiae* and *C. albicans*, for example) or ura4 and ura5 genes (e.g., for *S. pombe*, for example) and toxicity of the nucleotide analogue 5-Fluoroorotic acid (5-FOA). The ura3 or ura4 and ura5 genes encode orotine-5'-monophosphate (OMP) dicarboxylase. Yeast with an active ura3 or ura4 and ura5 gene (phenotypically Ura+) convert 5-FOA to fluorodeoxyuridine, which is toxic to yeast cells. Yeast carrying a mutation in the appropriate gene(s) or having a knock out of the appropriate gene(s) can grow in the presence of 5-FOA, if the media is also supplemented with uracil.

A nucleic acid engineering construct can be made which may comprise the URA3 gene or cassette (for *S. cerevisiae*), flanked on either side by the same nucleotide sequence in the same orientation. The ura3 cassette comprises a promoter, the ura3 gene and a functional transcription terminator. Target sequences which direct the construct to a particular nucleic acid region of interest in the organism to be engineered are added such that the target sequences are adjacent to and abut the flanking sequences on either side of the ura3 cassette. Yeast can be transformed with the engineering construct and plated on minimal media without uracil. Colonies can be screened by PCR to determine those transformants that have the engineering construct inserted in the proper location in the genome. Checking insertion location prior to selecting for recombination of the ura3 cassette may reduce the number of incorrect clones carried through to later stages of the procedure. Correctly inserted transformants can then be replica plated on minimal media containing 5-FOA to select for recombination of the ura3 cassette out of the construct, leaving a disrupted gene and an identifiable footprint (e.g., nucleic acid sequence) that can be use to verify the presence of the disrupted gene. The technique described is useful for disrupting or "knocking out" gene function, but also can be used to insert genes or constructs into a host organisms genome in a targeted, sequence specific manner. Further detail will be described below in the engineering section and in the example section.

In certain embodiments, a nucleic acid reagent includes one or more topoisomerase insertion sites. A topoisomerase insertion site is a defined nucleotide sequence recognized and bound by a site-specific topoisomerase. For example, the nucleotide sequence 5'-(C/T)CCTT-3' is a topoisomerase recognition site bound specifically by most poxvirus topoisomerases, including vaccinia virus DNA topoisomerase I. After binding to the recognition sequence, the topoisomerase cleaves the strand at the 3'-most thymidine of the recognition site to produce a nucleotide sequence comprising 5'-(C/T)CCTT-PO4-TOPO, a complex of the topoisomerase covalently bound to the 3' phosphate via a tyrosine in the topoisomerase (e.g., Shuman, J. Biol. Chem. 266: 11372-11379, 1991; Sekiguchi and Shuman, Nucl. Acids Res. 22:5360-5365, 1994; U.S. Pat. No. 5,766,891; PCT/US95/16099; and PCT/US98/12372). In comparison, the nucleotide sequence 5'-GCAACTT-3' is a topoisomerase recognition site for type IA *E. coli* topoisomerase III. An element to be inserted often is combined with topoisomerase-reacted template and thereby incorporated into the nucleic acid reagent (e.g., http address at world wide web uniform resource locator invitrogen.com/downloads/F-

13512_Topo_Flyer.pdf; http address at world wide web uniform resource locator invitrogen.com/content/sfs/brochures/710_021849%20_B_TOPOCloning_bro.pdf; TOPO TA Cloning® Kit and Zero Blunt® TOPO® Cloning Kit product information).

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent is of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (see, e.g., Biochemistry 1996 Jun. 25; 35(25):8429-38 and http address world wide web uniform resource locator devicelink.com/ivdt/archive/00/11/007.html). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

In some embodiments, a nucleic acid reagent, protein reagent, protein fragment reagent or other reagent described herein is isolated or purified. The term "isolated" as used herein refers to material removed from its original environment (e.g., the natural environment if it is naturally occurring, or a host cell if expressed exogenously), and thus is altered "by the hand of man" from its original environment. The term "purified" as used herein with reference to molecules does not refer to absolute purity. Rather, "purified" refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

Engineering and Alteration Methods

Methods and compositions (e.g., nucleic acid reagents) described herein can be used to generate engineered microorganisms. As noted above, the term "engineered microorganism" as used herein refers to a modified organism that includes one or more activities distinct from an activity present in a microorganism utilized as a starting point for modification (e.g., host microorganism or unmodified organism). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like. The term "mutagenesis" as used herein refers to any modification to a nucleic acid (e.g., nucleic acid reagent, or host chromosome, for example) that is subsequently used to generate a product in a host or modified organism. Non-limiting examples of mutagenesis include deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis, T., E. F. Fritsch and J. Sambrook (1982) Molecular Cloning: a Laboratory Manual; Cold Spring Harbor Laboratory, Cold Spring Harbor, N.Y.

The term "genetic modification" as used herein refers to any suitable nucleic acid addition, removal or alteration that facilitates production of a target product (e.g., phosphogluconate dehydratase activity, 2-keto-3-deoxygluconate-6-phosphate aldolase activity, xylose isomerase activity, or phosphoenolpyruvate carboxylase activity, for example). in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous polynucleotide" as used herein refers to a nucleotide sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous polynucleotide is from a different organism in some embodiments, and in certain embodiments, is from the same type of organism but from an outside source (e.g., a recombinant source).

The term "altered activity" as used herein refers to an activity in an engineered microorganism that is added or modified relative to the host microorganism (e.g., added, increased, reduced, inhibited, or removed activity). An activity can be altered by introducing a genetic modification to a host microorganism that yields an engineered microorganism having added, increased, reduced, inhibited, or removed activity.

An added activity often is an activity not detectable in a host microorganism. An increased activity generally is an activity detectable in a host microorganism that has been increased in an engineered microorganism. An activity can be increased to any suitable level for production of a target product (e.g., adipic acid, 6-hydroxyhexanoic acid), including but not limited to less than 2-fold (e.g., about 10% increase to about 99% increase; about 20%, 30%, 40%, 50%, 60%, 70%, 80%, 90% increase), 2-fold, 3-fold, 4-fold, 5-fold, 6-fold, 7-fold, 8-fold, 9-fold, of 10-fold increase, or greater than about 10-fold increase. A reduced or inhibited activity generally is an activity detectable in a host microorganism that has been reduced or inhibited in an engineered microorganism. An activity can be reduced to undetectable levels in some embodiments, or detectable levels in certain embodiments. An activity can be decreased to any suitable level for production of a target product (e.g., adipic acid, 6-hydroxyhexanoic acid), including but not limited to less than 2-fold (e.g., about 10% decrease to about 99% decrease; about 20%, 30%, 40%, 50%, 60%, 70%, 80%, 90% decrease), 2-fold, 3-fold, 4-fold, 5-fold, 6-fold, 7-fold, 8-fold, 9-fold, of 10-fold decrease, or greater than about 10-fold decrease.

An altered activity sometimes is an activity not detectable in a host organism and is added to an engineered organism. An altered activity also may be an activity detectable in a host organism and is increased in an engineered organism. An activity may be added or increased by increasing the number of copies of a polynucleotide that encodes a polypeptide having a target activity, in some embodiments. In certain embodiments an activity can be added or increased by inserting into a host microorganism a heterologous polynucleotide that encodes a polypeptide having the added activity. In certain embodiments, an activity can be added or increased by inserting into a host microorganism a heterologous polynucleotide that is (i) operably linked to another polynucleotide that encodes a polypeptide having the added activity, and (ii) up regulates production of the polynucleotide. Thus, an activity can be added or increased by inserting or modifying a regulatory polynucleotide operably linked to another polynucleotide that encodes a polypeptide having the target activity. In certain embodiments, an activity can be added or increased by subjecting a host microorganism to a selective environment and screening for microorganisms that have a detectable level of the target activity. Examples of a selective environment include, without limitation, a medium containing a substrate that a host organism can process and a medium lacking a substrate that a host organism can process.

An altered activity sometimes is an activity detectable in a host organism and is reduced, inhibited, or removed (i.e., not detectable) in an engineered organism. An activity may be reduced or removed by decreasing the number of copies of a polynucleotide that encodes a polypeptide having a target activity, in some embodiments. In some embodiments, an activity can be reduced or removed by (i) inserting a polynucleotide within a polynucleotide that encodes a polypeptide having the target activity (disruptive insertion), and/or (ii) removing a portion of or all of a polynucleotide that encodes a polypeptide having the target activity (deletion or knock out, respectively). In certain embodiments, an activity can be reduced or removed by inserting into a host microorganism a heterologous polynucleotide that is (i) operably linked to another polynucleotide that encodes a polypeptide having the target activity, and (ii) down regulates production of the polynucleotide. Thus, an activity can be reduced or removed by inserting or modifying a regulatory polynucleotide operably linked to another polynucleotide that encodes a polypeptide having the target activity.

An activity also can be reduced or removed by (i) inhibiting a polynucleotide that encodes a polypeptide having the activity or (ii) inhibiting a polynucleotide operably linked to another polynucleotide that encodes a polypeptide having the activity. A polynucleotide can be inhibited by a suitable technique known in the art, such as by contacting an RNA encoded by the polynucleotide with a specific inhibitory RNA (e.g., RNAi, siRNA, ribozyme). An activity also can be reduced or removed by contacting a polypeptide having the activity with a molecule that specifically inhibits the activity (e.g., enzyme inhibitor, antibody). In certain embodiments, an activity can be reduced or removed by subjecting a host microorganism to a selective environment and screening for microorganisms that have a reduced level or removal of the target activity.

In some embodiments, an untranslated ribonucleic acid, or a cDNA can be used to reduce the expression of a particular activity or enzyme. For example, a microorganism can be engineered by genetic modification to express a nucleic acid reagent that reduces the expression of an activity by producing an RNA molecule that is partially or substantially homologous to a nucleic acid sequence of interest which encodes the activity of interest. The RNA molecule can bind to the nucleic acid sequence of interest and inhibit the nucleic acid sequence from performing its natural function, in certain embodiments. In some embodiments, the RNA may alter the nucleic acid sequence of interest which encodes the activity of interest in a manner that the nucleic acid sequence of interest is no longer capable of performing its natural function (e.g., the action of a ribozyme for example).

In certain embodiments, nucleotide sequences sometimes are added to, modified, or removed from one or more of the nucleic acid reagent elements, such as the promoter, 5'UTR, target sequence, or 3'UTR elements, to enhance, potentially enhance, reduce, or potentially reduce transcription and/or translation before or after such elements are incorporated in a nucleic acid reagent. In some embodiments, one or more of the following sequences may be modified or removed if they are present in a 5'UTR: a sequence that forms a stable secondary structure (e.g., quadruplex structure or stem loop stem structure (e.g., EMBL sequences X12949, AF274954, AF139980, AF152961, S95936, U194144, AF116649 or substantially identical sequences that form such stem loop stem structures)); a translation initiation codon upstream of the target nucleotide sequence start codon; a stop codon upstream of the target nucleotide sequence translation initiation codon; an ORF upstream of the target nucleotide sequence translation initiation codon; an iron responsive element (IRE) or like sequence; and a 5' terminal oligopyrimidine tract (TOP, e.g., consisting of 5-15 pyrimidines adjacent to the cap). A translational enhancer sequence and/or an internal ribosome entry site (IRES) sometimes is inserted into a 5'UTR (e.g., EMBL nucleotide sequences J04513, X87949, M95825, M12783, AF025841, AF013263, AF006822, M17169, M13440, M22427, D14838 and M17446 and substantially identical nucleotide sequences).

An AU-rich element (ARE, e.g., AUUUA repeats) and/or splicing junction that follows a non-sense codon sometimes is removed from or modified in a 3'UTR. A polyadenosine tail sometimes is inserted into a 3'UTR if none is present, sometimes is removed if it is present, and adenosine moieties sometimes are added to or removed from a polyadenosine tail present in a 3'UTR. Thus, some embodiments are directed to a process comprising: determining whether any nucleotide sequences that increase, potentially increase, reduce, or potentially reduce translation efficiency are present in the elements, and adding, removing, or modifying one or more of such sequences if they are identified. Certain embodiments are directed to a process comprising: determining whether any nucleotide sequences that increase or potentially increase translation efficiency are not present in the elements, and incorporating such sequences into the nucleic acid reagent.

In some embodiments, an activity can be altered by modifying the nucleotide sequence of an ORF. An ORF sometimes is mutated or modified (for example, by point mutation, deletion mutation, insertion mutation, PCR based mutagenesis and the like) to alter, enhance or increase, reduce, substantially reduce, or eliminate the activity of the encoded protein or peptide. The protein or peptide encoded by a modified ORF sometimes is produced in a lower amount or may not be produced at detectable levels, and in other embodiments, the product or protein encoded by the modified ORF is produced at a higher level (e.g., codons sometimes are modified so they are compatible with tRNA's preferentially used in the host organism or engineered organism). To determine the relative activity, the activity from the product of the mutated ORF (or cell containing it) can be compared to the activity of the product or protein encoded by the unmodified ORF (or cell containing it).

In some embodiments, an ORF nucleotide sequence sometimes is mutated or modified to alter the triplet nucleotide sequences used to encode amino acids (e.g., amino acid codon triplets, for example). Modification of the nucleotide sequence of an ORF to alter codon triplets sometimes is used to change the codon found in the original sequence to better match the preferred codon usage of the organism in which the ORF or nucleic acid reagent will be expressed. For example, the codon usage, and therefore the codon triplets encoded by a nucleic acid sequence from bacteria may be different from the preferred codon usage in eukaryotes like yeast or plants. Preferred codon usage also may be different between bacterial species. In certain embodiments an ORF nucleotide sequences sometimes is modified to eliminate codon pairs and/or eliminate mRNA secondary structures that can cause pauses during translation of the mRNA encoded by the ORF nucleotide sequence. Translational pausing sometimes occurs when nucleic acid secondary structures exist in an mRNA, and sometimes occurs due to the presence of codon pairs that slow the rate of translation by causing ribosomes to pause. In some embodiments, the use of lower abundance codon triplets can reduce translational pausing due to a decrease in the pause time needed to load a charged tRNA into the ribosome translation machinery. Therefore, to increase transcriptional and translational efficiency in bacteria (e.g., where transcription and translation are concurrent, for example) or to increase translational efficiency in eukaryotes (e.g., where transcription and translation are functionally separated), the nucleotide sequence of a nucleotide sequence of interest can be altered to better suit the transcription and/or translational machinery of the host and/or genetically modified microorganism. In certain embodiment, slowing the rate of translation by the use of lower abundance codons, which slow or pause the ribosome, can lead to higher yields of the desired product due to an increase in correctly folded proteins and a reduction in the formation of inclusion bodies.

Codons can be altered and optimized according to the preferred usage by a given organism by determining the codon distribution of the nucleotide sequence donor organism and comparing the distribution of codons to the distribution of codons in the recipient or host organism. Techniques described herein (e.g., site directed mutagenesis and the like) can then be used to alter the codons accordingly. Comparisons of codon usage can be done by hand, or using nucleic acid analysis software commercially available to the artisan.

Modification of the nucleotide sequence of an ORF also can be used to correct codon triplet sequences that have diverged in different organisms. For example, certain yeast (e.g., *C. tropicalis* and *C. maltosa*) use the amino acid triplet CUG (e.g., CTG in the DNA sequence) to encode serine. CUG typically encodes leucine in most organisms. In order to maintain the correct amino acid in the resultant polypeptide or protein, the CUG codon must be altered to reflect the organism in which the nucleic acid reagent will be expressed. Thus, if an ORF from a bacterial donor is to be expressed in either *Candida* yeast strain mentioned above, the heterologous nucleotide sequence must first be altered or modified to the appropriate leucine codon. Therefore, in some embodiments, the nucleotide sequence of an ORF sometimes is altered or modified to correct for differences that have occurred in the evolution of the amino acid codon triplets between different organisms. In some embodiments, the nucleotide sequence can be left unchanged at a particular amino acid codon, if the amino acid encoded is a conservative or neutral change in amino acid when compared to the originally encoded amino acid.

In some embodiments, an activity can be altered by modifying translational regulation signals, like a stop codon for example. A stop codon at the end of an ORF sometimes is modified to another stop codon, such as an amber stop codon described above. In some embodiments, a stop codon is introduced within an ORF, sometimes by insertion or mutation of an existing codon. An ORF comprising a modified terminal stop codon and/or internal stop codon often is translated in a system comprising a suppressor tRNA that recognizes the stop codon. An ORF comprising a stop codon sometimes is translated in a system comprising a suppressor tRNA that incorporates an unnatural amino acid during translation of the target protein or target peptide. Methods for incorporating unnatural amino acids into a target protein or peptide are known, which include, for example, processes utilizing a heterologous tRNA/synthetase pair, where the tRNA recognizes an amber stop codon and is loaded with an unnatural amino acid (e.g., World Wide Web URL iupac.org/news/prize/2003/wang.pdf).

Depending on the portion of a nucleic acid reagent (e.g., Promoter, 5' or 3' UTR, ORI, ORF, and the like) chosen for alteration (e.g., by mutagenesis, introduction or deletion, for example) the modifications described above can alter a given activity by (i) increasing or decreasing feedback inhibition mechanisms, (ii) increasing or decreasing promoter initiation, (iii) increasing or decreasing translation initiation, (iv) increasing or decreasing translational efficiency, (v) modifying localization of peptides or products expressed from nucleic acid reagents described herein, or (vi) increasing or decreasing the copy number of a nucleotide sequence of interest, (vii) expression of an anti-sense RNA, RNAi, siRNA, ribozyme and the like. In some embodiments, alteration of a nucleic acid reagent or nucleotide sequence can alter a region involved in feedback inhibition (e.g., 5' UTR, promoter, and the like). A modification sometimes is made that can add or enhance binding of a feedback regulator and sometimes a modification is made that can reduce, inhibit, or eliminate binding of a feedback regulator.

In certain embodiments, alteration of a nucleic acid reagent or nucleotide sequence can alter sequences involved in transcription initiation (e.g., promoters, 5' UTR, and the like). A modification sometimes can be made that can enhance or increase initiation from an endogenous or heterologous promoter element. A modification sometimes can be made that removes or disrupts sequences that increase or enhance transcription initiation, resulting in a decrease or elimination of transcription from an endogenous or heterologous promoter element.

In some embodiments, alteration of a nucleic acid reagent or nucleotide sequence can alter sequences involved in translational initiation or translational efficiency (e.g., 5' UTR, 3' UTR, codon triplets of higher or lower abundance, translational terminator sequences and the like, for example). A modification sometimes can be made that can increase or decrease translational initiation, modifying a ribosome binding site for example. A modification sometimes can be made that can increase or decrease translational efficiency. Removing or adding sequences that form hairpins and changing codon triplets to a more or less preferred codon are non-limiting examples of genetic modifications that can be made to alter translation initiation and translation efficiency.

In certain embodiments, alteration of a nucleic acid reagent or nucleotide sequence can alter sequences involved in localization of peptides, proteins, or other desired products (e.g., adipic acid, for example). A modification sometimes can be made that can alter, add, or remove sequences responsible for targeting a polypeptide, protein or product to an intracellular organelle, the periplasm, cellular membranes, or extracellularly. Transport of a heterologous product to a different intracellular space or extracellularly sometimes can reduce or eliminate the formation of inclusion bodies (e.g., insoluble aggregates of the desired product).

In some embodiments, alteration of a nucleic acid reagent or nucleotide sequence can alter sequences involved in increasing or decreasing the copy number of a nucleotide sequence of interest. A modification sometimes can be made that increases or decreases the number of copies of an ORF stably integrated into the genome of an organism or on an epigenetic nucleic acid reagent. Non-limiting examples of alterations that can increase the number of copies of a sequence of interest include, adding copies of the sequence of interest by duplication of regions in the genome (e.g., adding additional copies by recombination or by causing gene amplification of the host genome, for example), cloning additional copies of a sequence onto a nucleic acid reagent, or altering an ORI to increase the number of copies of an epigenetic nucleic acid reagent. Non-limiting examples of alterations that can decrease the number of copies of a sequence of interest include, removing copies of the sequence of interest by deletion or disruption of regions in the genome, removing additional copies of the sequence from epigenetic nucleic acid reagents, or altering an ORI to decrease the number of copies of an epigenetic nucleic acid reagent.

In certain embodiments, increasing or decreasing the expression of a nucleotide sequence of interest can also be accomplished by altering, adding, or removing sequences involved in the expression of an anti-sense RNA, RNAi, siRNA, ribozyme, and the like. The methods described above can be used to modify expression of anti-sense RNA, RNAi, siRNA, ribozyme and the like.

Engineered microorganisms can be prepared by altering, introducing, or removing nucleotide sequences in the host genome or in stably maintained epigenetic nucleic acid reagents, as noted above. The nucleic acid reagents used to alter, introduce, or remove nucleotide sequences in the host genome or epigenetic nucleic acids can be prepared using the methods described herein or available to the artisan.

Nucleic acid sequences having a desired activity can be isolated from cells of a suitable organism using lysis and nucleic acid purification procedures available in Maniatis, T., E. F. Fritsch and J. Sambrook (1982) Molecular Cloning: a Laboratory Manual; Cold Spring Harbor Laboratory, Cold Spring Harbor, N.Y. or with commercially available cell lysis and DNA purification reagents and kits. In some embodiments, nucleic acids used to engineer microorganisms can be provided for conducting methods described herein after processing of the organism containing the nucleic acid. For example, the nucleic acid of interest may be extracted, isolated, purified or amplified from a sample (e.g., from an organism of interest or culture containing a plurality of organisms of interest, like yeast or bacteria for example). The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated sample nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to sample nucleic acid provided that contains fewer nucleic acid species than in the sample source from which the sample nucleic acid is derived. A composition comprising sample nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a cell, organism or sample to a process that linearly or exponentially generates amplicon nucleic acids having the same or substantially the same nucleotide sequence as the nucleotide sequence of the nucleic acid in the sample, or portion thereof. As noted above, the nucleic acids used to prepare nucleic acid reagents as described herein can be subjected to fragmentation or cleavage.

Amplification of nucleic acids is sometimes necessary when dealing with organisms that are difficult to culture. Where amplification may be desired, any suitable amplification technique can be utilized. Non-limiting examples of methods for amplification of polynucleotides include polymerase chain reaction (PCR); ligation amplification (or ligase chain reaction (LCR)); amplification methods based on the use of Q-beta replicase or template-dependent polymerase (see US Patent Publication Number US20050287592); helicase-dependent isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, combinations thereof, and the like. Reagents and hardware for conducting PCR are commercially available.

Protocols for conducting the various type of PCR listed above are readily available to the artisan. PCR conditions can be dependent upon primer sequences, target abundance, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. PCR often is carried out as an automated process with a thermostable enzyme. In this process, the temperature of the reaction mixture is cycled through a denaturing region, a primer-annealing region, and an extension reaction region automatically. Machines specifically adapted for this purpose are commercially available. A non-limiting example of a PCR protocol that may be suitable for embodiments described herein is, treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Additional PCR protocols are described in the example section. Multiple cycles frequently are performed using a commercially available thermal cycler. Suitable isothermal amplification processes known and selected by the person of ordinary skill in the art also may be applied, in certain embodiments. In some embodiments, nucleic acids encoding polypeptides with a desired activity can be isolated by amplifying the desired sequence from an organism having the desired activity using oligonucleotides or primers designed based on sequences described herein.

Amplified, isolated and/or purified nucleic acids can be cloned into the recombinant DNA vectors described in Figures herein or into suitable commercially available recombinant DNA vectors. Cloning of nucleic acid sequences of interest into recombinant DNA vectors can facilitate further manipulations of the nucleic acids for preparation of nucleic acid reagents, (e.g., alteration of nucleotide sequences by mutagenesis, homologous recombination, amplification, and the like, for example). Standard cloning procedures (e.g., enzymic digestion, ligation, and the like) are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

In some embodiments, nucleic acid sequences prepared by isolation or amplification can be used, without any further modification, to add an activity to a microorganism and thereby generate a genetically modified or engineered microorganism. In certain embodiments, nucleic acid sequences prepared by isolation or amplification can be genetically modified to alter (e.g., increase or decrease, for example) a desired activity. In some embodiments, nucleic acids, used to add an activity to an organism, sometimes are genetically modified to optimize the heterologous polynucleotide sequence encoding the desired activity (e.g., polypeptide or protein, for example). The term "optimize" as used herein can refer to alteration to increase or enhance expression by preferred codon usage. The term optimize can also refer to modifications to the amino acid sequence to increase the activity of a polypeptide or protein, such that the activity exhibits a higher catalytic activity as compared to the "natural" version of the polypeptide or protein.

Nucleic acid sequences of interest can be genetically modified using methods known in the art. Mutagenesis techniques are particularly useful for small scale (e.g., 1, 2, 5, 10 or more nucleotides) or large scale (e.g., 50, 100, 150, 200, 500, or more nucleotides) genetic modification. Mutagenesis allows the artisan to alter the genetic information of an organism in a stable manner, either naturally (e.g., isolation using selection and screening) or experimentally by the use of chemicals, radiation, or inaccurate DNA replication (e.g., PCR mutagenesis). In some embodiments, genetic modification can be performed by whole scale synthetic synthesis of nucleic acids, using a native nucleotide sequence as the reference sequence, and modifying nucleotides that can result in the desired alteration of activity. Mutagenesis methods sometimes are specific or targeted to specific regions or nucleotides (e.g., site-directed mutagenesis, PCR-based site-directed mutagenesis, and in vitro mutagenesis techniques such as transplacement and in vivo oligonucleotide site-directed mutagenesis, for example). Mutagenesis methods sometimes are non-specific or random with respect to the placement of genetic modifications (e.g., chemical mutagenesis, insertion element (e.g., insertion or transposon elements) and inaccurate PCR based methods, for example).

Site directed mutagenesis is a procedure in which a specific nucleotide or specific nucleotides in a DNA molecule are mutated or altered. Site directed mutagenesis typically is performed using a nucleic acid sequence of interest cloned into a circular plasmid vector. Site-directed mutagenesis requires that the wild type sequence be known and used as a platform for the genetic alteration. Site-directed mutagenesis sometimes is referred to as oligonucleotide-directed mutagenesis because the technique can be performed using oligonucleotides which have the desired genetic modification incorporated into the complement a nucleotide sequence of interest. The wild type sequence and the altered nucleotide are allowed to hybridize and the hybridized nucleic acids are extended and replicated using a DNA polymerase. The double stranded nucleic acids are introduced into a host (e.g., *E. coli*, for example) and further rounds of replication are carried out in vivo. The transformed cells carrying the mutated nucleic acid sequence are then selected and/or screened for those cells carrying the correctly mutagenized sequence. Cassette mutagenesis and PCR-based site-directed mutagenesis are further modifications of the site-directed mutagenesis technique. Site-directed mutagenesis can also be performed in vivo (e.g., transplacement "pop-in pop-out", In vivo site-directed mutagenesis with synthetic oligonucleotides and the like, for example).

PCR-based mutagenesis can be performed using PCR with oligonucleotide primers that contain the desired mutation or mutations. The technique functions in a manner similar to standard site-directed mutagenesis, with the exception that a thermocycler and PCR conditions are used to replace replication and selection of the clones in a microorganism host. As PCR-based mutagenesis also uses a circular plasmid vector, the amplified fragment (e.g., linear nucleic acid molecule) containing the incorporated genetic modifications can be separated from the plasmid containing the template sequence after a sufficient number of rounds of thermocycler amplification, using standard electrophoretic procedures. A modification of this method uses linear amplification methods and a pair of mutagenic primers that amplify the entire plasmid. The procedure takes advantage of the *E. coli* Dam methylase system which causes DNA replicated in vivo to be sensitive to the restriction endonucleases DpnI. PCR synthesized DNA is not methylated and is therefore resistant to DpnI. This approach allows the template plasmid to be digested, leaving the genetically modified, PCR synthesized plasmids to be isolated and transformed into a host bacteria for DNA repair and replication, thereby facilitating subsequent cloning and identification steps. A certain amount of randomness can be added to PCR-based sited directed mutagenesis by using partially degenerate primers.

Recombination sometimes can be used as a tool for mutagenesis. Homologous recombination allows the artisan to specifically target regions of known sequence for insertion of heterologous nucleotide sequences using the host organisms natural DNA replication and repair enzymes. Homologous recombination methods sometimes are referred to as "pop in pop out" mutagenesis, transplacement, knock out mutagenesis or knock in mutagenesis. Integration of a nucleic acid sequence into a host genome is a single cross over event, which inserts the entire nucleic acid reagent (e.g., pop in). A second cross over event excises all but a portion of the nucleic acid reagent, leaving behind a heterologous sequence, often referred to as a "footprint" (e.g., pop out). Mutagenesis by insertion (e.g., knock in) or by double recombination leaving behind a disrupting heterologous nucleic acid (e.g., knock out) both serve to disrupt or "knock out" the function of the gene or nucleic acid sequence in which insertion occurs. By combining selectable markers and/or auxotrophic markers with nucleic acid reagents designed to provide the appropriate nucleic acid target sequences, the artisan can target a selectable nucleic acid reagent to a specific region, and then select for recombination events that "pop out" a portion of the inserted (e.g., "pop in") nucleic acid reagent.

Such methods take advantage of nucleic acid reagents that have been specifically designed with known target nucleic acid sequences at or near a nucleic acid or genomic region of interest. Popping out typically leaves a "foot print" of left over sequences that remain after the recombination event. The left over sequence can disrupt a gene and thereby reduce or eliminate expression of that gene. In some embodiments, the method can be used to insert sequences, upstream or downstream of genes that can result in an enhancement or reduction in expression of the gene. In certain embodiments, new genes can be introduced into the genome of a host organism using similar recombination or "pop in" methods. An example of a yeast recombination system using the ura3 gene and 5-FOA were described briefly above and further detail is presented herein.

A method for modification is described in Alani et al., "A method for gene disruption that allows repeated use of URA3 selection in the construction of multiply disrupted yeast strains", Genetics 116(4):541-545 August 1987. The original method uses a Ura3 cassette with 1000 base pairs (bp) of the same nucleotide sequence cloned in the same orientation on either side of the URA3 cassette. Targeting sequences of about 50 bp are added to each side of the construct. The double stranded targeting sequences are complementary to sequences in the genome of the host organism. The targeting sequences allow site-specific recombination in a region of interest. The modification of the original technique replaces the two 1000 bp sequence direct repeats with two 200 bp direct repeats. The modified method also uses 50 bp targeting sequences. The modification reduces or eliminates recombination of a second knock out into the 1000 bp repeat left behind in a first mutagenesis, therefore allowing multiply knocked out yeast. Additionally, the 200 bp sequences used herein are uniquely designed, self-assembling sequences that leave behind identifiable footprints. The technique used to design the sequences incorporate design features such as low identity to the yeast genome, and low identity to each other. Therefore a library of the self-assembling sequences can be generated to allow multiple knockouts in the same organism, while reducing or eliminating the potential for integration into a previous knockout.

In yeast the cassettes are typically of two different overall structures, as follows:

<5' homology region—promoter—coding sequence—terminator—3' homology region>

<5' homology region—promoter—coding sequence—terminator—marker—3' homology region>

The parts of the DNA transformation cassette possess the following properties:

5' and 3' homology regions—these DNA sequences dictate the specific location in the chromosome where the DNA transformation cassette will insert through homologous recombination. The 5' homology region indicates the upstream boundary for insertion while the 3' homology indicates the downstream boundary. The homology regions may constitute a gene that rescues auxotrophy in an engineered microorganism, i.e. the homology regions mediate insertion into a non-functional gene that results in an auxotrophic phenotype and insertion of the cassette restores function to the gene. For example, the 5' and 3' homology regions may represent the two halves of the URA3 gene and direct homologous recombination in a mutant or loss-of-function ura3 gene, which rescues the loss-of-function.

Promoter—this DNA sequence drives transcription of the coding sequence immediately downstream of the promoter. A promoter will often be turned on or off when the microorganism is exposed to specific compounds or grown under certain conditions.

Coding sequence—the sequence of codons that are translated into the desired protein. The codons can be optimized to reflect the endogenous codon frequency of the engineered microorganism.

Terminator—this DNA sequence marks the end of the sequence to be transcribed, as indicated by the promoter. It may or may not contain sequences that positively or negatively regulate the activity of the promoter.

Marker—this DNA sequence encodes information that will confer properties to a yeast cell that mediate growth under selective or auxotrophic conditions. For example, if the initial cell line is auxotrophic for uracil and is transformed with a cassette containing a URA3 marker, any transformant that contains the URA3 marker will now be able to grow in the absence of uracil.

The DNA transformation cassette is generated through conventional molecular biology methods such as PCR, restriction enzyme digestion and DNA ligation and/or Gibson assembly. The cassette is transformed into the yeast and clones of interest are identified as colonies that grow on the appropriate selective or auxotrophic media, e.g. synthetic complete yeast media lacking uracil.

As noted above, the URA3 cassette makes use of the toxicity of 5-FOA in yeast carrying a functional URA3 gene. Uracil synthesis deficient yeast are transformed with the modified URA3 cassette, using standard yeast transformation protocols, and the transformed cells are plated on minimal media minus uracil. In some embodiments, PCR can be used to verify correct insertion into the region of interest in the host genome, and certain embodiments the PCR step can be omitted. Inclusion of the PCR step can reduce the number of transformants that need to be counter selected to “pop out” the URA3 cassette. The transformants (e.g., all or the ones determined to be correct by PCR, for example) can then be counter-selected on media containing 5-FOA, which will select for recombination out (e.g., popping out) of the URA3 cassette, thus rendering the yeast ura3 deficient again, and resistant to 5-FOA toxicity. Targeting sequences used to direct recombination events to specific regions are presented herein. A modification of the method described above can be used to integrate genes into the chromosome, where after recombination a functional gene is left in the chromosome next to the 200 bp footprint.

In some embodiments, other auxotrophic or dominant selection markers can be used in place of URA3 (e.g., an auxotrophic selectable marker), with the appropriate change in selection media and selection agents. Auxotrophic selectable markers are used in strains deficient for synthesis of a required biological molecule (e.g., amino acid or nucleoside, for example). Non-limiting examples of additional auxotrophic markers include; HIS3, TRP1, LEU2, LEU2-d, and LYS2. Certain auxotrophic markers (e.g., URA3 and LYS2) allow counter selection to select for the second recombination event that pops out all but one of the direct repeats of the recombination construct. HIS3 encodes an activity involved in histidine synthesis. TRP1 encodes an activity involved in tryptophan synthesis. LEU2 encodes an activity involved in leucine synthesis. LEU2-d is a low expression version of LEU2 that selects for increased copy number (e.g., gene or plasmid copy number, for example) to allow survival on minimal media without leucine. LYS2 encodes an activity involved in lysine synthesis and allows counter selection for recombination out of the LYS2 gene using alpha-amino adipate ($\alpha$-amino adipate).

Dominant selectable markers are useful because they also allow industrial and/or prototrophic strains to be used for genetic manipulations. Additionally, dominant selectable markers provide the advantage that rich medium can be used for plating and culture growth, and thus growth rates are markedly increased. Non-limiting examples of dominant selectable markers include; Tn903 $kan^r$, $Cm^r$, $Hyg^r$, CUP1, and DHFR. Tn903 $kan^r$ encodes an activity involved in kanamycin antibiotic resistance (e.g., typically neomycin phosphotransferase II or NPTII, for example). $Cm^r$ encodes an activity involved in chloramphenicol antibiotic resistance (e.g., typically chloramphenicol acetyl transferase or CAT, for example). $Hyg^r$ encodes an activity involved in hygromycin resistance by phosphorylation of hygromycin B (e.g., hygromycin phosphotransferase, or HPT). CUP1 encodes an activity involved in resistance to heavy metal (e.g., copper, for example) toxicity. DHFR encodes a dihydrofolate reductase activity which confers resistance to methotrexate and sulfanilamide compounds.

In contrast to site-directed or specific mutagenesis, random mutagenesis does not require any sequence information and can be accomplished by a number of widely different methods. Random mutagenesis often is used to generate mutant libraries that can be used to screen for the desired genotype or phenotype. Non-limiting examples of random mutagenesis include; chemical mutagenesis, UV-induced mutagenesis, insertion element or transposon-mediated mutagenesis, DNA shuffling, error-prone PCR mutagenesis, and the like.

Chemical mutagenesis often involves chemicals like ethyl methanesulfonate (EMS), nitrous acid, mitomycin C, N-methyl-N-nitrosourea (MNU), diepoxybutane (DEB), 1,2,7,8-diepoxyoctane (DEO), methyl methane sulfonate (MMS), N-methyl-N'-nitro-N-nitrosoguanidine (MNNG), 4-nitroquinoline 1-oxide (4-NQO), 2-methyloxy-6-chloro-9 (3-[ethyl-2-chloroethyl]-aminopropylamino)-acridinedihydrochloride (ICR-170), 2-amino purine (2AP), and hydroxylamine (HA), provided herein as non-limiting examples. These chemicals can cause base-pair substitutions, frameshift mutations, deletions, transversion mutations, transition mutations, incorrect replication, and the like. In some embodiments, the mutagenesis can be carried out in vivo. Sometimes the mutagenic process involves the use of the host organism's DNA replication and repair mechanisms to incorporate and replicate the mutagenized base or bases.

Another type of chemical mutagenesis involves the use of base-analogs. The use of base-analogs causes incorrect base pairing which in the following round of replication is corrected to a mismatched nucleotide when compared to the starting sequence. Base analog mutagenesis introduces a small amount of non-randomness to random mutagenesis, because specific base analogs can be chosen which can be incorporated at certain nucleotides in the starting sequence. Correction of the mispairing typically yields a known substitution. For example, Bromo-deoxyuridine (BrdU) can be incorporated into DNA and replaces T in the sequence. The host DNA repair and replication machinery can sometime correct the defect, but sometimes will mispair the BrdU with a G. The next round of replication then causes a G-C transversion from the original A-T in the native sequence.

Ultraviolet (UV) induced mutagenesis is caused by the formation of thymidine dimers when UV light irradiates chemical bonds between two adjacent thymine residues. Excision repair mechanism of the host organism corrects the lesion in the DNA, but occasionally the lesion is incorrectly repaired typically resulting in a C to T transition.

Insertion element or transposon-mediated mutagenesis makes use of naturally occurring or modified naturally occurring mobile genetic elements. Transposons often encode accessory activities in addition to the activities necessary for transposition (e.g., movement using a transposase activity, for example). In many examples, transposon accessory activities are antibiotic resistance markers (e.g., see Tn903 $kan^r$ described above, for example). Insertion elements typically only encode the activities necessary for movement of the nucleic acid sequence. Insertion element and transposon mediated mutagenesis often can occur randomly, however specific target sequences are known for some transposons. Mobile genetic elements like IS elements or Transposons (Tn) often have inverted repeats, direct repeats or both inverted and direct repeats flanking the region coding for the transposition genes. Recombination events catalyzed by the transposase cause the element to remove itself from the genome and move to a new location, leaving behind a portion of an inverted or direct repeat. Classic examples of transposons are the "mobile genetic elements" discovered in maize. Transposon mutagenesis kits are commercially available which are designed to leave behind a 5 codon insert (e.g., Mutation Generation System kit, Finnzymes, World Wide Web URL finnzymes.us, for example). This allows the artisan to identify the insertion site, without fully disrupting the function of most genes.

DNA shuffling is a method which uses DNA fragments from members of a mutant library and reshuffles the fragments randomly to generate new mutant sequence combinations. The fragments are typically generated using DNaseI, followed by random annealing and re-joining using self-priming PCR. The DNA overhanging ends, from annealing of random fragments, provide "primer" sequences for the PCR process. Shuffling can be applied to libraries generated by any of the above mutagenesis methods.

Error prone PCR and its derivative rolling circle error prone PCR uses increased magnesium and manganese concentrations in conjunction with limiting amounts of one or two nucleotides to reduce the fidelity of the Taq polymerase. The error rate can be as high as 2% under appropriate conditions, when the resultant mutant sequence is compared to the wild type starting sequence. After amplification, the library of mutant coding sequences must be cloned into a suitable plasmid. Although point mutations are the most common types of mutation in error prone PCR, deletions and frameshift mutations are also possible. There are a number of commercial error-prone PCR kits available, including those from Stratagene and Clontech (e.g., World Wide Web URL strategene.com and World Wide Web URL clontech-.com, respectively, for example). Rolling circle error-prone PCR is a variant of error-prone PCR in which wild-type sequence is first cloned into a plasmid, the whole plasmid is then amplified under error-prone conditions.

As noted above, organisms with altered activities can also be isolated using genetic selection and screening of organisms challenged on selective media or by identifying naturally occurring variants from unique environments. For example, 2-Deoxy-D-glucose is a toxic glucose analog. Growth of yeast on this substance yields mutants that are glucose-deregulated. A number of mutants have been isolated using 2-Deoxy-D-glucose including transport mutants, and mutants that ferment glucose and galactose simultaneously instead of glucose first then galactose when glucose is depleted. Similar techniques have been used to isolate mutant microorganisms that can metabolize plastics (e.g., from landfills), petrochemicals (e.g., from oil spills), and the like, either in a laboratory setting or from unique environments.

Similar methods can be used to isolate naturally occurring mutations in a desired activity when the activity exists at a relatively low or nearly undetectable level in the organism of choice, in some embodiments. The method generally consists of growing the organism to a specific density in liquid culture, concentrating the cells, and plating the cells on various concentrations of the substance to which an increase in metabolic activity is desired. The cells are incubated at a moderate growth temperature, for 5 to 10 days. To enhance the selection process, the plates can be stored for another 5 to 10 days at a low temperature. The low temperature sometimes can allow strains that have gained or increased an activity to continue growing while other strains are inhibited for growth at the low temperature. Following the initial selection and secondary growth at low temperature, the plates can be replica plated on higher or lower concentrations of the selection substance to further select for the desired activity.

A native, heterologous, or mutagenized polynucleotide can be introduced into a nucleic acid reagent for introduction into a host organism, thereby generating an engineered microorganism. Standard recombinant DNA techniques (restriction enzyme digests, ligation, and the like) can be used by the artisan to combine the mutagenized nucleic acid of interest into a suitable nucleic acid reagent capable of (i) being stably maintained by selection in the host organism, or (ii) being integrating into the genome of the host organism. As noted above, sometimes nucleic acid reagents comprise two replication origins to allow the same nucleic acid reagent to be manipulated in bacterial before final introduction of the final product into the host organism (e.g., yeast or fungus for example). Standard molecular biology and recombinant DNA methods available to one of skill in the art can be found in Maniatis, T., E. F. Fritsch and J. Sambrook (1982) Molecular Cloning: a Laboratory Manual; Cold Spring Harbor Laboratory, Cold Spring Harbor, N.Y.

Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances, the addition of carrier molecules (e.g., bis-benzimidazolyl compounds, for example, see U.S. Pat. No. 5,595,899) can increase the uptake of DNA in cells typically though to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y.

Usually a DNA piece is constructed (called cassette) for the integration of the gene of interest into the genome.

Culture, Production and Process Methods

Engineered microorganisms often are cultured under conditions that optimize yield of a target molecule. A non-limiting example of such a target molecule is ethanol. Culture conditions often can alter (e.g., add, optimize, reduce, or eliminate, for example) activity of one or more of the following activities: phosphofructokinase activity, phosphogluconate dehydratase activity, 2-keto-3-deoxygluconate-6-phosphate aldolase activity, xylose isomerase activity, phosphoenolpyruvate carboxylase activity, alcohol dehydrogenase 2 activity and thymidylate synthase activities. In general, conditions that may be optimized include the type and amount of carbon source, the type and amount of nitrogen source, the carbon-to-nitrogen ratio, the oxygen level, growth temperature, pH, length of the biomass production phase, length of target product accumulation phase, and time of cell harvest.

The term "fermentation conditions" as used herein refers to any culture conditions suitable for maintaining a microorganism (e.g., in a static or proliferative state). Fermentation conditions can include several parameters, including without limitation, temperature, oxygen content, nutrient content (e.g., glucose content), pH, agitation level (e.g., revolutions per minute), gas flow rate (e.g., air, oxygen, nitrogen gas), redox potential, cell density (e.g., optical density), cell viability and the like. A change in fermentation conditions (e.g., switching fermentation conditions) is an alteration, modification or shift of one or more fermentation parameters. For example, one can change fermentation conditions by increasing or decreasing temperature, increasing or decreasing pH (e.g., adding or removing an acid, a base or carbon dioxide), increasing or decreasing oxygen content (e.g., introducing air, oxygen, carbon dioxide, nitrogen) and/or adding or removing a nutrient (e.g., one or more sugars or sources of sugar, biomass, vitamin and the like), or combinations of the foregoing. Examples of fermentation conditions are described herein. Aerobic conditions often comprise greater than about 50% dissolved oxygen (e.g., about 52%, 54%, 56%, 58%, 60%, 62%, 64%, 66%, 68%, 70%, 72%, 74%, 76%, 78%, 80%, 82%, 84%, 86%, 88%, 90%, 91%, 92%, 93%, 94%, 95%, 96%, 97%, 98% or 99%, or greater than any one of the foregoing). Anaerobic conditions often comprise less than about 50% dissolved oxygen (e.g., about 1%, 2%, 4%, 6%, 8%, 10%, 12%, 14%, 16%, 18%, 20%, 22%, 24%, 26%, 28%, 30%, 32%, 34%, 36%, 38%, 40%, 42%, 44%, 46%, 48%, or less than any one of the foregoing).

Culture media generally contain a suitable carbon source. Carbon sources may include, but are not limited to, monosaccharides (e.g., glucose, fructose, xylose), disaccharides (e.g., lactose, sucrose), oligosaccharides, polysaccharides (e.g., starch, cellulose, hemicellulose, other lignocellulosic materials, or mixtures thereof), sugar alcohols (e.g., glycerol), and renewable feedstocks (e.g., cheese whey permeate, corn steep liquor, sugar beet molasses, barley malt). Carbon sources also can be selected from one or more of the following non-limiting examples: linear or branched alkanes (e.g., hexane), linear or branched alcohols (e.g., hexanol), fatty acids (e.g., about 10 carbons to about 22 carbons), esters of fatty acids, monoglycerides, diglycerides, triglycerides, phospholipids, and various commercial sources of fatty acids including vegetable oils (e.g., soybean oil) and animal fats. A carbon source may include one-carbon sources (e.g., carbon dioxide, methanol, formaldehyde, formate, and carbon-containing amines) from which metabolic conversion into key biochemical intermediates can occur. It is expected that the source of carbon utilized may encompass a wide variety of carbon-containing sources and will only be limited by the choice of the engineered microorganism(s).

Nitrogen may be supplied from an inorganic (e.g., (NH-.sub.4).sub.2SO.sub.4) or organic source (e.g., urea or glutamate). In addition to appropriate carbon and nitrogen sources, culture media also can contain suitable minerals, salts, cofactors, buffers, vitamins, metal ions (e.g., Mn.sup.+2, Co.sup.+2, Zn.sup.+2, Mg.sup.+2) and other components suitable for culture of microorganisms. Engineered microorganisms sometimes are cultured in complex media (e.g., yeast extract-peptone-dextrose broth (YPD)). In some embodiments, engineered microorganisms are cultured in a defined minimal media that lacks a component necessary for growth and thereby forces selection of a desired expression cassette (e.g., Yeast Nitrogen Base (DIFCO Laboratories, Detroit, Mich.)). Culture media in some embodiments are common commercially prepared media, such as Yeast Nitrogen Base (DIFCO Laboratories, Detroit, Mich.). Other defined or synthetic growth media may also be used and the appropriate medium for growth of the particular microorganism are known.

A variety of host organisms can be selected for the production of engineered microorganisms. Non-limiting examples include yeast and fungi. In specific embodiments, yeast are cultured in YPD media (10 g/L Bacto Yeast Extract, 20 g/L Bacto Peptone, and 20 g/L Dextrose). Filamentous fungi, in particular embodiments, are grown in CM (Complete Medium) containing 10 g/L Dextrose, 2 g/L Bacto Peptone, 1 g/L Bacto Yeast Extract, 1 g/L Casamino acids, 50 mL/L 20× Nitrate Salts (120 g/L $NaNO_3$, 10.4 g/L KCl, 10.4 g/L $MgSO_4 \cdot 7H_2O$), 1 mL/L 1000× Trace Elements (22 g/L $ZnSO_4 \cdot 7H_2O$, 11 g/L $H_3BO_3$, 5 g/L $MnCl_2 \cdot 7H_2O$, 5 g/L $FeSO_4 \cdot 7H_2O$, 1.7 g/L $CoCl_2 \cdot 6H_2O$, 1.6 g/L $CuSO_4 \cdot 5H_2O$, 1.5 g/L $Na_2MoO_4 \cdot 2H_2O$, and 50 g/L $Na_4EDTA$), and 1 mL/L Vitamin Solution (100 mg each of Biotin, pyridoxine, thiamine, riboflavin, p-aminobenzoic acid, and nicotinic acid in 100 mL water).

A suitable pH range for the fermentation often is between about pH 4.0 to about pH 8.0, where a pH in the range of about pH 5.5 to about pH 7.0 sometimes is utilized for initial culture conditions. Culturing may be conducted under aerobic or anaerobic conditions, where microaerobic conditions sometimes are maintained. A two-stage process may be utilized, where one stage promotes microorganism proliferation, and another state promotes production of target molecule. In a two-stage process, the first stage may be conducted under aerobic conditions (e.g., introduction of air and/or oxygen) and the second stage may be conducted under anaerobic conditions (e.g., air or oxygen are not introduced to the culture conditions).

A variety of fermentation processes may be applied for commercial biological production of a target product. In some embodiments, commercial production of a target product from a recombinant microbial host is conducted using a batch, fed batch or continuous fermentation process, for example.

A batch fermentation process often is a closed system where the media composition is fixed at the beginning of the process and not subject to further additions beyond those required for maintenance of pH and oxygen level during the process. At the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die.

A variation of the standard batch process is the fed-batch process, where the carbon source is continually added to the fermentor over the course of the fermentation process. Fed-batch processes are useful when catabolite repression is apt to inhibit the metabolism of the cells or where it is desirable to have limited amounts of carbon source in the media at any one time. Measurement of the carbon source concentration in fed-batch systems may be estimated on the basis of the changes of measurable factors such as pH, dissolved oxygen, and the partial pressure of waste gases (e.g., CO.sub.2). Batch and fed-batch culturing methods are known in the art. Examples of such methods may be found in Thomas D. Brock in Biotechnology: A Textbook of Industrial Microbiology, 2.sup.nd ed., (1989) Sinauer Associates Sunderland, Mass. and Deshpande, Mukund V., Appl. Biochem. Biotechnol., 36:227 (1992).

In continuous fermentation process a defined media often is continuously added to a bioreactor while an equal amount of culture volume is removed simultaneously for product recovery. Continuous cultures generally maintain cells in the log phase of growth at a constant cell density. Continuous or semi-continuous culture methods permit the modulation of one factor or any number of factors that affect cell growth or end product concentration. For example, an approach may limit the carbon source and allow all other parameters to moderate metabolism. In some systems, a number of factors affecting growth may be altered continuously while the cell concentration, measured by media turbidity, is kept constant. Continuous systems often maintain steady state growth and thus the cell growth rate often is balanced against cell loss due to media being drawn off the culture. Methods of modulating nutrients and growth factors for continuous culture processes, as well as techniques for maximizing the rate of product formation, are known and a variety of methods are detailed by Brock, supra.

In various embodiments ethanol may be purified from the culture media or extracted from the engineered microorganisms. Culture media may be tested for ethanol concentration and drawn off when the concentration reaches a predetermined level. Detection methods are known in the art, including but not limited to the use of a hydrometer and infrared measurement of vibrational frequency of dissolved ethanol using the CH band at 2900 $cm^{-1}$. Ethanol may be present at a range of levels as described herein.

A target product sometimes is retained within an engineered microorganism after a culture process is completed, and in certain embodiments, the target product is secreted out of the microorganism into the culture medium. For the latter embodiments, (i) culture media may be drawn from the culture system and fresh medium may be supplemented, and/or (ii) target product may be extracted from the culture media during or after the culture process is completed. Engineered microorganisms may be cultured on or in solid, semi-solid or liquid media. In some embodiments media is drained from cells adhering to a plate. In certain embodiments, a liquid-cell mixture is centrifuged at a speed sufficient to pellet the cells but not disrupt the cells and allow extraction of the media, as known in the art. The cells may then be resuspended in fresh media. Target product may be purified from culture media according to methods known in the art.

In certain embodiments, target product is extracted from the cultured engineered microorganisms. The microorganism cells may be concentrated through centrifugation at a speed sufficient to shear the cell membranes. In some embodiments, the cells may be physically disrupted (e.g., shear force, sonication) or chemically disrupted (e.g., contacted with detergent or other lysing agent).

The phases may be separated by centrifugation or other method known in the art and target product may be isolated according to known methods.

Commercial grade target product sometimes is provided in substantially pure form (e.g., 90% pure or greater, 95% pure or greater, 99% pure or greater or 99.5% pure or greater). In some embodiments, target product may be modified into any one of a number of downstream products. For example, cannabidiolic acid may be derivatized or further processed to be an ingredient in food, drinks, vape pens, gum, skin lotions, pharmaceuticals, and supplements.

Target product may be provided within cultured microbes containing target product, and cultured microbes may be supplied fresh or frozen in a liquid media or dried. Fresh or frozen microbes may be contained in appropriate moisture-proof containers that may also be temperature controlled as necessary. Target product sometimes is provided in culture medium that is substantially cell-free. In some embodiments target product or modified target product purified from microbes is provided, and target product sometimes is provided in substantially pure form. In certain embodiments, ethanol can be provided in anhydrous or hydrous forms. Ethanol may be transported in a variety of containers including pints, quarts, liters, gallons, drums (e.g., 10 gallon or 55 gallon, for example) and the like.

EXAMPLES

The examples set forth below illustrate certain embodiments and do not limit the technology. Certain examples set forth below utilize standard recombinant DNA and other biotechnology protocols known in the art. Many such techniques are described in detail in Maniatis, T., E. F. Fritsch and J. Sambrook (1982) Molecular Cloning: a Laboratory Manual; Cold Spring Harbor Laboratory, Cold Spring Harbor, N.Y. DNA mutagenesis can be accomplished using the Stratagene (San Diego, Calif) “QuickChange” kit according to the manufacturer’s instructions, or by one of the other types of mutagenesis described above. 5,000 bp DNA pieces can also be manufactured to order by companies such as Twist Biosciences.

Example 1—Construction of Plasmids for *Candida viswanathii*

Protein sequence was reverse translated into DNA sequence to reflect the use of yeast alternative genetic code and codon usage in *Candida viswanathii*, reduction of secondary structure, and absence of certain restriction enzyme recognition sites. Other DNA sequences that encode the same protein may also be used. The following sequences were used as open reading frames for genes used to genetically modify *Candida viswanathii*.

CvACO1P Gene (SEQ ID NO: 93)

ATGACAGAAGTAGTAGATAGAGCAAGTTCCCCAGCAAGTCCAGGATCTACGACCGC

CGCCGCAGACGGTGCTAAGGTGGCGGTGGAGCCACGCGTAGATGTAGCGGCCCTTG

GCGAGCAGTTGCTAGGGCGATGGGCTGACATCAGATTGCACGCACGAGACTTAGCA

GGCCGCGAAGTGGTCCAAAAGGTTGAAGGACTTACGCACACTGAGCATCGGAGTAG

AGTCTTTGGACAGTTGAAGTACTTGGTAGACAACAATGCTGTTCACAGAGCTTTTCC

CTCCAGGCTAGGTGGATCAGATGACCATGGCGGTAATATAGCTGGATTCGAGGAAT

TAGTTACTGCTGATCCATCATTGCAAATAAAGGCCGGCGTTCAGTGGGGTTTGTTTG

GTTCTGCAGTGATGCACTTGGGAACCCGTGAACATCATGACAAGTGGTTGCCAGGTA

TTATGTCGTTAGAAATACCGGGGTGTTTCGCGATGACAGAAACCGGGCACGGTAGC

GACGTGGCCTCTATTGCTACAACAGCAACTTATGATGAGGAAACCCAAGAGTTTGTT

ATTGATACCCCGTTCAGAGCCGCTTGGAAAGATTATATCGGTAATGCAGCGAACGAT

GGTTTGGCGGCAGTTGTTTTCGCACAATTAATCACGAGGAAAGTGAACCATGGTGTA

CACGCCTTTTACGTGGATCTCAGAGATCCTGCGACTGGAGACTTCCTACCCGGAATA

GGAGGAGAGGACGATGGAATCAAGGGGGGATTGAATGGCATTGACAACGGTAGAC

TACATTTTACGAACGTACGCATTCCTAGAACTAATCTTCTTAACAGATATGGCGATG

TGGCGGTCGACGGCACATACCTGTCGACCATCGAATCACCAGGGCGCCGGTTCTTTA

CGATGCTTGGTACTCTAGTCCAGGGTAGAGTTAGTCTCGATGGAGCAGCTGTCGCTG

CACTGAAGGTCGCATTGCAAAGTGCAATTCACTACGCTGCGGAGAGGAGACAATTT

AATGCGACTTCACCTACTGAAGAAGAGGTCCTTCTTGATTATCAGAGGCATCAAAGG

AGACTCTTTACACGACTTGCAACGACGTACGCCGCATCTTTCGCCCACGAGCAGCTA

TTGCAAAAGTTCGATGATGTCTTTTCAGGGGCACATGATACCGACGCCGACCGGCAG

GACTTGGAAACCCTAGCCGCCGCTTTGAAGCCATTGAGCACATGGCATGCACTTGAC

ACGTTACAAGAATGCAGAGAGGCCTGTGGGGGGGCCGGATTTTTGATAGAAAACCG

TTTCGCGAGCTTGCGTGCTGACTTGGACGTTTACGTCACATTCGAGGGTGATAACAC

AGTTTTATTGCAATTGGTTGCTAAACGGCTCTTGGCAGACTACGCAAAAGAGTTCAG

AGGGGCCAACTTCGGCGTTCTTGCCAGGTATGTGGTTGACCAAGCCGCGGGAGTGG

CGCTCCACCGAACAGGACTAAGGCAAGTCGCTCAATTTGTTGCAGACAGCGGGTCC

GTTCAGAAGTCGGCTCTTGCGCTTCGCGATGAAGAGGGTCAACGAACATTGTTAACG

GACAGAGTACAGAGCATGGTTGCCGAAGTGGGGGCTGCCTTGAAAGGCGCAGGCAA

ATTACCCCAACATCAAGCAGCTGCATTGTTCAACCAACACCAGAACGAACTTATTGA

GGCTGCCCAGGCCCATGCAGAACTCCTCCAATGGGAGGCATTTACAGAAGCTCTCG

CTAAAGTCGACGATGCTGGTACAAAGGAAGTGCTTACTCGATTGCGAGATCTCTTTG

GTTTGTCCTTGATTGAAAAACACTTGCTGTGGTATCTTATGAATGGACGTTTGTCCAT

GCAAAGAGGCAGGACAGTTGGAACTTACATTAATCGTTTACTTGTCAAGATCCGTCC

ACACGCACTAGACTTGGTTGATGCCTTCGGTTACGGCGCGGAGCATTTGCGTGCTGC

TATCGCCACCGGAGCGGAAGCAACCCGACAGGATGAAGCCCGAACGTATTTTAGAC

AACAACGGGCATCGGGACTGGCCCCGGCCGATGAAAAGACCTTACTCGCTATCAAA

GCTGGTAAATCAAGAGGGCGAAGGGCAAAGCTATGA

-continued

CvHXS1 Gene (SEQ ID NO: 94)

ATGGGAAAAAATTATAAATCTTTGGACTCAGTTGTGGCTAGTGACTTCATTGCACTT

GGGATCACATCAGAAGTTGCTGAGACATTGCACGGACGCTTGGCAGAGATAGTTTG

CAACTACGGCGCCGCAACACCTCAGACCTGGATTAACATCGCAAACCATATTCTAA

GTCCAGATCTTCCATTTAGTCTCCATCAGATGTTGTTCTACGGTTGTTATAAGGACTT

TGGTCCAGCACCCCCAGCTTGGATACCAGACCCCGAAAAAGTAAAGTCCACGAACT

TAGGTGCCTTGTTAGAAAAGCGGGGAAAGGAGTTTCTAGGCGTTAAGTATAAGGAC

CCAATAAGTCTGTTTTCTCACTTCCAGGAGTTTAGCGTTCGAAATCCGGAAGTCTACT

GGCGGACGGTACTTATGGATGAAATGAAGATACTGTTCAGCAAAGATCCCGAATGT

ATCCTCAGACGCGACGACATTAACAACCCAGGGGGCTCTGAGTGGCTACCAGGTGG

ATATCTCAACCTGGCCAAGAACTGTTTGAATGTAAATAGTAACAAAAAACTTAACG

ACACTATGATAGTGTGGAGAGATGAAGGAAATGACGATCTCCCATTGAATAAATTG

ACTCTTGATCAATTACGAAAACGAGTCTGGTTGGTTGGATACGCCCTAGAAGAGATG

GGCCTTGAGAAGGGATGTGCGATTGCAATTGACATGCCCATGCACGTAGATGCGGTT

GTGATCTATTTAGCTATCGTCTTGGCAGGCTACGTCGTTGTCTCCATTGCAGATTCAT

TCTCAGCACCGGAAATTTCCACAAGATTGCGTCTATCAAAGGCTAAGGCTATTTTTA

CACAAGATCATATCATCCGAGGGAAAAAGCGTATACCTTTGTACCTGCGTGTCGTCG

AGGCCAAGTCTCCGATGGCAATAGTTATCCCGTGTTCGGGTTCAAATATTGGTGCGG

AATTGCGGGATGGTGATATTCTGTGGGATTACTTCTTAGAACGCGCAAAGGAATTTA

AGAACTGCGAATTTACAGCCCGTGAACAGCCAGTGGACGCGTACACAAATATTTTGT

TCTCATCGGGAACCACCGGAGAGCCAAAGGCGATACCATGGACTCAAGCTACGCCT

CTCAAGGCGGCTGCTGATGGTTGGTCACACTTGGACATTAGAAAGGGTGACGTAATT

GTATGGCCTACCAATTTGGGGTGGATGATGGGGCCTTGGTTGGTCTATGCTTCACTC

CTTAACGGGGCAAGCATCGCATTGTATAACGGATCTCCACTAGTGTCCGGCTTTGCC

AAATTCGTTCAAGATGCGAAAGTTACTATGCTAGGAGTTGTCCCCTCCATCGTACGA

AGCTGGAAAAGCACTAATTGCGTTAGTGGGTACGATTGGTCTACAATCAGATGCTTC

TCCTCATCGGGTGAGGCATCGAATGTCGATGAATACTTATGGCTAATGGGAAGGGCT

AACTACAAACCGGTCATCGAAATGTGCGGTGGCACAGAGATCGGGGGTGCCTTCAG

CGCCGGTTCGTTTTTACAAGCCCAATCTTTGAGTAGCTTCTCATCCCAATGTATGGGA

TGCACCTTGTACATTCTCGACAAGAATGGCTACCCGATGCCAAAGAACAAGCCGGG

TATAGGTGAATTGGCCTTGGGACCCGTGATGTTCGGTGCTTCCAAGACTTTACTTAA

CGGAAACCATCATGACGTTTATTTCAAAGGCATGCCCACCTTGAACGGAGAAGTCTT

GAGGAGACACGGAGATATCTTCGAACTCACTTCGAACGGCTATTATCACGCTCATGG

TAGAGCAGATGACACGATGAATATCGGGGGGATTAAAATTTCCTCAATCGAGATTG

AAAGGGTGTGTAATGAAGTTGACGATAGAGTGTTTGAGACTACGGCCATTGGAGTG

CCTCCATTGGGCGGAGGTCCAGAGCAGCTCGTTATCTTTTTTGTTCTTAAGGACAGC

AATGATACGACCATCGACCTAAACCAATTGCGACTTAGTTTTAATCTTGGGTTACAA

AAGAAATTGAACCCACTTTTTAAGGTGACGAGGGTTGTGCCACTTTCGCTGTTGCCT

AGGACAGCCACCAACAAAATAATGAGAAGAGTGCTTAGACAGCAATTTAGTCATTT

CGAGTGA

-continued

CvTKS1 Gene (SEQ ID NO: 95)

ATGAATCATTTAAGAGCAGAAGGACCCGCATCAGTGTTAGCGATAGGTACAGCTAA

CCCAGAGAATATCTTAATCCAAGATGAATTTCCTGACTACTATTTCCGTGTTACTAA

ATCGGAACATATGACTCAACTTAAAGAGAAGTTCCGGAAAATCTGCGATAAATCCA

TGATCCGAAAGAGAAACTGTTTCCTTAACGAAGAACATCTCAAGCAAAACCCGAGG

TTGGTAGAGCACGAAATGCAGACCTTGGATGCTAGGCAGGACATGTTGGTGGTCGA

AGTGCCAAAACTCGGCAAGGACGCGTGCGCTAAGGCAATCAAGGAGTGGGGTCAAC

CGAAGTCTAAAATCACGCATCTAATATTTACATCTGCACTGACAACCGACATGCCGG

GTGCCGATTATCACTGCGCCAAGCTACTTGGATTGAGTCCACTGGTTAAGAGAGTTA

TGATGTATCAATTGGGGTGTTACGGAGGGGGCACAGTCCTCAGAATTGCTAAGGAT

ATTGCGGAAAATAACAAGGGCGCGAGGGTCCTTGCTGTATGTTGTGATATTATGGCC

TGTTTGTTTCGCGGGCCCTCGGATTCAGATTTGGAATTGCTTGTCGGACAGGCAATTT

TTGGTGACGGGGCCGCAGCAGTCATAGTGGGAGCCGAACCAGACGAAAGCGTGGGT

GAAAGACCAATCTTTGAGTTGGTTCTGACCGGACAAACGATCTTACCTAACTCGGAA

GGTACGATTGGAGGACATATTAGAGAAGCCGGCCTAATTTTCGATCTTCACAAAGAC

GTTCCAATGTTAATCTCCAATAACATAGAAAAGTGCTTGATAGAAGCATTTACTCCC

ATTGGTATTAGTGACTGGAACAGCATTTTCTGGATCACCCACCCTGGAGGAAAAGCT

ATACTCGATAAGGTTGAAGAGAAACTCGACTTGAAAAAGGAGAAATTCGTTGACTC

ACGACATGTGTTATCAGAGCACGGGAATATGAGTTCATCCACAGTCTTGTTCGTAAT

GGATGAATTGCGAAAACGCTCTCTTGAGGAGGGAAAGAGCACAACCGGTGACGGGT

TTGAGTGGGGCGTGCTATTCGGTTTTGGCCCAGGTTTGACTGTCGAGCGGGTTGTTG

TTCGTAGTGTACCAATTAAGTACTGA

CvTKS1P Gene (SEQ ID NO: 96)

ATGAATCATTTAAGAGCAGAAGGACCCGCATCAGTGTTAGCGATAGGTACAGCTAA

CCCAGAGAATATCTTAATCCAAGATGAATTTCCTGACTACTATTTCCGTGTTACTAA

ATCGGAACATATGACTCAACTTAAAGAGAAGTTCCGGAAAATCTGCGATAAATCCA

TGATCCGAAAGAGAAACTGTTTCCTTAACGAAGAACATCTCAAGCAAAACCCGAGG

TTGGTAGAGCACGAAATGCAGACCTTGGATGCTAGGCAGGACATGTTGGTGGTCGA

AGTGCCAAAACTCGGCAAGGACGCGTGCGCTAAGGCAATCAAGGAGTGGGGTCAAC

CGAAGTCTAAAATCACGCATCTAATATTTACATCTGCACTGACAACCGACATGCCGG

GTGCCGATTATCACTGCGCCAAGCTACTTGGATTGAGTCCACTGGTTAAGAGAGTTA

TGATGTATCAATTGGGGTGTTACGGAGGGGGCACAGTCCTCAGAATTGCTAAGGAT

ATTGCGGAAAATAACAAGGGCGCGAGGGTCCTTGCTGTATGTTGTGATATTATGGCC

TGTTTGTTTCGCGGGCCCTCGGATTCAGATTTGGAATTGCTTGTCGGACAGGCAATTT

TTGGTGACGGGGCCGCAGCAGTCATAGTGGGAGCCGAACCAGACGAAAGCGTGGGT

GAAAGACCAATCTTTGAGTTGGTTCTGACCGGACAAACGATCTTACCTAACTCGGAA

GGTACGATTGGAGGACATATTAGAGAAGCCGGCCTAATTTTCGATCTTCACAAAGAC

GTTCCAATGTTAATCTCCAATAACATAGAAAAGTGCTTGATAGAAGCATTTACTCCC

ATTGGTATTAGTGACTGGAACAGCATTTTCTGGATCACCCACCCTGGAGGAAAAGCT

ATACTCGATAAGGTTGAAGAGAAACTCGACTTGAAAAAGGAGAAATTCGTTGACTC

ACGACATGTGTTATCAGAGCACGGGAATATGAGTTCATCCACAGTCTTGTTCGTAAT

-continued

GGATGAATTGCGAAAACGCTCTCTTGAGGAGGGAAAGAGCACAACCGGTGACGGGT

TTGAGTGGGGCGTGCTATTCGGTTTTGGCCCAGGTTTGACTGTCGAGCGGGTTGTTG

TTCGTAGTGTACCAATTAAGTACGGAAGAAGGGCAAAGTTGTGA

CvOAC1 Gene (SEQ ID NO: 97)

ATGGCAGTCAAACACCTAATAGTTCTCAAATTTAAAGACGAGATTACTGAAGCTCAG

AAGGAAGAGTTCTTTAAGACATATGTTAACTTAGTCAACATCATCCCCGCGATGAAG

GACGTCTACTGGGGCAAGGATGTGACGCAAAAAAATAAGGAAGAAGGATACACAC

ATATCGTTGAGGTGACCTTTGAGAGTGTGGAAACTATTCAAGATTATATTATTCACC

CAGCCCATGTAGGGTTCGGTGACGTTTATCGATCATTCTGGGAAAAGTTGCTTATAT

TTGATTACACCCCAAGAAAATTGAAGCCTAAGTGA

CvOACP1 Gene (SEQ ID NO: 98)

ATGGCAGTCAAACACCTAATAGTTCTCAAATTTAAAGACGAGATTACTGAAGCTCAG

AAGGAAGAGTTCTTTAAGACATATGTTAACTTAGTCAACATCATCCCCGCGATGAAG

GACGTCTACTGGGGCAAGGATGTGACGCAAAAAAATAAGGAAGAAGGATACACAC

ATATCGTTGAGGTGACCTTTGAGAGTGTGGAAACTATTCAAGATTATATTATTCACC

CAGCCCATGTAGGGTTCGGTGACGTTTATCGATCATTCTGGGAAAAGTTGCTTATAT

TTGATTACACCCCAAGAAAATTGAAGCCTAAGGGAAGACGAGCTAAGTTGTGA

CvPTS1 Gene (SEQ ID NO: 99)

ATGGGTTTATCGTCAGTGTGCACTTTTTCTTTTCAAACAAACTACCACACCCTCCTAA

ACCCTCACAATAATAACCCAAAAACCTCCTTGCTATGTTACAGACATCCAAAGACAC

CGATCAAGTATTCATACAACAATTTTCCCAGTAAACATTGCTCAACGAAGTCCTTCC

ACTTGCAAAACAAATGCAGCGAATCATTGTCGATAGCTAAAAACTCGATACGTGCG

GCAACCACTAACCAAACTGAGCCACCAGAGAGCGATAATCATTCAGTCGCCACCAA

GATTTTGAACTTTGGAAAAGCCTGTTGGAAACTTCAAAGGCCTTACACCATTATCGC

ATTTACCAGTTGCGCATGTGGTTTGTTCGGGAAGGAATTATTACACAACACAAATTT

GATCAGCTGGAGCCTAATGTTTAAGGCATTTTTCTTCTTAGTTGCAATTTTGTGTATA

GCTTCGTTTACAACGACCATTAATCAGATTTACGACCTTCACATCGATCGGATCAAT

AAACCAGACTTGCCCCTTGCCTCTGGGGAAATCTCTGTAAATACTGCATGGATCATG

CTGATAATCGTGGCTTTGTTTGGATTGATTATTACAATTAAGATGAAGGGGGGTCCA

TTATATATATTCGGGTACTGCTTCGGCATTTTCGGTGGTATCGTTTACTCCGTCCCAC

CCTTTAGATGGAAACAGAACCCCAGTACGGCCTTTCTACTCAATTTCTTGGCTCATAT

CATCACAAACTTCACATTCTATTATGCAAGCCGAGCGGCGCTTGGTTTGCCGTTCGA

ACTCAGACCGAGTTTTACATTTCTCCTTGCCTTCATGAAACTGATGGGACTGGCCCTT

GCATTGATCAAGGATGCGTCAGATGTCGAAGGCGACACTAAGTTCGGCATTCTGAC

GCTTGCTTCCAAGTATGGAAGTAGAAATCTAACGCTTTTTTGTTCAGGAATAGTGCT

ACTTAGTTATGTTGCTGCTATACTCGCTGGCATTATTTGGCCTCAGGCCTTCAACTCT

AACGTAATGTTGTTATCCCATGCTATTTTGGCGTTCTGGTTGATCTTGCAAACGCGAG

ATTTTGCACTCACTAACTACGACCCAGAGGCAGGAAGGCGCTTTTACGAGTTTATGT

GGAAGTTGTATTATGCCGAATACTTGGTTTATGTTTTCATTTGA

-continued

CVPTS1dN Gene (SEQ ID NO: 100)

ATGGCGGCAACCACTAACCAAACTGAGCCACCAGAGAGCGATAATCATTCAGTCGC

CACCAAGATTTTGAACTTTGGAAAAGCCTGTTGGAAACTTCAAAGGCCTTACACCAT

TATCGCATTTACCAGTTGCGCATGTGGTTTGTTCGGGAAGGAATTATTACACAACAC

AAATTTGATCAGCTGGAGCCTAATGTTTAAGGCATTTTTCTTCTTAGTTGCAATTTTG

TGTATAGCTTCGTTTACAACGACCATTAATCAGATTTACGACCTTCACATCGATCGG

ATCAATAAACCAGACTTGCCCCTTGCCTCTGGGGAAATCTCTGTAAATACTGCATGG

ATCATGCTGATAATCGTGGCTTTGTTTGGATTGATTATTACAATTAAGATGAAGGGG

GGTCCATTATATATATTCGGGTACTGCTTCGGCATTTTCGGTGGTATCGTTTACTCCG

TCCCACCCTTTAGATGGAAACAGAACCCCAGTACGGCCTTTCTACTCAATTTCTTGG

CTCATATCATCACAAACTTCACATTCTATTATGCAAGCCGAGCGGCGCTTGGTTTGC

CGTTCGAACTCAGACCGAGTTTTACATTTCTCCTTGCCTTCATGAAACTGATGGGACT

GGCCCTTGCATTGATCAAGGATGCGTCAGATGTCGAAGGCGACACTAAGTTCGGCAT

TCTGACGCTTGCTTCCAAGTATGGAAGTAGAAATCTAACGCTTTTTTGTTCAGGAAT

AGTGCTACTTAGTTATGTTGCTGCTATACTCGCTGGCATTATTTGGCCTCAGGCCTTC

AACTCTAACGTAATGTTGTTATCCCATGCTATTTTGGCGTTCTGGTTGATCTTGCAAA

CGCGAGATTTTGCACTCACTAACTACGACCCAGAGGCAGGAAGGCGCTTTTACGAGT

TTATGTGGAAGTTGTATTATGCCGAATACTTGGTTTATGTTTTCATTTGA

CvPTS2 Gene (SEQ ID NO: 101)

ATGGGGTTGTCCTTAGTTTGTACGTTCAGTTTCCAAACTAACTACCACACACTACTAA

ATCCGCACAACAAAAACCCGAAAAATTCATTGCTCTCCTATCAGCACCCAAAAACA

CCCATTATCAAGTCTAGTTACGACAACTTTCCATCAAAATACTGTCTAACGAAAAAC

TTTCATTTGTTGGGCTTAAATTCTCATAATCGTATTTCCAGTCAGTCCCGATCGATCA

GGGCCGGGAGTGACCAAATTGAAGGTTCTCCACATCATGAAAGTGACAATTCAATT

GCTACGAAGATTTTAAACTTTGGGCATACATGCTGGAAGCTACAGCGACCGTATGTA

GTTAAGGGGATGATCAGCATTGCCTGCGGCCTATTCGGAAGGGAACTCTTCAATAAT

AGACATCTTTTTTCTTGGGGTTTAATGTGGAAAGCTTTTTTCGCTTTGGTTCCTATCCT

TAGTTTTAACTTCTTCGCCGCTATTATGAATCAAATTTACGATGTTGACATCGACCGT

ATTAACAAACCCGATCTCCCCCTTGTTTCAGGCGAGATGTCCATTGAAACGGCATGG

ATTTTGTCCATCATTGTTGCGCTTACTGGCTTGATTGTTACCATTAAGCTTAAAAGCG

CTCCCTTGTTCGTTTTTATATACATTTTCGGCATTTTTGCCGGATTCGCATACAGTGTC

CCGCCTATACGTTGGAAACAATATCCATTCACGAACTTCTTGATCACGATCTCATCA

CATGTTGGATTGGCCTTTACGTCCTACAGTGCTACCACATCTGCCCTTGGATTGCCTT

TCGTTTGGAGGCCTGCCTTCTCGTTTATCATTGCATTTATGACAGTGATGGGAATGAC

TATCGCATTTGCTAAAGATATCAGCGACATAGAGGGCGATGCAAAATATGGGGTGA

GTACTGTTGCGACGAAGTTGGGCGCCCGAAATATGACCTTCGTTGTTTCCGGCGTTC

TTTTACTTAACTATTTAGTATCGATTAGCATCGGGATCATCTGGCCACAGGTGTTTAA

ATCAAATATTATGATCTTGTCGCATGCCATCCTAGCTTTCTGTCTTATATTTCAAACA

-continued

AGAGAATTAGCCCTAGCGAACTACGCCTCAGCACCAAGTCGTCAGTTCTTCGAATTT

ATATGGCTACTCTACTACGCCGAATACTTCGTCTATGTCTTCATTTAG

CvCBD1 Gene (SEQ ID NO: 102)

ATGAAGTGTTCTACGTTTAGTTTTTGGTTTGTTTGTAAAATTATATTCTTCTTTTTTTC

CTTCAACATTCAGACATCAATCGCCAACCCAAGGGAAAACTTCCTTAAGTGTTTTCT

GCAGTACATCCCTAACAATGCAACAAACCTCAAGTTGGTGTACACTCAAAACAATC

CACTCTATATGAGCGTGCTTAATAGCACAATCCACAACTTGCGCTTCACGTCAGATA

CTACGCCTAAGCCACTAGTGATCGTTACACCATCACACGTCAGCCATATTCAAGGAA

CGATCCTATGTCTGAAAAAGGTCGGGTTGCAAATCAGGACTCGATCAGGAGGGCAC

GATAGTGAGGGAATGAGTTACATCTCGCAAGTACCCTTCGTGATAGTTGACTTGCGA

AATATGCGGTCTATTAAAATTGACGTACATAGCCAGACCGCCTGGGTTGAAGCAGG

GGCAACCTTGGGTGAAGTTTATTACTGGGTCAATGAAAAAAACGAAAACCTAAGTC

TTGCTGCTGGATATTGCCCCACCGTTTGCGCGGGTGGTCATTTTGGAGGCGGCGGAT

ATGGTCCGTTGATGAGAAATTATGGACTTGCAGCAGACAATATTATAGATGCCCACT

TGGTGAACGTTCATGGAAAGGTCTTGGACCGTAAGTCCATGGGTGAAGATCTTTTCT

GGGCCTTGAGAGGTGGTGGAGCGGAATCGTTTGGCATCATCGTTGCCTGGAAAATTA

GGTTGGTTGCGGTCCCGAAGAGTACAATGTTCTCCGTGAAGAAGATTATGGAAATAC

ATGAGCTTGTCAAGTTAGTTAACAAGTGGCAAAATATCGCTTATAAGTATGATAAAG

ACTTGCTTTTGATGACTCATTTTATTACGCGAAACATAACCGATAACCAGGGCAAGA

ACAAGACTGCTATTCACACGTACTTCTCCTCTGTATTTCTTGGAGGAGTAGACTCCTT

AGTTGACTTGATGAACAAGAGTTTCCCAGAATTGGGGATTAAGAAGACAGATTGCA

GACAATTATCGTGGATAGATACAATCATATTCTATAGCGGTGTCGTCAATTACGATA

CTGATAATTTTAATAAAGAAATCCTCCTAGATCGTTCAGCTGGGCAAAACGGGGCAT

TCAAAATTAAATTGGATTATGTGAAGAAACCAATTCCAGAGCTGGTGTTTGTTCAGA

TATTGGAAAAACTTTACGAAGAAGACATTGGCGCAGGTATGTACGCTTTGTATCCAT

ATGGAGGCATTATGGACGAGATCTCAGAGCTGGCGATCCCCTTCCCGCACAGAGCT

GGGATACTCTACGAGCTATGGTACATCTGCTCTTGGGAGAAACAAGAAGACAACGA

GAAACATCTCAATTGGATTCGGAACATATACAACTTTATGACCCCATACGTATCAAA

AAACCCGCGCTTAGCATACTTGAATTACAGAGACTTAGATATCGGTATCAATGATCC

TAAGAATCCTAACAATTACACCCAAGCCCGTATTTGGGGTGAGAAATATTTCGGCAA

GAATTTTGACAGATTAGTTAAGGTCAAAACACTCGTGGACCCCAACAACTTTTTCCG

AAACGAGCAGTCGATTCCACCACTACCCAGGCATAGACACTGA

CBD1dNS1

(SEQ ID NO: 103)

ATGTTCTTGAAACACATTTTTGTTGCTCTCGCTTTTGCCTTGTTAGCTGACGCTACCC

CAGCCCAGAAGAGATCTCCCGGCTTCGTTGCTTTAGACTTTGACATCGTCAAGGTTC

AAAAGAACGTGACTGCCAACGACGACGCCGCTGCCATTGTTGCCAAGAGACAGACC

AACCCAAGGGAAAACTTCCTTAAGTGTTTTCTGCAGTACATCCCTAACAATGCAACA

AACCTCAAGTTGGTGTACACTCAAAACAATCCACTCTATATGAGCGTGCTTAATAGC

ACAATCCACAACTTGCGCTTCACGTCAGATACTACGCCTAAGCCACTAGTGATCGTT

ACACCATCACACGTCAGCCATATTCAAGGAACGATCCTATGTCTGAAAAAGGTCGG

GTTGCAAATCAGGACTCGATCAGGAGGGCACGATAGTGAGGGAATGAGTTACATCT

-continued

CGCAAGTACCCTTCGTGATAGTTGACTTGCGAAATATGCGGTCTATTAAAATTGACG

TACATAGCCAGACCGCCTGGGTTGAAGCAGGGGCAACCTTGGGTGAAGTTTATTACT

GGGTCAATGAAAAAAACGAAAACCTAAGTCTTGCTGCTGGATATTGCCCCACCGTTT

GCGCGGGTGGTCATTTTGGAGGCGGCGGATATGGTCCGTTGATGAGAAATTATGGA

CTTGCAGCAGACAATATTATAGATGCCCACTTGGTGAACGTTCATGGAAAGGTCTTG

GACCGTAAGTCCATGGGTGAAGATCTTTTCTGGGCCTTGAGAGGTGGTGGAGCGGA

ATCGTTTGGCATCATCGTTGCCTGGAAAATTAGGTTGGTTGCGGTCCCGAAGAGTAC

AATGTTCTCCGTGAAGAAGATTATGGAAATACATGAGCTTGTCAAGTTAGTTAACAA

GTGGCAAAATATCGCTTATAAGTATGATAAAGACTTGCTTTTGATGACTCATTTTATT

ACGCGAAACATAACCGATAACCAGGGCAAGAACAAGACTGCTATTCACACGTACTT

CTCCTCTGTATTTCTTGGAGGAGTAGACTCCTTAGTTGACTTGATGAACAAGAGTTTC

CCAGAATTGGGGATTAAGAAGACAGATTGCAGACAATTATCGTGGATAGATACAAT

CATATTCTATAGCGGTGTCGTCAATTACGATACTGATAATTTTAATAAAGAAATCCT

CCTAGATCGTTCAGCTGGGCAAAACGGGGCATTCAAAATTAAATTGGATTATGTGAA

GAAACCAATTCCAGAGCTGGTGTTTGTTCAGATATTGGAAAAACTTTACGAAGAAG

ACATTGGCGCAGGTATGTACGCTTTGTATCCATATGGAGGCATTATGGACGAGATCT

CAGAGCTGGCGATCCCCTTCCCGCACAGAGCTGGGATACTCTACGAGCTATGGTACA

TCTGCTCTTGGGAGAAACAAGAAGACAACGAGAAACATCTCAATTGGATTCGGAAC

ATATACAACTTTATGACCCCATACGTATCAAAAAACCCGCGCTTAGCATACTTGAAT

TACAGAGACTTAGATATCGGTATCAATGATCCTAAGAATCCTAACAATTACACCCAA

GCCCGTATTTGGGGTGAGAAATATTTCGGCAAGAATTTTGACAGATTAGTTAAGGTC

AAAACACTCGTGGACCCCAACAACTTTTTCCGAAACGAGCAGTCGATTCCACCACTA

CCCAGGCATAGACACTGA

CBD1dNS2

(SEQ ID NO: 104)

ATGCAATTGTCATTGTCAGTTTTGTCAACAGTTGCAACAGCATTGTTGTCATTGACAA

CAGCAGTTGATGCAAAGTCACATAACCCAAGGGAAAACTTCCTTAAGTGTTTTCTGC

AGTACATCCCTAACAATGCAACAAACCTCAAGTTGGTGTACACTCAAAACAATCCA

CTCTATATGAGCGTGCTTAATAGCACAATCCACAACTTGCGCTTCACGTCAGATACT

ACGCCTAAGCCACTAGTGATCGTTACACCATCACACGTCAGCCATATTCAAGGAACG

ATCCTATGTCTGAAAAAGGTCGGGTTGCAAATCAGGACTCGATCAGGAGGGCACGA

TAGTGAGGGAATGAGTTACATCTCGCAAGTACCCTTCGTGATAGTTGACTTGCGAAA

TATGCGGTCTATTAAAATTGACGTACATAGCCAGACCGCCTGGGTTGAAGCAGGGG

CAACCTTGGGTGAAGTTTATTACTGGGTCAATGAAAAAAACGAAAACCTAAGTCTTG

CTGCTGGATATTGCCCCACCGTTTGCGCGGGTGGTCATTTTGGAGGCGGCGGATATG

GTCCGTTGATGAGAAATTATGGACTTGCAGCAGACAATATTATAGATGCCCACTTGG

TGAACGTTCATGGAAAGGTCTTGGACCGTAAGTCCATGGGTGAAGATCTTTTCTGGG

CCTTGAGAGGTGGTGGAGCGGAATCGTTTGGCATCATCGTTGCCTGGAAAATTAGGT

TGGTTGCGGTCCCGAAGAGTACAATGTTCTCCGTGAAGAAGATTATGGAAATACATG

AGCTTGTCAAGTTAGTTAACAAGTGGCAAAATATCGCTTATAAGTATGATAAAGACT

TGCTTTTGATGACTCATTTTATTACGCGAAACATAACCGATAACCAGGGCAAGAACA

-continued

AGACTGCTATTCACACGTACTTCTCCTCTGTATTTCTTGGAGGAGTAGACTCCTTAGT

TGACTTGATGAACAAGAGTTTCCCAGAATTGGGGATTAAGAAGACAGATTGCAGAC

AATTATCGTGGATAGATACAATCATATTCTATAGCGGTGTCGTCAATTACGATACTG

ATAATTTTAATAAAGAAATCCTCCTAGATCGTTCAGCTGGGCAAAACGGGGCATTCA

AAATTAAATTGGATTATGTGAAGAAACCAATTCCAGAGCTGGTGTTTGTTCAGATAT

TGGAAAAACTTTACGAAGAAGACATTGGCGCAGGTATGTACGCTTTGTATCCATATG

GAGGCATTATGGACGAGATCTCAGAGCTGGCGATCCCCTTCCCGCACAGAGCTGGG

ATACTCTACGAGCTATGGTACATCTGCTCTTGGGAGAAACAAGAAGACAACGAGAA

ACATCTCAATTGGATTCGGAACATATACAACTTTATGACCCCATACGTATCAAAAAA

CCCGCGCTTAGCATACTTGAATTACAGAGACTTAGATATCGGTATCAATGATCCTAA

GAATCCTAACAATTACACCCAAGCCCGTATTTGGGGTGAGAAATATTTCGGCAAGA

ATTTTGACAGATTAGTTAAGGTCAAAACACTCGTGGACCCCAACAACTTTTTCCGAA

ACGAGCAGTCGATTCCACCACTACCCAGGCATAGACACTGA

CBD1dNV1

(SEQ ID NO: 105)

ATGCAATTGTCCTTGTCGGTTTTATCAACCGTTGCCACGGCCTTGTTGTCCCTAACCA

CCGCCGTCGATGCTAAGTCCCACAACATCAAGTTGTCCAAGTTGTCCAACGAAGAA

ACATTGGACGCCTCCACATTCCAAGAATACACGAGCTCCTTGGCCAACAAGTACATG

AACTTGTTCAACGCCGCTCACGGTAACCCAACCAGCTTTGGCTTGCAACACGTCTTG

TCCAACCAAGAAGCTGAAGTCCCATTCGTTACCCCACAAAAGGGTGGCAACCCAAG

GGAAAACTTCCTTAAGTGTTTTCTGCAGTACATCCCTAACAATGCAACAAACCTCAA

GTTGGTGTACACTCAAAACAATCCACTCTATATGAGCGTGCTTAATAGCACAATCCA

CAACTTGCGCTTCACGTCAGATACTACGCCTAAGCCACTAGTGATCGTTACACCATC

ACACGTCAGCCATATTCAAGGAACGATCCTATGTCTGAAAAAGGTCGGGTTGCAAA

TCAGGACTCGATCAGGAGGGCACGATAGTGAGGGAATGAGTTACATCTCGCAAGTA

CCCTTCGTGATAGTTGACTTGCGAAATATGCGGTCTATTAAAATTGACGTACATAGC

CAGACCGCCTGGGTTGAAGCAGGGGCAACCTTGGGTGAAGTTTATTACTGGGTCAAT

GAAAAAAACGAAAACCTAAGTCTTGCTGCTGGATATTGCCCCACCGTTTGCGCGGGT

GGTCATTTTGGAGGCGGCGGATATGGTCCGTTGATGAGAAATTATGGACTTGCAGCA

GACAATATTATAGATGCCCACTTGGTGAACGTTCATGGAAAGGTCTTGGACCGTAAG

TCCATGGGTGAAGATCTTTTCTGGGCCTTGAGAGGTGGTGGAGCGGAATCGTTTGGC

ATCATCGTTGCCTGGAAAATTAGGTTGGTTGCGGTCCCGAAGAGTACAATGTTCTCC

GTGAAGAAGATTATGGAAATACATGAGCTTGTCAAGTTAGTTAACAAGTGGCAAAA

TATCGCTTATAAGTATGATAAAGACTTGCTTTTGATGACTCATTTTATTACGCGAAAC

ATAACCGATAACCAGGGCAAGAACAAGACTGCTATTCACACGTACTTCTCCTCTGTA

TTTCTTGGAGGAGTAGACTCCTTAGTTGACTTGATGAACAAGAGTTTCCCAGAATTG

GGGATTAAGAAGACAGATTGCAGACAATTATCGTGGATAGATACAATCATATTCTAT

AGCGGTGTCGTCAATTACGATACTGATAATTTTAATAAAGAAATCCTCCTAGATCGT

TCAGCTGGGCAAAACGGGGCATTCAAAATTAAATTGGATTATGTGAAGAAACCAAT

TCCAGAGCTGGTGTTTGTTCAGATATTGGAAAAACTTTACGAAGAAGACATTGGCGC

AGGTATGTACGCTTTGTATCCATATGGAGGCATTATGGACGAGATCTCAGAGCTGGC

GATCCCCTTCCCGCACAGAGCTGGGATACTCTACGAGCTATGGTACATCTGCTCTTG

-continued

GGAGAAACAAGAAGACAACGAGAAACATCTCAATTGGATTCGGAACATATACAACT

TTATGACCCCATACGTATCAAAAAACCCGCGCTTAGCATACTTGAATTACAGAGACT

TAGATATCGGTATCAATGATCCTAAGAATCCTAACAATTACACCCAAGCCCGTATTT

GGGGTGAGAAATATTTCGGCAAGAATTTTGACAGATTAGTTAAGGTCAAAACACTC

GTGGACCCCAACAACTTTTTCCGAAACGAGCAGTCGATTCCACCACTACCCAGGCAT

AGACACTGA

CvCBD1dNP1

(SEQ ID NO: 106)

ATGAACCCAAGGGAAAACTTCCTTAAGTGTTTTCTGCAGTACATCCCTAACAATGCA

ACAAACCTCAAGTTGGTGTACACTCAAAACAATCCACTCTATATGAGCGTGCTTAAT

AGCACAATCCACAACTTGCGCTTCACGTCAGATACTACGCCTAAGCCACTAGTGATC

GTTACACCATCACACGTCAGCCATATTCAAGGAACGATCCTATGTCTGAAAAAGGTC

GGGTTGCAAATCAGGACTCGATCAGGAGGGCACGATAGTGAGGGAATGAGTTACAT

CTCGCAAGTACCCTTCGTGATAGTTGACTTGCGAAATATGCGGTCTATTAAAATTGA

CGTACATAGCCAGACCGCCTGGGTTGAAGCAGGGGCAACCTTGGGTGAAGTTTATT

ACTGGGTCAATGAAAAAAACGAAAACCTAAGTCTTGCTGCTGGATATTGCCCCACC

GTTTGCGCGGGTGGTCATTTTGGAGGCGGCGGATATGGTCCGTTGATGAGAAATTAT

GGACTTGCAGCAGACAATATTATAGATGCCCACTTGGTGAACGTTCATGGAAAGGTC

TTGGACCGTAAGTCCATGGGTGAAGATCTTTTCTGGGCCTTGAGAGGTGGTGGAGCG

GAATCGTTTGGCATCATCGTTGCCTGGAAAATTAGGTTGGTTGCGGTCCCGAAGAGT

ACAATGTTCTCCGTGAAGAAGATTATGGAAATACATGAGCTTGTCAAGTTAGTTAAC

AAGTGGCAAAATATCGCTTATAAGTATGATAAAGACTTGCTTTTGATGACTCATTTT

ATTACGCGAAACATAACCGATAACCAGGGCAAGAACAAGACTGCTATTCACACGTA

CTTCTCCTCTGTATTTCTTGGAGGAGTAGACTCCTTAGTTGACTTGATGAACAAGAGT

TTCCCAGAATTGGGGATTAAGAAGACAGATTGCAGACAATTATCGTGGATAGATAC

AATCATATTCTATAGCGGTGTCGTCAATTACGATACTGATAATTTTAATAAAGAAAT

CCTCCTAGATCGTTCAGCTGGGCAAAACGGGGCATTCAAAATTAAATTGGATTATGT

GAAGAAACCAATTCCAGAGCTGGTGTTTGTTCAGATATTGGAAAAACTTTACGAAG

AAGACATTGGCGCAGGTATGTACGCTTTGTATCCATATGGAGGCATTATGGACGAGA

TCTCAGAGCTGGCGATCCCCTTCCCGCACAGAGCTGGGATACTCTACGAGCTATGGT

ACATCTGCTCTTGGGAGAAACAAGAAGACAACGAGAAACATCTCAATTGGATTCGG

AACATATACAACTTTATGACCCCATACGTATCAAAAAACCCGCGCTTAGCATACTTG

AATTACAGAGACTTAGATATCGGTATCAATGATCCTAAGAATCCTAACAATTACACC

CAAGCCCGTATTTGGGGTGAGAAATATTTCGGCAAGAATTTTGACAGATTAGTTAAG

GTCAAAACACTCGTGGACCCCAACAACTTTTTCCGAAACGAGCAGTCGATTCCACCA

CTACCCAGGCATAGACACGGAAGAAGGGCAAAGTTGTAA

CvTHC1 Gene (SEQ ID NO: 107)

ATGAATTGTTCAGCATTTAGTTTTTGGTTTGTTTGTAAGATTATTTTCTTCTTTTTGTC

ATTTAACATTCAAATTTCAATTGCAAACCCACAAGAAAACTTTTTGAAGTGTTTTTCA

GAATACATTCCAAACAATCCAGCTAACCCAAAGTTTATTTACACACAACATGATCAA

TTGTACATGTCAGTTTTGAACTCAACAATTCAAAACTTGAGATTTACATCAGATACC

ACACCAAAGCCATTGGTTATTGTTACACCATCAAACGTTTCCCATATTCAAGCATCA

ATCTTGTGTTCAAAGAAGGTTGGATTGCAAATTAGAACCAGATCAGGAGGACACGA

TGCAGAAGGAATGTCATACATTTCACAAGTTCCATTCGTTGTTGTTGATTTGAGAAA

CATGCACTCAATTAAGATTGATGTTCATTCACAAACAGCATGGGTTGAAGCAGGAGC

AACATTGGGTGAAGTTTACTACTGGATTAACGAAAAGAACGAAAACTTCAGTTTTCC

AGGAGGTTACTGTCCAACAGTTGGAGTTGGAGGACATTTTTCAGGTGGAGGATACG

GAGCATTGATGAGAAACTACGGATTGGCAGCAGATAACATTATTGATGCACACTTG

GTTAACGTTGATGGAAAGGTTTTGGATAGAAAGTCAATGGGAGAAGATTTGTTTTGG

GCAATTAGAGGAGGTGGTGGAGAGAACTTTGGAATTATTGCAGCATGGAAGATCAA

GTTGGTTGCAGTTCCATCAAAGTCAACAATCTTTTCAGTTAAGAAGAACATGGAAAT

TCATGGTTTGGTTAAGTTGTTTAACAAGTGGCAAAACATTGCATACAAGTACGATAA

GGATTTGGTTTTGATGACACATTTTATTACAAAGAACATTACAGATAACCATGGAAA

GAACAAGACAACAGTTCACGGATACTTTTCATCAATTTTTCACGGAGGAGTTGATTC

ATTGGTTGACTTGATGAACAAGTCATTTCCAGAATTGGGAATCAAGAAGACAGATTG

TAAGGAATTTTCATGGATTGATACAACAATTTTCTACTCAGGAGTTGTTAACTTTAAC

ACAGCAAACTTTAAGAAGGAAATTTTGTTGGACAGATCAGCAGGAAAGAAGACCGC

ATTTTCCATTAAGTTGGATTACGTTAAGAAACCAATTCCAGAAACAGCAATGGTTAA

GATTTTGGAAAAGTTGTACGAAGAAGATGTTGGTGTTGGAATGTACGTTTTGTACCC

ATACGGAGGAATTATGGAAGAAATCTCAGAATCAGCAATTCCATTTCCACATAGAG

CAGGTATTATGTACGAATTGTGGTACACAGCATCATGGGAAAAGCAAGAAGATAAT

GAAAAGCATATTAACTGGGTTAGATCAGTTTACAACTTTACAACACCATACGTTTCA

CAAAACCCAAGATTGGCATACTTGAACTACAGAGATTTGGATTTGGGAAAGACAAA

CCCAGAATCACCAAACAACTATACACAAGCTAGAATTTGGGGAGAAAAGTACTTTG

GTAAGAACTTCAACAGATTGGTTAAAGTTAAGACAAAGGCAGATCCAAATAACTTC

TTTAGAAACGAACAATCAATTCCACCATTGCCACCACATCATCATTAA

THC1dNS1 Gene (SEQ ID NO: 108)

ATGTTCTTGAAACACATTTTTGTTGCTCTCGCTTTTGCCTTGTTAGCTGACGCTACCC

CAGCCCAGAAGAGATCTCCCGGCTTCGTTGCTTTAGACTTTGACATCGTCAAGGTTC

AAAAGAACGTGACTGCCAACGACGACGCCGCTGCCATTGTTGCCAAGAGACAGACC

AACCCACAAGAAAACTTTTTGAAGTGTTTTTCAGAATACATTCCAAACAATCCAGCT

AACCCAAAGTTTATTTACACACAACATGATCAATTGTACATGTCAGTTTTGAACTCA

ACAATTCAAAACTTGAGATTTACATCAGATACCACACCAAAGCCATTGGTTATTGTT

ACACCATCAAACGTTTCCCATATTCAAGCATCAATCTTGTGTTCAAAGAAGGTTGGA

TTGCAAATTAGAACCAGATCAGGAGGACACGATGCAGAAGGAATGTCATACATTTC

ACAAGTTCCATTCGTTGTTGTTGATTTGAGAAACATGCACTCAATTAAGATTGATGTT

CATTCACAAACAGCATGGGTTGAAGCAGGAGCAACATTGGGTGAAGTTTACTACTG

GATTAACGAAAAGAACGAAAACTTCAGTTTTCCAGGAGGTTACTGTCCAACAGTTG

GAGTTGGAGGACATTTTTCAGGTGGAGGATACGGAGCATTGATGAGAAACTACGGA

TTGGCAGCAGATAACATTATTGATGCACACTTGGTTAACGTTGATGGAAAGGTTTTG

GATAGAAAGTCAATGGGAGAAGATTTGTTTTGGGCAATTAGAGGAGGTGGTGGAGA

GAACTTTGGAATTATTGCAGCATGGAAGATCAAGTTGGTTGCAGTTCCATCAAAGTC

-continued

AACAATCTTTTCAGTTAAGAAGAACATGGAAATTCATGGTTTGGTTAAGTTGTTTAA

CAAGTGGCAAAACATTGCATACAAGTACGATAAGGATTTGGTTTTGATGACACATTT

TATTACAAAGAACATTACAGATAACCATGGAAAGAACAAGACAACAGTTCACGGAT

ACTTTTCATCAATTTTTCACGGAGGAGTTGATTCATTGGTTGACTTGATGAACAAGTC

ATTTCCAGAATTGGGAATCAAGAAGACAGATTGTAAGGAATTTTCATGGATTGATAC

AACAATTTTCTACTCAGGAGTTGTTAACTTTAACACAGCAAACTTTAAGAAGGAAAT

TTTGTTGGACAGATCAGCAGGAAAGAAGACCGCATTTTCCATTAAGTTGGATTACGT

TAAGAAACCAATTCCAGAAACAGCAATGGTTAAGATTTTGGAAAAGTTGTACGAAG

AAGATGTTGGTGTTGGAATGTACGTTTTGTACCCATACGGAGGAATTATGGAAGAAA

TCTCAGAATCAGCAATTCCATTTCCACATAGAGCAGGTATTATGTACGAATTGTGGT

ACACAGCATCATGGGAAAAGCAAGAAGATAATGAAAAGCATATTAACTGGGTTAGA

TCAGTTTACAACTTTACAACACCATACGTTTCACAAAACCCAAGATTGGCATACTTG

AACTACAGAGATTTGGATTTGGGAAAGACAAACCCAGAATCACCAAACAACTATAC

ACAAGCTAGAATTTGGGGAGAAAAGTACTTTGGTAAGAACTTCAACAGATTGGTTA

AAGTTAAGACAAAGGCAGATCCAAATAACTTCTTTAGAAACGAACAATCAATTCCA

CCATTGCCACCACATCATCATTAATAA

THC1dNS2

(SEQ ID NO: 109)

ATGCAATTGTCATTGTCAGTTTTGTCAACAGTTGCAACAGCATTGTTGTCATTGACAA

CAGCAGTTGATGCAAAGTCACATAACCCACAAGAAAACTTTTTGAAGTGTTTTTCAG

AATACATTCCAAACAATCCAGCTAACCCAAAGTTTATTTACACACAACATGATCAAT

TGTACATGTCAGTTTTGAACTCAACAATTCAAAACTTGAGATTTACATCAGATACCA

CACCAAAGCCATTGGTTATTGTTACACCATCAAACGTTTCCCATATTCAAGCATCAA

TCTTGTGTTCAAAGAAGGTTGGATTGCAAATTAGAACCAGATCAGGAGGACACGAT

GCAGAAGGAATGTCATACATTTCACAAGTTCCATTCGTTGTTGTTGATTTGAGAAAC

ATGCACTCAATTAAGATTGATGTTCATTCACAAACAGCATGGGTTGAAGCAGGAGC

AACATTGGGTGAAGTTTACTACTGGATTAACGAAAAGAACGAAAACTTCAGTTTTCC

AGGAGGTTACTGTCCAACAGTTGGAGTTGGAGGACATTTTTCAGGTGGAGGATACG

GAGCATTGATGAGAAACTACGGATTGGCAGCAGATAACATTATTGATGCACACTTG

GTTAACGTTGATGGAAAGGTTTTGGATAGAAAGTCAATGGGAGAAGATTTGTTTTGG

GCAATTAGAGGAGGTGGTGGAGAGAACTTTGGAATTATTGCAGCATGGAAGATCAA

GTTGGTTGCAGTTCCATCAAAGTCAACAATCTTTTCAGTTAAGAAGAACATGGAAAT

TCATGGTTTGGTTAAGTTGTTTAACAAGTGGCAAAACATTGCATACAAGTACGATAA

GGATTTGGTTTTGATGACACATTTTATTACAAAGAACATTACAGATAACCATGGAAA

GAACAAGACAACAGTTCACGGATACTTTTCATCAATTTTTCACGGAGGAGTTGATTC

ATTGGTTGACTTGATGAACAAGTCATTTCCAGAATTGGGAATCAAGAAGACAGATTG

TAAGGAATTTTCATGGATTGATACAACAATTTTCTACTCAGGAGTTGTTAACTTTAAC

ACAGCAAACTTTAAGAAGGAAATTTTGTTGGACAGATCAGCAGGAAAGAAGACCGC

ATTTTCCATTAAGTTGGATTACGTTAAGAAACCAATTCCAGAAACAGCAATGGTTAA

GATTTTGGAAAAGTTGTACGAAGAAGATGTTGGTGTTGGAATGTACGTTTTGTACCC

ATACGGAGGAATTATGGAAGAAATCTCAGAATCAGCAATTCCATTTCCACATAGAG

-continued

CAGGTATTATGTACGAATTGTGGTACACAGCATCATGGGAAAAGCAAGAAGATAAT

GAAAAGCATATTAACTGGGTTAGATCAGTTTACAACTTTACAACACCATACGTTTCA

CAAAACCCAAGATTGGCATACTTGAACTACAGAGATTTGGATTTGGGAAAGACAAA

CCCAGAATCACCAAACAACTATACACAAGCTAGAATTTGGGGAGAAAAGTACTTTG

GTAAGAACTTCAACAGATTGGTTAAAGTTAAGACAAAGGCAGATCCAAATAACTTC

TTTAGAAACGAACAATCAATTCCACCATTGCCACCACATCATCATTAATAA

THC1dNV1

(SEQ ID NO: 110)

ATGCAATTGTCCTTGTCGGTTTTATCAACCGTTGCCACGGCCTTGTTGTCCCTAACCA

CCGCCGTCGATGCTAAGTCCCACAACATCAAGTTGTCCAAGTTGTCCAACGAAGAA

ACATTGGACGCCTCCACATTCCAAGAATACACGAGCTCCTTGGCCAACAAGTACATG

AACTTGTTCAACGCCGCTCACGGTAACCCAACCAGCTTTGGCTTGCAACACGTCTTG

TCCAACCAAGAAGCTGAAGTCCCATTCGTTACCCCACAAAAGGGTGGCAACCCACA

AGAAAACTTTTTGAAGTGTTTTTCAGAATACATTCCAAACAATCCAGCTAACCCAAA

GTTTATTTACACACAACATGATCAATTGTACATGTCAGTTTTGAACTCAACAATTCA

AAACTTGAGATTTACATCAGATACCACACCAAAGCCATTGGTTATTGTTACACCATC

AAACGTTTCCCATATTCAAGCATCAATCTTGTGTTCAAAGAAGGTTGGATTGCAAAT

TAGAACCAGATCAGGAGGACACGATGCAGAAGGAATGTCATACATTTCACAAGTTC

CATTCGTTGTTGTTGATTTGAGAAACATGCACTCAATTAAGATTGATGTTCATTCACA

AACAGCATGGGTTGAAGCAGGAGCAACATTGGGTGAAGTTTACTACTGGATTAACG

AAAAGAACGAAAACTTCAGTTTTCCAGGAGGTTACTGTCCAACAGTTGGAGTTGGA

GGACATTTTTCAGGTGGAGGATACGGAGCATTGATGAGAAACTACGGATTGGCAGC

AGATAACATTATTGATGCACACTTGGTTAACGTTGATGGAAAGGTTTTGGATAGAAA

GTCAATGGGAGAAGATTTGTTTTGGGCAATTAGAGGAGGTGGTGGAGAGAACTTTG

GAATTATTGCAGCATGGAAGATCAAGTTGGTTGCAGTTCCATCAAAGTCAACAATCT

TTTCAGTTAAGAAGAACATGGAAATTCATGGTTTGGTTAAGTTGTTTAACAAGTGGC

AAAACATTGCATACAAGTACGATAAGGATTTGGTTTTGATGACACATTTTATTACAA

AGAACATTACAGATAACCATGGAAAGAACAAGACAACAGTTCACGGATACTTTTCA

TCAATTTTTCACGGAGGAGTTGATTCATTGGTTGACTTGATGAACAAGTCATTTCCA

GAATTGGGAATCAAGAAGACAGATTGTAAGGAATTTTCATGGATTGATACAACAAT

TTTCTACTCAGGAGTTGTTAACTTTAACACAGCAAACTTTAAGAAGGAAATTTTGTT

GGACAGATCAGCAGGAAAGAAGACCGCATTTTCCATTAAGTTGGATTACGTTAAGA

AACCAATTCCAGAAACAGCAATGGTTAAGATTTTGGAAAAGTTGTACGAAGAAGAT

GTTGGTGTTGGAATGTACGTTTTGTACCCATACGGAGGAATTATGGAAGAAATCTCA

GAATCAGCAATTCCATTTCCACATAGAGCAGGTATTATGTACGAATTGTGGTACACA

GCATCATGGGAAAAGCAAGAAGATAATGAAAAGCATATTAACTGGGTTAGATCAGT

TTACAACTTTACAACACCATACGTTTCACAAAACCCAAGATTGGCATACTTGAACTA

CAGAGATTTGGATTTGGGAAAGACAAACCCAGAATCACCAAACAACTATACACAAG

CTAGAATTTGGGGAGAAAAGTACTTTGGTAAGAACTTCAACAGATTGGTTAAAGTTA

-continued

AGACAAAGGCAGATCCAAATAACTTCTTTAGAAACGAACAATCAATTCCACCATTG

CCACCACATCATCATTAATAA

CvCBC1 Gene (SEQ ID NO: 111)

ATGAATTGTAGCACTTTCTCATTCTGGTTTGTTTGTAAGATTATTTTCTTTTTCTTGTC

ATTTAACATTCAAATTTCAATTGCAAACCCACAAGAGAACTTTTTGAAGTGTTTCTC

AGAATACATTCCAAACAACCCAGCTAACCCAAAGTTTATTTACACCCAACACGATCA

ATTGTACATGTCAGTTTTGAACTCAACAATTCAAAACTTGAGATTTACATCAGATAC

AACACCAAAGCCATTGGTTATTGTTACACCATCAAACGTTAGTCATATTCAAGCATC

AATCTTGTGTTCAAAGAAGGTTGGATTGCAAATTAGAACTAGATCAGGAGGACATG

ATGCAGAAGGATTGTCATACATTTCACAAGTTCCATTTGCAATTGTTGATTTGAGAA

ACATGCACACAGTTAAGGTTGATATTCATTCACAAACAGCATGGGTTGAAGCAGGA

GCAACATTGGGTGAAGTTTACTACTGGATTAACGAAATGAACGAAAACTTCTCATTT

CCAGGAGGATACTGTCCAACAGTTGGTGTTGGAGGACACTTTTCAGGTGGTGGATAC

GGAGCATTGATGAGAAACTACGGATTGGCAGCAGATAACATTATTGATGCACATTT

GGTTAACGTTGATGGAAAGGTTTTGGATAGAAAGTCAATGGGAGAAGATTTGTTTTG

GGCAATTAGAGGAGGTGGAGGAGAAAACTTTGGAATCATTGCAGCATGTAAGATCA

AGTTGGTTGTTGTTCCATCAAAGGCAACAATCTTTTCAGTTAAGAAGAACATGGAAA

TCCATGGATTGGTTAAGTTGTTTAACAAGTGGCAAAACATTGCATACAAGTACGATA

AGGATTTGATGTTGACAACACATTTTAGAACAAGAAACATTACAGATAACCACGGA

AAGAATAAGACAACAGTTCATGGATACTTTTCATCAATTTTCTTGGGAGGAGTTGAT

TCATTGGTTGACTTGATGAACAAGAGTTTTCCAGAATTGGGAATCAAGAAGACAGAT

TGTAAGGAATTGTCATGGATCGATACAACCATTTTCTACTCAGGAGTTGTTAACTAC

AACACAGCTAACTTTAAGAAGGAAATTTTGTTGGACAGATCAGCAGGTAAAAAGAC

AGCATTTTCAATTAAGTTGGATTACGTTAAGAAATTGATTCCAGAAACAGCAATGGT

TAAGATTTTGGAAAAGTTGTACGAAGAAGAAGTTGGAGTTGGAATGTACGTTTTGTA

CCCATACGGAGGAATTATGGATGAAATTTCAGAATCAGCAATTCCATTTCCACATAG

AGCAGGTATTATGTACGAATTGTGGTACACAGCAACATGGGAAAAGCAAGAAGATA

ACGAAAAGCATATTAACTGGGTTAGATCAGTTTACAACTTTACAACCCCATACGTTT

CACAAAACCCAAGATTGGCATACTTGAACTACAGAGATTTGGATTTGGGAAAGACA

AACCCAGAATCACCAAATAACTACACACAAGCTAGAATTTGGGGAGAAAAGTACTT

TGGTAAGAACTTTAACAGATTGGTGAAGGTTAAGACAAAGGCAGACCCAAACAATT

TCTTTAGAAACGAACAATCAATTCCACCATTGCCACCAAGACATCATTAA

The following plasmids were constructed using modern molecular biology techniques described herein.

TABLE 1

| Plasmid | Seq ID | Important Features |
|---|---|---|
| pLD1 | 157 | Empty URA3 multi integration |
| pLD10 | 158 | PPOX4-CvTKS1 URA3 multi integration |
| pLD12 | 159 | PPOX4-CvOAC1 URA3 multi integration |
| pLD14 | 160 | PPOX4-CvOAC1P URA3 multi integration |

TABLE 1-continued

| Plasmid | Seq ID | Important Features |
|---|---|---|
| pLD16 | 161 | PPOX4-CvHXS1 URA3 multi integration |
| pLD19 | 180 | PPOX4-PTS1 URA3 multi integration |
| pLD20 | 162 | PPOX4-CvCBD1 URA3 multi integration |
| pLD22 | 163 | PPOX4-CvACO1P URA3 multi integration |
| pLD24 | 164 | PPOX4-CvTKS1P URA3 multi integration |
| pLD26 | 181 | PPOX4-PTS1dN URA3 multi integration |
| pLD56 | 165 | PPOX4-CvPTS2 URA3 multi integration |
| pLD111 | 169 | PPOX4-CvTHC1 URA3 multi integration |
| pLD112 | 170 | PPOX4-CvCBC1 URA3 multi integration |

TABLE 1-continued

| Plasmid | Seq ID | Important Features |
|---|---|---|
| pLD125 | 172 | PPOX4-CvCBD1dNS1 URA3 multi integration |
| pLD127 | 173 | PPOX4-CvCBD1dNV1 URA3 multi integration |
| pLD139 | 179 | PPOX4-CvCBD1dNP1 URA3 multi integration |

Example 2—Construction of Plasmids for *Yarrowia lipolytica*

Protein sequence was reverse translated into DNA sequence to reflect the use of a universal genetic code and codon usage in *Yarrowia lipolytica*, reduction of secondary structure, and absence of certain restriction enzyme recognition sites. Other DNA sequences that encode the same protein may also be used. The following sequences were used as open reading frames for genes used to genetically modify *Yarrowia lipolytica*.

```
YlACO1P Gene
                                        (SEQ ID NO: 112)
ATGACCGAAGTAGTTGACAGAGCCTCATCCCCCGC

ATCCCCTGGCTCAACTACGGCCGCCGCAGACGGTG

CTAAGGTGGCCGTCGAGCCCCGAGTAGATGTGGCT

GCGCTGGGAGAGCAGCTGCTGGGCCGATGGGCTGA

TATCCGTCTCCACGCCCGGGACCTTGCGGGACGAG

AGGTAGTTCAGAAGGTGGAGGGTCTGACTCATACA

GAGCACCGCTCTCGCGTCTTTGGCCAGCTCAAGTA

CTTGGTCGATAACAACGCAGTTCACCGAGCCTTTC

CTTCTCGACTGGGTGGTAGTGACGACCACGGCGGA

AACATCGCTGGTTTTGAGGAGCTTGTCACGGCGGA

CCCCTCCCTCCAGATCAAGGCCGGCGTCCAGTGGG

GACTGTTCGGCTCCGCTGTTATGCACTTGGGAACT

AGGGAGCACCACGACAAGTGGCTCCCAGGCATCAT

GTCTCTGGAAATCCCTGGTTGCTTTGCCATGACTG

AGACTGGCCATGGCTCCGATGTCGCTTCCATTGCT

ACAACGGCCACCTATGATGAGGAAACCCAGGAGTT

CGTTATTGACACCCCGTTCCGAGCCGCCTGGAAGG

ACTACATTGGAAACGCCGCTAACGACGGTTTGGCC

GCTGTCGTGTTTGCCCAACTGATTACTCGAAAGGT

TAACCATGGAGTGCACGCCTTCTACGTCGATCTGA

GAGATCCCGCCACCGGAGACTTTCTCCCTGGTATT

GGTGGAGAGGACGACGGTATTAAGGGGGGACTAAA

CGGAATTGATAACGGACGTCTCCATTTCACCAATG

TTCGCATTCCCCGAACCAACCTGCTTAACCGTTAC

GGCGATGTTGCCGTCGATGGCACCTACAGCTCAAC

                -continued
CATCGAATCTCCGGGGCGAAGATTCTTTACAATGC

TAGGTACGCTGGTCCAGGGCCGAGTCAGCCTGGAC

GGTGCTGCAGTGGCTGCATCGAAGGTTGCTCTGCA

ATCCGCCATCCACTACGCCGCTGAGCGAAGACAGT

TCAACGCCACTTCGCCCACAGAGGAGGAGGTGCTC

CTGGATTACCAGCGACACCAGCGGCGCCTCTTTAC

CCGACTCGCCACCACCTACGCCGCATCGTTCGCCC

ATGAGCAACTGCTGCAGAAATTCGACGACGTGTTC

TCGGGTGCTCATGATACTGACGCCGACCGTCAGGA

CCTTGAGACACTGGCTGCTGCTCTGAAGCCCCTTT

CTACCTGGCATGCTCTCGATACCCTACAAGAGTGC

CGAGAAGCGTGTGGGGGTGCAGGTTTTCTGATTGA

GAACCGATTCGCTTCTCTCCGGGCCGATCTCGACG

TCTACGTGACCTTCGAAGGAGACAACACCGTGCTT

CTTCAGTTGGTGGCCAAGAGGCTGCTCGCTGACTA

TGCTAAGGAGTTCCGAGGTGCCAACTTCGGCGTGC

TCGCGCGGTACGTCGTGGACCAGGCTGCCGGAGTC

GCGCTACACCGAACCGGACTGCGACAGGTCGCTCA

GTTCGTGGCCGACAGTGGATCTGTCCAGAAATCTG

CTCTTGCCCTCCGAGACGAAGAAGGTCAGCGAACT

CTGCTGACCGACAGAGTCCAGTCCATGGTTGCAGA

GGTTGGCGCTGCTCTCAAAGGCGCGGGCAAGCTCC

CCCAGCACCAGGCGGCAGCACTGTTCAATCAGCAT

CAAAACGAACTGATCGAGGCTGCCCAGGCCCACGC

TGAGCTTTTACAGTGGGAGGCCTTTACTGAGGCTT

TGGCCAAGGTGGACGACGCTGGCACTAAGGAAGTG

TTGACCCGATTGCGTGACCTTTTTGGTCTGTCCCT

TATCGAGAAGCACCTCAGCTGGTATCTGATGAACG

GTAGGCTCTCGATGCAGAGAGGCCGAACGGTCGGC

ACTTACATTAATCGTCTTCTCGTTAAGATCCGACC

ACACGCACTTGATCTGGTTGATGCCTTCGGCTACG

GAGCCGAGCACCTTCGGGCCGCTATCGCCACCGGC

GCTGAGGCCACCCGACAGGACGAGGCCCGAACCTA

CTTCAGACAGCAACGAGCCTCCGGTAGCGCCCCTG

CTGACGAGAAGACACTCCTCGCTATCAAGGCCGGC

AAGTCTCGGGGACGACGAGCCAAACTGTAA

YlHXS1 Gene
                                        (SEQ ID NO: 113)
ATGGGAAAGAATTACAAAAGTCTAGATTCTGTCGT

TGCCAGTGACTTCATCGCGTTAGGCATTACATCCG

AGGTCGCTGAGACTCTGCACGGACGGCTTGCCGAG

ATTGTGTGCAACTACGGAGCCGCTACCCCTCAGAC
```

TTGGATTAACATCGCCAACCACATTCTGTCGCCGG
ACCTCCCCTTCTCTTTGCACCAGATGTTATTCTAC
GGATGCTACAAGGATTTTGGCCCTGCACCTCCTGC
CTGGATTCCGGACCCCGAAAAAGTCAAGTCCACCA
ACCTAGGTGCCCTGCTGGAAAAGCGAGGAAAGGAG
TTCCTTGGTGTCAAGTACAAGGACCCCATTTCTTC
TTTTTCTCATTTCCAGGAATTTTCGGTGCGTAATC
CTGAGGTGTATTGGCGAACTGTGCTCATGGACGAG
ATGAAAATCTCCTTCAGCAAGGACCCAGAGTGTAT
CCTGCGACGAGACGACATTAACAACCCAGGAGGCT
CGGAGTGGCTTCCCGGCGGATACCTAAACTCAGCT
AAGAATTGTCTCAACGTGAACTCTAACAAGAAGTT
GAACGACACCATGATCGTGTGGCGTGACGAAGGCA
ACGACGACCTGCCCCTGAACAAGTTGACTCTGGAC
CAGCTGCGAAAGAGGGTCTGGTTGGTTGGCTACGC
CCTCGAAGAGATGGGCTTAGAGAAGGGTTGCGCTA
TTGCTATTGATATGCCCATGCACGTCGATGCTGTA
GTGATCTACCTTGCCATTGTGTTAGCCGGTTACGT
GGTCGTATCGATTGCCGATTCGTTCTCCGCTCCGG
AGATTTCCACCCGACTCAGACTTAGCAAGGCCAAG
GCAATCTTTACTCAAGATCACATCATCCGAGGTAA
GAAGAGAATCCCTCTCTATTCTCGCGTGGTTGAGG
CCAAGTCCCCAATGGCTATCGTCATACCTTGCAGC
GGATCAAACATCGGGGCTGAGCTACGGGACGGTGA
TATCTCCTGGGATTACTTCCTGGAGCGAGCCAAAG
AGTTCAAGAACTGCGAGTTTACAGCGCGTGAGCAG
CCCGTCGATGCCTACACGAACATTCTATTCTCATC
GGGCACAACGGGAGAGCCCAAGGCCATCCCCTGGA
CCCAAGCTACCCCCTTGAAAGCTGCCGCTGATGGT
TGGTCCCATCTCGACATCAGAAAAGGCGATGTGAT
CGTTTGGCCCACTAACCTGGGCTGGATGATGGGTC
CTTGGCTGGTATATGCCAGCCTACTGAACGGCGCT
TCAATCGCACTGTACAACGGATCTCCACTCGTCAG
CGGCTTTGCCAAGTTTGTTCAAGACGCCAAAGTCA
CCATGCTGGGTGTTGTTCCTTCAATCGTGCGAAGT
TGGAAGAGTACCAACTGTGTCTCTGGATACGACTG
GAGCACCATTCGATGCTTCAGTTCCTCCGGCGAGG
CTTCCAACGTTGATGAGTACCTCTGGCTTATGGGT
CGTGCGAATTACAAGCCTGTGATCGAGATGTGTGG
TGGAACAGAAATTGGTGGTGCTTTTTCGGCCGGGT

CCTTTCTTCAGGCTCAGTCTCTCTCCTCTTTCTCT
TCCCAGTGTATGGGATGCACCCTGTATATTCTCGA
CAAGAACGGTTACCCCATGCCGAAGAATAAACCCG
GTATTGGGGAGCTTGCTCTTGGCCCCGTCATGTTT
GGTGCATCGAAGACCCTCCTGAACGGAAACCATCA
CGACGTCTACTTCAAGGGCATGCCCACACTTAACG
GCGAAGTTCTTCGGCGACATGGAGACATTTTCGAA
CTTACATCGAACGGATACTACCACGCCCACGGGCG
AGCAGATGATACGATGAACATCGGGGGCATCAAGA
TATCTTCTATCGAGATTGAAAGAGTGTGTAACGAG
GTAGACGACCGCGTCTTCGAGACTACTGCGATCGG
CGTCCCCCCCCTGGGCGGTGGCCCGGAGCAGCTAG
TCATTTTTTTTGTGCTCAAGGACTCTAACGACACG
ACCATCGACCTCAATCAGCTGCGACTCTCCTTCAA
CCTTGGATTGCAGAAGAAGCTGAACCCTCTCTTCA
AGGTCACTCGGGTTGTTCCCTTGTCCTCTCTTCCT
CGAACCGCCACCAACAAGATTATGCGACGAGTGCT
CCGACAGCAGTTCTCCCACTTCGAGTAA

YlTKS1 Gene (SEQ ID NO: 114)

ATGAATCATCTAAGAGCCGAAGGACCAGCAAGTGT
ACTCGCTATTGGTACTGCTAACCCCGAGAACATTC
TTATTCAGGATGAGTTCCCGGACTACTATTTCAGG
GTTACCAAGAGCGAGCATATGACCCAGCTTAAAGA
GAAGTTCCGCAAGATATGCGACAAGTCCATGATCC
GAAAGCGGAACTGCTTTCTCAATGAGGAGCACTTG
AAGCAAAACCCCCGACTGGTTGAGCACGAGATGCA
GACCTTGGACGCGCGACAAGACATGCTCGTCGTCG
AGGTGCCCAAACTCGGTAAGGATGCTTGCGCTAAG
GCCATTAAGGAGTGGGGTCAGCCCAAGTCGAAGAT
TACCCACCTAATCTTCACCTCCGCAAGCACTACAG
ACATGCCCGGTGCAGACTACCACTGTGCCAAGCTG
CTCGGACTGTCACCGTCGGTCAAGCGAGTGATGAT
GTACCAGCTCGGCTGTTACGGGGGTGGAACCGTTC
TCCGTATCGCCAAGGATATCGCTGAGAACAACAAA
GGAGCTCGTGTCCTGGCTGTGTGTTGCGACATCAT
GGCCTGCTTGTTCAGAGGCCCTAGTGATTCCGATC
TGGAATTACTTGTCGGTCAGGCCATCTTTGGAGAT
GGCGCCGCCGCTGTCATCGTGGGTGCCGAACCCGA
CGAGTCTGTTGGAGAAAGACCCATCTTTGAGCTTG
TCTCCACGGGCCAGACCATCCTCCCTAACAGCGAG
GGCACAATTGGAGGCCATATTCGAGAGGCCGGTCT

-continued

GATTTTTGACCTGCATAAGGACGTGCCTATGCTGA
TTTCGAACAACATCGAGAAGTGTCTCATCGAGGCC
TTCACTCCCATCGGCATTTCGGACTGGAACTCAAT
CTTCTGGATCACCCACCCAGGAGGCAAGGCGATTC
TGGATAAAGTTGAGGAAAAGCTCGACCTTAAGAAG
GAGAAGTTTGTGGATTCTCGACACGTCCTGTCTGA
ACACGGTAACATGTCTTCCTCTACTGTCCTGTTCG
TAATGGACGAGCTTCGAAAGCGATCTCTGGAGGAA
GGAAAGTCCACGACCGGCGACGGTTTTGAGTGGGG
CGTGCTGTTCGGGTTCGGTCCTGGCCTCACTGTGG
AGCGAGTTGTTGTCCGGTCCGTGCCTATTAAGTAC
TAA

YlTKS1P Gene (SEQ ID NO: 115)

ATGAATCATCTAAGAGCCGAAGGACCAGCAAGTGT
ACTCGCTATTGGTACTGCTAACCCCGAGAACATTC
TTATTCAGGATGAGTTCCCGGACTACTATTTCAGG
GTTACCAAGAGCGAGCATATGACCCAGCTTAAAGA
GAAGTTCCGCAAGATATGCGACAAGTCCATGATCC
GAAAGCGGAACTGCTTTCTCAATGAGGAGCACTTG
AAGCAAAACCCCCGACTGGTTGAGCACGAGATGCA
GACCTTGGACGCGCGACAAGACATGCTCGTCGTCG
AGGTGCCCAAACTCGGTAAGGATGCTTGCGCTAAG
GCCATTAAGGAGTGGGGTCAGCCCAAGTCGAAGAT
TACCCACCTAATCTTCACCTCCGCAAGCACTACAG
ACATGCCCGGTGCAGACTACCACTGTGCCAAGCTG
CTCGGACTGTCACCGTCGGTCAAGCGAGTGATGAT
GTACCAGCTCGGCTGTTACGGGGGTGGAACCGTTC
TCCGTATCGCCAAGGATATCGCTGAGAACAACAAA
GGAGCTCGTGTCCTGGCTGTGTGTTGCGACATCAT
GGCCTGCTTGTTCAGAGGCCCTAGTGATTCCGATC
TGGAATTACTTGTCGGTCAGGCCATCTTTGGAGAT
GGCGCCGCCGCTGTCATCGTGGGTGCCGAACCCGA
CGAGTCTGTTGGAGAAAGACCCATCTTTGAGCTTG
TCTCCACGGGCCAGACCATCCTCCCTAACAGCGAG
GGCACAATTGGAGGCCATATTCGAGAGGCCGGTCT
GATTTTTGACCTGCATAAGGACGTGCCTATGCTGA
TTTCGAACAACATCGAGAAGTGTCTCATCGAGGCC
TTCACTCCCATCGGCATTTCGGACTGGAACTCAAT
CTTCTGGATCACCCACCCAGGAGGCAAGGCGATTC
TGGATAAAGTTGAGGAAAAGCTCGACCTTAAGAAG

-continued

GAGAAGTTTGTGGATTCTCGACACGTCCTGTCTGA
ACACGGTAACATGTCTTCCTCTACTGTCCTGTTCG
TAATGGACGAGCTTCGAAAGCGATCTCTGGAGGAA
GGAAAGTCCACGACCGGCGACGGTTTTGAGTGGGG
CGTGCTGTTCGGGTTCGGTCCTGGCCTCACTGTGG
AGCGAGTTGTTGTCCGGTCCGTGCCTATTAAGTAC
GGAAGAAGGGCAAAGTTGTAA

YlOAC1 Gene (SEQ ID NO: 116)

ATGGCCGTCAAACACCTTATTGTCCTCAAGTTCAA
AGATGAGATCACTGAAGCCCAGAAGGAGGAGTTTT
TCAAGACCTACGTCAATTTGGTCAACATCATTCCA
GCAATGAAGGATGTGTACTGGGGCAAGGACGTGAC
CCAGAAGAACAAGGAAGAGGGTTATACCCATATCG
TTGAGGTTACGTTCGAGTCTGTGGAGACAATCCAA
GACTACATCATTCACCCCGCTCACGTGGGCTTTGG
AGACGTTTACAGATCCTTCTGGGAGAAGCTCCTGA
TTTTTGACTACACTCCTCGAAAGCTGAAGCCCAAG
TAA

YlOAC1P Gene (SEQ ID NO: 117)

ATGGCCGTCAAACACCTTATTGTCCTCAAGTTCAA
AGATGAGATCACTGAAGCCCAGAAGGAGGAGTTTT
TCAAGACCTACGTCAATTTGGTCAACATCATTCCA
GCAATGAAGGATGTGTACTGGGGCAAGGACGTGAC
CCAGAAGAACAAGGAAGAGGGTTATACCCATATCG
TTGAGGTTACGTTCGAGTCTGTGGAGACAATCCAA
GACTACATCATTCACCCCGCTCACGTGGGCTTTGG
AGACGTTTACAGATCCTTCTGGGAGAAGCTCCTGA
TTTTTGACTACACTCCTCGAAAGCTGAAGCCCAAG
GGAAGAAGGGCAAAGTTGTAA

YlPTS2 Gene (SEQ ID NO: 118)

ATGGGCCTCTCTCTAGTATGTACCTTCTCTTTCCA
GACCAACTATCACACTCTACTGAACCCCCATAACA
AGAACCCTAAAAATTCTCTTCTCAGTTACCAGCAC
CCCAAGACGCCTATCATTAAGTCCTCCTACGACAA
CTTTCCCTCTAAGTACTGCCTGACCAAAAACTTCC
ATCTCCTGGGACTGAACTCTCATAACAGAATTAGT
AGCCAGTCCCGATCTATCCGAGCTGGCTCTGACCA
GATTGAGGGCTCCCCTCACCATGAATCCGACAACA
GCATCGCTACCAAGATTTTGAATTTTGGTCACACA
TGCTGGAAGCTCCAGCGACCGTACGTCGTGAAGGG
TATGATCTCGATTGCCTGTGGACTGTTCGGACGTG

-continued

AGCTTTTTAATAATCGACACTTGTTTTCATGGGGC
CTCATGTGGAAGGCTTTTTTCGCCCTCGTGCCCAT
TCTGTCTTTCAACTTCTTTGCCGCTATTATGAACC
AAATCTACGACGTTGATATTGATAGGATCAACAAG
CCTGACCTGCCGCTCGTCTCGGGGGAGATGTCTAT
CGAGACAGCGTGGATTCTTTCGATTATCGTCGCGC
TGACTGGCCTTATCGTTACCATAAAGTTGAAGTCT
GCACCCCTCTTCGTGTTTATCTACATTTTCGGTAT
TTTTGCTGGATTCGCGTACTCCGTTCCCCCTATCA
GATGGAAGCAGTACCCCTTTACTAACTTTCTGATT
ACTATCAGCAGCCACGTCGGTTTAGCCTTTACCTC
ATATTCGGCCACCACCAGTGCACTGGGCCTCCCCT
TCGTCTGGCGACCTGCATTTTCATTCATCATCGCC
TTCATGACTGTGATGGGTATGACCATCGCTTTCGC
TAAGGACATCTCCGACATCGAGGGTGATGCTAAAT
ATGGAGTGTCCACCGTGGCCACTAAGCTGGGAGCC
CGGAACATGACGTTCGTCGTCTCTGGTGTTCTGCT
CCTTAACTACTTGGTTTCGATCTCCATTGGCATTA
TCTGGCCACAAGTCTTCAAGTCCAACATTATGATT
CTGTCCCACGCCATTCTTGCCTTTTGCCTGATCTT
CCAGACACGCGAACTCGCTCTCGCTAACTACGCCT
CCGCCCCATCGCGACAGTTCTTCGAGTTCATCTGG
CTGCTTTACTACGCCGAGTACTTCGTTTACGTGTT
CATCTAA

YlCBD1 Gene (SEQ ID NO: 119)

ATGAAGTGTTCGACGTTTTCTTTTTGGTTTGTTTG
TAAAATCATTTTCTTTTTCTTTTCTTTCAACATCC
AAACGTCGATCGCAAACCCTAGAGAGAACTTTCTT
AAGTGCTTCTCGCAGTACATCCCTAATAACGCTAC
CAACCTTAAGCTGGTGTACACCCAGAACAACCCTC
TTTACATGTCTGTTCTAAACAGCACCATCCACAAT
CTTAGATTCACATCAGACACCACTCCCAAGCCGCT
CGTCATCGTGACCCCGAGTCATGTGTCCCATATCC
AAGGCACTATCCTGTGCTCTAAAAAGGTCGGTCTG
CAGATTCGGACTCGCTCCGGTGGACATGATTCGGA
GGGCATGTCCTACATTAGCCAGGTCCCCTTTGTGA
TCGTGGACCTGAGGAACATGCGGTCTATTAAGATT
GATGTGCACTCACAGACCGCTTGGGTCGAGGCTGG
TGCGACATTGGGTGAGGTGTACTACTGGGTGAACG
AGAAGAACGAGAACCTGAGCCTCGCCGCTGGCTAC

-continued

TGTCCCACCGTTTGTGCCGGTGGACACTTCGGCGG
AGGCGGATACGGTCCACTTATGCGAAACTACGGGC
TCGCAGCTGATAATATCATCGACGCACACCTTGTT
AACGTTCACGGCAAGGTGCTGGACCGAAAAAGCAT
GGGTGAGGACCTATTTTGGGCCTTGCGAGGCGGTG
GTGCCGAATCCTTCGGAATTATCGTGGCCTGGAAG
ATCCGACTGGTCGCTGTGCCAAAGTCCACTATGTT
CTCCGTCAAGAAAATTATGGAGATCCACGAACTCG
TAAAGCTCGTCAATAAGTGGCAGAACATCGCCTAC
AAGTATGACAAGGATCTGCTGCTCATGACTCACTT
CATCACGCGAAACATTACAGACAACCAGGGAAAGA
ACAAGACCGCTATCCATACCTACTTCTCCTCTGTC
TTCCTTGGGGGTGTCGATTCCCTCGTTGATCTCAT
GAACAAATCTTTTCCAGAGCTCGGAATCAAGAAGA
CCGACTGCCGACAGCTCTCTTGGATCGACACCATT
ATTTTCTACTCAGGAGTCGTAAACTACGATACTGA
CAACTTTAACAAGGAGATTCTGTTAGATCGATCGG
CCGGCCAGAACGGTGCCTTCAAGATCAAGCTCGAC
TATGTCAAAAAGCCCATTCCTGAATCCGTCTTCGT
TCAAATTCTTGAAAAGTTGTACGAGGAGGATATCG
GCGCCGGAATGTACGCGCTGTACCCCTACGGTGGC
ATTATGGACGAGATTTCTGAAAGTGCTATTCCCTT
CCCCCACCGTGCTGGCATTCTGTATGAGCTGTGGT
ACATTTGCTCCTGGGAAAAGCAGGAGGACAACGAG
AAGCACTTGAACTGGATACGAAACATTTACAATTT
CATGACCCCCTATGTTTCGAAGAACCCTCGACTGG
CCTACCTGAATTACCGCGACCTCGACATCGGAATT
AACGACCCTAAGAACCCCAATAACTATACTCAGGC
CAGAATCTGGGGCGAGAAGTACTTCGGCAAGAACT
TTGACCGTCTGGTTAAGGTCAAGACCCTCGTGGAC
CCTAACAACTTCTTCCGAAACGAGCAGTCTATCCC
CCCTCTGCCCCGACACCGGCATTAA

YlTHC1 Gene (SEQ ID NO: 120)

ATGAATTGTTCAGCTTTCTCTTTTTGGTTTGTCTG
TAAGATCATTTTCTTCTTTCTATCCTTTCACATCC
AAATTTCCATAGCCAACCCTCGTGAGAACTTCCTT
AAGTGCTTTTCCAAGCACATTCCAAATAACGTCGC
CAATCCCAAGCTGGTGTACACGCAGCATGACCAGC
TCTACATGTCGATCCTCAATTCCACCATTCAAAAC
CTTAGATTCATTAGTGACACCACTCCCAAGCCCCT
AGTCATTGTCACCCCTTCGAACAACTCGCATATTC

-continued

```
AGGCAACTATTCTCTGCTCCAAGAAGGTTGGTTTA
CAGATCCGAACCCGGTCAGGTGGTCACGACGCTGA
GGGCATGTCTTACATTTCCCAGGTCCCCTTTGTGG
TGGTCGATCTGCGCAACATGCACTCCATTAAAATC
GACGTCCACTCGCAGACTGCCTGGGTCGAGGCTGG
AGCCACCCTTGGCGAGGTCTACTACTGGATTAACG
AGAAGAACGAAAACCTGTCGTTCCCTGGCGGCTAC
TGTCCGACTGTTGGAGTCGGCGGACACTTTTCTGG
TGGCGGATATGGTGCTCTCATGCGAAACTACGGAC
TGGCGGCAGACAACATCATCGATGCCCACCTTGTG
AACGTTGACGGTAAGGTACTGGACCGAAAGTCTAT
GGGCGAGGACTTGTTTTGGGCCATCCGAGGTGGAG
GTGGTGAGAACTTCGGGATCATCGCCGCCTGGAAG
ATCAAGCTGGTGGATGTGCCCAGTAAGTCTACCAT
TTTTAGCGTGAAGAAGAACATGGAGATCCACGGGC
TGGTGAAGCTGTTCAACAAGTGGCAGAATATTGCG
TACAAATACGACAAGGACCTGGTGCTTATGACCCA
TTTCATCACCAAGAACATCACGGATAACCACGGTA
AAAACAAGACTACTGTTCACGGTTACTTCTCTTCA
ATTTTCCATGGTGGTGTGGATTCCCTCGTTGATTT
GATGAACAAGTCCTTCCCAGAGCTGGGCATTAAGA
AGACAGACTGCAAGGAATTTAGCTGGATTGATACC
ACCATCTTCTACTCTGGAGTTGTCAACTTCAACAC
CGCAAACTTCAAGAAGGAAATCCTCTTGGACCGAT
CTGCCGGCAAGAAGACAGCTTTTTCGATTAAACTG
GATTACGTGAAGAAGCCCATCCCTGAGACAGCTAT
GGTCAAGATCCTTGAAAAACTTTATGAGGAGGACG
TCGGAGCCGGAATGTACGTTCTCTATCCTTACGGC
GGCATCATGGAGGAAATTTCTGAGTCTGCTATCCC
CTTCCCCCATCGAGCCGGAATCATGTACGAGCTGT
GGTACACCGCTAGTTGGGAGAAGCAGGAGGATAAC
GAGAAACATATCAATTGGGTCCGTAGCGTATACAA
TTTCACGACACCCTACGTGTCCCAGAACCCTCGAC
TCGCTTACCTGAACTATAGGGACCTGGACCTCGGC
AAGACTAACCACGCTAGCCCGAACAACTACACCCA
GGCCAGAATTTGGGGCGAAAAGTACTTCGGAAAGA
ACTTCAACCGACTCGTTAAGGTTAAGACCAAAGTT
GACCCCAACAACTTTTTCCGGAACGAGCAGTCCAT
CCCTCCACTCCCTCCCCACCATCACTGA
```

The following plasmids were constructed using modern molecular biology techniques described herein.

TABLE 2

| Plasmid | Seq ID | Important Features |
|---|---|---|
| pLD87 | 166 | KU70 Disruption cassette with LoxP-URA3-LoxP |
| pLD101 | 167 | POX5 Disruption cassette with LoxP-URA3-LoxP |
| pLD102 | 168 | POX3 Disruption cassette with LoxP-URA3-LoxP |
| pLD131 | 174 | CEN-ARS LEU2 PPOX2-PTS2 |
| pLD132 | 175 | CEN-ARS URA3 PPOX-CBD1 |
| pLD135 | 176 | POX3 Disruption cassette URA3 ACO1P |
| pLD137 | 177 | CEN-ARS LEU |
| pLD138 | 178 | CEN-ARS URA |

Example 3—Transformation of *Candida viswanathii*

A starting *Candida viswanathii* strain, such as the uracil auxotroph produced in Example 2, is propagated in a 5 mL YPD culture that is incubated overnight at 30° C., 250 rpm. The next day, a 50 mL culture is initiated with part of the 5 mL YPD overnight culture and grown for a few hours to an OD (600 nm) absorbance of 1.0-2.0. The resulting cells are pelleted by centrifugation at 1000×g for 10 minutes. The cells are washed by resuspension in sterile water, centrifuged (10000×g, 1 min) and resuspended in 1 mL sterile TE/LiOAC solution, pH 7.5. The cells were centrifuged (10000×g, 1 min) again and resuspended in 500 μl of TE/LiOAC solution and incubated with shaking at 30° C. for 30 minutes.

For each transformation reaction, 50 μl aliquots of cell suspension are to be used. To 50 μl of cells, add 5 μl of carrier DNA (boiled and cooled salmon sperm DNA, 10 mg/mL) and incubate for 1-2 minutes at room temperature. The DNA that is to be used to transform the yeast is optimally inserted into the yeast genome as linearized DNA. Therefore, 2-5 μg of linearized DNA for integration is added to the mixture of cells and salmon sperm DNA. To this mixture, 300 μl of sterile PEG solution (40% PEG 3500, 1×TE, 1×LiOAC) is added and the final mixture is incubated at 30° C. for 30-60 minutes while being gently agitated. The cells are then pelleted by centrifugation at 1000×g 30 seconds, resuspended in 500 μl of YPD media and incubated at 30° C., 250 rpm for 1-2 hours.

After recovery in YPD the cells are then pelleted by centrifugation and washed twice with 1 mL of 1×TE before plating cells on the appropriate auxotrophic or selective media to identify transformants.

Example 4—Transformation of *Yarrowia lipolytica*

A starting *Yarrowia lipolytica* strain is propagated in 2 mL YPD culture that is incubated overnight (~20 hrs) at 30° C., 250 rpm. the resulting cells are pelleted by centrifugation at 6000×g. The cells are washed by resuspension in 250 μl of 0.3 M Li Acetate 10 mM Tris-HCl pH 8.0. The cells are then pelleted and resuspended in 100 μl of 0.3 M Li Acetate 10 mM Tris-HCl pH 8.0. To the cells 5 μl of salmon sperm DNA solution (8 mg/ml ssDNA 10 mM Tris-HCL pH 8.0 1 mM EDTA) is added, 1 to 10 μl of DNA (up to 1 μg) and 15 μl of triacetic solution (95 μl of triacetin+5 μl beta-mercaptoethanol). Cells are mixed by pipetting and incubated 30 min at room temperature.

150 μl of PEG solution is added (40% PEG 3500, 1×TE, 1×LiOAC) and mix via pipetting. Incubate at 30 min at 30 min at room temperature. Heat shock at 37° C. for 15 to 25 minutes in water batch. Add 1 ml water, mix well and then pellet at 6000×g. Decant, resuspend in 100 μl of TE (10 mM Tris-HCl pH 8.0+1 mM EDTA and plate in desired media.

Example 5—Production of an Uracil Auxotroph of ATCC 20962

ATCC 20962 is a prototrophic yeast strain that is able to grow in the absence of supplemented uracil. In order to utilize this strain for experiments, it must first be made auxotrophic for uracil. In the case of ATCC 20962, the URA3 gene must be inactivated to make the strain auxotrophic. This will allow for uracil auxotrophy to be rescued by the introduction of a functional URA3 gene via transformation, as described in Example 3.

To convert ATCC 20962 to a uracil auxotroph, an individual colony of the strain was grown in 5 mL of YPD overnight at 30° C., shaken at 250 rpm. From the overnight culture, 20 and 100 μl of culture were plated on plates containing 5-FOA (recipe). The chemical 5-FOA is converted into a toxic compound, fluorodeoxyuridine, by the enzyme encoded by the URA3 gene. Therefore, growth on 5-FOA selects for uracil auxotrophs that have spontaneously produced loss-of-function ura3 mutants. The plate was placed at 30° C. for 3-6 days to produce colonies. The resulting colonies were tested for growth on media lacking uracil, e.g. synthetic complete yeast media lacking uracil and 5-FOA plates. One of these colonies did not grow on media lacking uracil but grew on 5-FOA plates, it was confirmed as uracil auxotrophs and named LCV32.

Example 6—Genomic DNA Extraction for PCR Analysis

An overnight culture in YPD or selective media was grown at 30° C. 225 rpm. Cells were pelleted in a screw-cap 1.5 ml microcentrifuge tube. Supernatant was decanted and cells resuspended in 250 μl of extraction buffer (100 mM NaCl, 2% Triton X-100, 1% SDS, 10 mM Tris-Cl, 1 mM EDTA pH 8.0). 200 μl of acid washed glass-beads (425-600), and 300 μl of phenol:chorofom:isoamyl alcohol solution (25:24:1 ratio) that has been equilibrated with 100 mM Tris Cl pH 8.0 is added and vortexed for 5 min. The microcentrifuge is then centrifuge and the supernatant is removed. The supernatant then is extracted with 300 μl of chloroform. The aqueous solution is then transferred to a new microcentrifuge tube. 1.2 ml of ice-cold ethanol is added to the microcentrifuge tube. The tube is then mixed and placed at −20° C. or colder for 1 hr. The DNA is then pelleted by centrifugation at 10,000×G. The pellets are then air-dried and resuspended in 500 μl of TE (10 mM Tris-HCl 1 mM EDTA pH 8.0).

Example 7—Verification of Integrations in *Candida viswanathii*

To verify the integration of exogenous genes into the genome of *Candida viswanathii* a PCR based method was developed where one or two of different exogenous genes were amplified in the same reaction as a section of the actin gene that serves as a control.

TABLE 3

| Gene | Forward Primer | Reverse Primer | Length |
|---|---|---|---|
| CvACT1 | 4 | 5 | 859 |
| CvHXS1 | 6 | 7 | 612 |
| CvTKS1 | 8 | 9 | 617 |
| CvOAC1 | 10 | 11 | 461 |
| CvPTS1 | 12 | 13 | 611 |
| CvCBD1 | 14 | 15 | 411 |
| CvACO1 | 16 | 17 | 414 |
| CvPTS2 | 41 | 42 | 616 |
| CvTHC1 | 168 | 169 | 397 |

For a 25 μl reaction, 12.5 μl of the 2× Master Mix, 0.5 μl of primers (10 μM of each), 1 μl of DNA template, and 11 μl of water. Standard running reactions are 95° C. for 2 min, 30 cycles of 95° C. for 30 sec, 55° C. for 30 sec, and 72° C. for 1 min, and a final step of 72° C. for 2 min. 10 μl to 20 μl is loaded in a 1.4 to 2.0% agarose TAE gel.

TABLE 4

| Primer number | Sequence |
|---|---|
| 4 | CCCAATTCCTGTGGTGGGTTGATTCG (SEQ ID NO: 121) |
| 5 | CTCTCAATTCGTTGTAGAAGGTGTGGTGC (SEQ ID NO: 122) |
| 6 | CTTTGGACTCAGTTGTGGCTAGTGACTTC (SEQ ID NO: 123) |
| 7 | GATCAAGAGTCAATTTATTCAATGGGAGATCGTC (SEQ ID NO: 124) |
| 8 | GAGCAGAAGGACCCGCATCAGTG (SEQ ID NO: 125) |
| 9 | GTCACCAAAAATTGCCTGTCCGACAAGC (SEQ ID NO: 126) |
| 10 | CACGACATAATGGCAGTCAAACACCTAATAG (SEQ ID NO: 127) |
| 11 | CTAGTTTTGTGTTCGGAGTATGCATACAACG (SEQ ID NO: 128) |
| 12 | CTACCACACCCTCCTAAACCCTCAC (SEQ ID NO: 129) |
| 13 | CGAAGCAGTACCCGAATATATATAATGGACC (SEQ ID NO: 130) |
| 14 | CCTTCAACATTCAGACATCAATCGCCAAC (SEQ ID NO: 131) |
| 15 | CACCCAAGGTTGCCCCTGCTTC (SEQ ID NO: 132) |
| 16 | GAGCAAGTTCCCCAGCAAGTCCAG (SEQ ID NO: 133) |
| 17 | CATGATGTTCACGGGTTCCCAAGTGC (SEQ ID NO: 134) |
| 41 | CATACATGCTGGAAGCTACAGCGAC (SEQ ID NO: 135) |
| 42 | CAGTACTCACCCCATATTTTGCATCGC (SEQ ID NO: 136) |

TABLE 4-continued

| Primer number | Sequence |
|---|---|
| 168 | GTTAAGTTGTTTAACAAGTGGCAAAACATTGCATAC (SEQ ID NO: 137) |
| 169 | CCAAAATCTTAACCATTGCTGTTTCTGGAATTGG (SEQ ID NO: 138) |
| 170 | GATTTGTTTTGGGCAATTAGAGGAGGTGG (SEQ ID NO: 139) |
| 171 | CAACTCCTGAGTAGAAAATGGTTGTATCGATC (SEQ ID NO: 140) |

Example 8—Construction of Yeast Strains in *Candida viswanathii*

The following strains were constructed by transformation as described in the previous example with a PacI digested plasmid as shown in Table 5. Ura+ strains were tested for successful integration of the gene or genes of interest by using the PCR-based method described above. A correct strain was named according to Table 5.

TABLE 5

| Strain | Parental Strain | Plasmid Transformed |
|---|---|---|
| LCV13 | ATCC20913 | pLD1 |
| LCV14 | ATCC20913 | pLD1 |
| LCV22 | ATCC20913 | pLD10, pLD12, pLD16 |
| LCV34 and LCV35 | LCV32 | pLD22 |
| LCV36 | LCV32 | pLD14, pLD22, pLD24 |
| LCV38 | LCV32 | pLD10, pLD12, pLD116, pLD22 |
| LCV40 | LCV32 | pLD1 |
| LCV49 | LCV32 | pLD14, pLD22, pLD24, pLD26 |
| LCV50 | ATCC20913 | pLD56, pLD111 |
| LCV51 | ATCC20913 | pLD19 |
| LCV55 | ATCC20913 | pLD56 |
| LCV59 | ATCC20913 | pLD20, pLD56 |
| LCV61 | ATCC20913 | pLD56, pLD111 |
| LCV63 | ATCC20913 | pLD56, pLD126 |
| LCV67 | ATCC20913 | pLD56, pLD140 |
| LCV70 | ATCC20913 | pLD56, pLD139 |

Example 9—Construction of Yeast Strains in *Yarrowia lipolytica*

MYA-2613 (ATCC) was transformed with PacI digested pLD87 and Ura+ transformants selected by growth in ScD-ura plates. Genomic DNA from the ura+ strains was purified as described above. To identify the disruption of the KU70 gene a four oligo PCR method was designed. Two primers (61+87) amplifies a 796 bp piece of the actin gene, and primers 63 and 64 amplifies a 558 bp piece that is replaced by the URA3 gene if the KU70 gene is disrupted.

Using genomic DNA as the template for the method described allowed to identify if the strain still had the KU70 gene (presence of both PCR fragments) or if the strain had a disrupted KU70 (presence of only the actin PCR fragment). One strain was identified with the correct PCR profile and named YYL2.

YYL2 was transformed with pLD113 and Leu+ transformants selected by growth in ScD-leu plates. Leu+ transformant was then streaked in ScD+FOA plates. FOA resistant strains were isolated and its genomic DNA purified. To identify loss of the URA3 a four oligo PCR method was designed. Two primers (61+87) amplifies a 796 bp piece of the actin gene, and primers 115 and 116 amplifies a 594 bp piece ku70-URA3 piece that is lost if the URA3 piece is removed from the KU70 loci.

Using genomic DNA as the template for the method described allowed to identify if the strain still had the URA3 at the KU70 loci (presence of both PCR fragments) or if the strain had lost the URA3 at the KU70 loci (presence of only the actin PCR fragment). One strain was identified with the correct PCR profile and named YYL4.

TABLE 6

| Strain | Parental Strain | Plasmid Transform |
|---|---|---|
| YYL2 | MYA-2613 | Pac1 (pLD87) |
| YYL2L | YYL2 | pLD113 |
| YYL4 | YYL2L | |
| YYL6 | YYL4 | pLD101 |
| YYL27 | YYL25 | pLD102 |
| YYL29 | YYL25 | pLD135 |

TABLE 7

| Strain | Background | Plasmid |
|---|---|---|
| YYL7 | MYA-2613 | pLD131 |
| YYL9 | MYA-2613 | pLD132 |
| YYL11 | MYA-2613 | pLD137 |
| YYL13 | MYA-2613 | pLD138 |
| YYL17 | MYA-2613 | pLD131, pLD132 |
| YYL19 | MYA-2613 | pLD131, pLD138 |
| YYL21 | MYA-2613 | pLD137, pLD138 |

TABLE 8

| Primer number | Sequence |
|---|---|
| 61 | TTGTTACCAACTGGGATGACATGGAGAAG (SEQ ID NO: 141) |
| 63 | CTGATGGACGTGTTTTTCGACATGAACC (SEQ ID NO: 142) |
| 64 | GAAAGGAACATAGTCATTTCCAAACTTGAAAGTC (SEQ ID NO: 143) |
| 87 | CAGACGGAGTACTTTCGCTCGAGG (SEQ ID NO: 144) |
| 115 | CCCAAATTTAGCTGCATCATTCATCAACC (SEQ ID NO: 145) |
| 116 | CCGTGCTTAAGAGCAAGTTCCTTGAGG (SEQ ID NO: 146) |
| 177 | CTACGACATGCCCAAGGAGCAGC (SEQ ID NO: 147) |
| 178 | GGATTCGCACATTGGTGAACTGGATC (SEQ ID NO: 148) |
| 179 | CCAAGCGACGACAAGCTGTTGAGC (SEQ ID NO: 149) |
| 180 | CGTGTGGGTAGCAGAGTGGGC (SEQ ID NO: 150) |
| 181 | CTTTGCCATGACTGAGACTGGCCATG (SEQ ID NO: 151) |

TABLE 8-continued

| Primer number | Sequence |
|---|---|
| 182 | GAGGCGCCGCTGGTGTCG (SEQ ID NO: 152) |
| 183 | TCCGAAAGCGGAACTGCTTTCTCAATG (SEQ ID NO: 153) |
| 184 | CAGACCGGCCTCTCGAATATGGC (SEQ ID NO: 154) |
| 185 | CTAGACTACACGGGCAACCTTAACCC (SEQ ID NO: 155) |
| 186 | CTTGGGCTTCAGCTTTCGAGGAGTG (SEQ ID NO: 156) |

YYL4 was transformed with PacI digested pLD101 and Ura+ transformants selected by growth in ScD-ura plates. Genomic DNA from the ura+ strains was purified as described above. To identify the disruption of the POX5 gene a four oligo PCR method was designed. Two primers (61+87) amplifies a 796 bp piece of the actin gene, and primers 179 and 180 amplifies a 395 bp POX5 segment that is replaced by the URA3 gene.

Using genomic DNA as the template for the method described allowed to identify if the strain still had the PO5 gene (presence of both PCR fragments) or if the strain had been disrupted for POX5 (presence of only the actin PCR fragment). One strain was identified with the correct PCR profile and named YYL6.

YYL6 is transformed with pLD113 and Leu+ transformants are selected by growth in ScD-leu plates. Leu+ transformant was then streaked in ScD+FOA plates. FOA resistant strains will be isolated and its genomic DNA purified. To identify loss of the URA3 a four oligo PCR method was designed. Two primers (61+87) amplifies a 796 bp piece of the actin gene, and primers 116 and 237 amplifies a 598 bp piecePOX5-URA3 piece that is lost if the URA3 piece is removed from the URA loci. A strain with the correct PCR products was named YYL0025.

YYL25 is transformed with Pac digested pLD102 or pLD135, and Ura+ transformants selected by growth in ScD-ura plates. Genomic DNA from the ura+ strains is purified as described above. To identify the disruption of the POX4 gene a four oligo PCR method was designed. Two primers (61+87) amplifies a 796 bp piece of the actin gene, and primers 177 and 178 amplifies a 596 bp POX3 segment that is replaced by the URA3 gene. One strain transformed with either pLD102 or pLD135 is identified with the correct PCR profile and named YYL27 and YYL29, respectively.

Strain with plasmids were either transformed once (if containing one plasmid) or sequentially (if containing more than one plasmid).

Example 10—Quantification of Olivetolic Acid and Cannabinoids

To a 100 to 500 mg wet yeast pellet 50 μl of HCl was added and vortexed for 30 seconds. 400 μl of dichloromethane:ethyl ether (1:2) was added and vortexed for 1 min and centrifuged for 2 min at 10 k rpm. The top layer was removed, and the pellet was reextracted. The top layers were combined and dried under vacuum. The powder was reconstituted in 200 μl of acetonitrile and sonicated for 1 min. The solution was centrifuge for 2 min at 10 k rpm. Solution was then used for LC MS MS analysis.

For 0.5 ml of supernatant, 0.5 ml 1 M HCl was added and vortexed for 30 s. 500 μl of dichloromethane was added, vortexed for 30 sec and centrifuged for 2 min at 10 k rpm. The bottom layer was removed and the aqueous layer re-extracted. Both organic layer samples were combined and dried under vacuum. The powder was reconstituted in 200 μl of acetonitrile and sonicated for 1 min. The solution was centrifuge for 2 min at 10 k rpm. Solution was then used for LC MS MS analysis.

Example 11—Quantification of Hexanoic Acid and Fatty Acids

To 1 ml of supernatant, 0.8 ml of 6N HCl was added. 400 μl of dichloromethane:ethyl ether (1:2) was added, vortexed for 2 min and centrifuge for 2 min. The top layer was removed the extraction was repeated. The top layers were combined and dried under vacuum. The powder was reconstituted in 167 μl acetonitrile and 33 μl of acetonitrile with 20 mg/ml isopropyl alcohol and sonicated for 1 min. The solution was centrifuged for 2 m in at 10 k rpm. Solution was then used for GC FID analysis.

Example 12—Yeast Media

ScD-ura

1 L of liquid media was made by making a 100 ml solution of 20% dextrose and a 900 ml solution with 1.7 g of Yeast Nitrogen Base without ammonium sulfate and amino acids, 5 g of ammonium sulfate, and 2 g of dropout amino acid mix without uracil (Sunrise Science Products). Both solutions were combined, and filter sterilized or were autoclaved separately and combined.

1 L worth of plates (~40 plates) was made by making a 100 ml solution of 20% dextrose, a 450 ml solution with 1.7 g of Yeast Nitrogen Base without ammonium sulfate and amino acids, 5 g of ammonium sulfate, and 2 g of amino acid mix without uracil, and a 450 ml solution with 20 g of agar. The solutions were autoclaved separately and combined.

ScD-leu

1 L of liquid media was made by making a 100 ml solution of 20% dextrose and a 900 ml solution with 1.7 g of Yeast Nitrogen Base without ammonium sulfate and amino acids, 5 g of ammonium sulfate, and 2 g of dropout amino acid mix without leucine (Sunrise Science Products). Both solutions were combined, and filter sterilized or were autoclaved separately and combined.

1 L worth of plates (~40 plates) was made by making a 100 ml solution of 20% dextrose, a 450 ml solution with 1.7 g of Yeast Nitrogen Base without ammonium sulfate and amino acids, 5 g of ammonium sulfate, and 2 g of amino acid mix without leucine and a 450 ml solution with 20 g of agar. Both solutions were combined, and filter sterilized or autoclaved separately and combined.

ScD-ura-leu

1 L of liquid media was made by making a 100 ml solution of 20% dextrose and a 900 ml solution with 1.7 1.7 g of Yeast Nitrogen Base without ammonium sulfate and amino acids, 5 g of ammonium sulfate, and 2 g of dropout amino acid mix without leucine and uracil (Sunrise Science Products). Both solutions were combined, and filter sterilized or autoclaved separately and combined.

1 L worth of plates (~40 plates) was made by making a 100 ml solution of 20% dextrose, a 450 ml solution with 1.7 g of Yeast Nitrogen Base without ammonium sulfate and amino acids, 5 g of ammonium sulfate, and 2 g of amino acid mix without leucine and uracil, and a 450 ml solution with 20 g of agar were made. The solutions were autoclaved separately and combined.

ScG-ura, ScG-leu, ScG-ura-leu was made the same as ScD-ura, ScD-leu or ScD-ura-leu respectively except the dextrose was replaced with glycerol at a 40 g/L concentration. ScGP-ura, ScGP-leu, ScGP-ura-leu was the same is the same as ScG-ura, ScG-leu or ScG-ura-leu, except, monopotassium and dipotassium phosphate was added to a final concentration of 1 g/L.

YPD

1 L of liquid media was made by making a 100 ml solution of 20% dextrose and a 900 ml solution with 10 g yeast extract and 20 g of peptone. Both solutions were combined, and filter sterilized or autoclaved separately and combined.

1 L worth of plates (~40 plates) was made by making a 100 ml solution of 20% dextrose, a 450 ml solution with 10 g yeast extract and 20 g of peptone, and a 450 ml solution with 20 g of agar. The solutions were autoclaved separately and combined afterwards.

SD+FOA

1 L worth of plates (~40 plates) was made by making a 100 ml solution of 20% dextrose, a 450 ml solution with 1.7 g of yeast nitrogen base without ammonium sulfate and amino acids, 5 g of ammonium sulfate, and 2 g of amino acid mix without uracil, 0.5 g 5-FOA, 250 mg uracil, and a 450 ml solution with 20 g of agar. The solutions were autoclaved separately and combined.

SmP

1 L of liquid media was made by dissolving 1.7 g of yeast nitrogen base without ammonium sulfate and amino acids, 5 g of ammonium sulfate, 1 g potassium phosphate, monobasic and 1 g potassium phosphate, bibasic. The solution was then filter sterilized.

YNEP Media

1 L of YNEP was made by dissolving 3 g yeast extract, 1.7 g of yeast nitrogen base without ammonium sulfate and amino acids, 5 g of ammonium sulfate, 1 g potassium phosphate, monobasic and 1 g/l of dextrose or glycerol per liter. The solution was then filter sterilized.

MLM Media

1 L of MLM media was made by dissolving 3 g yeast extract, 1.7 g of yeast nitrogen base without ammonium sulfate and amino acids, 1 g potassium phosphate, monobasic and 1 g/l of dextrose or glycerol. Filter sterilized.

ScP-ura, ScP-leu, ScP-ura-leu was the same as Sc-ura, Sc-leu, Sc-ura-leu, respectively except monopotassium and dipotassium phosphate was added to a final concentration of 1 g/L.

For *Yarrowia* media a supplement of thiamine, biotin and Myo-inositol can be added to the media to a final concentration of 300 μg/L, 8 μg/L and 4 μg/L.

Example 13—Shake Flask Fermentation *Candida*

A shake flask fermentation is a small-scale culture to test for production of a cannabinoid or cannabinoid precursor. A yeast strain to be tested is grown on ScD-ura, or YPD for 2-3 days. Individual colonies from those plates are propagated overnight in 5 mL of YPD or ScD-ura (30° C., shaking at 250 rpm). The resulting culture is propagated overnight in 50 mL of YPD or 25 ml of YNEP media (30° C., shaking at 250 rpm). The biomass from the 50 mL culture is spun down and washed with water, then resuspended in 15 mL of 1×SMP or MLM media with 300 μl of oleic acid (technical grade, 90%). Yeast cells, media and oleic acid are placed into a 250 mL culture flask (it may be a baffled flask for increased aeration of the culture) and incubated at 30° C. while shaking (250 rpm) for a 48-72 hours. The contents of the shake flask are spun down to produce a cell pellet and a supernatant, which is the culture media. The cell pellet and/or supernatant are analyzed for their contents by the appropriate method(s) as needed for the analyte(s) of interest.

Example 14—Shake Flask Fermentation *Yarrowia*

A shake flask fermentation is a small-scale culture to test for production of a cannabinoid or cannabinoid precursor. A yeast strain to be tested is grown on ScD-ura, ScD-leu, ScD-ura-leu or YPD for 2-3 days. Individual colonies from those plates are propagated overnight in 5 mL of YPD, ScD-ura, ScD-leu, or ScD-ura-leu (30° C., shaking at 250 rpm). The resulting culture is propagated overnight in 25 mL ScGP, ScGP-ura, ScGP-leu, or ScGP-ura-leu (30° C., shaking at 250 rpm). The biomass from the 25 mL culture is spun down and washed with water, then resuspended in 20 mL of ScP, ScP-ura, ScP-leu or ScP-ura-leu media with 800 μl of oleic acid (technical grade, 90%). Yeast cells, media and oleic acid are placed into a 250 mL culture flask (it may be a baffled flask for increased aeration of the culture) and incubated at 30° C. while shaking (250 rpm) for a 24-72 hours. The contents of the shake flask are spun down to produce a cell pellet and a supernatant, which is the culture media. The cell pellet and/or supernatant are analyzed for their contents by the appropriate method(s) as needed for the analyte(s) of interest.

Example 15—Production of Olivetolic Acid from Hexanoic Acid or Hexanoate-Esters in *Candida*

Strain LCV22 (HXS1 TKS1 OAC) was grown overnight in 25 ml of YPD in a 250 ml flask at 225 rpm and 30° C. 3 ml of the overnight culture was used to inoculate 50 ml of YPD and grown overnight in a 250 ml flask at 225 rpm and 30° C. A total of seven flasks were started. The biomass from the 50 mL culture was spun down and washed with water, then resuspended in 15 mL of 1×SMP media with 300 μl of oleic acid (technical grade, 90%). Yeast cells, media and oleic acid are placed into a baffled 250 mL culture flask. Different amounts of hexanoic acid, ethyl hexanoate, and geranyl hexanoate were added to different flask as described in Table 9. and incubated at room temperature while shaking (250 rpm) for 72 hours. The contents of the shake flask were spun down to produce a cell pellet and a supernatant, which is the culture media. The cell pellets were analyzed for olivetolic acid using an LC-MS MS method.

As shown in Table 9, there was an increase in olivetolic production using hexanoate ester as opposed to hexanoic acid. This is consistent with hexanoic acid being more toxic per mole than geranyl hexanoate and ethyl hexanoate.

TABLE 9

| Flask | Addition | Amount (ul) | Olivetolic acid (Area per mg) |
|---|---|---|---|
| 1 | — | — | 5 |
| 2 | Hexanoic acid | 15 | 13 |
| 3 | Ethyl hexanoate | 20 | 56 |
| 4 | Geranyl hexanoate | 34 | 179 |
| 5 | Hexanoic acid | 30 | 101 |
| 6 | Ethyl hexanoate | 40 | 62 |
| 7 | Geranyl hexanoate | 68 | 344 |

Example 16—Production of Hexanoic Acid from Oleic Acid in *Candida*

Strain LCV14 (wildtype) and LCV35 (Δpox+ACO1P) were grown in 3 ml of YPD. These overnight cultures were used to inoculate 50 ml of YPD and grown overnight in a 250 ml flask at 225 rpm and 30° C. The biomass from the 50 mL culture was spun down and washed with water, then resuspended in 15 mL of 1×SMP media with 300 μl of oleic acid (technical grade, 90%). Yeast cells, media and oleic acid were placed into a 250 mL culture flask and incubated at 30° C. while shaking (250 rpm) for 48 hours. The contents of the shake flask were spun down to produce a cell pellet and a supernatant, which is the culture media. The cell pellets were analyzed for hexanoic using an LC-MS MS method. As shown in Table 10, LCV35 produced more hexanoic acid than LCV35, which is consistent with the presence of an active pathway making hexanoic acid from oleic acid.

TABLE 10

| Strain | Hexanoic Acid (mg/L) |
|---|---|
| LCV14 | 9.7 |
| LCV35 | 61.2 |

Example 17—Production of Hexanoic Acid from Soybean Oil in *Candida*

Strain LCV14 (wildtype) and LCV34 (Δpox+ACO1P) were grown in 3 ml of YPD. These overnight cultures were used to inoculate 50 ml of YPD and grown overnight in a 250 ml flask at 225 rpm and 30° C. The biomass from the 50 mL culture was spun down and washed with water, then resuspended in 15 mL of 1×SMP media with 300 μl of soybean oil. Yeast cells, media and soybean oil were placed into a 250 mL culture flask and incubated at 30° C. while shaking (250 rpm) for 48 hours. The contents of the shake flask were spun down to produce a cell pellet and a supernatant, which is the culture media. The cell pellets were analyzed for hexanoic acid using an LC-MS MS method. As shown in Table 11, LCV34 produced more hexanoic acid than LCV14 when using soybean and palm oil, consistent with the presence of an active pathway making hexanoic acid from soybean oil and palm oil.

Example 18—Production of Hexanoic Acid from Alkane in *Candida*

Strain LCV14 (wildtype) and LCV34 (Δpox+ACO1P) were grown in 3 ml of YPD. These overnight cultures were used to inoculate 50 ml of YPD and grown overnight in a 250 ml flask at 225 rpm and 30° C. The biomass from the 50 mL culture was spun down and washed with water, then resuspended in 15 mL of 1×SMP media with 300 μl of hexadecane or octadecane. Yeast cells, media and alkane were placed into a 250 mL culture flask and incubated at 30° C. while shaking (250 rpm) for 48 hours. The contents of the shake flask were spun down to produce a cell pellet and a supernatant, which is the culture media. The cell pellets were analyzed for hexanoic acid using an LC-MS MS method. As shown in Table 11, LCV34 produced more hexanoic acid than LCV14 from hexadecane, which is consistent with the presence of an active pathway making hexanoic acid from hexadecane. Octadecane may not be utilized effectively by the yeast strains.

TABLE 11

| Strain | Substrate | Hexanoic Acid (mg/L) |
|---|---|---|
| LCV14 | Soybean Oil | 70 |
| LCV34 | Soybean Oil | 190 |
| LCV14 | Palm Oil | 47 |
| LCV34 | Palm Oil | 222 |
| LCV14 | Octadecane | 10 |
| LCV34 | Octadecane | 3 |
| LCV14 | Hexadecane | 2 |
| LCV34 | Hexadecane | 174 |

Example 19—Production of Olivetolic Acid from Oleic Acid in *Candida*

Strain LCV14 (wildtype), LCV36 (Δpox+ACO1P+TKS1P+OAC1P), and LCV38 (Δpox+ACO1P+HKS1+TKS1+OAC1) were grown in 3 ml of YPD. These overnight cultures were used to inoculate 50 ml of YPD and grown overnight in a 250 ml flask at 225 rpm and 30° C. The biomass from the 50 mL culture was spun down and washed with water, then resuspended in 15 mL of 1×SMP media with 300 μl of oleic acid (technical grade, 90%). Yeast cells, media and oleic acid were placed into a 250 mL culture flask and incubated at 30° C. while shaking (250 rpm) for 48 hours. The contents of the shake flask were spun down to produce a cell pellet and a supernatant, which is the culture media. The supernatants were analyzed for olivetolic acid using an LC-MS MS method. As shown in Table 12, LCV36 and LCV38 produced more olivetolic acid than LCV14, which is consistent with the presence of an active pathway making olivetolic acid from oleic acid with either a peroxisomal TKS1P and OAC1P or a non-peroxisomal HKS1, TKS1 and OAC1.

TABLE 12

| Strain | Olivetolic Acid (Area/g) |
|---|---|
| LCV14 | 611 |
| LCV36 | 1094 |
| LCV38 | 1026 |

Example 20—Production of Olivetolic Acid from Soybean Oil and Palm Oil in *Candida*

Strain LCV14 (wildtype) and LCV36 (Δpox+ACO1P+TKS1P+OAC1P) are grown in 3 ml of YPD. These overnights are used to inoculate 50 ml of YPD and grown overnight in a 250 ml flask at 225 rpm and 30° C. The biomass from the 50 mL culture is spun down and washed with water. It is resuspended in 15 mL of 1×SMP media with 300 μl of soybean oil or 300 μl of palm oil. Yeast cells, media and soybean oil are placed into a 250 mL culture flask. and incubated at 30° C. while shaking (250 rpm) for 48 hours. The contents of the shake flask str spun down to produce a cell pellet and a supernatant, which is the culture media. The cell pellets and supernatants are analyzed for olivetolic acid using an LC-MS MS method.

Example 21—Production of Olivetolic Acid from Alkanes in *Candida*

Strain LCV14 (wildtype) and LCV36 (Δpox+ACO1P+TKS1P+OAC1P) are grown in 3 ml of YPD. These overnights are used to inoculate 50 ml of YPD and grown overnight in a 250 ml flask at 225 rpm and 30° C. The biomass from the 50 mL culture is spun down and washed with water. It is resuspended in 15 mL of 1×SMP media with 300 μl of hexadecane or octadecane. Yeast cells, media and alkane is placed into a 250 mL culture flask, and incubated at 30° C. while shaking (250 rpm) for 48 hours. The contents of the shake flask are spun down to produce a cell pellet and a supernatant, which is the culture media. The cell pellets and supernatant are analyzed for olivetolic acid using an LC-MS MS method.

Example 22—Production of CBGA from Olivetolic Acid in *Candida*

Strain LCV51 (PTS1), LCV55 (PTS2) and LCV13 (wild-type) were grown in 3 ml of YPD. These overnight cultures were used to inoculate 2× (for LCV55) or 1× (for LCV13 and LCV5150 ml cultures of YPD and grown overnight in a 250 ml flask at 225 rpm and 30° C. The biomass from the 50 mL cultures were spun down and washed with water, then resuspended in 15 mL of 1×SMP media with 300 μl of oleic acid. Yeast cells, media and oleic acid were placed into a 250 mL culture flask. To one of the LCV55 flasks and the LCV13 flask, olivetolic acid was added to a final concentration of 1 mM. The flasks were then incubated at 30° C. while shaking (250 rpm) for 48 hours. The contents of the shake flask were spun down to produce a cell pellet and a supernatant, which is the culture media. The cell supernatants were analyzed for CBGA using an LC-MS MS method. As shown in Table 13, LCV51 and LCV55 produced more CBGA than LCV13 and LCV55 without olivetolic acid, which is consistent with the presence of an active pathway making CBGA acid from oleic acid when either PTS1 or PTS2 is expressed.

TABLE 13

| StrainStrain | | CBGA Area/μl |
|---|---|---|
| LCV13 | Yes | 18,200 |
| LCV51 | Yes | 21,920 |
| LCV55 | No | 0 |
| LCV55 | Yes | 36,000 |

Example 23—Production of CBDA from Olivetolic Acid in *Candida*

Strain LCV55 (PTS2) and LCV59 (PTS2 CBD1) is grown in 3 ml of YPD. These overnights are used to inoculate 2× (for LCV59) or 1× (for LCV55) 50 ml of YPD and grown overnight in a 250 ml flask at 225 rpm and 30° C. The biomass from the 50 mL culture is spun down and washed with water, then resuspended in 15 mL of 1×SMP media with 300 μl of oleic acid. Yeast cells, media and oleic acid are placed into a 250 mL culture flask. To one of the LCV59 flasks and the LCV55 flask, olivetolic acid is added to a final concentration of 1 mM. The flasks are then incubated at 30° C. while shaking (250 rpm) for 48 hours. The contents of the shake flask are spun down to produce a cell pellet and a supernatant, which is the culture media. The cell pellets and supernatants are analyzed for CBDA using an LC-MS MS method.

Example 24—Production of THCA from Olivetolic Acid in *Candida*

Strain LCV55 (PTS2) and LC61 (PTS2 THC1) are grown in 3 ml of YPD. These overnight cultures are used to inoculate 2× (for LCV61) or 1× (for LCV155) 50 ml of YPD and grown overnight in a 250 ml flask at 225 rpm and 30° C. The biomass from the 50 mL culture is spun down and washed with water, then resuspended in 15 mL of 1×SMP media with 300 μl of oleic acid. Yeast cells, media and oleic acid are placed into a 250 mL culture flask. To one of the LCV61 flasks and the LCV55 flask, olivetolic acid is added to a final concentration of 1 mM. The flasks are then incubated at 30° C. while shaking (250 rpm) for 48 hours. The contents of the shake flask are spun down to produce a cell pellet and a supernatant, which is the culture media. The cell pellets and supernatants are analyzed for THCA using an LC-MS MS method.

Example 25—Production of CBGA from Fatty Acids in *Candida*

Strain LCV36 (Δpox+ACO1P+TKS1P+OAC1P) and LCV49 (Δpox+ACO1P+TKS1P+OAC1P+PTS1dN), were grown in 3 ml of YPD. These overnight cultures were used to inoculate 50 ml of YPD and grown overnight in a 250 ml flask at 225 rpm and 30° C. The biomass from the 50 mL culture was spun down and washed with water, then resuspended in 15 mL of 1×SMP media with 300 μl of oleic acid (technical grade, 90%). Yeast cells, media and oleic acid were placed into a 250 mL culture flask and incubated at 30° C. while shaking (250 rpm) for 48 hours. The contents of the shake flask were spun down to produce a cell pellet and a supernatant, which is the culture media. The supernatants were analyzed for CBGA using an LC-MS MS method. As shown in Table, LCV49 produced more CBGA than LCV36, which is consistent with the presence of an active pathway making CBGA from oleic acid.

TABLE 14

| Strain | CBGA Area/ul |
|---|---|
| LCV36 | 1,058 |
| LCV49 | 2,000 |

Example 26—Production of CBDA from Fatty Acids in *Candida*

A strain is created that expresses ACO1P, TKS1P, AOC1P, PTS2 and CBD1 in a pox deleted background. This strain is grown overnight in 3 mol of YPD. This overnight culture is used to inoculate 50 ml of YPD and grown overnight in a 250 ml flask at 225 rpm and 30° C. The biomass from the 50 mL culture is spun down and washed with water. It is resuspended in 15 mL of 1×SMP media supplemented with 300 μl of oleic acid. Yeast cells, media and oleic are placed into a 250 mL culture flask. The flasks are then incubated at 30° C. while shaking (250 rpm) for 48 hours. The contents of the shake flask are spun down to produce a cell pellet and a supernatant. The cell pellet and supernatants are analyzed for CBDA acid using an LC-MS MS method.

Example 27—Production of THCA from Fatty Acids in *Candida*

A strain is created that expresses ACO1P, TKS1P, AOC1P, PTS2 and THC1 or ACO1, HXS1, TKS1, AOC1, PTS2, and THC1 in a pox deleted background. This strain is grown overnight in 3 mol of YPD. This overnight is used to inoculate 50 ml of YPD and grown overnight in a 250 ml flask at 225 rpm and 30° C. The biomass from the 50 mL culture is spun down and washed with water. It is resuspended in 15 mL of 1×SMP media with 300 μl of oleic acid. Yeast cells, media and oleic acid are placed into a 250 mL culture flask. The flask is then incubated at 30° C. while shaking (250 rpm) for 48 hours. The contents of the shake flask are spun down to produce a cell pellet and a supernatant, which is the culture media. The cell pellet and supernatant is analyzed for THCA acid using an LC-MS MS method.

Example 28—Enhanced Secretion of CBDA in *Candida*

Strain LCV59 (PTS2 CBD1), LCV63 (PTS2 CBD1dNS1), LCV67 (PTS2 CBDdNV1), and LCV70 (PTS2 CBD1dNP1) are grown in 3 ml of ScD-ura. These overnight cultures are used to inoculate 50 ml of YPD and grown overnight in 1 250 ml flask at 225 rpm and 30° C. The biomass from the 50 mL culture is spun down and washed with water, then resuspended in 15 mL of 1×SMP media with 300 μl of oleic acid. Yeast cells, media and oleic acid is placed into a 250 mL culture flask. Olivetolic acid is added to a final concentration of 1 mM. The flasks are then incubated at 30° C. while shaking (250 rpm) for 48 hours. The contents of the shake flask are spun down to produce a cell pellet and a supernatant, which is the culture media. The cell pellets and supernatants are analyzed for CBDA using an LC-MS MS method.

Example 29—Enhanced Secretion of THCA in *Candida*

Strains expressing either (PTS2 THC1), (PTS2 THC1dNS1), (PTS2 THCdNV1), or (PTS2 THC1dNP1) were grown in 3 ml of ScD-ura. These overnight cultures are used to inoculate 50 ml of YPD and grown overnight in a 250 ml flask at 225 rpm and 30° C. The biomass from the 50 mL culture is spun down and washed with water, then resuspended in 15 mL of 1×SMP media with 300 μl of oleic acid. Yeast cells, media and oleic acid is placed into a 250 mL culture flask. Olivetolic acid is added to a final concentration of 1 mM. The flasks are then incubated at 30° C. while shaking (250 rpm) for 48 hours. The contents of the shake flask are spun down to produce a cell pellet and a supernatant, which is the culture media. The cell pellets and supernatants are analyzed for THCA using an LC-MS MS method.

Example 30—Production of CBCA in *Candida* from Fatty Acids

A strain is created that expresses ACO1P, TKS1P, OAC1P, PTS2 and CBC1 or ACO1P, HXS1, TKS1, OAC1, PTS2, and CBC1 in a pox deleted background. This strain is grown overnight in 3 mol of YPD. This overnight culture is used to inoculate 50 ml of YPD and grown overnight in a 250 ml flask at 225 rpm and 30° C. The biomass from the 50 mL culture is spun down and washed with water, then resuspended in 15 mL of 1×SMP media with 300 μl of oleic acid. Yeast cells, media and oleic acid are placed into a 250 mL culture flask. The flask is then incubated at 30° C. while shaking (250 rpm) for 48 hours. The contents of the shake flask are spun down to produce a cell pellet and a supernatant, which is the culture media. The cell pellet and supernatant are analyzed for CBCA acid using an LC-MS MS method.

Example 31—Production of Hexanoic Acid from Fatty Acids in *Yarrowia*

Strain YYL2 (wildtype), YYL6 (Δpox5), YYL27(Δpox3 Δpox5), and YYL29(Δpox3 Δpox5+ACO1P) are grown in 3 ml of YPD. These overnight cultures are used to inoculate 25 ml of ScGP and grown overnight in a 250 ml flask at 225 rpm and 30° C. The biomass from the 25 mL culture was spun down and washed with water, then resuspended in 20 mL of ScP media with 800 μl of oleic acid (technical grade, 90%). Yeast cells, media and oleic acid were placed into a 250 mL culture flask and incubated at 30° C. while shaking (250 rpm) for 48 hours. The fermentation is analyzed for hexanoic acid using a GC-FID method.

Example 32—Production of Hexanoic Acid from Soybean Oil and Palm Oil in *Yarrowia*

Strain YYL2 (wildtype), YYL6 (Δpox5), YYL27(Δpox3 Δpox5), and YYL29(Δpox3 Δpox5+ACO1P) are grown in 3 ml of YPD. These overnight cultures are used to inoculate 25 ml of ScGP and grown overnight in a 250 ml flask at 225 rpm and 30° C. The biomass from the 25 mL culture was spun down and washed with water, then resuspended in 20 mL of ScP media with 800 μl of oleic acid (technical grade, 90%). Yeast cells, media and vegetable oil were placed into a 250 mL culture flask and incubated at 30° C. while shaking (250 rpm) for 48 hours. The fermentation is analyzed for hexanoic acid using a GC-FID method.

Example 33—Production of Hexanoic Acid from Alkanes in *Yarrowia*

Strain YYL2 (wildtype), YYL6 (Δpox5), YYL27(Δpox3 Δpox5), and YYL29(Δpox3 Δpox5+ACO1P) are grown in 3 ml of YPD. These overnight cultures are used to inoculate 25 ml of ScGP and grown overnight in a 250 ml flask at 225 rpm and 30° C. The biomass from the 25 mL culture is spun down and washed with water, then resuspended in 20 mL of ScP media with 800 μl of either hexadecane and octadecane. Yeast cells, media and oleic acid are placed into a 250 mL culture flask and incubated at 30° C. while shaking (250 rpm) for 48 hours. The fermentation is analyzed for hexanoic acid using a GC-FID method.

Example 34—Production of Olivetolic Acid from Hexanoic Acid or Hexanoate-Esters in *Yarrowia*

A strain is created that expresses HXS1, TKS1 and OAC1 is grown overnight in 3 ml of YPD. This overnight culture is used to inoculate 25 ml of ScGP and grown overnight in a 250 ml flask at 225 rpm and 30° C. The biomass from the 25 mL culture is spun down and washed with water, then resuspended in 20 mL of ScP media with 800 μl oleic acid. Yeast cells, media and oleic acid is placed into a 250 mL culture flask. Hexanoic acid, ethyl-hexanoate, geranyl hexanoate or other hexanoate ester is added to the flask. The culture flask is incubated at 30° C. while shaking (250 rpm) for 48 hours. The contents of the shake flask are spun down to produce a cell pellet and a supernatant. The cell pellets and supernatants are analyzed for olivetolic acid using an LC-MS MS method.

Example 35—Production of Olivetolic Acid from Fatty Acids in *Yarrowia*

A strain that produces hexanoic acid that expresses TKS1P and OAC1P or HXS1 TKS1 OAC1 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water. It is resuspended in 20 mL of ScP media with 800 µl oleic acid. Yeast cells, media and oleic acid is placed into a 250 mL culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for olivetolic acid using an LC-MS MS method.

Example 36—Production of Olivetolic Acid 1 from Soybean Oil or Palm Oil in *Yarrowia*

A strain that produces hexanoic acid that expresses TKS1P and OAC1P or HXS1 TKS1 OAC1 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water, then resuspended in 20 mL of ScP media with 800 µl soybean or palm oil. Yeast cells, media and vegetable oil is placed into a 250 mL culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for olivetolic acid using an LC MS MS method.

Example 37—Production of Olivetolic Acid from Alkanes in *Yarrowia*

A strain that produces hexanoic acid that expresses TKS1P and OAC1P or HXS1 TKS1 OAC1 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water. It is resuspended in 20 mL of ScP media with 800 µl of hexadecane or octadecane. Yeast cells, media and alkane are placed into a 250 mL culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for olivetolic acid using an LC MS MS method.

Example 38—Production of CBGA from Olivetolic Acid in *Yarrowia*

YYL7 is grown overnight in 3 ml of ScD-leu. This overnight culture is used to inoculate 25 ml of ScGP-leu and grown overnight in a 250 ml flask at 225 rpm and 30° C. The biomass from the 25 mL culture is spun down and is washed with water, then resuspended in 20 mL of Sc-leu media with 800 µl oleic acid. Yeast cells, media and oleic are placed into a 250 mL culture flask. Olivetolic acid is added to a final concentration of 1 mM to the culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for CBGA using an LC-MS MS method.

Example 39—Production of CBDA from Olivetolic Acid in *Yarrowia*

YYL17 is grown overnight in 3 ml of ScD-leu-ura. This overnight culture is used to inoculate 25 ml of ScGP-leu-ura and grown overnight in a 250 ml flask at 225 rpm and 30° C. The biomass from the 25 mL culture is spun down and is washed with water, then resuspended in 20 mL of ScP-ura-leu media with 800 µl oleic acid. Yeast cells, media and oleic are placed into a 250 mL culture flask. Olivetolic acid is added to a final concentration of 1 mM to the culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for CBDA using an LC-MS MS method.

Example 40—Production of THCA from Olivetolic Acid in *Yarrowia*

A strain expressing PTS2 and THC1 is grown overnight in 3 ml of ScD-leu-ura (if genes are in a plasmid) or YPD (if genes are integrated). This overnight is used to inoculate 25 ml of ScGP-leu-ura if genes are in a plasmid) or ScGP (if genes are integrated) and grown overnight in a 250 ml flask at 225 rpm and 30° C. The biomass from the 25 mL culture is spun down and is washed with water, then resuspended in 20 mL of ScP-ura-leu media with 800 µl oleic acid (if genes are in a plasmid) or ScP (if genes are integrated) media with 800 µl oleic acid. Yeast cells, media and oleic are placed into a 250 mL culture flask. Olivetolic acid is added to a final concentration of 1 mM to the culture flask. The culture flask is incubated at 30° C. while shaking (250 rpm) for 48 hours. The contents of the shake flask are spun down to produce a cell pellet and a supernatant. The cell pellets and supernatants are analyzed for THCA using an LC-MS MS method.

Example 41—Production of CBGA from Fatty Acids in *Yarrowia*

A strain that produces hexanoic acid that expresses TKS1P OAC1P PTS2 or HXS1 TKS1 OAC1 PTS2 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water, then resuspended in 20 mL of ScP media with 800 µl oleic acid. Yeast cells, media and oleic acid are placed into a 250 mL culture flask. The culture flask is incubated at 30° C. while shaking (250 rpm) for 48 hours. The contents of the shake flask are spun down to produce a cell pellet and a supernatant. The cell pellets and supernatants are analyzed for CBGA using an LC-MS MS method.

Example 42—Production of CBDA from Fatty Acids in *Yarrowia*

A strain that produces hexanoic acid that expresses TKS1P OAC1P PTS2 CBD1 or HXS1 TKS1 OAC1 PTS2 CBD1 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water, then resuspended in 20 mL of ScP media with 800 µl oleic acid. Yeast cells, media and oleic acid are placed into a 250 mL culture flask. The culture flask is incubated at 30° C. while shaking (250 rpm) for 48 hours. The contents of the shake flask are spun down to produce a cell pellet and a supernatant. The cell pellets and supernatants are analyzed for CBDA using an LC-MS MS method.

Example 43—Production of THCA from Fatty Acids in *Yarrowia*

A strain that produces hexanoic acid that expresses TKS1P OAC1P PTS2 THC1 or HXS1 TKS1 OAC1 PTS2 THC1 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water, then resuspended in 20 mL of ScP media with 800 μl oleic acid. Yeast cells, media and oleic acid are placed into a 250 mL culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for THCA using an LC MS MS method.

Example 44—Production of CBCA from Fatty Acids in *Yarrowia*

A strain that produces hexanoic acid that expresses TKS1P OAC1P PTS2 CBC1 or HXS1 TKS1 OAC1 PTS2 CBC1 is grown overnight in 3 ml of YPD. This overnight culture is used to inoculate 25 ml of ScGP and grown overnight in a 250 ml flask at 225 rpm and 30° C. The biomass from the 25 mL culture is spun down and is washed with water, then resuspended in 20 mL of ScP media with 800 μl oleic acid. Yeast cells, media and oleic acid are placed into a 250 mL culture flask. The culture flask is incubated at 30° C. while shaking (250 rpm) for 48 hours. The contents of the shake flask are spun down to produce a cell pellet and a supernatant, which is the culture media. The cell pellets and supernatants are analyzed for CBC1 using an LC MS MS method.

Sequences (*Yarrowia*)
pLD1

(SEQ ID NO: 157)

```
TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT
```

-continued

```
CCCCACTAACATTGTTCAAATCTTCACGACATAAGAAGAGCCCGGGTCTAGATGTGT
GCTCTTCCGAGTGACTCTTTTGATAAGAGTCGCAAATTTGATTTCATAAGTATATATT
CATTATGTAAAGTAGTAAATGGAAAATTCATTAAAAAAAAAGCAAATTTCCGTTGTA
TGCATACTCCGAACACAAAACTAGCCCCGGAAAAACCCTTAGTTGATAGTTGCGAAT
TTAGGTCGACCATATGCGACGGGTACAACGAGAATTGTATTGAATTGATCAAGAAC
ATGATCTTGGTGTTACAGAACATCAAGTTCTTGGACCAGACTGAGAATGCACAGATA
TACAAGGCGTCATGTGATAAAATGGATGAGATTTATCCACAATTGAAGAAAGAGTT
TATGGAAAGTGGTCAACCAGAAGCTAAACAGGAAGAAGCAAACGAAGAGGTGAAA
CAAGAAGAAGAAGGTAAATAAGTATTTTGTATTATATAACAAACAAAGTAAGGAAT
ACAGATTTATACAATAAATTGCCATACTAGTCACGTGAGATATCTCATCCATTCCCC
AACTCCCAAGAAAATAAAAAAGTGAAAAATAAAATCAAACCCAAAGATCAACCTCC
CCATCATCATCGTCATCAAACCCCCAGCTCAATTCGCAATGGTTAGCACAAAAACAT
ACACAGAAAGGGCATCAGCACACCCCTCCAAGGTTGCCCAACGTTTATTAATTAAA
GGCTAGGTGGAGGCTCAGTGATGATAAGTCTGCGATGGTGGATGCATGTGTCATGGT
CATAGCTGTTTCCTGTGTGAAATTGTTATCCGCTCAGAGGGCACAATCCTATTCCGC
GCTATCCGACAATCTCCAAGACATTAGGTGGAGTTCAGTTCGGCGTATGGCATATGT
CGCTGGAAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGA
AGAACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCT
ACGGGGTCTGACGCTCTATTCAACAAAGCCGCCGTCCCGTCAAGTCAGCGTAAATG
GGTAGGGGGCTTCAAATCGTCCGCTCTGCCAGTGTTACAACCAATTAACAAATTCTG
ATTAGAAAAACTCATCGAGCATCAAATGAAACTGCAATTTATTCATATCAGGATTAT
CAATACCATATTTTTGAAAAAGCCGTTTCTGTAATGAAGGAGAAAACTCACCGAGGC
AGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCAC
CATGAGTGACGACTGAATCCGGTGAGAATGGCAAAAGCTTATGCATTTCTTTCCAGA
CTTGTTCAACAGGCCAGCCATTACGCTCGTCATCAAAATCACTCGCATCAACCAAAC
CGTTATTCATTCGTGATTGCGCCTGAGCGAGACGAAATACGCGATCGCTGTTAAAAG
GACAATTACAAACAGGAATCGAATGCAACCGGCGCAGGAACACTGCCAGCGCATCA
ACAATATTTTCACCTGAATCAGGATATTCTTCTAATACCTGGAATGCTGTTTTCCCGG
GGATCGCAGTGGTGAGTAACCATGCATCATCAGGAGTACGGATAAAATGCTTGATG
```

GTCGGAAGAGGCATAAATTCCGTCAGCCAGTTTAGTCTGACCATCTCATCTGTAACA

TCATTGGCAACGCTACCTTTGCCATGTTTCAGAAACAACTCTGGCGCATCGGGCTTC

CCATACAATCGATAGATTGTCGCACCTGATTGCCCGACATTATCGCGAGCCCATTTA

TACCCATATAAATCAGCATCCATGTTGGAATTTAATCGCGGCCTCGAGCAAGACGTT

TCCCGTTGAATATGGCTCATAACACCCCTTGTATTACTGTTTATGTAAGCAGACAGTT

TTATTGTTCATGATGATATATTTTTATCTTGTGCAATGTAACATCAGAGATTTTGAGA

CACAACGTGGCTTTCCCCCGCCGCTCTAGAACTAGTGGATCCAAATAAAACGAAAG

GCTCAGTCGAAAGACTGGGCCTTTCGTTTTATCTGTTGTTTGTCGCATTATACGAGAC

GTCCAGGTTGGGATACCTGAAACAAAACCCATCGTACGGCCAAGGAAGTCTCCAAT

AACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCT pLD10

(SEQ ID NO: 158)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATCATTTAAGAGCAGAAGGAC

-continued

CCGCATCAGTGTTAGCGATAGGTACAGCTAACCCAGAGAATATCTTAATCCAAGATG

AATTTCCTGACTACTATTTCCGTGTTACTAAATCGGAACATATGACTCAACTTAAAG

AGAAGTTCCGGAAAATCTGCGATAAATCCATGATCCGAAAGAGAAACTGTTTCCTTA

ACGAAGAACATCTCAAGCAAAACCCGAGGTTGGTAGAGCACGAAATGCAGACCTTG

GATGCTAGGCAGGACATGTTGGTGGTCGAAGTGCCAAAACTCGGCAAGGACGCGTG

CGCTAAGGCAATCAAGGAGTGGGGTCAACCGAAGTCTAAAATCACGCATCTAATAT

TTACATCTGCACTGACAACCGACATGCCGGGTGCCGATTATCACTGCGCCAAGCTAC

TTGGATTGAGTCCACTGGTTAAGAGAGTTATGATGTATCAATTGGGGTGTTACGGAG

GGGGCACAGTCCTCAGAATTGCTAAGGATATTGCGGAAAATAACAAGGGCGCGAGG

GTCCTTGCTGTATGTTGTGATATTATGGCCTGTTTGTTTCGCGGGCCCTCGGATTCAG

ATTTGGAATTGCTTGTCGGACAGGCAATTTTTGGTGACGGGGCCGCAGCAGTCATAG

TGGGAGCCGAACCAGACGAAAGCGTGGGTGAAAGACCAATCTTTGAGTTGGTTCTG

ACCGGACAAACGATCTTACCTAACTCGGAAGGTACGATTGGAGGACATATTAGAGA

AGCCGGCCTAATTTTCGATCTTCACAAAGACGTTCCAATGTTAATCTCCAATAACAT

AGAAAAGTGCTTGATAGAAGCATTTACTCCCATTGGTATTAGTGACTGGAACAGCAT

TTTCTGGATCACCCACCCTGGAGGAAAAGCTATACTCGATAAGGTTGAAGAGAAAC

TCGACTTGAAAAAGGAGAAATTCGTTGACTCACGACATGTGTTATCAGAGCACGGG

AATATGAGTTCATCCACAGTCTTGTTCGTAATGGATGAATTGCGAAAACGCTCTCTT

GAGGAGGGAAAGAGCACAACCGGTGACGGGTTTGAGTGGGGCGTGCTATTCGGTTT

TGGCCCAGGTTTGACTGTCGAGCGGGTTGTTGTTCGTAGTGTACCAATTAAGTACTG

ATAAGAGTGACTCTTTTGATAAGAGTCGCAAATTTGATTTCATAAGTATATATTCATT

ATGTAAAGTAGTAAATGGAAAATTCATTAAAAAAAAAGCAAATTTCCGTTGTATGC

ATACTCCGAACACAAAACTAGCCCCGGAAAAACCCTTAGTTGATAGTTGCGAATTTA

GGTCGACCATATGCGACGGGTACAACGAGAATTGTATTGAATTGATCAAGAACATG

ATCTTGGTGTTACAGAACATCAAGTTCTTGGACCAGACTGAGAATGCACAGATATAC

AAGGCGTCATGTGATAAAATGGATGAGATTTATCCACAATTGAAGAAAGAGTTTAT

GGAAAGTGGTCAACCAGAAGCTAAACAGGAAGAAGCAAACGAAGAGGTGAAACAA

GAAGAAGAAGGTAAATAAGTATTTTGTATTATATAACAAACAAAGTAAGGAATACA

GATTTATACAATAAATTGCCATACTAGTCACGTGAGATATCTCATCCATTCCCCAAC

TCCCAAGAAAATAAAAAAGTGAAAAATAAAATCAAACCCAAAGATCAACCTCCCCA

TCATCATCGTCATCAAACCCCCAGCTCAATTCGCAATGGTTAGCACAAAAACATACA

CAGAAAGGGCATCAGCACACCCCTCCAAGGTTGCCCAACGTTTATTAATTAAAGGCT

AGGTGGAGGCTCAGTGATGATAAGTCTGCGATGGTGGATGCATGTGTCATGGTCATA

GCTGTTTCCTGTGTGAAATTGTTATCCGCTCAGAGGGCACAATCCTATTCCGCGCTAT

CCGACAATCTCCAAGACATTAGGTGGAGTTCAGTTCGGCGTATGGCATATGTCGCTG

GAAAGAACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAAAATCGACG

CTCAAGTCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTAGGTATCTC

-continued

AGTTCGGTGTAGGTCGTTCGCTCCAAGCTGGGCTGTGTGCACGAACCCCCCGTTCAG

CCCGACCGCTGCGCCTTATCCGGTAACTATCGTCTTGAGTCCAACCCGGTAAGACAC

GACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGAA

CAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGG

GGTCTGACGCTCTATTCAACAAAGCCGCCGTCCCGTCAAGTCAGCGTAAATGGGTAG

GGGGCTTCAAATCGTCCGCTCTGCCAGTGTTACAACCAATTAACAAATTCTGATTAG

AAAAACTCATCGAGCATCAAATGAAACTGCAATTTATTCATATCAGGATTATCAATA

CCATATTTTTGAAAAAGCCGTTTCTGTAATGAAGGAGAAAACTCACCGAGGCAGTTC

CATAGGATGGCAAGATCCTGGTATCGGTCTGCGATTCCGACTCGTCCAACATCAATA

CAACCTATTAATTTCCCCTCGTCAAAAATAAGGTTATCAAGTGAGAAATCACCATGA

GTGACGACTGAATCCGGTGAGAATGGCAAAAGCTTATGCATTTCTTTCCAGACTTGT

TCAACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGACA

ATTACAAACAGGAATCGAATGCAACCGGCGCAGGAACACTGCCAGCGCATCAACAA

TATTTTCACCTGAATCAGGATATTCTTCTAATACCTGGAATGCTGTTTTCCCGGGGAT

CGCAGTGGTGAGTAACCATGCATCATCAGGAGTACGGATAAAATGCTTGATGGTCG

GAAGAGGCATAAATTCCGTCAGCCAGTTTAGTCTGACCATCTCATCTGTAACATCAT

TGGCAACGCTACCTTTGCCATGTTTCAGAAACAACTCTGGCGCATCGGGCTTCCCAT

ACAATCGATAGATTGTCGCACCTGATTGCCCGACATTATCGCGAGCCCATTTATACC

CATATAAATCAGCATCCATGTTGGAATTTAATCGCGGCCTCGAGCAAGACGTTTCCC

GTTGAATATGGCTCATAACACCCCTTGTATTACTGTTTATGTAAGCAGACAGTTTTAT

TGTTCATGATGATATATTTTTATCTTGTGCAATGTAACATCAGAGATTTTGAGACACA

ACGTGGCTTTCCCCCGCCGCTCTAGAACTAGTGGATCCAAATAAAACGAAAGGCTC

AGTCGAAAGACTGGGCCTTTCGTTTTATCTGTTGTTTGTCGCATTATACGAGACGTCC

AGGTTGGGATACCTGAAACAAAACCCATCGTACGGCCAAGGAAGTCTCCAATAACT

GTGATCCACCACAAGCGCCAGGGTTTTCCCAGTCACGACGTTGTAAAACGACGGCC

AGTCATGCATAATCCGCACGCATCTGGAATAAGGAAGTGCCATTCCGCCTGACCT pLD12

(SEQ ID NO: 159)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

-continued

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGCAGTCAAACACCTAATAGTTCT

CAAATTTAAAGACGAGATTACTGAAGCTCAGAAGGAAGAGTTCTTTAAGACATATG

TTAACTTAGTCAACATCATCCCCGCGATGAAGGACGTCTACTGGGGCAAGGATGTGA

CGCAAAAAAATAAGGAAGAAGGATACACACATATCGTTGAGGTGACCTTTGAGAGT

GTGGAAACTATTCAAGATTATATTATTCACCCAGCCCATGTAGGGTTCGGTGACGTT

TATCGATCATTCTGGGAAAAGTTGCTTATATTTGATTACACCCCAAGAAAATTGAAG

CCTAAGTGATAAGAGTGACTCTTTTGATAAGAGTCGCAAATTTGATTTCATAAGTAT

ATATTCATTATGTAAAGTAGTAAATGGAAAATTCATTAAAAAAAAAGCAAATTTCCG

TTGTATGCATACTCCGAACACAAAACTAGCCCCGGAAAAACCCTTAGTTGATAGTTG

CGAATTTAGGTCGACCATATGCGACGGGTACAACGAGAATTGTATTGAATTGATCAA

GAACATGATCTTGGTGTTACAGAACATCAAGTTCTTGGACCAGACTGAGAATGCACA

GATATACAAGGCGTCATGTGATAAAATGGATGAGATTTATCCACAATTGAAGAAAG

AGTTTATGGAAAGTGGTCAACCAGAAGCTAAACAGGAAGAAGCAAACGAAGAGGT

GAAACAAGAAGAAGAAGGTAAATAAGTATTTTGTATTATATAACAAACAAAGTAAG

GAATACAGATTTATACAATAAATTGCCATACTAGTCACGTGAGATATCTCATCCATT

CCCCAACTCCCAAGAAAATAAAAAAGTGAAAAATAAAATCAAACCCAAAGATCAA

CCTCCCCATCATCATCGTCATCAAACCCCCAGCTCAATTCGCAATGGTTAGCACAAA

AACATACACAGAAAGGGCATCAGCACACCCCTCCAAGGTTGCCCAACGTTTATTAA

TTAAAGGCTAGGTGGAGGCTCAGTGATGATAAGTCTGCGATGGTGGATGCATGTGTC

ATGGTCATAGCTGTTTCCTGTGTGAAATTGTTATCCGCTCAGAGGGCACAATCCTATT

CCGCGCTATCCGACAATCTCCAAGACATTAGGTGGAGTTCAGTTCGGCGTATGGCAT

ATGTCGCTGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAA

-continued

AAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACAC

TAGAAGAACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTTTTTTTGT

TTGCAAGCAGCAGATTACGCGCAGAAAAAAAGGATCTCAAGAAGATCCTTTGATCT

TTTCTACGGGGTCTGACGCTCTATTCAACAAAGCCGCCGTCCCGTCAAGTCAGCGTA

AATGGGTAGGGGGCTTCAAATCGTCCGCTCTGCCAGTGTTACAACCAATTAACAAAT

TCTGATTAGAAAAACTCATCGAGCATCAAATGAAACTGCAATTTATTCATATCAGGA

TTATCAATACCATATTTTTGAAAAAGCCGTTTCTGTAATGAAGGAGAAAACTCACCG

AGGCAGTTCCATAGGATGGCAAGATCCTGGTATCGGTCTGCGATTCCGACTCGTCCA

ACATCAATACAACCTATTAATTTCCCCTCGTCAAAAATAAGGTTATCAAGTGAGAAA

TCACCATGAGTGACGACTGAATCCGGTGAGAATGGCAAAAGCTTATGCATTTCTTTC

CAGACTTGTTCAACAGGCCAGCCATTACGCTCGTCATCAAAATCACTCGCATCAACC

AAACCGTTATTCATTCGTGATTGCGCCTGAGCGAGACGAAATACGCGATCGCTGTTA

AAAGGACAATTACAAACAGGAATCGAATGCAACCGGCGCAGGAACACTGCCAGCG

CATCAACAATATTTTCACCTGAATCAGGATATTCTTCTAATACCTGGAATGCTGTTTT

CCCGGGGATCGCAGTGGTGAGTAACCATGCATCATCAGGAGTACGGATAAAATGCT

TGATGGTCGGAAGAGGCATAAATTCCGTCAGCCAGTTTAGTCTGACCATCTCATCTG

TAACATCATTGGCAACGCTACCTTTGCCATGTTTCAGAAACAACTCTGGCGCATCGG

GCTTCCCATACAATCGATAGATTGTCGCACCTGATTGCCCGACATTATCGCGAGCCC

ATTTATACCCATATAAATCAGCATCCATGTTGGAATTTAATCGCGGCCTCGAGCAAG

ACGTTTCCCGTTGAATATGGCTCATAACACCCCTTGTATTACTGTTTATGTAAGCAGA

CAGTTTTATTGTTCATGATGATATATTTTTATCTTGTGCAATGTAACATCAGAGATTT

TGAGACACAACGTGGCTTTCCCCCGCCGCTCTAGAACTAGTGGATCCAAATAAAAC

GAAAGGCTCAGTCGAAAGACTGGGCCTTTCGTTTTATCTGTTGTTTGTCGCATTATAC

GAGACGTCCAGGTTGGGATACCTGAAACAAAACCCATCGTACGGCCAAGGAAGTCT

CCAATAACTGTGATCCACCACAAGCGCCAGGGTTTTCCCAGTCACGACGTTGTAAAA

CGACGGCCAGTCATGCATAATCCGCACGCATCTGGAATAAGGAAGTGCCATTCCGC

CTGACCT pLD14

(SEQ ID NO: 160)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGCAGTCAAACACCTAATAGTTCT

CAAATTTAAAGACGAGATTACTGAAGCTCAGAAGGAAGAGTTCTTTAAGACATATG

TTAACTTAGTCAACATCATCCCCGCGATGAAGGACGTCTACTGGGGCAAGGATGTGA

CGCAAAAAAATAAGGAAGAAGGATACACACATATCGTTGAGGTGACCTTTGAGAGT

GTGGAAACTATTCAAGATTATATTATTCACCCAGCCCATGTAGGGTTCGGTGACGTT

TATCGATCATTCTGGGAAAAGTTGCTTATATTTGATTACACCCCAAGAAAATTGAAG

CCTAAGGGAAGACGAGCTAAGTTGTGATAAGAGTGACTCTTTTGATAAGAGTCGCA

AATTTGATTTCATAAGTATATATTCATTATGTAAAGTAGTAAATGGAAAATTCATTA

AAAAAAAAGCAAATTTCCGTTGTATGCATACTCCGAACACAAAACTAGCCCCGGAA

AAACCCTTAGTTGATAGTTGCGAATTTAGGTCGACCATATGCGACGGGTACAACGAG

AATTGTATTGAATTGATCAAGAACATGATCTTGGTGTTACAGAACATCAAGTTCTTG

GACCAGACTGAGAATGCACAGATATACAAGGCGTCATGTGATAAAATGGATGAGAT

TTATCCACAATTGAAGAAAGAGTTTATGGAAAGTGGTCAACCAGAAGCTAAACAGG

AAGAAGCAAACGAAGAGGTGAAACAAGAAGAAGAAGGTAAATAAGTATTTTGTAT

TATATAACAAACAAAGTAAGGAATACAGATTTATACAATAAATTGCCATACTAGTC

ACGTGAGATATCTCATCCATTCCCCAACTCCCAAGAAAATAAAAAAGTGAAAAATA

AAATCAAACCCAAAGATCAACCTCCCCATCATCATCGTCATCAAACCCCCAGCTCAA

TTCGCAATGGTTAGCACAAAAACATACACAGAAAGGGCATCAGCACACCCCTCCAA

GGTTGCCCAACGTTTATTAATTAAAGGCTAGGTGGAGGCTCAGTGATGATAAGTCTG

-continued

CGATGGTGGATGCATGTGTCATGGTCATAGCTGTTTCCTGTGTGAAATTGTTATCCGC

TCAGAGGGCACAATCCTATTCCGCGCTATCCGACAATCTCCAAGACATTAGGTGGAG

TTCAGTTCGGCGTATGGCATATGTCGCTGGAAAGAACATGTGAGCAAAAGGCCAGC

AAAAGGCCAGGAACCGTAAAAAGGCCGCGTTGCTGGCGTTTTTCCATAGGCTCCGC

CCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGT

TCCGACCCTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTCGCTCCAAG

CTGGGCTGTGTGCACGAACCCCCCGTTCAGCCCGACCGCTGCGCCTTATCCGGTAAC

TATCGTCTTGAGTCCAACCCGGTAAGACACGACTTATCGCCACTGGCAGCAGCCACT

GGTAACAGGATTAGCAGAGCGAGGTATGTAGGCGGTGCTACAGAGTTCTTGAAGTG

GTGGCCTAACTACGGCTACACTAGAAGAACAGTATTTGGTATCTGCGCTCTGCTGAA

GCCAGTTACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAAAAAAGGAT

CTCAAGAAGATCCTTTGATCTTTTCTACGGGGTCTGACGCTCTATTCAACAAAGCCG

CCGTCCCGTCAAGTCAGCGTAAATGGGTAGGGGGCTTCAAATCGTCCGCTCTGCCAG

TGTTACAACCAATTAACAAATTCTGATTAGAAAAACTCATCGAGCATCAAATGAAAC

TGCAATTTATTCATATCAGGATTATCAATACCATATTTTTGAAAAAGCCGTTTCTGTA

ATGAAGGAGAAAACTCACCGAGGCAGTTCCATAGGATGGCAAGATCCTGGTATCGG

TCTGCGATTCCGACTCGTCCAACATCAATACAACCTATTAATTTCCCCTCGTCAAAA

ATAAGGTTATCAAGTGAGAAATCACCATGAGTGACGACTGAATCCGGTGAGAATGG

CAAAAGCTTATGCATTTCTTTCCAGACTTGTTCAACAGGCCAGCCATTACGCTCGTC

ATCAAAATCACTCGCATCAACCAAACCGTTATTCATTCGTGATTGCGCCTGAGCGAG

ACGAAATACGCGATCGCTGTTAAAAGGACAATTACAAACAGGAATCGAATGCAACC

GGCGCAGGAACACTGCCAGCGCATCAACAATATTTTCACCTGAATCAGGATATTCTT

CTAATACCTGGAATGCTGTTTTCCCGGGGATCGCAGTGGTGAGTAACCATGCATCAT

CAGGAGTACGGATAAAATGCTTGATGGTCGGAAGAGGCATAAATTCCGTCAGCCAG

TTTAGTCTGACCATCTCATCTGTAACATCATTGGCAACGCTACCTTTGCCATGTTTCA

GAAACAACTCTGGCGCATCGGGCTTCCCATACAATCGATAGATTGTCGCACCTGATT

GCCCGACATTATCGCGAGCCCATTTATACCCATATAAATCAGCATCCATGTTGGAAT

TTAATCGCGGCCTCGAGCAAGACGTTTCCCGTTGAATATGGCTCATAACACCCCTTG

TATTACTGTTTATGTAAGCAGACAGTTTTATTGTTCATGATGATATATTTTTATCTTGT

GCAATGTAACATCAGAGATTTTGAGACACAACGTGGCTTTCCCCCGCCGCTCTAGAA

CTAGTGGATCCAAATAAAACGAAAGGCTCAGTCGAAAGACTGGGCCTTTCGTTTTAT

CTGTTGTTTGTCGCATTATACGAGACGTCCAGGTTGGGATACCTGAAACAAAACCCA

TCGTACGGCCAAGGAAGTCTCCAATAACTGTGATCCACCACAAGCGCCAGGGTTTTC

CCAGTCACGACGTTGTAAAACGACGGCCAGTCATGCATAATCCGCACGCATCTGGA

ATAAGGAAGTGCCATTCCGCCTGACCT pLD16

(SEQ ID NO: 161)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

-continued

TCGTGAAGACGCACATCGATATCATCTCAGACTTCAGCTACGAGGGCACGATTGAGC
CGTTGCTTGTGCTTGCAGAGCGCCACGGGTTCTTGATATTCGAGGACAGGAAGTTTG
CTGATATCGGAAACACCGTGATGTTGCAGTACACCTCGGGGGTATACCGGATCGCG
GCGTGGAGTGACATCACGAACGCGCACGGAGTGACTGGGAAGGGCGTCGTTGAAGG
GTTGAAACGCGGTGCGGAGGGGGTAGAAAAGGAAAGGGGCGTGTTGATGTTGGCG
GAGTTGTCGAGTAAAGGCTCGTTGGCGCATGGTGAATATACCCGTGAGACGATCGA
GATTGCGAAGAGTGATCGGGAGTTCGTGATTGGGTTCATCGCGCAGCGGGACATGG
GGGGTAGAGAAGAAGGGTTTGATTGGATCATCATGACGCCTGGTGTGGGGTTGGAT
GATAAAGGCGATGCGTTGGGCCAGCAGTATAGGACTGTTGATGAGGTGGTTCTGAC
TGGTACCGATGTGATTATTGTCGGGAGAGGGTTGTTTGGAAAAGGAAGAGACCCTG
AGGTGGAGGGAAAGAGATACAGGGATGCTGGATGGAAGGCATACTTGAAGAGAAC
TGGTCAGTTAGAATAAATATTGTAATAAATAGGTCTATATACATACACTAAGCTTCT
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG
GCATGGCAGATCATCATGCCTGCAGGAGCTCCAATTGTAATATTTCGGGAGAAATAT
CGTTGGGGTAAAACAACAGAGAGAGAGAGGGAGAGATGGTTCTGGTAGAATTATAA
TCTGGTTGTTGCAAATGCTACTGATCGACTCTGGCAATGTCTGTAGCTCGCTAGTTGT
ATGCAACTTAGGTGTTATGCATACACACGGTTATTCGGTTGAATTGTGGAGTAAAAA
TTGTCTGAGTTGTGTCTTAGCTACTGGCTGGCCCCCCGCGAAAGATAATCAAAATTA
CACTTGTGAATTTTTGCACACACACCGATTAACATTTCCCTTTTTTGTCCACCGATAC
ACGCTTGCCTCTTCTTATTTTCTCTGTGCTTCCCCCTCCTGTGACTTTTTCCACCATTG
ATATAAAATCAACTCCATTTCCCTAAAATCTCCCCAGATTCTAAAAACAACTTCTTCT
CTTCTGCTTTTCCTTATTTTTGTTATATTTATTTACCATCCCTTATTTTGAATAGTTATT
CCCCACTAACATTGTTCAAATCTTCACGACataATGGGAAAAAATTATAAATCTTTGG
ACTCAGTTGTGGCTAGTGACTTCATTGCACTTGGGATCACATCAGAAGTTGCTGAGA
CATTGCACGGACGCTTGGCAGAGATAGTTTGCAACTACGGCGCCGCAACACCTCAG
ACCTGGATTAACATCGCAAACCATATTCTAAGTCCAGATCTTCCATTTAGTCTCCATC
AGATGTTGTTCTACGGTTGTTATAAGGACTTTGGTCCAGCACCCCCAGCTTGGATAC
CAGACCCCGAAAAAGTAAAGTCCACGAACTTAGGTGCCTTGTTAGAAAAGCGGGGA
AAGGAGTTTCTAGGCGTTAAGTATAAGGACCCAATAAGTCTGTTTTCTCACTTCCAG
GAGTTTAGCGTTCGAAATCCGGAAGTCTACTGGCGGACGGTACTTATGGATGAAATG
AAGATACTGTTCAGCAAAGATCCCGAATGTATCCTCAGACGCGACGACATTAACAA
CCCAGGGGGCTCTGAGTGGCTACCAGGTGGATATCTCAACCTGGCCAAGAACTGTTT
GAATGTAAATAGTAACAAAAAACTTAACGACACTATGATAGTGTGGAGAGATGAAG
GAAATGACGATCTCCCATTGAATAAATTGACTCTTGATCAATTACGAAAACGAGTCT
GGTTGGTTGGATACGCCCTAGAAGAGATGGGCCTTGAGAAGGGATGTGCGATTGCA
ATTGACATGCCCATGCACGTAGATGCGGTTGTGATCTATTTAGCTATCGTCTTGGCA
GGCTACGTCGTTGTCTCCATTGCAGATTCATTCTCAGCACCGGAAATTTCCACAAGA -continued

TTGCGTCTATCAAAGGCTAAGGCTATTTTTACACAAGATCATATCATCCGAGGGAAA

AAGCGTATACCTTTGTACCTGCGTGTCGTCGAGGCCAAGTCTCCGATGGCAATAGTT

ATCCCGTGTTCGGGTTCAAATATTGGTGCGGAATTGCGGGATGGTGATATTCTGTGG

GATTACTTCTTAGAACGCGCAAAGGAATTTAAGAACTGCGAATTTACAGCCCGTGAA

CAGCCAGTGGACGCGTACACAAATATTTTGTTCTCATCGGGAACCACCGGAGAGCC

AAAGGCGATACCATGGACTCAAGCTACGCCTCTCAAGGCGGCTGCTGATGGTTGGTC

ACACTTGGACATTAGAAAGGGTGACGTAATTGTATGGCCTACCAATTTGGGGTGGAT

GATGGGGCCTTGGTTGGTCTATGCTTCACTCCTTAACGGGGCAAGCATCGCATTGTA

TAACGGATCTCCACTAGTGTCCGGCTTTGCCAAATTCGTTCAAGATGCGAAAGTTAC

TATGCTAGGAGTTGTCCCCTCCATCGTACGAAGCTGGAAAAGCACTAATTGCGTTAG

TGGGTACGATTGGTCTACAATCAGATGCTTCTCCTCATCGGGTGAGGCATCGAATGT

CGATGAATACTTATGGCTAATGGGAAGGGCTAACTACAAACCGGTCATCGAAATGT

GCGGTGGCACAGAGATCGGGGGTGCCTTCAGCGCCGGTTCGTTTTTACAAGCCCAAT

CTTTGAGTAGCTTCTCATCCCAATGTATGGGATGCACCTTGTACATTCTCGACAAGA

ATGGCTACCCGATGCCAAAGAACAAGCCGGGTATAGGTGAATTGGCCTTGGGACCC

GTGATGTTCGGTGCTTCCAAGACTTTACTTAACGGAAACCATCATGACGTTTATTTCA

AAGGCATGCCCACCTTGAACGGAGAAGTCTTGAGGAGACACGGAGATATCTTCGAA

CTCACTTCGAACGGCTATTATCACGCTCATGGTAGAGCAGATGACACGATGAATATC

GGGGGGATTAAAATTTCCTCAATCGAGATTGAAAGGGTGTGTAATGAAGTTGACGA

TAGAGTGTTTGAGACTACGGCCATTGGAGTGCCTCCATTGGGCGGAGGTCCAGAGC

AGCTCGTTATCTTTTTTGTTCTTAAGGACAGCAATGATACGACCATCGACCTAAACC

AATTGCGACTTAGTTTTAATCTTGGGTTACAAAAGAAATTGAACCCACTTTTTAAGG

TGACGAGGGTTGTGCCACTTTCGCTGTTGCCTAGGACAGCCACCAACAAAATAATGA

GAAGAGTGCTTAGACAGCAATTTAGTCATTTCGAGTGATAAGAGTGACTCTTTTGAT

AAGAGTCGCAAATTTGATTTCATAAGTATATATTCATTATGTAAAGTAGTAAATGGA

AAATTCATTAAAAAAAAAGCAAATTTCCGTTGTATGCATACTCCGAACACAAAACTA

GCCCCGGAAAAACCCTTAGTTGATAGTTGCGAATTTAGGTCGACCATATGCGACGGG

TACAACGAGAATTGTATTGAATTGATCAAGAACATGATCTTGGTGTTACAGAACATC

AAGTTCTTGGACCAGACTGAGAATGCACAGATATACAAGGCGTCATGTGATAAAAT

GGATGAGATTTATCCACAATTGAAGAAAGAGTTTATGGAAAGTGGTCAACCAGAAG

CTAAACAGGAAGAAGCAAACGAAGAGGTGAAACAAGAAGAAGAAGGTAAATAAGT

ATTTTGTATTATATAACAAACAAAGTAAGGAATACAGATTTATACAATAAATTGCCA

TACTAGTCACGTGAGATATCTCATCCATTCCCCAACTCCCAAGAAAATAAAAAAGTG

AAAAATAAAATCAAACCCAAAGATCAACCTCCCCATCATCATCGTCATCAAACCCC

CAGCTCAATTCGCAATGGTTAGCACAAAAACATACACAGAAAGGGCATCAGCACAC

CCCTCCAAGGTTGCCCAACGTTTATTAATTAAAGGCTAGGTGGAGGCTCAGTGATGA

TAAGTCTGCGATGGTGGATGCATGTGTCATGGTCATAGCTGTTTCCTGTGTGAAATT

GTTATCCGCTCAGAGGGCACAATCCTATTCCGCGCTATCCGACAATCTCCAAGACAT

TAGGTGGAGTTCAGTTCGGCGTATGGCATATGTCGCTGGAAAGAACATGTGAGCAA

AAGGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGGCG

-continued

AAACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTCGGG

AAGCGTGGCGCTTTCTCATAGCTCACGCTGTAGGTATCTCAGTTCGGTGTAGGTCGT

TCGCTCCAAGCTGGGCTGTGTGCACGAACCCCCCGTTCAGCCCGACCGCTGCGCCTT

ATCCGGTAACTATCGTCTTGAGTCCAACCCGGTAAGACACGACTTATCGCCACTGGC

AGCAGCCACTGGTAACAGGATTAGCAGAGCGAGGTATGTAGGCGGTGCTACAGAGT

TCTTGAAGTGGTGGCCTAACTACGGCTACACTAGAAGAACAGTATTTGGTATCTGCG

CTCTGCTGAAGCCAGTTACCTTCGGAAAAAGAGTTGGTAGCTCTTGATCCGGCAAAC

AAACCACCGCTGGTAGCGGTGGTTTTTTTGTTTGCAAGCAGCAGATTACGCGCAGAA

AAAAAGGATCTCAAGAAGATCCTTTGATCTTTTCTACGGGGTCTGACGCTCTATTCA

ACAAAGCCGCCGTCCCGTCAAGTCAGCGTAAATGGGTAGGGGGCTTCAAATCGTCC

GCTCTGCCAGTGTTACAACCAATTAACAAATTCTGATTAGAAAAACTCATCGAGCAT

CAAATGAAACTGCAATTTATTCATATCAGGATTATCAATACCATATTTTTGAAAAAG

CCGTTTCTGTAATGAAGGAGAAAACTCACCGAGGCAGTTCCATAGGATGGCAAGAT

CCTGGTATCGGTCTGCGATTCCGACTCGTCCAACATCAATACAACCTATTAATTTCCC

CTCGTCAAAAATAAGGTTATCAAGTGAGAAATCACCATGAGTGACGACTGAATCCG

GTGAGAATGGCAAAAGCTTATGCATTTCTTTCCAGACTTGTTCAACAGGCCAGCCAT

TACGCTCGTCATCAAAATCACTCGCATCAACCAAACCGTTATTCATTCGTGATTGCG

CCTGAGCGAGACGAAATACGCGATCGCTGTTAAAAGGACAATTACAAACAGGAATC

GAATGCAACCGGCGCAGGAACACTGCCAGCGCATCAACAATATTTTCACCTGAATC

AGGATATTCTTCTAATACCTGGAATGCTGTTTTCCCGGGGATCGCAGTGGTGAGTAA

CCATGCATCATCAGGAGTACGGATAAAATGCTTGATGGTCGGAAGAGGCATAAATT

CCGTCAGCCAGTTTAGTCTGACCATCTCATCTGTAACATCATTGGCAACGCTACCTTT

GCCATGTTTCAGAAACAACTCTGGCGCATCGGGCTTCCCATACAATCGATAGATTGT

CGCACCTGATTGCCCGACATTATCGCGAGCCCATTTATACCCATATAAATCAGCATC

CATGTTGGAATTTAATCGCGGCCTCGAGCAAGACGTTTCCCGTTGAATATGGCTCAT

AACACCCCTTGTATTACTGTTTATGTAAGCAGACAGTTTTATTGTTCATGATGATATA

TTTTTATCTTGTGCAATGTAACATCAGAGATTTTGAGACACAACGTGGCTTTCCCCCG

CCGCTCTAGAACTAGTGGATCCAAATAAAACGAAAGGCTCAGTCGAAAGACTGGGC

CTTTCGTTTTATCTGTTGTTTGTCGCATTATACGAGACGTCCAGGTTGGGATACCTGA

AACAAAACCCATCGTACGGCCAAGGAAGTCTCCAATAACTGTGATCCACCACAAGC

GCCAGGGTTTTCCCAGTCACGACGTTGTAAAACGACGGCCAGTCATGCATAATCCGC

ACGCATCTGGAATAAGGAAGTGCCATTCCGCCTGACCT pLD20

(SEQ ID NO: 162)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

-continued

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAAGTGTTCTACGTTTAGTTTTTG

GTTTGTTTGTAAAATTATATTCTTCTTTTTTTCCTTCAACATTCAGACATCAATCGCCA

ACCCAAGGGAAAACTTCCTTAAGTGTTTTCTGCAGTACATCCCTAACAATGCAACAA

ACCTCAAGTTGGTGTACACTCAAAACAATCCACTCTATATGAGCGTGCTTAATAGCA

CAATCCACAACTTGCGCTTCACGTCAGATACTACGCCTAAGCCACTAGTGATCGTTA

CACCATCACACGTCAGCCATATTCAAGGAACGATCCTATGTCTGAAAAAGGTCGGGT

TGCAAATCAGGACTCGATCAGGAGGGCACGATAGTGAGGGAATGAGTTACATCTCG

CAAGTACCCTTCGTGATAGTTGACTTGCGAAATATGCGGTCTATTAAAATTGACGTA

CATAGCCAGACCGCCTGGGTTGAAGCAGGGGCAACCTTGGGTGAAGTTTATTACTG

GGTCAATGAAAAAAACGAAAACCTAAGTCTTGCTGCTGGATATTGCCCCACCGTTTG

CGCGGGTGGTCATTTTGGAGGCGGCGGATATGGTCCGTTGATGAGAAATTATGGACT

TGCAGCAGACAATATTATAGATGCCCACTTGGTGAACGTTCATGGAAAGGTCTTGGA

CCGTAAGTCCATGGGTGAAGATCTTTTCTGGGCCTTGAGAGGTGGTGGAGCGGAATC

GTTTGGCATCATCGTTGCCTGGAAAATTAGGTTGGTTGCGGTCCCGAAGAGTACAAT

GTTCTCCGTGAAGAAGATTATGGAAATACATGAGCTTGTCAAGTTAGTTAACAAGTG

GCAAAATATCGCTTATAAGTATGATAAAGACTTGCTTTTGATGACTCATTTTATTACG

CGAAACATAACCGATAACCAGGGCAAGAACAAGACTGCTATTCACACGTACTTCTC

CTCTGTATTTCTTGGAGGAGTAGACTCCTTAGTTGACTTGATGAACAAGAGTTTCCC

AGAATTGGGGATTAAGAAGACAGATTGCAGACAATTATCGTGGATAGATACAATCA

TATTCTATAGCGGTGTCGTCAATTACGATACTGATAATTTTAATAAAGAAATCCTCCT

-continued

AGATCGTTCAGCTGGGCAAAACGGGGCATTCAAAATTAAATTGGATTATGTGAAGA

AACCAATTCCAGAGCTGGTGTTTGTTCAGATATTGGAAAAACTTTACGAAGAAGACA

TTGGCGCAGGTATGTACGCTTTGTATCCATATGGAGGCATTATGGACGAGATCTCAG

AGCTGGCGATCCCCTTCCCGCACAGAGCTGGGATACTCTACGAGCTATGGTACATCT

GCTCTTGGGAGAAACAAGAAGACAACGAGAAACATCTCAATTGGATTCGGAACATA

TACAACTTTATGACCCCATACGTATCAAAAAACCCGCGCTTAGCATACTTGAATTAC

AGAGACTTAGATATCGGTATCAATGATCCTAAGAATCCTAACAATTACACCCAAGCC

CGTATTTGGGGTGAGAAATATTTCGGCAAGAATTTTGACAGATTAGTTAAGGTCAAA

ACACTCGTGGACCCCAACAACTTTTTCCGAAACGAGCAGTCGATTCCACCACTACCC

AGGCATAGACACTGATAAGAGTGACTCTTTTGATAAGAGTCGCAAATTTGATTTCAT

AAGTATATATTCATTATGTAAAGTAGTAAATGGAAAATTCATTAAAAAAAAAGCAA

ATTTCCGTTGTATGCATACTCCGAACACAAAACTAGCCCCGGAAAAACCCTTAGTTG

ATAGTTGCGAATTTAGGTCGACCATATGCGACGGGTACAACGAGAATTGTATTGAAT

TGATCAAGAACATGATCTTGGTGTTACAGAACATCAAGTTCTTGGACCAGACTGAGA

ATGCACAGATATACAAGGCGTCATGTGATAAAATGGATGAGATTTATCCACAATTG

AAGAAAGAGTTTATGGAAAGTGGTCAACCAGAAGCTAAACAGGAAGAAGCAAACG

AAGAGGTGAAACAAGAAGAAGAAGGTAAATAAGTATTTTGTATTATATAACAAACA

AAGTAAGGAATACAGATTTATACAATAAATTGCCATACTAGTCACGTGAGATATCTC

ATCCATTCCCCAACTCCCAAGAAAATAAAAAAGTGAAAAATAAAATCAAACCCAAA

GATCAACCTCCCCATCATCATCGTCATCAAACCCCCAGCTCAATTCGCAATGGTTAG

CACAAAAACATACACAGAAAGGGCATCAGCACACCCCTCCAAGGTTGCCCAACGTT

TATTAATTAAAGGCTAGGTGGAGGCTCAGTGATGATAAGTCTGCGATGGTGGATGC

ATGTGTCATGGTCATAGCTGTTTCCTGTGTGAAATTGTTATCCGCTCAGAGGGCACA

ATCCTATTCCGCGCTATCCGACAATCTCCAAGACATTAGGTGGAGTTCAGTTCGGCG

TATGGCATATGTCGCTGGAAAGAACATGTGAGCAAAAGGCCAGCAAAAGGCCAGGA

ACCGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTC

GGAAAAAGAGTTGGTAGCTCTTGATCCGGCAAACAAACCACCGCTGGTAGCGGTGG

TTTTTTTGTTTGCAAGCAGCAGATTACGCGCAGAAAAAAAGGATCTCAAGAAGATCC

TTTGATCTTTTCTACGGGGTCTGACGCTCTATTCAACAAAGCCGCCGTCCCGTCAAGT

CAGCGTAAATGGGTAGGGGGCTTCAAATCGTCCGCTCTGCCAGTGTTACAACCAATT

AACAAATTCTGATTAGAAAAACTCATCGAGCATCAAATGAAACTGCAATTTATTCAT

ATCAGGATTATCAATACCATATTTTTGAAAAAGCCGTTTCTGTAATGAAGGAGAAAA

-continued

CTCACCGAGGCAGTTCCATAGGATGGCAAGATCCTGGTATCGGTCTGCGATTCCGAC

TCGTCCAACATCAATACAACCTATTAATTTCCCCTCGTCAAAAATAAGGTTATCAAG

TGAGAAATCACCATGAGTGACGACTGAATCCGGTGAGAATGGCAAAAGCTTATGCA

TTTCTTTCCAGACTTGTTCAACAGGCCAGCCATTACGCTCGTCATCAAAATCACTCGC

ATCAACCAAACCGTTATTCATTCGTGATTGCGCCTGAGCGAGACGAAATACGCGATC

GCTGTTAAAAGGACAATTACAAACAGGAATCGAATGCAACCGGCGCAGGAACACTG

CCAGCGCATCAACAATATTTTCACCTGAATCAGGATATTCTTCTAATACCTGGAATG

CTGTTTTCCCGGGGATCGCAGTGGTGAGTAACCATGCATCATCAGGAGTACGGATAA

AATGCTTGATGGTCGGAAGAGGCATAAATTCCGTCAGCCAGTTTAGTCTGACCATCT

CATCTGTAACATCATTGGCAACGCTACCTTTGCCATGTTTCAGAAACAACTCTGGCG

CATCGGGCTTCCCATACAATCGATAGATTGTCGCACCTGATTGCCCGACATTATCGC

GAGCCCATTTATACCCATATAAATCAGCATCCATGTTGGAATTTAATCGCGGCCTCG

AGCAAGACGTTTCCCGTTGAATATGGCTCATAACACCCCTTGTATTACTGTTTATGTA

AGCAGACAGTTTTATTGTTCATGATGATATATTTTTATCTTGTGCAATGTAACATCAG

AGATTTTGAGACACAACGTGGCTTTCCCCCGCCGCTCTAGAACTAGTGGATCCAAAT

AAAACGAAAGGCTCAGTCGAAAGACTGGGCCTTTCGTTTTATCTGTTGTTTGTCGCA

TTATACGAGACGTCCAGGTTGGGATACCTGAAACAAAACCCATCGTACGGCCAAGG

AAGTCTCCAATAACTGTGATCCACCACAAGCGCCAGGGTTTTCCCAGTCACGACGTT

GTAAAACGACGGCCAGTCATGCATAATCCGCACGCATCTGGAATAAGGAAGTGCCA

TTCCGCCTGACCT pLD22

(SEQ ID NO: 163)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

-continued

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGACAGAAGTAGTAGATAGAGCAA

GTTCCCCAGCAAGTCCAGGATCTACGACCGCCGCCGCAGACGGTGCTAAGGTGGCG

GTGGAGCCACGCGTAGATGTAGCGGCCCTTGGCGAGCAGTTGCTAGGGCGATGGGC

TGACATCAGATTGCACGCACGAGACTTAGCAGGCCGCGAAGTGGTCCAAAAGGTTG

AAGGACTTACGCACACTGAGCATCGGAGTAGAGTCTTTGGACAGTTGAAGTACTTG

GTAGACAACAATGCTGTTCACAGAGCTTTTCCCTCCAGGCTAGGTGGATCAGATGAC

CATGGCGGTAATATAGCTGGATTCGAGGAATTAGTTACTGCTGATCCATCATTGCAA

ATAAAGGCCGGCGTTCAGTGGGGTTTGTTTGGTTCTGCAGTGATGCACTTGGGAACC

CGTGAACATCATGACAAGTGGTTGCCAGGTATTATGTCGTTAGAAATACCGGGGTGT

TTCGCGATGACAGAAACCGGGCACGGTAGCGACGTGGCCTCTATTGCTACAACAGC

AACTTATGATGAGGAAACCCAAGAGTTTGTTATTGATACCCCGTTCAGAGCCGCTTG

GAAAGATTATATCGGTAATGCAGCGAACGATGGTTTGGCGGCAGTTGTTTTCGCACA

ATTAATCACGAGGAAAGTGAACCATGGTGTACACGCCTTTTACGTGGATCTCAGAGA

TCCTGCGACTGGAGACTTCCTACCCGGAATAGGAGGAGAGGACGATGGAATCAAGG

GGGGATTGAATGGCATTGACAACGGTAGACTACATTTTACGAACGTACGCATTCCTA

GAACTAATCTTCTTAACAGATATGGCGATGTGGCGGTCGACGGCACATACCTGTCGA

CCATCGAATCACCAGGGCGCCGGTTCTTTACGATGCTTGGTACTCTAGTCCAGGGTA

GAGTTAGTCTCGATGGAGCAGCTGTCGCTGCACTGAAGGTCGCATTGCAAAGTGCA

ATTCACTACGCTGCGGAGAGGAGACAATTTAATGCGACTTCACCTACTGAAGAAGA

GGTCCTTCTTGATTATCAGAGGCATCAAAGGAGACTCTTTACACGACTTGCAACGAC

GTACGCCGCATCTTTCGCCCACGAGCAGCTATTGCAAAAGTTCGATGATGTCTTTTC

AGGGGCACATGATACCGACGCCGACCGGCAGGACTTGGAAACCCTAGCCGCCGCTT

TGAAGCCATTGAGCACATGGCATGCACTTGACACGTTACAAGAATGCAGAGAGGCC

TGTGGGGGGGCCGGATTTTTGATAGAAAACCGTTTCGCGAGCTTGCGTGCTGACTTG

GACGTTTACGTCACATTCGAGGGTGATAACACAGTTTTATTGCAATTGGTTGCTAAA

CGGCTCTTGGCAGACTACGCAAAAGAGTTCAGAGGGGCCAACTTCGGCGTTCTTGCC

AGGTATGTGGTTGACCAAGCCGCGGGAGTGGCGCTCCACCGAACAGGACTAAGGCA

AGTCGCTCAATTTGTTGCAGACAGCGGGTCCGTTCAGAAGTCGGCTCTTGCGCTTCG

CGATGAAGAGGGTCAACGAACATTGTTAACGGACAGAGTACAGAGCATGGTTGCCG

AAGTGGGGGCTGCCTTGAAAGGCGCAGGCAAATTACCCCAACATCAAGCAGCTGCA

TTGTTCAACCAACACCAGAACGAACTTATTGAGGCTGCCCAGGCCCATGCAGAACTC

CTCCAATGGGAGGCATTTACAGAAGCTCTCGCTAAAGTCGACGATGCTGGTACAAA

GGAAGTGCTTACTCGATTGCGAGATCTCTTTGGTTTGTCCTTGATTGAAAAACACTTG

-continued

CTGTGGTATCTTATGAATGGACGTTTGTCCATGCAAAGAGGCAGGACAGTTGGAACT

TACATTAATCGTTTACTTGTCAAGATCCGTCCACACGCACTAGACTTGGTTGATGCCT

TCGGTTACGGCGCGGAGCATTTGCGTGCTGCTATCGCCACCGGAGCGGAAGCAACC

CGACAGGATGAAGCCCGAACGTATTTTAGACAACAACGGGCATCGGGACTGGCCCC

GGCCGATGAAAAGACCTTACTCGCTATCAAAGCTGGTAAATCAAGAGGGCGAAGGG

CAAAGCTATGATAAGAGTGACTCTTTTGATAAGAGTCGCAAATTTGATTTCATAAGT

ATATATTCATTATGTAAAGTAGTAAATGGAAAATTCATTAAAAAAAAAGCAAATTTC

CGTTGTATGCATACTCCGAACACAAAACTAGCCCCGGAAAAACCCTTAGTTGATAGT

TGCGAATTTAGGTCGACCATATGCGACGGGTACAACGAGAATTGTATTGAATTGATC

AAGAACATGATCTTGGTGTTACAGAACATCAAGTTCTTGGACCAGACTGAGAATGC

ACAGATATACAAGGCGTCATGTGATAAAATGGATGAGATTTATCCACAATTGAAGA

AAGAGTTTATGGAAAGTGGTCAACCAGAAGCTAAACAGGAAGAAGCAAACGAAGA

GGTGAAACAAGAAGAAGAAGGTAAATAAGTATTTTGTATTATATAACAAACAAAGT

AAGGAATACAGATTTATACAATAAATTGCCATACTAGTCACGTGAGATATCTCATCC

ATTCCCCAACTCCCAAGAAAATAAAAAAGTGAAAAATAAAATCAAACCCAAAGATC

AACCTCCCCATCATCATCGTCATCAAACCCCCAGCTCAATTCGCAATGGTTAGCACA

AAAACATACACAGAAAGGGCATCAGCACACCCCTCCAAGGTTGCCCAACGTTTATT

AATTAAAGGCTAGGTGGAGGCTCAGTGATGATAAGTCTGCGATGGTGGATGCATGT

GTCATGGTCATAGCTGTTTCCTGTGTGAAATTGTTATCCGCTCAGAGGGCACAATCC

TATTCCGCGCTATCCGACAATCTCCAAGACATTAGGTGGAGTTCAGTTCGGCGTATG

GCATATGTCGCTGGAAAGAACATGTGAGCAAAAGGCCAGCAAAAGGCCAGGAACC

GTAAAAAGGCCGCGTTGCTGGCGTTTTTCCATAGGCTCCGCCCCCCTGACGAGCATC

ACAAAAATCGACGCTCAAGTCAGAGGTGGCGAAACCCGACAGGACTATAAAGATAC

CAGGCGTTTCCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCACGA

ACCCCCCGTTCAGCCCGACCGCTGCGCCTTATCCGGTAACTATCGTCTTGAGTCCAA

CCCGGTAAGACACGACTTATCGCCACTGGCAGCAGCCACTGGTAACAGGATTAGCA

GAGCGAGGTATGTAGGCGGTGCTACAGAGTTCTTGAAGTGGTGGCCTAACTACGGC

TACACTAGAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGGTGGTTTT

TTTGTTTGCAAGCAGCAGATTACGCGCAGAAAAAAAGGATCTCAAGAAGATCCTTT

GATCTTTTCTACGGGGTCTGACGCTCTATTCAACAAAGCCGCCGTCCCGTCAAGTCA

GCGTAAATGGGTAGGGGGCTTCAAATCGTCCGCTCTGCCAGTGTTACAACCAATTAA

CAAATTCTGATTAGAAAAACTCATCGAGCATCAAATGAAACTGCAATTTATTCATAT

CAGGATTATCAATACCATATTTTTGAAAAAGCCGTTTCTGTAATGAAGGAGAAAACT

CACCGAGGCAGTTCCATAGGATGGCAAGATCCTGGTATCGGTCTGCGATTCCGACTC

GTCCAACATCAATACAACCTATTAATTTCCCCTCGTCAAAAATAAGGTTATCAAGTG

AGAAATCACCATGAGTGACGACTGAATCCGGTGAGAATGGCAAAAGCTTATGCATT

TCTTTCCAGACTTGTTCAACAGGCCAGCCATTACGCTCGTCATCAAAATCACTCGCA

TCAACCAAACCGTTATTCATTCGTGATTGCGCCTGAGCGAGACGAAATACGCGATCG

-continued

CTGTTAAAAGGACAATTACAAACAGGAATCGAATGCAACCGGCGCAGGAACACTGC

CAGCGCATCAACAATATTTTCACCTGAATCAGGATATTCTTCTAATACCTGGAATGC

TGTTTTCCCGGGGATCGCAGTGGTGAGTAACCATGCATCATCAGGAGTACGGATAAA

ATGCTTGATGGTCGGAAGAGGCATAAATTCCGTCAGCCAGTTTAGTCTGACCATCTC

ATCTGTAACATCATTGGCAACGCTACCTTTGCCATGTTTCAGAAACAACTCTGGCGC

ATCGGGCTTCCCATACAATCGATAGATTGTCGCACCTGATTGCCCGACATTATCGCG

AGCCCATTTATACCCATATAAATCAGCATCCATGTTGGAATTTAATCGCGGCCTCGA

GCAAGACGTTTCCCGTTGAATATGGCTCATAACACCCCTTGTATTACTGTTTATGTAA

GCAGACAGTTTTATTGTTCATGATGATATATTTTTATCTTGTGCAATGTAACATCAGA

GATTTTGAGACACAACGTGGCTTTCCCCCGCCGCTCTAGAACTAGTGGATCCAAATA

AAACGAAAGGCTCAGTCGAAAGACTGGGCCTTTCGTTTTATCTGTTGTTTGTCGCAT

TATACGAGACGTCCAGGTTGGGATACCTGAAACAAAACCCATCGTACGGCCAAGGA

AGTCTCCAATAACTGTGATCCACCACAAGCGCCAGGGTTTTCCCAGTCACGACGTTG

TAAAACGACGGCCAGTCATGCATAATCCGCACGCATCTGGAATAAGGAAGTGCCAT

TCCGCCTGACCT pLD24

(SEQ ID NO: 164)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

-continued

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATCATTTAAGAGCAGAAGGAC

CCGCATCAGTGTTAGCGATAGGTACAGCTAACCCAGAGAATATCTTAATCCAAGATG

AATTTCCTGACTACTATTTCCGTGTTACTAAATCGGAACATATGACTCAACTTAAAG

AGAAGTTCCGGAAAATCTGCGATAAATCCATGATCCGAAAGAGAAACTGTTTCCTTA

ACGAAGAACATCTCAAGCAAAACCCGAGGTTGGTAGAGCACGAAATGCAGACCTTG

GATGCTAGGCAGGACATGTTGGTGGTCGAAGTGCCAAAACTCGGCAAGGACGCGTG

CGCTAAGGCAATCAAGGAGTGGGGTCAACCGAAGTCTAAAATCACGCATCTAATAT

TTACATCTGCACTGACAACCGACATGCCGGGTGCCGATTATCACTGCGCCAAGCTAC

TTGGATTGAGTCCACTGGTTAAGAGAGTTATGATGTATCAATTGGGGTGTTACGGAG

GGGGCACAGTCCTCAGAATTGCTAAGGATATTGCGGAAAATAACAAGGGCGCGAGG

GTCCTTGCTGTATGTTGTGATATTATGGCCTGTTTGTTTCGCGGGCCCTCGGATTCAG

ATTTGGAATTGCTTGTCGGACAGGCAATTTTTGGTGACGGGGCCGCAGCAGTCATAG

TGGGAGCCGAACCAGACGAAAGCGTGGGTGAAAGACCAATCTTTGAGTTGGTTCTG

ACCGGACAAACGATCTTACCTAACTCGGAAGGTACGATTGGAGGACATATTAGAGA

AGCCGGCCTAATTTTCGATCTTCACAAAGACGTTCCAATGTTAATCTCCAATAACAT

AGAAAAGTGCTTGATAGAAGCATTTACTCCCATTGGTATTAGTGACTGGAACAGCAT

TTTCTGGATCACCCACCCTGGAGGAAAAGCTATACTCGATAAGGTTGAAGAGAAAC

TCGACTTGAAAAAGGAGAAATTCGTTGACTCACGACATGTGTTATCAGAGCACGGG

AATATGAGTTCATCCACAGTCTTGTTCGTAATGGATGAATTGCGAAAACGCTCTCTT

GAGGAGGGAAAGAGCACAACCGGTGACGGGTTTGAGTGGGGCGTGCTATTCGGTTT

TGGCCCAGGTTTGACTGTCGAGCGGGTTGTTGTTCGTAGTGTACCAATTAAGTACGG

AAGAAGGGCAAAGTTGTGATAAGAGTGACTCTTTTGATAAGAGTCGCAAATTTGATT

TCATAAGTATATATTCATTATGTAAAGTAGTAAATGGAAAATTCATTAAAAAAAAAG

CAAATTTCCGTTGTATGCATACTCCGAACACAAAACTAGCCCCGGAAAAACCCTTAG

TTGATAGTTGCGAATTTAGGTCGACCATATGCGACGGGTACAACGAGAATTGTATTG

AATTGATCAAGAACATGATCTTGGTGTTACAGAACATCAAGTTCTTGGACCAGACTG

AGAATGCACAGATATACAAGGCGTCATGTGATAAAATGGATGAGATTTATCCACAA

TTGAAGAAAGAGTTTATGGAAAGTGGTCAACCAGAAGCTAAACAGGAAGAAGCAA

ACGAAGAGGTGAAACAAGAAGAAGAAGGTAAATAAGTATTTTGTATTATATAACAA

ACAAAGTAAGGAATACAGATTTATACAATAAATTGCCATACTAGTCACGTGAGATA

TCTCATCCATTCCCCAACTCCCAAGAAAATAAAAAAGTGAAAAATAAAATCAAACC

CAAAGATCAACCTCCCCATCATCATCGTCATCAAACCCCCAGCTCAATTCGCAATGG

TTAGCACAAAAACATACACAGAAAGGGCATCAGCACACCCCTCCAAGGTTGCCCAA

CGTTTATTAATTAAAGGCTAGGTGGAGGCTCAGTGATGATAAGTCTGCGATGGTGGA

TGCATGTGTCATGGTCATAGCTGTTTCCTGTGTGAAATTGTTATCCGCTCAGAGGGC

ACAATCCTATTCCGCGCTATCCGACAATCTCCAAGACATTAGGTGGAGTTCAGTTCG

GCGTATGGCATATGTCGCTGGAAAGAACATGTGAGCAAAAGGCCAGCAAAAGGCCA

GGAACCGTAAAAAGGCCGCGTTGCTGGCGTTTTTCCATAGGCTCCGCCCCCCTGACG

-continued

AGCATCACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTATCGTCTTG

AGTCCAACCCGGTAAGACACGACTTATCGCCACTGGCAGCAGCCACTGGTAACAGG

ATTAGCAGAGCGAGGTATGTAGGCGGTGCTACAGAGTTCTTGAAGTGGTGGCCTAA

CTACGGCTACACTAGAAGAACAGTATTTGGTATCTGCGCTCTGCTGAAGCCAGTTAC

CTTCGGAAAAAGAGTTGGTAGCTCTTGATCCGGCAAACAAACCACCGCTGGTAGCG

GTGGTTTTTTTGTTTGCAAGCAGCAGATTACGCGCAGAAAAAAAGGATCTCAAGAA

GATCCTTTGATCTTTTCTACGGGGTCTGACGCTCTATTCAACAAAGCCGCCGTCCCGT

CAAGTCAGCGTAAATGGGTAGGGGGCTTCAAATCGTCCGCTCTGCCAGTGTTACAAC

CAATTAACAAATTCTGATTAGAAAAACTCATCGAGCATCAAATGAAACTGCAATTTA

TTCATATCAGGATTATCAATACCATATTTTTGAAAAAGCCGTTTCTGTAATGAAGGA

GAAAACTCACCGAGGCAGTTCCATAGGATGGCAAGATCCTGGTATCGGTCTGCGATT

CCGACTCGTCCAACATCAATACAACCTATTAATTTCCCCTCGTCAAAAATAAGGTTA

TCAAGTGAGAAATCACCATGAGTGACGACTGAATCCGGTGAGAATGGCAAAAGCTT

ATGCATTTCTTTCCAGACTTGTTCAACAGGCCAGCCATTACGCTCGTCATCAAAATC

ACTCGCATCAACCAAACCGTTATTCATTCGTGATTGCGCCTGAGCGAGACGAAATAC

GCGATCGCTGTTAAAAGGACAATTACAAACAGGAATCGAATGCAACCGGCGCAGGA

ACACTGCCAGCGCATCAACAATATTTTCACCTGAATCAGGATATTCTTCTAATACCT

GGAATGCTGTTTTCCCGGGGATCGCAGTGGTGAGTAACCATGCATCATCAGGAGTAC

GGATAAAATGCTTGATGGTCGGAAGAGGCATAAATTCCGTCAGCCAGTTTAGTCTGA

CCATCTCATCTGTAACATCATTGGCAACGCTACCTTTGCCATGTTTCAGAAACAACTC

TGGCGCATCGGGCTTCCCATACAATCGATAGATTGTCGCACCTGATTGCCCGACATT

ATCGCGAGCCCATTTATACCCATATAAATCAGCATCCATGTTGGAATTTAATCGCGG

CCTCGAGCAAGACGTTTCCCGTTGAATATGGCTCATAACACCCCTTGTATTACTGTTT

ATGTAAGCAGACAGTTTTATTGTTCATGATGATATATTTTTATCTTGTGCAATGTAAC

ATCAGAGATTTTGAGACACAACGTGGCTTTCCCCCGCCGCTCTAGAACTAGTGGATC

CAAATAAAACGAAAGGCTCAGTCGAAAGACTGGGCCTTTCGTTTTATCTGTTGTTTG

TCGCATTATACGAGACGTCCAGGTTGGGATACCTGAAACAAAACCCATCGTACGGC

CAAGGAAGTCTCCAATAACTGTGATCCACCACAAGCGCCAGGGTTTTCCCAGTCACG

ACGTTGTAAAACGACGGCCAGTCATGCATAATCCGCACGCATCTGGAATAAGGAAG

TGCCATTCCGCCTGACCT pLD56

(SEQ ID NO: 165)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

-continued
GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGGGTTGTCCTTAGTTTGTACGTT

CAGTTTCCAAACTAACTACCACACACTACTAAATCCGCACAACAAAAACCCGAAAA

ATTCATTGCTCTCCTATCAGCACCCAAAAACACCCATTATCAAGTCTAGTTACGACA

ACTTTCCATCAAAATACTGTCTAACGAAAAACTTTCATTTGTTGGGCTTAAATTCTCA

TAATCGTATTTCCAGTCAGTCCCGATCGATCAGGGCCGGGAGTGACCAAATTGAAGG

TTCTCCACATCATGAAAGTGACAATTCAATTGCTACGAAGATTTTAAACTTTGGGCA

TACATGCTGGAAGCTACAGCGACCGTATGTAGTTAAGGGGATGATCAGCATTGCCTG

CGGCCTATTCGGAAGGGAACTCTTCAATAATAGACATCTTTTTTCTTGGGGTTTAATG

TGGAAAGCTTTTTTCGCTTTGGTTCCTATCCTTAGTTTTAACTTCTTCGCCGCTATTAT

GAATCAAATTTACGATGTTGACATCGACCGTATTAACAAACCCGATCTCCCCCTTGT

TTCAGGCGAGATGTCCATTGAAACGGCATGGATTTTGTCCATCATTGTTGCGCTTACT

GGCTTGATTGTTACCATTAAGCTTAAAAGCGCTCCCTTGTTCGTTTTTATATACATTT

TCGGCATTTTTGCCGGATTCGCATACAGTGTCCCGCCTATACGTTGGAAACAATATC

CATTCACGAACTTCTTGATCACGATCTCATCACATGTTGGATTGGCCTTTACGTCCTA

CAGTGCTACCACATCTGCCCTTGGATTGCCTTTCGTTTGGAGGCCTGCCTTCTCGTTT

ATCATTGCATTTATGACAGTGATGGGAATGACTATCGCATTTGCTAAAGATATCAGC

GACATAGAGGGCGATGCAAAATATGGGGTGAGTACTGTTGCGACGAAGTTGGGCGC

CCGAAATATGACCTTCGTTGTTTCCGGCGTTCTTTTACTTAACTATTTAGTATCGATT

AGCATCGGGATCATCTGGCCACAGGTGTTTAAATCAAATATTATGATCTTGTCGCAT

-continued

GCCATCCTAGCTTTCTGTCTTATATTTCAAACAAGAGAATTAGCCCTAGCGAACTAC

GCCTCAGCACCAAGTCGTCAGTTCTTCGAATTTATATGGCTACTCTACTACGCCGAA

TACTTCGTCTATGTCTTCATTTAGTAATAAGAGTGACTCTTTTGATAAGAGTCGCAAA

TTTGATTTCATAAGTATATATTCATTATGTAAAGTAGTAAATGGAAAATTCATTAAA

AAAAAAGCAAATTTCCGTTGTATGCATACTCCGAACACAAAACTAGCCCCGGAAAA

ACCCTTAGTTGATAGTTGCGAATTTAGGTCGACCATATGCGACGGGTACAACGAGAA

TTGTATTGAATTGATCAAGAACATGATCTTGGTGTTACAGAACATCAAGTTCTTGGA

CCAGACTGAGAATGCACAGATATACAAGGCGTCATGTGATAAAATGGATGAGATTT

ATCCACAATTGAAGAAAGAGTTTATGGAAAGTGGTCAACCAGAAGCTAAACAGGAA

GAAGCAAACGAAGAGGTGAAACAAGAAGAAGAAGGTAAATAAGTATTTTGTATTAT

ATAACAAACAAAGTAAGGAATACAGATTTATACAATAAATTGCCATACTAGTCACG

TGAGATATCTCATCCATTCCCCAACTCCCAAGAAAATAAAAAAGTGAAAAATAAAA

TCAAACCCAAAGATCAACCTCCCCATCATCATCGTCATCAAACCCCCAGCTCAATTC

GCAATGGTTAGCACAAAAACATACACAGAAAGGGCATCAGCACACCCCTCCAAGGT

TGCCCAACGTTTATTAATTAAAGGCTAGGTGGAGGCTCAGTGATGATAAGTCTGCGA

TGGTGGATGCATGTGTCATGGTCATAGCTGTTTCCTGTGTGAAATTGTTATCCGCTCA

GAGGGCACAATCCTATTCCGCGCTATCCGACAATCTCCAAGACATTAGGTGGAGTTC

AGTTCGGCGTATGGCATATGTCGCTGGAAAGAACATGTGAGCAAAAGGCCAGCAAA

AGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCG

ACCCTGCCGCTTACCGGATACCTGTCCGCCTTTCTCCCTTCGGGAAGCGTGGCGCTTT

CTCATAGCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTCAA

GAAGATCCTTTGATCTTTTCTACGGGGTCTGACGCTCTATTCAACAAAGCCGCCGTC

CCGTCAAGTCAGCGTAAATGGGTAGGGGGCTTCAAATCGTCCGCTCTGCCAGTGTTA

CAACCAATTAACAAATTCTGATTAGAAAAACTCATCGAGCATCAAATGAAACTGCA

ATTTATTCATATCAGGATTATCAATACCATATTTTTGAAAAAGCCGTTTCTGTAATGA

AGGAGAAAACTCACCGAGGCAGTTCCATAGGATGGCAAGATCCTGGTATCGGTCTG

CGATTCCGACTCGTCCAACATCAATACAACCTATTAATTTCCCCTCGTCAAAAATAA

GGTTATCAAGTGAGAAATCACCATGAGTGACGACTGAATCCGGTGAGAATGGCAAA

AGCTTATGCATTTCTTTCCAGACTTGTTCAACAGGCCAGCCATTACGCTCGTCATCAA

AATCACTCGCATCAACCAAACCGTTATTCATTCGTGATTGCGCCTGAGCGAGACGAA

ATACGCGATCGCTGTTAAAAGGACAATTACAAACAGGAATCGAATGCAACCGGCGC

AGGAACACTGCCAGCGCATCAACAATATTTTCACCTGAATCAGGATATTCTTCTAAT

ACCTGGAATGCTGTTTTCCCGGGGATCGCAGTGGTGAGTAACCATGCATCATCAGGA

GTACGGATAAAATGCTTGATGGTCGGAAGAGGCATAAATTCCGTCAGCCAGTTTAGT

CTGACCATCTCATCTGTAACATCATTGGCAACGCTACCTTTGCCATGTTTCAGAAAC

AACTCTGGCGCATCGGGCTTCCCATACAATCGATAGATTGTCGCACCTGATTGCCCG

ACATTATCGCGAGCCCATTTATACCCATATAAATCAGCATCCATGTTGGAATTTAAT

CGCGGCCTCGAGCAAGACGTTTCCCGTTGAATATGGCTCATAACACCCCTTGTATTA

CTGTTTATGTAAGCAGACAGTTTTATTGTTCATGATGATATATTTTTATCTTGTGCAA

TGTAACATCAGAGATTTTGAGACACAACGTGGCTTTCCCCCGCCGCTCTAGAACTAG

TGGATCCAAATAAAACGAAAGGCTCAGTCGAAAGACTGGGCCTTTCGTTTTATCTGT

TGTTTGTCGCATTATACGAGACGTCCAGGTTGGGATACCTGAAACAAAACCCATCGT

ACGGCCAAGGAAGTCTCCAATAACTGTGATCCACCACAAGCGCCAGGGTTTTCCCA

GTCACGACGTTGTAAAACGACGGCCAGTCATGCATAATCCGCACGCATCTGGAATA

AGGAAGTGCCATTCCGCCTGACCT pLD87

(SEQ ID NO: 166)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

-continued

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTTTAATTAAGTCGACTTGATGTTTAGAGTGTCCAGATCCGCAAGATCGGCTCGCA

CTTGTGTTGTGTTGTTTCAAATCAGCCTGTCGTTTTGTGTCGTTTGAGATCATTCTGTC

TCACTCTTAGGCTCGCTTAGAACCGACAACGGAGAATCCGGGCTCGGTTTTTCGGTC

GGCCTTGATCTGGGCCTTGGACTTGTACTGGTCGGCCATCTCCACGTTGACCAGCTC

CTTGACCTTGTAGAGCTGACCGGCGATACCAGGAGACACCTTGTAGTACTTCTGGGA

GCCGACCTTGCCCAGACCGAGGGTCTTGAGCACGTCACGTGTTCTCCACGGCATTCG

CAGGATAGATCGGACCTGTGTGACTTTGTAGAACATGGCGTTTCAGGTGGTTGCGTG

AGTGTGTAAAATCGTGTCTTTCAGAAGTTACAAATTTCACCGCATTTAGAGTTTATG

CAGATGGGCGGTGTGTGGTTGGGAGTTCGATTTCCGTGCGTGCATTTGATCTTGATG

AATTGGATTTGTACATGGGGAATAGCACGTCAAGAACCGCCTACTGCAAACTCGTG

AATATTGAGATTATTGAGGAAATTCAAGGAAAATTCAGATCAGATTTGAGAGCAAA

GTCCAACAATACTACACAATCCCTTTCCTGTATTCTTCCACCATCGTCATCGTCGTCT

GTCTTCTCTTCAGCTTTTTAATTTCACTCCCCACAAACCCAAATTTAGCTGCATCATT

CATCAACCTCCAATTATAACTATACATCGCGACACGAACACGAAACACGAACCACG

AACCGCCGCTTTGTCGACGGAGTGAGACGGGAGAGAGACCATGGTCTCTCGCTCGT

CTCACGCTTAGCGGCCGCGTCGACATAACTTCGTATAGCATACATTATACGAAGTTA

TTTTCTAATTTGGACCGATAGCCGTATAGTCCAGTCTATCTATAAGTTCAACTAACTC

GTAACTATTACCATAACATATACTTCACTGCCCCAGATAAGGTTCCGATAAAAAGTT

GTGCAGACTAAATTTATTTCAGTCTCCTCTTCACCACCAAAATGCCCTCCTACGAAG

CGCGAGCTAACGTCCACAAGTCCGCCTTTGCCGCCCGAGTGCTCAAGCTCGTGGCAG

CCAAGAAAACCAACCTGTGTGCTTCTCTGGATGTTACCACCACCAAGGAGCTCATTG

AGCTTGCCGATAAGGTCGGACCTTATGTGTGCATGATCAAGACCCATATCGACATCA

TTGACGACTTCACCTACGCCGGAACTGTGCTCCCCCTCAAGGAACTTGCTCTTAAGC

ACGGTTTCTTCCTGTTCGAGGACAGAAAGTTCGCAGATATTGGCAACACTGTCAAGC

ACCAGTACAAGAACGGTGTCTACCGAATCGCCGAGTGGTCCGATATCACCAACGCC

CACGGTGTACCCGGAACCGGAATCATTGCTGGCCTGCGAGCTGGTGCCGAGGAAAC

TGTCTCTGAACAGAAGAAGGAGGATGTCTCTGACTACGAGAACTCCCAGTACAAGG

AGTTCCTGGTCCCCTCTCCCAACGAGAAGCTGGCCAGAGGTCTGCTCATGCTGGCCG

AGCTGTCTTGCAAGGGCTCTCTGGCCACTGGCGAGTACTCCAAGCAGACCATTGAGC

-continued

TTGCCCGATCCGACCCCGAGTTTGTGGTTGGCTTCATTGCCCAGAACCGACCTAAGG

GCGACTCTGAGGACTGGCTTATTCTGACCCCCGGGGTGGGTCTTGACGACAAGGGA

GATGCTCTCGGACAGCAGTACCGAACTGTTGAGGATGTCATGTCTACCGGAACGGAT

ATCATAATTGTCGGCCGAGGTCTGTACGGCCAGAACCGAGATCCTATTGAGGAGGC

CAAGCGATACCAGAAGGCTGGCTGGGAGGCTTACCAGAAGATTAACTGTTAGAGGT

TAGACTATGGATATGTCATTTAACTGTGTATATAGAGAGCGTGCAAGTATGGAGCGC

TTGTTCAGCTTGTATGATGGTCAGACGACCTGTCTGATCGAGTATGTATGATACTGC

ACAACCTGATAACTTCGTATAGCATACATTATACGAAGTTATCTCGAGGGATCCCTA

GGGAGGCACATCTAAACGAATAACGAATATTAATGATACCATCATATCTCAGAACA

TGTATGACTGCTGCTTCCAAACGATATGAGGATGAGTCCTCTTTCAGATTAAGATAG

AGTACAAATATATTATCTATATACTGGTGTCTGTGCGATGTCGTATGAGCGGTGAAT

CATGTGACTGTCACGTGGTTTGGCCCAAGTTACACCGTAGCTACGCCTTTCTTGACC

GACTCCATGGTCTTCTGGGCGGGTTGACAGTTTCCACTGGATGAGCGTCCGCCTCCT

GTTCCTGTCGTTGTCCCTGCAGCTCAGCCTCAATCTTCTGACCGAGCTCGGAGTCCA

GGGAAATGCCAACAGGTTGTCCAAGCAACATCATGGTTTGGTGGGCAGCCGTGATC

TCATCGTCGTTGGATACCATTCGGTACTTGGCCTCAATCTGCACAAAGTAGCGGTAC

CACTGGTTTCGAGCAAACCGCTCCAATTGAGCCTCTCCGTCGAGAGAGAGAGTAGGT

GATTGCTCCAACTTGCGGCCAAAATGAAGTTCTCGACTCACCTTTTTGAAGCGGTTC

TTCTTGCCCATCTTGGTGGCGAAAGTAGTGGCTAGTGGTGGATGACTTTGTATAATG

TACCGATGAAGAGGGTTGTATTTGCTCAGTAAGAAGTAGCGAGTGAAATCAGATCA

CTTAACGAGAGCAAAGGGCAATGGAATACCTGCTGCCTGATTAACAACAGCTTCTGT

GTCGTTTCTCTCTTGTGAATGAGTGTGTTGCTAGAGGTAGGTTGGCACTCCAATGTTA

CTTAATTAA pLD101

(SEQ ID NO: 167)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCTCGTGATACCAATTCGGAGCCTGCTTTTTTGTAC

-continued

AAACTTGTTGATAATGGCAATTCAAGGATCTTCACCTAGATCCTTTTAAATTAAAAA

TGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCCCCA

GTGCTGCAATGATACCGCGAGAGCCACGCTCACCGGCTCCAGATTTATCAGCAATA

AACCAGCCAGCCGGAAGGGCCGAGCGCAGAAGTGGTCCTGCAACTTTATCCGCCTC

CATCCAGTCTATTAATTGTTGCCGGGAAGCTAGAGTAAGTAGTTCGCCAGTTAATAG

TTTGCGCAACGTTGTTGCCATTGCTACAGGCATCGTGGTGTCACGCTCGTCGTTTGGT

ATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCGC

CACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGG

ATACATATTTGAATGTATTTAGAAAAATAAACAAATAGGGGTTCCGCGCACATTTCC

CCGAAAAGTGCCAGATACCTGAAACAAAACCCATCGTACGGCCAAGGAAGTCTCCA

ATAACTGTGATCCACCACAAGCGCCAGGGTTTTCCCAGTCACGACGTTGTAAAACGA

CGGCCAGTCATGCATAATCCGCACGCATCTGGAATAAGGAAGTGCCATTCCGCCTG

ACCTTTAATTAACGATCCGCGTAAATTCAGAGCAATGCCAAGATCCTTATTTCCGAT

AACAGCGAGATACACATCAGAAGAGGTGGAGACTCTGGCCCCGCACGACCACCACG

TCGTCACTCAAAGCAAAGTCACGATGTAGAAATCACAATCGTCCCCATAAGCACGT

GGATTCCCCTGGTTTTGTTTCGGCCTCGGCAGTGGCAATTCTGGGGTATATAAACCA

GCAAGGTTATGACCTGATTGACCTGCTTGTGGCCTGATAAACCGCCTGACTTTTGTG

ATAAGGTTGGGAGCATGCGGCTCGGGCCATTGTGAGCATTTTCGTCAAGGACTGGCC

AAGTCCAACTGGAAGAGACATGGGCAAAATGTCGACTTTACAGATGTACCCGAAAT

TGCTTCAATTGCTCTCAGCTGCCGGAACCGGATCTATCGGTGCAAGTATCGTACAGT

AGACATGTGCTATTGGTAACCCTCGGTATTGGCTAGGTTTCGTATCAGGGATACAGT

TCAACGCTGATCGCATATGGCATGATTCCGGCTCGACACAGCGACCAAGAACCAAG

CGTGTATGTCGTAGACTTGCAAATCATGTGGGGCTTATCCCCGGATTTCCCCAAGTC

ACGTTTTCACAAAGGCTGTCTCCCGAATGCATGAGCCGAGGCAGGCTAAACTGGTTT

GTTCATGTACCCCACACAACGTAAAGATGCACCCCATGTGCAGTGAAATACCACAA

GTATATATATACCGACCTACCCGAGATAGCAAATTGATTCTACACTTACACTACCAA

TTCTTACATCAAACCAAACCGCTTGAGACCATCCGGTCTCTGATCATCCTCGAGATA

ACTTCGTATAATGTATGCTATACGAAGTTATCAGGTTGTGCAGTATCATACATACTC

GATCAGACAGGTCGTCTGACCATCATACAAGCTGAACAAGCGCTCCATACTTGCAC

GCTCTCTATATACACAGTTAAATGACATATCCATAGTCTAACCTCTAACAGTTAATCT

-continued
TCTGGTAAGCCTCCCAGCCAGCCTTCTGGTATCGCTTGGCCTCCTCAATAGGATCTC

GGTTCTGGCCGTACAGACCTCGGCCGACAATTATGATATCCGTTCCGGTAGACATGA

CATCCTCAACAGTTCGGTACTGCTGTCCGAGAGCATCTCCCTTGTCGTCAAGACCCA

CCCCGGGGGTCAGAATAAGCCAGTCCTCAGAGTCGCCCTTAGGTCGGTTCTGGGCA

ATGAAGCCAACCACAAACTCGGGGTCGGATCGGGCAAGCTCAATGGTCTGCTTGGA

GTACTCGCCAGTGGCCAGAGAGCCCTTGCAAGACAGCTCGGCCAGCATGAGCAGAC

CTCTGGCCAGCTTCTCGTTGGGAGAGGGGACCAGGAACTCCTTGTACTGGGAGTTCT

CGTAGTCAGAGACATCCTCCTTCTTCTGTTCAGAGACAGTTTCCTCGGCACCAGCTC

GCAGGCCAGCAATGATTCCGGTTCCGGGTACACCGTGGGCGTTGGTGATATCGGACC

ACTCGGCGATTCGGTAGACACCGTTCTTGTACTGGTGCTTGACAGTGTTGCCAATAT

CTGCGAACTTTCTGTCCTCGAACAGGAAGAAACCGTGCTTAAGAGCAAGTTCCTTGA

GGGGGAGCACAGTTCCGGCGTAGGTGAAGTCGTCAATGATGTCGATATGGGTCTTG

ATCATGCACACATAAGGTCCGACCTTATCGGCAAGCTCAATGAGCTCCTTGGTGGTG

GTAACATCCAGAGAAGCACACAGGTTGGTTTTCTTGGCTGCCACGAGCTTGAGCACT

CGGGCGGCAAAGGCGGACTTGTGGACGTTAGCTCGCGCTTCGTAGGAGGGCATTTT

GGTGGTGAAGAGGAGACTGAAATAAATTTAGTCTGCACAACTTTTTATCGGAACCTT

ATCTGGGGCAGTGAAGTATATGTTATGGTAATAGTTACGAGTTAGTTGAACTTATAG

ATAGACTGGACTATACGGCTATCGGTCCAAATTAGAAAATAACTTCGTATAATGTAT

GCTATACGAAGTTATGTCGACGCGGCCGCACAAGCACTACATGGACGAGGTCAAGG

CTGCCAACAACCCTCGTAACACCCATGCTCCTTACTACGAGACAAAGCTGCGACCCT

TCCTGTTCCGACCCGATGAGGACGAGGAGATTTGCGACCTGGACGAGTAGGTTGTTG

TAATACTATGATTTATTGTGTTTATATGTTATTGATACTATTGAAAGAGTTATTGTGT

AATTTTAGATGCTGTATGTTAACTAGAAGCTCAGATTCTACAAAGAGATCCTCAGAT

CTGAGGAATGATCTACGTTCTGCAATAGAAGGGACAACTGCAGCTCTGAATGACCA

CAAAAAGAATACACCACAAGCAGTTGTAACTGAGCTATTAGCCTTGCTTTCGCACCA

TTCGCTTTTCTGGATGGTAGCCCTTTACTACAAGTAGCTAATATGGAATGTACATTAC

CGTCTCATTACAATATGTATATGCAAGTTCATGGCACTTCATGCACACCAGCCCCTTC

GTTAAGTACCTTCCAAAAAGTGATCAATGATAAGTGATATATCTAATTTAGAGATCT

GGACACACGAACAAGTCGGGAACACAAATCCCGAGATGATTGCCTGCTCAGAGGAG

TCCAATTAGTCTTTACACCATTCGTGCTAATGAAGGGCACAGAATATTCCACTTTGA

AAGTTTAAGATTAAGCTCGGCTCGCAATTATGCATGAAAAATATGTAGGGAGAGAA

CGATCCCACGAGTTCTGTTTGGTTGCGAGAGTGTTCGGGTTTTCTCCTAAAAAGAAT

AGGGGAGGGAAAAATTATCGCCTAAGTCACCATTAATTAA pLD102

(SEQ ID NO: 168)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

-continued

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCTCGTGATACCAATTCGGAGCCTGCTTTTTTGTAC

AAACTTGTTGATAATGGCAATTCAAGGATCTTCACCTAGATCCTTTTAAATTAAAAA

TGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCCCCA

GTGCTGCAATGATACCGCGAGAGCCACGCTCACCGGCTCCAGATTTATCAGCAATA

AACCAGCCAGCCGGAAGGGCCGAGCGCAGAAGTGGTCCTGCAACTTTATCCGCCTC

CATCCAGTCTATTAATTGTTGCCGGGAAGCTAGAGTAAGTAGTTCGCCAGTTAATAG

TTTGCGCAACGTTGTTGCCATTGCTACAGGCATCGTGGTGTCACGCTCGTCGTTTGGT

ATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCGC

CACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGG

ATACATATTTGAATGTATTTAGAAAAATAAACAAATAGGGGTTCCGCGCACATTTCC

CCGAAAAGTGCCAGATACCTGAAACAAAACCCATCGTACGGCCAAGGAAGTCTCCA

ATAACTGTGATCCACCACAAGCGCCAGGGTTTTCCCAGTCACGACGTTGTAAAACGA

CGGCCAGTCATGCATAATCCGCACGCATCTGGAATAAGGAAGTGCCATTCCGCCTG

ACCTTTAATTAATTGGCAAATTTTACTGTGGCCTTCAGAACGGTAAAAATAGACCAA

TCAGAATTCTGAAAAGCACATCTTGATCTCCTCATTGCGGGGAGTCCAACGGTGGTC

TTATTCCCCCGAATTTCCCGCTCAATCTCGTTCCAGACCGACCCGGACACAGTGCTT

AACGCCGTTCCGAAACTCTACCGCAGATATGCTCCAACGGACTGGGCTGCATAGAT

GTGATCCTCGGCTTGGAGAAATGGATAAAAGCCGGCCAAAAAAAAAGCGGAAAAA

AGCGGAAAAAAAGAGAAAAAAAATCGCAAAATTTGAAAAATAGGGGGAAAAGACG

CAAAAACGCAAGGAGGGGGGAGTATATGACACTGATAAGCAAGCTCACAACGGTTC

CTCTTATTTTTTTCCTCATCTTCTGCCTAGGTTCCCAAAATCCCAGATGCTTCTCTCCA

-continued
GTGCCAAAAGTAAGTACCCCACAGGTTTTCGGCCGAAAATTCCACGTGCAGCAACG

TCGTGTGGGGTGTTAAAATGTGGGGGCGGGGAACCAGGACAAGAGGCTCTTGTGGG

AGCCGAATGAGAGCACAAAGCGGGCGGGTGTGATAAGGGCATTTTTGCCCATTTTC

CCTTCTCCTGTCTCTCCGACGGTGATGGCGTTGTGCGTCCTCTATCTATTTCTTTTTAT

TTCTTTTTGTTTTATTTCTCTGACTACCGATTTGGCTTGATTTCCTCAACCCCACACAA

ATAAGCTCGGGCCGAGGAATATATATATACACGGACACAGTCGCCCTGTGGACAAC

ACGTCACTACCTCTACGACGCTTGAGACCATCCGGTCTCTGATCATCCTCGAGATAA

CTTCGTATAATGTATGCTATACGAAGTTATCAGGTTGTGCAGTATCATACATACTCG

ATCAGACAGGTCGTCTGACCATCATACAAGCTGAACAAGCGCTCCATACTTGCACGC

TCTCTATATACACAGTTAAATGACATATCCATAGTCTAACCTCTAACAGTTAATCTTC

TGGTAAGCCTCCCAGCCAGCCTTCTGGTATCGCTTGGCCTCCTCAATAGGATCTCGG

TTCTGGCCGTACAGACCTCGGCCGACAATTATGATATCCGTTCCGGTAGACATGACA

TCCTCAACAGTTCGGTACTGCTGTCCGAGAGCATCTCCCTTGTCGTCAAGACCCACC

CCGGGGGTCAGAATAAGCCAGTCCTCAGAGTCGCCCTTAGGTCGGTTCTGGGCAATG

AAGCCAACCACAAACTCGGGGTCGGATCGGGCAAGCTCAATGGTCTGCTTGGAGTA

CTCGCCAGTGGCCAGAGAGCCCTTGCAAGACAGCTCGGCCAGCATGAGCAGACCTC

TGGCCAGCTTCTCGTTGGGAGAGGGGACCAGGAACTCCTTGTACTGGGAGTTCTCGT

AGTCAGAGACATCCTCCTTCTTCTGTTCAGAGACAGTTTCCTCGGCACCAGCTCGCA

GGCCAGCAATGATTCCGGTTCCGGGTACACCGTGGGCGTTGGTGATATCGGACCACT

CGGCGATTCGGTAGACACCGTTCTTGTACTGGTGCTTGACAGTGTTGCCAATATCTG

CGAACTTTCTGTCCTCGAACAGGAAGAAACCGTGCTTAAGAGCAAGTTCCTTGAGGG

GGAGCACAGTTCCGGCGTAGGTGAAGTCGTCAATGATGTCGATATGGGTCTTGATCA

TGCACACATAAGGTCCGACCTTATCGGCAAGCTCAATGAGCTCCTTGGTGGTGGTAA

CATCCAGAGAAGCACACAGGTTGGTTTTCTTGGCTGCCACGAGCTTGAGCACTCGGG

CGGCAAAGGCGGACTTGTGGACGTTAGCTCGCGCTTCGTAGGAGGGCATTTTGGTGG

TGAAGAGGAGACTGAAATAAATTTAGTCTGCACAACTTTTTATCGGAACCTTATCTG

GGGCAGTGAAGTATATGTTATGGTAATAGTTACGAGTTAGTTGAACTTATAGATAGA

CTGGACTATACGGCTATCGGTCCAAATTAGAAAATAACTTCGTATAATGTATGCTAT

ACGAAGTTATGTCGACGCGGCCGCATGGAGCGTGTGTTCTGAGTCGATGTTTTCTAT

GGAGTTGTGAGTGTTAGTAGACATGATGGGTTTATATATGATGAATGAATAGATGTG

ATTTTGATTTGCACGATGGAATTGAGAACTTTGTAAACGTACATGGGAATGTATGAA

TGTGGGGGTTTTGTGACTGGATAACTGACGGTCAGTGGACGCCGTTGTTCAAATATC

CAAGAGATGCGAGAAACTTTGGGTCAAGTGAACATGTCCTCTCTGTTCAAGTAAACC

ATCAACTATGGGTAGTATATTTAGTAAGGACAAGAGTTGAGATTCTTTGGAGTCCTA

GAAACGTATTTTCGCGTTCCAAGATCAAATTAGTAGAGTAATACGGGCACGGGAAT

CCATTCATAGTCTCAATTTTCCCATAGGTGTGCTACAAGGTGTTGAGATGTGGTACA

GTACCACCATGATTCGAGGTAAAGAGCCCAGAAGTCATTGATGAGGTCAAGAAATA

CACAGATCTACAGCTCAATACAATGAATATCTTCTTTCATATTCTTCAGGTGACACC

AAGGGTGTCTATTTTCCCCAGAAATGCGTGAAAAGGCGCGTGTGTAGCGTGGAGTAT

GGGTTCGGTTGGCGTATCCTTCATATATCGACGAAATAGTAGGGCAAGAGATGACA

AAAAGTATCTATATGTAGACAGCGTAGAATATGGATTTGATTGGTATAAATTCATTT

-continued

ATTGCGTGTCTCACAAATACTCTCGATAAGTTGGGGTTAAACTGGAGATGGAACAAT

GTCGATATCTCGACATATTTTGATATTTGTTAATTAA pLD111

(SEQ ID NO: 169)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATTGTTCAGCATTTAGTTTTTG

GTTTGTTTGTAAGATTATTTTCTTCTTTTTGTCATTTAACATTCAAATTTCAATTGCAA

ACCCACAAGAAAACTTTTTGAAGTGTTTTTCAGAATACATTCCAAACAATCCAGCTA

ACCCAAAGTTTATTTACACACAACATGATCAATTGTACATGTCAGTTTTGAACTCAA

CAATTCAAAACTTGAGATTTACATCAGATACCACACCAAAGCCATTGGTTATTGTTA

CACCATCAAACGTTTCCCATATTCAAGCATCAATCTTGTGTTCAAAGAAGGTTGGAT

TGCAAATTAGAACCAGATCAGGAGGACACGATGCAGAAGGAATGTCATACATTTCA

CAAGTTCCATTCGTTGTTGTTGATTTGAGAAACATGCACTCAATTAAGATTGATGTTC

ATTCACAAACAGCATGGGTTGAAGCAGGAGCAACATTGGGTGAAGTTTACTACTGG

ATTAACGAAAAGAACGAAAACTTCAGTTTTCCAGGAGGTTACTGTCCAACAGTTGG

-continued

AGTTGGAGGACATTTTTCAGGTGGAGGATACGGAGCATTGATGAGAAACTACGGAT

TGGCAGCAGATAACATTATTGATGCACACTTGGTTAACGTTGATGGAAAGGTTTTGG

ATAGAAAGTCAATGGGAGAAGATTTGTTTTGGGCAATTAGAGGAGGTGGTGGAGAG

AACTTTGGAATTATTGCAGCATGGAAGATCAAGTTGGTTGCAGTTCCATCAAAGTCA

ACAATCTTTTCAGTTAAGAAGAACATGGAAATTCATGGTTTGGTTAAGTTGTTTAAC

AAGTGGCAAAACATTGCATACAAGTACGATAAGGATTTGGTTTTGATGACACATTTT

ATTACAAAGAACATTACAGATAACCATGGAAAGAACAAGACAACAGTTCACGGATA

CTTTTCATCAATTTTTCACGGAGGAGTTGATTCATTGGTTGACTTGATGAACAAGTCA

TTTCCAGAATTGGGAATCAAGAAGACAGATTGTAAGGAATTTTCATGGATTGATACA

ACAATTTTCTACTCAGGAGTTGTTAACTTTAACACAGCAAACTTTAAGAAGGAAATT

TTGTTGGACAGATCAGCAGGAAAGAAGACCGCATTTTCCATTAAGTTGGATTACGTT

AAGAAACCAATTCCAGAAACAGCAATGGTTAAGATTTTGGAAAAGTTGTACGAAGA

AGATGTTGGTGTTGGAATGTACGTTTTGTACCCATACGGAGGAATTATGGAAGAAAT

CTCAGAATCAGCAATTCCATTTCCACATAGAGCAGGTATTATGTACGAATTGTGGTA

CACAGCATCATGGGAAAAGCAAGAAGATAATGAAAAGCATATTAACTGGGTTAGAT

CAGTTTACAACTTTACAACACCATACGTTTCACAAAACCCAAGATTGGCATACTTGA

ACTACAGAGATTTGGATTTGGGAAAGACAAACCCAGAATCACCAAACAACTATACA

CAAGCTAGAATTTGGGGAGAAAAGTACTTTGGTAAGAACTTCAACAGATTGGTTAA

AGTTAAGACAAAGGCAGATCCAAATAACTTCTTTAGAAACGAACAATCAATTCCAC

CATTGCCACCACATCATCATTAATAAGAGTGACTCTTTTGATAAGAGTCGCAAATTT

GATTTCATAAGTATATATTCATTATGTAAAGTAGTAAATGGAAAATTCATTAAAAAA

AAAGCAAATTTCCGTTGTATGCATACTCCGAACACAAAACTAGCCCCGGAAAAACC

CTTAGTTGATAGTTGCGAATTTAGGTCGACCATATGCGACGGGTACAACGAGAATTG

TATTGAATTGATCAAGAACATGATCTTGGTGTTACAGAACATCAAGTTCTTGGACCA

GACTGAGAATGCACAGATATACAAGGCGTCATGTGATAAAATGGATGAGATTTATC

CACAATTGAAGAAAGAGTTTATGGAAAGTGGTCAACCAGAAGCTAAACAGGAAGA

AGCAAACGAAGAGGTGAAACAAGAAGAAGAAGGTAAATAAGTATTTTGTATTATAT

AACAAACAAAGTAAGGAATACAGATTTATACAATAAATTGCCATACTAGTCACGTG

AGATATCTCATCCATTCCCCAACTCCCAAGAAAATAAAAAAGTGAAAAATAAAATC

AAACCCAAAGATCAACCTCCCCATCATCATCGTCATCAAACCCCCAGCTCAATTCGC

AATGGTTAGCACAAAAACATACACAGAAAGGGCATCAGCACACCCCTCCAAGGTTG

CCCAACGTTTATTAATTAAAGGCTAGGTGGAGGCTCAGTGATGATAAGTCTGCGATG

GTGGATGCATGTGTCATGGTCATAGCTGTTTCCTGTGTGAAATTGTTATCCGCTCAGA

GGGCACAATCCTATTCCGCGCTATCCGACAATCTCCAAGACATTAGGTGGAGTTCAG

TTCGGCGTATGGCATATGTCGCTGGAAAGAACATGTGAGCAAAAGGCCAGCAAAAG

GCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAACTATCGT

-continued

CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGGTCTGACGCTCTATTCAACAAAGCCGCCGTCCC

GTCAAGTCAGCGTAAATGGGTAGGGGGCTTCAAATCGTCCGCTCTGCCAGTGTTACA

ACCAATTAACAAATTCTGATTAGAAAAACTCATCGAGCATCAAATGAAACTGCAATT

TATTCATATCAGGATTATCAATACCATATTTTTGAAAAAGCCGTTTCTGTAATGAAG

GAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGG

TTATCAAGTGAGAAATCACCATGAGTGACGACTGAATCCGGTGAGAATGGCAAAAG

CTTATGCATTTCTTTCCAGACTTGTTCAACAGGCCAGCCATTACGCTCGTCATCAAAA

TCACTCGCATCAACCAAACCGTTATTCATTCGTGATTGCGCCTGAGCGAGACGAAAT

ACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGT

ACGGATAAAATGCTTGATGGTCGGAAGAGGCATAAATTCCGTCAGCCAGTTTAGTCT

GACCATCTCATCTGTAACATCATTGGCAACGCTACCTTTGCCATGTTTCAGAAACAA

CTCTGGCGCATCGGGCTTCCCATACAATCGATAGATTGTCGCACCTGATTGCCCGAC

ATTATCGCGAGCCCATTTATACCCATATAAATCAGCATCCATGTTGGAATTTAATCG

CGGCCTCGAGCAAGACGTTTCCCGTTGAATATGGCTCATAACACCCCTTGTATTACT

GTTTATGTAAGCAGACAGTTTTATTGTTCATGATGATATATTTTTATCTTGTGCAATG

TAACATCAGAGATTTTGAGACACAACGTGGCTTTCCCCCGCCGCTCTAGAACTAGTG

GATCCAAATAAAACGAAAGGCTCAGTCGAAAGACTGGGCCTTTCGTTTTATCTGTTG

TTTGTCGCATTATACGAGACGTCCAGGTTGGGATACCTGAAACAAAACCCATCGTAC

GGCCAAGGAAGTCTCCAATAACTGTGATCCACCACAAGCGCCAGGGTTTTCCCAGTC

ACGACGTTGTAAAACGACGGCCAGTCATGCATAATCCGCACGCATCTGGAATAAGG

AAGTGCCATTCCGCCTGACCT pLD112

(SEQ ID NO: 170)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

-continued

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGAATTGTAGCACTTTCTCATTCTG

GTTTGTTTGTAAGATTATTTTCTTTTTCTTGTCATTTAACATTCAAATTTCAATTGCAA

ACCCACAAGAGAACTTTTTGAAGTGTTTCTCAGAATACATTCCAAACAACCCAGCTA

ACCCAAAGTTTATTTACACCCAACACGATCAATTGTACATGTCAGTTTTGAACTCAA

CAATTCAAAACTTGAGATTTACATCAGATACAACACCAAAGCCATTGGTTATTGTTA

CACCATCAAACGTTAGTCATATTCAAGCATCAATCTTGTGTTCAAAGAAGGTTGGAT

TGCAAATTAGAACTAGATCAGGAGGACATGATGCAGAAGGATTGTCATACATTTCA

CAAGTTCCATTTGCAATTGTTGATTTGAGAAACATGCACACAGTTAAGGTTGATATT

CATTCACAAACAGCATGGGTTGAAGCAGGAGCAACATTGGGTGAAGTTTACTACTG

GATTAACGAAATGAACGAAAACTTCTCATTTCCAGGAGGATACTGTCCAACAGTTGG

TGTTGGAGGACACTTTTCAGGTGGTGGATACGGAGCATTGATGAGAAACTACGGATT

GGCAGCAGATAACATTATTGATGCACATTTGGTTAACGTTGATGGAAAGGTTTTGGA

TAGAAAGTCAATGGGAGAAGATTTGTTTTGGGCAATTAGAGGAGGTGGAGGAGAAA

ACTTTGGAATCATTGCAGCATGTAAGATCAAGTTGGTTGTTGTTCCATCAAAGGCAA

CAATCTTTTCAGTTAAGAAGAACATGGAAATCCATGGATTGGTTAAGTTGTTTAACA

AGTGGCAAAACATTGCATACAAGTACGATAAGGATTTGATGTTGACAACACATTTTA

GAACAAGAAACATTACAGATAACCACGGAAAGAATAAGACAACAGTTCATGGATAC

TTTTCATCAATTTTCTTGGGAGGAGTTGATTCATTGGTTGACTTGATGAACAAGAGTT

TTCCAGAATTGGGAATCAAGAAGACAGATTGTAAGGAATTGTCATGGATCGATACA

ACCATTTTCTACTCAGGAGTTGTTAACTACAACACAGCTAACTTTAAGAAGGAAATT

TTGTTGGACAGATCAGCAGGTAAAAAGACAGCATTTTCAATTAAGTTGGATTACGTT

AAGAAATTGATTCCAGAAACAGCAATGGTTAAGATTTTGGAAAAGTTGTACGAAGA

AGAAGTTGGAGTTGGAATGTACGTTTTGTACCCATACGGAGGAATTATGGATGAAAT

TTCAGAATCAGCAATTCCATTTCCACATAGAGCAGGTATTATGTACGAATTGTGGTA

-continued

CACAGCAACATGGGAAAAGCAAGAAGATAACGAAAAGCATATTAACTGGGTTAGAT

CAGTTTACAACTTTACAACCCCATACGTTTCACAAAACCCAAGATTGGCATACTTGA

ACTACAGAGATTTGGATTTGGGAAAGACAAACCCAGAATCACCAAATAACTACACA

CAAGCTAGAATTTGGGGAGAAAAGTACTTTGGTAAGAACTTTAACAGATTGGTGAA

GGTTAAGACAAAGGCAGACCCAAACAATTTCTTTAGAAACGAACAATCAATTCCAC

CATTGCCACCAAGACATCATTAATAAGAGTGACTCTTTTGATAAGAGTCGCAAATTT

GATTTCATAAGTATATATTCATTATGTAAAGTAGTAAATGGAAAATTCATTAAAAAA

AAAGCAAATTTCCGTTGTATGCATACTCCGAACACAAAACTAGCCCCGGAAAAACC

CTTAGTTGATAGTTGCGAATTTAGGTCGACCATATGCGACGGGTACAACGAGAATTG

TATTGAATTGATCAAGAACATGATCTTGGTGTTACAGAACATCAAGTTCTTGGACCA

GACTGAGAATGCACAGATATACAAGGCGTCATGTGATAAAATGGATGAGATTTATC

CACAATTGAAGAAAGAGTTTATGGAAAGTGGTCAACCAGAAGCTAAACAGGAAGA

AGCAAACGAAGAGGTGAAACAAGAAGAAGAAGGTAAATAAGTATTTTGTATTATAT

AACAAACAAAGTAAGGAATACAGATTTATACAATAAATTGCCATACTAGTCACGTG

AGATATCTCATCCATTCCCCAACTCCCAAGAAAATAAAAAAGTGAAAAATAAAATC

AAACCCAAAGATCAACCTCCCCATCATCATCGTCATCAAACCCCCAGCTCAATTCGC

AATGGTTAGCACAAAAACATACACAGAAAGGGCATCAGCACACCCCTCCAAGGTTG

CCCAACGTTTATTAATTAAAGGCTAGGTGGAGGCTCAGTGATGATAAGTCTGCGATG

GTGGATGCATGTGTCATGGTCATAGCTGTTTCCTGTGTGAAATTGTTATCCGCTCAGA

GGGCACAATCCTATTCCGCGCTATCCGACAATCTCCAAGACATTAGGTGGAGTTCAG

TTCGGCGTATGGCATATGTCGCTGGAAAGAACATGTGAGCAAAAGGCCAGCAAAAG

GCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGGTCTGACGCTCTATTCAACAAAGCCGCCGTCCC

GTCAAGTCAGCGTAAATGGGTAGGGGGCTTCAAATCGTCCGCTCTGCCAGTGTTACA

ACCAATTAACAAATTCTGATTAGAAAAACTCATCGAGCATCAAATGAAACTGCAATT

TATTCATATCAGGATTATCAATACCATATTTTTGAAAAAGCCGTTTCTGTAATGAAG

GAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGG

TTATCAAGTGAGAAATCACCATGAGTGACGACTGAATCCGGTGAGAATGGCAAAAG

CTTATGCATTTCTTTCCAGACTTGTTCAACAGGCCAGCCATTACGCTCGTCATCAAAA

-continued

TCACTCGCATCAACCAAACCGTTATTCATTCGTGATTGCGCCTGAGCGAGACGAAAT

ACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGT

ACGGATAAAATGCTTGATGGTCGGAAGAGGCATAAATTCCGTCAGCCAGTTTAGTCT

GACCATCTCATCTGTAACATCATTGGCAACGCTACCTTTGCCATGTTTCAGAAACAA

CTCTGGCGCATCGGGCTTCCCATACAATCGATAGATTGTCGCACCTGATTGCCCGAC

ATTATCGCGAGCCCATTTATACCCATATAAATCAGCATCCATGTTGGAATTTAATCG

CGGCCTCGAGCAAGACGTTTCCCGTTGAATATGGCTCATAACACCCCTTGTATTACT

GTTTATGTAAGCAGACAGTTTTATTGTTCATGATGATATATTTTTATCTTGTGCAATG

TAACATCAGAGATTTTGAGACACAACGTGGCTTTCCCCCGCCGCTCTAGAACTAGTG

GATCCAAATAAAACGAAAGGCTCAGTCGAAAGACTGGGCCTTTCGTTTTATCTGTTG

TTTGTCGCATTATACGAGACGTCCAGGTTGGGATACCTGAAACAAAACCCATCGTAC

GGCCAAGGAAGTCTCCAATAACTGTGATCCACCACAAGCGCCAGGGTTTTCCCAGTC

ACGACGTTGTAAAACGACGGCCAGTCATGCATAATCCGCACGCATCTGGAATAAGG

AAGTGCCATTCCGCCTGACCT pLD113

(SEQ ID NO: 171)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

-continued

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

AGGGATTTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTTAAATTATTGGCCCGAAAATTAATCAGTGTAGACTGGATCCTC

GAGAACCATTTAATTAACAAGTCGAGAACGTACCACTGTCCTCCACTACAAACACA

CCCAATCTGCTTCTTCTAGTCAAGGTTGCTACACCGGTAAATTATAAATCATCATTTC

ATTAGCAGGGCTGGGCCCTTTTTATAGAGTCTTATACACTAGCGGACCCTGCCGGTA

-continued

GACCAACCCGCAGGCGCGTCAGTTTGCTCCTTCCATCAATGCGTCGTAGAAACGACT

TACTCCTTCTTGAGCAGCTCCTTGACCTTGTTGGCAACAAAGTCTCCGACCTCGGAG

GTGGAGGAGGAGCCTCCGATATCGGCGGTAGTGATACCAGCCTCGACGGACTCCTT

GACGGCAGCCTCAACAGCGTCACCGGCGGGCTTCATGTTAAGAGAGAACTTGAGCA

TCATGGCGGCAGACAGAATGGTGGCAATGGGGTTGACCTTCTGCTTGCCGAGATCG

GGGGCAGATCCGTGACAGGGCTCGTACAGACCGAACGCCTCGTTGGTGTCGGGCAG

AGAAGCCAGAGAGGCGGAGGGCAGCAGACCCAGAGAACCGGGGATGACGGAGGCC

TCGTCGGAGATGATATCGCCAAACATGTTGGTGGTGATGATGATACCATTCATCTTG

GAGGGCTGCTTGATGAGGATCATGGCGGCCGAGTCGATCAGCTGGTGGTTGAGCTC

CAGCTGGGGGAATTCGTCCTTGAGGACTCGGGTGACGGTCTTTCGCCAAAGTCGAGA

GGAGGCCAGCACGTTGGCCTTGTCAAGGGACCACACGGGAAGAGGGGGGTTGTGCT

GAAGGGCCAGGAAGGCGGCCATTCGGGCAATTCGCTCAACCTCAGGAACGGAGTAA

GTCTCAGTGTCGGAAGCGACGCCAGATCCGTCATCCTCCTTTCGCTCTCCAAAGTAG

ATACCTCCGACGAGCTCTCGGACAATGATGAAGTCGGTGCCCTCAACGTTTCGGATG

GGGGAGAGATCGGCGAGCTTGGGCGACAGCAGCTGGCAGGGTCGCAGGTTGGCGTA

CAGGTTCAGGTCCTTTCGCAGCTTGAGAAGACCCTGCTCGGGTCGCACGTCGGTTCG

TCCGTCGGGAGTGGTCCATACGGTGTTGGCAGCGCCTCCGACAGCACCGAGCATAA

TAGAGTCAGCCTTTCGGCAGATGTCGAGAGTAGCGTCGGTGATGGGCTCGCCCTCCT

TCTCAATGGCAGCTCCTCCAATGAGTCGGTCCTCAAACACAAACTCGGTGCCGGAGG

CCTCAGCAACAGACTTGAGCACCTTGACGGCCTCGGCAATCACCTCGGGGCCACAG

AAGTCGCCGCCGAGAAGAACAATCTTCTTGGAGTCAGTCTTGGTCTTCTTAGTTTCG

GGTTCCATTGTGGATGTGTGTGGTTGTATGTGTGATGTGGTGTGTGGAGTGAAAATC

TGTGGCTGGCAAACGCTCTTGTATATATACGCACTTTTGCCCGTGCTATGTGGAAGA

CTAAACCTCCGAAGATTGTGACTCAGGTAGTGCGGTATCGGCTAGGGACCCAAACCT

TGTCGATGCCGATAGCGCTATCGAACGTACCCCAGCCGGCCGGGAGTATGTCGGAG

GGGACATACGAGATCGTCAAGGGTTTGTGGCCAACTGGTAAATAAATGATGACTCA

GGCGACGACGGAATTCGACAGCAACTACTCCTTTCACCAACCATGTGCATTTTAGCT

CGAATAACATTCACAGGCTTGGTGATCTACATCCATGGTGTCTGGCCGATTACCGTG

GTGTTTTGGCAGTAACGAGAATATTGAGTGAACTCTTCCCATCACCAATAAAGACTC

ATACTACAATCACGAGCGCTTCAGCTGCCACTATAGTGTTGGTGACACAATACCCCT

CGATGCTGGGCATTACTGTAGCAAGAGATATTATTTCATGGCGCATTTTCCAGTCTA

CCTGACTTTTTAGTGTGATTTCTTCTCCACATTTTATGCTCAGTGTGAAAAGTTGGAG

TGCACACTTAATTATCGCCGGTTTTCGGAAAGTACTATGTGCTCAAGGTTGCACCCC

ACGTTACGTATGCAGCACATTGAGCAGCCTTTGGACCGTGGAGATAACGGTGTGGA

GATAGCAACGGGTAGTCTTCGTATTAATTCAATGCATTGTTAGTTTTATATGATATGG

TGTCGAGCGGCCGCGACCGGGTTGGCGGCGCATTTGTGTCCCAAAAAACAGCCCCA

ATTGCCCCAATTGACCCCAAATTGACCCAGTAGCGGGCCCAACCCCGGCGAGAGCC

CCCTTCTCCCCACATATCAAACCTCCCCCGGTTCCCACACTTGCCGTTAAGGGCGTA

GGGTACTGCAGTCTGGAATCTACGCTTGTTCAGACTTTGTACTAGTTTCTTTGTCTGG

CCATCCGGGTAACCCATGCCGGACGCAAAATAGACTACTGAAAATTTTTTTGCTTTG

TGGTTGGGACTTTAGCCAAGGGTATAAAAGACCACCGTCCCCGAATTACCTTTCCTC

-continued

TTCTTTTCTCTCTCTCCTTGTCAACTCACACCCGAAATCGTTAAGCATTTCCTTCTGAG

TATAAGAATCATTCAAAATGTCCAACCTCCTCACCGTCCACCAGAACCTTCCCGCCC

TTCCCGTGGACGCCACCTCCGACGAGGTCCGAAAGAACCTCATGGACATGTTCCGA

GATCGACAGGCCTTCTCCGAGCACACTTGGAAGATGCTCCTCTCCGTCTGCCGATCC

TGGGCCGCCTGGTGCAAGCTCAACAACCGAAAGTGGTTCCCCGCCGAGCCCGAGGA

CGTCCGAGACTACCTCCTTTACCTCCAGGCCCGAGGCCTCGCCGTCAAGACCATCCA

GCAGCACCTCGGCCAGCTCAACATGCTCCACCGACGATCCGGCCTCCCCCGACCCTC

CGACTCCAACGCCGTGTCCCTCGTCATGCGACGAATCCGAAAGGAGAACGTGGACG

CCGGCGAGCGAGCCAAGCAGGCCCTTGCCTTCGAGCGAACCGACTTCGACCAGGTC

CGATCCCTCATGGAGAACTCCGACCGATGCCAGGACATCCGAAACCTCGCCTTCCTT

GGCATCGCCTACAACACCCTCCTTCGAATCGCCGAGATCGCCCGAATCCGAGTCAAG

GACATCTCCCGAACCGACGGCGGCCGAATGCTCATCCACATCGGCCGAACCAAGAC

CCTCGTGTCCACCGCCGGCGTCGAGAAGGCCCTCTCCCTCGGCGTCACCAAGCTCGT

CGAGCGATGGATCTCCGTGTCCGGCGTCGCTGACGACCCCAACAACTACCTCTTCTG

CCGAGTCCGAAAGAACGGCGTCGCTGCTCCCTCCGCCACCTCCCAGCTCTCCACCCG

AGCCCTTGAGGGCATCTTCGAGGCCACCCACCGACTCATCTACGGCGCCAAGGACG

ACTCCGGCCAGCGATACCTCGCCTGGTCCGGCCACTCTGCTCGAGTCGGTGCCGCCC

GAGACATGGCCCGAGCCGGTGTCTCCATCCCCGAGATCATGCAGGCCGGCGGCTGG

ACCAACGTCAACATCGTCATGAACTACATCCGAAACCTCGACTCCGAGACTGGCGC

CATGGTCCGACTTCTTGAGGACGGCGACTGATGATCATATGATTACATTAATAGCTA

ATTACGTGTATCCGATATATATACTAATTACAATAGTACATATTAGAACATACAATA

GTTTTAATTAA pLD125

(SEQ ID NO: 172)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

-continued

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACATAATGTTCTTGAAACACATTTTTGTTG

CTCTCGCTTTTGCCTTGTTAGCTGACGCTACCCCAGCCCAGAAGAGATCTCCCGGCTT

CGTTGCTTTAGACTTTGACATCGTCAAGGTTCAAAAGAACGTGACTGCCAACGACGA

CGCCGCTGCCATTGTTGCCAAGAGACAGACCAACCCAAGGGAAAACTTCCTTAAGT

GTTTTCTGCAGTACATCCCTAACAATGCAACAAACCTCAAGTTGGTGTACACTCAAA

ACAATCCACTCTATATGAGCGTGCTTAATAGCACAATCCACAACTTGCGCTTCACGT

CAGATACTACGCCTAAGCCACTAGTGATCGTTACACCATCACACGTCAGCCATATTC

AAGGAACGATCCTATGTCTGAAAAAGGTCGGGTTGCAAATCAGGACTCGATCAGGA

GGGCACGATAGTGAGGGAATGAGTTACATCTCGCAAGTACCCTTCGTGATAGTTGAC

TTGCGAAATATGCGGTCTATTAAAATTGACGTACATAGCCAGACCGCCTGGGTTGAA

GCAGGGGCAACCTTGGGTGAAGTTTATTACTGGGTCAATGAAAAAAACGAAAACCT

AAGTCTTGCTGCTGGATATTGCCCCACCGTTTGCGCGGGTGGTCATTTTGGAGGCGG

CGGATATGGTCCGTTGATGAGAAATTATGGACTTGCAGCAGACAATATTATAGATGC

CCACTTGGTGAACGTTCATGGAAAGGTCTTGGACCGTAAGTCCATGGGTGAAGATCT

TTTCTGGGCCTTGAGAGGTGGTGGAGCGGAATCGTTTGGCATCATCGTTGCCTGGAA

AATTAGGTTGGTTGCGGTCCCGAAGAGTACAATGTTCTCCGTGAAGAAGATTATGGA

AATACATGAGCTTGTCAAGTTAGTTAACAAGTGGCAAAATATCGCTTATAAGTATGA

TAAAGACTTGCTTTTGATGACTCATTTTATTACGCGAAACATAACCGATAACCAGGG

CAAGAACAAGACTGCTATTCACACGTACTTCTCCTCTGTATTTCTTGGAGGAGTAGA

CTCCTTAGTTGACTTGATGAACAAGAGTTTCCCAGAATTGGGGATTAAGAAGACAGA

TTGCAGACAATTATCGTGGATAGATACAATCATATTCTATAGCGGTGTCGTCAATTA

CGATACTGATAATTTTAATAAAGAAATCCTCCTAGATCGTTCAGCTGGGCAAAACGG

GGCATTCAAAATTAAATTGGATTATGTGAAGAAACCAATTCCAGAGCTGGTGTTTGT

TCAGATATTGGAAAAACTTTACGAAGAAGACATTGGCGCAGGTATGTACGCTTTGTA

TCCATATGGAGGCATTATGGACGAGATCTCAGAGCTGGCGATCCCCTTCCCGCACAG

AGCTGGGATACTCTACGAGCTATGGTACATCTGCTCTTGGGAGAAACAAGAAGACA

ACGAGAAACATCTCAATTGGATTCGGAACATATACAACTTTATGACCCCATACGTAT

CAAAAAACCCGCGCTTAGCATACTTGAATTACAGAGACTTAGATATCGGTATCAATG

ATCCTAAGAATCCTAACAATTACACCCAAGCCCGTATTTGGGGTGAGAAATATTTCG

GCAAGAATTTTGACAGATTAGTTAAGGTCAAAACACTCGTGGACCCCAACAACTTTT

TCCGAAACGAGCAGTCGATTCCACCACTACCCAGGCATAGACACTGAGAGTGACTC

-continued

TTTTGATAAGAGTCGCAAATTTGATTTCATAAGTATATATTCATTATGTAAAGTAGTA

AATGGAAAATTCATTAAAAAAAAAGCAAATTTCCGTTGTATGCATACTCCGAACAC

AAAACTAGCCCCGGAAAAACCCTTAGTTGATAGTTGCGAATTTAGGTCGACCATATG

CGACGGGTACAACGAGAATTGTATTGAATTGATCAAGAACATGATCTTGGTGTTACA

GAACATCAAGTTCTTGGACCAGACTGAGAATGCACAGATATACAAGGCGTCATGTG

ATAAAATGGATGAGATTTATCCACAATTGAAGAAAGAGTTTATGGAAAGTGGTCAA

CCAGAAGCTAAACAGGAAGAAGCAAACGAAGAGGTGAAACAAGAAGAAGAAGGTA

AATAAGTATTTTGTATTATATAACAAACAAAGTAAGGAATACAGATTTATACAATAA

ATTGCCATACTAGTCACGTGAGATATCTCATCCATTCCCCAACTCCCAAGAAAATAA

AAAAGTGAAAAATAAAATCAAACCCAAAGATCAACCTCCCCATCATCATCGTCATC

AAACCCCCAGCTCAATTCGCAATGGTTAGCACAAAAACATACACAGAAAGGGCATC

AGCACACCCCTCCAAGGTTGCCCAACGTTTATTAATTAAAGGCTAGGTGGAGGCTCA

GTGATGATAAGTCTGCGATGGTGGATGCATGTGTCATGGTCATAGCTGTTTCCTGTG

TGAAATTGTTATCCGCTCAGAGGGCACAATCCTATTCCGCGCTATCCGACAATCTCC

AAGACATTAGGTGGAGTTCAGTTCGGCGTATGGCATATGTCGCTGGAAAGAACATG

TGAGCAAAAGGCCAGCAAAAGGCCAGGAACCGTAAAAAGGCCGCGTTGCTGGCGTT

TTTCCATAGGCTCCGCCCCCCTGACGAGCATCACAAAAATCGACGCTCAAGTCAGAG

GTGGCGAAACCCGACAGGACTATAAAGATACCAGGCGTTTCCCCCTGGAAGCTCCC

TCGTGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGCTG

CGCCTTATCCGGTAACTATCGTCTTGAGTCCAACCCGGTAAGACACGACTTATCGCC

ACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGAACAGTATTTGGTA

TCTGCGCTCTGCTGAAGCCAGTTACCTTCGGAAAAAGAGTTGGTAGCTCTTGATCCG

GCAAACAAACCACCGCTGGTAGCGGTGGTTTTTTTGTTTGCAAGCAGCAGATTACGC

GCAGAAAAAAAGGATCTCAAGAAGATCCTTTGATCTTTTCTACGGGGTCTGACGCTC

TATTCAACAAAGCCGCCGTCCCGTCAAGTCAGCGTAAATGGGTAGGGGGCTTCAAA

TCGTCCGCTCTGCCAGTGTTACAACCAATTAACAAATTCTGATTAGAAAAACTCATC

GAGCATCAAATGAAACTGCAATTTATTCATATCAGGATTATCAATACCATATTTTTG

AAAAAGCCGTTTCTGTAATGAAGGAGAAAACTCACCGAGGCAGTTCCATAGGATGG

CAAGATCCTGGTATCGGTCTGCGATTCCGACTCGTCCAACATCAATACAACCTATTA

ATTTCCCCTCGTCAAAAATAAGGTTATCAAGTGAGAAATCACCATGAGTGACGACTG

AATCCGGTGAGAATGGCAAAAGCTTATGCATTTCTTTCCAGACTTGTTCAACAGGCC

AGCCATTACGCTCGTCATCAAAATCACTCGCATCAACCAAACCGTTATTCATTCGTG

ATTGCGCCTGAGCGAGACGAAATACGCGATCGCTGTTAAAAGGACAATTACAAACA

GGAATCGAATGCAACCGGCGCAGGAACACTGCCAGCGCATCAACAATATTTTCACC

TGAATCAGGATATTCTTCTAATACCTGGAATGCTGTTTTCCCGGGGATCGCAGTGGT

GAGTAACCATGCATCATCAGGAGTACGGATAAAATGCTTGATGGTCGGAAGAGGCA

TAAATTCCGTCAGCCAGTTTAGTCTGACCATCTCATCTGTAACATCATTGGCAACGCT

-continued

ACCTTTGCCATGTTTCAGAAACAACTCTGGCGCATCGGGCTTCCCATACAATCGATA

GATTGTCGCACCTGATTGCCCGACATTATCGCGAGCCCATTTATACCCATATAAATC

AGCATCCATGTTGGAATTTAATCGCGGCCTCGAGCAAGACGTTTCCCGTTGAATATG

GCTCATAACACCCCTTGTATTACTGTTTATGTAAGCAGACAGTTTTATTGTTCATGAT

GATATATTTTTATCTTGTGCAATGTAACATCAGAGATTTTGAGACACAACGTGGCTTT

CCCCCGCCGCTCTAGAACTAGTGGATCCAAATAAAACGAAAGGCTCAGTCGAAAGA

CTGGGCCTTTCGTTTTATCTGTTGTTTGTCGCATTATACGAGACGTCCAGGTTGGGAT

ACCTGAAACAAAACCCATCGTACGGCCAAGGAAGTCTCCAATAACTGTGATCCACC

ACAAGCGCCAGGGTTTTCCCAGTCACGACGTTGTAAAACGACGGCCAGTCATGCAT

AATCCGCACGCATCTGGAATAAGGAAGTGCCATTCCGCCTGACCT pLD127

(SEQ ID NO: 173)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGCAATTGTCCTTGTCGGTTTTATC

AACCGTTGCCACGGCCTTGTTGTCCCTAACCACCGCCGTCGATGCTAAGTCCCACAA

CATCAAGTTGTCCAAGTTGTCCAACGAAGAAACATTGGACGCCTCCACATTCCAAGA

-continued

ATACACGAGCTCCTTGGCCAACAAGTACATGAACTTGTTCAACGCCGCTCACGGTAA
CCCAACCAGCTTTGGCTTGCAACACGTCTTGTCCAACCAAGAAGCTGAAGTCCCATT
CGTTACCCCACAAAAGGGTggcAACCCAAGGGAAAACTTCCTTAAGTGTTTTCTGCAG
TACATCCCTAACAATGCAACAAACCTCAAGTTGGTGTACACTCAAAACAATCCACTC
TATATGAGCGTGCTTAATAGCACAATCCACAACTTGCGCTTCACGTCAGATACTACG
CCTAAGCCACTAGTGATCGTTACACCATCACACGTCAGCCATATTCAAGGAACGATC
CTATGTCTGAAAAAGGTCGGGTTGCAAATCAGGACTCGATCAGGAGGGCACGATAG
TGAGGGAATGAGTTACATCTCGCAAGTACCCTTCGTGATAGTTGACTTGCGAAATAT
GCGGTCTATTAAAATTGACGTACATAGCCAGACCGCCTGGGTTGAAGCAGGGGCAA
CCTTGGGTGAAGTTTATTACTGGGTCAATGAAAAAAACGAAAACCTAAGTCTTGCTG
CTGGATATTGCCCCACCGTTTGCGCGGGTGGTCATTTTGGAGGCGGCGGATATGGTC
CGTTGATGAGAAATTATGGACTTGCAGCAGACAATATTATAGATGCCCACTTGGTGA
ACGTTCATGGAAAGGTCTTGGACCGTAAGTCCATGGGTGAAGATCTTTTCTGGGCCT
TGAGAGGTGGTGGAGCGGAATCGTTTGGCATCATCGTTGCCTGGAAAATTAGGTTGG
TTGCGGTCCCGAAGAGTACAATGTTCTCCGTGAAGAAGATTATGGAAATACATGAG
CTTGTCAAGTTAGTTAACAAGTGGCAAAATATCGCTTATAAGTATGATAAAGACTTG
CTTTTGATGACTCATTTTATTACGCGAAACATAACCGATAACCAGGGCAAGAACAAG
ACTGCTATTCACACGTACTTCTCCTCTGTATTTCTTGGAGGAGTAGACTCCTTAGTTG
ACTTGATGAACAAGAGTTTCCCAGAATTGGGGATTAAGAAGACAGATTGCAGACAA
TTATCGTGGATAGATACAATCATATTCTATAGCGGTGTCGTCAATTACGATACTGAT
AATTTTAATAAAGAAATCCTCCTAGATCGTTCAGCTGGGCAAAACGGGGCATTCAAA
ATTAAATTGGATTATGTGAAGAAACCAATTCCAGAGCTGGTGTTTGTTCAGATATTG
GAAAAACTTTACGAAGAAGACATTGGCGCAGGTATGTACGCTTTGTATCCATATGGA
GGCATTATGGACGAGATCTCAGAGCTGGCGATCCCCTTCCCGCACAGAGCTGGGAT
ACTCTACGAGCTATGGTACATCTGCTCTTGGGAGAAACAAGAAGACAACGAGAAAC
ATCTCAATTGGATTCGGAACATATACAACTTTATGACCCCATACGTATCAAAAAACC
CGCGCTTAGCATACTTGAATTACAGAGACTTAGATATCGGTATCAATGATCCTAAGA
ATCCTAACAATTACACCCAAGCCCGTATTTGGGGTGAGAAATATTTCGGCAAGAATT
TTGACAGATTAGTTAAGGTCAAAACACTCGTGGACCCCAACAACTTTTTCCGAAACG
AGCAGTCGATTCCACCACTACCCAGGCATAGACACTGAGAGTGACTCTTTTGATAAG
AGTCGCAAATTTGATTTCATAAGTATATATTCATTATGTAAAGTAGTAAATGGAAAA
TTCATTAAAAAAAAAGCAAATTTCCGTTGTATGCATACTCCGAACACAAAACTAGCC
CCGGAAAAACCCTTAGTTGATAGTTGCGAATTTAGGTCGACCATATGCGACGGGTAC
AACGAGAATTGTATTGAATTGATCAAGAACATGATCTTGGTGTTACAGAACATCAAG
TTCTTGGACCAGACTGAGAATGCACAGATATACAAGGCGTCATGTGATAAAATGGA
TGAGATTTATCCACAATTGAAGAAAGAGTTTATGGAAAGTGGTCAACCAGAAGCTA
AACAGGAAGAAGCAAACGAAGAGGTGAAACAAGAAGAAGAAGGTAAATAAGTATT
TTGTATTATATAACAAACAAAGTAAGGAATACAGATTTATACAATAAATTGCCATAC
TAGTCACGTGAGATATCTCATCCATTCCCCAACTCCCAAGAAAATAAAAAAGTGAA
AAATAAAATCAAACCCAAAGATCAACCTCCCCATCATCATCGTCATCAAACCCCCA -continued

GCTCAATTCGCAATGGTTAGCACAAAAACATACACAGAAAGGGCATCAGCACACCC

CTCCAAGGTTGCCCAACGTTTATTAATTAAAGGCTAGGTGGAGGCTCAGTGATGATA

AGTCTGCGATGGTGGATGCATGTGTCATGGTCATAGCTGTTTCCTGTGTGAAATTGTT

ATCCGCTCAGAGGGCACAATCCTATTCCGCGCTATCCGACAATCTCCAAGACATTAG

GTGGAGTTCAGTTCGGCGTATGGCATATGTCGCTGGAAAGAACATGTGAGCAAAAG

GCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCCTTATCCG

GTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTG

AAGTGGTGGCCTAACTACGGCTACACTAGAAGAACAGTATTTGGTATCTGCGCTCTG

CTGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCTATTCAACAA

AGCCGCCGTCCCGTCAAGTCAGCGTAAATGGGTAGGGGGCTTCAAATCGTCCGCTCT

GCCAGTGTTACAACCAATTAACAAATTCTGATTAGAAAAACTCATCGAGCATCAAAT

GAAACTGCAATTTATTCATATCAGGATTATCAATACCATATTTTTGAAAAAGCCGTT

TCTGTAATGAAGGAGAAAACTCACCGAGGCAGTTCCATAGGATGGCAAGATCCTGG

TATCGGTCTGCGATTCCGACTCGTCCAACATCAATACAACCTATTAATTTCCCCTCGT

CAAAAATAAGGTTATCAAGTGAGAAATCACCATGAGTGACGACTGAATCCGGTGAG

AATGGCAAAAGCTTATGCATTTCTTTCCAGACTTGTTCAACAGGCCAGCCATTACGC

TCGTCATCAAAATCACTCGCATCAACCAAACCGTTATTCATTCGTGATTGCGCCTGA

GCGAGACGAAATACGCGATCGCTGTTAAAAGGACAATTACAAACAGGAATCGAATG

CAACCGGCGCAGGAACACTGCCAGCGCATCAACAATATTTTCACCTGAATCAGGAT

ATTCTTCTAATACCTGGAATGCTGTTTTCCCGGGGATCGCAGTGGTGAGTAACCATG

CATCATCAGGAGTACGGATAAAATGCTTGATGGTCGGAAGAGGCATAAATTCCGTC

AGCCAGTTTAGTCTGACCATCTCATCTGTAACATCATTGGCAACGCTACCTTTGCCAT

GTTTCAGAAACAACTCTGGCGCATCGGGCTTCCCATACAATCGATAGATTGTCGCAC

CTGATTGCCCGACATTATCGCGAGCCCATTTATACCCATATAAATCAGCATCCATGT

TGGAATTTAATCGCGGCCTCGAGCAAGACGTTTCCCGTTGAATATGGCTCATAACAC

CCCTTGTATTACTGTTTATGTAAGCAGACAGTTTTATTGTTCATGATGATATATTTTT

ATCTTGTGCAATGTAACATCAGAGATTTTGAGACACAACGTGGCTTTCCCCCGCCGC

TCTAGAACTAGTGGATCCAAATAAAACGAAAGGCTCAGTCGAAAGACTGGGCCTTT

CGTTTTATCTGTTGTTTGTCGCATTATACGAGACGTCCAGGTTGGGATACCTGAAAC

-continued

AAAACCCATCGTACGGCCAAGGAAGTCTCCAATAACTGTGATCCACCACAAGCGCC

AGGGTTTTCCCAGTCACGACGTTGTAAAACGACGGCCAGTCATGCATAATCCGCACG

CATCTGGAATAAGGAAGTGCCATTCCGCCTGACCT pLD131

(SEQ ID NO: 174)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

-continued

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

AGGGATTTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTTAAATTATTGGCCCGAAAATTAATCAGTGTAGACTGGATCCTC

GAGAACCATTTAATTAAGATCGTCGACGATTCCGCCAAGTGAGACTGGCGATCGGG

AGAAGGGTTGGTGGTCATGGGGGATAGAATTTGTACAAGTGGAAAAACCACTACGA

GTAGCGGATTTGATACCACAAGTAGCAGAGATATACAGCAATGGTGGGAGTGCAAG

TATCGGAATGTACTGTACCTCCTGTACTCGTACTCGTACGGCACTCGTAGAAACGGG

GCAATACGGGGGAGAAGCGATCGCCCGTCTGTTCAATCGCCACAAGTCCGAGTAAT

GCTTGAGTATCGAAGTCTTGTACCTCCCTGTCAATCATGGCACCACTGGTCTTGACTT

GTCTATTCATACTGGACAAGCGCCAGAGTTAAGCTTGTAGCGAATTTCGCCCTCGGA

CATCACCCCATACGACGGACACACATGCCCGACAAACAGCCTCTCTTATTGTAGCTG

AAAGTATATTGAATGTGAACGTGTACAATATCAGGTACCAGCGGGAGGTTACGGCC

AAGGTGATACCGGAATAACCCTGGCTTGGAGATGGTCGGTCCATTGTACTGAAGTGT

CCGTGTCGTTTCCGTCACTGCCCCAATTGGACATGTTTGTTTTTCCGATCTTTCGGGC

GCCCTCTCCTTGTCTCCTTGTCTGTCTCCTGGACTGTTGCTACCCCATTTCTTTGGCCT

CCATTGGTTCCTCCCCGTCTTTCACGTCGTCTATGGTTGCATGGTTTCCCTTATACTTT

TCCCCACAGTCACATGTTATGGAGGGGTCTAGATGGAGGCCTAATTTTGACGTGCAA

GGGGCGAATTGGGGCGAGAAACACGTCGTGGACATGGTGCAAGGCCCGCAGGGTTG

ATTCGACGCTTTTCCGCGAAAAAAACAAGTCCAAATACCCCCGTTATTCTCCCTCG

-continued

GCTCTCGGTATTTCACATGAAAACTATAACCTAGACTACACGGGCAACCTTAACCCC

AGAGTATACTTATATACCAAAGGGATGGGTCCTCAAAAATCACACAAGCAACGACG

CCATGGGCCTCTCTCTAGTATGTACCTTCTCTTTCCAGACCAACTATCACACTCTACT

GAACCCCCATAACAAGAACCCTAAAAATTCTCTTCTCAGTTACCAGCACCCCAAGAC

GCCTATCATTAAGTCCTCCTACGACAACTTTCCCTCTAAGTACTGCCTGACCAAAAA

CTTCCATCTCCTGGGACTGAACTCTCATAACAGAATTAGTAGCCAGTCCCGATCTAT

CCGAGCTGGCTCTGACCAGATTGAGGGCTCCCCTCACCATGAATCCGACAACAGCAT

CGCTACCAAGATTTTGAATTTTGGTCACACATGCTGGAAGCTCCAGCGACCGTACGT

CGTGAAGGGTATGATCTCGATTGCCTGTGGACTGTTCGGACGTGAGCTTTTTAATAA

TCGACACTTGTTTTCATGGGGCCTCATGTGGAAGGCTTTTTTCGCCCTCGTGCCCATT

CTGTCTTTCAACTTCTTTGCCGCTATTATGAACCAAATCTACGACGTTGATATTGATA

GGATCAACAAGCCTGACCTGCCGCTCGTCTCGGGGGAGATGTCTATCGAGACAGCG

TGGATTCTTTCGATTATCGTCGCGCTGACTGGCCTTATCGTTACCATAAAGTTGAAGT

CTGCACCCCTCTTCGTGTTTATCTACATTTTCGGTATTTTTGCTGGATTCGCGTACTCC

GTTCCCCCTATCAGATGGAAGCAGTACCCCTTTACTAACTTTCTGATTACTATCAGCA

GCCACGTCGGTTTAGCCTTTACCTCATATTCGGCCACCACCAGTGCACTGGGCCTCC

CCTTCGTCTGGCGACCTGCATTTTCATTCATCATCGCCTTCATGACTGTGATGGGTAT

GACCATCGCTTTCGCTAAGGACATCTCCGACATCGAGGGTGATGCTAAATATGGAGT

GTCCACCGTGGCCACTAAGCTGGGAGCCCGGAACATGACGTTCGTCGTCTCTGGTGT

TCTGCTCCTTAACTACTTGGTTTCGATCTCCATTGGCATTATCTGGCCACAAGTCTTC

AAGTCCAACATTATGATTCTGTCCCACGCCATTCTTGCCTTTTGCCTGATCTTCCAGA

CACGCGAACTCGCTCTCGCTAACTACGCCTCCGCCCCATCGCGACAGTTCTTCGAGT

TCATCTGGCTGCTTTACTACGCCGAGTACTTCGTTTACGTGTTCATCTAATAAGAGTA

GGCAATTAACAGATAGTTTGCCGGTGATAATTCTCTTAACCTCCCACACTCCTTTGAC

ATAACGATTTATGTAACGAAACTGAAATTTGACCAGATATTGTTGTAAATAGAAAAT

CTGGCTTGTAGGTGGCAAAATGCGGCGTCTTTGTTCATCAATTCCCTCTGTGACTACT

CGTCATCCCTTTATGTTCGACTGTCGTATTTCTTATTTTCCATACATATGCAAGTGAG

ATGCCCGTGTCCGAATTCGCTATGGATCCATAGCGTCGACACCATATCATATAAAAC

TAACAATGCATTGAATTAATACGAAGACTACCCGTTGCTATCTCCACACCGTTATCT

CCACGGTCCAAAGGCTGCTCAATGTGCTGCATACGTAACGTGGGGTGCAACCTTGAG

CACATAGTACTTTCCGAAAACCGGCGATAATTAAGTGTGCACTCCAACTTTTCACAC

TGAGCATAAAATGTGGAGAAGAAATCACACTAAAAAGTCAGGTAGACTGGAAAATG

CGCCATGAAATAATATCTCTTGCTACAGTAATGCCCAGCATCGAGGGGTATTGTGTC

ACCAACACTATAGTGGCAGCTGAAGCGCTCGTGATTGTAGTATGAGTCTTTATTGGT

GATGGGAAGAGTTCACTCAATATTCTCGTTACTGCCAAAACACCACGGTAATCGGCC

AGACACCATGGATGTAGATCACCAAGCCTGTGAATGTTATTCGAGCTAAAATGCAC

ATGGTTGGTGAAAGGAGTAGTTGCTGTCGAATTCCGTCGTCGCCTGAGTCATCATTT

ATTTACCAGTTGGCCACAAACCCTTGACGATCTCGTATGTCCCCTCCGACATACTCC

CGGCCGGCTGGGGTACGTTCGATAGCGCTATCGGCATCGACAAGGTTTGGGTCCCTA

GCCGATACCGCACTACCTGAGTCACAATCTTCGGAGGTTTAGTCTTCCACATAGCAC

GGGCAAAAGTGCGTATATATACAAGAGCGTTTGCCAGCCACAGATTTTCACTCCACA

-continued

CACCACATCACACATACAACCACACACATCCACAATGGAACCCGAAACTAAGAAGA

CCAAGACTGACTCCAAGAAGATTGTTCTTCTCGGCGGCGACTTCTGTGGCCCCGAGG

TGATTGCCGAGGCCGTCAAGGTGCTCAAGTCTGTTGCTGAGGCCTCCGGCACCGAGT

TTGTGTTTGAGGACCGACTCATTGGAGGAGCTGCCATTGAGAAGGAGGGCGAGCCC

ATCACCGACGCTACTCTCGACATCTGCCGAAAGGCTGACTCTATTATGCTCGGTGCT

GTCGGAGGCGCTGCCAACACCGTATGGACCACTCCCGACGGACGAACCGACGTGCG

ACCCGAGCAGGGTCTTCTCAAGCTGCGAAAGGACCTGAACCTGTACGCCAACCTGC

GACCCTGCCAGCTGCTGTCGCCCAAGCTCGCCGATCTCTCCCCCATCCGAAACGTTG

AGGGCACCGACTTCATCATTGTCCGAGAGCTCGTCGGAGGTATCTACTTTGGAGAGC

GAAAGGAGGATGACGGATCTGGCGTCGCTTCCGACACTGAGACTTACTCCGTTCCTG

AGGTTGAGCGAATTGCCCGAATGGCCGCCTTCCTGGCCCTTCAGCACAACCCCCCTC

TTCCCGTGTGGTCCCTTGACAAGGCCAACGTGCTGGCCTCCTCTCGACTTTGGCGAA

AGACCGTCACCCGAGTCCTCAAGGACGAATTCCCCCAGCTGGAGCTCAACCACCAG

CTGATCGACTCGGCCGCCATGATCCTCATCAAGCAGCCCTCCAAGATGAATGGTATC

ATCATCACCACCAACATGTTTGGCGATATCATCTCCGACGAGGCCTCCGTCATCCCC

GGTTCTCTGGGTCTGCTGCCCTCCGCCTCTCTGGCTTCTCTGCCCGACACCAACGAGG

CGTTCGGTCTGTACGAGCCCTGTCACGGATCTGCCCCCGATCTCGGCAAGCAGAAGG

TCAACCCCATTGCCACCATTCTGTCTGCCGCCATGATGCTCAAGTTCTCTCTTAACAT

GAAGCCCGCCGGTGACGCTGTTGAGGCTGCCGTCAAGGAGTCCGTCGAGGCTGGTA

TCACTACCGCCGATATCGGAGGCTCCTCCTCCACCTCCGAGGTCGGAGACTTTGTTG

CCAACAAGGTCAAGGAGCTGCTCAAGAAGGAGTAAGTCGTTTCTACGACGCATTGA

TGGAAGGAGCAAACTGACGCGCCTGCGGGTTGGTCTACCGGCAGGGTCCGCTAGTG

TATAAGACTCTATAAAAAGGGCCCAGCCCTGCTAATGAAATGATGATTTATAATTTA

CCGGTGTAGCAACCTTGACTAGAAGAAGCAGATTGGGTGTGTTTGTAGTGGAGGAC

AGTGGTACGTTTTAATTAA pLD132

(SEQ ID NO: 175)

TTAATTAAGATCGTCGACGATTCCGCCAAGTGAGACTGGCGATCGGGAGAAGGGTT

GGTGGTCATGGGGGATAGAATTTGTACAAGTGGAAAAACCACTACGAGTAGCGGAT

TTGATACCACAAGTAGCAGAGATATACAGCAATGGTGGGAGTGCAAGTATCGGAAT

GTACTGTACCTCCTGTACTCGTACTCGTACGGCACTCGTAGAAACGGGGCAATACGG

GGGAGAAGCGATCGCCCGTCTGTTCAATCGCCACAAGTCCGAGTAATGCTTGAGTAT

CGAAGTCTTGTACCTCCCTGTCAATCATGGCACCACTGGTCTTGACTTGTCTATTCAT

ACTGGACAAGCGCCAGAGTTAAGCTTGTAGCGAATTTCGCCCTCGGACATCACCCCA

TACGACGGACACACATGCCCGACAAACAGCCTCTCTTATTGTAGCTGAAAGTATATT

GAATGTGAACGTGTACAATATCAGGTACCAGCGGGAGGTTACGGCCAAGGTGATAC

CGGAATAACCCTGGCTTGGAGATGGTCGGTCCATTGTACTGAAGTGTCCGTGTCGTT

TCCGTCACTGCCCCAATTGGACATGTTTGTTTTTCCGATCTTTCGGGCGCCCTCTCCT

TGTCTCCTTGTCTGTCTCCTGGACTGTTGCTACCCCATTTCTTTGGCCTCCATTGGTTC

CTCCCCGTCTTTCACGTCGTCTATGGTTGCATGGTTTCCCTTATACTTTTCCCCACAGT

CACATGTTATGGAGGGGTCTAGATGGAGGCCTAATTTTGACGTGCAAGGGGCGAAT

-continued

TGGGGCGAGAAACACGTCGTGGACATGGTGCAAGGCCCGCAGGGTTGATTCGACGC

TTTTCCGCGAAAAAAACAAGTCCAAATACCCCCGTTTATTCTCCCTCGGCTCTCGGT

ATTTCACATGAAAACTATAACCTAGACTACACGGGCAACCTTAACCCCAGAGTATAC

TTATATACCAAAGGGATGGGTCCTCAAAAATCACACAAGCAACGACGCCATGAAGT

GTTCGACGTTTTCTTTTTGGTTTGTTTGTAAAATCATTTTCTTTTTCTTTTCTTTCAACA

TCCAAACGTCGATCGCAAACCCTAGAGAGAACTTTCTTAAGTGCTTCTCGCAGTACA

TCCCTAATAACGCTACCAACCTTAAGCTGGTGTACACCCAGAACAACCCTCTTTACA

TGTCTGTTCTAAACAGCACCATCCACAATCTTAGATTCACATCAGACACCACTCCCA

AGCCGCTCGTCATCGTGACCCCGAGTCATGTGTCCCATATCCAAGGCACTATCCTGT

GCTCTAAAAAGGTCGGTCTGCAGATTCGGACTCGCTCCGGTGGACATGATTCGGAGG

GCATGTCCTACATTAGCCAGGTCCCCTTTGTGATCGTGGACCTGAGGAACATGCGGT

CTATTAAGATTGATGTGCACTCACAGACCGCTTGGGTCGAGGCTGGTGCGACATTGG

GTGAGGTGTACTACTGGGTGAACGAGAAGAACGAGAACCTGAGCCTCGCCGCTGGC

TACTGTCCCACCGTTTGTGCCGGTGGACACTTCGGCGGAGGCGGATACGGTCCACTT

ATGCGAAACTACGGGCTCGCAGCTGATAATATCATCGACGCACACCTTGTTAACGTT

CACGGCAAGGTGCTGGACCGAAAAAGCATGGGTGAGGACCTATTTTGGGCCTTGCG

AGGCGGTGGTGCCGAATCCTTCGGAATTATCGTGGCCTGGAAGATCCGACTGGTCGC

TGTGCCAAAGTCCACTATGTTCTCCGTCAAGAAAATTATGGAGATCCACGAACTCGT

AAAGCTCGTCAATAAGTGGCAGAACATCGCCTACAAGTATGACAAGGATCTGCTGC

TCATGACTCACTTCATCACGCGAAACATTACAGACAACCAGGGAAAGAACAAGACC

GCTATCCATACCTACTTCTCCTCTGTCTTCCTTGGGGGTGTCGATTCCCTCGTTGATCT

CATGAACAAATCTTTTCCAGAGCTCGGAATCAAGAAGACCGACTGCCGACAGCTCT

CTTGGATCGACACCATTATTTTCTACTCAGGAGTCGTAAACTACGATACTGACAACT

TTAACAAGGAGATTCTGTTAGATCGATCGGCCGGCCAGAACGGTGCCTTCAAGATCA

AGCTCGACTATGTCAAAAAGCCCATTCCTGAATCCGTCTTCGTTCAAATTCTTGAAA

AGTTGTACGAGGAGGATATCGGCGCCGGAATGTACGCGCTGTACCCCTACGGTGGC

ATTATGGACGAGATTTCTGAAAGTGCTATTCCCTTCCCCCACCGTGCTGGCATTCTGT

ATGAGCTGTGGTACATTTGCTCCTGGGAAAAGCAGGAGGACAACGAGAAGCACTTG

AACTGGATACGAAACATTTACAATTTCATGACCCCCTATGTTTCGAAGAACCCTCGA

CTGGCCTACCTGAATTACCGCGACCTCGACATCGGAATTAACGACCCTAAGAACCCC

AATAACTATACTCAGGCCAGAATCTGGGGCGAGAAGTACTTCGGCAAGAACTTTGA

CCGTCTGGTTAAGGTCAAGACCCTCGTGGACCCTAACAACTTCTTCCGAAACGAGCA

GTCTATCCCCCCTCTGCCCCGACACCGGCATTAATAAGAGTAGGCAATTAACAGATA

GTTTGCCGGTGATAATTCTCTTAACCTCCCACACTCCTTTGACATAACGATTTATGTA

ACGAAACTGAAATTTGACCAGATATTGTTGTAAATAGAAAATCTGGCTTGTAGGTGG

CAAAATGCGGCGTCTTTGTTCATCAATTCCCTCTGTGACTACTCGTCATCCCTTTATG

TTCGACTGTCGTATTTCTTATTTTCCATACATATGCAAGTGAGATGCCCGTGTCCGAA

TTCGCTATGGATCCATAGCGCAGGTTGTGCAGTATCATACATACTCGATCAGACAGG

TCGTCTGACCATCATACAAGCTGAACAAGCGCTCCATACTTGCACGCTCTCTATATA

CACAGTTAAATGACATATCCATAGTCTAACCTCTAACAGTTAATCTTCTGGTAAGCC

TCCCAGCCAGCCTTCTGGTATCGCTTGGCCTCCTCAATAGGATCTCGGTTCTGGCCGT

-continued

ACAGACCTCGGCCGACAATTATGATATCCGTTCCGGTAGACATGACATCCTCAACAG

TTCGGTACTGCTGTCCGAGAGCATCTCCCTTGTCGTCAAGACCCACCCCGGGGGTCA

GAATAAGCCAGTCCTCAGAGTCGCCCTTAGGTCGGTTCTGGGCAATGAAGCCAACC

ACAAACTCGGGGTCGGATCGGGCAAGCTCAATGGTCTGCTTGGAGTACTCGCCAGT

GGCCAGAGAGCCCTTGCAAGACAGCTCGGCCAGCATGAGCAGACCTCTGGCCAGCT

TCTCGTTGGGAGAGGGGACCAGGAACTCCTTGTACTGGGAGTTCTCGTAGTCAGAGA

CATCCTCCTTCTTCTGTTCAGAGACAGTTTCCTCGGCACCAGCTCGCAGGCCAGCAA

TGATTCCGGTTCCGGGTACACCGTGGGCGTTGGTGATATCGGACCACTCGGCGATTC

GGTAGACACCGTTCTTGTACTGGTGCTTGACAGTGTTGCCAATATCTGCGAACTTTCT

GTCCTCGAACAGGAAGAAACCGTGCTTAAGAGCAAGTTCCTTGAGGGGGAGCACAG

TTCCGGCGTAGGTGAAGTCGTCAATGATGTCGATATGGGTCTTGATCATGCACACAT

AAGGTCCGACCTTATCGGCAAGCTCAATGAGCTCCTTGGTGGTGGTAACATCCAGAG

AAGCACACAGGTTGGTTTTCTTGGCTGCCACGAGCTTGAGCACTCGGGCGGCAAAG

GCGGACTTGTGGACGTTAGCTCGCGCTTCGTAGGAGGGCATTTTGGTGGTGAAGAGG

AGACTGAAATAAATTTAGTCTGCACAACTTTTTATCGGAACCTTATCTGGGGCAGTG

AAGTATATGTTATGGTAATAGTTACGAGTTAGTTGAACTTATAGATAGACTGGACTA

TACGGCTATCGGTCCAAATTAGAAATTAATTAAATGGTTCTCGAGGATCCAGTCTAC

ACTGATTAATTTTCGGGCCAATAATTTAAAAAAATCGTGTTATATAATATTATATGT

ATTATATATATACATATGATGATACTGACAGTCATGTCCCATTGCTAAATAGACAGA

CTCCATCTGCCGCCTCCAACTGATGTTCTCAATATTTAAGGGGTCATCTCGCATTGTT

TAATAATAAACAGACTCCATCTACCGCCTCCAAATGATGTTCTCAAAATATATTGTA

TGAACTTATTTTTATTACTTAGTATTATTAGACAACTTACTTGCTTTATGAAAAACAC

TTCCTATTTAGGAAACAATTTATAATGGCAGTTCGTTCATTTAACAATTTATGTAGAA

TAAATGTTATAAATGCGTATGGGAAATCTTAAATATGGATAGCATAAATGATATCTG

CATTGCCTAATTCGAAATCAACAGCAACGAAAAAAATCCCTTGTACAACATAAATA

GTCATCGAGAAATATCAACTATCAAAGAACAGCTATTCACACGTTACTATTGAGATT

ATTATTGGACGAGAATCACACACTCAACTGTCTTTCTCTCTTCTAGAAATACAGGTA

CAAGTATGTACTATTCTCATTGTTCATACTTCTAGTCATTTCATCCCACATATTCCTTG

GATTTCTCTCCAATGAATGACATTCTATCTTGCAAATTCAACAATTATAATAAGATAT

ACCAAAGTAGCGGTATAGTGGCAATCAAAAAGCTTCTCTGGTGTGCTTCTCGTATTT

ATTTTTATTCTAATGATCCATTAAAGGTATATATTTATTTCTTGTTATATAATCCTTTT

GTTTATTACATGGGCTGGATACATAAAGGTATTTTGATTTAATTTTTTGCTTAAATTC

AATCCCCCCTCGTTCAGTGTCAACTGTAATGGTAGGAAATTACCATACTTTTGAAGA

AGCAAAAAAAATGAAAGAAATAAAAAATCGTATTTCCAGGTTAGACGTTCCGCAGA

ATCTAGAATGCGGTATGCGGTACATTGTTCTTCGAACGTAAAAGTTGCGCTCCCTGA

GATATTGTACATTTTTGCTTTTACAAGTACAAGTACATCGTACAACTATGTACTACTG

TTGATGCATCCACAACAGTTTGTTTTGTTTTTTTTTGTTTTTTATTTTTCTAATGATTC

ATTACCGCTATGTATACCTACTTGTACTTGTAGTAAGCCGGGTTATTGGCGTTCAATT

AATCATAGACTTATGAATCTGCACGGTGTGCGCTGCGAGTTACTTTTAGCTTATGCA

TGCTACTTGGGTGTAATATTGGGATCAGGTCAGGCGGAATGGCACTTCCTTATTCCA

-continued

GATGCGTGCGGATTATGCATGACTGGCCGTCGTTTTACAACGTCGTGACTGGGAAAA

CCCTGGCGCTTGTGGTGGATCACAGTTATTGGAGACTTCCTTGGCCGTACGATGGGT

TTTGTTTCAGGTATCCCAACCTGGACGTCTCGTATAATGCGACAAACAACAGATAAA

ACGAAAGGCCCAGTCTTTCGACTGAGCCTTTCGTTTTATTTGGATCCACTAGTTCTAG

AGCGGCGGGGGAAAGCCACGTTGTGTCTCAAAATCTCTGATGTTACATTGCACAAG

ATAAAAATATATCATCATGAACAATAAAACTGTCTGCTTACATAAACAGTAATACAA

GGGGTGTTATGAGCCATATTCAACGGGAAACGTCTTGCTCGAGGCCGCGATTAAATT

CCAACATGGATGCTGATTTATATGGGTATAAATGGGCTCGCGATAATGTCGGGCAAT

CAGGTGCGACAATCTATCGATTGTATGGGAAGCCCGATGCGCCAGAGTTGTTTCTGA

AACATGGCAAAGGTAGCGTTGCCAATGATGTTACAGATGAGATGGTCAGACTAAAC

TGGCTGACGGAATTTATGCCTCTTCCGACCATCAAGCATTTTATCCGTACTCCTGATG

ATGCATGGTTACTCACCACTGCGATCCCCGGGAAAACAGCATTCCAGGTATTAGAAG

AATATCCTGATTCAGGTGAAAATATTGTTGATGCGCTGGCAGTGTTCCTGCGCCGGT

TGCATTCGATTCCTGTTTGTAATTGTCCTTTTAACAGCGATCGCGTATTTCGTCTCGC

TCAGGCGCAATCACGAATGAATAACGGTTTGGTTGATGCGAGTGATTTTGATGACGA

GCGTAATGGCTGGCCTGTTGAACAAGTCTGGAAAGAAATGCATAAGCTTTTGCCATT

CTCACCGGATTCAGTCGTCACTCATGGTGATTTCTCACTTGATAACCTTATTTTTGAC

GAGGGGAAATTAATAGGTTGTATTGATGTTGGACGAGTCGGAATCGCAGACCGATA

CCAGGATCTTGCCATCCTATGGAACTGCCTCGGTGAGTTTTCTCCTTCATTACAGAAA

CGGCTTTTTCAAAAATATGGTATTGATAATCCTGATATGAATAAATTGCAGTTTCATT

TGATGCTCGATGAGTTTTTCTAATCAGAATTTGTTAATTGGTTGTAACACTGGCAGA

GCGGACGATTTGAAGCCCCCTACCCATTTACGCTGACTTGACGGGACGGCGGCTTTG

TTGAATAGAGCGTCAGACCCCGTAGAAAAGATCAAAGGATCTTCTTGAGATCCTTTT

TTTCTGCGCGTAATCTGCTGCTTGCAAACAAAAAAACCACCGCTACCAGCGGTGGTT

TGTTTGCCGGATCAAGAGCTACCAACTCTTTTTCCGAAGGTAACTGGCTTCAGCAGA

GCGCAGATACCAAATACTGTTCTTCTAGTGTAGCCGTAGTTAGGCCACCACTTCAAG

AACTCTGTAGCACCGCCTACATACCTCGCTCTGCTAATCCTGTTACCAGTGGCTGCT

GCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCG

AACGACCTACACCGAACTGAGATACCTACAGCGTGAGCTATGAGAAAGCGCCACGC

TTCCCGAAGGGAGAAAGGCGGACAGGTATCCGGTAAGCGGCAGGGTCGGAACAGG

AGAGCGCACGAGGGAGCTTCCAGGGGGAAACGCCTGGTATCTTTATAGTCCTGTCG

GGTTTCGCCACCTCTGACTTGAGCGTCGATTTTTGTGATGCTCGTCAGGGGGGCGGA

GCCTATGGAAAAACGCCAGCAACGCGGCCTTTTTACGGTTCCTGGCCTTTTGCTGGC

CTTTTGCTCACATGTTCTTTCCAGCGACATATGCCATACGCCGAACTGAACTCCACCT

AATGTCTTGGAGATTGTCGGATAGCGCGGAATAGGATTGTGCCCTCTGAGCGGATAA

CAATTTCACACAGGAAACAGCTATGACCATGACACATGCATCCACCATCGCAGACTT

ATCATCACTGAGCCTCCACCTAGCCT pLD135

(SEQ ID NO: 176)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

-continued

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCTCGTGATACCAATTCGGAGCCTGCTTTTTTGTAC

AAACTTGTTGATAATGGCAATTCAAGGATCTTCACCTAGATCCTTTTAAATTAAAAA

TGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCCCCA

GTGCTGCAATGATACCGCGAGAGCCACGCTCACCGGCTCCAGATTTATCAGCAATA

AACCAGCCAGCCGGAAGGGCCGAGCGCAGAAGTGGTCCTGCAACTTTATCCGCCTC

CATCCAGTCTATTAATTGTTGCCGGGAAGCTAGAGTAAGTAGTTCGCCAGTTAATAG

TTTGCGCAACGTTGTTGCCATTGCTACAGGCATCGTGGTGTCACGCTCGTCGTTTGGT

ATGGCTTCATTCAGCTCCGGTTCCCAACGATCAAGGCGAGTTACATGATCCCCCATG

TTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAAT

AGTGTATGCGGCGACCGAGTTGCTCTTGCCCGGCGTCAATACGGGATAATACCGCGC

CACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCC

AACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGG

ATACATATTTGAATGTATTTAGAAAAATAAACAAATAGGGGTTCCGCGCACATTTCC

CCGAAAAGTGCCAGATACCTGAAACAAAACCCATCGTACGGCCAAGGAAGTCTCCA

ATAACTGTGATCCACCACAAGCGCCAGGGTTTTCCCAGTCACGACGTTGTAAAACGA

CGGCCAGTCATGCATAATCCGCACGCATCTGGAATAAGGAAGTGCCATTCCGCCTG

ACCTTTAATTAATTGGCAAATTTTACTGTGGCCTTCAGAACGGTAAAAATAGACCAA

TCAGAATTCTGAAAAGCACATCTTGATCTCCTCATTGCGGGGAGTCCAACGGTGGTC

TTATTCCCCCGAATTTCCCGCTCAATCTCGTTCCAGACCGACCCGGACACAGTGCTT

-continued

AACGCCGTTCCGAAACTCTACCGCAGATATGCTCCAACGGACTGGGCTGCATAGAT

GTGATCCTCGGCTTGGAGAAATGGATAAAAGCCGGCCAAAAAAAAAGCGGAAAAA

AGCGGAAAAAAAGAGAAAAAAAATCGCAAAATTTGAAAAATAGGGGGAAAAGACG

CAAAAACGCAAGGAGGGGGGAGTATATGACACTGATAAGCAAGCTCACAACGGTTC

CTCTTATTTTTTTCCTCATCTTCTGCCTAGGTTCCCAAAATCCCAGATGCTTCTCTCCA

GTGCCAAAAGTAAGTACCCCACAGGTTTTCGGCCGAAAATTCCACGTGCAGCAACG

TCGTGTGGGGTGTTAAAATGTGGGGGCGGGGAACCAGGACAAGAGGCTCTTGTGGG

AGCCGAATGAGAGCACAAAGCGGGCGGGTGTGATAAGGGCATTTTTGCCCATTTTC

CCTTCTCCTGTCTCTCCGACGGTGATGGCGTTGTGCGTCCTCTATCTATTTCTTTTTAT

TTCTTTTTGTTTTATTTCTCTGACTACCGATTTGGCTTGATTTCCTCAACCCCACACAA

ATAAGCTCGGGCCGAGGAATATATATATACACGGACACAGTCGCCCTGTGGACAAC

ACGTCACTACCTCTACGACGCTATGGATCCATAGCGAATTCGGACACGGGCATCTCA

CTTGCATATGTATGGAAAATAAGAAATACGACAGTCGAACATAAAGGGATGACGAG

TAGTCACAGAGGGAATTGATGAACAAAGACGCCGCATTTTGCCACCTACAAGCCAG

ATTTTCTATTTACAACAATATCTGGTCAAATTTCAGTTTCGTTACATAAATCGTTATG

TCAAAGGAGTGTGGGAGGTTAAGAGAATTATCACCGGCAAACTATCTGTTAATTGCC

TACTCTTATTACAGTTTGGCTCGTCGTCCCCGAGACTTGCCGGCCTTGATAGCGAGG

AGTGTCTTCTCGTCAGCAGGGGCGCTACCGGAGGCTCGTTGCTGTCTGAAGTAGGTT

CGGGCCTCGTCCTGTCGGGTGGCCTCAGCGCCGGTGGCGATAGCGGCCCGAAGGTG

CTCGGCTCCGTAGCCGAAGGCATCAACCAGATCAAGTGCGTGTGGTCGGATCTTAAC

GAGAAGACGATTAATGTAAGTGCCGACCGTTCGGCCTCTCTGCATCGAGAGCCTACC

GTTCATCAGATACCAGCTGAGGTGCTTCTCGATAAGGGACAGACCAAAAAGGTCAC

GCAATCGGGTCAACACTTCCTTAGTGCCAGCGTCGTCCACCTTGGCCAAAGCCTCAG

TAAAGGCCTCCCACTGTAAAAGCTCAGCGTGGGCCTGGGCAGCCTCGATCAGTTCGT

TTTGATGCTGATTGAACAGTGCTGCCGCCTGGTGCTGGGGGAGCTTGCCCGCGCCTT

TGAGAGCAGCGCCAACCTCTGCAACCATGGACTGGACTCTGTCGGTCAGCAGAGTT

CGCTGACCTTCTTCGTCTCGGAGGGCAAGAGCAGATTTCTGGACAGATCCACTGTCG

GCCACGAACTGAGCGACCTGTCGCAGTCCGGTTCGGTGTAGCGCGACTCCGGCAGC

CTGGTCCACGACGTACCGCGCGAGCACGCCGAAGTTGGCACCTCGGAACTCCTTAG

CATAGTCAGCGAGCAGCCTCTTGGCCACCAACTGAAGAAGCACGGTGTTGTCTCCTT

CGAAGGTCACGTAGACGTCGAGATCGGCCCGGAGAGAAGCGAATCGGTTCTCAATC

AGAAAACCTGCACCCCCACACGCTTCTCGGCACTCTTGTAGGGTATCGAGAGCATGC

CAGGTAGAAAGGGGCTTCAGAGCAGCAGCCAGTGTCTCAAGGTCCTGACGGTCGGC

GTCAGTATCATGAGCACCCGAGAACACGTCGTCGAATTTCTGCAGCAGTTGCTCATG

GGCGAACGATGCGGCGTAGGTGGTGGCGAGTCGGGTAAAGAGGCGCCGCTGGTGTC

GCTGGTAATCCAGGAGCACCTCCTCCTCTGTGGGCGAAGTGGCGTTGAACTGTCTTC

GCTCAGCGGCGTAGTGGATGGCGGATTGCAGAGCAACCTTCGATGCAGCCACTGCA

GCACCGTCCAGGCTGACTCGGCCCTGGACCAGCGTACCTAGCATTGTAAAGAATCTT

CGCCCCGGAGATTCGATGGTTGAGCTGTAGGTGCCATCGACGGCAACATCGCCGTA

ACGGTTAAGCAGGTTGGTTCGGGGAATGCGAACATTGGTGAAATGGAGACGTCCGT

TATCAATTCCGTTTAGTCCCCCCTTAATACCGTCGTCCTCTCCACCAATACCAGGGAG

-continued

AAAGTCTCCGGTGGCGGGATCTCTCAGATCGACGTAGAAGGCGTGCACTCCATGGTT

AACCTTTCGAGTAATCAGTTGGGCAAACACGACAGCGGCCAAACCGTCGTTAGCGG

CGTTTCCAATGTAGTCCTTCCAGGCGGCTCGGAACGGGGTGTCAATAACGAACTCCT

GGGTTTCCTCATCATAGGTGGCCGTTGTAGCAATGGAAGCGACATCGGAGCCATGGC

CAGTCTCAGTCATGGCAAAGCAACCAGGGATTTCCAGAGACATGATGCCTGGGAGC

CACTTGTCGTGGTGCTCCCTAGTTCCCAAGTGCATAACAGCGGAGCCGAACAGTCCC

CACTGGACGCCGGCCTTGATCTGGAGGGAGGGGTCCGCCGTGACAAGCTCCTCAAA

ACCAGCGATGTTTCCGCCGTGGTCGTCACTACCACCCAGTCGAGAAGGAAAGGCTC

GGTGAACTGCGTTGTTATCGACCAAGTACTTGAGCTGGCCAAAGACGCGAGAGCGG

TGCTCTGTATGAGTCAGACCCTCCACCTTCTGAACTACCTCTCGTCCCGCAAGGTCCC

GGGCGTGGAGACGGATATCAGCCCATCGGCCCAGCAGCTGCTCTCCCAGCGCAGCC

ACATCTACTCGGGGCTCGACGGCCACCTTAGCACCGTCTGCGGCGGCCGTAGTTGAG

CCAGGGGATGCGGGGGATGAGGCTCTGTCAACTACTTCGGTCATGGCGTCGTTGCTT

GTGTGATTTTTGAGGACCCATCCCTTTGGTATATAAGTATACTCTGGGGTTAAGGTTG

CCCGTGTAGTCTAGGTTATAGTTTTCATGTGAAATACCGAGAGCCGAGGGAGAATAA

ACGGGGGTATTTGGACTTGTTTTTTTCGCGGAAAAGCGTCGAATCAACCCTGCGGGC

CTTGCACCATGTCCACGACGTGTTTCTCGCCCCAATTCGCCCCTTGCACGTCAAAATT

AGGCCTCCATCTAGACCCCTCCATAACATGTGACTGTGGGGAAAAGTATAAGGGAA

ACCATGCAACCATAGACGACGTGAAAGACGGGGAGGAACCAATGGAGGCCAAAGA

AATGGGGTAGCAACAGTCCAGGAGACAGACAAGGAGACAAGGAGAGGGCGCCCGA

AAGATCGGAAAAACAAACATGTCCAATTGGGGCAGTGACGGAAACGACACGGACA

CTTCAGTACAATGGACCGACCATCTCCAAGCCAGGGTTATTCCGGTATCACCTTGGC

CGTAACCTCCCGCTGGTACCTGATATTGTACACGTTCACATTCAATATACTTTCAGCT

ACAATAAGAGAGGCTGTTTGTCGGGCATGTGTGTCCGTCGTATGGGGTGATGTCCGA

GGGCGAAATTCGCTACAAGCTTAACTCTGGCGCTTGTCCAGTATGAATAGACAAGTC

AAGACCAGTGGTGCCATGATTGACAGGGAGGTACAAGACTTCGATACTCAAGCATT

ACTCGGACTTGTGGCGATTGAACAGACGGGCGATCGCTTCTCCCCCGTATTGCCCCG

TTTCTACGAGTGCCGTACGAGTACGAGTACAGGAGGTACAGTACATTCCGATACTTG

CACTCCCACCATTGCTGTATATCTCTGCTACTTGTGGTATCAAATCCGCTACTCGTAG

TGGTTTTTCCACTTGTACAAATTCTATCCCCCATGACCACCAACCCTTCTCCCGATCG

CCAGTCTCACTTGGCGGAATCGTCGACGATCATCCTCGAGATGCGGCCGCGTCGACA

TAACTTCGTATAGCATACATTATACGAAGTTATTTTCTAATTTGGACCGATAGCCGTA

TAGTCCAGTCTATCTATAAGTTCAACTAACTCGTAACTATTACCATAACATATACTTC

ACTGCCCCAGATAAGGTTCCGATAAAAAGTTGTGCAGACTAAATTTATTTCAGTCTC

CTCTTCACCACCAAAATGCCCTCCTACGAAGCGCGAGCTAACGTCCACAAGTCCGCC

TTTGCCGCCCGAGTGCTCAAGCTCGTGGCAGCCAAGAAAACCAACCTGTGTGCTTCT

CTGGATGTTACCACCACCAAGGAGCTCATTGAGCTTGCCGATAAGGTCGGACCTTAT

GTGTGCATGATCAAGACCCATATCGACATCATTGACGACTTCACCTACGCCGGAACT

GTGCTCCCCCTCAAGGAACTTGCTCTTAAGCACGGTTTCTTCCTGTTCGAGGACAGA

AAGTTCGCAGATATTGGCAACACTGTCAAGCACCAGTACAAGAACGGTGTCTACCG

-continued

AATCGCCGAGTGGTCCGATATCACCAACGCCCACGGTGTACCCGGAACCGGAATCA

TTGCTGGCCTGCGAGCTGGTGCCGAGGAAACTGTCTCTGAACAGAAGAAGGAGGAT

GTCTCTGACTACGAGAACTCCCAGTACAAGGAGTTCCTGGTCCCCTCTCCCAACGAG

AAGCTGGCCAGAGGTCTGCTCATGCTGGCCGAGCTGTCTTGCAAGGGCTCTCTGGCC

ACTGGCGAGTACTCCAAGCAGACCATTGAGCTTGCCCGATCCGACCCCGAGTTTGTG

GTTGGCTTCATTGCCCAGAACCGACCTAAGGGCGACTCTGAGGACTGGCTTATTCTG

ACCCCCGGGGTGGGTCTTGACGACAAGGGAGATGCTCTCGGACAGCAGTACCGAAC

TGTTGAGGATGTCATGTCTACCGGAACGGATATCATAATTGTCGGCCGAGGTCTGTA

CGGCCAGAACCGAGATCCTATTGAGGAGGCCAAGCGATACCAGAAGGCTGGCTGGG

AGGCTTACCAGAAGATTAACTGTTAGAGGTTAGACTATGGATATGTCATTTAACTGT

GTATATAGAGAGCGTGCAAGTATGGAGCGCTTGTTCAGCTTGTATGATGGTCAGACG

ACCTGTCTGATCGAGTATGTATGATACTGCACAACCTGATAACTTCGTATAGCATAC

ATTATACGAAGTTATCTCGAGGCGGCCGCATGGAGCGTGTGTTCTGAGTCGATGTTT

TCTATGGAGTTGTGAGTGTTAGTAGACATGATGGGTTTATATATGATGAATGAATAG

ATGTGATTTTGATTTGCACGATGGAATTGAGAACTTTGTAAACGTACATGGGAATGT

ATGAATGTGGGGGTTTTGTGACTGGATAACTGACGGTCAGTGGACGCCGTTGTTCAA

ATATCCAAGAGATGCGAGAAACTTTGGGTCAAGTGAACATGTCCTCTCTGTTCAAGT

AAACCATCAACTATGGGTAGTATATTTAGTAAGGACAAGAGTTGAGATTCTTTGGAG

TCCTAGAAACGTATTTTCGCGTTCCAAGATCAAATTAGTAGAGTAATACGGGCACGG

GAATCCATTCATAGTCTCAATTTTCCCATAGGTGTGCTACAAGGTGTTGAGATGTGG

TACAGTACCACCATGATTCGAGGTAAAGAGCCCAGAAGTCATTGATGAGGTCAAGA

AATACACAGATCTACAGCTCAATACAATGAATATCTTCTTTCATATTCTTCAGGTGA

CACCAAGGGTGTCTATTTTCCCCAGAAATGCGTGAAAAGGCGCGTGTGTAGCGTGG

AGTATGGGTTCGGTTGGCGTATCCTTCATATATCGACGAAATAGTAGGGCAAGAGAT

GACAAAAAGTATCTATATGTAGACAGCGTAGAATATGGATTTGATTGGTATAAATTC

ATTTATTGCGTGTCTCACAAATACTCTCGATAAGTTGGGGTTAAACTGGAGATGGAA

CAATGTCGATATCTCGACATATTTTGATATTTGTTAATTAA pLD137

(SEQ ID NO: 177)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

-continued

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

-continued

AGGGATTTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTTAAATTATTGGCCCGAAAATTAATCAGTGTAGACTGGATCCTC

GAGAACCATTTAATTAAGATCAGAGACCGGATGGTCTCAAGCGTCGACACCATATC

ATATAAAACTAACAATGCATTGAATTAATACGAAGACTACCCGTTGCTATCTCCACA

CCGTTATCTCCACGGTCCAAAGGCTGCTCAATGTGCTGCATACGTAACGTGGGGTGC

AACCTTGAGCACATAGTACTTTCCGAAAACCGGCGATAATTAAGTGTGCACTCCAAC

TTTTCACACTGAGCATAAAATGTGGAGAAGAAATCACACTAAAAAGTCAGGTAGAC

TGGAAAATGCGCCATGAAATAATATCTCTTGCTACAGTAATGCCCAGCATCGAGGG

GTATTGTGTCACCAACACTATAGTGGCAGCTGAAGCGCTCGTGATTGTAGTATGAGT

CTTTATTGGTGATGGGAAGAGTTCACTCAATATTCTCGTTACTGCCAAAACACCACG

GTAATCGGCCAGACACCATGGATGTAGATCACCAAGCCTGTGAATGTTATTCGAGCT

AAAATGCACATGGTTGGTGAAAGGAGTAGTTGCTGTCGAATTCCGTCGTCGCCTGAG

TCATCATTTATTTACCAGTTGGCCACAAACCCTTGACGATCTCGTATGTCCCCTCCGA

CATACTCCCGGCCGGCTGGGGTACGTTCGATAGCGCTATCGGCATCGACAAGGTTTG

GGTCCCTAGCCGATACCGCACTACCTGAGTCACAATCTTCGGAGGTTTAGTCTTCCA

CATAGCACGGGCAAAAGTGCGTATATATACAAGAGCGTTTGCCAGCCACAGATTTTC

ACTCCACACACCACATCACACATACAACCACACACATCCACAATGGAACCCGAAAC

TAAGAAGACCAAGACTGACTCCAAGAAGATTGTTCTTCTCGGCGGCGACTTCTGTGG

CCCCGAGGTGATTGCCGAGGCCGTCAAGGTGCTCAAGTCTGTTGCTGAGGCCTCCGG

CACCGAGTTTGTGTTTGAGGACCGACTCATTGGAGGAGCTGCCATTGAGAAGGAGG

GCGAGCCCATCACCGACGCTACTCTCGACATCTGCCGAAAGGCTGACTCTATTATGC

TCGGTGCTGTCGGAGGCGCTGCCAACACCGTATGGACCACTCCCGACGGACGAACC

GACGTGCGACCCGAGCAGGGTCTTCTCAAGCTGCGAAAGGACCTGAACCTGTACGC

CAACCTGCGACCCTGCCAGCTGCTGTCGCCCAAGCTCGCCGATCTCTCCCCCATCCG

AAACGTTGAGGGCACCGACTTCATCATTGTCCGAGAGCTCGTCGGAGGTATCTACTT

TGGAGAGCGAAAGGAGGATGACGGATCTGGCGTCGCTTCCGACACTGAGACTTACT

CCGTTCCTGAGGTTGAGCGAATTGCCCGAATGGCCGCCTTCCTGGCCCTTCAGCACA

ACCCCCCTCTTCCCGTGTGGTCCCTTGACAAGGCCAACGTGCTGGCCTCCTCTCGACT

TTGGCGAAAGACCGTCACCCGAGTCCTCAAGGACGAATTCCCCCAGCTGGAGCTCA

ACCACCAGCTGATCGACTCGGCCGCCATGATCCTCATCAAGCAGCCCTCCAAGATGA

ATGGTATCATCATCACCACCAACATGTTTGGCGATATCATCTCCGACGAGGCCTCCG

TCATCCCCGGTTCTCTGGGTCTGCTGCCCTCCGCCTCTCTGGCTTCTCTGCCCGACAC

CAACGAGGCGTTCGGTCTGTACGAGCCCTGTCACGGATCTGCCCCCGATCTCGGCAA

GCAGAAGGTCAACCCCATTGCCACCATTCTGTCTGCCGCCATGATGCTCAAGTTCTC

TCTTAACATGAAGCCCGCCGGTGACGCTGTTGAGGCTGCCGTCAAGGAGTCCGTCGA

-continued

GGCTGGTATCACTACCGCCGATATCGGAGGCTCCTCCTCCACCTCCGAGGTCGGAGA

CTTTGTTGCCAACAAGGTCAAGGAGCTGCTCAAGAAGGAGTAAGTCGTTTCTACGAC

GCATTGATGGAAGGAGCAAACTGACGCGCCTGCGGGTTGGTCTACCGGCAGGGTCC

GCTAGTGTATAAGACTCTATAAAAAGGGCCCAGCCCTGCTAATGAAATGATGATTTA

TAATTTACCGGTGTAGCAACCTTGACTAGAAGAAGCAGATTGGGTGTGTTTGTAGTG

GAGGACAGTGGTACGTTTTAATTAA pLD138

(SEQ ID NO: 178)

AGGCTAGGTGGAGGCTCAGTGATGATAAGTCTGCGATGGTGGATGCATGTGTCATG

GTCATAGCTGTTTCCTGTGTGAAATTGTTATCCGCTCAGAGGGCACAATCCTATTCCG

CGCTATCCGACAATCTCCAAGACATTAGGTGGAGTTCAGTTCGGCGTATGGCATATG

TCGCTGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

CTACGGGGTCTGACGCTCTATTCAACAAAGCCGCCGTCCCGTCAAGTCAGCGTAAAT

GGGTAGGGGGCTTCAAATCGTCCGCTCTGCCAGTGTTACAACCAATTAACAAATTCT

GATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGG

CAGTTCCATAGGATGGCAAGATCCTGGTATCGGTCTGCGATTCCGACTCGTCCAACA

TCAATACAACCTATTAATTTCCCCTCGTCAAAAATAAGGTTATCAAGTGAGAAATCA

CCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAA

CCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATC

AACAATATTTTCACCTGAATCAGGATATTCTTCTAATACCTGGAATGCTGTTTTCCCG

GGGATCGCAGTGGTGAGTAACCATGCATCATCAGGAGTACGGATAAAATGCTTGAT

GGTCGGAAGAGGCATAAATTCCGTCAGCCAGTTTAGTCTGACCATCTCATCTGTAAC

ATCATTGGCAACGCTACCTTTGCCATGTTTCAGAAACAACTCTGGCGCATCGGGCTT

CCCATACAATCGATAGATTGTCGCACCTGATTGCCCGACATTATCGCGAGCCCATTT

ATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGCAGACAGT

TTTATTGTTCATGATGATATATTTTTATCTTGTGCAATGTAACATCAGAGATTTTGAG

-continued
ACACAACGTGGCTTTCCCCCGCCGCTCTAGAACTAGTGGATCCAAATAAAACGAAA

GGCTCAGTCGAAAGACTGGGCCTTTCGTTTTATCTGTTGTTTGTCGCATTATACGAGA

CGTCCAGGTTGGGATACCTGAAACAAAACCCATCGTACGGCCAAGGAAGTCTCCAA

TAACTGTGATCCACCACAAGCGCCAGGGTTTTCCCAGTCACGACGTTGTAAAACGAC

GGCCAGTCATGCATAATCCGCACGCATCTGGAATAAGGAAGTGCCATTCCGCCTGA

CCTGATCCCAATATTACACCCAAGTAGCATGCATAAGCTAAAAGTAACTCGCAGCG

CACACCGTGCAGATTCATAAGTCTATGATTAATTGAACGCCAATAACCCGGCTTACT

ACAAGTACAAGTAGGTATACATAGCGGTAATGAATCATTAGAAAAATAAAAAACAA

AAAAAAACAAAACAAACTGTTGTGGATGCATCAACAGTAGTACATAGTTGTACGAT

GTACTTGTACTTGTAAAAGCAAAAATGTACAATATCTCAGGGAGCGCAACTTTTACG

TTCGAAGAACAATGTACCGCATACCGCATTCTAGATTCTGCGGAACGTCTAACCTGG

AAATACGATTTTTTATTTCTTTCATTTTTTTTGCTTCTTCAAAAGTATGGTAATTTCCT

ACCATTACAGTTGACACTGAACGAGGGGGGATTGAATTTAAGCAAAAAATTAAATC

AAAATACCTTTATGTATCCAGCCCATGTAATAAACAAAAGGATTATATAACAAGAA

ATAAATATATACCTTTAATGGATCATTAGAATAAAAATAAATACGAGAAGCACACC

AGAGAAGCTTTTTGATTGCCACTATACCGCTACTTTGGTATATCTTATTATAATTGTT

GAATTTGCAAGATAGAATGTCATTCATTGGAGAGAAATCCAAGGAATATGTGGGAT

GAAATGACTAGAAGTATGAACAATGAGAATAGTACATACTTGTACCTGTATTTCTAG

AAGAGAGAAAGACAGTTGAGTGTGTGATTCTCGTCCAATAATAATCTCAATAGTAA

CGTGTGAATAGCTGTTCTTTGATAGTTGATATTTCTCGATGACTATTTATGTTGTACA

AGGGATTTTTTTCGTTGCTGTTGATTTCGAATTAGGCAATGCAGATATCATTTATGCT

ATCCATATTTAAGATTTCCCATACGCATTTATAACATTTATTCTACATAAATTGTTAA

ATGAACGAACTGCCATTATAAATTGTTTCCTAAATAGGAAGTGTTTTTCATAAAGCA

AGTAAGTTGTCTAATAATACTAAGTAATAAAAATAAGTTCATACAATATATTTTGAG

AACATCATTTGGAGGCGGTAGATGGAGTCTGTTTATTATTAAACAATGCGAGATGAC

CCCTTAAATATTGAGAACATCAGTTGGAGGCGGCAGATGGAGTCTGTCTATTTAGCA

ATGGGACATGACTGTCAGTATCATCATATGTATATATATAATACATATAATATTATA

TAACACGATTTTTTTAAATTATTGGCCCGAAAATTAATCAGTGTAGACTGGATCCTC

GAGAACCATTTAATTAATTTCTAATTTGGACCGATAGCCGTATAGTCCAGTCTATCT

ATAAGTTCAACTAACTCGTAACTATTACCATAACATATACTTCACTGCCCCAGATAA

GGTTCCGATAAAAAGTTGTGCAGACTAAATTTATTTCAGTCTCCTCTTCACCACCAA

AATGCCCTCCTACGAAGCGCGAGCTAACGTCCACAAGTCCGCCTTTGCCGCCCGAGT

GCTCAAGCTCGTGGCAGCCAAGAAAACCAACCTGTGTGCTTCTCTGGATGTTACCAC

CACCAAGGAGCTCATTGAGCTTGCCGATAAGGTCGGACCTTATGTGTGCATGATCAA

GACCCATATCGACATCATTGACGACTTCACCTACGCCGGAACTGTGCTCCCCCTCAA

GGAACTTGCTCTTAAGCACGGTTTCTTCCTGTTCGAGGACAGAAAGTTCGCAGATAT

TGGCAACACTGTCAAGCACCAGTACAAGAACGGTGTCTACCGAATCGCCGAGTGGT

CCGATATCACCAACGCCCACGGTGTACCCGGAACCGGAATCATTGCTGGCCTGCGA

GCTGGTGCCGAGGAAACTGTCTCTGAACAGAAGAAGGAGGATGTCTCTGACTACGA

GAACTCCCAGTACAAGGAGTTCCTGGTCCCCTCTCCCAACGAGAAGCTGGCCAGAG

GTCTGCTCATGCTGGCCGAGCTGTCTTGCAAGGGCTCTCTGGCCACTGGCGAGTACT

-continued

CCAAGCAGACCATTGAGCTTGCCCGATCCGACCCCGAGTTTGTGGTTGGCTTCATTG
CCCAGAACCGACCTAAGGGCGACTCTGAGGACTGGCTTATTCTGACCCCCGGGGTG
GGTCTTGACGACAAGGGAGATGCTCTCGGACAGCAGTACCGAACTGTTGAGGATGT
CATGTCTACCGGAACGGATATCATAATTGTCGGCCGAGGTCTGTACGGCCAGAACCG
AGATCCTATTGAGGAGGCCAAGCGATACCAGAAGGCTGGCTGGGAGGCTTACCAGA
AGATTAACTGTTAGAGGTTAGACTATGGATATGTCATTTAACTGTGTATATAGAGAG
CGTGCAAGTATGGAGCGCTTGTTCAGCTTGTATGATGGTCAGACGACCTGTCTGATC
GAGTATGTATGATACTGCACAACCTGCGCTTGAGACCATCCGGTCTCTGATCTTAAT
TAA pLD139

(SEQ ID NO: 179)

TTAATTAATTCCGCTTAATGGAGTCCAAAAAGACCAACCTCTGCGCCTCGATCGACG
TGACCACAACCGCCGAGTTCCTTTCGCTCATCGACAAGCTCGGTCCCCACATCTGTC
TCGTGAAGACGCACATCGATATCATCTCAGACTTCAGCTACGAGGGCACGATTGAGC
CGTTGCTTGTGCTTGCAGAGCGCCACGGGTTCTTGATATTCGAGGACAGGAAGTTTG
CTGATATCGGAAACACCGTGATGTTGCAGTACACCTCGGGGGTATACCGGATCGCG
GCGTGGAGTGACATCACGAACGCGCACGGAGTGACTGGGAAGGGCGTCGTTGAAGG
GTTGAAACGCGGTGCGGAGGGGGTAGAAAAGGAAAGGGGCGTGTTGATGTTGGCG
GAGTTGTCGAGTAAAGGCTCGTTGGCGCATGGTGAATATACCCGTGAGACGATCGA
GATTGCGAAGAGTGATCGGGAGTTCGTGATTGGGTTCATCGCGCAGCGGGACATGG
GGGGTAGAGAAGAAGGGTTTGATTGGATCATCATGACGCCTGGTGTGGGGTTGGAT
GATAAAGGCGATGCGTTGGGCCAGCAGTATAGGACTGTTGATGAGGTGGTTCTGAC
TGGTACCGATGTGATTATTGTCGGGAGAGGGTTGTTTGGAAAAGGAAGAGACCCTG
AGGTGGAGGGAAAGAGATACAGGGATGCTGGATGGAAGGCATACTTGAAGAGAAC
TGGTCAGTTAGAATAAATATTGTAATAAATAGGTCTATATACATACACTAAGCTTCT
AGGACGTCATTGTAGTCTTCGAAGTTGTCTGCTAGTTTAGTTCTCATGATTTCGAAAA
CCAATAACGCAATGGATGTAGCAGGGATGGTGGTTAGTGCGTTCCTGACAAACCCA
GAGTACGCCGCCTCAAACCACGTCACATTCGCCCTTTGCTTCATCCGCATCACTTGCT
TGAAGGTATCCACGTACGAGTTGTAATACACCTTGAAGAACGGCTTCGTCTAGTTCG
GCATGGCAGATCATCATGCCTGCAGGAGCTCCAATTGTAATATTTCGGGAGAAATAT
CGTTGGGGTAAAACAACAGAGAGAGAGAGGGAGAGATGGTTCTGGTAGAATTATAA
TCTGGTTGTTGCAAATGCTACTGATCGACTCTGGCAATGTCTGTAGCTCGCTAGTTGT
ATGCAACTTAGGTGTTATGCATACACACGGTTATTCGGTTGAATTGTGGAGTAAAAA
TTGTCTGAGTTGTGTCTTAGCTACTGGCTGGCCCCCCGCGAAAGATAATCAAAATTA
CACTTGTGAATTTTTGCACACACACCGATTAACATTTCCCTTTTTTGTCCACCGATAC
ACGCTTGCCTCTTCTTATTTTCTCTGTGCTTCCCCCTCCTGTGACTTTTTCCACCATTG
ATATAAAATCAACTCCATTTCCCTAAAATCTCCCCAGATTCTAAAAACAACTTCTTCT
CTTCTGCTTTTCCTTATTTTTGTTATATTTATTTACCATCCCTTATTTTGAATAGTTATT
CCCCACTAACATTGTTCAAATCTTCACGACATAATGAACCCAAGGGAAAACTTCCTT
AAGTGTTTTCTGCAGTACATCCCTAACAATGCAACAAACCTCAAGTTGGTGTACACT
CAAAACAATCCACTCTATATGAGCGTGCTTAATAGCACAATCCACAACTTGCGCTTC

ACGTCAGATACTACGCCTAAGCCACTAGTGATCGTTACACCATCACACGTCAGCCAT

ATTCAAGGAACGATCCTATGTCTGAAAAAGGTCGGGTTGCAAATCAGGACTCGATC

AGGAGGGCACGATAGTGAGGGAATGAGTTACATCTCGCAAGTACCCTTCGTGATAG

TTGACTTGCGAAATATGCGGTCTATTAAAATTGACGTACATAGCCAGACCGCCTGGG

TTGAAGCAGGGGCAACCTTGGGTGAAGTTTATTACTGGGTCAATGAAAAAAACGAA

AACCTAAGTCTTGCTGCTGGATATTGCCCCACCGTTTGCGCGGGTGGTCATTTTGGA

GGCGGCGGATATGGTCCGTTGATGAGAAATTATGGACTTGCAGCAGACAATATTAT

AGATGCCCACTTGGTGAACGTTCATGGAAAGGTCTTGGACCGTAAGTCCATGGGTGA

AGATCTTTTCTGGGCCTTGAGAGGTGGTGGAGCGGAATCGTTTGGCATCATCGTTGC

CTGGAAAATTAGGTTGGTTGCGGTCCCGAAGAGTACAATGTTCTCCGTGAAGAAGAT

TATGGAAATACATGAGCTTGTCAAGTTAGTTAACAAGTGGCAAAATATCGCTTATAA

GTATGATAAAGACTTGCTTTTGATGACTCATTTTATTACGCGAAACATAACCGATAA

CCAGGGCAAGAACAAGACTGCTATTCACACGTACTTCTCCTCTGTATTTCTTGGAGG

AGTAGACTCCTTAGTTGACTTGATGAACAAGAGTTTCCCAGAATTGGGGATTAAGAA

GACAGATTGCAGACAATTATCGTGGATAGATACAATCATATTCTATAGCGGTGTCGT

CAATTACGATACTGATAATTTTAATAAAGAAATCCTCCTAGATCGTTCAGCTGGGCA

AAACGGGGCATTCAAAATTAAATTGGATTATGTGAAGAAACCAATTCCAGAGCTGG

TGTTTGTTCAGATATTGGAAAAACTTTACGAAGAAGACATTGGCGCAGGTATGTACG

CTTTGTATCCATATGGAGGCATTATGGACGAGATCTCAGAGCTGGCGATCCCCTTCC

CGCACAGAGCTGGGATACTCTACGAGCTATGGTACATCTGCTCTTGGGAGAAACAA

GAAGACAACGAGAAACATCTCAATTGGATTCGGAACATATACAACTTTATGACCCC

ATACGTATCAAAAAACCCGCGCTTAGCATACTTGAATTACAGAGACTTAGATATCGG

TATCAATGATCCTAAGAATCCTAACAATTACACCCAAGCCCGTATTTGGGGTGAGAA

ATATTTCGGCAAGAATTTTGACAGATTAGTTAAGGTCAAAACACTCGTGGACCCCAA

CAACTTTTTCCGAAACGAGCAGTCGATTCCACCACTACCCAGGCATAGACACGGAA

GAAGGGCAAAGTTGTAAGAGTGACTCTTTTGATAAGAGTCGCAAATTTGATTTCATA

AGTATATATTCATTATGTAAAGTAGTAAATGGAAAATTCATTAAAAAAAAAGCAAA

TTTCCGTTGTATGCATACTCCGAACACAAAACTAGCCCCGGAAAAACCCTTAGTTGA

TAGTTGCGAATTTAGGTCGACCATATGCGACGGGTACAACGAGAATTGTATTGAATT

GATCAAGAACATGATCTTGGTGTTACAGAACATCAAGTTCTTGGACCAGACTGAGA

ATGCACAGATATACAAGGCGTCATGTGATAAAATGGATGAGATTTATCCACAATTG

AAGAAAGAGTTTATGGAAAGTGGTCAACCAGAAGCTAAACAGGAAGAAGCAAACG

AAGAGGTGAAACAAGAAGAAGAAGGTAAATAAGTATTTTGTATTATATAACAAACA

AAGTAAGGAATACAGATTTATACAATAAATTGCCATACTAGTCACGTGAGATATCTC

ATCCATTCCCCAACTCCCAAGAAAATAAAAAAGTGAAAAATAAAATCAAACCCAAA

GATCAACCTCCCCATCATCATCGTCATCAAACCCCCAGCTCAATTCGCAATGGTTAG

CACAAAAACATACACAGAAAGGGCATCAGCACACCCCTCCAAGGTTGCCCAACGTT

TATTAATTAAAGGCTAGGTGGAGGCTCAGTGATGATAAGTCTGCGATGGTGGATGC

ATGTGTCATGGTCATAGCTGTTTCCTGTGTGAAATTGTTATCCGCTCAGAGGGCACA

ATCCTATTCCGCGCTATCCGACAATCTCCAAGACATTAGGTGGAGTTCAGTTCGGCG

TATGGCATATGTCGCTGGAAAGAACATGTGAGCAAAAGGCCAGCAAAAGGCCAGGA

-continued

ACCGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCA

CGAACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGTTACCTTC

GGAAAAAGAGTTGGTAGCTCTTGATCCGGCAAACAAACCACCGCTGGTAGCGGTGG

TTTTTTTGTTTGCAAGCAGCAGATTACGCGCAGAAAAAAAGGATCTCAAGAAGATCC

TTTGATCTTTTCTACGGGGTCTGACGCTCTATTCAACAAAGCCGCCGTCCCGTCAAGT

CAGCGTAAATGGGTAGGGGGCTTCAAATCGTCCGCTCTGCCAGTGTTACAACCAATT

AACAAATTCTGATTAGAAAAACTCATCGAGCATCAAATGAAACTGCAATTTATTCAT

ATCAGGATTATCAATACCATATTTTTGAAAAAGCCGTTTCTGTAATGAAGGAGAAAA

CTCACCGAGGCAGTTCCATAGGATGGCAAGATCCTGGTATCGGTCTGCGATTCCGAC

TCGTCCAACATCAATACAACCTATTAATTTCCCCTCGTCAAAAATAAGGTTATCAAG

TGAGAAATCACCATGAGTGACGACTGAATCCGGTGAGAATGGCAAAAGCTTATGCA

TTTCTTTCCAGACTTGTTCAACAGGCCAGCCATTACGCTCGTCATCAAAATCACTCGC

ATCAACCAAACCGTTATTCATTCGTGATTGCGCCTGAGCGAGACGAAATACGCGATC

GCTGTTAAAAGGACAATTACAAACAGGAATCGAATGCAACCGGCGCAGGAACACTG

CCAGCGCATCAACAATATTTTCACCTGAATCAGGATATTCTTCTAATACCTGGAATG

CTGTTTTCCCGGGGATCGCAGTGGTGAGTAACCATGCATCATCAGGAGTACGGATAA

AATGCTTGATGGTCGGAAGAGGCATAAATTCCGTCAGCCAGTTTAGTCTGACCATCT

CATCTGTAACATCATTGGCAACGCTACCTTTGCCATGTTTCAGAAACAACTCTGGCG

CATCGGGCTTCCCATACAATCGATAGATTGTCGCACCTGATTGCCCGACATTATCGC

GAGCCCATTTATACCCATATAAATCAGCATCCATGTTGGAATTTAATCGCGGCCTCG

AGCAAGACGTTTCCCGTTGAATATGGCTCATAACACCCCTTGTATTACTGTTTATGTA

AGCAGACAGTTTTATTGTTCATGATGATATATTTTTATCTTGTGCAATGTAACATCAG

AGATTTTGAGACACAACGTGGCTTTCCCCCGCCGCTCTAGAACTAGTGGATCCAAAT

AAAACGAAAGGCTCAGTCGAAAGACTGGGCCTTTCGTTTTATCTGTTGTTTGTCGCA

TTATACGAGACGTCCAGGTTGGGATACCTGAAACAAAACCCATCGTACGGCCAAGG

AAGTCTCCAATAACTGTGATCCACCACAAGCGCCAGGGTTTTCCCAGTCACGACGTT

GTAAAACGACGGCCAGTCATGCATAATCCGCACGCATCTGGAATAAGGAAGTGCCA

TTCCGCCTGACCT pLD19

(SEQ ID NO: 180)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

-continued

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

CTTCTGCTTTTCCTTATTTTTGTTATATTTATTTACCATCCCTTATTTTGAATAGTTATT

CCCCACTAACATTGTTCAAATCTTCACGACataATGGGTTTATCGTCAGTGTGCACTTT

TTCTTTTCAAACAAACTACCACACCCTCCTAAACCCTCACAATAATAACCCAAAAAC

CTCCTTGCTATGTTACAGACATCCAAAGACACCGATCAAGTATTCATACAACAATTT

TCCCAGTAAACATTGCTCAACGAAGTCCTTCCACTTGCAAAACAAATGCAGCGAATC

ATTGTCGATAGCTAAAAACTCGATACGTGCGGCAACCACTAACCAAACTGAGCCAC

CAGAGAGCGATAATCATTCAGTCGCCACCAAGATTTTGAACTTTGGAAAAGCCTGTT

GGAAACTTCAAAGGCCTTACACCATTATCGCATTTACCAGTTGCGCATGTGGTTTGT

TCGGGAAGGAATTATTACACAACACAAATTTGATCAGCTGGAGCCTAATGTTTAAGG

CATTTTTCTTCTTAGTTGCAATTTTGTGTATAGCTTCGTTTACAACGACCATTAATCA

GATTTACGACCTTCACATCGATCGGATCAATAAACCAGACTTGCCCCTTGCCTCTGG

GGAAATCTCTGTAAATACTGCATGGATCATGCTGATAATCGTGGCTTTGTTTGGATT

GATTATTACAATTAAGATGAAGGGGGGTCCATTATATATATTCGGGTACTGCTTCGG

CATTTTCGGTGGTATCGTTTACTCCGTCCCACCCTTTAGATGGAAACAGAACCCCAG

TACGGCCTTTCTACTCAATTTCTTGGCTCATATCATCACAAACTTCACATTCTATTAT

GCAAGCCGAGCGGCGCTTGGTTTGCCGTTCGAACTCAGACCGAGTTTTACATTTCTC

CTTGCCTTCATGAAACTGATGGGACTGGCCCTTGCATTGATCAAGGATGCGTCAGAT

GTCGAAGGCGACACTAAGTTCGGCATTCTGACGCTTGCTTCCAAGTATGGAAGTAGA

AATCTAACGCTTTTTTGTTCAGGAATAGTGCTACTTAGTTATGTTGCTGCTATACTCG

-continued

CTGGCATTATTTGGCCTCAGGCCTTCAACTCTAACGTAATGTTGTTATCCCATGCTAT

TTTGGCGTTCTGGTTGATCTTGCAAACGCGAGATTTTGCACTCACTAACTACGACCC

AGAGGCAGGAAGGCGCTTTTACGAGTTTATGTGGAAGTTGTATTATGCCGAATACTT

GGTTTATGTTTTCATTTGATAAgagTGACTCTTTTGATAAGAGTCGCAAATTTGATTTC

ATAAGTATATATTCATTATGTAAAGTAGTAAATGGAAAATTCATTAAAAAAAAAGC

AAATTTCCGTTGTATGCATACTCCGAACACAAAACTAGCCCCGGAAAAACCCTTAGT

TGATAGTTGCGAATTTAGGTCGACCATATGCGACGGGTACAACGAGAATTGTATTGA

ATTGATCAAGAACATGATCTTGGTGTTACAGAACATCAAGTTCTTGGACCAGACTGA

GAATGCACAGATATACAAGGCGTCATGTGATAAAATGGATGAGATTTATCCACAAT

TGAAGAAAGAGTTTATGGAAAGTGGTCAACCAGAAGCTAAACAGGAAGAAGCAAA

CGAAGAGGTGAAACAAGAAGAAGAAGGTAAATAAGTATTTTGTATTATATAACAAA

CAAAGTAAGGAATACAGATTTATACAATAAATTGCCATACTAGTCACGTGAGATATC

TCATCCATTCCCCAACTCCCAAGAAAATAAAAAAGTGAAAAATAAAATCAAACCCA

AAGATCAACCTCCCCATCATCATCGTCATCAAACCCCCAGCTCAATTCGCAATGGTT

AGCACAAAAACATACACAGAAAGGGCATCAGCACACCCCTCCAAGGTTGCCCAACG

TTTATTAATTAAAGGCTAGGTGGAGGCTCAGTGATGATAAGTCTGCGATGGTGGATG

CATGTGTCATGGTCATAGCTGTTTCCTGTGTGAAATTGTTATCCGCTCAGAGGGCAC

AATCCTATTCCGCGCTATCCGACAATCTCCAAGACATTAGGTGGAGTTCAGTTCGGC

GTATGGCATATGTCGCTGGAAAGAACATGTGAGCAAAAGGCCAGCAAAAGGCCAGG

AACCGTAAAAAGGCCGCGTTGCTGGCGTTTTTCCATAGGCTCCGCCCCCCTGACGAG

CATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAGCT

CACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATT

AGCAGAGCGAGGTATGTAGGCGGTGCTACAGAGTTCTTGAAGTGGTGGCCTAACTA

CGGCTACACTAGAAGAACAGTATTTGGTATCTGCGCTCTGCTGAAGCCAGTTACCTT

CGGAAAAAGAGTTGGTAGCTCTTGATCCGGCAAACAAACCACCGCTGGTAGCGGTG

GTTTTTTTGTTTGCAAGCAGCAGATTACGCGCAGAAAAAAAGGATCTCAAGAAGATC

CTTTGATCTTTTCTACGGGGTCTGACGCTCTATTCAACAAAGCCGCCGTCCCGTCAAG

TCAGCGTAAATGGGTAGGGGGCTTCAAATCGTCCGCTCTGCCAGTGTTACAACCAAT

TAACAAATTCTGATTAGAAAAACTCATCGAGCATCAAATGAAACTGCAATTTATTCA

TATCAGGATTATCAATACCATATTTTTGAAAAAGCCGTTTCTGTAATGAAGGAGAAA

ACTCACCGAGGCAGTTCCATAGGATGGCAAGATCCTGGTATCGGTCTGCGATTCCGA

CTCGTCCAACATCAATACAACCTATTAATTTCCCCTCGTCAAAAATAAGGTTATCAA

GTGAGAAATCACCATGAGTGACGACTGAATCCGGTGAGAATGGCAAAAGCTTATGC

ATTTCTTTCCAGACTTGTTCAACAGGCCAGCCATTACGCTCGTCATCAAAATCACTCG

CATCAACCAAACCGTTATTCATTCGTGATTGCGCCTGAGCGAGACGAAATACGCGAT

CGCTGTTAAAAGGACAATTACAAACAGGAATCGAATGCAACCGGCGCAGGAACACT

-continued

GCCAGCGCATCAACAATATTTTCACCTGAATCAGGATATTCTTCTAATACCTGGAAT

GCTGTTTTCCCGGGGATCGCAGTGGTGAGTAACCATGCATCATCAGGAGTACGGATA

AAATGCTTGATGGTCGGAAGAGGCATAAATTCCGTCAGCCAGTTTAGTCTGACCATC

TCATCTGTAACATCATTGGCAACGCTACCTTTGCCATGTTTCAGAAACAACTCTGGC

GCATCGGGCTTCCCATACAATCGATAGATTGTCGCACCTGATTGCCCGACATTATCG

CGAGCCCATTTATACCCATATAAATCAGCATCCATGTTGGAATTTAATCGCGGCCTC

GAGCAAGACGTTTCCCGTTGAATATGGCTCATAACACCCCTTGTATTACTGTTTATGT

AAGCAGACAGTTTTATTGTTCATGATGATATATTTTTATCTTGTGCAATGTAACATCA

GAGATTTTGAGACACAACGTGGCTTTCCCCCGCCGCTCTAGAACTAGTGGATCCAAA

TAAAACGAAAGGCTCAGTCGAAAGACTGGGCCTTTCGTTTTATCTGTTGTTTGTCGC

ATTATACGAGACGTCCAGGTTGGGATACCTGAAACAAAACCCATCGTACGGCCAAG

GAAGTCTCCAATAACTGTGATCCACCACAAGCGCCAGGGTTTTCCCAGTCACGACGT

TGTAAAACGACGGCCAGTCATGCATAATCCGCACGCATCTGGAATAAGGAAGTGCC

ATTCCGCCTGACCT pLD26

(SEQ ID NO: 181)

TTAATTAATTCCGCTTAATGGAGTCCAAAAAGACCAACCTCTGCGCCTCGATCGACG

TGACCACAACCGCCGAGTTCCTTTCGCTCATCGACAAGCTCGGTCCCCACATCTGTC

TCGTGAAGACGCACATCGATATCATCTCAGACTTCAGCTACGAGGGCACGATTGAGC

CGTTGCTTGTGCTTGCAGAGCGCCACGGGTTCTTGATATTCGAGGACAGGAAGTTTG

CTGATATCGGAAACACCGTGATGTTGCAGTACACCTCGGGGGTATACCGGATCGCG

GCGTGGAGTGACATCACGAACGCGCACGGAGTGACTGGGAAGGGCGTCGTTGAAGG

GTTGAAACGCGGTGCGGAGGGGGTAGAAAAGGAAAGGGGCGTGTTGATGTTGGCG

GAGTTGTCGAGTAAAGGCTCGTTGGCGCATGGTGAATATACCCGTGAGACGATCGA

GATTGCGAAGAGTGATCGGGAGTTCGTGATTGGGTTCATCGCGCAGCGGGACATGG

GGGGTAGAGAAGAAGGGTTTGATTGGATCATCATGACGCCTGGTGTGGGGTTGGAT

GATAAAGGCGATGCGTTGGGCCAGCAGTATAGGACTGTTGATGAGGTGGTTCTGAC

TGGTACCGATGTGATTATTGTCGGGAGAGGGTTGTTTGGAAAAGGAAGAGACCCTG

AGGTGGAGGGAAAGAGATACAGGGATGCTGGATGGAAGGCATACTTGAAGAGAAC

TGGTCAGTTAGAATAAATATTGTAATAAATAGGTCTATATACATACACTAAGCTTCT

AGGACGTCATTGTAGTCTTCGAAGTTGTCTGCTAGTTTAGTTCTCATGATTTCGAAAA

CCAATAACGCAATGGATGTAGCAGGGATGGTGGTTAGTGCGTTCCTGACAAACCCA

GAGTACGCCGCCTCAAACCACGTCACATTCGCCCTTTGCTTCATCCGCATCACTTGCT

TGAAGGTATCCACGTACGAGTTGTAATACACCTTGAAGAACGGCTTCGTCTAGTTCG

GCATGGCAGATCATCATGCCTGCAGGAGCTCCAATTGTAATATTTCGGGAGAAATAT

CGTTGGGGTAAAACAACAGAGAGAGAGAGGGAGAGATGGTTCTGGTAGAATTATAA

TCTGGTTGTTGCAAATGCTACTGATCGACTCTGGCAATGTCTGTAGCTCGCTAGTTGT

ATGCAACTTAGGTGTTATGCATACACACGGTTATTCGGTTGAATTGTGGAGTAAAAA

TTGTCTGAGTTGTGTCTTAGCTACTGGCTGGCCCCCCGCGAAAGATAATCAAAATTA

CACTTGTGAATTTTTGCACACACACCGATTAACATTTCCCTTTTTTGTCCACCGATAC

ACGCTTGCCTCTTCTTATTTTCTCTGTGCTTCCCCCTCCTGTGACTTTTTCCACCATTG

ATATAAAATCAACTCCATTTCCCTAAAATCTCCCCAGATTCTAAAAACAACTTCTTCT

-continued

CTTCTGCTTTTCCTTATTTTTGTTATATTTATTTACCATCCCTTATTTTGAATAGTTATT

CCCCACTAACATTGTTCAAATCTTCACGACataATGGCGGCAACCACTAACCAAACTG

AGCCACCAGAGAGCGATAATCATTCAGTCGCCACCAAGATTTTGAACTTTGGAAAA

GCCTGTTGGAAACTTCAAAGGCCTTACACCATTATCGCATTTACCAGTTGCGCATGT

GGTTTGTTCGGGAAGGAATTATTACACAACACAAATTTGATCAGCTGGAGCCTAATG

TTTAAGGCATTTTTCTTCTTAGTTGCAATTTTGTGTATAGCTTCGTTTACAACGACCA

TTAATCAGATTTACGACCTTCACATCGATCGGATCAATAAACCAGACTTGCCCCTTG

CCTCTGGGGAAATCTCTGTAAATACTGCATGGATCATGCTGATAATCGTGGCTTTGT

TTGGATTGATTATTACAATTAAGATGAAGGGGGGTCCATTATATATATTCGGGTACT

GCTTCGGCATTTTCGGTGGTATCGTTTACTCCGTCCCACCCTTTAGATGGAAACAGA

ACCCCAGTACGGCCTTTCTACTCAATTTCTTGGCTCATATCATCACAAACTTCACATT

CTATTATGCAAGCCGAGCGGCGCTTGGTTTGCCGTTCGAACTCAGACCGAGTTTTAC

ATTTCTCCTTGCCTTCATGAAACTGATGGGACTGGCCCTTGCATTGATCAAGGATGC

GTCAGATGTCGAAGGCGACACTAAGTTCGGCATTCTGACGCTTGCTTCCAAGTATGG

AAGTAGAAATCTAACGCTTTTTTGTTCAGGAATAGTGCTACTTAGTTATGTTGCTGCT

ATACTCGCTGGCATTATTTGGCCTCAGGCCTTCAACTCTAACGTAATGTTGTTATCCC

ATGCTATTTTGGCGTTCTGGTTGATCTTGCAAACGCGAGATTTTGCACTCACTAACTA

CGACCCAGAGGCAGGAAGGCGCTTTTACGAGTTTATGTGGAAGTTGTATTATGCCGA

ATACTTGGTTTATGTTTTCATTTGATAAgagTGACTCTTTTGATAAGAGTCGCAAATTT

GATTTCATAAGTATATATTCATTATGTAAAGTAGTAAATGGAAAATTCATTAAAAAA

AAAGCAAATTTCCGTTGTATGCATACTCCGAACACAAAACTAGCCCCGGAAAAACC

CTTAGTTGATAGTTGCGAATTTAGGTCGACCATATGCGACGGGTACAACGAGAATTG

TATTGAATTGATCAAGAACATGATCTTGGTGTTACAGAACATCAAGTTCTTGGACCA

GACTGAGAATGCACAGATATACAAGGCGTCATGTGATAAAATGGATGAGATTTATC

CACAATTGAAGAAAGAGTTTATGGAAAGTGGTCAACCAGAAGCTAAACAGGAAGA

AGCAAACGAAGAGGTGAAACAAGAAGAAGAAGGTAAATAAGTATTTTGTATTATAT

AACAAACAAAGTAAGGAATACAGATTTATACAATAAATTGCCATACTAGTCACGTG

AGATATCTCATCCATTCCCCAACTCCCAAGAAAATAAAAAAGTGAAAAATAAAATC

AAACCCAAAGATCAACCTCCCCATCATCATCGTCATCAAACCCCCAGCTCAATTCGC

AATGGTTAGCACAAAAACATACACAGAAAGGGCATCAGCACACCCCTCCAAGGTTG

CCCAACGTTTATTAATTAAAGGCTAGGTGGAGGCTCAGTGATGATAAGTCTGCGATG

GTGGATGCATGTGTCATGGTCATAGCTGTTTCCTGTGTGAAATTGTTATCCGCTCAGA

GGGCACAATCCTATTCCGCGCTATCCGACAATCTCCAAGACATTAGGTGGAGTTCAG

TTCGGCGTATGGCATATGTCGCTGGAAAGAACATGTGAGCAAAAGGCCAGCAAAAG

GCCAGGAACCGTAAAAAGGCCGCGTTGCTGGCGTTTTTCCATAGGCTCCGCCCCCCT

GACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGC

TGTGTGCACGAACCCCCCGTTCAGCCCGACCGCTGCGCCTTATCCGGTAACTATCGT

-continued

```
CTTGAGTCCAACCCGGTAAGACACGACTTATCGCCACTGGCAGCAGCCACTGGTAA

CAGGATTAGCAGAGCGAGGTATGTAGGCGGTGCTACAGAGTTCTTGAAGTGGTGGC

CTAACTACGGCTACACTAGAAGAACAGTATTTGGTATCTGCGCTCTGCTGAAGCCAG

TTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAG

AAGATCCTTTGATCTTTTCTACGGGGTCTGACGCTCTATTCAACAAAGCCGCCGTCCC

GTCAAGTCAGCGTAAATGGGTAGGGGGCTTCAAATCGTCCGCTCTGCCAGTGTTACA

ACCAATTAACAAATTCTGATTAGAAAAACTCATCGAGCATCAAATGAAACTGCAATT

TATTCATATCAGGATTATCAATACCATATTTTTGAAAAAGCCGTTTCTGTAATGAAG

GAGAAAACTCACCGAGGCAGTTCCATAGGATGGCAAGATCCTGGTATCGGTCTGCG

ATTCCGACTCGTCCAACATCAATACAACCTATTAATTTCCCCTCGTCAAAAATAAGG

TTATCAAGTGAGAAATCACCATGAGTGACGACTGAATCCGGTGAGAATGGCAAAAG

CTTATGCATTTCTTTCCAGACTTGTTCAACAGGCCAGCCATTACGCTCGTCATCAAAA

TCACTCGCATCAACCAAACCGTTATTCATTCGTGATTGCGCCTGAGCGAGACGAAAT

ACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATAC

CTGGAATGCTGTTTTCCCGGGGATCGCAGTGGTGAGTAACCATGCATCATCAGGAGT

ACGGATAAAATGCTTGATGGTCGGAAGAGGCATAAATTCCGTCAGCCAGTTTAGTCT

GACCATCTCATCTGTAACATCATTGGCAACGCTACCTTTGCCATGTTTCAGAAACAA

CTCTGGCGCATCGGGCTTCCCATACAATCGATAGATTGTCGCACCTGATTGCCCGAC

ATTATCGCGAGCCCATTTATACCCATATAAATCAGCATCCATGTTGGAATTTAATCG

CGGCCTCGAGCAAGACGTTTCCCGTTGAATATGGCTCATAACACCCCTTGTATTACT

GTTTATGTAAGCAGACAGTTTTATTGTTCATGATGATATATTTTTATCTTGTGCAATG

TAACATCAGAGATTTTGAGACACAACGTGGCTTTCCCCCGCCGCTCTAGAACTAGTG

GATCCAAATAAAACGAAAGGCTCAGTCGAAAGACTGGGCCTTTCGTTTTATCTGTTG

TTTGTCGCATTATACGAGACGTCCAGGTTGGGATACCTGAAACAAAACCCATCGTAC

GGCCAAGGAAGTCTCCAATAACTGTGATCCACCACAAGCGCCAGGGTTTTCCCAGTC

ACGACGTTGTAAAACGACGGCCAGTCATGCATAATCCGCACGCATCTGGAATAAGG

AAGTGCCATTCCGCCTGACCT
```

References including disclosure related to compartmentalization of an enzyme through signal sequences include the following, each of which is incorporated by reference herein in its entirety: Agarwal et al. 2001 "Gene isolation and characterization of two acyl CoA oxidases from soybean with broad substrate specificities and enhanced expression in the growing seedling axis." Plant Mol Biol. 2001 November; 47(4):519-31; Alconado and Juarez 2006. "Acyl-CoA oxidase activity from *Beauveria bassiana*, an entomopathogenic fungus". J Basic Microbiol. 2006; 46(6):435-43; Aizpurua-Olaizola et al. "Identification and quantification of cannabinoids in *Cannabis sativa* L. plants by high performance liquid chromatography-mass spectrometry." Anal Bioanal Chem. 2014 November; 406(29):7549-60; Backer et al. "Innovative development and validation of an HPLC/DAD method for the qualitative and quantitative determination of major cannabinoids in *cannabis* plant material." J Chromatogr B Analyt Technol Biomed Life Sci. 2009 Dec. 15; 877(32):4115-24; Bakke et al. "N-ethylmaleimide-resistant acyl-coenzyme A oxidase from *Arthrobacter ureafaciens* NBRC 12140: molecular cloning, gene expression and characterization of the recombinant enzyme." Biochim Biophys Acta. 2007 January; 1774(1):65-71; Barth and Gaillardin. "Physiology and genetics of the dimorphic fungus *Yarrowia lipolytica*." FEMS Microbiol Rev. 1997 April; 19(4):219-37; Beggah et al. "Intra- and intermolecular events direct the propeptide-mediated maturation of the *Candida albicans* secreted aspartic proteinase Sap1p." Microbiology. 2000 November; 146 (Pt 11):2765-73; Brocard and Hartig. "Peroxisome targeting signal 1: is it really a simple tripeptide?" Biochim Biophys Acta. 2006 December; 1763(12):1565-73; Brown et al. "*Aspergillus* has distinct fatty acid synthases for primary and secondary metabolism: Proc Natl Acad Sci USA. 1996 Dec. 10; 93(25):14873-7; Carbalho et al. "Designing microorganisms for heterologous biosynthesis of cannabinoids." FEMS Yeast Res. 2017 Jun. 1; 17(4); Gagne et al. "Identification of olivetolic acid cyclase from *Cannabis sativa* reveals a unique catalytic route to plant polyketides." Proc Natl Acad Sci USA. 2012 Jul. 31; 109(31):12811-6; Gajewski et al. "Engineering fungal de novo fatty acid synthesis for short chain fatty acid production." Nat Commun. 2017 Mar. 10; 8:14650; Gao et al. "Iterative integration of multiple-copy pathway genes in *Yarrowia lipolytica* for heterologous 0-carotene production". Metab Eng. 2017 May; 41:192-201; Gietz and Woods "Transformation of Yeast by Lithium Acetate/Single-Stranded Carrier DNA/Polyethylene Glycol Method". Methods Enzymol. 2002; 350:87-96; Hong et al. "Engineering *Yarrowia lipolytica* to express secretory invertase with strong FBA1IN promoter". Yeast. 2012 February; 29(2):59-72; Hooks et al. "Long-chain acyl-CoA oxidases of *Arabidopsis*." Plant J. 1999 October; 20(1):1-13; Hunkova and Fenci. "Toxic effects of fatty acids on yeast cells: dependence of inhibitory effects on fatty acid concentration." Biotechnol Bioeng. 1977 November; 19(11):1623-41; Kistler and Boz "Cellular compartmentalization of secondary metabolism" Front. Microbiology February 2015; Klionsky et al. "Intracellular sorting and processing of a yeast vacuolar hydrolase: proteinase A propeptide contains vacuolar targeting information." Mol Cell Biol. 1988 May; 8(5):2105-16; Krink-Koutsoubelis et al." Engineered Production of Short-Chain Acyl-Coenzyme A Esters in *Saccharomyces cerevisiae*." ACS Synth Biol. 2018 Apr. 20; 7(4): 1105-1115; Lametschwandtner et al. "The difference in recognition of terminal tripeptides as peroxisomal targeting signal 1 between yeast and human is due to different affinities of their receptor Pex5p to the cognate signal and to residues adjacent to it." J Biol Chem. 1998 Dec. 11; 273 (50):33635-43; Ledesma-Amaro and Nicaud. "*Yarrowia lipolytica* as a biotechnological chassis to produce usual and unusual fatty acids." Prog Lipid Res. 2016 January; 61:40-50; Liang et al. "Structure, mechanism and function of prenyltransferase." Eur J Biochem. 2002 July; 269(14): 3339-54; Lui et al. "Membrane stress caused by octanoic acid in *Saccharomyces cerevisiae*" Appl Microbiol Biotechnol. 2013 April; 97(7):3239-51; Luo et. al 2002 "The acyl-CoA oxidases from the yeast *Yarrowia lipolytica*: characterization of Aox2p." Arch Biochem Biophys. November 1; 407(1):32-8; Luo et al 2019 "Complete biosynthesis of cannabinoids and their unnatural analogues in yeast." Nature. 2019 March; 567(7746):123-126; Pamplaniyi "Identification, isolation, and functional characterization of prenyltransferases in *Cannabis sativa* "Dissertation Dortmund 2016; Reiser et. al 2009 "AoxA is a major peroxisomal long chain fattyacyl-CoA oxidase required for beta-oxidation in *A. nidulans*". Curr Genet. 2010 April; 56(2): 139-50; Setoyama et. al 1995 "Functional expression of two forms of rat acyl-CoA oxidase and their substrate specificities" December 14; 217(2):482-7; Shimiu et al. "Type III Polyketide Synthases: Functional Classification and Phylogenomics. Chembiochem. 2017 Jan. 3; 18(1):50-65; Stout et al. "The hexanoyl-CoA precursor for cannabinoid biosynthesis is formed by an acyl-activating enzyme in *Cannabis sativa* trichomes." Plant J. 2012 August; 71(3):353-65; Tan et al. "Synthetic Pathway for the Production of Olivetolic Acid in *Escherichia coli*". ACS Synth Biol. 2018 Aug. 17; 7(8):1886-1896; Taura et al. "Characterization of olivetol synthase, a polyketide synthase putatively involved in cannabinoid biosynthetic pathway." FEBS Lett. 2009 Jun. 18; 583(12):2061-6; Zirpel et al. "Production of Δ9-tetrahydrocannabinolic acid from cannabigerolic acid by whole cells of *Pichia* (Komagataella) *pastoris* expressing Δ9-tetrahydrocannabinolic acid synthase from *Cannabis sativa* L." Biotechnol Lett. 2015 September; 37(9):1869-75; Zirpel et al. "Optimization of Δ9-tetrahydrocannabinolic acid synthase production in Komagataella phaffii via post-translational bottleneck identification." J Biotechnol. 2018 Apr. 20; 272-273:40-47; Zirpel "Recombinant Expression and Functional Characterization of Cannabinoid Producing Enzymes in Komagataella phaffii" Dissertation Dortmund 2018; Yang et al "Structural basis for olivetolic acid formation by a polyketide cyclase from *Cannabis sativa*." FEBS J. 2016 March; 283(6):1088-106; U.S. Pat. Nos. 7,851,199; 8,884,100; 9,546,362; 9,611,460; 9,765,308; 9,822,384; 10,059,971; 10,287,557; U.S. Pat. Publ. No. 2014/0228586 A1; U.S. Pat. Publ. No. 2016/0010126 A1; U.S. Pat. Publ. No. 2016/0298151 A1; U.S. Pat. Publ. No. 2017/0211049 A1; U.S. Pat. Publ. No. 2018/0073043 A1; U.S. Pat. Publ. No. 2018/0155748 A1; U.S. Pat. Publ. No. 2018/0334692A1; PCT Publ. No. WO2017139496A1; PCT Publ. No. WO2018200888A1; PCT Publ. No. WO2018219995A1; PCT Publ. No. WO2018148849A1; PCT Publ. No. WO2018148848A1; and PCT Publ. No. WO2019071000A1.

Exemplary Methods, Microorganisms, and Compositions (e.g., Polyketides)

Method 1: A method, comprising: providing a microorganism selected from the group consisting of a fungi and a yeast, wherein the microorganism has been modified to produce a polyketide in fermentation, wherein at least one of the enzymes that mediate the polyketide production have been targeted to at least one compartment within a secretory pathway resulting in an increase in secretion of the polyketide.

Method 2: Method 1, wherein the polyketide is a cannabinoid.

Method 3: Method 2, wherein the polyketide is a cannabinoid that is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Method 4: Method 1, wherein the polyketide is olivetolic acid.

Method 5: Method 1, wherein the microorganism is a yeast.

Method 6: Method 5, wherein the yeast is from a genus selected from the group consisting of *Candida, Arxula, Pichia, Scheffersomyces, Kluyveromyces, Saccharomyces, Yarrowia*, or *Schizosaccharomyces.*

Method 7: Method 5, wherein the yeast is a *Candida viswanathii.*

Method 8: Method 5, wherein the yeast is *Arxula adeninivorans.*

Method 9: Method 5, wherein the yeast is *Yarrowia lipolytica.*

Method 10: Method 1, wherein the microorganism is a fungi.

Method 11: Method 10, wherein the fungi is from a genus selected from the group consisting of *Aspergillus, Trichoderma* or *Myceliophthora.*

Method 12: Method 10, wherein the fungi is *Aspergillus niger.*

Method 13: Method 10, wherein the fungi is *Aspergillus terreus.*

Method 14: Method 10, wherein the fungi is *Trichoderma harzianum.*

Method 15: Method 10, wherein the fungi is *Myceliophthora thermophila.*

Method 16: Method 1, wherein the compartment within the secretory pathway is an endoplasmic reticulum.

Method 17: Method 1, wherein the compartment within the secretory pathway is a Golgi apparatus.

Method 18: Method 1, wherein the compartment within the secretory pathway is a vacuole.

Method 19: Method 1, wherein the compartment within the secretory pathway is an endosome.

Method 20: Method 1, wherein the enzyme is removed of its endogenous amino-terminal localization sequence and/or carboxyl-terminal localization sequence.

Method 21: Method 16, whereby the enzyme has been modified with the N-terminal addition of the N-terminal 24 amino acids (MMWKFLIAIGHLIFSYCCNAQLLDS) from OST1 and a C-terminal addition of the amino acids HDEL to localize the enzyme to the endoplasmic reticulum.

Method 22: Method 18, whereby the enzyme has been modified by an N-terminal addition of N-terminal 73 amino acids (MGITNETQALLGGDSLSCLNKKKSNTKRNL-SYLLNIITVSfIAYLCFFATHNHHNDSGIPK VDPHKK-KNIIMM) of PHO8 to localize the enzyme to the vacuole.

Method 23: Method 18, whereby the enzyme has been modified with the N-terminal fusion with Sna4 to localize the enzyme to the vacuole.

Method 24: Method 18, whereby the enzyme has been modified with the N-terminal addition of N-terminal 92 amino acids (MQLSLSVLSTVATALLSLTTAVDAK-SHNIKLSKLSNEETLDASTFQEYTSSLANKYMNL FNAAHGNPTSFGLQHVLSNQEAEVPFVTPQKGG) from vacuolar aspartic protease to localize the enzyme to the vacuole.

Method 25: Method 19, whereby the enzyme has been modified with the N-terminal addition of N-terminal 305 amino acids from DOA4 (MTLLLKPTSELDAGSRKIIER-IQSNSPTFQHLFDLLLNLLPFFDKTVSLLSI-GYCDYEVA YVTYQTCI-QVVGLMKPKTNSLNQDIFKGVQLQTRKRASTFKAILSYFAE-PETQEEDPLLN RFKSLSGGGSKTKSSQDEVFHEWITS-SELQRLSSKKVLLIDFRPRKDYLNNHIKYKDLV HIEPTQLETLLDSASDQDLETLVKKSAPYDQYHI-FLERHKYDLIVVYNYNYGSESTDRLL GIIDVV-SKPNPFTKLITILMNNKYIS-SRLKVKPLFLSGGVLNWYKTFGIEYLERTLVQNGV AHT) to localize the enzyme to an endosomal compartment.

Method 26: Method 17, whereby the enzyme has been modified with the N-terminal addition of N-terminal 81 amino acids of beta-galactosyltransferase (MRLREPIIS-GSAAMPGASLQRACRIIVAVCALIILGVTLVYY-LAGRDLSRLPQLVGVS TPLQGGSN-SAAAIGQSSGELRTGG) to localize the enzyme to a Golgi compartment.

Method 27: Method 17, whereby the enzyme has been modified with N-terminal 34 amino acids of rat liver alpha-2,6-sialyltransferase (MIHTNLKKKFSLFILVFLLFAV-ICVWKKGSDYEA) to localize the enzyme to a Golgi compartment.

Method 28: Method 16 whereby the enzyme has been modified the N-terminal addition of the N-terminal 31 amino acids (MKFGVLFSVFAAIVSALPLQEGPLNKRAYPS) from glucoamylase and a C-terminal addition of the amino acids HDEL to localize the enzyme to the endoplasmic reticulum.

Method 29: Method 1, wherein the fermentation uses a fatty acid and/or sugar as a carbon source.

Method 30: Method 1, wherein the fermentation uses dextrose or sucrose as a carbon source.

Method 31: Method 1, wherein the enzyme is prenyltransferase.

Method 32: Method 1, wherein the enzyme is cannabidiolic acid synthase.

Method 33: Method 32, wherein the microorganism has been modified to express the protein sequence SEQ. ID *53, 54, 55 or 56.

Method 34: Method 1, wherein the enzyme is tetrahydrocannabidiolic acid synthase.

Method 35: Method 34, wherein the microorganism has been modified to express the protein sequence SEQ. ID *58, 59, 60 or 61.

Method 36: Method 1, wherein the enzyme is cannabichromenic acid synthase.

Microorganism 37: A microorganism selected from the group consisting of a fungi and a yeast, wherein the microorganism has been modified to produce a polyketide in fermentation, wherein at least one of the enzymes that mediate the polyketide production have been targeted to at least one compartment within a secretory pathway resulting in an increase in secretion of the one polyketide.

Microorganism 38: Microorganism 37, wherein the microorganism is a yeast.

Microorganism 39: Microorganism 38, wherein the yeast is from a genus selected from the group consisting of *Candida, Arxula, Pichia, Scheffersomyces, Kluyveromyces, Saccharomyces, Yarrowia*, or *Schizosaccharomyces.*

Microorganism 40: Microorganism 38, wherein the yeast is a *Candida viswanathii.*

Microorganism 41: Microorganism 38, wherein the yeast is *Arxula adeninivorans.*

Microorganism 42: Microorganism 38, wherein the yeast is *Yarrowia lipolytica.*

Microorganism 43: Microorganism 37, wherein the microorganism is a fungi.

Microorganism 44: Microorganism 43, wherein the fungi is from a genus selected from the group consisting of *Aspergillus, Trichoderma* or *Myceliophthora.*

Microorganism 45: Microorganism 43, wherein the fungi is *Aspergillus niger.*

Microorganism 46: Microorganism 43, wherein the fungi is *Aspergillus terreus.*

Microorganism 47: Microorganism 43, wherein the fungi is *Trichoderma harzianum.*

Microorganism 48: Microorganism 43, wherein the fungi is *Myceliophthora thermophila.*

Microorganism 49: Microorganism 37, wherein the polyketide is a cannabinoid.

Microorganism 50: Microorganism 37, wherein the polyketide is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Microorganism 51: Microorganism 37, wherein the polyketide is olivetolic acid.

Microorganism 52: Microorganism 37, wherein the compartment within the secretory pathway is an endoplasmic reticulum.

Microorganism 53: Microorganism 37, wherein the compartment within the secretory pathway is a Golgi apparatus.

Microorganism 54: Microorganism 37, wherein the compartment within the secretory pathway is a vacuole.

Microorganism 55: Microorganism 37, wherein the compartment within the secretory pathway is an endosome.

Microorganism 56: Microorganism 37, wherein the enzyme is removed of its endogenous amino-terminal localization sequence and/or carboxyl-terminal localization sequence.

Microorganism 57: Microorganism 52, whereby the enzyme has been modified with the N-terminal addition of the N-terminal 24 amino acids (MMWKFLIAIGLIFSYCCNAQLLDS) from OST1 and a C-terminal addition of the amino acids HDEL to localize the enzyme to the endoplasmic reticulum.

Microorganism 58: Microorganism 54, whereby the enzyme has been modified by an N-terminal addition of N-terminal 73 amino acids (MGITNETQALLGGDSLSCLNKKKSNTKRNLSYLLNIITVSIIAYLCFFATHNHHNDSGIPK VDPHKKKNIMM) of PHO8 to localize the enzyme to the vacuole.

Microorganism 59: Microorganism 54, whereby the enzyme has been modified with the N-terminal fusion with Sna4 to localize the enzyme to the vacuole.

Microorganism 60: Microorganism 54, whereby the enzyme has been modified with the N-terminal addition of N-terminal 92 amino acids (MQLSLSVLSTVATALLSLTTAVDAKSHNIKLSKLSNEETLDASTFQEYTSSLANKYMNL FNAAHGNPTSFGLQHVLSNQEAEVPFVTPQKGG) from vacuolar aspartic protease to localize the enzyme to the vacuole.

Microorganism 61: Microorganism 55, whereby the enzyme has been modified with the N-terminal addition of N-terminal 305 amino acids from DOA4 (MTLLLIKPTSELDATSRKIIERIQSNSPTFQI-ILFDLLLNLLPFFDKTVSLLGSIGYCDYEVA YVTYQTCIQVVGLMKPKTNSLNQDIFKGVQLQTRKRASTFKAILSYFAEPETQEEDPLLN RFKSLSGGGSKTKSSQDEVFHEWITSSELQRELSSKKVIILDFRPRKDYLNNHIKYKDLV HIEPTQLETLLDSASDQDLETLVKKSAPYDQYHIFLERHKYDLIVVYNYNYGSESTDRLL GIIDVVSKPNPFTKLITILMNNKYISSRLKVKPLFLSGGVLNWYKTFGIEYLERTLVQNGV AHT) to localize the enzyme to an endosomal compartment.

Microorganism 62: Microorganism 53, whereby the enzyme has been modified with the N-terminal addition of N-terminal 81 amino acids of beta-galactosyltransferase (MRLREPLLSGSAAMPGASLQRACRLLVAVCALHLGVTLVYYLAGRDLSRLPQLVGVS TPLQGGSNSAAAIGQSSGELRTGG) to localize the enzyme to a Golgi compartment.

Microorganism 63: Microorganism 53, whereby the enzyme has been modified with N-terminal 34 amino acids of rat liver alpha-2,6-sialyltransferase (MIHTNLKKKFSLFILVFLLFAVICVWKKGSDYEA) to localize the enzyme to a Golgi compartment.

Microorganism 64: Microorganism 52, whereby the enzyme has been modified the N-terminal addition of the N-terminal 31 amino acids (MKFGVLFSVFAAIVSALPLQEGPLNKRAYPS) from glucoamylase and a C-terminal addition of the amino acids HDEL to localize the enzyme to the endoplasmic reticulum.

Microorganism 65: Microorganism 37, wherein the fermentation uses a fatty acid and/or sugar as a carbon source.

Microorganism 66: Microorganism 37, wherein the fermentation uses dextrose or sucrose as a carbon source.

Microorganism 67: Microorganism 37, wherein the enzyme is prenyltransferase.

Microorganism 68: Microorganism 37, wherein the enzyme is cannabidiolic acid synthase.

Microorganism 69: Microorganism 68, wherein the microorganism has been modified to express the protein sequence SEQ. ID *53, 54, 55 or 56.

Microorganism 70: Microorganism 37, wherein the enzyme is tetrahydrocannabidiolic acid synthase.

Microorganism 71: Microorganism 70, wherein the microorganism has been modified to express the protein sequence SEQ. ID *58, 59, 60 or 61.

Microorganism 72: Microorganism 37, wherein the enzyme is cannabichromenic acid synthase.

Polyketide 73: A polyketide produced by any one of Methods 1-36.

Polyketide 74: A polyketide produced by any one of Microorganisms 37-72.

Method 75: A method, comprising: providing as a feedstock at least one of a fatty acid, vegetable oil, or an alkane to a microorganism which has a modified beta-oxidation pathway, wherein the beta-oxidation pathway has been modified by a modification to produce a fatty acid or a fatty acid-CoA that is a substrate for an acyl-CoA synthase or a polyketide synthase, respectively, wherein the microorganism produces a polyketide.

Method 76: Method 75, wherein at least one of an acyl-coA oxidase, enoyl CoA hydratase, 3-hydroxyacyl-CoA dehydrogenase, B-ketothiolase or thiolase has been modified and/or replaced in the microorganism.

Method 77: Method 75, wherein the modification is one or more of a deletion, a mutation, a replacement, or an expression of one of acyl-coA oxidase, enoyl CoA hydratase, 3-hydroxyacyl-CoA dehydrogenase, B-ketholiase, or thiolase.

Method 78: Method 75, wherein the modification is of acyl-coA oxidase.

Method 79: Method 75, wherein the microorganism has been modified to include wherein the microorganism has been modified to express the protein sequence SEQ. ID 10.

Method 80: Method 75, wherein the feedstock is a fatty acid or a vegetable oil.

Method 81: Method 80, wherein the fatty acid is selected from the group consisting of oleic acid, palmitic acid, stearic acid, linoleic acid, alpha-linolenic acid, palmitoleic acid, tridecanoic acid, pentadecanoic acid, and nonanoic acid.

Method 82: Method 80, wherein the vegetable oil is selected from the group consisting of palm oil, soybean oil, corn oil, canola oil, coconut oil, sunflower oil, olive oil, palm kernel oil, lard, castor oil, peanut oil, sesame oil, grapeseed, avocado oil, and flaxseed oil.

Method 83: Method 75, wherein the fatty acid is in a form of a methyl ester or ethyl ester.

Method 84: Method 75, wherein the alkane is selected from the group consisting of octadecane, heptadecane, hexadecane, pentadecane, tetradecane, tridecane, dodecane, and undecane.

Method 85: Method 75, wherein the polyketide synthase is a tetraketide synthase.

Method 86: Method 75, wherein the polyketide synthase is TKS1 or TKS1p.

Method 87: Method 75, wherein the polyketide synthase is targeted to the peroxisome.

Method 88: Method 75, wherein an olivetolic acid synthase is expressed.

Method 89: Method 88, wherein the olivetolic acid synthase is CsOAC1.

Method 90: Method 88, where the olivetolic acid synthase is targeted to the peroxisome.

Method 91: Method 75, wherein an endogenous acyl-coA oxidase has been mutated.

Method 92: Method 75, wherein an endogenous acyl-coA oxidase has been replaced with a non-native acyl-coA oxidase.

Method 93: Method 92, wherein the non-native acyl-coA oxidase is selected from the group consisting of ACO1P, ACO2, ACO3, ACO4, ACO5, ACO6, ACO7, ACO8, ACO9 and ACO10.

Method 94: Method 75, wherein the polyketide is a cannabinoid.

Method 95: Method 75, wherein the polyketide is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Method 96: Method 75, wherein the polyketide is olivetolic acid.

Method 97: Method 75, wherein a polyketide synthase is expressed.

Method 98: Method 97, wherein the polyketide synthase is a tetraketide synthase.

Method 99: Method 97, wherein the polyketide synthase is TKS1 or TKS1p

Method 100: Method 97, wherein the polyketide synthase is targeted to the peroxisome.

Method 101: Method 75, wherein an olivetolic acid synthase is expressed.

Method 102: Method 101, wherein the olivetolic acid synthase is CsOAC1.

Method 103: Method 101, where the olivetolic acid synthase is targeted to the peroxisome.

Method 104: Method 75, wherein beta-oxidation has been modified.

Method 105: Method 104, wherein an endogenous acyl-coA oxidase has been mutated.

Method 106: Method 104, wherein an endogenous acyl-coA oxidase has been replaced with a non-native acyl-coA oxidase.

Method 107: Method 106, wherein the non-native acyl-coA oxidase is selected from the group consisting of ACO1P, ACO2, ACO3, ACO4, ACO5, ACO6, ACO7, ACO8, ACO9, and ACO10.

Method 108: Method 75, wherein the microorganism is a yeast.

Method 109: Method 108, wherein the yeast is from a genus selected from the group consisting of *Candida, Arxula, Pichia, Scheffersomyces, Kluyveromyces, Saccharomyces, Yarrowia*, or *Schizosaccharomyces.*

Method 110: Method 108, wherein the yeast is a *Candida viswanathii.*

Method 111: Method 108, wherein the yeast is *Arxula adeninivorans.*

Method 112: Method 108, wherein the yeast is *Yarrowia lipolytica.*

Method 113: Method 75, wherein the microorganism is a fungi.

Method 114: Method 113, wherein the fungi is from a genus selected from the group consisting of *Aspergillus, Trichoderma* or *Myceliophthora.*

Method 115: Method 113, wherein the fungi is *Aspergillus niger.*

Method 116: Method 113, wherein the fungi is *Aspergillus terreus.*

Method 117: Method 113, wherein the fungi is *Trichoderma harzianum.*

Method 118: Method 113, wherein the fungi is *Myceliophthora thermophila.*

Microorganism 119: A microorganism, wherein the microorganism is a yeast or a fungi having a modified beta-oxidation pathway, wherein the beta-oxidation pathway has been modified by a modification to produce a fatty acid or a fatty acid-CoA that is a substrate for an acyl-CoA synthase or a polyketide synthase, respectively, wherein the microorganism produces a polyketide.

Microorganism 120: Microorganism 119, wherein the microorganism is a yeast.

Microorganism 121: Microorganism 120, wherein the yeast is from a genus selected from the group consisting of *Candida, Arxula, Pichia, Scheffersomyces, Kluyveromyces, Saccharomyces, Yarrowia*, or *Schizosaccharomyces.*

Microorganism 122: Microorganism 120, wherein the yeast is a *Candida viswanathii.*

Microorganism 123: Microorganism 120, wherein the yeast is *Arxula adeninivorans.*

Microorganism 124: Microorganism 120, wherein the yeast is *Yarrowia lipolytica.*

Microorganism 125: Microorganism 119, wherein the microorganism is a fungi.

Microorganism 126: Microorganism 125, wherein the fungi is from a genus selected from the group consisting of *Aspergillus, Trichoderma* or *Myceliophthora.*

Microorganism 127: Microorganism 125, wherein the fungi is *Aspergillus niger.*

Microorganism 128: Microorganism 125, wherein the fungi is *Aspergillus terreus.*

Microorganism 129: Microorganism 125, wherein the fungi is *Trichoderma harzianum.*

Microorganism 130: Microorganism 125, wherein the fungi is *Myceliophthora thermophila.*

Microorganism 131: Microorganism 119, wherein at least one of an acyl-coA oxidase, enoyl CoA hydratase, 3-hydroxyacyl-CoA dehydrogenase, B-ketholiase or thiolase has been modified and/or replaced in the microorganism.

Microorganism 132: Microorganism 119, wherein the modification is one or more of a deletion, a mutation, a replacement, or an expression of one of acyl-coA oxidase, enoyl CoA hydratase, 3-hydroxyacyl-CoA dehydrogenase, B-ketholiase, or thiolase.

Microorganism 133: Microorganism 119, wherein the modification is of acyl-coA oxidase.

Microorganism 134: Microorganism 119, wherein the microorganism has been modified to include SEQ. ID 10.

Microorganism 135: Microorganism 119, wherein the polyketide synthase is a tetraketide synthase.

Microorganism 136: Microorganism 119, wherein the polyketide synthase is TKS1 or TKS1p.

Microorganism 137: Microorganism 119, wherein the polyketide synthase is targeted to the peroxisome.

Microorganism 138: Microorganism 119, wherein an olivetolic acid synthase is expressed.

Microorganism 139: Microorganism 138, wherein the olivetolic acid synthase is CsOAC1.

Microorganism 140: Microorganism 119, where the olivetolic acid synthase is targeted to the peroxisome.

Microorganism 141: Microorganism 119, wherein an endogenous acyl-coA oxidase has been mutated.

Microorganism 142: Microorganism 119, wherein an endogenous acyl-coA oxidase has been replaced with a non-native acyl-coA oxidase.

Microorganism 143: Microorganism 142, wherein the non-native acyl-coA oxidase is selected from the group consisting of ACO1P, ACO2, ACO3, ACO4, ACO5, ACO6, ACO7, ACO8, ACO9, and ACO10.

Microorganism 144: Microorganism 119, wherein the polyketide is a cannabinoid.

Microorganism 145: Microorganism 119, wherein the polyketide is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Microorganism 146: Microorganism 119, wherein the polyketide is olivetolic acid.

Polyketide 147: A polyketide produced by any one of Methods 75-118.

Polyketide 148: A polyketide produced by any one of Microorganisms 119-146.

Method 149: A method, comprising: providing a microorganism that has been modified to produce a polyketide; and providing the microorganism with a C5-11 fatty acid ester in fermentation to yield a corresponding C5-9 fatty acid, wherein the C5-9 fatty acid is activated by an Acyl-CoA synthase and is used as a substrate for a polyketide synthase, from which the polyketide is obtained.

Method 150: Method 149, wherein the microorganism has been genetically modified.

Method 151: Method 149, wherein the polyketide is a cannabinoid.

Method 152: Method 151, wherein the cannabinoid is selected from the group consisting of cannabigerolic acid, Δ9-tetrahydrocannabinolic acid, cannabidiolic acid, cannabichromenic acid, cannabigerovarinic acid, tetrahydrocannabivarin acid, cannabidivarinic acid, and cannabichromevarinic acid.

Method 153: Method 149, wherein the polyketide is olivetolic acid.

Method 154: Method 149, wherein the microorganism is a yeast.

Method 155: Method 154, wherein the yeast is from a genus selected from the group consisting of *Candida, Arxula, Pichia, Scheffersomyces, Kluyveromyces, Saccharomyces, Yarrowia*, or *Schizosaccharomyces.*

Method 156: Method 154, wherein the yeast is a *Candida viswanathii.*

Method 157: Method 154, wherein the yeast is *Arxula adeninivorans.*

Method 158: Method 154, wherein the yeast is *Yarrowia lipolytica.*

Method 159: Method 149, wherein the microorganism is a fungi.

Method 160: Method 159, wherein the fungi is from a genus selected from the group consisting of *Aspergillus, Trichoderma* or *Myceliophthora.*

Method 162: Method 159, wherein the fungi is *Aspergillus niger.*

Method 163: Method 159, wherein the fungi is *Aspergillus terreus.*

Method 164: Method 159, wherein the fungi is *Trichoderma harzianum.*

Method 164: Method 159, wherein the fungi is *Myceliophthora thermophila.*

Method 165: Method 159, wherein the $C_{5-11}$ fatty acid ester is a $C_6$ fatty acid ester.

Method 166: Method 159, wherein the $C_{5-11}$ fatty acid ester is an ester of an acid selected from the group consisting of pentanoic acid, hexanoic acid, heptanoic acid, octanoic acid, nonanoic acid, decanoic acid, and undecanoic acid.

Method 167: Method 159, wherein the $C_{5-11}$ fatty acid ester is an ester selected from the group consisting of methyl ester, ethyl ester, and geranyl ester.

Polyketide 168: A polyketide produced by any one of Methods 149-167.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction ‘or’ should not be read as requiring mutual exclusivity among that group, but rather should be read as ‘and/or’ unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article ‘a’ or ‘an’ does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases ‘at least one’ and “one or more’ to introduce claim recitations. However, the use of such phrases should not be construed to imply that the introduction of a claim recitation by the indefinite articles ‘a’ or ‘an’ limits any particular claim containing such introduced claim recitation to embodiments containing only one such recitation, even when the same claim includes the introductory phrases ‘one or more’ or ‘at least one’ and indefinite articles such as ‘a’ or ‘an’ (e.g., ‘a’ and/or ‘an’ should typically be interpreted to mean ‘at least one’ or ‘one or more’); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of ‘two recitations,’ without other modifiers, typically means at least two recitations, or two or more recitations). Furthermore, in those instances where a convention analogous to ‘at least one of A, B, and C, etc.’ is used, in general such a construction is intended in the sense one having skill in the art would understand the convention (e.g., ‘a system having at least one of A, B, and C’ would include but not be limited to systems that have A alone, B alone, C alone, A and B together, A and C together, B and C together, and/or A, B, and C together, etc.). In those instances where a convention analogous to ‘at least one of A, B, or C, etc.’ is used, in general such a construction is intended in the sense one having skill in the art would understand the convention (e.g., ‘a system having at least one of A, B, or C’ would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase ‘A or B’ will be understood to include the possibilities of ‘A’ or ‘B’ or ‘A and B.’

All numbers expressing quantities of ingredients, reaction conditions, and so forth used in the specification are to be understood as being modified in all instances by the term ‘about.’ Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of producing a fatty acyl-CoA in a peroxisome, the method comprising:

providing a fatty acid to a genetically modified microorganism, wherein the genetically modified organism is a yeast or a fungus, wherein the microorganism comprises a biosynthetic enzyme targeted to the peroxisome, wherein the biosynthetic enzyme is capable of catabolizing the fatty acid into the fatty acyl-CoA;

culturing the microorganism under conditions sufficient to produce the fatty acyl-CoA in the peroxisome; and isolating the fatty acyl-CoA.

2. The method of claim 1, wherein the fatty acyl-CoA is acetyl-CoA, malonyl-CoA, or hexanoyl-CoA.

3. The method of claim 1, wherein the yeast is from a genus selected from the group consisting of *Candida, Arxula, Pichia, Scheffersomyces, Kluyveromyces, Saccharomyces, Yarrowia*, or *Schizosaccharomyces.*

4. The method of claim 1, wherein the fungus is *Aspergillus parasiticus, Aspergillus nidulans*, Thraustochytrium, Schizochytrium, *Rhizopus arrhizus, Rhizopus oryzae*, or *Rhizopus nigricans.*

5. The method of claim 1, wherein the biosynthetic enzyme is a fatty acyl-CoA synthetase, fatty acyl activating enzyme, acyl-CoA oxidase, acyl-CoA thioesterase, hexanoyl-CoA synthetase, acetyl-CoA carboxylase, enoyl-CoA hydratase, 3-hydroxyacyl-CoA dehydrogenase, beta-ketothiolase, thiolase, acyl-CoA synthase, cannabidiolic acid synthase, tetrahydrocannabidiolic acid, olivetolic acid synthase, or polyketide synthase.

6. The method of claim 5, wherein the polyketide synthase is a Type III polyketide synthase.

7. The method of claim 6, wherein the Type III polyketide synthase is tetraketide synthase, TKS1, or TKS1p.

8. The method of claim 1, wherein the biosynthetic enzyme comprises a peroxisomal targeting sequence.

9. The method of claim 8, wherein the peroxisomal targeting sequence has a consensus sequence of [S/A/H/C/E/P/Q/V]-[K/R/H/Q]-[L/F] as set forth in SEQ ID NO: 7, or GRRAKL as set forth in SEQ ID NO: 6.

10. The method of claim 1, wherein the enzyme is removed of its endogenous amino-terminal localization sequence and/or carboxyl-terminal localization sequence.

11. A genetically modified microorganism, comprising a biosynthetic enzyme targeted to a peroxisome in the microorganism, wherein the genetically modified microorganism is a yeast or a fungus, wherein the biosynthetic enzyme is capable of catabolizing a fatty acid into a fatty acyl-CoA.

12. The genetically modified microorganism of claim 11, wherein the yeast is from a genus selected from the group consisting of *Candida, Arxula, Pichia, Scheffersomyces, Kluyveromyces, Saccharomyces, Yarrowia*, or *Schizosaccharomyces.*

13. The genetically modified microorganism of claim 11, wherein the fungus is *Aspergillus parasiticus, Aspergillus nidulans*, Thraustochytrium, Schizochytrium, *Rhizopus arrhizus, Rhizopus oryzae*, or *Rhizopus nigricans*.

14. The genetically modified microorganism of claim 11, wherein the biosynthetic enzyme is a fatty acyl-CoA synthetase, fatty acyl activating enzyme, acyl-CoA oxidase, acyl-CoA thioesterase, hexanoyl-CoA synthetase, acetyl-CoA carboxylase, enoyl-CoA hydratase, 3-hydroxyacyl-CoA dehydrogenase, beta-ketothiolase, thiolase, acyl-CoA synthase, cannabidiolic acid synthase, tetrahydrocannabidiolic acid, olivetolic acid synthase, or polyketide synthase.

15. The genetically modified microorganism of claim 11, wherein the biosynthetic enzyme comprises a peroxisomal targeting sequence.

16. The genetically modified microorganism of claim 15, wherein the peroxisomal targeting sequence has a consensus sequence of [S/A/H/C/E/P/Q/V]-[K/R/H/Q]-[L/F] as set forth in SEQ ID NO: 7, or GRRAKL as set forth in SEQ ID NO: 6.

17. The genetically modified microorganism of claim 11, wherein the microorganism is capable of producing in the peroxisome a fatty acyl-CoA.

18. The genetically modified microorganism of claim 17, wherein the fatty acyl-CoA is acetyl-CoA, malonyl-CoA, or hexanoyl-CoA.

19. The genetically modified microorganism of claim 11, wherein the enzyme is removed of its endogenous amino-terminal localization sequence and/or carboxyl-terminal localization sequence.

* * * * *

SEQUENCE LISTING

```
Sequence total quantity: 182
SEQ ID NO: 1            moltype = AA  length = 22
FEATURE                 Location/Qualifiers
source                  1..22
                        mol_type = protein
                        organism = Saccharomyces cerevisiae
SEQUENCE: 1
MFSLKALLPL ALLLVSANQV AA                                          22

SEQ ID NO: 2            moltype = AA  length = 54
FEATURE                 Location/Qualifiers
source                  1..54
                        mol_type = protein
                        organism = Saccharomyces cerevisiae
SEQUENCE: 2
KVHKAKIYKH ELSDEMKEVT FEQHLAHLGQ KYLTQFEKAN PEVVFSREHP FFTE        54

SEQ ID NO: 3            moltype = AA  length = 18
FEATURE                 Location/Qualifiers
source                  1..18
                        mol_type = protein
                        organism = Homo sapiens
SEQUENCE: 3
```

```
MVRMVPVLLS LLLLLGPA                                                18

SEQ ID NO: 4            moltype = AA  length = 19
FEATURE                 Location/Qualifiers
source                  1..19
                        mol_type = protein
                        organism = Kluyveromyces marxianus
SEQUENCE: 4
MLFSNTLLIA AASALLAEA                                               19

SEQ ID NO: 5            moltype = AA  length = 19
FEATURE                 Location/Qualifiers
source                  1..19
                        mol_type = protein
                        organism = Saccharomycopsis fibuligera
SEQUENCE: 5
MKFGVLFSVF AAIVSALPA                                               19

SEQ ID NO: 6            moltype = AA  length = 6
FEATURE                 Location/Qualifiers
source                  1..6
                        mol_type = protein
                        organism = Saccharomyces cerevisiae
SEQUENCE: 6
GRRAKL                                                             6

SEQ ID NO: 7            moltype =   length =
SEQUENCE: 7
000

SEQ ID NO: 8            moltype =   length =
SEQUENCE: 8
000

SEQ ID NO: 9            moltype = AA  length = 9
FEATURE                 Location/Qualifiers
source                  1..9
                        mol_type = protein
                        organism = Saccharomyces cerevisiae
SEQUENCE: 9
RRMLSSKQL                                                          9

SEQ ID NO: 10           moltype = AA  length = 709
FEATURE                 Location/Qualifiers
REGION                  1..709
                        note = Arthrobacter
source                  1..709
                        mol_type = protein
                        organism = synthetic construct
SEQUENCE: 10
MTEVVDRASS PASPGSTTAA ADGAKVAVEP RVDVAALGEQ LLGRWADIRL HARDLAGREV  60
VQKVEGLTHT EHRSRVFGQL KYLVDNNAVH RAFPSRLGGS DDHGGNIAGF EELVTADPSL  120
QIKAGVQWGL FGSAVMHLGT REHHDKWLPG IMSLEIPGCF AMTETGHGSD VASIATTATY  180
DEETQEFVID TPFRAAWKDY IGNAANDGLA AVVFAQLITR KVNHGVHAFY VDLRDPATGD  240
FLPGIGGEDD GIKGGLNGID NGRLHFTNVR IPRTNLLNRY GDVAVDGTYS STIESPGRRF  300
FTMLGTLVQG RVSLDGAAVA ASKVALQSAI HYAAERRQFN ATSPTEEEVL LDYQRHQRRL  360
FTRLATTYAA SFAHEQLLQK FDDVFSGAHD TDADRQDLET LAAALKPLST WHALDTLQEC  420
REACGGAGFL IENRFASLRA DLDVYVTFEG DNTVLLQLVA KRLLADYAKE FRGANFGVLA  480
RYVVDQAAGV ALHRTGLRQV AQFVADSGSV QKSALALRDE EGQRTLLTDR VQSMVAEVGA  540
ALKGAGKLPQ HQAAALFNQH QNELIEAAQA HAELLQWEAF TEALAKVDDA GTKEVLTRLR  600
DLFGLSLIEK HLSWYLMNGR LSMQRGRTVG TYINRLLVKI RPHALDLVDA FGYGAEHLRA  660
AIATGAEATR QDEARTYFRQ QRASGSAPAD EKTLLAIKAG KSRGRRAKL             709

SEQ ID NO: 11           moltype = AA  length = 700
FEATURE                 Location/Qualifiers
source                  1..700
                        mol_type = protein
                        organism = Yarrowia lipolytica
SEQUENCE: 11
MNPNNTGTIE INGKEYNTFT EPPVAMAQER AKTSFPVREM TYFLDGGEKN TLKNEQIMEE  60
IERDPLFNND NYYDLNKEQI RELTMERVAK LSLFVRDQPE DDIKKRFALI GIADMGTYTR  120
LGVHYGLFFG AVRGTGTAEQ FGHWISKGAG DLRKFYGCFS MTELGHGSNL AGLETTAIYD  180
EETDEFIINT PHIAATKWWI GGAAHTATHT VVFARLIVKG KDYGVKTFVV QLRNINDHSL  240
KVGISIGDIG KKMGRDGIDN GWIQFTNVRI PRQNLLMKYT KVDREGNVTQ PPLAQLTYGS  300
LITGRVSMAS DSHQVGKRFI TIALRYACIR RQFSTTPGQP ETKIIDYPYH QRRLLPLLAY  360
VYALKMTADE VGALFSRTML KMDDLKPDDK AGLNEVVSDV KELFSVSAGL KAFSTWACAD  420
VIDKTRQACG GHGYSGYNGF GQAYADWVVQ CTWEGDNNIL TLSAGRALIQ SAVALRKGEP  480
VGNAVSYLKR YKDLANAKLN GRSLTDPKVL VEAWEVAAGN IINRATDQYE KLIGEGLNAD  540
QAFEVLSQQR FQAAKVHTRR HLIAAFFSRI DTEAGEAIKQ PLLNLALLFA LWSIEEDSGL  600
```

```
FLREGFLEPK DIDTVTELVN KYCTTVREEV IGYTDAFNLS DYFINAPIGC YDGDAYRHYF  660
QKVNEQNPAR DPRPPYYAST LKPFLFREEE DDDICELDEE                        700

SEQ ID NO: 12          moltype = AA  length = 661
FEATURE                Location/Qualifiers
source                 1..661
                       mol_type = protein
                       organism = Rattus norvegicus
SEQUENCE: 12
MNPDLRKERA SATFNPELIT HILDGSPENT RRRREIENLI LNDPDFQHED YNFLTRSQRY  60
EVAVKKSATM VKKMREYGIS DPEEIMWFKK LYLANFVEPV GLNYSMFIPT LLNQGTTAQQ  120
EKWMRPSQEL QIIGTYAQTE MGHGTHLRGL ETTATYDPKT QEFILNSPTV TSIKWWPGGL  180
GKTSNHAIVL AQLITQGECY GLHAFVVPIR EIGTHKPLPG ITVGDIGPKF GYEEMDNGYL  240
KMDNYRIPRE NMLMKYAQVK PDGTYVKPLS NKLTYGTMVF VRSFLVGNAA QSLSKACTIA  300
IRYSAVRRQS EIKQSEPEPQ ILDFQTQQYK LFPLLATAYA FHFVGRYMKE TYLRINESIG  360
QGDLSELPEL HALTAGLKAF TTWTANAGIE ECRMACGGHG YSHSSGIPNI YVTFTPACTF  420
EGENTVMMLQ TARFLMKIYD QVRSGKLVGG MVSYLNDLPS QRIQPQQVAV WPTMVDINSL  480
EGLTEAYKLR AARLVEIAAK NLQTHVSHRK SKEVAWNLTS VDLVRASEAH CHYVVVKVFS  540
DKLPKIQDKA VQAVLRNLCL LYSLYGISQK GGDFLEGSII TGAQLSQVNA RILELLTLIR  600
PNAVALVDAF DFKDMTLGSV LGRYDGNVYE NLFEWAKKSP LNKTEVHESY HKHLKPLQSK  660
L                                                                  661

SEQ ID NO: 13          moltype = AA  length = 661
FEATURE                Location/Qualifiers
source                 1..661
                       mol_type = protein
                       organism = Rattus norvegicus
SEQUENCE: 13
MNPDLRKERA SATFNPELIT HILDGSPENT RRRREIENLI LNDPDFQHED YNFLTRSQRY  60
EVAVKKSATM VKKMREYGIS DPEEIMWFKN SVHRGHPEPL DLHLGMFLPT LLHQATAEQQ  120
ERFFMPAWNL EITGTYAQTE MGHGTHLRGL ETTATYDPKT QEFILNSPTV TSIKWWPGGL  180
GKTSNHAIVL AQLITQGECY GLHAFVVPIR EIGTHKPLPG ITVGDIGPKF GYEEMDNGYL  240
KMDNYRIPRE NMLMKYAQVK PDGTYVKPLS NKLTYGTMVF VRSFLVGNAA QSLSKACTIA  300
IRYSAVRRQS EIKQSEPEPQ ILDFQTQQYK LFPLLATAYA FHFVGRYMKE TYLRINESIG  360
QGDLSELPEL HALTAGLKAF TTWTANAGIE ECRMACGGHG YSHSSGIPNI YVTFTPACTF  420
EGENTVMMLQ TARFLMKIYD QVRSGKLVGG MVSYLNDLPS QRIQPQQVAV WPTMVDINSL  480
EGLTEAYKLR AARLVEIAAK NLQTHVSHRK SKEVAWNLTS VDLVRASEAH CHYVVVKVFS  540
DKLPKIQDKA VQAVLRNLCL LYSLYGISQK GGDFLEGSII TGAQLSQVNA RILELLTLIR  600
PNAVALVDAF DFKDMTLGSV LGRYDGNVYE NLFEWAKKSP LNKTEVHESY HKHLKPLQSK  660
L                                                                  661

SEQ ID NO: 14          moltype = AA  length = 664
FEATURE                Location/Qualifiers
source                 1..664
                       mol_type = protein
                       organism = Glycine max
SEQUENCE: 14
MEDGVDHLAF ERNKAQFDVE DMKIIWAGSR QDFELSDRIS RLVASDPAFR KDDRTRLIGR  60
LFKNTLRKAA YAWKRINELR LNEQEAYKLR SFVDQPAFTD LHWGMFVPAI QGQGTDEQQQ  120
KWLPLAYGMQ IIGCYAQTEL GHGSNVQGLE TTATFDPKTD EFVIHSPTLT SSKWWPGGLG  180
KISTHAVAYA RLIIGGEDHG VHGFIVQLRS LDDHLPLPGI TIGDIGMKFG NAAYNTMDNG  240
VLRFDHVRIP RNQMLMRVSQ VTREGRYVSS NVPRQLVYGT MVNVRQKIVA DASVALSRAV  300
CIATRYSAVR RQFGSHNGGL ETQVIDYKTQ QARLFPLLAS AYAFRFVGGW LKWLYMDVTE  360
RLQANDFSTL PEAHACTAGL KSLTTTATAD GIEECRKLCG GHGYLCSSGL PELFAVYVPA  420
CTYEGDNVVL LLQVARHLMK TVSQLGSGNK PVGTTAYMAR VEQLMQYHSD VEKAEDWLKP  480
NVVLEAFEAR ASRMSVACAQ NLSKFANPEE GFQELAADLV DAAVAHCQLI VVSKFIEKLQ  540
QDIPGKGVKK QLEVLCSIYA LFLLHKHLGD FLSTGCINPK QGSLASEQLR NLYSQVRPNA  600
IALVDAFNYT DHYLGSILGR YDGNVYPKMN EEAWKDPLND SVVPDGFKEY IQPMLKQQLR  660
NARL                                                               664

SEQ ID NO: 15          moltype = AA  length = 665
FEATURE                Location/Qualifiers
source                 1..665
                       mol_type = protein
                       organism = Glycine max
SEQUENCE: 15
MEGMVDHLAF ERNNSQFDVD EMKIVWAGSR HAFEVSDKMA RLVASDPAFR KDDRVVLDRK  60
ALFKNTLRKA AYAWKRIIEL RLSEEEAAML RSFVDQPAFT DLHWGMFVPA IKGQGTEEQQ  120
KKWLPLAHKM QIIGCYAQTE LGHGSNVQGL ETTATFDPRT DEFVIHSPTL TSSKWWPGGL  180
GKVSTHAVVY ARLITDGQDH GVHGFIVQLR SLDDHLPLPG ITVGDIGMKF GNGAYNSMDN  240
GMLRFDHVRI PRNQMLMRVS QVTREGKYVQ SSVPRQLVYG TMVYVRQTIV SDASVALSRA  300
VCIATRYSAV RRQFGSKEGG LETQVIDYKT QQARLFPLLA SAYAFRFVGE WLKWLYMDVM  360
KRLQASDFST LPEAHACTAG LKSLTTSATA DGIEECRKLC GGHGYLCSSG LPELFAVYIP  420
TCTYEGDNTV LLLQVARHLI KTISQLGSRN KPVGTTSYIG RVEQLMQYRS DVQKVEDWLK  480
PNAVLGAFEA RAAKKVVACA QNLSKFTNPE EGFQELSVDL VEAAVAHCQL IVVSKFIEKL  540
QQDIPGKGVK QQLELLCSIY ALFLLHKHLG DFLATGCITP KQGSLANELL RSLYSQVRPN  600
AIALVDAFNY TDHYLGSVLG RYDGDVYPKL YEEAWKDPLN DSVVPDGFQE YIRPMLKQQL  660
RNARL                                                              665
```

```
SEQ ID NO: 16          moltype = AA  length = 684
FEATURE                Location/Qualifiers
source                 1..684
                       mol_type = protein
                       organism = Beuvaria bassiana
SEQUENCE: 16
MSFPDNLKPK EPSGSSLLEK ERRQSPVDVD ALGKHIFAGT SFLERQARVL RAIEQEPLFD  60
KSRQQQLSRV ERVKLGLARG KLMRRLQDRH GWDMDDYHMA AYLVGEQSPY RLHVGMFRTT  120
VEEQSSDAQR AYWMPRVNGW EVSGAYSQTE LGHGSNVRGV ELEARWDPAA REFVVHSPTL  180
TAAKWWNGSL GRTANHAILM AQLMVPDPKR EGQYISHGPQ AFIAQIRDLK TNLPLEGVVI  240
GDIGVKIGFT SMDNGYMLFN QFRIPHSALL SRYVQLDPET GVFSKSPNPA LAYGTMTSIR  300
TMLVEEAGTH LARAVTIAIR YTAIRQQFRD KDSQDPSSAE LQVLDYPTVQ VRLFPLLAAA  360
FALQYTGKVM RQDYAKTRGE VEKGNLEGLA VMHSNSSGLK SLSTEITNAG IETCRRAMGG  420
HGYGSGSGLV EMQKDYQAKP ILEGDNWMIT QQTSSFLIKR MTAAAKTRNE PPKDQIDAQL  480
KTFLHQKDKG RTFDILNSDS DIEESFKWRA ASMTYDAYEA RVIKKKRHND LLIQFHKLSH  540
AHSQSIMVSS FLTTLTSSND LAHETKEIVF DLYRLFAYTT IQAESYEFLR CGAASSKDLD  600
ALPERIQALL TRIRPHAVKL VDAWKIPDYL LDSALGRYDG NVYEDLFNRA HRLNPLNDIV  660
FNPDYKDDEI VKGSGERKPL SPKL                                       684

SEQ ID NO: 17          moltype = AA  length = 696
FEATURE                Location/Qualifiers
source                 1..696
                       mol_type = protein
                       organism = Aspergillus nidulans
SEQUENCE: 17
MPNPPPAWVQ ALKPASPQGT ELLTQERAQS NIDVDTLGDL LHTKEALKKQ DEILSVLKSE  60
KVFDKSRNHV LGRTEKIQLA LARGKRLQQL KKAHNWSDED VHVANDLVSE PTPYGLHASM  120
FLVTLREQGT PEQHKLFYER ARNYEIIGCY AQTELGHGSN VRGLETTATW DPSDQTFIIH  180
SPTLTASKWW IGSLGRTANH AVVMAQLYIG GKNYGPHPFV VQIRDMETHQ PLENVYVGDI  240
GPKFGYNTMD NGFLLFNKLK IPHVNMLARF AQVDKATNKY IRPASPSLMY GTMTWVRSNI  300
VLQAGGVLAR GVTIAVRYCA VRRQFQDRDA KANAEENQVL NYKMVQIRLL PLLAAMYALH  360
FTGRGMMRLY EENQERMKAA AQADQEKRGA GPEQLRAGSD LLADLHATSC GLKALASTTA  420
GEGLEVCRRA CGGHGYSNYS GIGPWYADYL PTLTWEGDNY MLTQQVARYL LKSARAVLAG  480
KGTANDTSRI LQAYLARRDK GASFDILGND ADIVAAFAWR TAHLTFETLK YRDVEKRSWN  540
SLLINFWRLS TALSQYLVVK NFYEAVNSPE IRSSLDKDTA STLRSLFRLH ALHTLDREAS  600
EFFSSAAVTV RQIGLTQTSE VPKLLDEIRP HAVRLVDSWK IPDWQLDSAL GRSDGDVYPD  660
LFKRASMQNP VNDLVFDPYP WNENVLKNAG EIKSKL                           696

SEQ ID NO: 18          moltype = AA  length = 646
FEATURE                Location/Qualifiers
source                 1..646
                       mol_type = protein
                       organism = Arabidopsis thaliana
SEQUENCE: 18
MESRREKNPM TEEESDGLIA ARRIQRLSLH LSPSLTPSPS LPLVQTETCS ARSKKLDVNG  60
EALSLYMRGK HIDIQEKIFD FFNSRPDLQT PIEISKDDHR ELCMNQLIGL VREAGVRPFR  120
YVADDPEKYF AIMEAVGSVD MSLGIKMGVQ YSLWGGSVIN LGTKKHRDKY FDGIDNLDYT  180
GCFAMTELHH GSNVQGLQTT ATFDPLKDEF VIDTPNDGAI KWWIGNAAVH GKFATVFARL  240
ILPTHDSKGV SDMGVHAFIV PIRDMKTHQT LPGVEIQDCG HKVGLNGVDN GALRFRSVRI  300
PRDNLLNRFG DVSRDGTYTS SLPTINKRFG ATLGELVGGR VGLAYASVGV LKISATIAIR  360
YSLLRQQFGP PKQPEVSILD YQSQQHKLMP MLASTYAYHF ATVYLVEKYS EMKKTHDEQL  420
VADVHALSAG LKSYVTSYTA KALSVCREAC GGHGYAAVNR FGSLRNDHDI FQTFEGDNTV  480
LLQQVAADLL KRYKEKFQGG TLTVTWSYLR ESMNTYLSQP NPVTARWEGE DHLRDPKFQL  540
DAFRYRTSRL LQNVAARLQK HSKTLGGFGA WNRCLNHLLT LAESHIETVI LAKFIEAVKN  600
CPDPSAKAAL KLACDLYALD RIWKDIGTYR NVDYVAPNKA KVCFLV                646

SEQ ID NO: 19          moltype = AA  length = 692
FEATURE                Location/Qualifiers
source                 1..692
                       mol_type = protein
                       organism = Arabidopsis thaliana
SEQUENCE: 19
MESRREKNPM TEEESDGLIA ARRIQRLSLH LSPSLTPSPS LPLVQTETCS ARSKKLDVNG  60
EALSLYMRGK HIDIQEKIFD FFNSRPDLQT PIEISKDDHR ELCMNQLIGL VREAGVRPFR  120
YVADDPEKYF AIMEAVGSVD MSLGIKMGVQ YSLWGGSVIN LGTKKHRDKY FDGIDNLDYT  180
GCFAMTELHH GSNVQGLQTT ATFDPLKDEF VIDTPNDGAI KWWIGNAAVH GKFATVFARL  240
ILPTHDSKGV SDMGVHAFIV PIRDMKTHQT LPGVEIQDCG HKVGLNGVDN GALRFRSVRI  300
PRDNLLNRFG DVSRDGTYTS SLPTINKRFG ATLGELVGGR VGLAYASVGV LKISATIAIR  360
YSLLRQQFGP PKQPEVSILD YQSQQHKLMP MLASTYAYHF ATVYLVEKYS EMKKTHDEQL  420
VADVHALSAG LKSYVTSYTA KALSVCREAC GGHGYAAVNR FGSLRNDHDI FQTFEGDNTV  480
LLQQVAADLL KRYKEKFQGG TLTVTWSYLR ESMNTYLSQP NPVTARWEGE DHLRDPKFQL  540
DAFRYRTSRL LQNVAARLQK HSKTLGGFGA WNRCLNHLLT LAESHIETVI LAKFIEAVKN  600
CPDPSAKAAL KLACDLYALD RIWKDIGTYR NVDYVAPNKA KAIHKLTEYL SFQVRNVAKE  660
LVDAFELPDH VTRAPIAMQS DAYSQYTQVV GF                               692

SEQ ID NO: 20          moltype = AA  length = 711
FEATURE                Location/Qualifiers
VARIANT                711
                       note = Xaa = Any Amino Acid
```

```
VARIANT              711
                     note = Xaa = Any Amino Acid
source               1..711
                     mol_type = protein
                     organism = Candida viswanathii
SEQUENCE: 20
MTFTKKNVSV SQGPDPRTSI QTERANSKFD PVTMNYFLEG SKERSELMKS LAQQIERDPI  60
LFTDGSYYDL TKDQQRELTV LKINRLSRYR EGDSVDTFNK RLSIMGVVDP QVATRIGVNL  120
GLFLSCISGN GTAEQFKYWA IDKGTHNIQG LYGCFGMTEL GHGSNVAGVE TTATFDKETD  180
EFVINTPHIG ATKWWIGGAA HSATHCSVYA RLVVDGKDYG VKTFVVPLRD SNHDLMPGVT  240
VGDIGAKMGR DGIDNGWIQF SNVRIPRFFM LQKFCKVSAE GEVVLPPLEQ LSYSALLGGR  300
VMMVLDSYRM LARVSTIALR YAIGRRQFKG DNVDQNDPNA LETQLIDYPL HQKRLFPYLA  360
AAYVVSTGAL KVEHTIQSTL ATLDAAVENN DTTAIFKSID DMKSLFIDSG SLKATTTWLA  420
AEAIDQCRQA CGGHGYSSYN GFAKAFNDWV VQCTWEGDNN VLSLSVGKPI IKQIIGIEDN  480
GKTVRGSTAF LNQVKDFTGS NASKVVLNNT SDLNDINKVI KSIEVAIIRL AHEAAISVRK  540
ESLDFAGAEL VQISKLKAHH YLLTEFVKRV GEFEHKELVP FLNTIGRLYS ATVVLDKFAG  600
VFLTFNVASP QAITDLASTQ IPKLCAEVRP NVVAYTDSFQ QSDMVINSAI GKYDGDVYEN  660
YFDLVKQLNP PKNTKAPYTA ALEGMLNRPS LEARERYEKS DETAAILSKP X           711

SEQ ID NO: 21        moltype = AA  length = 662
FEATURE              Location/Qualifiers
source               1..662
                     mol_type = protein
                     organism = Candida viswanathii
SEQUENCE: 21
MPTELQKERE LTKFNPKELN YFLEGSQERS EIISNMVEQM QKDPILKVDA SYYNLTKDQQ  60
REVTAKKIAR LSRYFEHEYP DQQAQRLSIL GVFDPQVFTR IGVNLGLFVS CVRGNGTNSQ  120
FFYWTINKGI DKLRGIYGCF GMTELAHGSN VQGIETTATF DEDTDEFVIN TPHIGATKWW  180
IGGAAHSATH CSVYARLKVK GKDYGVKTFV VPLRDSNHDL EPGVTVGDIG AKMGRDGIDN  240
GWIQFSNVRI PRFFMLQKYC KVSRSGEVTM PPSEQLSYSA LIGGRVTMMM DSYRMTSRFI  300
TIALRYAIHR RQFKKKDTDT IETKLIDYPL HQKRLFPFLA AAYLFSQGAL YLEQTMNATN  360
DKLDEAVSAG EKEAIDAAIV ESKKLFVASG CLKSTCTWLT AEAIDEARQA CGGHGYSSYN  420
GFGKAYSDWV VQCTWEGDNN ILAMNVAKPM VRDLLKEPEQ KGLVLSSVAD LDDPAKLVKA  480
FDHALSGLAR DIGAVAEDKG FDITGPSLVL VSKLNAHRFL IDGFFKRITP EWSEVLRPLG  540
FLYADWILTN FGATFLQYGI ITPDVSRKIS SEHFPALCAK VRPNVVGLTD GFNLTDMMTN  600
AAIGRYDGNV YEHYFETVKA LNPPENTKAP YSKALEDMLN RPDLEVRERG EKSEEAAEIL  660
SS                                                                662

SEQ ID NO: 22        moltype = AA  length = 689
FEATURE              Location/Qualifiers
source               1..689
                     mol_type = protein
                     organism = Yarrowia lipolytica
SEQUENCE: 22
MTTNTFTDPP VEMAKERGKT QFTVRDVTNF LNGGEEETQI VEKIMSSIER DPVLSVTADY  60
DCNLQQARKQ TMERVAALSP YLVTDTEKLS LWRAQLHGMV DMSTRTRLSI HNNLFIGSIR  120
GSGTPEQFKY WVKKGAVAVK QFYGCFAMTE LGHGSNLKGL ETTATYDQDS DQFIINTPHI  180
GATKWWIGGA AHTSTHCVCF AKLIVHGKDY GTRNFVVPLR NVHDHSLKVG VSIGDIGKKM  240
GRDGVDNGWI QFTNVRIPRQ NMLMRYAKVS DTGVVTKPAL DQLTYGALIR GRVSMIADSF  300
HVSKRFLTIA LRYACVRRQF GTSGDTKETK IIDYPYHQRR LLPLLAYCYA MKMGADEAQK  360
TWIETTDRIL ALNPNDPAQK NDLEKAVTDT KELFAASAGM KAFTTWGCAK IIDECRQACG  420
GHGYSGYNGF GQGYADWVVQ CTWEGDNNVL CLSMGRGLVQ SALQILAGKH VGASIQYVGD  480
KSKISQNGQG TPREQLLSPE FLVEAFRTAS RNNILRTTDK YQELVKTLNP DQAFEELSQQ  540
RFQCARIHTR QHLISSFYAR IATAKDDIKP HLLKLANLFA LWSIEEDTGI FLRENILTPG  600
DIDLINSLVD ELCVAVRDQV IGLTDAFGLS DFFINAPIGS YDGNVYEKYF AKVNQQNPAT  660
NPRPPYYEST LKPFLFREEE DDEICDLDE                                   689

SEQ ID NO: 23        moltype = AA  length = 700
FEATURE              Location/Qualifiers
source               1..700
                     mol_type = protein
                     organism = Yarrowia lipolytica
SEQUENCE: 23
MNPNNTGTIE INGKEYNTFT EPPVAMAQER AKTSFPVREM TYFLDGGEKN TLKNEQIMEE  60
IERDPLFNND NYYDLNKEQI RELTMERVAK LSLFVRDQPE DDIKKRFALI GIADMGTYTR  120
LGVHYGLFFG AVRGTGTAEQ FGHWISKGAG DLRKFYGCFS MTELGHGSNL AGLETTAIYD  180
EETDEFIINT PHIAATKWWI GGAAHTATHT VVFARLIVKG KDYGVKTFVV QLRNINDHSL  240
KVGISIGDIG KKMGRDGIDN GWIQFTNVRI PRQNLLMKYT KVDREGNVTQ PPLAQLTYGS  300
LITGRVSMAS DSHQVGKRFI TIALRYACIR RQFSTTPGQP ETKIIDYPYH QRRLLPLLAY  360
VYALKMTADE VGALFSRTML KMDDLKPDDK AGLNEVVSDV KELFSVSAGL KAFSTWACAD  420
VIDKTRQACG GHGYSGYNGF GQAYADWVVQ CTWEGDNNIL TLSAGRALIQ SAVALRKGEP  480
VGNAVSYLKR YKDLANAKLN GRSLTDPKVL VEAWEVAAGN IINRATDQYE KLIGEGLNAD  540
QAFEVLSQQR FQAAKVHTRR HLIAAFFSRI DTEAGEAIKQ PLLNLALLFA LWSIEEDSGL  600
FLREGFLEPK DIDTVTELVN KYCTTVREEV IGYTDAFNLS DYFINAPIGC YDGDAYRHYF  660
QKVNEQNPAR DPRPPYYAST LKPFLFREEE DDDICELDEE                       700

SEQ ID NO: 24        moltype = AA  length = 700
FEATURE              Location/Qualifiers
source               1..700
```

```
                        mol_type = protein
                        organism = Yarrowia lipolytica
SEQUENCE: 24
MISPNLTANV EIDGKQYNTF TEPPKALAGE RAKVKFPIKD MTEFLHGGEE NVTMIERLMT  60
ELERDPVLNV SGDYDMPKEQ LRETAVARIA ALSGHWKKDT EKEALLRSQL HGIVDMGTRI  120
RLGVHTGLFM GAIRGSGTKE QYDYWVRKGA ADVKGFYGCF AMTELGHGSN VAGLETTATY  180
IQDTDEFIIN TPNTGATKWW IGGAAHSATH TACFARLLVD GKDYGVKIFV VQLRDVSSHS  240
LMPGIALGDI GKKMGRDAID NGWIQFTNVR IPRQNMLMKY AKVSSTGKVS QPPLAQLTYG  300
ALIGGRVTMI ADSFFVSQRF ITIALRYACV RRQFGTTPGQ PETKIIDYPY HQRRLLPLLA  360
FTYAMKMAAD QSQIQYDQTT DLLQTIDPKD KGALGKAIVD LKELFASSAG LKAFTTWTCA  420
NIIDQCRQAC GGHGYSGYNG FGQAYADWVV QCTWEGDNNV LCLSMGRGLI QSCLGHRKGK  480
PLGSSVGYLA NKGLEQATLS GRDLKDPKVL IEAWEKVANG AIQRATDKFV ELTKGGLSPD  540
QAFEELSQQR FQCAKIHTRK HLVTAFYERI NASAKADVKP YLINLANLFT LWSIEEDSGL  600
FLREGFLQPK DIDQVTELVN HYCKEVRDQV AGYTDAPFGLS DWFINAPIGN YDGDVYKHYF  660
AKVNQQNPAQ NPRPPYYEST LRPFLFREDE DDDICELDEE                        700

SEQ ID NO: 25           moltype = AA  length = 701
FEATURE                 Location/Qualifiers
source                  1..701
                        mol_type = protein
                        organism = Yarrowia lipolytica
SEQUENCE: 25
MITPNPANDI VHDGKLYDTF TEPPKLMAQE RAQLDFDPRD ITYFLDGSKE ETELLESLML  60
MYERDPLFNN QNEYDESFET LRERSVKRIF QLSKSIAMDP EPMSFRKIGF LGILDMGTYA  120
RLGVHYALFC NSIRGQGTPD QLMYWLDQGA MVIKGFYGCF AMTEMGHGSN LSRLETIATF  180
DKETDEFIIN TPHVGATKWW IGGAAHTATH TLAFARLQVD GKDYGVKSFV VPLRNLDDHS  240
LRPGIATGDI GKKMGRDAVD NGWIQFTNVR VPRNYMLMKH TKVLRDGTVK QPPLAQLTYG  300
SLITGRVQMT TDSHNVSKKF LTIALRYATI RRQFSSTPGE PETRLIDYLY HQRRLLPLMA  360
YSYAMKLAGD HVRELFFASQ EKAESLKEDD KAGVESYVQD IKELFSVSAG LKAATTWACA  420
DIIDKARQAC GGHGYSAYNG FGQAFQDWVV QCTWEGDNTV LTLSAGRALI QSALVYRKEG  480
KLGNATKYLS RSKELANAKR NGRSLEDPKL LVEAWEAVSA GAINAATDAY EELSKQGVSV  540
DECFEQVSQE RFQAARIHTR RALIEAFYSR IATADEKVKP HLIPLANLFA LWSIEEDSAL  600
FLAEGYFEPE DIIEVTSLVN KYCGIVRKNV IGYTDAFNLS DYFINAAIGR YDGDVYKNYF  660
EKVKQQYPPE GGKPHYYEDV MKPFLHRERI PDVPMEPEDI Q                      701

SEQ ID NO: 26           moltype = AA  length = 699
FEATURE                 Location/Qualifiers
source                  1..699
                        mol_type = protein
                        organism = Yarrowia lipolytica
SEQUENCE: 26
MNNNPTNVIL GGKEYDTFTE PPAQMELERA KTQFKVRDVT NFLTGSEQET LLTERIMREI  60
ERDPVLNVAG DYDADLPTKR RQAVERIGAL ARYLPKDSEK EAILRGQLHG IVDMGTRTRI  120
AVHYGLFMGA IRGSGTKEQY DYWVAKGAAT LHKFYGCFAM TELGHGSNVA GLETTATLDK  180
DTDEFIINTP NSGATKWWIG GAAHSATHTA CLARLIVDGK DYGVKIFIVQ LRDLNSHSLL  240
NGIAIGDIGK KMGRDAIDNG WIQFTDVRIP RQNMLMRYDR VSRDGEVTTS ELAQLTYGAL  300
LSGRVTMIAE SHLLSARFLT IALRYACIRR QFGAVPDKPE TKLIDYPYHQ RRLLPLLAYT  360
YAMKMGADEA QQQYNSSFGA LLKLNPVKDA EKFAVATADL KALFASSAGM KAFTTWAAAK  420
IIDECRQACG GHGYSGYNGF GQAYADWVVQ CTWEGDNNVL CLSMGRSLIQ SCIAMRKKKG  480
HVGKSVEYLQ RRDELQNARV DNKPLTDPAV LITAWEKVAC EAINRATDSF IKLTQEGLSP  540
DQAFEELSQQ RFECARIHTR KHLITSFYAR ISKAKARVKP HLTVLANLFA VWSIEEDSGL  600
FLREGCFEPA EMDEITALVD ELCCEAREQV IGFTDAFNLS DFFINAPIGR FDGDAYKHYM  660
DEVKAANNPR NTHAPYYETK LRPFLFRPDE DEEICDLDE                         699

SEQ ID NO: 27           moltype = AA  length = 689
FEATURE                 Location/Qualifiers
source                  1..689
                        mol_type = protein
                        organism = Yarrowia lipolytica
SEQUENCE: 27
MLSQQSLNTF TEPPVEMARE RNQTSFNPRL LTYFLDGGEK NTLLMDRLMQ EYERDPVFRN  60
EGDYDITDVA QSRELAFKRI AKLIEYVHTD DEETYLYRCM LLGQIDMGAF ARYAIHHGVW  120
GGAIRGAGTP EQYEFWVKKG SLSVKKFYGS FSMTELGHGS NLVGLETTAT LDKNADEFVI  180
NTPNVAATKW WIGGAADTAT HTAVFARLIV DGEDHGVKTF VVQLRDVETH NLMPGIAIGD  240
CGKKMGRQGT DNGWIQFTHV RIPRQNMLMR YCHVDSDGNV TEPMMAQMAY GALLAGRVGM  300
AMDSYFTSRK FLTIALRYAT IRRAFAAGGG QETKLIDYPY HQRRLLPLMA QTYAIKCTAD  360
KVRDQFVKVT DMLLNLDVSD QEAVPKAIAE AKELFSVSAG VKATTTWACA HTIDQCRQAC  420
GGHGYSAYNG FGRAYSDWVI QCTWEGDNNI LCLSAGRALV QSNRAVRAGK PIGGPTAYLA  480
APAGSPKLAG RNLYDPKVMI GAWETVSRAL INRTTDEFEV LAKKGLSTAQ AYEELSQQRF  540
LCTRIHTRLY MVKNFYERIA EEGTEFTKEP LTRLANLYAF WSVEEEAGIF LREGYITPQE  600
LKYISAEIRK QLLEVRKDVI GYTDAFNVPD FFLNSAIGRA DGDVYKNYFK VVNTQNPPQD  660
PRPPYYESVI RPFLFRKDED EEICSLEDE                                    689

SEQ ID NO: 28           moltype = AA  length = 906
FEATURE                 Location/Qualifiers
source                  1..906
                        mol_type = protein
                        organism = Candida viswanathii
SEQUENCE: 28
```

```
MSPVDFKDKV VIITGAGGGL GKYYSLEFAK LGAKVVVNDL GGALNGQGGN SKAADVVVDE  60
IVKNGGVAVA DYNNVLDGDK IVETAVKNFG TVHVIINNAG ILRDASMKKM TEKDYKLVID  120
VHLNGAFAVT KAAWPYFQKQ KYGRIVNTSS PAGLYGNFGQ ANYASAKSAL LGFAETLAKE  180
GAKYNIKANA IAPLARSRMT ESILPPPMLE KLGPEKVAPL VLYLSSAENE LTGQFFEVAA  240
GFYAQIRWER SGGVLFKPDQ SFTAEVVAKR FSEILDYDDS RKPEYLKNQY PFMLNDYATL  300
TNEARKLPAN DASGAPTVSL KDKVVLITGA GAGLGKEYAK WFAKYGAKVV VNDFKDATKT  360
VDEIKAAGGE AWPDQHDVAK DSEAIIKNVI DKYGTIDILV NNAGILRDRS FAKMSKQEWD  420
SVQQVHLIGT FNLSRLAWPY FVEKQFGRII NITSTSGIYG NFGQANYSSS KAGILGLSKT  480
MAIEGAKNNI KVNIVAPHAE TAMTLTIFRE QDKNLYHADQ VAPLLVYLGT DDVPVTGETF  540
EIGGGWIGNT RWQRAKGAVS HDEHTTVEFI KEHLNEITDF TTDTENPKST TESSMAILSA  600
VGGDDDDDDE DEEEDEGDEE EDEEDEEEDD PVWRFDDRDV ILYNIALGAT TKQLKYVYEN  660
DSDFQVIPTF GHLITFNSGK SQNSFAKLLR NFNPMLLLHG EHYLKVHSWP PTEGEIKTT   720
FEPIATTPKG TNVVIVHGSK SVDNKSGELI YSNEATYFIR NCQADNKVYA DRPAFATNQF  780
LAPKRAPDYQ VDVPVSEDLA ALYRLSGDRN PLHIDPNFAK GAKFPKPILH GMCTYGLSAK  840
ALIDKFGMFN EIKARFTGIV FPGETLRVLA WKESDDTIVF QTHVVDRGTI AINNAAIKLV  900
GDKAKI                                                            906

SEQ ID NO: 29          moltype = AA  length = 472
FEATURE                Location/Qualifiers
source                 1..472
                       mol_type = protein
                       organism = Candida viswanathii
SEQUENCE: 29
MMWKFLIAIG LIFSYCCNAQ LLDSLSFDNN WVNTHYIRTI DLSKGFVKET DLIQIKNIND  60
KPQDEYYFVV NDGFDSIDEL SIFSAFVGDQ ALEVEVDEVV PDKVFKLKLP VPIAPNSDLE  120
LRINFVYIDS LVSVPSKIAM DATQQLLYKT NKFPFSPYVT QEYTLALSGM SKGQEMDLHI  180
DVEDTPGLPD LKPRVESQVL KYGPIAEDIP AFALKPMGLM YDHNRPLTKA VSLNRSIWLP  240
ASDINKVSIE EYYELTNTGA ELDKGFSRVD WMKGRFESTR NHWALSHLEI PLLERGFDDY  300
YYTDKVGVVS THKIFKNHLL LQPRYPVFGG WKYNFTLGWS EELSKFLHKL HDNQDEYIIK  360
FPILNSLRDV TYQDVYLEFY LPENAEFQNI SSPIAFESIS IENELSYLDV SKGHTKITVH  420
YTNLFDDLHK LDVFVKYQYT QVAFIYKIAK ISGFVFLGLV SYYLLGLLDL SI          472

SEQ ID NO: 30          moltype = AA  length = 519
FEATURE                Location/Qualifiers
source                 1..519
                       mol_type = protein
                       organism = Saccharomyces fibuligera
SEQUENCE: 30
MKFGVLFSVF AAIVSALPLQ EGPLNKRAYP SFEAYSNYKV DRTDLETFLD KQKEVSLYYL  60
LQNIAYPEGQ FNNGVPGTVI ASPSTSNPDY YYQWTRDSAI TFLTVLSELE DNNFNTTLAK  120
AVEYYINTSY NLQRTSNPSG SFDDENHKGL GEPKFNTDGS AYTGAWGRPQ NDGPALRAYA  180
ISRYLNDVNS LNEGKLVLTD SGDINFSSTE DIYKNIIKPD LEYVIGYWDS TGFDLWEENQ  240
GRHFFTSLVQ QKALAYAVDI AKSFDDGDFA NTLSSTASTL ESYLSGSDGG FVNTDVNHIV  300
ENPDLLQQNS RQGLDSATYI GPLLTHDIGE SSSTPFDVDN EYVLQSYYLL LEDNKDRYSV  360
NSAYSAGAAI GRYPEDVYNG DGSSEGNPWF LATAYAAQVP YKLAYDAKSA SNDITINKIN  420
YDFFNKYIVD LSTINSAYQS SDSVTIKSGS DEFNTVADNL VTFGDSFLQV ILDHINDDGS  480
LNEQLNRYTG YSTGAYSLTW SSGALLEAIR LRNKVKALA                        519

SEQ ID NO: 31          moltype = AA  length = 403
FEATURE                Location/Qualifiers
source                 1..403
                       mol_type = protein
                       organism = Rattus norvegicus
SEQUENCE: 31
MIHTNLKKKF SLFILVFLLF AVICVWKKGS DYEALTLQAK EFQMPKSQEK VAMGSASQVV  60
FSNSKQDPKE DIPILSYHRV TAKVKPQPSF QVWDKDSTYS KLNPRLLKIW RNYLNMNKYK  120
VSYKGPGPGV KFSVEALRCH LRDHVNVSMI EATDFPFNTT EWEGYLPKEN FRTKVGPWQR  180
CAVVSSAGSL KNSQLGREID NHDAVLRFNG APTDNFQQDV GSKTTIRLMN SQLVTTEKRF  240
LKDSLYTEGI LIVWDPSVYH ADIPKWYQKP DYNFFETYKS YRRLNPSQPF YILKPQMPWE  300
LWDIIQEISA DLIQPNPPSS GMLGIIIMMT LCDQVDIYEF LPSKRKTDVC YYHQKFFDSA  360
CTMGAYDPLL FEKNMVKHLN EGTDEDIYLF GKATLSGFRN IRC                    403

SEQ ID NO: 32          moltype = AA  length = 219
FEATURE                Location/Qualifiers
source                 1..219
                       mol_type = protein
                       organism = Homo sapiens
SEQUENCE: 32
MRLREPLLSG SAAMPGASLQ RACRLLVAVC ALHLGVTLVY YLAGRDLSRL PQLVGVSTPL  60
QGGSNSAAAI GQSSGELRTG GARPPPPLGA SSQPRPGGDS SPVVDSGPGP ASNLTSVPVP  120
HTTALSLPAC PEESPLLVGP MLIEFNMPVD LELVAKQNPN VKMGGRYAPR DCVSPHKVAI  180
IIPFRNRQEH LKYWLYYLHP VLQRQQLDYG IYVINQISF                         219

SEQ ID NO: 33          moltype = AA  length = 815
FEATURE                Location/Qualifiers
source                 1..815
                       mol_type = protein
                       organism = Candida viswanathii
SEQUENCE: 33
```

```
MTLLLKPTSE LDATSRKIIE RIQSNSPTFQ HLFDLLLNLL PFFDKTVSLL GSIGYCDYEV  60
AYVTYQTCIQ VVGLMKPKTN SLNQDIFKGV QLQTRKRAST FKAILSYFAE PETQEEDPLL  120
NRFKSLSGGG SKTKSSQDEV FHEWITSSEL QRELSSKKVL LIDFRPRKDY LNNHIKYKDL  180
VHIEPTQLET LLDSASDQDL ETLVKKSAPY DQYHIFLERH KYDLIVVYNY NYGSESTDRL  240
LGIIDVVSKP NPFTKLITIL MNNKYISSRL KVKPLFLSGG VLNWYKTFGI EYLERTLVQN  300
GVAHTSDNQY LKSFNDYVST SKETPKTQVK TQNGDYIRPS QRKVNQFDPV PVKSGPTVFA  360
SAKVDLPPTP GSPAVSTPSP PRAPAPPTKT TSLTHVPEKE AKSPSPVTKE VTVSSKKSQF  420
LELYTTGLVN LGNSCYMNCV VQCLAAAPQL TSFFFPTITE SFSDHSYRQH INSNNKLGTK  480
GELTTSFVEL ILNMLNNNGK AFSPTKFKRT MGSLSPSQQF LTYDQQDCIE FLNFLLDALH  540
EDLNNVTITD PSERKLITDL SPEQEKSRET LPVRLASTIE WERYLKLNFS VIVDYFQGQH  600
LSQLKCLECG FTSTTYNAFS ILSLPIPQKL NNLGKVLLKD CLEEFVTTEL LDDNNKWYCP  660
QCKRFTRLTK KIAITRLPQV LIVNFNRFKM TNTGGFNKLE TFVTYPVNEE LDMTPYWPDV  720
GSRINENSTM SIEMEQDLLQ SFPIRNQTPP FKYKLFGVAN HFGNLTTGHY TSYVYKHSDS  780
KKTRNWCYFD DSKITYNVSP SQVVNKNAYC LFFQR                            815

SEQ ID NO: 34           moltype = AA  length = 421
FEATURE                 Location/Qualifiers
source                  1..421
                        mol_type = protein
                        organism = Candida viswanathii
SEQUENCE: 34
MQLSLSVLST VATALLSLTT AVDAKSHNIK LSKLSNEETL DASTFQEYTS SLANKYMNLF  60
NAAHGNPTSF GLQHVLSNQE AEVPFVTPQK GGKYDAPLTN YLNAQYFTEI EIGTPGQPFK  120
VILDTGSSNL WVPSQDCTSL ACFLHSKYDH DASSTYKANG SEFSIQYGSG SMEGYISQDI  180
LTIGDLVIPK QDFAEATSEP GLAFAFGKFD GILGLAYDSI SVNHIVPPVY NAINQGLLDK  240
PQVSFYLGNT EKDENDGGLA TFGGYDASLF QGKITWLPVR RKAYWEVSFE GIGLGDEYAE  300
LQKTGAAIDT GTSLITLPSS LAEIINAKIG ATKSWSGQYQ IDCAKRDELP DLTLTFAGHN  360
FTLTAHDYIL EVSGSCISVF TPMDFPKPIG DLAIIGDAFL RKYYSIYDLD KNAVGLAPSK  420
A                                                                 421

SEQ ID NO: 35           moltype = AA  length = 551
FEATURE                 Location/Qualifiers
source                  1..551
                        mol_type = protein
                        organism = Candida viswanathii
SEQUENCE: 35
MGITNETQAL LGGDSLSCLN KKKSNTKRNL SYLLNIITVS IIAYLCFFAT HNHHNDSGIP  60
KVDPHKKKNI IMMVTDGMGP ASLSAARSFR QFRDKLAIND ILTLDQYLIG SSRTRSSSSL  120
VTDSAAGATA FSCALKSYNG AIGVSPDKSP CGTILEALKL QGYYTGLVVT TRITDATPAA  180
FSAHVDYRFQ EDLIAEHQLG EYPFGRAVDL ILGGGRCHFL PTAQGGCRAD DRNLIKESSD  240
TWQYVGDRQQ FDQLKGGKNV SLPLLGLLAN TDIPYAIDRD EKEYPSLAEQ VKVALTALSD  300
ATKDSDQGFF LLIEGSRIDH AGHHNDPTAQ VREVLAYDEA FGEVIKFIDS TDVETVAIST  360
SDHETGGLVV SRQVTPEYPD YIWYPEVLLN STHSGDYLAH KIADYKNKDD TAKLTKFIKH  420
EILETDLGVT DYTDKDVQAI LDKVNDPANL LYVLNDIVSF RAQIGWTTHG HSAVDVNIYA  480
HTNSPAIRAK LASAKAYHGL SGNHENIEIG AFMEEITGSN LSRVTELIKK TAHSPSLSKK  540
EFSVDEFHGN V                                                      551

SEQ ID NO: 36           moltype = AA  length = 140
FEATURE                 Location/Qualifiers
source                  1..140
                        mol_type = protein
                        organism = Saccharomyces cerevisiae
SEQUENCE: 36
MCCYCVCCTV SDFILYIVAF FFPPAAVLLR SGPCSSDFLL NVLLTLLGFL PGMLHAFYYI  60
TITSPLRNAE YVYYYQQGWV DSERNVPSNR PQNSQTPQNR PQQGSSARNV YPSVETPLLQ  120
GAAPHDNKQS LVESPPPYVP                                             140

SEQ ID NO: 37           moltype = AA  length = 377
FEATURE                 Location/Qualifiers
source                  1..377
                        mol_type = protein
                        organism = Candida viswanathii
SEQUENCE: 37
MRLKDIKLIL IGILTISVTY FLISSFSGPR AYTTSDPNSS KMQFLRALES HPNWKETGLN  60
FQPTKKLEVD DSSTPVRQQL AARFPYDPTQ PFPKNIWQTW KVGIEDETFP KRYLKFQLSW  120
DTKNPEYKHH VIPDDQCDEL VAQLFEDVPD VARAYKVMPK SILKADFFRY LILFARGGVY  180
TDIDTVGLKP IDTWMSNMEL LWGEPNRAGL VVGIEADPDR PDWADWYARR IQFCQWTIQL  240
KKGHPMLREL ITKITDITLT REKRNELKKV LGKDEGGDIM NWTGPGIFTD TVFSYMNAIL  300
QAPEVITGKY KWDNIVDWKV FTGMQMPIAI DDVLVLPITS FSPDVSQMGS KSSTDPMAYA  360
KHMFLGSWKD DGMPEME                                                377

SEQ ID NO: 38           moltype = AA  length = 720
FEATURE                 Location/Qualifiers
source                  1..720
                        mol_type = protein
                        organism = Cannabis sativa
SEQUENCE: 38
MGKNYKSLDS VVASDFIALG ITSEVAETLH GRLAEIVCNY GAATPQTWIN IANHILSPDL  60
PFSLHQMLFY GCYKDFGPAP PAWIPDPEKV KSTNLGALLE KRGKEFLGVK YKDPISSFSH  120
```

```
FQEFSVRNPE VYWRTVLMDE MKISFSKDPE CILRRDDINN PGGSEWLPGG YLNSAKNCLN  180
VNSNKKLNDT MIVWRDEGND DLPLNKLTLD QLRKRVWLVG YALEEMGLEK GCAIAIDMPM  240
HVDAVVIYLA IVLAGYVVVS IADSFSAPEI STRLRLSKAK AIFTQDHIIR GKKRIPLYSR  300
VVEAKSPMAI VIPCSGSNIG AELRDGDISW DYFLERAKEF KNCEFTAREQ PVDAYTNILF  360
SSGTTGEPKA IPWTQATPLK AAADGWSHLD IRKGDVIVWP TNLGWMMGPW LVYASLLNGA  420
SIALYNGSPL VSGFAKFVQD AKVTMLGVVP SIVRSWKSTN CVSGYDWSTI RCFSSSGEAS  480
NVDEYLWLMG RANYKPVIEM CGGTEIGGAF SAGSFLQAQS LSSFSSQCMG CTLYILDKNG  540
YPMPKNKPGI GELALGPVMF GASKTLLNGN HHDVYFKGMP TLNGEVLRRH GDIFELTSNG  600
YYHAHGRADD TMNIGGIKIS SIEIERVCNE VDDRVFETTA IGVPPLGGGP EQLVIFFVLK  660
DSNDTTIDLN QLRLSFNLGL QKKLNPLFKV TRVVPLSSLP RTATNKIMRR VLRQQFSHFE  720

SEQ ID NO: 39          moltype = AA  length = 385
FEATURE                Location/Qualifiers
source                 1..385
                       mol_type = protein
                       organism = Cannabis sativa
SEQUENCE: 39
MNHLRAEGPA SVLAIGTANP ENILIQDEFP DYYFRVTKSE HMTQLKEKFR KICDKSMIRK  60
RNCFLNEEHL KQNPRLVEHE MQTLDARQDM LVVEVPKLGK DACAKAIKEW GQPKSKITHL  120
IFTSASTTDM PGADYHCAKL LGLSPSVKRV MMYQLGCYGG GTVLRIAKDI AENNKGARVL  180
AVCCDIMACL FRGPSDSDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LDLKKEKFVD SRHVLSEHGN MSSSTVLFVM DELRKRSLEE GKSTTGDGFE  360
WGVLFGFGPG LTVERVVVRS VPIKY                                      385

SEQ ID NO: 40          moltype = AA  length = 391
FEATURE                Location/Qualifiers
REGION                 1..391
                       note = Cannabis sativa
source                 1..391
                       mol_type = protein
                       organism = synthetic construct
SEQUENCE: 40
MNHLRAEGPA SVLAIGTANP ENILIQDEFP DYYFRVTKSE HMTQLKEKFR KICDKSMIRK  60
RNCFLNEEHL KQNPRLVEHE MQTLDARQDM LVVEVPKLGK DACAKAIKEW GQPKSKITHL  120
IFTSASTTDM PGADYHCAKL LGLSPSVKRV MMYQLGCYGG GTVLRIAKDI AENNKGARVL  180
AVCCDIMACL FRGPSDSDLE LLVGQAIFGD GAAAVIVGAE PDESVGERPI FELVSTGQTI  240
LPNSEGTIGG HIREAGLIFD LHKDVPMLIS NNIEKCLIEA FTPIGISDWN SIFWITHPGG  300
KAILDKVEEK LDLKKEKFVD SRHVLSEHGN MSSSTVLFVM DELRKRSLEE GKSTTGDGFE  360
WGVLFGFGPG LTVERVVVRS VPIKYGRRAK L                                391

SEQ ID NO: 41          moltype = AA  length = 105
FEATURE                Location/Qualifiers
source                 1..105
                       mol_type = protein
                       organism = Cannabis sativa
SEQUENCE: 41
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR KLKPK                 105

SEQ ID NO: 42          moltype = AA  length = 111
FEATURE                Location/Qualifiers
REGION                 1..111
                       note = Cannabis sativa
source                 1..111
                       mol_type = protein
                       organism = synthetic construct
SEQUENCE: 42
MAVKHLIVLK FKDEITEAQK EEFFKTYVNL VNIIPAMKDV YWGKDVTQKN KEEGYTHIVE  60
VTFESVETIQ DYIIHPAHVG FGDVYRSFWE KLLIFDYTPR KLKPKGRRAK L          111

SEQ ID NO: 43          moltype = AA  length = 393
FEATURE                Location/Qualifiers
source                 1..393
                       mol_type = protein
                       organism = Cannabis sativa
SEQUENCE: 43
MGLSSVCTFS FQTNYHTLLN PHNNNPKTSL LCYRHPKTPI KYSYNNFPSK HTKSFHLQNK  60
CSESLSIAKN SIRAATTNQT EPPESDNHSV ATKILNFGKA CWKLQRPYTI IAFTSCACGL  120
FGKELLHNTN LISWSLMFKA FFFLVAILCI ASFTTTINQI YDLHIDRINK PDLPLASGEI  180
SVNTAWIMSI IVALFGLIIT IKMKGGPLYI FGYCFGIFGG IVYSVPPFRW KQNPSTAFLL  240
NFLAHIITNF TFYYASRAAL GLPFELRPSF TFLLAFMKSM GSALALIKDA SDVEGDTKFG  300
ISTLASKYGS RNLTLFCSGI VLLSYVAAIL AGIIWPQAFN SNVMLLSHAI LAFWLILQTR  360
DFALTNYDPE AGRRFYEFMW KLYYAEYLVY VFI                              393

SEQ ID NO: 44          moltype = AA  length = 321
FEATURE                Location/Qualifiers
REGION                 1..321
                       note = Cannabis sativa
```

```
source                  1..321
                        mol_type = protein
                        organism = synthetic construct
SEQUENCE: 44
MAATTNQTEP PESDNHSVAT KILNFGKACW KLQRPYTIIA FTSCACGLFG KELLHNTNLI  60
SWSLMFKAFF FLVAILCIAS FTTTINQIYD LHIDRINKPD LPLASGEISV NTAWIMSIIV  120
ALFGLIITIK MKGGPLYIFG YCFGIFGGIV YSVPPFRWKQ NPSTAFLLNF LAHIITNFTF  180
YYASRAALGL PFELRPSFTF LLAFMKSMGS ALALIKDASD VEGDTKFGIS TLASKYGSRN  240
LTLFCSGIVL LSYVAAILAG IIWPQAFNSN VMLLSHAILA FWLILQTRDF ALTNYDPEAG  300
RRFYEFMWKL YYAEYLVYVF I                                            321

SEQ ID NO: 45           moltype = AA  length = 398
FEATURE                 Location/Qualifiers
source                  1..398
                        mol_type = protein
                        organism = Cannabis sativa
SEQUENCE: 45
MGLSLVCTFS FQTNYHTLLN PHNKNPKNSL LSYQHPKTPI IKSSYDNFPS KYCLTKNFHL  60
LGLNSHNRIS SQSRSIRAGS DQIEGSPHHE SDNSIATKIL NFGHTCWKLQ RPYVVKGMIS  120
IACGLFGREL FNNRHLFSWG LMWKAFFALV PILSFNFFAA IMNQIYDVDI DRINKPDLPL  180
VSGEMSIETA WILSIIVALT GLIVTIKLKS APLFVFIYIF GIFAGFAYSV PPIRWKQYPF  240
TNFLITISSH VGLAFTSYSA TTSALGLPFV WRPAFSFIIA FMTVMGMTIA FAKDISDIEG  300
DAKYGVSTVA TKLGARNMTF VVSGVLLLNY LVSISIGIIW PQVFKSNIMI LSHAILAFCL  360
IFQTRELALA NYASAPSRQF FEFIWLLYYA EYFVYVFI                          398

SEQ ID NO: 46           moltype = AA  length = 394
FEATURE                 Location/Qualifiers
source                  1..394
                        mol_type = protein
                        organism = Cannabis sativa
SEQUENCE: 46
MGLSSVCTFS FQTNYHTLLN PHNNNPKTSL LYRHPKTPIK YSYNNFPSKH CSTKSFHLQN  60
KCSESLSIAK NSIRAATTNQ TEPPESDNHS VATKILNFGK ACWKLQRPYT IIAFTSCACG  120
LFGKELLHNT NLISWSLMFK AFFFLVAVLC IASFTTTINQ IYDLHIDRIN KPDLPLASGE  180
ISVNTAWIMS IIVALFGLII TIKMKGGPLY IFGYCFGIFG GTVYSVPPFR WKQNPSTAFL  240
LNFLAHIITN FTFYHASRAA LGLPFELRPS FTFLLAFMKS MGSALALIKD ASDVEGDTKF  300
GISTLASKYG SRNLTLFCSG IVLLSYVAAI LAGIIWPQAF NSNVMLLSHA ILAFWLILQT  360
RDFALTNYDP EAGRRFYEFM WKLYYAEYLV YVFI                              394

SEQ ID NO: 47           moltype = AA  length = 397
FEATURE                 Location/Qualifiers
source                  1..397
                        mol_type = protein
                        organism = Cannabis sativa
SEQUENCE: 47
MELSSICNFS FQTNYHTLLN PHNKNPKSSL LSHQHPKTPI ITSSYNNFPS NYCSNKNFHL  60
QNRCSKSLLI AKNSIRTDTA NQTEPPESNT KYSVVTKILS FGHTCWKLQR PYTFIGVISC  120
ACGLFGRELF HNTNLLSWSL MLKAFSSLMV ILSVNLCTNI INQITDLDID RINKPDLPLA  180
SGEMSIETAW IMSIIVALTG LILTIKLNCG PLFISLYCVS ILVGALYSVP PFRWKQNPNT  240
AFSSYFMGLV IVNFTCYYAS RAAFGLPFEM SPPFTFILAF VKSMGSALFL CKDVSDIEGD  300
SKHGISTLAT RYGAKNITFL CSGIVLLTYV SAILAAIIWP QAFKSNVMLL SHATLAFWLI  360
FQTREFALTN YNPEAGRKFY EFMWKLHYAE YLVYVFI                           397

SEQ ID NO: 48           moltype = AA  length = 400
FEATURE                 Location/Qualifiers
source                  1..400
                        mol_type = protein
                        organism = Cannabis sativa
SEQUENCE: 48
MVFSSVCSFP SSLGTNFKLV PRSNFKASSS HYHEINNFIN NKPIKFSYFS SRLYCSAKPI  60
VHRENKFTKS FSLSHLQRKS SIKAHGEIEA DGSNGTSEFN VMKSGNAIWR FVRPYAAKGV  120
LFNSAAMFAK ELVGNLNLFS WPLMFKILSF TLVILCIFVS TSGINQIYDL DIDRLNKPNL  180
PVASGEISVE LAWLLTIVCT ISGLTLTIIT NSGPFFPFLY SASIFFGFLY SAPPFRWKKN  240
PFTACFCNVM LYVGTSVGVY YACKASLGLP ANWSPAFCLL FWFISLLSIP ISIAKDLSDI  300
EGDRKFGIIT FSTKFGAKPI AYICHGLMLL NYVSVMAAAI IWPQFFNSSV ILLSHAFMAI  360
WVLYQAWILE KSNYATETCQ KYYIFLWIIF SLEHAFYLFM                        400

SEQ ID NO: 49           moltype = AA  length = 384
FEATURE                 Location/Qualifiers
source                  1..384
                        mol_type = protein
                        organism = Cannabis sativa
SEQUENCE: 49
MELSLSLGGP TIFPRYRASY TSTKLTTHFS NFPSKFSTKN FHQTLSFYGP TRGSKSLLNT  60
HQWRNSIRAC AEAGAAGSNP VLNKVSDFRD ACWRFLRPHT IRGTTLGSIA LVARALIENP  120
NLIKWSLLLK AFSGLLALIC GNGYIVGINQ IYDIGIDKVN KPYLPIAAGD LSVQSAWYLV  180
ILFAVAGLLT VGFNFGPFIT SLYCLGLVLG TIYSVPPFRM KRFPVAAFLI IATVRGFLLN  240
FGVYYATRAA LGLTFEWSSA VAFITTFVTL FALVIAITKD LPDVEGDRKF QISTFATKLG  300
VRNIAYLGSG LLLLNYIGAI AAAIYMPQAF KRNLMLPIHT ILALSLVFQA WVLEQANYTK  360
```

```
EAIAGFYRFI WNLFYVEYII FPFI                                         384

SEQ ID NO: 50          moltype = AA  length = 387
FEATURE                Location/Qualifiers
source                 1..387
                       mol_type = protein
                       organism = Cannabis sativa
SEQUENCE: 50
MAIALWLPRI SRSTTRRFLK PSSSLTLFSV SHSHNYIVTS NRSPIPRLFT VPNQSHGREW  60
VSVSEVRLGY VSHISTAGKS DENRSRDAQV ADVSWIDLYL PRQIHPYVRL ARLDKPIGTW  120
LLAWPCMWSI SLAANPGHLP DIKMMTLFGC GALLLRGAGC TINDLLDRDI DTMVERTKLR  180
PVASGIITPF QGICFLGFQL LLGLGILLQL NNYSRILGAS SLLLVFSYPL MKRLTFWPQA  240
YLGLTFNWGA LLGWAAVKGN IDPAIVLPLY ASGVFWTLVY DTIYAHQDKE DDVRVGIKST  300
ALRFGDLTKQ WNMGFGAACI SSLALSGYNA EIGWPFYASL VAASGQLAWQ ISTVDLSSRD  360
DCNKKFVSNK WFGAIIFSGI VLARISS                                      387

SEQ ID NO: 51          moltype = AA  length = 308
FEATURE                Location/Qualifiers
source                 1..308
                       mol_type = protein
                       organism = Cannabis sativa
SEQUENCE: 51
MSEAADVERV YAAMEEAAGL LGVACARDKI YPLLSTFQDT LVEGGSVVVF SMASGRHSTE  60
LDFSISVPTS HGDPYATVVE KGLFPATGHP VDDLLADTQK HLPVSMFAID GEVTGGFKKT  120
YAFFPTDNMP GVAELSAIPS MPPAVAENAE LFARYGLDKV QMTSMDYKKR QVNLYFSELS  180
AQTLEAESVL ALVRELGLHV PNELGLKFCK RSFSVYPTLN WETGKIDRLC FAVISNDPTL  240
VPSSDEGDIE KFHNYATKAP YAYVGEKRTL VYGLTLSPKE EYYKLGAYYH ITDVQRGLLK  300
AFDSLEDG                                                           308

SEQ ID NO: 52          moltype = AA  length = 852
FEATURE                Location/Qualifiers
source                 1..852
                       mol_type = protein
                       organism = Streptomyces
SEQUENCE: 52
MSEAADVERV YAAMEEAAGL LGVACARDKI YPLLSTFQDT LVEGGSVVVF SMASGRHSTE  60
LDFSISVPTS HGDPYATVVE KGLFPATGHP VDDLLADTQK HLPVSMFAID GEVTGGFKKT  120
YAFFPTDNMP GVAELSAIPS MPPAVAENAE LFARYGLDKV QMTSMDYKKR QVNLYFSELS  180
AQTLEAESVL ALVRELGLHV PNELGLKFCK RSFSVYPTLN WETGKIDRLC FAVISNDPTL  240
VPSSDEGDIE KFHNYATKAP YAYVGEKRTL VYGLTLSPKE EYYKLGAYYH ITDVQRGLLK  300
AFDSLEDGMK CSTFSFWFVC KIIFFFFSFN IQTSIANPRE NFLKCFSQYI PNNATNLKLV  360
YTQNNPLYMS VLNSTIHNLR FTSDTTPKPL VIVTPSHVSH IQGTILCSKK VGLQIRTRSG  420
GHDSEGMSYI SQVPFVIVDL RNMRSIKIDV HSQTAWVEAG ATLGEVYYWV NEKNENLSLA  480
AGYCPTVCAG GHFGGGGYGP LMRNYGLAAD NIIDAHLVNV HGKVLDRKSM GEDLFWALRG  540
GGAESFGIIV AWKIRLVAVP KSTMFSVKKI MEIHELVKLV NKWQNIAYKY DKDLLLMTHF  600
ITRNITDNQG KNKTAIHTYF SSVFLGGVDS LVDLMNKSFP ELGIKKTDCR QLSWIDTIIF  660
YSGVVNYDTD NFNKEILLDR SAGQNGAFKI KLDYVKKPIP ESVFVQILEK LYEEDIGAGM  720
YALYPYGGIM DEISESAIPF PHRAGILYEL WYICSWEKQE DNEKHLNWIR NIYNFMTPYV  780
SKNPRLAYLN YRDLDIGIND PKNPNNYTQA RIWGEKYFGK NFDRLVKVKT LVDPNNFFRN  840
EQSIPPLPRH RH                                                      852

SEQ ID NO: 53          moltype = AA  length = 573
FEATURE                Location/Qualifiers
REGION                 1..573
                       note = Cannabis sativa
source                 1..573
                       mol_type = protein
                       organism = synthetic construct
SEQUENCE: 53
MFLKHIFVAL AFALLADATP AQKRSPGFVA LDFDIVKVQK NVTANDDAAA IVAKRQTNPR  60
ENFLKCFSQY IPNNATNLKL VYTQNNPLYM SVLNSTIHNL RFTSDTTPKP LVIVTPSHVS  120
HIQGTILCSK KVGLQIRTRS GGHDSEGMSY ISQVPFVIVD LRNMRSIKID VHSQTAWVEA  180
GATLGEVYYW VNEKNENLSL AAGYCPTVCA GGHFGGGGYG PLMRNYGLAA DNIIDAHLVN  240
VHGKVLDRKS MGEDLFWALR GGGAESFGII VAWKIRLVAV PKSTMFSVKK IMEIHELVKL  300
VNKWQNIAYK YDKDLLLMTH FITRNITDNQ GKNKTAIHTY FSSVFLGGVD SLVDLMNKSF  360
PELGIKKTDC RQLSWIDTII FYSGVVNYDT DNFNKEILLD RSAGQNGAFK IKLDYVKKPI  420
PESVFVQILE KLYEEDIGAG MYALYPYGGI MDEISESAIP FPHRAGILYE LWYICSWEKQ  480
EDNEKHLNWI RNIYNFMTPY VSKNPRLAYL NYRDLDIGIN DPKNPNNYTQ ARIWGEKYFG  540
KNFDRLVKVK TLVDPNNFFR NEQSIPPLPR HRH                               573

SEQ ID NO: 54          moltype = AA  length = 543
FEATURE                Location/Qualifiers
REGION                 1..543
                       note = Cannabis sativa
source                 1..543
                       mol_type = protein
                       organism = synthetic construct
SEQUENCE: 54
MQLSLSVLST VATALLSLTT AVDAKSHNPR ENFLKCFSQY IPNNATNLKL VYTQNNPLYM  60
```

```
SVLNSTIHNL RFTSDTTPKP LVIVTPSHVS HIQGTILCSK KVGLQIRTRS GGHDSEGMSY  120
ISQVPFVIVD LRNMRSIKID VHSQTAWVEA GATLGEVYYW VNEKNENLSL AAGYCPTVCA  180
GGHFGGGGYG PLMRNYGLAA DNIIDAHLVN VHGKVLDRKS MGEDLFWALR GGGAESFGII  240
VAWKIRLVAV PKSTMFSVKK IMEIHELVKL VNKWQNIAYK YDKDLLLMTH FITRNITDNQ  300
GKNKTAIHTY FSSVFLGGVD SLVDLMNKSF PELGIKKTDC RQLSWIDTII FYSGVVNYDT  360
DNFNKEILLD RSAGQNGAFK IKLDYVKKPI PESVFVQILE KLYEEDIGAG MYALYPYGGI  420
MDEISESAIP FPHRAGILYE LWYICSWEKQ EDNEKHLNWI RNIYNFMTPY VSKNPRLAYL  480
NYRDLDIGIN DPKNPNNYTQ ARIWGEKYFG KNFDRLVKVK TLVDPNNFFR NEQSIPPLPR  540
HRH                                                                543

SEQ ID NO: 55          moltype = AA  length = 608
FEATURE                Location/Qualifiers
REGION                 1..608
                       note = Cannabis sativa
source                 1..608
                       mol_type = protein
                       organism = synthetic construct
SEQUENCE: 55
MQLSLSVLST VATALLSLTT AVDAKSHNIK LSKLSNEETL DASTFQEYTS SLANKYMNLF  60
NAAHGNPTSF GLQHVLSNQE AEVPFVTPQK GGNPRENFLK CFSQYIPNNA TNLKLVYTQN  120
NPLYMSVLNS TIHNLRFTSD TTPKPLVIVT PSHVSHIQGT ILCSKKVGLQ IRTRSGGHDS  180
EGMSYISQVP FVIVDLRNMR SIKIDVHSQT AWVEAGATLG EVYYWVNEKN ENLSLAAGYC  240
PTVCAGGHFG GGGYGPLMRN YGLAADNIID AHLVNVHGKV LDRKSMGEDL FWALRGGGAE  300
SFGIIVAWKI RLVAVPKSTM FSVKKIMEIH ELVKLVNKWQ NIAYKYDKDL LLMTHFITRN  360
ITDNQGKNKT AIHTYFSSVF LGGVDSLVDL MNKSFPELGI KKTDCRQLSW IDTIIFYSGV  420
VNYDTDNFNK EILLDRSAGQ NGAFKIKLDY VKKPIPESVF VQILEKLYEE DIGAGMYALY  480
PYGGIMDEIS ESAIPFPHRA GILYELWYIC SWEKQEDNEK HLNWIRNIYN FMTPYVSKNP  540
RLAYLNYRDL DIGINDPKNP NNYTQARIWG EKYFGKNFDR LVKVKTLVDP NNFFRNEQSI  600
PPLPRHRH                                                           608

SEQ ID NO: 56          moltype = AA  length = 523
FEATURE                Location/Qualifiers
REGION                 1..523
                       note = Cannabis sativa
source                 1..523
                       mol_type = protein
                       organism = synthetic construct
SEQUENCE: 56
MNPRENFLKC FSQYIPNNAT NLKLVYTQNN PLYMSVLNST IHNLRFTSDT TPKPLVIVTP  60
SHVSHIQGTI LCSKKVGLQI RTRSGGHDSE GMSYISQVPF VIVDLRNMRS IKIDVHSQTA  120
WVEAGATLGE VYYWVNEKNE NLSLAAGYCP TVCAGGHFGG GGYGPLMRNY GLAADNIIDA  180
HLVNVHGKVL DRKSMGEDLF WALRGGGAES FGIIVAWKIR LVAVPKSTMF SVKKIMEIHE  240
LVKLVNKWQN IAYKYDKDLL LMTHFITRNI TDNQGKNKTA IHTYFSSVFL GGVDSLVDLM  300
NKSFPELGIK KTDCRQLSWI DTIIFYSGVV NYDTDNFNKE ILLDRSAGQN GAFKIKLDYV  360
KKPIPESVFV QILEKLYEED IGAGMYALYP YGGIMDEISE SAIPFPHRAG ILYELWYICS  420
WEKQEDNEKH LNWIRNIYNF MTPYVSKNPR LAYLNYRDLD IGINDPKNPN NYTQARIWGE  480
KYFGKNFDRL VKVKTLVDPN NFFRNEQSIP PLPRHRHGRR AKL                    523

SEQ ID NO: 57          moltype = AA  length = 545
FEATURE                Location/Qualifiers
source                 1..545
                       mol_type = protein
                       organism = Cannabis sativa
SEQUENCE: 57
MNCSAFSFWF VCKIIFFFLS FNIQISIANP QENFLKCFSE YIPNNPANPK FIYTQHDQLY  60
MSVLNSTIQN LRFTSDTTPK PLVIVTPSNV SHIQASILCS KKVGLQIRTR SGGHDAEGMS  120
YISQVPFVVV DLRNMHSIKI DVHSQTAWVE AGATLGEVYY WINEKNENFS FPGGYCPTVG  180
VGGHFSGGGY GALMRNYGLA ADNIIDAHLV NVDGKVLDRK SMGEDLFWAI RGGGGENFGI  240
IAAWKIKLVA VPSKSTIFSV KKNMEIHGLV KLFNKWQNIA YKYDKDLVLM THFITKNITD  300
NHGKNKTTVH GYFSSIFHGG VDSLVDLMNK SFPELGIKKT DCKEFSWIDT TIFYSGVVNF  360
NTANFKKEIL LDRSAGKKTA FSIKLDYVKK PIPETAMVKI LEKLYEEDVG VGMYVLYPYG  420
GIMEEISESA IPFPHRAGIM YELWYTASWE KQEDNEKHIN WVRSVYNFTT PYVSQNPRLA  480
YLNYRDLDLG KTNPESPNNY TQARIWGEKY FGKNFNRLVK VKTKADPNNF FRNEQSIPPL  540
PPHHH                                                              545

SEQ ID NO: 58          moltype = AA  length = 574
FEATURE                Location/Qualifiers
REGION                 1..574
                       note = Cannabis sativa
source                 1..574
                       mol_type = protein
                       organism = synthetic construct
SEQUENCE: 58
MFLKHIFVAL AFALLADATP AQKRSPGFVA LDFDIVKVQK NVTANDDAAA IVAKRQTNPQ  60
ENFLKCFSEY IPNNPANPKF IYTQHDQLYM SVLNSTIQNL RFTSDTTPKP LVIVTPSNVS  120
HIQASILCSK KVGLQIRTRS GGHDAEGMSY ISQVPFVVVD LRNMHSIKID VHSQTAWVEA  180
GATLGEVYYW INEKNENFSF PGGYCPTVGV GGHFSGGGYG ALMRNYGLAA DNIIDAHLVN  240
VDGKVLDRKS MGEDLFWAIR GGGGENFGII AAWKIKLVAV PSKSTIFSVK KNMEIHGLVK  300
LFNKWQNIAY KYDKDLVLMT HFITKNITDN HGKNKTTVHG YFSSIFHGGV DSLVDLMNKS  360
```

```
FPELGIKKTD CKEFSWIDTT IFYSGVVNFN TANFKKEILL DRSAGKKTAF SIKLDYVKKP  420
IPETAMVKIL EKLYEEDVGV GMYVLYPYGG IMEEISESAI PFPHRAGIMY ELWYTASWEK  480
QEDNEKHINW VRSVYNFTTP YVSQNPRLAY LNYRDLDLGK TNPESPNNYT QARIWGEKYF  540
GKNFNRLVKV KTKADPNNFF RNEQSIPPLP PHHH                             574

SEQ ID NO: 59          moltype = AA  length = 544
FEATURE                Location/Qualifiers
REGION                 1..544
                       note = Cannabis sativa
source                 1..544
                       mol_type = protein
                       organism = synthetic construct
SEQUENCE: 59
MQLSLSVLST VATALLSLTT AVDAKSHNPQ ENFLKCFSEY IPNNPANPKF IYTQHDQLYM  60
SVLNSTIQNL RFTSDTTPKP LVIVTPSNVS HIQASILCSK KVGLQIRTRS GGHDAEGMSY  120
ISQVPFVVVD LRNMHSIKID VHSQTAWVEA GATLGEVYYW INEKNENFSF PGGYCPTVGV  180
GGHFSGGGYG ALMRNYGLAA DNIIDAHLVN VDGKVLDRKS MGEDLFWAIR GGGGENFGII  240
AAWKIKLVAV PSKSTIFSVK KNMEIHGLVK LFNKWQNIAY KYDKDLVLMT HFITKNITDN  300
HGKNKTTVHG YFSSIFHGGV DSLVDLMNKS FPELGIKKTD CKEFSWIDTT IFYSGVVNFN  360
TANFKKEILL DRSAGKKTAF SIKLDYVKKP IPETAMVKIL EKLYEEDVGV GMYVLYPYGG  420
IMEEISESAI PFPHRAGIMY ELWYTASWEK QEDNEKHINW VRSVYNFTTP YVSQNPRLAY  480
LNYRDLDLGK TNPESPNNYT QARIWGEKYF GKNFNRLVKV KTKADPNNFF RNEQSIPPLP  540
PHHH                                                              544

SEQ ID NO: 60          moltype = AA  length = 609
FEATURE                Location/Qualifiers
REGION                 1..609
                       note = Cannabis sativa
source                 1..609
                       mol_type = protein
                       organism = synthetic construct
SEQUENCE: 60
MQLSLSVLST VATALLSLTT AVDAKSHNIK LSKLSNEETL DASTFQEYTS SLANKYMNLF  60
NAAHGNPTSF GLQHVLSNQE AEVPFVTPQK GGNPQENFLK CFSEYIPNNP ANPKFIYTQH  120
DQLYMSVLNS TIQNLRFTSD TTPKPLVIVT PSNVSHIQAS ILCSKKVGLQ IRTRSGGHDA  180
EGMSYISQVP FVVVDLRNMH SIKIDVHSQT AWVEAGATLG EVYYWINEKN ENFSFPGGYC  240
PTVGVGGHFS GGGYGALMRN YGLAADNIID AHLVNVDGKV LDRKSMGEDL FWAIRGGGGE  300
NFGIIAAWKI KLVAVPSKST IFSVKKNMEI HGLVKLFNKW QNIAYKYDKD LVLMTHFITK  360
NITDNHGKNK TTVHGYFSSI FHGGVDSLVD LMNKSFPELG IKKTDCKEFS WIDTTIFYSG  420
VVNFNTANFK KEILLDRSAG KKTAFSIKLD YVKKPIPETA MVKILEKLYE EDVGVGMYVL  480
YPYGGIMEEI SESAIPFPHR AGIMYELWYT ASWEKQEDNE KHINWVRSVY NFTTPYVSQN  540
PRLAYLNYRD LDLGKTNPES PNNYTQARIW GEKYFGKNFN RLVKVKTKAD PNNFFRNEQS  600
IPPLPPHHH                                                         609

SEQ ID NO: 61          moltype = AA  length = 525
FEATURE                Location/Qualifiers
REGION                 1..525
                       note = Cannabis sativa
source                 1..525
                       mol_type = protein
                       organism = synthetic construct
SEQUENCE: 61
MSNPQENFLK CFSEYIPNNP ANPKFIYTQH DQLYMSVLNS TIQNLRFTSD TTPKPLVIVT  60
PSNVSHIQAS ILCSKKVGLQ IRTRSGGHDA EGMSYISQVP FVVVDLRNMH SIKIDVHSQT  120
AWVEAGATLG EVYYWINEKN ENFSFPGGYC PTVGVGGHFS GGGYGALMRN YGLAADNIID  180
AHLVNVDGKV LDRKSMGEDL FWAIRGGGGE NFGIIAAWKI KLVAVPSKST IFSVKKNMEI  240
HGLVKLFNKW QNIAYKYDKD LVLMTHFITK NITDNHGKNK TTVHGYFSSI FHGGVDSLVD  300
LMNKSFPELG IKKTDCKEFS WIDTTIFYSG VVNFNTANFK KEILLDRSAG KKTAFSIKLD  360
YVKKPIPETA MVKILEKLYE EDVGVGMYVL YPYGGIMEEI SESAIPFPHR AGIMYELWYT  420
ASWEKQEDNE KHINWVRSVY NFTTPYVSQN PRLAYLNYRD LDLGKTNPES PNNYTQARIW  480
GEKYFGKNFN RLVKVKTKAD PNNFFRNEQS IPPLPPHHHG RRAKL                 525

SEQ ID NO: 62          moltype = AA  length = 545
FEATURE                Location/Qualifiers
source                 1..545
                       mol_type = protein
                       organism = Cannabis sativa
SEQUENCE: 62
MNCSTFSFWF VCKIIFFFLS FNIQISIANP QENFLKCFSE YIPNNPANPK FIYTQHDQLY  60
MSVLNSTIQN LRFTSDTTPK PLVIVTPSNV SHIQASILCS KKVGLQIRTR SGGHDAEGLS  120
YISQVPFAIV DLRNMHTVKV DIHSQTAWVE AGATLGEVYY WINEMNENFS FPGGYCPTVG  180
VGGHFSGGGY GALMRNYGLA ADNIIDAHLV NVDGKVLDRK SMGEDLFWAI RGGGGENFGI  240
IAACKIKLVV VPSKATIFSV KKNMEIHGLV KLFNKWQNIA YKYDKDLMLT THFRTRNITD  300
NHGKNKTTVH GYFSSIFLGG VDSLVDLMNK SFPELGIKKT DCKELSWIDT TIFYSGVVNY  360
NTANFKKEIL LDRSAGKKTA FSIKLDYVKK LIPETAMVKI LEKLYEEEVG VGMYVLYPYG  420
GIMDEISESA IPFPHRAGIM YELWYTATWE KQEDNEKHIN WVRSVYNFTT PYVSQNPRLA  480
YLNYRDLDLG KTNPESPNNY TQARIWGEKY FGKNFNRLVK VKTKADPNNF FRNEQSIPPL  540
PPRHH                                                             545
```

```
SEQ ID NO: 63           moltype = DNA  length = 567
FEATURE                 Location/Qualifiers
source                  1..567
                        mol_type = other DNA
                        organism = Candida viswanathii
SEQUENCE: 63
gaggatgaag aagacgaaga cgaattggat gaagatgaag cgtatgagta ttatgagtac  60
tgtcggacgt tggaaggtgg cagagttaag cccgagaaag caaggaagga gtgggagatg  120
atgagtgatg cggccaagag gatgtgaagg ctgcgtatct gtttttgata gctggtggta  180
gccgaataga ggaaggcaag cttgttcata ttggatgatg atggtagatg gtggctgcca  240
aagtggttgt aaatagaaaa aagtgggttt gggtctgttg atagttagtg gtggcggctg  300
tctgtgatta cgtcagcaag tagcacctcg gcagttaaaa cagcagcaac agaaaaaaaa  360
tgtgtgaaag tttgattccc ccacagtcta ccacacccag agttccattt atccataata  420
tcacaagcaa tagaaaaata aaaaattatc aacaaatcac aacgaaaaga ttctgcaaaa  480
ttattttcac ttcttctttt gacttcctct tcttcttgtt aggttctttc catattttcc  540
ccttaaaccc atacacaacg cagccat                                     567

SEQ ID NO: 64           moltype = DNA  length = 529
FEATURE                 Location/Qualifiers
misc_feature            1..529
                        note = PoX4_Promoter_CV
source                  1..529
                        mol_type = other DNA
                        organism = synthetic construct
SEQUENCE: 64
gagctccaat tgtaatattt cgggagaaat atcgttgggg taaaacaaca gagagagaga  60
gggagagatg gttctggtag aattataatc tggttgttgc aaatgctact gatcgactct  120
ggcaatgtct gtagctcgct agttgtatgc aacttaggtg ttatgcatac acacggttat  180
tcggttgaat tgtggagtaa aaattgtctg agttgtgtct tagctactgg ctggcccccc  240
gcgaaagata atcaaaatta cacttgtgaa tttttgcaca cacaccgatt aacatttccc  300
ttttttgtcc accgatacac gcttgcctct tcttattttc tctgtgcttc cccctcctgt  360
gactttttcc accattgata taaaatcaac tccatttccc taaaatctcc ccagattcta  420
aaaacaactt cttctcttct gcttttcctt atttttgtta tatttattta ccatccctta  480
ttttgaatag ttattcccca ctaacattgt tcaaatcttc acgacataa              529

SEQ ID NO: 65           moltype = DNA  length = 861
FEATURE                 Location/Qualifiers
source                  1..861
                        mol_type = other DNA
                        organism = Candida viswanathii
SEQUENCE: 65
gtgccgacgg agtaacaaaa atgttacagt gcgcactact tatcccgcta aggtgataaa  60
ctgcaaaaac acaccgtcaa ggagaagtcg acgttttgcc gccacttgtg aagggaagaa  120
gagtcgttga gttgatgtaa ttaagctggc acgtagatac cagaaggttc tagagtagag  180
cttgggtggt gtttggccct gtttggacca cggatagaga tggagaatcc cttggttaga  240
gcggagagga aaaaattgaa actttgcata tcccacttca ttatccttga tgtaaccgtt  300
ttatggggta attaaagtgt ggaaaaataa tcagggagac atattcccga tcaattgggt  360
ggtggtcgct caatttctgt gagtagtagg ctcagtggtg tgtattggga ttggtagtag  420
tctgtataag cagtgttata taacccattg cttgttgatt cctattttgc tggcaaaagt  480
gacaactgta gttgtgagat aatcctcggt tattacgcct ggggggcag acagccaaag  540
ttgtgcccgt gcgacaatgg catcagaaga aacagaaaaa aaaaacacag gcatttttat  600
ccacatgcac actaccccca ctattcctgt ctgcagtgtg cttgtgtgtg gcccccgca  660
gaatcaacag ggcaaactct ggagcctgaa tctttatata aacttcaggc attggccccc  720
cttttcacaa ttcttcacat ccaccatttt ttttcttctt tcctaccata ttagtttttt  780
tttattcttt tcctacctat ctgattatta tcaaacatct ggtcatcctc aaaagaaaga  840
aagaaactat aacaatcaat c                                           861

SEQ ID NO: 66           moltype = DNA  length = 599
FEATURE                 Location/Qualifiers
source                  1..599
                        mol_type = unassigned DNA
                        organism = Candida viswanathii
SEQUENCE: 66
tggattatgt aatcacaggc tgtttctcca ttcctgcatg taggctggcc cgcggtatca  60
accatcgtcc cgcttcttct ggtttttttt ttttttccgc tatgatattt ttgatctctt  120
gggggatttg gtgggtctgc cccccccgct actacaagct caaacacccg aaaccttaca  180
acacacacac acacatcccg cttagttgcg ggttgaagaa cgtgtattcc cgtagggtta  240
atggtgtgtc ccccccctagt cacccgcttc tgccattctg ggtttgcctt caaagctggc  300
ataaatgacg aaaaaaaagc acagcatcct gcacacaacc ctgctcagtg tgacaggtgg  360
tggtgtaata gaaaacctcg gcttaaaacc tctggtcaga gcatcaactg caatcttgtc  420
tttttctgct gccctcacat tctccccaca cattccccacc ctcaagattt cacaggcaaa  480
aactgcaaat atatataaat ctacaaccaa ttctttcccc agatggaaaa tctaattttt  540
gttcaccctt tttctttctc ctgctatcac tgctactgca catattcaac accacaacc   599

SEQ ID NO: 67           moltype = DNA  length = 502
FEATURE                 Location/Qualifiers
misc_feature            1..502
                        note = TEF1_promoter_CV
source                  1..502
```

```
                         mol_type = other DNA
                         organism = synthetic construct
SEQUENCE: 67
gactgggaga acagaccaag gatgcccata caccattaat aacaagcaca ccttgataaa  60
tctctagtgt tgacaaattg gtgatttgaa catgactgta gagagagaga caagtaacca  120
ctgatggatt ggtggtggca aataaccact ttaaataaag accaactcac acacaaagac  180
agcaggtcgt gttcctattt ccaattttca caaggagaag aataaaaatt tttcaatgag  240
attaactaaa gaaacagaca ggcagcccac aagaagaaga agaagaagag gaagaggaag  300
aagaagaaga agaagaagaa gaagagaaaa aaaatttttc cctctgcgtt gcgttgggct  360
tgggttgcca gcacccacca tatataactc tcatcaaata cccagtagag aaaaattttt  420
cctccctctt tttctttctt tcttctcctt cttttgctac tctttctgtt tttcatcaaa  480
aagatatata taatcaatca tg                                          502

SEQ ID NO: 68            moltype = DNA  length = 502
FEATURE                  Location/Qualifiers
source                   1..502
                         mol_type = other DNA
                         organism = Candida viswanathii
SEQUENCE: 68
accaaacgtt actttttttt tgcaatcgga tggtatgggt ctggggttca cctgttttgt  60
aaagctacag aaggtggcat atttctctga tcaggtgttt ttttttttcgg ctgctgctgc  120
tcgtggtggt gtagtggtag tggtgtgtgt gtgtgtgtgt gcgtgcgtgt ggaaggacgc  180
tttttgctct ctgactcctc ccaatcagaa gttgctatag tggtgaaaca acaatggatg  240
ataatgcccc gggcggtgcg tgtccgacac aaaccactac attttttagc tgggagccta  300
ctgccactac gacccaccca cccatggtca acaaaaaaat tctgacaaat tataaaataa  360
cccttgaatt ccccccttgga aaaattttttg gtatttctct ctctcttttc ctttccctct  420
tctttttctc tccatcaatc aattgacgtt cagtaactca attaattaca tcacatccct  480
caattaaaga atttaaacaa tg                                          502

SEQ ID NO: 69            moltype = DNA  length = 1006
FEATURE                  Location/Qualifiers
misc_feature             1..1006
                         note = POX2_Promoter_Yl
source                   1..1006
                         mol_type = other DNA
                         organism = synthetic construct
SEQUENCE: 69
acgattccgc caagtgagac tggcgatcgg gagaagggtt ggtggtcatg gggatagaa  60
tttgtacaag tggaaaaacc actacgagta gcggatttga taccacaagt agcagagata  120
tacagcaatg gtgggagtgc aagtatcgga atgtactgta cctcctgtac tcgtactcgt  180
acggcactcg tagaaacggg gcaatacggg ggagaagcga tcgcccgtct gttcaatcgc  240
cacaagtccg agtaatgctt gagtatcgaa gtcttgtacc tccctgtcaa tcatggcacc  300
actggtcttg acttgtctat tcatactgga caagcgccag agttaagctt gtagcgaatt  360
tcgccctcgg acatcacccc atacgacgga cacacatgcc cgacaaacag cctctcttat  420
tgtagctgaa agtatattga atgtgaacgt gtacaatatc aggtaccagc gggaggttac  480
ggccaaggtg ataccggaat aaccctggct tggagatggt cggtccattg tactgaagtg  540
tccgtgtcgt ttccgtcact gccccaattg gacatgtttg tttttccgat ctttcgggcg  600
ccctctcctt gtctccttgt ctgtctcctg gactgttgct accccatttc tttggcctcc  660
attggttcct ccccgtcttt cacgtcgtct atggttgcat ggtttccctt atacttttcc  720
ccacagtcac atgttatgga ggggtctaga tggaggccta attttgacgt gcaaggggcg  780
aattggggcg agaaacacgt cgtggacatg gtgcaaggcc cgcagggttg attcgacgct  840
tttccgcgaa aaaaacaagt ccaaataccc ccgtttattc tccctcggct ctcggtattt  900
cacatgaaaa ctataaccta gactacacgg gcaaccttaa ccccagagta tacttatata  960
ccaaagggat gggtcctcaa aaatcacaca agcaacgacg ccatga                1006

SEQ ID NO: 70            moltype = DNA  length = 1004
FEATURE                  Location/Qualifiers
source                   1..1004
                         mol_type = other DNA
                         organism = Yarrowia lipolytica
SEQUENCE: 70
aaacttctcc gagtctgtgc cttcaggtgg gcatagttga tgggtgtttt gaagttaata  60
gtggggaaga actatggcaa acaagcagat gcaggcacct tgtaactgca gaccggttct  120
tgtctaccga ctccgctgca cctgtgccgc ggtacatgtc gtcacaggct gcggggttcg  180
gaggccccct tgcaacctcc tttgatagtt gctatggccc caaagagtta tacgagatag  240
acccacagat ctacttgact gttgtcacag aacctgctag gtttgcttat tgtacccgct  300
ttgtagctac tgtacaacga caacgtcaaa aattgagacg cgaacaaact ccagatgcag  360
aacccaaacc tctctctcag agtttcgagt gcttctacct cacagtaaag tggaggtgga  420
cctgcaaggg aattcagtca caaggccccg aatgtctccg aaactccaat cggaccgttt  480
aaacagacta atatcacgtc attgattgat attagcatcc ggcaagagcc gcaaggttat  540
ctcctcacca atgagcctgt tgtacggctc attccgcatc tgcggctgat tcagtttcga  600
gtggggatgg tagacttcat tgcagcattc ctaaccttct acttggtccg tggagatgtc  660
atggacatcg attttgggct gagaagcctt ttgacgatgt tgatatcact gaccgctaat  720
ttactctggc agtttctccg gctctcgagg catcgtcgat caccaaacac tatctgctag  780
tctaaatgtc cgacacgaca gcttttgatc gccgtgaacg gcgcagacct catgcaccat  840
gcaccagggc caaatcaatt acgggtcgct tagcgttgca gtcggggcat tatggtggaa  900
gttccgatac ggcacagaca cattccatag tggggggatt ggattataaa agggccatag  960
aaagccctca attgataccc aagtaccagc tctcctcact atga                  1004
```

```
SEQ ID NO: 71          moltype = DNA  length = 1367
FEATURE                Location/Qualifiers
misc_feature           1..1367
                       note = ICL1_Promoter_Yk
source                 1..1367
                       mol_type = other DNA
                       organism = synthetic construct
SEQUENCE: 71
gaccccctcc ttttgccagt atatccaccg caacacccac catgagcgac atctgatacc  60
gtgccgcgac cactacccca aataagctcc aactaatatg ccgaggcagg tgggaaacta  120
tgcactccag acgacgctgt agaagcacat ggaaggtgcg gaggcggtgg caacgagggg  180
catgagccat caacgagtaa ccacagacaa ggcaaggggg gaaacgcgac cggaatctct  240
cgcggtcacg tgacccgccc gggttccact cgtccatgtt gtgtctctgg tgtcttcggc  300
cgactcgcat tggttaaact tccaccaccg caatcacgtc ccactggcca aactttttct  360
gctttctctg actttttctg gccaaaaggc aacgtcggaa agggtcggga ggattcggaa  420
ccgacgaaaa tcggccggct ccagcggggg tagttcggca gtcctggtgg gagctctagg  480
ggagctgtgg tctgtgtagg gcgcgggtcc gggtttgttg ggtgtcaaat cacgtgtttt  540
tgcccccccg ctgagccgga ctccgacaac cgtgtctcca acggcctgac taagctgctc  600
ccagcactct gccgtagcgt tggtctgtcc tgtcgcactc tgttcaaaga cagaagaaag  660
aaaaagctaa cctccacgtc agagacaatg gtagaaggct tgttccttgc aaccgaggag  720
agtgagtgtt ctcggcacga gcatcatggg cgatctggag ggtatttttg aggggaaaaa  780
acgggatcag gacaaacaga ggccacagac cgggaatctg ggccccaaaa cggccttttc  840
ccgtcgcaaa accggtctac atacacccct tcggcccgcc acaggccggt gtgaaaaacc  900
ctaaagcttg cttcaaacca gacggacgca cagcaagaca catcatgaag agtcacctgc  960
agtatatata gatctgggga ttcccagtag actgaccaag catacaaaag tgagtatcca  1020
acagcgacac gtgagatggc agagacacag agacgtgtct acatggttgg acaagtctcc  1080
acattcgcca gagacgtatc cacatacaaa cacaatctca cagctgatct gctcctgtga  1140
cagcacagta catgttagtg gatgaggtgt tgtgtagtgg gttaaatggg tggactgatt  1200
cagtggcatc ggtggcgaca ccctctactc ttcatgtcgt cacctaccgt tcggaatccc  1260
aattatctga tgaactaaac gatttctggc caaaacacaa ttttgccaaa gaagtcgttc  1320
tcaccaatgc aagtgtcaca tcaaacatct gtcccgtact aacccag               1367

SEQ ID NO: 72          moltype = DNA  length = 1004
FEATURE                Location/Qualifiers
misc_feature           1..1004
                       note = POT1_Promoter+Yl
source                 1..1004
                       mol_type = other DNA
                       organism = synthetic construct
SEQUENCE: 72
ccacaatacc ccacagtgtg catatcaaac ctaccggttg ttgctctctc cagccttact  60
aagaaggagg cgacgtggca gtggctcgcg ggaggatcgg cgggaaactc cgggatatcc  120
gtcgagagtt tacacgtgaa tgggcagcgc aatccgttga cgacgatacg actggcaaag  180
tagcgacgat acctgccaga caggtgacat gtgcaggccg cactaacaag gaaacgggcg  240
ctggggggggg cgggcttcta gactttgccc ttgaacagga atctagtggg ggcttgtctt  300
tccgccaatg gggggagcgcc tgttgagcga ccgtgcatgc tggaacgcca agtgtatgta  360
cagctggtgt tctcgcagcg gtatgtgacg ggacttacat ctctcgtttt ttcatgacca  420
cgttttcaca ggctcggagg tacgttaaag ttttgaaggc tgcatctgaa ccgaggtatg  480
ggggagtttg aggagcaaca gtgttggggc tgagggggcc aagatcgggg caagcagagg  540
tcttagatca attgtgggaa tcccaaaggg ctcgttatca ccttttttcca cccaattcgg  600
gtcccaattg atccactact ggcttgccca agttacccca gaaatgccgc cccggatttc  660
tccaaaaacc taataagctt catggaactt ggtggaagtg actttctaca gagtggagag  720
aaccgtggac acgtggcaat ggcgctgacc gtgtccccga gccgaatcga cgtgaggggga  780
gaacggagta tctgcggtca tgtgaccttc cagagcggcg tcgccagtgt gcacgcggtg  840
acccccagtt tggttctctg tcacacgcat actacctcgg ctctccacat gctgaacttt  900
atctttcgtg ggatcatac cgaaagttgc aactaccagg tgtatataaa gcctggtaga  960
ctccccccac tttggacctc atccaaccaa gacacacaaa aatg              1004

SEQ ID NO: 73          moltype = DNA  length = 174
FEATURE                Location/Qualifiers
source                 1..174
                       mol_type = other DNA
                       organism = Candida viswanathii
SEQUENCE: 73
gagtgactct tttgataaga gtcgcaaatt tgatttcata agtatatatt cattatgtaa  60
agtagtaaat ggaaaattca ttaaaaaaaa agcaaatttc cgttgtatgc atactccgaa  120
cacaaaacta gccccggaaa aacccttagt tgatagttgc gaatttaggt cgac       174

SEQ ID NO: 74          moltype = DNA  length = 200
FEATURE                Location/Qualifiers
source                 1..200
                       mol_type = other DNA
                       organism = Candida viswanathii
SEQUENCE: 74
agctccaggc ttgttatgac tctagagaga agtgtgtgtg tttgcgtttg ttttactata  60
cattcaacat gttctttttc ttttttgata tttattccaa ctataattat acacagattc  120
gtatatactt tactttaccc tctttcgtag ttttttaatt tgatgatttt tgagtttcat  180
atccaaggtc aaaacccgac                                              200
```

```
SEQ ID NO: 75          moltype = DNA  length = 251
FEATURE                Location/Qualifiers
source                 1..251
                       mol_type = other DNA
                       organism = Yarrowia lipolytica
SEQUENCE: 75
taggcaatta acagatagtt tgccggtgat aattctctta acctcccaca ctcctttgac  60
ataacgattt atgtaacgaa actgaaattt gaccagatat tgttgtaaat agaaaatctg  120
gcttgtaggt ggcaaaatgc ggcgtctttg ttcatcaatt ccctctgtga ctactcgtca  180
tccctttatg ttcgactgtc gtatttctta ttttccatac atatgcaagt gagatgcccg  240
tgtccgaatt c                                                       251

SEQ ID NO: 76          moltype = DNA  length = 308
FEATURE                Location/Qualifiers
misc_feature           1..308
                       note = TDH3_terminator_YL
source                 1..308
                       mol_type = other DNA
                       organism = synthetic construct
SEQUENCE: 76
cttccgagta gctatccgaa gatcaagagc gaagcaagtt gtaagtccag gacatgtttc  60
ccgcccacgc gagtgattta taacacctct ctttttgac acccgctcgc cttgaaattc  120
atgtcacata aattatagtc aacgacgttt gaataacttg tcttgtagtt cgatgatgat  180
catatgatta cattaatagt aattactgta tttgatatat atactaatta caatagtaca  240
tattagaaca tacaatagtt agtgccgtga agtggcttaa aataccgcga gtcgattacg  300
taatatta                                                           308

SEQ ID NO: 77          moltype = DNA  length = 2133
FEATURE                Location/Qualifiers
misc_feature           1..2133
                       note = LEU2_Marker_Yl
source                 1..2133
                       mol_type = other DNA
                       organism = synthetic construct
SEQUENCE: 77
aacgtaccac tgtcctccac tacaaacaca cccaatctgc ttcttctagt caaggttgct  60
acaccggtaa attataaatc atcatttcat tagcagggct gggccctttt tatagagtct  120
tatacactag cggaccctgc cggtagacca acccgcaggc gcgtcagttt gctccttcca  180
tcaatgcgtc gtagaaacga cttactcctt cttgagcagc tccttgacct tgttggcaac  240
aaagtctccg acctcggagg tggaggagga gcctccgata tcggcggtag tgataccagc  300
ctcgacggac tccttgacgg cagcctcaac agcgtcaccg gcgggcttca tgttaagaga  360
gaacttgagc atcatggcgg cagacagaat ggtggcaatg gggttgacct tctgcttgcc  420
gagatcgggg gcagatccgt gacagggctc gtacagaccg aacgcctcgt tggtgtcggg  480
cagagaagcc agagaggcgg agggcagcag acccagagaa ccggggatga cggaggcctc  540
gtcggagatg atatcgccaa acatgttggt ggtgatgatg ataccattca tcttggaggg  600
ctgcttgatg aggatcatgg cggccgagtc gatcagctgg tggttgagct ccagctgggg  660
gaattcgtcc ttgaggactc gggtgacggt ctttcgccaa agtcgagagg aggccagcac  720
gttggccttg tcaagggacc acacgggaag aggggggttg tgctgaaggg ccaggaaggc  780
ggccattcgg gcaattcgct caacctcagg aacggagtaa gtctcagtgt cggaagcgac  840
gccagatccg tcatcctcct ttcgctctcc aaagtagata cctccgacga gctctcggac  900
aatgatgaag tcggtgccct caacgtttcg gatgggggag agatcggcga gcttgggcga  960
cagcagctgg cagggtcgca ggttggcgta caggttcagg tcctttcgca gcttgagaag  1020
accctgctcg ggtcgcacgt cggttcgtcc gtcgggagtg gtccatacgg tgttggcagc  1080
gcctccgaca gcaccgagca taatagagtc agcctttcgg cagatgtcga gagtagcgtc  1140
ggtgatgggc tcgccctcct tctcaatggc agctcctcca atgagtcggt cctcaaacac  1200
aaactcggtg ccggaggcct cagcaacaga cttgagcacc ttgacggcct cggcaatcac  1260
ctcggggcca cagaagtcgc cgccgagaag aacaatcttc ttggagtcag tcttggtctt  1320
cttagtttcg ggttccattg tggatgtgtg tggttgtatg tgtgatgtgg tgtgtggagt  1380
gaaaatctgt ggctggcaaa cgctcttgta tatatacgca cttttgcccg tgctatgtgg  1440
aagactaaac ctccgaagat tgtgactcag gtagtgcggt atcggctagg gacccaaacc  1500
ttgtcgatgc cgatagcgct atcgaacgta ccccagccgg ccgggagtat gtcggagggg  1560
acatacgaga tcgtcaaggg tttgtggcca actggtaaat aaatgatgac tcaggcgacg  1620
acggaattcg acagcaacta ctcctttcac caaccatgtg cattttagct cgaataacat  1680
tcacaggctt ggtgatctac atccatggtg tctggccgat taccgtggtg ttttggcagt  1740
aacgagaata ttgagtgaac tcttcccatc accaataaag actcatacta caatcacgag  1800
cgcttcagct gccactatag tgttggtgac acaataccc tcgatgctgg gcattactgt  1860
agcaagagat attatttcat ggcgcatttt ccagtctacc tgacttttta gtgtgatttc  1920
ttctccacat tttatgctca gtgtgaaaag ttggagtgca cacttaatta tcgccggttt  1980
tcggaaagta ctatgtgctc aaggttgcac cccacgttac gtatgcagca cattgagcag  2040
cctttggacc gtggagataa cggtgtggag atagcaacgg gtagtcttcg tattaattca  2100
atgcattgtt agttttatat gatatggtgt cga                               2133

SEQ ID NO: 78          moltype = DNA  length = 1142
FEATURE                Location/Qualifiers
misc_feature           1..1142
                       note = URA3_Marker_Yl
source                 1..1142
                       mol_type = other DNA
                       organism = synthetic construct
```

```
SEQUENCE: 78
tttctaattt ggaccgatag ccgtatagtc cagtctatct ataagttcaa ctaactcgta  60
actattacca taacatatac ttcactgccc cagataaggt tccgataaaa agttgtgcag  120
actaaattta tttcagtctc ctcttcacca ccaaaatgcc ctcctacgaa gcgcgagcta  180
acgtccacaa gtccgccttt gccgcccgag tgctcaagct cgtggcagcc aagaaaacca  240
acctgtgtgc ttctctggat gttaccacca ccaaggagct cattgagctt gccgataagg  300
tcggacctta tgtgtgcatg atcaagaccc atatcgacat cattgacgac ttcacctacg  360
ccggaactgt gctcccctc aaggaacttg ctcttaagca cggtttcttc ctgttcgagg  420
acagaaagtt cgcagatatt ggcaacactg tcaagcacca gtacaagaac ggtgtctacc  480
gaatcgccga gtggtccgat atcaccaacg cccacggtgt acccggaacc ggaatcattg  540
ctggcctgcg agctggtgcc gaggaaactg tctctgaaca gaagaaggag gatgtctctg  600
actacgagaa ctcccagtac aaggagttcc tggtcccctc tcccaacgag aagctggcca  660
gaggtctgct catgctggcc gagctgtctt gcaagggctc tctggccact ggcgagtact  720
ccaagcagac cattgagctt gcccgatccg accccgagtt tgtggttggc ttcattgccc  780
agaaccgacc taagggcgac tctgaggact ggcttattct gacccccggg gtgggtcttg  840
acgacaaggg agatgctctc ggacagcagt accgaactgt tgaggatgtc atgtctaccg  900
gaacggatat cataattgtc ggccgaggtc tgtacggcca gaaccgagat cctattgagg  960
aggccaagcg ataccagaag gctggctggg aggcttacca gaagattaac tgttagaggt  1020
tagactatgg atatgtcatt taactgtgta tatagagagc gtgcaagtat ggagcgcttg  1080
ttcagcttgt atgatggtca gacgacctgt ctgatcgagt atgtatgata ctgcacaacc  1140
tg                                                                1142

SEQ ID NO: 79          moltype = AA  length = 9
FEATURE                Location/Qualifiers
REGION                 1..9
                       note = FLAG
source                 1..9
                       mol_type = protein
                       organism = synthetic construct
SEQUENCE: 79
DYKDDDDKG                                                         9

SEQ ID NO: 80          moltype = AA  length = 14
FEATURE                Location/Qualifiers
source                 1..14
                       mol_type = protein
                       organism = paramyxovirus simian parainfluenza virus 5
SEQUENCE: 80
GKPIPNPLLG LDST                                                   14

SEQ ID NO: 81          moltype = AA  length = 10
FEATURE                Location/Qualifiers
source                 1..10
                       mol_type = protein
                       organism = Homo sapiens
SEQUENCE: 81
EQKLISEEDL                                                        10

SEQ ID NO: 82          moltype = AA  length = 11
FEATURE                Location/Qualifiers
source                 1..11
                       mol_type = protein
                       organism = Herpes simplex virus
SEQUENCE: 82
QPELAPEDPE D                                                      11

SEQ ID NO: 83          moltype = AA  length = 9
FEATURE                Location/Qualifiers
source                 1..9
                       mol_type = protein
                       organism = Vesicular stomatitis virus
SEQUENCE: 83
YPYDVPDYA                                                         9

SEQ ID NO: 84          moltype = AA  length = 261
FEATURE                Location/Qualifiers
source                 1..261
                       mol_type = protein
                       organism = Influenza
SEQUENCE: 84
MTKFIGCIDL HNGEVKQIVG GTLTSKKEDV PKTNFVSQHP SSYYAKLYKD RDVQGCHVIK  60
LGPNNDDAAR EALQESPQFL QVGGGINDTN CLEWLKWASK VIVTSWLFTK EGHFQLKRLE  120
RLTELCGKDR IVVDLSCRKT QDGRWIVAMN KWQTLTDLEL NADTFRELRK YTNEFLIHAA  180
DVEGLCGGID ELLVSKLFEW TKDYDDLKIV YAGGAKSVDD LKLVDELSHG KVDLTFGSSL  240
DIFGGNLVKF EDCCRWNEKQ G                                           261

SEQ ID NO: 85          moltype = AA  length = 5
FEATURE                Location/Qualifiers
VARIANT                3
```

```
                         note = Xaa = Any Amino Acid
REGION                   1..5
                         note = Cysteine-rich tag
source                   1..5
                         mol_type = protein
                         organism = synthetic construct
SEQUENCE: 85
CCXCC                                                                5

SEQ ID NO: 86            moltype = AA  length = 6
FEATURE                  Location/Qualifiers
REGION                   1..6
                         note = VSV-G
source                   1..6
                         mol_type = protein
                         organism = synthetic construct
SEQUENCE: 86
CCPGCC                                                               6

SEQ ID NO: 87            moltype = AA  length = 6
FEATURE                  Location/Qualifiers
REGION                   1..6
                         note = polyhistidine element
source                   1..6
                         mol_type = protein
                         organism = synthetic construct
SEQUENCE: 87
CCPGCC                                                               6

SEQ ID NO: 88            moltype = AA  length = 261
FEATURE                  Location/Qualifiers
source                   1..261
                         mol_type = protein
                         organism = Saccharomyces cerevisiae
SEQUENCE: 88
MTKFIGCIDL HNGEVKQIVG GTLTSKKEDV PKTNFVSQHP SSYYAKLYKD RDVQGCHVIK  60
LGPNNDDAAR EALQESPQFL QVGGGINDTN CLEWLKWASK VIVTSWLFTK EGHFQLKRLE  120
RLTELCGKDR IVVDLSCRKT QDGRWIVAMN KWQTLTDLEL NADTFRELRK YTNEFLIHAA  180
DVEGLCGGID ELLVSKLFEW TKDYDDLKIV YAGGAKSVDD LKLVDELSHG KVDLTFGSSL  240
DIFGGNLVKF EDCCRWNEKQ G                                              261

SEQ ID NO: 89            moltype = AA  length = 6
FEATURE                  Location/Qualifiers
source                   1..6
                         mol_type = protein
                         organism = Cricetulus griseus
SEQUENCE: 89
LVPRGS                                                               6

SEQ ID NO: 90            moltype = AA  length = 5
FEATURE                  Location/Qualifiers
REGION                   1..5
                         note = enterokinase
source                   1..5
                         mol_type = protein
                         organism = synthetic construct
SEQUENCE: 90
DDDDK                                                                5

SEQ ID NO: 91            moltype = AA  length = 7
FEATURE                  Location/Qualifiers
REGION                   1..7
                         note = TEV protease
source                   1..7
                         mol_type = protein
                         organism = synthetic construct
SEQUENCE: 91
ENLYFQG                                                              7

SEQ ID NO: 92            moltype = AA  length = 8
FEATURE                  Location/Qualifiers
REGION                   1..8
                         note = PreScission protease
source                   1..8
                         mol_type = protein
                         organism = synthetic construct
SEQUENCE: 92
LEVLFQGP                                                             8
```

```
SEQ ID NO: 93           moltype = DNA  length = 2130
FEATURE                 Location/Qualifiers
misc_feature            1..2130
                        note = CvACO1P Gene
source                  1..2130
                        mol_type = other DNA
                        organism = synthetic construct
SEQUENCE: 93
atgacagaag tagtagatag agcaagttcc ccagcaagtc caggatctac gaccgccgcc  60
gcagacggtg ctaaggtggc ggtggagcca cgcgtagatg tagcggccct tggcgagcag  120
ttgctagggc gatgggctga catcagattg cacgcacgag acttagcagg ccgcgaagtg  180
gtccaaaagg ttgaaggact tacgcacact gagcatcgga gtagagtctt tggacagttg  240
aagtacttgg tagacaacaa tgctgttcac agagcttttc cctccaggct aggtggatca  300
gatgaccatg gcggtaatat agctggattc gaggaattag ttactgctga tccatcattg  360
caaataaagg ccggcgttca gtggggtttg tttggttctg cagtgatgca cttgggaacc  420
cgtgaacatc atgacaagtg gttgccaggt attatgtcgt tagaaatacc ggggtgtttc  480
gcgatgacag aaaccgggca cggtagcgac gtggcctcta ttgctacaac agcaacttat  540
gatgaggaaa cccaagagtt tgttattgat accccgttca gagccgcttg gaaagattat  600
atcggtaatg cagcgaacga tggtttggcg gcagttgttt tcgcacaatt aatcacgagg  660
aaagtgaacc atggtgtaca cgccttttac gtggatctca gagatcctgc gactggagac  720
ttcctacccg gaataggagg agaggacgat ggaatcaagg ggggattgaa tggcattgac  780
aacggtagac tacattttac gaacgtacgc attcctagaa ctaatcttct taacagatat  840
ggcgatgtgg cggtcgacgg cacatacctg tcgaccatcg aatcaccagg gcgccggttc  900
tttacgatgc ttggtactct agtccagggt agagttagtc tcgatggagc agctgtcgct  960
gcactgaagg tcgcattgca aagtgcaatt cactacgctg cggagaggag acaatttaat  1020
gcgacttcac ctactgaaga agaggtcctt cttgattatc agaggcatca aaggagactc  1080
tttacacgac ttgcaacgac gtacgccgca tctttcgccc acgagcagct attgcaaaag  1140
ttcgatgatg tcttttcagg ggcacatgat accgacgccg accggcagga cttggaaacc  1200
ctagccgccg ctttgaagcc attgagcaca tggcatgcac ttgacacgtt acaagaatgc  1260
agagaggcct gtgggggggc cggatttttg atagaaaacc gtttcgcgag cttgcgtgct  1320
gacttggacg tttacgtcac attcgagggt gataacacag ttttattgca attggttgct  1380
aaacggctct tggcagacta cgcaaaagag ttcagagggg ccaacttcgg cgttcttgcc  1440
aggtatgtgg ttgaccaagc cgcgggagtg gcgctccacc gaacaggact aaggcaagtc  1500
gctcaatttg ttgcagacag cgggtccgtt cagaagtcgg ctcttgcgct tcgcgatgaa  1560
gagggtcaac gaacattgtt aacggacaga gtacagagca tggttgccga agtgggggct  1620
gccttgaaag gcgcaggcaa attaccccaa catcaagcag ctgcattgtt caaccaacac  1680
cagaacgaac ttattgaggc tgcccaggcc catgcagaac tcctccaatg ggaggcattt  1740
acagaagctc tcgctaaagt cgacgatgct ggtacaaagg aagtgcttac tcgattgcga  1800
gatctctttg gtttgtcctt gattgaaaaa cacttgctgt ggtatcttat gaatggacgt  1860
ttgtccatgc aaagaggcag gacagttgga acttacatta atcgtttact tgtcaagatc  1920
cgtccacacg cactagactt ggttgatgcc ttcggttacg gcgcggagca tttgcgtgct  1980
gctatcgcca ccggagcgga agcaacccga caggatgaag cccgaacgta ttttagacaa  2040
caacgggcat cgggactggc cccggccgat gaaaagacct tactcgctat caaagctggt  2100
aaatcaagag ggcgaagggc aaagctatga                                   2130

SEQ ID NO: 94           moltype = DNA  length = 2163
FEATURE                 Location/Qualifiers
misc_feature            1..2163
                        note = CvHXS1 Gene
source                  1..2163
                        mol_type = other DNA
                        organism = synthetic construct
SEQUENCE: 94
atgggaaaaa attataaatc tttggactca gttgtggcta gtgacttcat tgcacttggg  60
atcacatcag aagttgctga gacattgcac ggacgcttgg cagagatagt ttgcaactac  120
ggcgccgcaa cacctcagac ctggattaac atcgcaaacc atattctaag tccagatctt  180
ccatttagtc tccatcagat gttgttctac ggttgttata aggactttgg tccagcaccc  240
ccagcttgga taccagaccc cgaaaaagta aagtccacga acttaggtgc cttgttagaa  300
aagcggggaa aggagtttct aggcgttaag tataaggacc caataagtct gttttctcac  360
ttccaggagt ttagcgttcg aaatccggaa gtctactggc ggacggtact tatggatgaa  420
atgaagatac tgttcagcaa agatcccgaa tgtatcctca gacgcgacga cattaacaac  480
ccagggggct ctgagtggct accaggtgga tatctcaacc tggccaagaa ctgtttgaat  540
gtaaatagta acaaaaaact taacgacact atgatagtgt ggagagatga aggaaatgac  600
gatctcccat tgaataaatt gactcttgat caattacgaa aacgagtctg gttggttgga  660
tacgccctag aagagatggg ccttgagaag ggatgtgcga ttgcaattga catgcccatg  720
cacgtagatg cggttgtgat ctatttagct atcgtcttgg caggctacgt cgttgtctcc  780
attgcagatt cattctcagc accggaaatt tccacaagat tgcgtctatc aaaggctaag  840
gctattttta cacaagatca tatcatccga gggaaaaagc gtatacettt gtacctgcgt  900
gtcgtcgagg ccaagtctcc gatggcaata gttatcccgt gttcgggttc aaatattggt  960
gcggaattgc gggatggtga tattctgtgg gattacttct tagaacgcgc aaaggaattt  1020
aagaactgcg aatttacagc ccgtgaacag ccagtggacg cgtacacaaa tattttgttc  1080
tcatcgggaa ccaccggaga gccaaaggcg ataccatgga ctcaagctac gcctctcaag  1140
gcggctgctg atggttggtc acacttggac attagaaagg gtgacgtaat tgtatggcct  1200
accaatttgg ggtggatgat ggggccttgg ttggtctatg cttcactcct taacggggca  1260
agcatcgcat tgtataacgg atctccacta gtgtccggct ttgccaaatt cgttcaagat  1320
gcgaaagtta ctatgctagg agttgtcccc tccatcgtac gaagctggaa aagcactaat  1380
tgcgttagtg ggtacgattg gtctacaatc agatgcttct cctcatcggg tgaggcatcg  1440
aatgtcgatg aatacttatg gctaatggga agggctaact acaaaccggt catcgaaatg  1500
tgcggtggca cagagatcgg gggtgccttc agcgccggtt cgtttttaca agcccaatct  1560
```

```
ttgagtagct tctcatccca atgtatggga tgcaccttgt acattctcga caagaatggc  1620
tacccgatgc caaagaacaa gccgggtata ggtgaattgg ccttgggacc cgtgatgttc  1680
ggtgcttcca agactttact taacggaaac catcatgacg tttatttcaa aggcatgccc  1740
accttgaacg gagaagtctt gaggagacac ggagatatct tcgaactcac ttcgaacggc  1800
tattatcacg ctcatggtag agcagatgac acgatgaata tcggggggat taaaatttcc  1860
tcaatcgaga ttgaaagggt gtgtaatgaa gttgacgata gagtgtttga gactacggcc  1920
attggagtgc ctccattggg cggaggtcca gagcagctcg ttatcttttt tgttcttaag  1980
gacagcaatg atacgaccat cgacctaaac caattgcgac ttagttttaa tcttgggtta  2040
caaaagaaat tgaacccact ttttaaggtg acgagggttg tgccactttc gctgttgcct  2100
aggacagcca ccaacaaaat aatgagaaga gtgcttagac agcaatttag tcatttcgag  2160
tga                                                                2163
```

```
SEQ ID NO: 95          moltype = DNA  length = 1158
FEATURE                Location/Qualifiers
misc_feature           1..1158
                       note = CvTKS1 Gene
source                 1..1158
                       mol_type = other DNA
                       organism = synthetic construct
SEQUENCE: 95
atgaatcatt taagagcaga aggacccgca tcagtgttag cgataggtac agctaaccca  60
gagaatatct taatccaaga tgaatttcct gactactatt tccgtgttac taaatcggaa  120
catatgactc aacttaaaga gaagttccgg aaaatctgcg ataaatccat gatccgaaag  180
agaaactgtt tccttaacga agaacatctc aagcaaaacc cgaggttggt agagcacgaa  240
atgcagacct tggatgctag gcaggacatg ttggtggtcg aagtgccaaa actcggcaag  300
gacgcgtgcg ctaaggcaat caaggagtgg ggtcaaccga agtctaaaat cacgcatcta  360
atatttacat ctgcactgac aaccgacatg ccgggtgccg attatcactg cgccaagcta  420
cttggattga gtccactggt taagagagtt atgatgtatc aattggggtg ttacggaggg  480
ggcacagtcc tcagaattgc taaggatatt gcggaaaata acaagggcgc gagggtcctt  540
gctgtatgtt gtgatattat ggcctgtttg tttcgcgggc cctcggattc agatttggaa  600
ttgcttgtcg gacaggcaat ttttggtgac ggggccgcag cagtcatagt gggagccgaa  660
ccagacgaaa gcgtgggtga aagaccaatc tttgagttgg ttctgaccgg acaaacgatc  720
ttacctaact cggaaggtac gattggagga catattagag aagccggcct aattttcgat  780
cttcacaaag acgttccaat gttaatctcc aataacatag aaaagtgctt gatagaagca  840
tttactccca ttggtattag tgactggaac agcattttct ggatcaccca ccctggagga  900
aaagctatac tcgataaggt tgaagagaaa ctcgacttga aaaaggagaa attcgttgac  960
tcacgacatg tgttatcaga gcacgggaat atgagttcat ccacagtctt gttcgtaatg  1020
gatgaattgc gaaaacgctc tcttgaggag ggaaagagca caaccggtga cgggtttgag  1080
tggggcgtgc tattcggttt tggcccaggt ttgactgtcg agcgggttgt tgttcgtagt  1140
gtaccaatta agtactga                                              1158
```

```
SEQ ID NO: 96          moltype = DNA  length = 1176
FEATURE                Location/Qualifiers
misc_feature           1..1176
                       note = CvTKS1P Gene
source                 1..1176
                       mol_type = other DNA
                       organism = synthetic construct
SEQUENCE: 96
atgaatcatt taagagcaga aggacccgca tcagtgttag cgataggtac agctaaccca  60
gagaatatct taatccaaga tgaatttcct gactactatt tccgtgttac taaatcggaa  120
catatgactc aacttaaaga gaagttccgg aaaatctgcg ataaatccat gatccgaaag  180
agaaactgtt tccttaacga agaacatctc aagcaaaacc cgaggttggt agagcacgaa  240
atgcagacct tggatgctag gcaggacatg ttggtggtcg aagtgccaaa actcggcaag  300
gacgcgtgcg ctaaggcaat caaggagtgg ggtcaaccga agtctaaaat cacgcatcta  360
atatttacat ctgcactgac aaccgacatg ccgggtgccg attatcactg cgccaagcta  420
cttggattga gtccactggt taagagagtt atgatgtatc aattggggtg ttacggaggg  480
ggcacagtcc tcagaattgc taaggatatt gcggaaaata acaagggcgc gagggtcctt  540
gctgtatgtt gtgatattat ggcctgtttg tttcgcgggc cctcggattc agatttggaa  600
ttgcttgtcg gacaggcaat ttttggtgac ggggccgcag cagtcatagt gggagccgaa  660
ccagacgaaa gcgtgggtga aagaccaatc tttgagttgg ttctgaccgg acaaacgatc  720
ttacctaact cggaaggtac gattggagga catattagag aagccggcct aattttcgat  780
cttcacaaag acgttccaat gttaatctcc aataacatag aaaagtgctt gatagaagca  840
tttactccca ttggtattag tgactggaac agcattttct ggatcaccca ccctggagga  900
aaagctatac tcgataaggt tgaagagaaa ctcgacttga aaaaggagaa attcgttgac  960
tcacgacatg tgttatcaga gcacgggaat atgagttcat ccacagtctt gttcgtaatg  1020
gatgaattgc gaaaacgctc tcttgaggag ggaaagagca caaccggtga cgggtttgag  1080
tggggcgtgc tattcggttt tggcccaggt ttgactgtcg agcgggttgt tgttcgtagt  1140
gtaccaatta agtacggaag aagggcaaag ttgtga                          1176
```

```
SEQ ID NO: 97          moltype = DNA  length = 318
FEATURE                Location/Qualifiers
misc_feature           1..318
                       note = CvOAC1 Gene
source                 1..318
                       mol_type = other DNA
                       organism = synthetic construct
SEQUENCE: 97
atggcagtca aacacctaat agttctcaaa tttaaagacg agattactga agctcagaag  60
```

```
gaagagttct ttaagacata tgttaactta gtcaacatca tccccgcgat gaaggacgtc  120
tactggggca aggatgtgac gcaaaaaaat aaggaagaag gatacacaca tatcgttgag  180
gtgacctttg agagtgtgga aactattcaa gattatatta ttcacccagc ccatgtaggg  240
ttcggtgacg tttatcgatc attctgggaa aagttgctta tatttgatta caccccaaga  300
aaattgaagc ctaagtga                                                318

SEQ ID NO: 98          moltype = DNA  length = 336
FEATURE                Location/Qualifiers
misc_feature           1..336
                       note = CvOACP1 Gene
source                 1..336
                       mol_type = other DNA
                       organism = synthetic construct
SEQUENCE: 98
atggcagtca aacacctaat agttctcaaa tttaaagacg agattactga agctcagaag  60
gaagagttct ttaagacata tgttaactta gtcaacatca tccccgcgat gaaggacgtc  120
tactggggca aggatgtgac gcaaaaaaat aaggaagaag gatacacaca tatcgttgag  180
gtgacctttg agagtgtgga aactattcaa gattatatta ttcacccagc ccatgtaggg  240
ttcggtgacg tttatcgatc attctgggaa aagttgctta tatttgatta caccccaaga  300
aaattgaagc ctaagggaag acgagctaag ttgtga                            336

SEQ ID NO: 99          moltype = DNA  length = 1188
FEATURE                Location/Qualifiers
misc_feature           1..1188
                       note = CvPTS1 Gene
source                 1..1188
                       mol_type = other DNA
                       organism = synthetic construct
SEQUENCE: 99
atgggtttat cgtcagtgtg cactttttct tttcaaacaa actaccacac cctcctaaac  60
cctcacaata ataacccaaa aacctccttg ctatgttaca gacatccaaa gacaccgatc  120
aagtattcat acaacaattt tcccagtaaa cattgctcaa cgaagtcctt ccacttgcaa  180
aacaaatgca gcgaatcatt gtcgatagct aaaaactcga tacgtgcggc aaccactaac  240
caaactgagc caccagagag cgataatcat tcagtcgcca ccaagatttt gaactttgga  300
aaagcctgtt ggaaacttca aaggccttac accattatcg catttaccag ttgcgcatgt  360
ggtttgttcg ggaaggaatt attacacaac acaaatttga tcagctggag cctaatgttt  420
aaggcatttt tcttcttagt tgcaattttg tgtatagctt cgtttacaac gaccattaat  480
cagatttacg accttcacat cgatcggatc aataaaccag acttgcccct tgcctctggg  540
gaaatctctg taaatactgc atggatcatg ctgataatcg tggctttgtt tggattgatt  600
attacaatta agatgaaggg ggtccatta tatatattcg ggtactgctt cggcattttc  660
ggtggtatcg tttactccgt cccacccttt agatggaaac agaaccccag tacggccttt  720
ctactcaatt tcttggctca tatcatcaca aacttcacat tctattatgc aagccgagcg  780
gcgcttggtt tgccgttcga actcagaccg agttttacat ttctccttgc cttcatgaaa  840
ctgatgggac tggcccttgc attgatcaag gatgcgtcag atgtcgaagg cgacactaag  900
ttcggcattc tgacgcttgc ttccaagtat ggaagtagaa atctaacgct tttttgttca  960
ggaatagtgc tacttagtta tgttgctgct atactcgctg gcattatttg gcctcaggcc  1020
ttcaactcta acgtaatgtt gttatcccat gctattttgg cgttctggtt gatcttgcaa  1080
acgcgagatt ttgcactcac taactacgac ccagaggcag gaaggcgctt ttacgagttt  1140
atgtggaagt tgtattatgc cgaatacttg gtttatgttt tcatttga               1188

SEQ ID NO: 100         moltype = DNA  length = 966
FEATURE                Location/Qualifiers
misc_feature           1..966
                       note = CVPTS1dN Gene
source                 1..966
                       mol_type = other DNA
                       organism = synthetic construct
SEQUENCE: 100
atggcggcaa ccactaacca aactgagcca ccagagagcg ataatcattc agtcgccacc  60
aagattttga actttggaaa agcctgttgg aaacttcaaa ggccttacac cattatcgca  120
tttaccagtt gcgcatgtgg tttgttcggg aaggaattat tacacaacac aaatttgatc  180
agctggagcc taatgtttaa ggcatttttc ttcttagttg caattttgtg tatagcttcg  240
tttacaacga ccattaatca gatttacgac cttcacatcg atcggatcaa taaaccagac  300
ttgccccttg cctctgggga aatctctgta aatactgcat ggatcatgct gataatcgtg  360
gctttgtttg gattgattat tacaattaag atgaaggggg gtccattata tatattcggg  420
tactgcttcg gcattttcgg tggtatcgtt tactccgtcc caccctttag atggaaacag  480
aaccccagta cggcctttct actcaatttc ttggctcata tcatcacaaa cttcacattc  540
tattatgcaa gccgagcggc gcttggtttg ccgttcgaac tcagaccgag ttttacattt  600
ctccttgcct tcatgaaact gatgggactg gcccttgcat tgatcaagga tgcgtcagat  660
gtcgaaggcg acactaagtt cggcattctg acgcttgctt ccaagtatgg aagtagaaat  720
ctaacgcttt tttgttcagg aatagtgcta cttagttatg ttgctgctat actcgctggc  780
attatttggc ctcaggcctt caactctaac gtaatgttgt tatcccatgc tattttggcg  840
ttctggttga tcttgcaaac gcgagatttt gcactcacta actacgaccc agaggcagga  900
aggcgctttt acgagtttat gtggaagttg tattatgccg aatacttggt ttatgttttc  960
atttga                                                             966

SEQ ID NO: 101         moltype = DNA  length = 1197
FEATURE                Location/Qualifiers
misc_feature           1..1197
```

```
                        note = CvPTS2 Gene
source                  1..1197
                        mol_type = other DNA
                        organism = synthetic construct
SEQUENCE: 101
atggggttgt ccttagtttg tacgttcagt ttccaaacta actaccacac actactaaat  60
ccgcacaaca aaaacccgaa aaattcattg ctctcctatc agcacccaaa aacacccatt  120
atcaagtcta gttacgacaa ctttccatca aaatactgtc taacgaaaaa ctttcatttg  180
ttgggcttaa attctcataa tcgtatttcc agtcagtccc gatcgatcag ggccgggagt  240
gaccaaattg aaggttctcc acatcatgaa agtgacaatt caattgctac gaagatttta  300
aactttgggc atacatgctg gaagctacag cgaccgtatg tagttaaggg gatgatcagc  360
attgcctgcg gcctattcgg aagggaactc ttcaataata gacatctttt ttcttggggt  420
ttaatgtgga aagctttttt cgctttggtt cctatcctta gttttaactt cttcgccgct  480
attatgaatc aaatttacga tgttgacatc gaccgtatta acaaacccga tctcccccttt  540
gtttcaggcg agatgtccat tgaaacggca tggattttgt ccatcattgt tgcgcttact  600
ggcttgattg ttaccattaa gcttaaaagc gctcccttgt tcgtttttat atacattttc  660
ggcatttttg ccggattcgc atacagtgtc ccgcctatac gttggaaaca atatccattc  720
acgaacttct tgatcacgat ctcatcacat gttggattgg cctttacgtc ctacagtgct  780
accacatctg cccttggatt gcctttcgtt tggaggcctg ccttctcgtt tatcattgca  840
tttatgacag tgatgggaat gactatcgca tttgctaaag atatcagcga catagagggc  900
gatgcaaaat atggggtgag tactgttgcg acgaagttgg gcgcccgaaa tatgaccttc  960
gttgtttccg gcgttctttt acttaactat ttagtatcga ttagcatcgg gatcatctgg  1020
ccacaggtgt ttaaatcaaa tattatgatc ttgtcgcatg ccatcctagc tttctgtctt  1080
atatttcaaa caagagaatt agccctagcg aactacgcct cagcaccaag tcgtcagttc  1140
ttcgaattta tatggctact ctactacgcc gaatacttcg tctatgtctt catttag    1197

SEQ ID NO: 102          moltype = DNA  length = 1635
FEATURE                 Location/Qualifiers
misc_feature            1..1635
                        note = CvCBD1 Gene
source                  1..1635
                        mol_type = other DNA
                        organism = synthetic construct
SEQUENCE: 102
atgaagtgtt ctacgtttag tttttggttt gtttgtaaaa ttatattctt cttttttttcc  60
ttcaacattc agacatcaat cgccaaccca agggaaaact tccttaagtg ttttctgcag  120
tacatcccta acaatgcaac aaacctcaag ttggtgtaca ctcaaaacaa tccactctat  180
atgagcgtgc ttaatagcac aatccacaac ttgcgcttca cgtcagatac tacgcctaag  240
ccactagtga tcgttacacc atcacacgtc agccatattc aaggaacgat cctatgtctg  300
aaaaaggtcg ggttgcaaat caggactcga tcaggagggc acgatagtga gggaatgagt  360
tacatctcgc aagtaccctt cgtgatagtt gacttgcgaa atatgcggtc tattaaaatt  420
gacgtacata gccagaccgc ctgggttgaa gcaggggcaa ccttgggtga agtttattac  480
tgggtcaatg aaaaaaacga aaacctaagt cttgctgctg gatattgccc caccgtttgc  540
gcgggtggtc attttggagg cggcggatat ggtccgttga tgagaaatta tggacttgca  600
gcagacaata ttatagatgc ccacttggtg aacgttcatg gaaaggtctt ggaccgtaag  660
tccatgggtg aagatctttt ctgggccttg agaggtggtg gagcggaatc gtttggcatc  720
atcgttgcct ggaaaattag gttggttgcg gtcccgaaga gtacaatgtt ctccgtgaag  780
aagattatgg aaatacatga gcttgtcaag ttagttaaca agtggcaaaa tatcgcttat  840
aagtatgata aagacttgct tttgatgact cattttatta cgcgaaacat aaccgataac  900
cagggcaaga acaagactgc tattcacacg tacttctcct ctgtatttct tggaggagta  960
gactccttag ttgacttgat gaacaagagt ttcccagaat tggggattaa gaagacagat  1020
tgcagacaat tatcgtggat agatacaatc atattctata gcggtgtcgt caattacgat  1080
actgataatt ttaataaaga aatcctccta gatcgttcag ctgggcaaaa cggggcattc  1140
aaaattaaat tggattatgt gaagaaacca attccagagc tggtgtttgt tcagatattg  1200
gaaaaacttt acgaagaaga cattggcgca ggtatgtacg ctttgtatcc atatggaggc  1260
attatggacg agatctcaga gctggcgatc cccttcccgc acagagctgg gatactctac  1320
gagctatggt acatctgctc ttgggagaaa caagaagaca acgagaaaca tctcaattgg  1380
attcggaaca tatacaactt tatgacccca tacgtatcaa aaaacccgcg cttagcatac  1440
ttgaattaca gagacttaga tatcggtatc aatgatccta agaatcctaa caattacacc  1500
caagcccgta tttggggtga gaaatatttc ggcaagaatt ttgacagatt agttaaggtc  1560
aaaacactcg tggaccccaa caactttttc cgaaacgagc agtcgattcc accactaccc  1620
aggcatagac actga                                                    1635

SEQ ID NO: 103          moltype = DNA  length = 1722
FEATURE                 Location/Qualifiers
misc_feature            1..1722
                        note = CBD1dNS1
source                  1..1722
                        mol_type = other DNA
                        organism = synthetic construct
SEQUENCE: 103
atgttcttga aacacatttt tgttgctctc gcttttgcct tgttagctga cgctacccca  60
gcccagaaga gatctcccgg cttcgttgct ttagactttg acatcgtcaa ggttcaaaag  120
aacgtgactg ccaacgacga cgccgctgcc attgttgcca agagacagac caacccaagg  180
gaaaacttcc ttaagtgttt tctgcagtac atccctaaca atgcaacaaa cctcaagttg  240
gtgtacactc aaaacaatcc actctatatg agcgtgctta atagcacaat ccacaacttg  300
cgcttcacgt cagatactac gcctaagcca ctagtgatcg ttacaccatc acacgtcagc  360
catattcaag gaacgatcct atgtctgaaa aaggtcgggt tgcaaatcag gactcgatca  420
ggagggcacg atagtgaggg aatgagttac atctcgcaag tacccttcgt gatagttgac  480
```

```
ttgcgaaata tgcggtctat taaaattgac gtacatagcc agaccgcctg ggttgaagca  540
ggggcaacct tgggtgaagt ttattactgg gtcaatgaaa aaaacgaaaa cctaagtctt  600
gctgctggat attgccccac cgtttgcgcg ggtggtcatt ttggaggcgg cggatatggt  660
ccgttgatga gaaattatgg acttgcagca gacaatatta tagatgccca cttggtgaac  720
gttcatggaa aggtcttgga ccgtaagtcc atgggtgaag atcttttctg ggccttgaga  780
ggtggtggag cggaatcgtt tggcatcatc gttgcctgga aaattaggtt ggttgcggtc  840
ccgaagagta caatgttctc cgtgaagaag attatggaaa tacatgagct tgtcaagtta  900
gttaacaagt ggcaaaatat cgcttataag tatgataaag acttgctttt gatgactcat  960
tttattacgc gaaacataac cgataaccag ggcaagaaca agactgctat tcacacgtac  1020
ttctcctctg tatttcttgg aggagtagac tccttagttg acttgatgaa caagagtttc  1080
ccagaattgg ggattaagaa gacagattgc agacaattat cgtggataga tacaatcata  1140
ttctatagcg gtgtcgtcaa ttacgatact gataatttta ataaagaaat cctcctagat  1200
cgttcagctg ggcaaaacgg ggcattcaaa attaaattgg attatgtgaa gaaaccaatt  1260
ccagagctgg tgtttgttca gatattggaa aaactttacg aagaagacat tggcgcaggt  1320
atgtacgctt tgtatccata tggaggcatt atggacgaga tctcagagct ggcgatcccc  1380
ttcccgcaca gagctgggat actctacgag ctatggtaca tctgctcttg ggagaaacaa  1440
gaagacaacg agaaacatct caattggatt cggaacatat acaactttat gaccccatac  1500
gtatcaaaaa acccgcgctt agcatacttg aattacagag acttagatat cggtatcaat  1560
gatcctaaga atcctaacaa ttacacccaa gcccgtattt ggggtgagaa atatttcggc  1620
aagaattttg acagattagt taaggtcaaa acactcgtgg accccaacaa ctttttccga  1680
aacgagcagt cgattccacc actacccagg catagacact ga                     1722

SEQ ID NO: 104         moltype = DNA  length = 1632
FEATURE                Location/Qualifiers
misc_feature           1..1632
                       note = CBD1dNS2
source                 1..1632
                       mol_type = other DNA
                       organism = synthetic construct
SEQUENCE: 104
atgcaattgt cattgtcagt tttgtcaaca gttgcaacag cattgttgtc attgacaaca  60
gcagttgatg caaagtcaca taacccaagg gaaaacttcc ttaagtgttt tctgcagtac  120
atccctaaca atgcaacaaa cctcaagttg gtgtacactc aaaacaatcc actctatatg  180
agcgtgctta atagcacaat ccacaacttg cgcttcacgt cagatactac gcctaagcca  240
ctagtgatcg ttacaccatc acacgtcagc catattcaag gaacgatcct atgtctgaaa  300
aaggtcgggt tgcaaatcag gactcgatca ggagggcacg atagtgaggg aatgagttac  360
atctcgcaag taccettcgt gatagttgac ttgcgaaata tgcggtctat taaaattgac  420
gtacatagcc agaccgcctg ggttgaagca ggggcaacct tgggtgaagt ttattactgg  480
gtcaatgaaa aaaacgaaaa cctaagtctt gctgctggat attgccccac cgtttgcgcg  540
ggtggtcatt ttggaggcgg cggatatggt ccgttgatga gaaattatgg acttgcagca  600
gacaatatta tagatgccca cttggtgaac gttcatggaa aggtcttgga ccgtaagtcc  660
atgggtgaag atcttttctg ggccttgaga ggtggtggag cggaatcgtt tggcatcatc  720
gttgcctgga aaattaggtt ggttgcggtc ccgaagagta caatgttctc cgtgaagaag  780
attatggaaa tacatgagct tgtcaagtta gttaacaagt ggcaaaatat cgcttataag  840
tatgataaag acttgctttt gatgactcat tttattacgc gaaacataac cgataaccag  900
ggcaagaaca agactgctat tcacacgtac ttctcctctg tatttcttgg aggagtagac  960
tccttagttg acttgatgaa caagagtttc ccagaattgg ggattaagaa gacagattgc  1020
agacaattat cgtggataga tacaatcata ttctatagcg gtgtcgtcaa ttacgatact  1080
gataatttta ataaagaaat cctcctagat cgttcagctg ggcaaaacgg ggcattcaaa  1140
attaaattgg attatgtgaa gaaaccaatt ccagagctgg tgtttgttca gatattggaa  1200
aaactttacg aagaagacat tggcgcaggt atgtacgctt tgtatccata tggaggcatt  1260
atggacgaga tctcagagct ggcgatcccc ttcccgcaca gagctgggat actctacgag  1320
ctatggtaca tctgctcttg ggagaaacaa gaagacaacg agaaacatct caattggatt  1380
cggaacatat acaactttat gaccccatac gtatcaaaaa acccgcgctt agcatacttg  1440
aattacagag acttagatat cggtatcaat gatcctaaga atcctaacaa ttacacccaa  1500
gcccgtattt ggggtgagaa atatttcggc aagaattttg acagattagt taaggtcaaa  1560
acactcgtgg accccaacaa ctttttccga aacgagcagt cgattccacc actacccagg  1620
catagacact ga                                                      1632

SEQ ID NO: 105         moltype = DNA  length = 1827
FEATURE                Location/Qualifiers
misc_feature           1..1827
                       note = CBD1dNV1
source                 1..1827
                       mol_type = other DNA
                       organism = synthetic construct
SEQUENCE: 105
atgcaattgt ccttgtcggt tttatcaacc gttgccacgg ccttgttgtc cctaaccacc  60
gccgtcgatg ctaagtccca caacatcaag ttgtccaagt tgtccaacga agaaacattg  120
gacgcctcca cattccaaga atacacgagc tccttggcca acaagtacat gaacttgttc  180
aacgccgctc acggtaaccc aaccagcttt ggcttgcaac acgtcttgtc caaccaagaa  240
gctgaagtcc cattcgttac ccccacaaaag ggtggcaacc caagggaaaa cttccttaag  300
tgttttctgc agtacatccc taacaatgca acaaacctca agttggtgta cactcaaaac  360
aatccactct atatgagcgt gcttaatagc acaatccaca acttgcgctt cacgtcagat  420
actacgccta agccactagt gatcgttaca ccatcacacg tcagccatat tcaaggaacg  480
atcctatgtc tgaaaaaggt cgggttgcaa atcaggactc gatcaggagg gcacgatagt  540
gagggaatga gttacatctc gcaagtaccc ttcgtgatag ttgacttgcg aaatatgcgg  600
tctattaaaa ttgacgtaca tagccagacc gcctgggttg aagcaggggc aaccttgggt  660
gaagtttatt actgggtcaa tgaaaaaaac gaaaacctaa gtcttgctgc tggatattgc  720
```

```
cccaccgttt gcgcgggtgg tcattttgga ggcggcggat atggtccgtt gatgagaaat  780
tatggacttg cagcagacaa tattatagat gcccacttgg tgaacgttca tggaaaggtc  840
ttggaccgta agtccatggg tgaagatctt ttctgggcct tgagaggtgg tggagcggaa  900
tcgtttggca tcatcgttgc ctggaaaatt aggttggttg cggtcccgaa gagtacaatg  960
ttctccgtga agaagattat ggaaatacat gagcttgtca agttagttaa caagtggcaa  1020
aatatcgctt ataagtatga taaagacttg cttttgatga ctcattttat tacgcgaaac  1080
ataaccgata accagggcaa gaacaagact gctattcaca cgtacttctc ctctgtattt  1140
cttggaggag tagactcctt agttgacttg atgaacaaga gtttcccaga attggggatt  1200
aagaagacag attgcagaca attatcgtgg atagatacaa tcatattcta tagcggtgtc  1260
gtcaattacg atactgataa ttttaataaa gaaatcctcc tagatcgttc agctgggcaa  1320
aacggggcat tcaaaattaa attggattat gtgaagaaac caattccaga gctggtgttt  1380
gttcagatat tggaaaaact ttacgaagaa gacattggcg caggtatgta cgctttgtat  1440
ccatatggag gcattatgga cgagatctca gagctggcga tccccttccc gcacagagct  1500
gggatactct acgagctatg gtacatctgc tcttgggaga aacaagaaga caacgagaaa  1560
catctcaatt ggattcggaa catatacaac tttatgaccc catacgtatc aaaaaacccg  1620
cgcttagcat acttgaatta cagagactta gatatcggta tcaatgatcc taagaatcct  1680
aacaattaca cccaagcccg tatttggggt gagaaatatt tcggcaagaa ttttgacaga  1740
ttagttaagg tcaaaacact cgtggacccc aacaactttt tccgaaacga gcagtcgatt  1800
ccaccactac ccaggcatag acactga                                     1827

SEQ ID NO: 106         moltype = DNA  length = 1572
FEATURE                Location/Qualifiers
misc_feature           1..1572
                       note = CvCBD1dNP1
source                 1..1572
                       mol_type = other DNA
                       organism = synthetic construct
SEQUENCE: 106
atgaacccaa gggaaaactt ccttaagtgt tttctgcagt acatccctaa caatgcaaca  60
aacctcaagt tggtgtacac tcaaaacaat ccactctata tgagcgtgct taatagcaca  120
atccacaact tgcgcttcac gtcagatact acgcctaagc cactagtgat cgttacacca  180
tcacacgtca gccatattca aggaacgatc ctatgtctga aaaaggtcgg gttgcaaatc  240
aggactcgat caggagggca cgatagtgag ggaatgagtt acatctcgca agtacccttc  300
gtgatagttg acttgcgaaa tatgcggtct attaaaattg acgtacatag ccagaccgcc  360
tgggttgaag caggggcaac cttgggtgaa gtttattact gggtcaatga aaaaaacgaa  420
aacctaagtc ttgctgctgg atattgcccc accgtttgcg cgggtggtca ttttggaggc  480
ggcggatatg gtccgttgat gagaaattat ggacttgcag cagacaatat tatagatgcc  540
cacttggtga acgttcatgg aaaggtcttg gaccgtaagt ccatgggtga agatcttttc  600
tgggccttga gaggtggtgg agcggaatcg tttggcatca tcgttgcctg gaaaattagg  660
ttggttgcgg tcccgaagag tacaatgttc tccgtgaaga agattatgga aatacatgag  720
cttgtcaagt tagttaacaa gtggcaaaat atcgcttata agtatgataa agacttgctt  780
ttgatgactc attttattac gcgaaacata accgataacc agggcaagaa caagactgct  840
attcacacgt acttctcctc tgtatttctt ggaggagtag actccttagt tgacttgatg  900
aacaagagtt tcccagaatt ggggattaag aagacagatt gcagacaatt atcgtggata  960
gatacaatca tattctatag cggtgtcgtc aattacgata ctgataattt taataaagaa  1020
atcctcctag atcgttcagc tgggcaaaac ggggcattca aaattaaatt ggattatgtg  1080
aagaaaccaa ttccagagct ggtgtttgtt cagatattgg aaaaacttta cgaagaagac  1140
attggcgcag gtatgtacgc tttgtatcca tatggaggca ttatggacga gatctcagag  1200
ctggcgatcc ccttcccgca cagagctggg atactctacg agctatggta catctgctct  1260
tgggagaaac aagaagacaa cgagaaacat ctcaattgga ttcggaacat atacaacttt  1320
atgaccccat acgtatcaaa aaacccgcgc ttagcatact tgaattacag agacttagat  1380
atcggtatca atgatcctaa gaatcctaac aattacaccc aagcccgtat ttggggtgag  1440
aaatatttcg gcaagaattt tgacagatta gttaaggtca aaacactcgt ggaccccaac  1500
aacttttccc gaaacgagca gtcgattcca ccactaccca ggcatagaca cggaagaagg  1560
gcaaagttgt aa                                                     1572

SEQ ID NO: 107         moltype = DNA  length = 1638
FEATURE                Location/Qualifiers
misc_feature           1..1638
                       note = CvTHC1 Gene
source                 1..1638
                       mol_type = other DNA
                       organism = synthetic construct
SEQUENCE: 107
atgaattgtt cagcatttag tttttggttt gtttgtaaga ttattttctt ctttttgtca  60
tttaacattc aaatttcaat tgcaaaccca caagaaaact tttgaagtg tttttcagaa  120
tacattccaa acaatccagc taacccaaag tttatttaca cacaacatga tcaattgtac  180
atgtcagttt tgaactcaac aattcaaaac ttgagattta catcagatac cacaccaaag  240
ccattggtta ttgttacacc atcaaacgtt tcccatattc aagcatcaat cttgtgttca  300
aagaaggttg gattgcaaat tagaaccaga tcaggaggac acgatgcaga aggaatgtca  360
tacatttcac aagttccatt cgttgttgtt gatttgagaa acatgcactc aattaagatt  420
gatgttcatt cacaaacagc atgggttgaa gcaggagcaa cattgggtga agtttactac  480
tggattaacg aaaagaacga aaacttcagt tttccaggag gttactgtcc aacagttgga  540
gttggaggac atttttcagg tggaggatac ggagcattga tgagaaacta cggattggca  600
gcagataaca ttattgatgc acacttggtt aacgttgatg gaaaggtttt ggatagaaag  660
tcaatgggag aagatttgtt ttgggcaatt agaggaggtg gtggagagaa ctttggaatt  720
attgcagcat ggaagatcaa gttggttgca gttccatcaa agtcaacaat cttttcagtt  780
aagaagaaca tggaaattca tggtttggtt aagttgttta acaagtggca aaacattgca  840
tacaagtacg ataaggattt ggttttgatg acacatttta ttacaaagaa cattacagat  900
```

```
aaccatggaa agaacaagac aacagttcac ggatactttt catcaatttt tcacggagga  960
gttgattcat tggttgactt gatgaacaag tcatttccag aattgggaat caagaagaca  1020
gattgtaagg aattttcatg gattgataca acaattttct actcaggagt tgttaacttt  1080
aacacagcaa actttaagaa ggaaattttg ttggacagat cagcaggaaa gaagaccgca  1140
ttttccatta agttggatta cgttaagaaa ccaattccag aaacagcaat ggttaagatt  1200
ttggaaaagt tgtacgaaga agatgttggt gttggaatgt acgttttgta cccatacgga  1260
ggaattatgg aagaaatctc agaatcagca attccatttc cacatagagc aggtattatg  1320
tacgaattgt ggtacacagc atcatgggaa aagcaagaag ataatgaaaa gcatattaac  1380
tgggttagat cagtttacaa ctttacaaca ccatacgttt cacaaaaccc aagattggca  1440
tacttgaact acagagattt ggatttggga aagacaaacc cagaatcacc aaacaactat  1500
acacaagcta gaatttgggg agaaaagtac tttggtaaga acttcaacag attggttaaa  1560
gttaagacaa aggcagatcc aaataacttc tttagaaacg aacaatcaat tccaccattg  1620
ccaccacatc atcattaa                                                1638
```

```
SEQ ID NO: 108         moltype = DNA  length = 1728
FEATURE                Location/Qualifiers
misc_feature           1..1728
                       note = THC1dNS1 Gene
source                 1..1728
                       mol_type = other DNA
                       organism = synthetic construct
SEQUENCE: 108
atgttcttga aacacatttt tgttgctctc gcttttgcct tgttagctga cgctacccca  60
gcccagaaga gatctcccgg cttcgttgct ttagactttg acatcgtcaa ggttcaaaag  120
aacgtgactg ccaacgacga cgccgctgcc attgttgcca agagacagac caacccacaa  180
gaaaactttt tgaagtgttt ttcagaatac attccaaaca atccagctaa cccaaagttt  240
atttacacac aacatgatca attgtacatg tcagttttga actcaacaat tcaaaacttg  300
agatttacat cagataccac accaaagcca ttggttattg ttacaccatc aaacgtttcc  360
catattcaag catcaatctt gtgttcaaag aaggttggat tgcaaattag aaccagatca  420
ggaggacacg atgcagaagg aatgtcatac atttcacaag ttccattcgt tgttgttgat  480
ttgagaaaca tgcactcaat taagattgat gttcattcac aaacagcatg ggttgaagca  540
ggagcaacat tgggtgaagt ttactactgg attaacgaaa agaacgaaaa cttcagtttt  600
ccaggaggtt actgtccaac agttggagtt ggaggacatt tttcaggtgg aggatacgga  660
gcattgatga gaaactacgg attggcagca gataacatta ttgatgcaca cttggttaac  720
gttgatggaa aggttttgga tagaaagtca atgggagaag atttgttttg ggcaattaga  780
ggaggtggtg gagagaactt tggaattatt gcagcatgga agatcaagtt ggttgcagtt  840
ccatcaaagt caacaatctt ttcagttaag aagaacatgg aaattcatgg tttggttaag  900
ttgtttaaca agtggcaaaa cattgcatac aagtacgata aggatttggt tttgatgaca  960
cattttatta caaagaacat tacagataac catggaaaga acaagacaac agttcacgga  1020
tacttttcat caatttttca cggaggagtt gattcattgg ttgacttgat gaacaagtca  1080
tttccagaat tgggaatcaa gaagacagat tgtaaggaat tttcatggat tgatacaaca  1140
attttctact caggagttgt taactttaac acagcaaact ttaagaagga aattttgttg  1200
gacagatcag caggaaagaa gaccgcattt tccattaagt tggattacgt taagaaacca  1260
attccagaaa cagcaatggt taagattttg gaaaagttgt acgaagaaga tgttggtgtt  1320
ggaatgtacg ttttgtaccc atacggagga attatggaag aaatctcaga atcagcaatt  1380
ccatttccac atagagcagg tattatgtac gaattgtggt acacagcatc atgggaaaag  1440
caagaagata atgaaaagca tattaactgg gttagatcag tttacaactt tacaacacca  1500
tacgtttcac aaaacccaag attggcatac ttgaactaca gagatttgga tttgggaaag  1560
acaaacccag aatcaccaaa caactataca caagctagaa tttggggaga aaagtacttt  1620
ggtaagaact tcaacagatt ggttaaagtt aagacaaagg cagatccaaa taacttcttt  1680
agaaacgaac aatcaattcc accattgcca ccacatcatc attaataa              1728
```

```
SEQ ID NO: 109         moltype = DNA  length = 1638
FEATURE                Location/Qualifiers
misc_feature           1..1638
                       note = THC1dNS2
source                 1..1638
                       mol_type = other DNA
                       organism = synthetic construct
SEQUENCE: 109
atgcaattgt cattgtcagt tttgtcaaca gttgcaacag cattgttgtc attgacaaca  60
gcagttgatg caaagtcaca taacccacaa gaaaactttt tgaagtgttt ttcagaatac  120
attccaaaca atccagctaa cccaaagttt atttacacac aacatgatca attgtacatg  180
tcagttttga actcaacaat tcaaaacttg agatttacat cagataccac accaaagcca  240
ttggttattg ttacaccatc aaacgtttcc catattcaag catcaatctt gtgttcaaag  300
aaggttggat tgcaaattag aaccagatca ggaggacacg atgcagaagg aatgtcatac  360
atttcacaag ttccattcgt tgttgttgat ttgagaaaca tgcactcaat taagattgat  420
gttcattcac aaacagcatg ggttgaagca ggagcaacat tgggtgaagt ttactactgg  480
attaacgaaa agaacgaaaa cttcagtttt ccaggaggtt actgtccaac agttggagtt  540
ggaggacatt tttcaggtgg aggatacgga gcattgatga gaaactacgg attggcagca  600
gataacatta ttgatgcaca cttggttaac gttgatggaa aggttttgga tagaaagtca  660
atgggagaag atttgttttg ggcaattaga ggaggtggtg gagagaactt tggaattatt  720
gcagcatgga agatcaagtt ggttgcagtt ccatcaaagt caacaatctt ttcagttaag  780
aagaacatgg aaattcatgg tttggttaag ttgtttaaca agtggcaaaa cattgcatac  840
aagtacgata aggatttggt tttgatgaca cattttatta caaagaacat tacagataac  900
catggaaaga acaagacaac agttcacgga tacttttcat caatttttca cggaggagtt  960
gattcattgg ttgacttgat gaacaagtca tttccagaat tgggaatcaa gaagacagat  1020
tgtaaggaat tttcatggat tgatacaaca attttctact caggagttgt taactttaac  1080
acagcaaact ttaagaagga aattttgttg gacagatcag caggaaagaa gaccgcattt  1140
```

```
tccattaagt tggattacgt taagaaacca attccagaaa cagcaatggt taagattttg  1200
gaaaagttgt acgaagaaga tgttggtgtt ggaatgtacg ttttgtaccc atacggagga  1260
attatggaag aaatctcaga atcagcaatt ccatttccac atagagcagg tattatgtac  1320
gaattgtggt acacagcatc atgggaaaag caagaagata atgaaaagca tattaactgg  1380
gttagatcag tttacaactt tacaacacca tacgtttcac aaaacccaag attggcatac  1440
ttgaactaca gagatttgga tttgggaaag acaaacccag aatcaccaaa caactataca  1500
caagctagaa tttggggaga aaagtacttt ggtaagaact tcaacagatt ggttaaagtt  1560
aagacaaagg cagatccaaa taacttcttt agaaacgaac aatcaattcc accattgcca  1620
ccacatcatc attaataa                                                1638
```

```
SEQ ID NO: 110          moltype = DNA  length = 1833
FEATURE                 Location/Qualifiers
misc_feature            1..1833
                        note = THC1dNV1
source                  1..1833
                        mol_type = other DNA
                        organism = synthetic construct
SEQUENCE: 110
atgcaattgt ccttgtcggt tttatcaacc gttgccacgg ccttgttgtc cctaaccacc  60
gccgtcgatg ctaagtccca caacatcaag ttgtccaagt tgtccaacga agaaacattg  120
gacgcctcca cattccaaga atacacgagc tccttggcca acaagtacat gaacttgttc  180
aacgccgctc acggtaaccc aaccagcttt ggcttgcaac acgtcttgtc caaccaagaa  240
gctgaagtcc cattcgttac cccacaaaag ggtggcaacc cacaagaaaa ctttttgaag  300
tgtttttcag aatacattcc aaacaatcca gctaacccaa agtttattta cacacaacat  360
gatcaattgt acatgtcagt tttgaactca acaattcaaa acttgagatt tacatcagat  420
accacaccaa agccattggt tattgttaca ccatcaaacg tttcccatat tcaagcatca  480
atcttgtgtt caaagaaggt tggattgcaa attagaacca gatcaggagg acacgatgca  540
gaaggaatgt catacatttc acaagttcca ttcgttgttg ttgatttgag aaacatgcac  600
tcaattaaga ttgatgttca ttcacaaaca gcatgggttg aagcaggagc aacattgggt  660
gaagtttact actggattaa cgaaaagaac gaaaacttca gttttccagg aggttactgt  720
ccaacagttg gagttggagg acatttttca ggtggaggat acggagcatt gatgagaaac  780
tacggattgg cagcagataa cattattgat gcacacttgg ttaacgttga tggaaaggtt  840
ttggatagaa agtcaatggg agaagatttg ttttgggcaa ttagaggagg tggtggagag  900
aactttggaa ttattgcagc atggaagatc aagttggttg cagttccatc aaagtcaaca  960
atcttttcag ttaagaagaa catggaaatt catggtttgg ttaagttgtt taacaagtgg  1020
caaaacattg catacaagta cgataaggat ttggttttga tgacacattt tattacaaag  1080
aacattacag ataaccatgg aaagaacaag acaacagttc acggatactt ttcatcaatt  1140
tttcacggag gagttgattc attggttgac ttgatgaaca agtcatttcc agaattggga  1200
atcaagaaga cagattgtaa ggaattttca tggattgata caacaatttt ctactcagga  1260
gttgttaact ttaacacagc aaactttaag aaggaaattt tgttggacag atcagcagga  1320
aagaagaccg cattttccat taagttggat tacgttaaga aaccaattcc agaaacagca  1380
atggttaaga ttttggaaaa gttgtacgaa gaagatgttg gtgttggaat gtacgttttg  1440
tacccatacg gaggaattat ggaagaaatc tcagaatcag caattccatt tccacataga  1500
gcaggtatta tgtacgaatt gtggtacaca gcatcatggg aaaagcaaga agataatgaa  1560
aagcatatta actgggttag atcagtttac aactttacaa caccatacgt ttcacaaaac  1620
ccaagattgg catacttgaa ctacagagat ttggatttgg gaaagacaaa cccagaatca  1680
ccaaacaact atacacaagc tagaatttgg ggagaaaagt actttggtaa gaacttcaac  1740
agattggtta aagttaagac aaaggcagat ccaaataact tctttagaaa cgaacaatca  1800
attccaccat tgccaccaca tcatcattaa taa                              1833
```

```
SEQ ID NO: 111          moltype = DNA  length = 1638
FEATURE                 Location/Qualifiers
misc_feature            1..1638
                        note = CvCBC1 Gene
source                  1..1638
                        mol_type = other DNA
                        organism = synthetic construct
SEQUENCE: 111
atgaattgta gcactttctc attctggttt gtttgtaaga ttattttctt tttcttgtca  60
tttaacattc aaatttcaat tgcaaaccca caagagaact tttgaagtg tttctcagaa  120
tacattccaa acaacccagc taacccaaag tttatttaca cccaacacga tcaattgtac  180
atgtcagttt tgaactcaac aattcaaaac ttgagattta catcagatac aacaccaaag  240
ccattggtta ttgttacacc atcaaacgtt agtcatattc aagcatcaat cttgtgttca  300
aagaaggttg gattgcaaat tagaactaga tcaggaggac atgatgcaga aggattgtca  360
tacatttcac aagttccatt tgcaattgtt gatttgagaa acatgcacac agttaaggtt  420
gatattcatt cacaaacagc atgggttgaa gcaggagcaa cattgggtga agtttactac  480
tggattaacg aaatgaacga aaacttctca tttccaggag gatactgtcc aacagttggt  540
gttggaggac acttttcagg tggtggatac ggagcattga tgagaaacta cggattggca  600
gcagataaca ttattgatgc acatttggtt aacgttgatg gaaaggtttt ggatagaaag  660
tcaatgggag aagatttgtt ttgggcaatt agaggaggtg gaggagaaaa ctttggaatc  720
attgcagcat gtaagatcaa gttggttgtt gttccatcaa aggcaacaat cttttcagtt  780
aagaagaaca tggaaatcca tggattggtt aagttgttta acaagtggca aaacattgca  840
tacaagtacg ataaggattt gatgttgaca acacatttta gaacaagaaa cattacagat  900
aaccacggaa agaataagac aacagttcat ggatactttt catcaatttt cttgggagga  960
gttgattcat tggttgactt gatgaacaag agttttccag aattgggaat caagaagaca  1020
gattgtaagg aattgtcatg gatcgataca accattttct actcaggagt tgttaactac  1080
aacacagcta actttaagaa ggaaattttg ttggacagat cagcaggtaa aaagacagca  1140
ttttcaatta agttggatta cgttaagaaa ttgattccag aaacagcaat ggttaagatt  1200
ttggaaaagt tgtacgaaga agaagttgga gttggaatgt acgttttgta cccatacgga  1260
```

```
ggaattatgg atgaaatttc agaatcagca attccatttc cacatagagc aggtattatg  1320
tacgaattgt ggtacacagc aacatgggaa aagcaagaag ataacgaaaa gcatattaac  1380
tgggttagat cagtttacaa ctttacaacc ccatacgttt cacaaaaccc aagattggca  1440
tacttgaact acagagattt ggatttggga aagacaaacc cagaatcacc aaataactac  1500
acacaagcta gaatttgggg agaaaagtac tttggtaaga actttaacag attggtgaag  1560
gttaagacaa aggcagaccc aaacaatttc tttagaaacg aacaatcaat tccaccattg  1620
ccaccaagac atcattaa                                                1638

SEQ ID NO: 112          moltype = DNA  length = 2130
FEATURE                 Location/Qualifiers
misc_feature            1..2130
                        note = YlACO1P Gene
source                  1..2130
                        mol_type = other DNA
                        organism = synthetic construct
SEQUENCE: 112
atgaccgaag tagttgacag agcctcatcc cccgcatccc ctggctcaac tacggccgcc  60
gcagacggtg ctaaggtggc cgtcgagccc cgagtagatg tggctgcgct gggagagcag  120
ctgctgggcc gatgggctga tatccgtctc cacgcccggg accttgcggg acgagaggta  180
gttcagaagg tggagggtct gactcataca gagcaccgct ctcgcgtctt tggccagctc  240
aagtacttgg tcgataacaa cgcagttcac cgagcctttc cttctcgact gggtggtagt  300
gacgaccacg gcggaaacat cgctggtttt gaggagcttg tcacggcgga cccctccctc  360
cagatcaagg ccggcgtcca gtggggactg ttcggctccg ctgttatgca cttgggaact  420
agggagcacc acgacaagtg gctcccaggc atcatgtctc tggaaatccc tggttgcttt  480
gccatgactg agactggcca tggctccgat gtcgcttcca ttgctacaac ggccacctat  540
gatgaggaaa cccaggagtt cgttattgac accccgttcc gagccgcctg gaaggactac  600
attggaaacg ccgctaacga cggtttggcc gctgtcgtgt ttgcccaact gattactcga  660
aaggttaacc atggagtgca cgccttctac gtcgatctga gagatcccgc caccggagac  720
tttctccctg gtattggtgg agaggacgac ggtattaagg ggggactaaa cggaattgat  780
aacggacgtc tccatttcac caatgttcgc attccccgaa ccaacctgct taaccgttac  840
ggcgatgttg ccgtcgatgg cacctacagc tcaaccatcg aatctccggg gcgaagattc  900
tttacaatgc taggtacgct ggtccagggc cgagtcagcc tggacggtgc tgcagtggct  960
gcatcgaagg ttgctctgca atccgccatc cactacgccg ctgagcgaag acagttcaac  1020
gccacttcgc ccacagagga ggaggtgctc ctggattacc agcgacacca gcggcgcctc  1080
tttacccgac tcgccaccac ctacgccgca tcgttcgccc atgagcaact gctgcagaaa  1140
ttcgacgacg tgttctcggg tgctcatgat actgacgccg accgtcagga ccttgagaca  1200
ctggctgctg ctctgaagcc cctttctacc tggcatgctc tcgataccct acaagagtgc  1260
cgagaagcgt gtgggggtgc aggttttctg attgagaacc gattcgcttc tctccgggcc  1320
gatctcgacg tctacgtgac cttcgaagga gacaacaccg tgcttcttca gttggtggcc  1380
aagaggctgc tcgctgacta tgctaaggag ttccgaggtg ccaacttcgg cgtgctcgcg  1440
cggtacgtcg tggaccaggc tgccggagtc gcgctacacc gaaccggact gcgacaggtc  1500
gctcagttcg tggccgacag tggatctgtc cagaaatctg ctcttgccct ccgagacgaa  1560
gaaggtcagc gaactctgct gaccgacaga gtccagtcca tggttgcaga ggttggcgct  1620
gctctcaaag gcgcgggcaa gctcccccag caccaggcgg cagcactgtt caatcagcat  1680
caaaacgaac tgatcgaggc tgcccaggcc cacgctgagc ttttacagtg ggaggccttt  1740
actgaggctt tggccaaggt ggacgacgct ggcactaagg aagtgttgac ccgattgcgt  1800
gaccttttg gtctgtccct tatcgagaag cacctcagct ggtatctgat gaacggtagg  1860
ctctcgatgc agagaggccg aacggtcggc acttacatta atcgtcttct cgttaagatc  1920
cgaccacacg cacttgatct ggttgatgcc ttcggctacg gagccgagca ccttcgggcc  1980
gctatcgcca ccggcgctga ggccacccga caggacgagg cccgaaccta cttcagacag  2040
caacgagcct ccggtagcgc ccctgctgac gagaagacac tcctcgctat caaggccggc  2100
aagtctcggg gacgacgagc caaactgtaa                                   2130

SEQ ID NO: 113          moltype = DNA  length = 2163
FEATURE                 Location/Qualifiers
misc_feature            1..2163
                        note = YlHXS1 Gene
source                  1..2163
                        mol_type = other DNA
                        organism = synthetic construct
SEQUENCE: 113
atgggaaaga attacaaaag tctagattct gtcgttgcca gtgacttcat cgcgttaggc  60
attacatccg aggtcgctga gactctgcac ggacggcttg ccgagattgt gtgcaactac  120
ggagccgcta cccctcagac ttggattaac atcgccaacc acattctgtc gccggacctc  180
cccttctctt tgcaccagat gttattctac ggatgctaca aggattttgg ccctgcacct  240
cctgcctgga ttccggaccc cgaaaaagtc aagtccacca acctaggtgc cctgctggaa  300
aagcgaggaa aggagttcct tggtgtcaag tacaaggacc ccatttcttc tttttctcat  360
ttccaggaat tttcggtgcg taatcctgag gtgtattggc gaactgtgct catggacgag  420
atgaaaatct ccttcagcaa ggacccagag tgtatcctgc gacgagacga cattaacaac  480
ccaggaggct cggagtggct tcccggcgga tacctaaact cagctaagaa ttgtctcaac  540
gtgaactcta acaagaagtt gaacgacacc atgatcgtgt ggcgtgacga aggcaacgac  600
gacctgcccc tgaacaagtt gactctggac cagctgcgaa agagggtctg gttggttggc  660
tacgccctcg aagagatggg cttagagaag ggttgcgcta ttgctattga tatgcccatg  720
cacgtcgatg ctgtagtgat ctaccttgcc attgtgttag ccggttacgt ggtcgtatcg  780
attgccgatt cgttctccgc tccggagatt tccacccgac tcagacttag caaggccaag  840
gcaatcttta ctcaagatca catcatccga ggtaagaaga gaatccctct ctattctcgc  900
gtggttgagg ccaagtcccc aatggctatc gtcatacctt gcagcggatc aaacatcggg  960
gctgagctac gggacggtga tatctcctgg gattacttcc tggagcgagc caaagagttc  1020
aagaactgcg agtttacagc gcgtgagcag cccgtcgatg cctacacgaa cattctattc  1080
```

```
tcatcgggca caacgggaga gcccaaggcc atcccctgga cccaagctac ccccttgaaa  1140
gctgccgctg atggttggtc ccatctcgac atcagaaaag gcgatgtgat cgtttggccc  1200
actaacctgg gctggatgat gggtccttgg ctggtatatg ccagcctact gaacggcgct  1260
tcaatcgcac tgtacaacgg atctccactc gtcagcggct ttgccaagtt tgttcaagac  1320
gccaaagtca ccatgctggg tgttgttcct tcaatcgtgc gaagttggaa gagtaccaac  1380
tgtgtctctg gatacgactg gagcaccatt cgatgcttca gttcctccgg cgaggcttcc  1440
aacgttgatg agtacctctg gcttatgggt cgtgcgaatt acaagcctgt gatcgagatg  1500
tgtggtggaa cagaaattgg tggtgctttt tcggccgggt cctttcttca ggctcagtct  1560
ctctcctctt tctcttccca gtgtatggga tgcaccctgt atattctcga caagaacggt  1620
taccccatgc cgaagaataa acccggtatt ggggagcttg ctcttggccc cgtcatgttt  1680
ggtgcatcga agaccctcct gaacggaaac catcacgacg tctacttcaa gggcatgccc  1740
acacttaacg gcgaagttct tcggcgacat ggagacattt tcgaacttac atcgaacgga  1800
tactaccacg cccacgggcg agcagatgat acgatgaaca tcgggggcat caagatatct  1860
tctatcgaga ttgaaagagt gtgtaacgag gtagacgacc gcgtcttcga gactactgcg  1920
atcggcgtcc ccccccctggg cggtggcccg gagcagctag tcattttttt tgtgctcaag  1980
gactctaacg acacgaccat cgacctcaat cagctgcgac tctccttcaa ccttggattg  2040
cagaagaagc tgaaccctct cttcaaggtc actcgggttg ttcccttgtc ctctcttcct  2100
cgaaccgcca ccaacaagat tatgcgacga gtgctccgac agcagttctc ccacttcgag  2160
taa                                                                2163

SEQ ID NO: 114          moltype = DNA  length = 1158
FEATURE                 Location/Qualifiers
misc_feature            1..1158
                        note = YlTKS1 Gene
source                  1..1158
                        mol_type = other DNA
                        organism = synthetic construct
SEQUENCE: 114
atgaatcatc taagagccga aggaccagca agtgtactcg ctattggtac tgctaacccc  60
gagaacattc ttattcagga tgagttcccg gactactatt tcagggttac caagagcgag  120
catatgaccc agcttaaaga gaagttccgc aagatatgcg acaagtccat gatccgaaag  180
cggaactgct ttctcaatga ggagcacttg aagcaaaacc cccgactggt tgagcacgag  240
atgcagacct tggacgcgcg acaagacatg ctcgtcgtcg aggtgcccaa actcggtaag  300
gatgcttgcg ctaaggccat taaggagtgg ggtcagccca agtcgaagat tacccaccta  360
atcttcacct ccgcaagcac tacagacatg cccggtgcag actaccactg tgccaagctg  420
ctcggactgt caccgtcggt caagcgagtg atgatgtacc agctcggctg ttacgggggt  480
ggaaccgttc tccgtatcgc caaggatatc gctgagaaca acaaaggagc tcgtgtcctg  540
gctgtgtgtt gcgacatcat ggcctgcttg ttcagaggcc ctagtgattc cgatctggaa  600
ttacttgtcg gtcaggccat ctttggagat ggcgccgccg ctgtcatcgt gggtgccgaa  660
cccgacgagt ctgttggaga aagacccatc tttgagcttg tctccacggg ccagaccatc  720
ctccctaaca gcgagggcac aattggaggc catattcgag aggccggtct gatttttgac  780
ctgcataagg acgtgcctat gctgatttcg aacaacatcg agaagtgtct catcgaggcc  840
ttcactccca tcggcatttc ggactggaac tcaatcttct ggatcaccca cccaggaggc  900
aaggcgattc tggataaagt tgaggaaaag ctcgacctta agaaggagaa gtttgtggat  960
tctcgacacg tcctgtctga acacggtaac atgtcttcct ctactgtcct gttcgtaatg  1020
gacgagcttc gaaagcgatc tctggaggaa ggaaagtcca cgaccggcga cggttttgag  1080
tggggcgtgc tgttcgggtt cggtcctggc ctcactgtgg agcgagttgt tgtccggtcc  1140
gtgcctatta agtactaa                                                1158

SEQ ID NO: 115          moltype = DNA  length = 1176
FEATURE                 Location/Qualifiers
misc_feature            1..1176
                        note = YlTKS1P Gene
source                  1..1176
                        mol_type = other DNA
                        organism = synthetic construct
SEQUENCE: 115
atgaatcatc taagagccga aggaccagca agtgtactcg ctattggtac tgctaacccc  60
gagaacattc ttattcagga tgagttcccg gactactatt tcagggttac caagagcgag  120
catatgaccc agcttaaaga gaagttccgc aagatatgcg acaagtccat gatccgaaag  180
cggaactgct ttctcaatga ggagcacttg aagcaaaacc cccgactggt tgagcacgag  240
atgcagacct tggacgcgcg acaagacatg ctcgtcgtcg aggtgcccaa actcggtaag  300
gatgcttgcg ctaaggccat taaggagtgg ggtcagccca agtcgaagat tacccaccta  360
atcttcacct ccgcaagcac tacagacatg cccggtgcag actaccactg tgccaagctg  420
ctcggactgt caccgtcggt caagcgagtg atgatgtacc agctcggctg ttacgggggt  480
ggaaccgttc tccgtatcgc caaggatatc gctgagaaca acaaaggagc tcgtgtcctg  540
gctgtgtgtt gcgacatcat ggcctgcttg ttcagaggcc ctagtgattc cgatctggaa  600
ttacttgtcg gtcaggccat ctttggagat ggcgccgccg ctgtcatcgt gggtgccgaa  660
cccgacgagt ctgttggaga aagacccatc tttgagcttg tctccacggg ccagaccatc  720
ctccctaaca gcgagggcac aattggaggc catattcgag aggccggtct gatttttgac  780
ctgcataagg acgtgcctat gctgatttcg aacaacatcg agaagtgtct catcgaggcc  840
ttcactccca tcggcatttc ggactggaac tcaatcttct ggatcaccca cccaggaggc  900
aaggcgattc tggataaagt tgaggaaaag ctcgacctta agaaggagaa gtttgtggat  960
tctcgacacg tcctgtctga acacggtaac atgtcttcct ctactgtcct gttcgtaatg  1020
gacgagcttc gaaagcgatc tctggaggaa ggaaagtcca cgaccggcga cggttttgag  1080
tggggcgtgc tgttcgggtt cggtcctggc ctcactgtgg agcgagttgt tgtccggtcc  1140
gtgcctatta agtacggaag aagggcaaag ttgtaa                            1176

SEQ ID NO: 116          moltype = DNA  length = 318
```

```
FEATURE                 Location/Qualifiers
misc_feature            1..318
                        note = YlOAC1 Gene
source                  1..318
                        mol_type = other DNA
                        organism = synthetic construct
SEQUENCE: 116
atggccgtca aacaccttat tgtcctcaag ttcaaagatg agatcactga agcccagaag  60
gaggagtttt tcaagaccta cgtcaatttg gtcaacatca ttccagcaat gaaggatgtg  120
tactggggca aggacgtgac ccagaagaac aaggaagagg gttataccca tatcgttgag  180
gttacgttcg agtctgtgga gacaatccaa gactacatca ttcaccccgc tcacgtgggc  240
tttggagacg tttacagatc cttctgggag aagctcctga tttttgacta cactcctcga  300
aagctgaagc ccaagtaa                                                 318

SEQ ID NO: 117          moltype = DNA  length = 336
FEATURE                 Location/Qualifiers
misc_feature            1..336
                        note = YlOAC1P Gene
source                  1..336
                        mol_type = other DNA
                        organism = synthetic construct
SEQUENCE: 117
atggccgtca aacaccttat tgtcctcaag ttcaaagatg agatcactga agcccagaag  60
gaggagtttt tcaagaccta cgtcaatttg gtcaacatca ttccagcaat gaaggatgtg  120
tactggggca aggacgtgac ccagaagaac aaggaagagg gttataccca tatcgttgag  180
gttacgttcg agtctgtgga gacaatccaa gactacatca ttcaccccgc tcacgtgggc  240
tttggagacg tttacagatc cttctgggag aagctcctga tttttgacta cactcctcga  300
aagctgaagc ccaagggaag aagggcaaag ttgtaa                             336

SEQ ID NO: 118          moltype = DNA  length = 1197
FEATURE                 Location/Qualifiers
misc_feature            1..1197
                        note = YlPTS2 Gene
source                  1..1197
                        mol_type = other DNA
                        organism = synthetic construct
SEQUENCE: 118
atgggcctct ctctagtatg taccttctct ttccagacca actatcacac tctactgaac  60
ccccataaca agaaccctaa aaattctctt ctcagttacc agcaccccaa gacgcctatc  120
attaagtcct cctacgacaa ctttccctct aagtactgcc tgaccaaaaa cttccatctc  180
ctgggactga actctcataa cagaattagt agccagtccc gatctatccg agctggctct  240
gaccagattg agggctcccc tcaccatgaa tccgacaaca gcatcgctac caagattttg  300
aattttggtc acacatgctg gaagctccag cgaccgtacg tcgtgaaggg tatgatctcg  360
attgcctgtg gactgttcgg acgtgagctt tttaataatc gacacttgtt ttcatggggc  420
ctcatgtgga aggctttttt cgccctcgtg cccattctgt ctttcaactt ctttgccgct  480
attatgaacc aaatctacga cgttgatatt gataggatca acaagcctga cctgccgctc  540
gtctcggggg agatgtctat cgagacagcg tggattcttt cgattatcgt cgcgctgact  600
ggccttatcg ttaccataaa gttgaagtct gcacccctct tcgtgtttat ctacattttc  660
ggtatttttg ctggattcgc gtactccgtt ccccctatca gatggaagca gtacccctt  720
actaactttc tgattactat cagcagccac gtcggtttag cctttacctc atattcggcc  780
accaccagtg cactgggcct ccccttcgtc tggcgacctg cattttcatt catcatcgcc  840
ttcatgactg tgatgggtat gaccatcgct ttcgctaagg acatctccga catcgagggt  900
gatgctaaat atggagtgtc caccgtggcc actaagctgg gagcccggaa catgacgttc  960
gtcgtctctg gtgttctgct ccttaactac ttggtttcga tctccattgg cattatctgg  1020
ccacaagtct tcaagtccaa cattatgatt ctgtcccacg ccattcttgc cttttgcctg  1080
atcttccaga cacgcgaact cgctctcgct aactacgcct ccgccccatc gcgacagttc  1140
ttcgagttca tctggctgct ttactacgcc gagtacttcg tttacgtgtt catctaa      1197

SEQ ID NO: 119          moltype = DNA  length = 1635
FEATURE                 Location/Qualifiers
misc_feature            1..1635
                        note = YlCBD1 Gene
source                  1..1635
                        mol_type = other DNA
                        organism = synthetic construct
SEQUENCE: 119
atgaagtgtt cgacgttttc tttttggttt gtttgtaaaa tcatttttctt tttcttttct  60
ttcaacatcc aaacgtcgat cgcaaaccct agagagaact ttcttaagtg cttctcgcag  120
tacatcccta ataacgctac caaccttaag ctggtgtaca cccagaacaa ccctctttac  180
atgtctgttc taaacagcac catccacaat cttagattca catcagacac cactcccaag  240
ccgctcgtca tcgtgacccc gagtcatgtg tcccatatcc aaggcactat cctgtgctct  300
aaaaaggtcg gtctgcagat tcggactcgc tccggtggac atgattcgga gggcatgtcc  360
tacattagcc aggtcccctt tgtgatcgtg gacctgagga acatgcggtc tattaagatt  420
gatgtgcact cacagaccgc ttgggtcgag gctggtgcga cattgggtga ggtgtactac  480
tgggtgaacg agaagaacga gaacctgagc ctcgccgctg gctactgtcc caccgtttgt  540
gccggtggac acttcggcgg aggcggatac ggtccactta tgcgaaacta cgggctcgca  600
gctgataata tcatcgacgc acaccttgtt aacgttcacg gcaaggtgct ggaccgaaaa  660
agcatgggtg aggacctatt ttgggccttg cgaggcggtg gtgccgaatc cttcggaatt  720
atcgtggcct ggaagatccg actggtcgct gtgccaaagt ccactatgtt ctccgtcaag  780
```

```
aaaattatgg agatccacga actcgtaaag ctcgtcaata agtggcagaa catcgcctac  840
aagtatgaca aggatctgct gctcatgact cacttcatca cgcgaaacat tacagacaac  900
cagggaaaga acaagaccgc tatccatacc tacttctcct ctgtcttcct tgggggtgtc  960
gattccctcg ttgatctcat gaacaaatct tttccagagc tcggaatcaa gaagaccgac  1020
tgccgacagc tctcttggat cgacaccatt attttctact caggagtcgt aaactacgat  1080
actgacaact ttaacaagga gattctgtta gatcgatcgg ccggccagaa cggtgccttc  1140
aagatcaagc tcgactatgt caaaaagccc attcctgaat ccgtcttcgt tcaaattctt  1200
gaaaagttgt acgaggagga tatcggcgcc ggaatgtacg cgctgtaccc ctacggtggc  1260
attatggacg agatttctga aagtgctatt cccttccccc accgtgctgg cattctgtat  1320
gagctgtggt acatttgctc ctgggaaaag caggaggaca acgagaagca cttgaactgg  1380
atacgaaaca tttacaattt catgaccccc tatgtttcga agaaccctcg actggcctac  1440
ctgaattacc gcgacctcga catcggaatt aacgacccta agaaccccaa taactatact  1500
caggccagaa tctggggcga gaagtacttc ggcaagaact ttgaccgtct ggttaaggtc  1560
aagaccctcg tggaccctaa caacttcttc cgaaacgagc agtctatccc ccctctgccc  1620
cgacaccggc attaa                                                   1635
```

```
SEQ ID NO: 120         moltype = DNA  length = 1638
FEATURE                Location/Qualifiers
misc_feature           1..1638
                       note = YlTHC1 Gene
source                 1..1638
                       mol_type = other DNA
                       organism = synthetic construct
SEQUENCE: 120
atgaattgtt cagctttctc tttttggttt gtctgtaaga tcatttttctt ctttctatcc  60
tttcacatcc aaatttccat agccaaccct cgtgagaact tccttaagtg cttttccaag  120
cacattccaa ataacgtcgc caatcccaag ctggtgtaca cgcagcatga ccagctctac  180
atgtcgatcc tcaattccac cattcaaaac cttagattca ttagtgacac cactcccaag  240
cccctagtca ttgtcacccc ttcgaacaac tcgcatattc aggcaactat tctctgctcc  300
aagaaggttg gtttacagat ccgaacccgg tcaggtggtc acgacgctga gggcatgtct  360
tacatttccc aggtcccctt tgtggtggtc gatctgcgca acatgcactc cattaaaatc  420
gacgtccact cgcagactgc ctgggtcgag gctggagcca cccttggcga ggtctactac  480
tggattaacg agaagaacga aaacctgtcg ttccctggcg gctactgtcc gactgttgga  540
gtcggcggac acttttctgg tggcggatat ggtgctctca tgcgaaacta cggactggcg  600
gcagacaaca tcatcgatgc ccaccttgtg aacgttgacg gtaaggtact ggaccgaaag  660
tctatgggcg aggacttgtt ttgggccatc cgaggtggag gtggtgagaa cttcgggatc  720
atcgccgcct ggaagatcaa gctggtggat gtgcccagta agtctaccat ttttagcgtg  780
aagaagaaca tggagatcca cgggctggtg aagctgttca acaagtggca gaatattgcg  840
tacaaatacg acaaggacct ggtgcttatg acccatttca tcaccaagaa catcacggat  900
aaccacggta aaaacaagac tactgttcac ggttacttct cttcaatttt ccatggtggt  960
gtggattccc tcgttgattt gatgaacaag tccttcccag agctgggcat taagaagaca  1020
gactgcaagg aatttagctg gattgatacc accatcttct actctggagt tgtcaacttc  1080
aacaccgcaa acttcaagaa ggaaatcctc ttggaccgat ctgccggcaa gaagacagct  1140
ttttcgatta aactggatta cgtgaagaag cccatccctg agacagctat ggtcaagatc  1200
cttgaaaaac tttatgagga ggacgtcgga gccggaatgt acgttctcta tccttacggc  1260
ggcatcatgg aggaaatttc tgagtctgct atccccttcc cccatcgagc cggaatcatg  1320
tacgagctgt ggtacaccgc tagttgggag aagcaggagg ataacgagaa acatatcaat  1380
tgggtccgta gcgtatacaa tttcacgaca ccctacgtgt cccagaaccc tcgactcgct  1440
tacctgaact atagggacct ggacctcggc aagactaacc acgctagccc gaacaactac  1500
acccaggcca gaatttgggg cgaaaagtac ttcggaaaga acttcaaccg actcgttaag  1560
gttaagacca aagttgaccc caacaacttt ttccggaacg agcagtccat ccctccactc  1620
cctccccacc atcactga                                                1638
```

```
SEQ ID NO: 121         moltype = DNA  length = 26
FEATURE                Location/Qualifiers
misc_feature           1..26
                       note = CvACT1
source                 1..26
                       mol_type = other DNA
                       organism = synthetic construct
SEQUENCE: 121
cccaattcct gtggtgggtt gattcg                                       26
```

```
SEQ ID NO: 122         moltype = DNA  length = 29
FEATURE                Location/Qualifiers
misc_feature           1..29
                       note = CvACT1
source                 1..29
                       mol_type = other DNA
                       organism = synthetic construct
SEQUENCE: 122
ctctcaattc gttgtagaag gtgtggtgc                                    29
```

```
SEQ ID NO: 123         moltype = DNA  length = 29
FEATURE                Location/Qualifiers
misc_feature           1..29
                       note = CvHXS1
source                 1..29
                       mol_type = other DNA
```

```
                         organism = synthetic construct
SEQUENCE: 123
ctttggactc agttgtggct agtgacttc                                        29

SEQ ID NO: 124           moltype = DNA  length = 34
FEATURE                  Location/Qualifiers
misc_feature             1..34
                         note = CvHXS1
source                   1..34
                         mol_type = other DNA
                         organism = synthetic construct
SEQUENCE: 124
gatcaagagt caatttattc aatgggagat cgtc                                  34

SEQ ID NO: 125           moltype = DNA  length = 23
FEATURE                  Location/Qualifiers
misc_feature             1..23
                         note = CvTKS1
source                   1..23
                         mol_type = other DNA
                         organism = synthetic construct
SEQUENCE: 125
gagcagaagg acccgcatca gtg                                              23

SEQ ID NO: 126           moltype = DNA  length = 28
FEATURE                  Location/Qualifiers
misc_feature             1..28
                         note = CvTKS1
source                   1..28
                         mol_type = other DNA
                         organism = synthetic construct
SEQUENCE: 126
gtcaccaaaa attgcctgtc cgacaagc                                         28

SEQ ID NO: 127           moltype = DNA  length = 31
FEATURE                  Location/Qualifiers
misc_feature             1..31
                         note = CvOAC1
source                   1..31
                         mol_type = other DNA
                         organism = synthetic construct
SEQUENCE: 127
cacgacataa tggcagtcaa acacctaata g                                     31

SEQ ID NO: 128           moltype = DNA  length = 31
FEATURE                  Location/Qualifiers
misc_feature             1..31
                         note = CvOAC1
source                   1..31
                         mol_type = other DNA
                         organism = synthetic construct
SEQUENCE: 128
ctagttttgt gttcggagta tgcatacaac g                                     31

SEQ ID NO: 129           moltype = DNA  length = 25
FEATURE                  Location/Qualifiers
misc_feature             1..25
                         note = CvPTS1
source                   1..25
                         mol_type = other DNA
                         organism = synthetic construct
SEQUENCE: 129
ctaccacacc ctcctaaacc ctcac                                            25

SEQ ID NO: 130           moltype = DNA  length = 31
FEATURE                  Location/Qualifiers
misc_feature             1..31
                         note = CvPTS1
source                   1..31
                         mol_type = other DNA
                         organism = synthetic construct
SEQUENCE: 130
cgaagcagta cccgaatata tataatggac c                                     31

SEQ ID NO: 131           moltype = DNA  length = 29
FEATURE                  Location/Qualifiers
misc_feature             1..29
                         note = CvCBD1
source                   1..29
```

```
                        mol_type = other DNA
                        organism = synthetic construct
SEQUENCE: 131
ccttcaacat tcagacatca atcgccaac                                     29

SEQ ID NO: 132          moltype = DNA  length = 22
FEATURE                 Location/Qualifiers
misc_feature            1..22
                        note = CvCBD1
source                  1..22
                        mol_type = other DNA
                        organism = synthetic construct
SEQUENCE: 132
cacccaaggt tgcccctgct tc                                            22

SEQ ID NO: 133          moltype = DNA  length = 24
FEATURE                 Location/Qualifiers
misc_feature            1..24
                        note = CvACO1
source                  1..24
                        mol_type = other DNA
                        organism = synthetic construct
SEQUENCE: 133
gagcaagttc cccagcaagt ccag                                          24

SEQ ID NO: 134          moltype = DNA  length = 26
FEATURE                 Location/Qualifiers
misc_feature            1..26
                        note = CvACO1
source                  1..26
                        mol_type = other DNA
                        organism = synthetic construct
SEQUENCE: 134
catgatgttc acgggttccc aagtgc                                        26

SEQ ID NO: 135          moltype = DNA  length = 25
FEATURE                 Location/Qualifiers
misc_feature            1..25
                        note = CvPTS2
source                  1..25
                        mol_type = other DNA
                        organism = synthetic construct
SEQUENCE: 135
catacatgct ggaagctaca gcgac                                         25

SEQ ID NO: 136          moltype = DNA  length = 27
FEATURE                 Location/Qualifiers
misc_feature            1..27
                        note = CvPTS2
source                  1..27
                        mol_type = other DNA
                        organism = synthetic construct
SEQUENCE: 136
cagtactcac cccatatttt gcatcgc                                       27

SEQ ID NO: 137          moltype = DNA  length = 36
FEATURE                 Location/Qualifiers
misc_feature            1..36
                        note = CvTHC1
source                  1..36
                        mol_type = other DNA
                        organism = synthetic construct
SEQUENCE: 137
gttaagttgt ttaacaagtg gcaaaacatt gcatac                             36

SEQ ID NO: 138          moltype = DNA  length = 34
FEATURE                 Location/Qualifiers
misc_feature            1..34
                        note = CvTHC1
source                  1..34
                        mol_type = other DNA
                        organism = synthetic construct
SEQUENCE: 138
ccaaaatctt aaccattgct gtttctggaa ttgg                               34

SEQ ID NO: 139          moltype = DNA  length = 29
FEATURE                 Location/Qualifiers
misc_feature            1..29
                        note = Candida viswanathii
```

```
source                  1..29
                        mol_type = other DNA
                        organism = synthetic construct
SEQUENCE: 139
gatttgtttt gggcaattag aggaggtgg                                       29

SEQ ID NO: 140          moltype = DNA  length = 32
FEATURE                 Location/Qualifiers
misc_feature            1..32
                        note = Candida viswanathii
source                  1..32
                        mol_type = other DNA
                        organism = synthetic construct
SEQUENCE: 140
caactcctga gtagaaaatg gttgtatcga tc                                   32

SEQ ID NO: 141          moltype = DNA  length = 29
FEATURE                 Location/Qualifiers
misc_feature            1..29
                        note = Yarrowia lipolytica
source                  1..29
                        mol_type = other DNA
                        organism = synthetic construct
SEQUENCE: 141
ttgttaccaa ctgggatgac atggagaag                                       29

SEQ ID NO: 142          moltype = DNA  length = 28
FEATURE                 Location/Qualifiers
misc_feature            1..28
                        note = Yarrowia lipolytica
source                  1..28
                        mol_type = other DNA
                        organism = synthetic construct
SEQUENCE: 142
ctgatggacg tgtttttcga catgaacc                                        28

SEQ ID NO: 143          moltype = DNA  length = 34
FEATURE                 Location/Qualifiers
misc_feature            1..34
                        note = Yarrowia lipolytica
source                  1..34
                        mol_type = other DNA
                        organism = synthetic construct
SEQUENCE: 143
gaaaggaaca tagtcatttc caaacttgaa agtc                                 34

SEQ ID NO: 144          moltype = DNA  length = 24
FEATURE                 Location/Qualifiers
misc_feature            1..24
                        note = Yarrowia lipolytica
source                  1..24
                        mol_type = other DNA
                        organism = synthetic construct
SEQUENCE: 144
cagacggagt actttcgctc gagg                                            24

SEQ ID NO: 145          moltype = DNA  length = 29
FEATURE                 Location/Qualifiers
misc_feature            1..29
                        note = Yarrowia lipolytica
source                  1..29
                        mol_type = other DNA
                        organism = synthetic construct
SEQUENCE: 145
cccaaattta gctgcatcat tcatcaacc                                       29

SEQ ID NO: 146          moltype = DNA  length = 27
FEATURE                 Location/Qualifiers
misc_feature            1..27
                        note = Yarrowia lipolytica
source                  1..27
                        mol_type = other DNA
                        organism = synthetic construct
SEQUENCE: 146
ccgtgcttaa gagcaagttc cttgagg                                         27

SEQ ID NO: 147          moltype = DNA  length = 23
FEATURE                 Location/Qualifiers
misc_feature            1..23
```

```
                        note = Yarrowia lipolytica
source                  1..23
                        mol_type = other DNA
                        organism = synthetic construct
SEQUENCE: 147
ctacgacatg cccaaggagc agc                                              23

SEQ ID NO: 148          moltype = DNA  length = 26
FEATURE                 Location/Qualifiers
misc_feature            1..26
                        note = Yarrowia lipolytica
source                  1..26
                        mol_type = other DNA
                        organism = synthetic construct
SEQUENCE: 148
ggattcgcac attggtgaac tggatc                                           26

SEQ ID NO: 149          moltype = DNA  length = 24
FEATURE                 Location/Qualifiers
misc_feature            1..24
                        note = Yarrowia lipolytica
source                  1..24
                        mol_type = other DNA
                        organism = synthetic construct
SEQUENCE: 149
ccaagcgacg acaagctgtt gagc                                             24

SEQ ID NO: 150          moltype = DNA  length = 21
FEATURE                 Location/Qualifiers
misc_feature            1..21
                        note = Yarrowia lipolytica
source                  1..21
                        mol_type = other DNA
                        organism = synthetic construct
SEQUENCE: 150
cgtgtgggta gcagagtggg c                                                21

SEQ ID NO: 151          moltype = DNA  length = 26
FEATURE                 Location/Qualifiers
misc_feature            1..26
                        note = Yarrowia lipolytica
source                  1..26
                        mol_type = other DNA
                        organism = synthetic construct
SEQUENCE: 151
ctttgccatg actgagactg gccatg                                           26

SEQ ID NO: 152          moltype = DNA  length = 18
FEATURE                 Location/Qualifiers
misc_feature            1..18
                        note = Yarrowia lipolytica
source                  1..18
                        mol_type = other DNA
                        organism = synthetic construct
SEQUENCE: 152
gaggcgccgc tggtgtcg                                                    18

SEQ ID NO: 153          moltype = DNA  length = 27
FEATURE                 Location/Qualifiers
misc_feature            1..27
                        note = Yarrowia lipolytica
source                  1..27
                        mol_type = other DNA
                        organism = synthetic construct
SEQUENCE: 153
tccgaaagcg gaactgcttt ctcaatg                                          27

SEQ ID NO: 154          moltype = DNA  length = 23
FEATURE                 Location/Qualifiers
misc_feature            1..23
                        note = Yarrowia lipolytica
source                  1..23
                        mol_type = other DNA
                        organism = synthetic construct
SEQUENCE: 154
cagaccggcc tctcgaatat ggc                                              23

SEQ ID NO: 155          moltype = DNA  length = 26
FEATURE                 Location/Qualifiers
```

```
misc_feature           1..26
                       note = Yarrowia lipolytica
source                 1..26
                       mol_type = other DNA
                       organism = synthetic construct
SEQUENCE: 155
ctagactaca cgggcaacct taaccc                                        26

SEQ ID NO: 156         moltype = DNA  length = 25
FEATURE                Location/Qualifiers
misc_feature           1..25
                       note = Yarrowia lipolytica
source                 1..25
                       mol_type = other DNA
                       organism = synthetic construct
SEQUENCE: 156
cttgggcttc agctttcgag gagtg                                         25

SEQ ID NO: 157         moltype = DNA  length = 4435
FEATURE                Location/Qualifiers
misc_feature           1..4435
                       note = pLD1
source                 1..4435
                       mol_type = other DNA
                       organism = synthetic construct
SEQUENCE: 157
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt cccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa gaagagcccg ggtctagatg tgtgctcttc cgagtgactc ttttgataag  1620
agtcgcaaat ttgatttcat aagtatatat tcattatgta aagtagtaaa tggaaaattc  1680
attaaaaaaa aagcaaattt ccgttgtatg catactccga acacaaaact agccccggaa  1740
aaacccttag ttgatagttg cgaatttagg tcgaccatat gcgacgggta caacgagaat  1800
tgtattgaat tgatcaagaa catgatcttg gtgttacaga acatcaagtt cttggaccag  1860
actgagaatg cacagatata caaggcgtca tgtgataaaa tggatgagat ttatccacaa  1920
ttgaagaaag agtttatgga aagtggtcaa ccagaagcta aacaggaaga agcaaacgaa  1980
gaggtgaaac aagaagaaga aggtaaataa gtattttgta ttatataaca aacaaagtaa  2040
ggaatacaga tttatacaat aaattgccat actagtcacg tgagatatct catccattcc  2100
ccaactccca agaaaataaa aaagtgaaaa ataaaatcaa acccaaagat caacctcccc  2160
atcatcatcg tcatcaaacc cccagctcaa ttcgcaatgg ttagcacaaa aacatacaca  2220
gaaagggcat cagcacaccc ctccaaggtt gcccaacgtt tattaattaa aggctaggtg  2280
gaggctcagt gatgataagt ctgcgatggt ggatgcatgt gtcatggtca tagctgtttc  2340
ctgtgtgaaa ttgttatccg ctcagagggc acaatcctat tccgcgctat ccgacaatct  2400
ccaagacatt aggtggagtt cagttcggcg tatggcatat gtcgctggaa agaacatgtg  2460
agcaaaaggc cagcaaaagg ccaggaaccg taaaaaggcc gcgttgctgg cgtttttcca  2520
taggctccgc ccccctgacg agcatcacaa aaatcgacgc tcaagtcaga ggtggcgaaa  2580
cccgacagga ctataaagat accaggcgtt tccccctgga agctccctcg tgcgctctcc  2640
tgttccgacc ctgccgctta ccggatacct gtccgccttt ctcccttcgg gaagcgtggc  2700
gctttctcat agctcacgct gtaggtatct cagttcggtg taggtcgttc gctccaagct  2760
gggctgtgtg cacgaacccc ccgttcagcc cgaccgctgc gccttatccg gtaactatcg  2820
tcttgagtcc aacccggtaa gacacgactt atcgccactg gcagcagcca ctggtaacag  2880
gattagcaga gcgaggtatg taggcggtgc tacagagttc ttgaagtggt ggcctaacta  2940
cggctacact agaagaacag tatttggtat ctgcgctctg ctgaagccag ttaccttcgg  3000
aaaaagagtt ggtagctctt gatccggcaa acaaaccacc gctggtagcg gtggtttttt  3060
tgtttgcaag cagcagatta cgcgcagaaa aaaggatct caagaagatc ctttgatctt  3120
ttctacgggg tctgacgctc tattcaacaa agccgccgtc ccgtcaagtc agcgtaaatg  3180
```

```
ggtagggggc ttcaaatcgt ccgctctgcc agtgttacaa ccaattaaca aattctgatt  3240
agaaaaactc atcgagcatc aaatgaaact gcaatttatt catatcagga ttatcaatac  3300
catatttttg aaaaagccgt ttctgtaatg aaggagaaaa ctcaccgagg cagttccata  3360
ggatggcaag atcctggtat cggtctgcga ttccgactcg tccaacatca atacaaccta  3420
ttaatttccc ctcgtcaaaa ataaggttat caagtgagaa atcaccatga gtgacgactg  3480
aatccggtga gaatggcaaa agcttatgca tttctttcca gacttgttca acaggccagc  3540
cattacgctc gtcatcaaaa tcactcgcat caaccaaacc gttattcatt cgtgattgcg  3600
cctgagcgag acgaaatacg cgatcgctgt taaaaggaca attacaaaca ggaatcgaat  3660
gcaaccggcg caggaacact gccagcgcat caacaatatt ttcacctgaa tcaggatatt  3720
cttctaatac ctggaatgct gttttcccgg ggatcgcagt ggtgagtaac catgcatcat  3780
caggagtacg gataaaatgc ttgatggtcg gaagaggcat aaattccgtc agccagttta  3840
gtctgaccat ctcatctgta acatcattgg caacgctacc tttgccatgt ttcagaaaca  3900
actctggcgc atcgggcttc ccatacaatc gatagattgt cgcacctgat tgcccgacat  3960
tatcgcgagc ccatttatac ccatataaat cagcatccat gttggaattt aatcgcggcc  4020
tcgagcaaga cgtttcccgt tgaatatggc tcataacacc ccttgtatta ctgtttatgt  4080
aagcagacag ttttattgtt catgatgata tatttttatc ttgtgcaatg taacatcaga  4140
gattttgaga cacaacgtgg ctttcccccg ccgctctaga actagtggat ccaaataaaa  4200
cgaaaggctc agtcgaaaga ctgggccttt cgttttatct gttgtttgtc gcattatacg  4260
agacgtccag gttgggatac ctgaaacaaa acccatcgta cggccaagga agtctccaat  4320
aactgtgatc caccacaagc gccagggttt tcccagtcac gacgttgtaa aacgacggcc  4380
agtcatgcat aatccgcacg catctggaat aaggaagtgc cattccgcct gacct       4435

SEQ ID NO: 158          moltype = DNA  length = 5564
FEATURE                 Location/Qualifiers
misc_feature            1..5564
                        note = pLD10
source                  1..5564
                        mol_type = other DNA
                        organism = synthetic construct
SEQUENCE: 158
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgcccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgaatcattt aagagcagaa ggacccgcat cagtgttagc gataggtaca  1620
gctaacccag agaatatctt aatccaagat gaatttcctg actactattt ccgtgttact  1680
aaatcggaac atatgactca acttaaagag aagttccgga aaatctgcga taaatccatg  1740
atccgaaaga gaaactgttt ccttaacgaa gaacatctca agcaaaaccc gaggttggta  1800
gagcacgaaa tgcagacctt ggatgctagg caggacatgt tggtggtcga agtgccaaaa  1860
ctcggcaagg acgcgtgcgc taaggcaatc aaggagtggg gtcaaccgaa gtctaaaatc  1920
acgcatctaa tatttacatc tgcactgaca accgacatgc cgggtgccga ttatcactgc  1980
gccaagctac ttggattgag tccactggtt aagagagtta tgatgtatca attggggtgt  2040
tacggagggg gcacagtcct cagaattgct aaggatattg cggaaaataa caagggcgcg  2100
agggtccttg ctgtatgttg tgatattatg gcctgtttgt ttcgcgggcc ctcggattca  2160
gatttggaat tgcttgtcgg acaggcaatt tttggtgacg gggccgcagc agtcatagtg  2220
ggagccgaac cagacgaaag cgtgggtgaa agaccaatct ttgagttggt tctgaccgga  2280
caaacgatct tacctaactc ggaaggtacg attggaggac atattagaga agccggccta  2340
attttcgatc ttcacaaaga cgttccaatg ttaatctcca ataacataga aaagtgcttg  2400
atagaagcat ttactcccat tggtattagt gactggaaca gcattttctg gatcacccac  2460
cctggaggaa aagctatact cgataaggtt gaagagaaac tcgacttgaa aaaggagaaa  2520
ttcgttgact cacgacatgt gttatcagag cacgggaata tgagttcatc cacagtcttg  2580
ttcgtaatgg atgaattgcg aaaacgctct cttgaggagg gaaagagcac aaccggtgac  2640
gggtttgagt ggggcgtgct attcggtttt ggcccaggtt tgactgtcga gcgggttgtt  2700
gttcgtagtg taccaattaa gtactgataa gagtgactct tttgataaga gtcgcaaatt  2760
tgatttcata agtatatatt cattatgtaa agtagtaaat ggaaaattca ttaaaaaaaa  2820
agcaaatttc cgttgtatgc atactccgaa cacaaaacta gccccggaaa aacccttagt  2880
tgatagttgc gaatttaggt cgaccatatg cgacgggtac aacgagaatt gtattgaatt  2940
```

```
gatcaagaac atgatcttgg tgttacagaa catcaagttc ttggaccaga ctgagaatgc  3000
acagatatac aaggcgtcat gtgataaaat ggatgagatt tatccacaat tgaagaaaga  3060
gtttatggaa agtggtcaac cagaagctaa acaggaagaa gcaaacgaag aggtgaaaca  3120
agaagaagaa ggtaaataag tattttgtat tatataacaa acaaagtaag gaatacagat  3180
ttatacaata aattgccata ctagtcacgt gagatatctc atccattccc caactcccaa  3240
gaaaataaaa aagtgaaaaa taaaatcaaa cccaaagatc aacctcccca tcatcatcgt  3300
catcaaaccc ccagctcaat tcgcaatggt tagcacaaaa acatacacag aaagggcatc  3360
agcacacccc tccaaggttg cccaacgttt attaattaaa ggctaggtgg aggctcagtg  3420
atgataagtc tgcgatggtg gatgcatgtg tcatggtcat agctgtttcc tgtgtgaaat  3480
tgttatccgc tcagagggca caatcctatt ccgcgctatc cgacaatctc caagacatta  3540
ggtggagttc agttcggcgt atggcatatg tcgctggaaa gaacatgtga gcaaaaggcc  3600
agcaaaaggc caggaaccgt aaaaaggccg cgttgctggc gtttttccat aggctccgcc  3660
cccctgacga gcatcacaaa aatcgacgct caagtcagag gtggcgaaac ccgacaggac  3720
tataaagata ccaggcgttt ccccctggaa gctccctcgt gcgctctcct gttccgaccc  3780
tgccgcttac cggatacctg tccgcctttc tcccttcggg aagcgtggcg ctttctcata  3840
gctcacgctg taggtatctc agttcggtgt aggtcgttcg ctccaagctg ggctgtgtgc  3900
acgaaccccc cgttcagccc gaccgctgcg ccttatccgg taactatcgt cttgagtcca  3960
acccggtaag acacgactta tcgccactgg cagcagccac tggtaacagg attagcagag  4020
cgaggtatgt aggcggtgct acagagttct tgaagtggtg gcctaactac ggctacacta  4080
gaagaacagt atttggtatc tgcgctctgc tgaagccagt taccttcgga aaaagagttg  4140
gtagctcttg atccggcaaa caaaccaccg ctggtagcgg tggttttttt gtttgcaagc  4200
agcagattac gcgcagaaaa aaaggatctc aagaagatcc tttgatcttt tctacggggt  4260
ctgacgctct attcaacaaa gccgccgtcc cgtcaagtca gcgtaaatgg gtagggggct  4320
tcaaatcgtc cgctctgcca gtgttacaac caattaacaa attctgatta gaaaaactca  4380
tcgagcatca aatgaaactg caatttattc atatcaggat tatcaatacc atatttttga  4440
aaaagccgtt tctgtaatga aggagaaaac tcaccgaggc agttccatag gatggcaaga  4500
tcctggtatc ggtctgcgat tccgactcgt ccaacatcaa tacaacctat taatttcccc  4560
tcgtcaaaaa taaggttatc aagtgagaaa tcaccatgag tgacgactga atccggtgag  4620
aatggcaaaa gcttatgcat ttctttccag acttgttcaa caggccagcc attacgctcg  4680
tcatcaaaat cactcgcatc aaccaaaccg ttattcattc gtgattgcgc ctgagcgaga  4740
cgaaatacgc gatcgctgtt aaaaggacaa ttacaaacag gaatcgaatg caaccggcgc  4800
aggaacactg ccagcgcatc aacaatattt tcacctgaat caggatattc ttctaatacc  4860
tggaatgctg ttttcccggg gatcgcagtg gtgagtaacc atgcatcatc aggagtacgg  4920
ataaaatgct tgatggtcgg aagaggcata aattccgtca gccagtttag tctgaccatc  4980
tcatctgtaa catcattggc aacgctacct ttgccatgtt tcagaaacaa ctctggcgca  5040
tcgggcttcc catacaatcg atagattgtc gcacctgatt gcccgacatt atcgcgagcc  5100
catttatacc catataaatc agcatccatg ttggaattta atcgcggcct cgagcaagac  5160
gtttcccgtt gaatatggct cataacaccc cttgtattac tgtttatgta agcagacagt  5220
tttattgttc atgatgatat atttttatct tgtgcaatgt aacatcagag attttgagac  5280
acaacgtggc tttccccgc cgctctagaa ctagtggatc caaataaaac gaaaggctca  5340
gtcgaaagac tgggcctttc gttttatctg ttgtttgtcg cattatacga gacgtccagg  5400
ttgggatacc tgaaacaaaa cccatcgtac ggccaaggaa gtctccaata actgtgatcc  5460
accacaagcg ccagggtttt cccagtcacg acgttgtaaa acgacggcca gtcatgcata  5520
atccgcacgc atctggaata aggaagtgcc attccgcctg acct                    5564

SEQ ID NO: 159          moltype = DNA  length = 4724
FEATURE                 Location/Qualifiers
misc_feature            1..4724
                        note = pLD12
source                  1..4724
                        mol_type = other DNA
                        organism = synthetic construct
SEQUENCE: 159
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
```

```
cacgacataa tggcagtcaa acacctaata gttctcaaat ttaaagacga gattactgaa  1620
gctcagaagg aagagttctt taagacatat gttaacttag tcaacatcat ccccgcgatg  1680
aaggacgtct actggggcaa ggatgtgacg caaaaaaata aggaagaagg atacacacat  1740
atcgttgagg tgacctttga gagtgtggaa actattcaag attatattat tcacccagcc  1800
catgtagggt tcggtgacgt ttatcgatca ttctgggaaa agttgcttat atttgattac  1860
accccaagaa aattgaagcc taagtgataa gagtgactct tttgataaga gtcgcaaatt  1920
tgatttcata agtatatatt cattatgtaa agtagtaaat ggaaaattca ttaaaaaaaa  1980
agcaaatttc cgttgtatgc atactccgaa cacaaaacta gccccggaaa aacccttagt  2040
tgatagttgc gaatttaggt cgaccatatg cgacgggtac aacgagaatt gtattgaatt  2100
gatcaagaac atgatcttgg tgttacagaa catcaagttc ttggaccaga ctgagaatgc  2160
acagatatac aaggcgtcat gtgataaaat ggatgagatt tatccacaat tgaagaaaga  2220
gtttatggaa agtggtcaac cagaagctaa acaggaagaa gcaaacgaag aggtgaaaca  2280
agaagaagaa ggtaaataag tattttgtat tatataacaa acaaagtaag gaatacagat  2340
ttatacaata aattgccata ctagtcacgt gagatatctc atccattccc caactcccaa  2400
gaaaataaaa aagtgaaaaa taaaatcaaa cccaaagatc aacctcccca tcatcatcgt  2460
catcaaaccc ccagctcaat tcgcaatggt tagcacaaaa acatacacag aaagggcatc  2520
agcacacccc tccaaggttg cccaacgttt attaattaaa ggctaggtgg aggctcagtg  2580
atgataagtc tgcgatggtg gatgcatgtg tcatggtcat agctgtttcc tgtgtgaaat  2640
tgttatccgc tcagagggca caatcctatt ccgcgctatc cgacaatctc caagacatta  2700
ggtggagttc agttcggcgt atggcatatg tcgctggaaa gaacatgtga gcaaaaggcc  2760
agcaaaaggc caggaaccgt aaaaaggccg cgttgctggc gtttttccat aggctccgcc  2820
cccctgacga gcatcacaaa aatcgacgct caagtcagag gtggcgaaac ccgacaggac  2880
tataaagata ccaggcgttt ccccctggaa gctccctcgt gcgctctcct gttccgaccc  2940
tgccgcttac cggatacctg tccgcctttc tcccttcggg aagcgtggcg ctttctcata  3000
gctcacgctg taggtatctc agttcggtgt aggtcgttcg ctccaagctg ggctgtgtgc  3060
acgaaccccc cgttcagccc gaccgctgcg ccttatccgg taactatcgt cttgagtcca  3120
acccggtaag acacgactta tcgccactgg cagcagccac tggtaacagg attagcagag  3180
cgaggtatgt aggcggtgct acagagttct tgaagtggtg gcctaactac ggctacacta  3240
gaagaacagt atttggtatc tgcgctctgc tgaagccagt taccttcgga aaaagagttg  3300
gtagctcttg atccggcaaa caaaccaccg ctggtagcgg tggttttttt gtttgcaagc  3360
agcagattac gcgcagaaaa aaaggatctc aagaagatcc tttgatcttt tctacggggt  3420
ctgacgctct attcaacaaa gccgccgtcc cgtcaagtca gcgtaaatgg gtagggggct  3480
tcaaatcgtc cgctctgcca gtgttacaac caattaacaa attctgatta gaaaaactca  3540
tcgagcatca aatgaaactg caatttattc atatcaggat tatcaatacc atatttttga  3600
aaaagccgtt tctgtaatga aggagaaaac tcaccgaggc agttccatag gatggcaaga  3660
tcctggtatc ggtctgcgat tccgactcgt ccaacatcaa tacaacctat taatttcccc  3720
tcgtcaaaaa taaggttatc aagtgagaaa tcaccatgag tgacgactga atccggtgag  3780
aatggcaaaa gcttatgcat ttctttccag acttgttcaa caggccagcc attacgctcg  3840
tcatcaaaat cactcgcatc aaccaaaccg ttattcattc gtgattgcgc ctgagcgaga  3900
cgaaatacgc gatcgctgtt aaaaggacaa ttacaaacag gaatcgaatg caaccggcgc  3960
aggaacactg ccagcgcatc aacaatattt tcacctgaat caggatattc ttctaatacc  4020
tggaatgctg ttttcccggg gatcgcagtg gtgagtaacc atgcatcatc aggagtacgg  4080
ataaaatgct tgatggtcgg aagaggcata aattccgtca gccagtttag tctgaccatc  4140
tcatctgtaa catcattggc aacgctacct ttgccatgtt tcagaaacaa ctctggcgca  4200
tcgggcttcc catacaatcg atagattgtc gcacctgatt gcccgacatt atcgcgagcc  4260
catttatacc catataaatc agcatccatg ttggaattta atcgcggcct cgagcaagac  4320
gtttcccgtt gaatatggct cataacaccc cttgtattac tgtttatgta agcagacagt  4380
tttattgttc atgatgatat atttttatct tgtgcaatgt aacatcagag attttgagac  4440
acaacgtggc tttccccccgc cgctctagaa ctagtggatc caaataaaac gaaaggctca  4500
gtcgaaagac tgggcctttc gttttatctg ttgtttgtcg cattatacga gacgtccagg  4560
ttgggatacc tgaaacaaaa cccatcgtac ggccaaggaa gtctccaata actgtgatcc  4620
accacaagcg ccagggtttt cccagtcacg acgttgtaaa acgacggcca gtcatgcata  4680
atccgcacgc atctggaata aggaagtgcc attccgcctg acct                   4724

SEQ ID NO: 160          moltype = DNA  length = 4742
FEATURE                 Location/Qualifiers
misc_feature            1..4742
                        note = pLD14
source                  1..4742
                        mol_type = other DNA
                        organism = synthetic construct
SEQUENCE: 160
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
```

```
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc ctttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tggcagtcaa acacctaata gttctcaaat ttaaagacga gattactgaa  1620
gctcagaagg aagagttctt taagacatat gttaacttag tcaacatcat ccccgcgatg  1680
aaggacgtct actggggcaa ggatgtgacg caaaaaaata aggaagaagg atacacacat  1740
atcgttgagg tgacctttga gagtgtggaa actattcaag attatattat tcacccagcc  1800
catgtagggt tcggtgacgt ttatcgatca ttctgggaaa agttgcttat atttgattac  1860
accccaagaa aattgaagcc taagggaaga cgagctaagt tgtgataaga gtgactcttt  1920
tgataagagt cgcaaatttg atttcataag tatatattca ttatgtaaag tagtaaatgg  1980
aaaattcatt aaaaaaaaag caaatttccg ttgtatgcat actccgaaca caaaactagc  2040
cccggaaaaa cccttagttg atagttgcga atttaggtcg accatatgcg acgggtacaa  2100
cgagaattgt attgaattga tcaagaacat gatcttggtg ttacagaaca tcaagttctt  2160
ggaccagact gagaatgcac agatatacaa ggcgtcatgt gataaaatgg atgagattta  2220
tccacaattg aagaaagagt ttatggaaag tggtcaacca gaagctaaac aggaagaagc  2280
aaacgaagag gtgaaacaag aagaagaagg taaataagta ttttgtatta tataacaaac  2340
aaagtaagga atacagattt atacaataaa ttgccatact agtcacgtga gatatctcat  2400
ccattcccca actcccaaga aaataaaaaa gtgaaaaata aaatcaaacc caaagatcaa  2460
cctccccatc atcatcgtca tcaaaccccc agctcaattc gcaatggtta gcacaaaaac  2520
atacacagaa agggcatcag cacacccctc caaggttgcc caacgtttat taattaaagg  2580
ctaggtggag gctcagtgat gataagtctg cgatggtgga tgcatgtgtc atggtcatag  2640
ctgtttcctg tgtgaaattg ttatccgctc agagggcaca atcctattcc gcgctatccg  2700
acaatctcca agacattagg tggagttcag ttcggcgtat ggcatatgtc gctggaaaga  2760
acatgtgagc aaaaggccag caaaaggcca ggaaccgtaa aaaggccgcg ttgctggcgt  2820
ttttccatag gctccgcccc cctgacgagc atcacaaaaa tcgacgctca agtcagaggt  2880
ggcgaaaccc gacaggacta taaagatacc aggcgtttcc ccctggaagc tccctcgtgc  2940
gctctcctgt tccgaccctg ccgcttaccg gatacctgtc cgcctttctc ccttcgggaa  3000
gcgtggcgct ttctcatagc tcacgctgta ggtatctcag ttcggtgtag gtcgttcgct  3060
ccaagctggg ctgtgtgcac gaaccccccg ttcagcccga ccgctgcgcc ttatccggta  3120
actatcgtct tgagtccaac ccggtaagac acgacttatc gccactggca gcagccactg  3180
gtaacaggat tagcagagcg aggtatgtag gcggtgctac agagttcttg aagtggtggc  3240
ctaactacgg ctacactaga agaacagtat ttggtatctg cgctctgctg aagccagtta  3300
ccttcggaaa aagagttggt agctcttgat ccggcaaaca aaccaccgct ggtagcggtg  3360
gtttttttgt ttgcaagcag cagattacgc gcagaaaaaa aggatctcaa gaagatcctt  3420
tgatcttttc tacggggtct gacgctctat tcaacaaagc cgccgtcccg tcaagtcagc  3480
gtaaatgggt agggggcttc aaatcgtccg ctctgccagt gttacaacca attaacaaat  3540
tctgattaga aaaactcatc gagcatcaaa tgaaactgca atttattcat atcaggatta  3600
tcaataccat atttttgaaa aagccgtttc tgtaatgaag gagaaaactc accgaggcag  3660
ttccatagga tggcaagatc ctggtatcgg tctgcgattc cgactcgtcc aacatcaata  3720
caacctatta atttcccctc gtcaaaaata aggttatcaa gtgagaaatc accatgagtg  3780
acgactgaat ccggtgagaa tggcaaaagc ttatgcattt ctttccagac ttgttcaaca  3840
ggccagccat tacgctcgtc atcaaaatca ctcgcatcaa ccaaaccgtt attcattcgt  3900
gattgcgcct gagcgagacg aaatacgcga tcgctgttaa aaggacaatt acaaacagga  3960
atcgaatgca accggcgcag gaacactgcc agcgcatcaa caatattttc acctgaatca  4020
ggatattctt ctaatacctg gaatgctgtt ttcccgggga tcgcagtggt gagtaaccat  4080
gcatcatcag gagtacggat aaaatgcttg atggtcggaa gaggcataaa ttccgtcagc  4140
cagtttagtc tgaccatctc atctgtaaca tcattggcaa cgctaccttt gccatgtttc  4200
agaaacaact ctggcgcatc gggcttccca tacaatcgat agattgtcgc acctgattgc  4260
ccgacattat cgcgagccca tttataccca tataaatcag catccatgtt ggaatttaat  4320
cgcggcctcg agcaagacgt ttcccgttga atatggctca taacacccct tgtattactg  4380
tttatgtaag cagacagttt tattgttcat gatgatatat ttttatcttg tgcaatgtaa  4440
catcagagat tttgagacac aacgtggctt tccccccgccg ctctagaact agtggatcca  4500
aataaaacga aaggctcagt cgaaagactg ggcctttcgt tttatctgtt gtttgtcgca  4560
ttatacgaga cgtccaggtt gggatacctg aaacaaaacc catcgtacgg ccaaggaagt  4620
ctccaataac tgtgatccac cacaagcgcc agggttttcc cagtcacgac gttgtaaaac  4680
gacggccagt catgcataat ccgcacgcat ctggaataag gaagtgccat tccgcctgac  4740
ct                                                                4742
```

```
SEQ ID NO: 161          moltype = DNA  length = 6569
FEATURE                 Location/Qualifiers
misc_feature            1..6569
                        note = pLD16
source                  1..6569
                        mol_type = other DNA
                        organism = synthetic construct
SEQUENCE: 161
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
```

```
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgacttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgggaaaaaa ttataaatct ttggactcag ttgtggctag tgacttcatt  1620
gcacttggga tcacatcaga agttgctgag acattgcacg gacgcttggc agagatagtt  1680
tgcaactacg gcgccgcaac acctcagacc tggattaaca tcgcaaacca tattctaagt  1740
ccagatcttc catttagtct ccatcagatg ttgttctacg gttgttataa ggactttggt  1800
ccagcacccc cagcttggat accagacccc gaaaaagtaa agtccacgaa cttaggtgcc  1860
ttgttagaaa agcggggaaa ggagtttcta ggcgttaagt ataaggaccc aataagtctg  1920
ttttctcact tccaggagtt tagcgttcga aatccggaag tctactggcg gacggtactt  1980
atggatgaaa tgaagatact gttcagcaaa gatcccgaat gtatcctcag acgcgacgac  2040
attaacaacc caggggggctc tgagtggcta ccaggtggat atctcaacct ggccaagaac  2100
tgtttgaatg taaatagtaa caaaaaaactt aacgacacta tgatagtgtg gagagatgaa  2160
ggaaatgacg atctcccatt gaataaattg actcttgatc aattacgaaa acgagtctgg  2220
ttggttggat acgccctaga agagatgggc cttgagaagg gatgtgcgat tgcaattgac  2280
atgcccatgc acgtagatgc ggttgtgatc tatttagcta tcgtcttggc aggctacgtc  2340
gttgtctcca ttgcagattc attctcagca ccggaaattt ccacaagatt gcgtctatca  2400
aaggctaagg ctatttttac acaagatcat atcatccgag ggaaaaagcg tatacctttg  2460
tacctgcgtg tcgtcgaggc caagtctccg atggcaatag ttatcccgtg ttcgggttca  2520
aatattggtg cggaattgcg ggatggtgat attctgtggg attacttctt agaacgcgca  2580
aaggaattta agaactgcga atttacagcc cgtgaacagc cagtggacgc gtacacaaat  2640
attttgttct catcgggaac caccggagag ccaaaggcga taccatggac tcaagctacg  2700
cctctcaagg cggctgctga tggttggtca cacttggaca ttagaaaggg tgacgtaatt  2760
gtatggccta ccaatttggt gtggatgatg gggccttggt tggtctatgc ttcactcctt  2820
aacggggcaa gcatcgcatt gtataacgga tctccactag tgtccggctt tgccaaattc  2880
gttcaagatg cgaaagttac tatgctagga gttgtcccct ccatcgtacg aagctggaaa  2940
agcactaatt gcgttagtgg gtacgattgg tctacaatca gatgcttctc ctcatcgggt  3000
gaggcatcga atgtcgatga atacttatgg ctaatgggaa gggctaacta caaaccggtc  3060
atcgaaatgt gcggtggcac agagatcggg ggtgccttca gcgccggttc gtttttacaa  3120
gcccaatctt tgagtagctt ctcatcccaa tgtatgggat gcaccttgta cattctcgac  3180
aagaatggct acccgatgcc aaagaacaag ccgggtatag gtgaattggc cttgggaccc  3240
gtgatgttcg gtgcttccaa gactttactt aacggaaacc atcatgacgt ttatttcaaa  3300
ggcatgccca ccttgaacgg agaagtcttg aggagacacg gagatatctt cgaactcact  3360
tcgaacggct attatcacgc tcatggtaga gcagatgaca cgatgaatat cggggggatt  3420
aaaatttcct caatcgagat tgaaagggtg tgtaatgaag ttgacgatag agtgtttgag  3480
actacggcca ttggagtgcc tccattgggc ggaggtccag agcagctcgt tatctttttt  3540
gttcttaagg acagcaatga tacgaccatc gacctaaacc aattgcgact tagttttaat  3600
cttgggttac aaaagaaatt gaacccactt tttaaggtga cgagggttgt gccactttcg  3660
ctgttgccta ggacagccac caacaaaata atgagaagag tgcttagaca gcaatttagt  3720
catttcgagt gataagagtg actcttttga taagagtcgc aaatttgatt tcataagtat  3780
atattcatta tgtaaagtag taaatggaaa attcattaaa aaaaaagcaa atttccgttg  3840
tatgcatact ccgaacacaa aactagcccc ggaaaaaccc ttagttgata gttgcgaatt  3900
taggtcgacc atatgcgacg ggtacaacga gaattgtatt gaattgatca agaacatgat  3960
cttggtgtta cagaacatca agttcttgga ccagactgag aatgcacaga tatacaaggc  4020
gtcatgtgat aaaatggatg agatttatcc acaattgaag aaagagttta tggaaagtgg  4080
tcaaccagaa gctaaacagg aagaagcaaa cgaagaggtg aaacaagaag aagaaggtaa  4140
ataagtattt tgtattatat aacaaacaaa gtaaggaata cagatttata caataaattg  4200
ccatactagt cacgtgagat atctcatcca ttccccaact cccaagaaaa taaaaaagtg  4260
aaaaataaaa tcaaacccaa agatcaacct ccccatcatc atcgtcatca aaccccccagc  4320
tcaattcgca atggttagca caaaaacata cacagaaagg gcatcagcac accctccaa  4380
ggttgcccaa cgtttattaa ttaaaggcta ggtggaggct cagtgatgat aagtctgcga  4440
tggtggatgc atgtgtcatg gtcatagctg tttcctgtgt gaaattgtta tccgctcaga  4500
gggcacaatc ctattccgcg ctatccgaca atctccaaga cattaggtgg agttcagttc  4560
ggcgtatggc atatgtcgct ggaaagaaca tgtgagcaaa aggccagcaa aaggccagga  4620
accgtaaaaa ggccgcgttg ctggcgtttt tccataggct ccgcccccct gacgagcatc  4680
acaaaaatcg acgctcaagt cagaggtggc gaaacccgac aggactataa agataccagg  4740
cgtttccccc tggaagctcc ctcgtgcgct ctcctgttcc gaccctgccg cttaccggat  4800
acctgtccgc ctttctccct tcgggaagcg tggcgctttc tcatagctca cgctgtaggt  4860
atctcagttc ggtgtaggtc gttcgctcca agctgggctg tgtgcacgaa ccccccgttc  4920
agcccgaccg ctgcgcctta tccggtaact atcgtcttga gtccaacccg gtaagacacg  4980
acttatcgcc actggcagca gccactggta acaggattag cagagcgagg tatgtaggcg  5040
gtgctacaga gttcttgaag tggtggccta actacggcta cactagaaga acagtatttg  5100
gtatctgcgc tctgctgaag ccagttacct tcggaaaaag agttggtagc tcttgatccg  5160
```

```
gcaaacaaac caccgctggt agcggtggtt tttttgtttg caagcagcag attacgcgca  5220
gaaaaaaagg atctcaagaa gatcctttga tcttttctac ggggtctgac gctctattca  5280
acaaagccgc cgtcccgtca agtcagcgta aatgggtagg gggcttcaaa tcgtccgctc  5340
tgccagtgtt acaaccaatt aacaaattct gattagaaaa actcatcgag catcaaatga  5400
aactgcaatt tattcatatc aggattatca ataccatatt tttgaaaaag ccgtttctgt  5460
aatgaaggag aaaactcacc gaggcagttc cataggatgg caagatcctg gtatcggtct  5520
gcgattccga ctcgtccaac atcaatacaa cctattaatt tcccctcgtc aaaaataagg  5580
ttatcaagtg agaaatcacc atgagtgacg actgaatccg gtgagaatgg caaaagctta  5640
tgcatttctt tccagacttg ttcaacaggc cagccattac gctcgtcatc aaaatcactc  5700
gcatcaacca aaccgttatt cattcgtgat tgcgcctgag cgagacgaaa tacgcgatcg  5760
ctgttaaaag gacaattaca aacaggaatc gaatgcaacc ggcgcaggaa cactgccagc  5820
gcatcaacaa tattttcacc tgaatcagga tattcttcta atacctggaa tgctgttttc  5880
ccggggatcg cagtggtgag taaccatgca tcatcaggag tacggataaa atgcttgatg  5940
gtcggaagag gcataaattc cgtcagccag tttagtctga ccatctcatc tgtaacatca  6000
ttggcaacgc tacctttgcc atgtttcaga aacaactctg gcgcatcggg cttcccatac  6060
aatcgataga ttgtcgcacc tgattgcccg acattatcgc gagcccattt atacccatat  6120
aaatcagcat ccatgttgga atttaatcgc ggcctcgagc aagacgtttc ccgttgaata  6180
tggctcataa caccccttgt attactgttt atgtaagcag acagttttat tgttcatgat  6240
gatatatttt tatcttgtgc aatgtaacat cagagatttt gagacacaac gtggctttcc  6300
cccgccgctc tagaactagt ggatccaaat aaaacgaaag gctcagtcga aagactgggc  6360
ctttcgtttt atctgttgtt tgtcgcatta tacgagacgt ccaggttggg atacctgaaa  6420
caaaacccat cgtacggcca aggaagtctc caataactgt gatccaccac aagcgccagg  6480
gttttcccag tcacgacgtt gtaaaacgac ggccagtcat gcataatccg cacgcatctg  6540
gaataaggaa gtgccattcc gcctgacct                                   6569
```

```
SEQ ID NO: 162          moltype = DNA  length = 6041
FEATURE                 Location/Qualifiers
misc_feature            1..6041
                        note = pLD20
source                  1..6041
                        mol_type = other DNA
                        organism = synthetic construct
SEQUENCE: 162
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc ctttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgaagtgttc tacgtttagt ttttggtttg tttgtaaaat tatattcttc  1620
tttttttcct tcaacattca gacatcaatc gccaacccaa gggaaaactt ccttaagtgt  1680
tttctgcagt acatccctaa caatgcaaca aacctcaagt tggtgtacac tcaaaacaat  1740
ccactctata tgagcgtgct taatagcaca atccacaact tgcgcttcac gtcagatact  1800
acgcctaagc cactagtgat cgttacacca tcacacgtca gccatattca aggaacgatc  1860
ctatgtctga aaaaggtcgg gttgcaaatc aggactcgat caggagggca cgatagtgag  1920
ggaatgagtt acatctcgca agtacccttc gtgatagttg acttgcgaaa tatgcggtct  1980
attaaaattg acgtacatag ccagaccgcc tgggttgaag caggggcaac cttgggtgaa  2040
gtttattact gggtcaatga aaaaaacgaa aacctaagtc ttgctgctgg atattgcccc  2100
accgtttgcg cgggtggtca ttttggaggc ggcggatatg gtccgttgat gagaaattat  2160
ggacttgcag cagacaatat tatagatgcc cacttggtga acgttcatgg aaaggtcttg  2220
gaccgtaagt ccatgggtga agatcttttc tgggccttga gaggtggtgg agcggaatcg  2280
tttggcatca tcgttgcctg gaaaattagg ttggttgcgg tcccgaagag tacaatgttc  2340
tccgtgaaga agattatgga aatacatgag cttgtcaagt tagttaacaa gtggcaaaat  2400
atcgcttata agtatgataa agacttgctt ttgatgactc attttattac gcgaaacata  2460
accgataacc agggcaagaa caagactgct attcacacgt acttctcctc tgtatttctt  2520
ggaggagtag actccttagt tgacttgatg aacaagagtt tcccagaatt ggggattaag  2580
aagacagatt gcagacaatt atcgtggata gatacaatca tattctatag cggtgtcgtc  2640
aattacgata ctgataattt taataaagaa atcctcctag atcgttcagc tgggcaaaac  2700
ggggcattca aaattaaatt ggattatgtg aagaaaccaa ttccagagct ggtgtttgtt  2760
```

```
cagatattgg aaaaacttta cgaagaagac attggcgcag gtatgtacgc tttgtatcca  2820
tatggaggca ttatggacga gatctcagag ctggcgatcc ccttcccgca cagagctggg  2880
atactctacg agctatggta catctgctct tgggagaaac aagaagacaa cgagaaacat  2940
ctcaattgga ttcggaacat atacaacttt atgaccccat acgtatcaaa aaacccgcgc  3000
ttagcatact tgaattacag agacttagat atcggtatca atgatcctaa gaatcctaac  3060
aattacaccc aagcccgtat ttggggtgag aaatatttcg gcaagaattt tgacagatta  3120
gttaaggtca aaacactcgt ggaccccaac aactttttcc gaaacgagca gtcgattcca  3180
ccactaccca ggcatagaca ctgataagag tgactctttt gataagagtc gcaaatttga  3240
tttcataagt atatattcat tatgtaaagt agtaaatgga aaattcatta aaaaaaaagc  3300
aaatttccgt tgtatgcata ctccgaacac aaaactagcc ccggaaaaac ccttagttga  3360
tagttgcgaa tttaggtcga ccatatgcga cgggtacaac gagaattgta ttgaattgat  3420
caagaacatg atcttggtgt tacagaacat caagttcttg gaccagactg agaatgcaca  3480
gatatacaag gcgtcatgtg ataaaatgga tgagatttat ccacaattga agaaagagtt  3540
tatggaaagt ggtcaaccag aagctaaaca ggaagaagca aacgaagagg tgaaacaaga  3600
agaagaaggt aaataagtat tttgtattat ataacaaaca aagtaaggaa tacagattta  3660
tacaataaat tgccatacta gtcacgtgag atatctcatc cattccccaa ctcccaagaa  3720
aataaaaaag tgaaaaataa aatcaaaccc aaagatcaac ctccccatca tcatcgtcat  3780
caaacccccca gctcaattcg caatggttag cacaaaaaca tacacagaaa gggcatcagc  3840
acacccctcc aaggttgccc aacgtttatt aattaaaggc taggtggagg ctcagtgatg  3900
ataagtctgc gatggtggat gcatgtgtca tggtcatagc tgtttcctgt gtgaaattgt  3960
tatccgctca gagggcacaa tcctattccg cgctatccga caatctccaa gacattaggt  4020
ggagttcagt tcggcgtatg gcatatgtcg ctggaaagaa catgtgagca aaaggccagc  4080
aaaaggccag gaaccgtaaa aaggccgcgt tgctggcgtt tttccatagg ctccgccccc  4140
ctgacgagca tcacaaaaat cgacgctcaa gtcagaggtg gcgaaacccg acaggactat  4200
aaagatacca ggcgtttccc cctggaagct ccctcgtgcg ctctcctgtt ccgaccctgc  4260
cgcttaccgg atacctgtcc gcctttctcc cttcgggaag cgtggcgctt tctcatagct  4320
cacgctgtag gtatctcagt tcggtgtagg tcgttcgctc caagctgggc tgtgtgcacg  4380
aaccccccgt tcagcccgac cgctgcgcct tatccggtaa ctatcgtctt gagtccaacc  4440
cggtaagaca cgacttatcg ccactggcag cagccactgg taacaggatt agcagagcga  4500
ggtatgtagg cggtgctaca gagttcttga agtggtggcc taactacggc tacactagaa  4560
gaacagtatt tggtatctgc gctctgctga agccagttac cttcggaaaa agagttggta  4620
gctcttgatc cggcaaacaa accaccgctg gtagcggtgg tttttttgtt tgcaagcagc  4680
agattacgcg cagaaaaaaa ggatctcaag aagatccttt gatcttttct acggggtctg  4740
acgctctatt caacaaagcc gccgtcccgt caagtcagcg taaatgggta gggggcttca  4800
aatcgtccgc tctgccagtg ttacaaccaa ttaacaaatt ctgattagaa aaactcatcg  4860
agcatcaaat gaaactgcaa tttattcata tcaggattat caataccata tttttgaaaa  4920
agccgtttct gtaatgaagg agaaaactca ccgaggcagt tccataggat ggcaagatcc  4980
tggtatcggt ctgcgattcc gactcgtcca acatcaatac aacctattaa tttcccctcg  5040
tcaaaaataa ggttatcaag tgagaaatca ccatgagtga cgactgaatc cggtgagaat  5100
ggcaaaagct tatgcatttc tttccagact tgttcaacag gccagccatt acgctcgtca  5160
tcaaaatcac tcgcatcaac caaaccgtta ttcattcgtg attgcgcctg agcgagacga  5220
aatacgcgat cgctgttaaa aggacaatta caaacaggaa tcgaatgcaa ccggcgcagg  5280
aacactgcca gcgcatcaac aatattttca cctgaatcag gatattcttc taatacctgg  5340
aatgctgttt tcccggggat cgcagtggtg agtaaccatg catcatcagg agtacggata  5400
aaatgcttga tggtcggaag aggcataaat tccgtcagcc agtttagtct gaccatctca  5460
tctgtaacat cattggcaac gctacctttg ccatgtttca gaaacaactc tggcgcatcg  5520
ggcttcccat acaatcgata gattgtcgca cctgattgcc cgacattatc gcgagcccat  5580
ttatacccat ataaatcagc atccatgttg gaatttaatc gcggcctcga gcaagacgtt  5640
tcccgttgaa tatggctcat aacacccctt gtattactgt ttatgtaagc agacagtttt  5700
attgttcatg atgatatatt tttatcttgt gcaatgtaac atcagagatt ttgagacaca  5760
acgtggcttt ccccccgccgc tctagaacta gtggatccaa ataaaacgaa aggctcagtc  5820
gaaagactgg gcctttcgtt ttatctgttg tttgtcgcat tatacgagac gtccaggttg  5880
ggatacctga aacaaaaccc atcgtacggc caaggaagtc tccaataact gtgatccacc  5940
acaagcgcca gggttttccc agtcacgacg ttgtaaaacg acggccagtc atgcataatc  6000
cgcacgcatc tggaataagg aagtgccatt ccgcctgacc t                      6041

SEQ ID NO: 163         moltype = DNA  length = 6536
FEATURE                Location/Qualifiers
misc_feature           1..6536
                       note = pLD22
source                 1..6536
                       mol_type = other DNA
                       organism = synthetic construct
SEQUENCE: 163
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
```

```
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt cccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgacagaagt agtagataga gcaagttccc cagcaagtcc aggatctacg  1620
accgccgccg cagacggtgc taaggtggcg gtggagccac gcgtagatgt agcggccctt  1680
ggcgagcagt tgctagggcg atgggctgac atcagattgc acgcacgaga cttagcaggc  1740
cgcgaagtgg tccaaaaggt tgaaggactt acgcacactg agcatcggag tagagtcttt  1800
ggacagttga agtacttggt agacaacaat gctgttcaca gagcttttcc ctccaggcta  1860
ggtggatcag atgaccatgg cggtaatata gctggattcg aggaattagt tactgctgat  1920
ccatcattgc aaataaaggc cggcgttcag tggggtttgt ttggttctgc agtgatgcac  1980
ttgggaaccc gtgaacatca tgacaagtgg ttgccaggta ttatgtcgtt agaaataccg  2040
gggtgtttcg cgatgacaga aaccgggcac ggtagcgacg tggcctctat tgctacaaca  2100
gcaacttatg atgaggaaac ccaagagttt gttattgata ccccgttcag agccgcttgg  2160
aaagattata tcggtaatgc agcgaacgat ggtttggcgg cagttgtttt cgcacaatta  2220
atcacgagga aagtgaacca tggtgtacac gccttttacg tggatctcag agatcctgcg  2280
actggagact tcctacccgg aataggagga gaggacgatg gaatcaaggg gggattgaat  2340
ggcattgaca acggtagact acattttacg aacgtacgca ttcctagaac taatcttctt  2400
aacagatatg gcgatgtggc ggtcgacggc acatacctgt cgaccatcga atcaccaggg  2460
cgccggttct ttacgatgct tggtactcta gtccagggta gagttagtct cgatggagca  2520
gctgtcgctg cactgaaggt cgcattgcaa agtgcaattc actacgctgc ggagaggaga  2580
caatttaatg cgacttcacc tactgaagaa gaggtccttc ttgattatca gaggcatcaa  2640
aggagactct ttacacgact tgcaacgacg tacgccgcat ctttcgccca cgagcagcta  2700
ttgcaaaagt tcgatgatgt cttttcaggg gcacatgata ccgacgccga ccggcaggac  2760
ttggaaaccc tagccgccgc tttgaagcca ttgagcacat ggcatgcact tgacacgtta  2820
caagaatgca gagaggcctg tgggggggcc ggatttttga tagaaaaccg tttcgcgagc  2880
ttgcgtgctg acttggacgt ttacgtcaca ttcgagggtg ataacacagt tttattgcaa  2940
ttggttgcta aacggctctt ggcagactac gcaaaagagt tcagaggggc caacttcggc  3000
gttcttgcca ggtatgtggt tgaccaagcc gcgggagtgg cgctccaccg aacaggacta  3060
aggcaagtcg ctcaatttgt tgcagacagc gggtccgttc agaagtcggc tcttgcgctt  3120
cgcgatgaag agggtcaacg aacattgtta acggacagag tacagagcat ggttgccgaa  3180
gtgggggctg ccttgaaagg cgcaggcaaa ttaccccaac atcaagcagc tgcattgttc  3240
aaccaacacc agaacgaact tattgaggct gcccaggccc atgcagaact cctccaatgg  3300
gaggcattta cagaagctct cgctaaagtc gacgatgctg gtacaaagga agtgcttact  3360
cgattgcgag atctctttgg tttgtccttg attgaaaaac acttgctgtg gtatcttatg  3420
aatggacgtt tgtccatgca aagaggcagg acagttggaa cttacattaa tcgtttactt  3480
gtcaagatcc gtccacacgc actagacttg gttgatgcct tcggttacgg cgcggagcat  3540
ttgcgtgctg ctatcgccac cggagcggaa gcaacccgac aggatgaagc ccgaacgtat  3600
tttagacaac aacgggcatc gggactggcc ccggccgatg aaaagacctt actcgctatc  3660
aaagctggta aatcaagagg gcgaagggca aagctatgat aagagtgact cttttgataa  3720
gagtcgcaaa tttgatttca taagtatata ttcattatgt aaagtagtaa atggaaaatt  3780
cattaaaaaa aaagcaaatt tccgttgtat gcatactccg aacacaaaac tagccccgga  3840
aaaaccctta gttgatagtt gcgaatttag gtcgaccata tgcgacgggt acaacgagaa  3900
ttgtattgaa ttgatcaaga acatgatctt ggtgttacag aacatcaagt tcttggacca  3960
gactgagaat gcacagatat acaaggcgtc atgtgataaa atggatgaga tttatccaca  4020
attgaagaaa gagtttatgg aaagtggtca accagaagct aaacaggaag aagcaaacga  4080
agaggtgaaa caagaagaag aaggtaaata agtattttgt attatataac aaacaaagta  4140
aggaatacag atttatacaa taaattgcca tactagtcac gtgagatatc tcatccattc  4200
cccaactccc aagaaaataa aaaagtgaaa aataaaatca aacccaaaga tcaacctccc  4260
catcatcatc gtcatcaaac ccccagctca attcgcaatg gttagcacaa aaacatacac  4320
agaaagggca tcagcacacc cctccaaggt tgcccaacgt ttattaatta aaggctaggt  4380
ggaggctcag tgatgataag tctgcgatgg tggatgcatg tgtcatggtc atagctgttt  4440
cctgtgtgaa attgttatcc gctcagaggg cacaatccta ttccgcgcta tccgacaatc  4500
tccaagacat taggtggagt tcagttcggc gtatggcata tgtcgctgga aagaacatgt  4560
gagcaaaagg ccagcaaaag gccaggaacc gtaaaaaggc cgcgttgctg gcgtttttcc  4620
ataggctccg cccccctgac gagcatcaca aaaatcgacg ctcaagtcag aggtggcgaa  4680
acccgacagg actataaaga taccaggcgt ttccccctgg aagctccctc gtgcgctctc  4740
ctgttccgac cctgccgctt accggatacc tgtccgcctt tctcccttcg ggaagcgtgg  4800
cgctttctca tagctcacgc tgtaggtatc tcagttcggt gtaggtcgtt cgctccaagc  4860
tgggctgtgt gcacgaaccc cccgttcagc ccgaccgctg cgccttatcc ggtaactatc  4920
gtcttgagtc caacccggta agacacgact tatcgccact ggcagcagcc actggtaaca  4980
ggattagcag agcgaggtat gtaggcggtg ctacagagtt cttgaagtgg tggcctaact  5040
acggctacac tagaagaaca gtatttggta tctgcgctct gctgaagcca gttaccttcg  5100
gaaaaagagt tggtagctct tgatccggca aacaaaccac cgctggtagc ggtggttttt  5160
ttgtttgcaa gcagcagatt acgcgcagaa aaaaaggatc tcaagaagat cctttgatct  5220
tttctacggg gtctgacgct ctattcaaca aagccgccgt cccgtcaagt cagcgtaaat  5280
gggtaggggg cttcaaatcg tccgctctgc cagtgttaca accaattaac aaattctgat  5340
tagaaaaact catcgagcat caaatgaaac tgcaatttat tcatatcagg attatcaata  5400
ccatattttt gaaaaagccg tttctgtaat gaaggagaaa actcaccgag gcagttccat  5460
aggatggcaa gatcctggta tcggtctgcg attccgactc gtccaacatc aatacaacct  5520
attaatttcc cctcgtcaaa aataaggtta tcaagtgaga aatcaccatg agtgacgact  5580
gaatccggtg agaatggcaa aagcttatgc atttctttcc agacttgttc aacaggccag  5640
```

```
ccattacgct cgtcatcaaa atcactcgca tcaaccaaac cgttattcat tcgtgattgc  5700
gcctgagcga gacgaaatac gcgatcgctg ttaaaaggac aattacaaac aggaatcgaa  5760
tgcaaccggc gcaggaacac tgccagcgca tcaacaatat tttcacctga atcaggatat  5820
tcttctaata cctggaatgc tgttttcccg gggatcgcag tggtgagtaa ccatgcatca  5880
tcaggagtac ggataaaatg cttgatggtc ggaagaggca taaattccgt cagccagttt  5940
agtctgacca tctcatctgt aacatcattg gcaacgctac ctttgccatg tttcagaaac  6000
aactctggcg catcgggctt cccatacaat cgatagattg tcgcacctga ttgcccgaca  6060
ttatcgcgag cccatttata cccatataaa tcagcatcca tgttggaatt taatcgcggc  6120
ctcgagcaag acgtttcccg ttgaatatgg ctcataacac cccttgtatt actgtttatg  6180
taagcagaca gttttattgt tcatgatgat atatttttat cttgtgcaat gtaacatcag  6240
agattttgag acacaacgtg gctttccccc gccgctctag aactagtgga tccaaataaa  6300
acgaaaggct cagtcgaaag actgggcctt tcgttttatc tgttgtttgt cgcattatac  6360
gagacgtcca ggttgggata cctgaaacaa aacccatcgt acggccaagg aagtctccaa  6420
taactgtgat ccaccacaag cgccagggtt ttcccagtca cgacgttgta aaacgacggc  6480
cagtcatgca taatccgcac gcatctggaa taaggaagtg ccattccgcc tgacct      6536
```

```
SEQ ID NO: 164          moltype = DNA  length = 5582
FEATURE                 Location/Qualifiers
misc_feature            1..5582
                        note = pLD24
source                  1..5582
                        mol_type = other DNA
                        organism = synthetic construct
SEQUENCE: 164
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgcccttt gc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgaatcattt aagagcagaa ggacccgcat cagtgttagc gataggtaca  1620
gctaacccag agaatatctt aatccaagat gaatttcctg actactattt ccgtgttact  1680
aaatcggaac atatgactca acttaaagag aagttccgga aaatctgcga taaatccatg  1740
atccgaaaga gaaactgttt ccttaacgaa gaacatctca agcaaaaccc gaggttggta  1800
gagcacgaaa tgcagacctt ggatgctagg caggacatgt tggtggtcga agtgccaaaa  1860
ctcggcaagg acgcgtgcgc taaggcaatc aaggagtggg gtcaaccgaa gtctaaaatc  1920
acgcatctaa tatttacatc tgcactgaca accgacatgc cgggtgccga ttatcactgc  1980
gccaagctac ttggattgag tccactggtt aagagagtta tgatgtatca attggggtgt  2040
tacggagggg gcacagtcct cagaattgct aaggatattg cggaaaataa caagggcgcg  2100
agggtccttg ctgtatgttg tgatattatg gcctgtttgt ttcgcgggcc ctcggattca  2160
gatttggaat tgcttgtcgg acaggcaatt tttggtgacg gggccgcagc agtcatagtg  2220
ggagccgaac cagacgaaag cgtgggtgaa agaccaatct ttgagttggt tctgaccgga  2280
caaacgatct tacctaactc ggaaggtacg attggaggac atattagaga agccggccta  2340
attttcgatc ttcacaaaga cgttccaatg ttaatctcca ataacataga aaagtgcttg  2400
atagaagcat ttactcccat tggtattagt gactggaaca gcattttctg gatcacccac  2460
cctggaggaa aagctatact cgataaggtt gaagagaaac tcgacttgaa aaaggagaaa  2520
ttcgttgact cacgacatgt gttatcagag cacgggaata tgagttcatc cacagtcttg  2580
ttcgtaatgg atgaattgcg aaaacgctct cttgaggagg gaaagagcac aaccggtgac  2640
gggtttgagt ggggcgtgct attcggtttt ggcccaggtt tgactgtcga gcgggttgtt  2700
gttcgtagtg taccaattaa gtacggaaga agggcaaagt tgtgataaga gtgactcttt  2760
tgataagagt cgcaaatttg atttcataag tatatattca ttatgtaaag tagtaaatgg  2820
aaaattcatt aaaaaaaaag caaatttccg ttgtatgcat actccgaaca caaaactagc  2880
cccggaaaaa cccttagttg atagttgcga atttaggtcg accatatgcg acgggtacaa  2940
cgagaattgt attgaattga tcaagaacat gatcttggtg ttacagaaca tcaagttctt  3000
ggaccagact gagaatgcac agatatacaa ggcgtcatgt gataaaatgg atgagattta  3060
tccacaattg aagaaagagt ttatggaaag tggtcaacca gaagctaaac aggaagaagc  3120
aaacgaagag gtgaaacaag aagaagaagg taaataagta ttttgtatta tataacaaac  3180
aaagtaagga atacagattt atacaataaa ttgccatact agtcacgtga gatatctcat  3240
ccattcccca actcccaaga aaataaaaaa gtgaaaaata aaatcaaacc caaagatcaa  3300
```

```
cctccccatc atcatcgtca tcaaaccccc agctcaattc gcaatggtta gcacaaaaac  3360
atacacagaa agggcatcag cacacccctc caaggttgcc caacgtttat taattaaagg  3420
ctaggtggag gctcagtgat gataagtctg cgatggtgga tgcatgtgtc atggtcatag  3480
ctgtttcctg tgtgaaattg ttatccgctc agagggcaca atcctattcc gcgctatccg  3540
acaatctcca agacattagg tggagttcag ttcggcgtat ggcatatgtc gctggaaaga  3600
acatgtgagc aaaaggccag caaaaggcca ggaaccgtaa aaaggccgcg ttgctggcgt  3660
ttttccatag gctccgcccc cctgacgagc atcacaaaaa tcgacgctca agtcagaggt  3720
ggcgaaaccc gacaggacta taaagatacc aggcgtttcc ccctggaagc tccctcgtgc  3780
gctctcctgt tccgaccctg ccgcttaccg gatacctgtc cgcctttctc ccttcgggaa  3840
gcgtggcgct ttctcatagc tcacgctgta ggtatctcag ttcggtgtag gtcgttcgct  3900
ccaagctggg ctgtgtgcac gaaccccccg ttcagcccga ccgctgcgcc ttatccggta  3960
actatcgtct tgagtccaac ccggtaagac acgacttatc gccactggca gcagccactg  4020
gtaacaggat tagcagagcg aggtatgtag gcggtgctac agagttcttg aagtggtggc  4080
ctaactacgg ctacactaga agaacagtat ttggtatctg cgctctgctg aagccagtta  4140
ccttcggaaa aagagttggt agctcttgat ccggcaaaca aaccaccgct ggtagcggtg  4200
gtttttttgt ttgcaagcag cagattacgc gcagaaaaaa aggatctcaa gaagatcctt  4260
tgatcttttc tacggggtct gacgctctat tcaacaaagc cgccgtcccg tcaagtcagc  4320
gtaaatgggt agggggcttc aaatcgtccg ctctgccagt gttacaacca attaacaaat  4380
tctgattaga aaaactcatc gagcatcaaa tgaaactgca atttattcat atcaggatta  4440
tcaataccat atttttgaaa aagccgtttc tgtaatgaag gagaaaactc accgaggcag  4500
ttccatagga tggcaagatc ctggtatcgg tctgcgattc cgactcgtcc aacatcaata  4560
caacctatta atttcccctc gtcaaaaata aggttatcaa gtgagaaatc accatgagtg  4620
acgactgaat ccggtgagaa tggcaaaagc ttatgcattt ctttccagac ttgttcaaca  4680
ggccagccat tacgctcgtc atcaaaatca ctcgcatcaa ccaaaccgtt attcattcgt  4740
gattgcgcct gagcgagacg aaatacgcga tcgctgttaa aaggacaatt acaaacagga  4800
atcgaatgca accggcgcag gaacactgcc agcgcatcaa caatattttc acctgaatca  4860
ggatattctt ctaatacctg gaatgctgtt ttcccgggga tcgcagtggt gagtaaccat  4920
gcatcatcag gagtacggat aaaatgcttg atggtcggaa gaggcataaa ttccgtcagc  4980
cagtttagtc tgaccatctc atctgtaaca tcattggcaa cgctaccttt gccatgtttc  5040
agaaacaact ctggcgcatc gggcttccca tacaatcgat agattgtcgc acctgattgc  5100
ccgacattat cgcgagccca tttataccca tataaatcag catccatgtt ggaatttaat  5160
cgcggcctcg agcaagacgt ttcccgttga atatggctca taacacccct tgtattactg  5220
tttatgtaag cagacagttt tattgttcat gatgatatat ttttatcttg tgcaatgtaa  5280
catcagagat tttgagacac aacgtggctt tcccccgccg ctctagaact agtggatcca  5340
aataaaacga aaggctcagt cgaaagactg ggcctttcgt tttatctgtt gtttgtcgca  5400
ttatacgaga cgtccaggtt gggatacctg aaacaaaacc catcgtacgg ccaaggaagt  5460
ctccaataac tgtgatccac cacaagcgcc agggttttcc cagtcacgac gttgtaaaac  5520
gacggccagt catgcataat ccgcacgcat ctggaataag gaagtgccat tccgcctgac  5580
ct                                                                 5582
```

```
SEQ ID NO: 165          moltype = DNA  length = 5606
FEATURE                 Location/Qualifiers
misc_feature            1..5606
                        note = pLD56
source                  1..5606
                        mol_type = other DNA
                        organism = synthetic construct
SEQUENCE: 165
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgcccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tggggttgtc cttagtttgt acgttcagtt tccaaactaa ctaccacaca  1620
ctactaaatc cgcacaacaa aaacccgaaa aattcattgc tctcctatca gcacccaaaa  1680
acacccatta tcaagtctag ttacgacaac tttccatcaa aatactgtct aacgaaaaac  1740
tttcatttgt tgggcttaaa ttctcataat cgtatttcca gtcagtcccg atcgatcagg  1800
gccgggagtg accaaattga aggttctcca catcatgaaa gtgacaattc aattgctacg  1860
```

```
aagattttaa actttgggca tacatgctgg aagctacagc gaccgtatgt agttaagggg  1920
atgatcagca ttgcctgcgg cctattcgga agggaactct tcaataatag acatcttttt  1980
tcttggggtt taatgtggaa agcttttttc gctttggttc ctatccttag ttttaacttc  2040
ttcgccgcta ttatgaatca aatttacgat gttgacatcg accgtattaa caaacccgat  2100
ctccccccttg tttcaggcga gatgtccatt gaaacggcat ggattttgtc catcattgtt  2160
gcgcttactg gcttgattgt taccattaag cttaaaagcg ctcccttgtt cgtttttata  2220
tacattttcg gcatttttgc cggattcgca tacagtgtcc cgcctatacg ttggaaacaa  2280
tatccattca cgaacttctt gatcacgatc tcatcacatg ttggattggc ctttacgtcc  2340
tacagtgcta ccacatctgc ccttggattg cctttcgttt ggaggcctgc cttctcgttt  2400
atcattgcat ttatgacagt gatgggaatg actatcgcat ttgctaaaga tatcagcgac  2460
atagagggcg atgcaaaata tggggtgagt actgttgcga cgaagttggg cgcccgaaat  2520
atgaccttcg ttgtttccgg cgttctttta cttaactatt tagtatcgat tagcatcggg  2580
atcatctggc cacaggtgtt taaatcaaat attatgatct tgtcgcatgc catcctagct  2640
ttctgtctta tatttcaaac aagagaatta gccctagcga actacgcctc agcaccaagt  2700
cgtcagttct tcgaatttat atggctactc tactacgccg aatacttcgt ctatgtcttc  2760
atttagtaat aagagtgact cttttgataa gagtcgcaaa tttgatttca taagtatata  2820
ttcattatgt aaagtagtaa atggaaaatt cattaaaaaa aaagcaaatt tccgttgtat  2880
gcatactccg aacacaaaac tagccccgga aaaaccctta gttgatagtt gcgaatttag  2940
gtcgaccata tgcgacgggt acaacgagaa ttgtattgaa ttgatcaaga acatgatctt  3000
ggtgttacag aacatcaagt tcttggacca gactgagaat gcacagatat acaaggcgtc  3060
atgtgataaa atggatgaga tttatccaca attgaagaaa gagtttatgg aaagtggtca  3120
accagaagct aaacaggaag aagcaaacga agaggtgaaa caagaagaag aaggtaaata  3180
agtattttgt attatataac aaacaaagta aggaatacag atttatacaa taaattgcca  3240
tactagtcac gtgagatatc tcatccattc cccaactccc aagaaaataa aaaagtgaaa  3300
aataaaatca aacccaaaga tcaacctccc catcatcatc gtcatcaaac ccccagctca  3360
attcgcaatg gttagcacaa aaacatacac agaaagggca tcagcacacc cctccaaggt  3420
tgcccaacgt ttattaatta aaggctaggt ggaggctcag tgatgataag tctgcgatgg  3480
tggatgcatg tgtcatggtc atagctgttt cctgtgtgaa attgttatcc gctcagaggg  3540
cacaatccta ttccgcgcta tccgacaatc tccaagacat taggtggagt tcagttcggc  3600
gtatggcata tgtcgctgga aagaacatgt gagcaaaagg ccagcaaaag gccaggaacc  3660
gtaaaaaggc cgcgttgctg gcgtttttcc ataggctccg ccccccctgac gagcatcaca  3720
aaaatcgacg ctcaagtcag aggtggcgaa acccgacagg actataaaga taccaggcgt  3780
ttccccctgg aagctccctc gtgcgctctc ctgttccgac cctgccgctt accggatacc  3840
tgtccgcctt tctcccttcg ggaagcgtgg cgctttctca tagctcacgc tgtaggtatc  3900
tcagttcggt gtaggtcgtt cgctccaagc tgggctgtgt gcacgaaccc cccgttcagc  3960
ccgaccgctg cgccttatcc ggtaactatc gtcttgagtc caacccggta agacacgact  4020
tatcgccact ggcagcagcc actggtaaca ggattagcag agcgaggtat gtaggcggtg  4080
ctacagagtt cttgaagtgg tggcctaact acggctacac tagaagaaca gtatttggta  4140
tctgcgctct gctgaagcca gttaccttcg gaaaaagagt tggtagctct tgatccggca  4200
aacaaaccac cgctggtagc ggtggttttt ttgtttgcaa gcagcagatt acgcgcagaa  4260
aaaaaggatc tcaagaagat cctttgatct tttctacggg gtctgacgct ctattcaaca  4320
aagccgccgt cccgtcaagt cagcgtaaat gggtaggggg cttcaaatcg tccgctctgc  4380
cagtgttaca accaattaac aaattctgat tagaaaaact catcgagcat caaatgaaac  4440
tgcaatttat tcatatcagg attatcaata ccatattttt gaaaaagccg tttctgtaat  4500
gaaggagaaa actcaccgag gcagttccat aggatggcaa gatcctggta tcggtctgcg  4560
attccgactc gtccaacatc aatacaacct attaatttcc cctcgtcaaa aataaggtta  4620
tcaagtgaga aatcaccatg agtgacgact gaatccggtg agaatggcaa aagcttatgc  4680
atttctttcc agacttgttc aacaggccag ccattacgct cgtcatcaaa atcactcgca  4740
tcaaccaaac cgttattcat tcgtgattgc gcctgagcga gacgaaatac gcgatcgctg  4800
ttaaaaggac aattacaaac aggaatcgaa tgcaaccggc gcaggaacac tgccagcgca  4860
tcaacaatat tttcacctga atcaggatat tcttctaata cctggaatgc tgttttcccg  4920
gggatcgcag tggtgagtaa ccatgcatca tcaggagtac ggataaaatg cttgatggtc  4980
ggaagaggca taaattccgt cagccagttt agtctgacca tctcatctgt aacatcattg  5040
gcaacgctac ctttgccatg tttcagaaac aactctggcg catcgggctt cccatacaat  5100
cgatagattg tcgcacctga ttgcccgaca ttatcgcgag cccatttata cccatataaa  5160
tcagcatcca tgttggaatt taatcgcggc ctcgagcaag acgtttcccg ttgaatatgg  5220
ctcataacac cccttgtatt actgtttatg taagcagaca gttttattgt tcatgatgat  5280
atatttttat cttgtgcaat gtaacatcag agattttgag acacaacgtg gctttccccc  5340
gccgctctag aactagtgga tccaaataaa acgaaaggct cagtcgaaag actgggcctt  5400
tcgttttatc tgttgtttgt cgcattatac gagacgtcca ggttgggata cctgaaacaa  5460
aacccatcgt acggccaagg aagtctccaa taactgtgat ccaccacaag cgccagggtt  5520
ttcccagtca cgacgttgta aaacgacggc cagtcatgca taatccgcac gcatctggaa  5580
taaggaagtg ccattccgcc tgacct                                        5606
```

```
SEQ ID NO: 166          moltype = DNA  length = 5071
FEATURE                 Location/Qualifiers
misc_feature            1..5071
                        note = pLD87
source                  1..5071
                        mol_type = other DNA
                        organism = synthetic construct
SEQUENCE: 166
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc ccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
```

-continued

```
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaaggatct caagaagatc  840
ctttgatctt ttctacgggg tctgacgctc tattcaacaa agccgccgtc ccgtcaagtc  900
agcgtaaatg ggtagggggc ttcaaatcgt ccgctctgcc agtgttacaa ccaattaaca  960
aattctgatt agaaaaactc atcgagcatc aaatgaaact gcaatttatt catatcagga  1020
ttatcaatac catatttttg aaaaagccgt ttctgtaatg aaggagaaaa ctcaccgagg  1080
cagttccata ggatggcaag atcctggtat cggtctgcga ttccgactcg tccaacatca  1140
atacaaccta ttaatttccc ctcgtcaaaa ataaggttat caagtgagaa atcaccatga  1200
gtgacgactg aatccggtga gaatggcaaa agcttatgca tttctttcca gacttgttca  1260
acaggccagc cattacgctc gtcatcaaaa tcactcgcat caaccaaacc gttattcatt  1320
cgtgattgcg cctgagcgag acgaaatacg cgatcgctgt taaaaggaca attacaaaca  1380
ggaatcgaat gcaaccggcg caggaacact gccagcgcat caacaatatt ttcacctgaa  1440
tcaggatatt cttctaatac ctggaatgct gttttcccgg ggatcgcagt ggtgagtaac  1500
catgcatcat caggagtacg gataaaatgc ttgatggtcg gaagaggcat aaattccgtc  1560
agccagttta gtctgaccat ctcatctgta acatcattgg caacgctacc tttgccatgt  1620
ttcagaaaca actctggcgc atcgggcttc ccatacaatc gatagattgt cgcacctgat  1680
tgcccgacat tatcgcgagc ccatttatac ccatataaat cagcatccat gttggaattt  1740
aatcgcggcc tcgagcaaga cgtttcccgt tgaatatggc tcataacacc ccttgtatta  1800
ctgtttatgt aagcagacag ttttattgtt catgatgata tatttttatc ttgtgcaatg  1860
taacatcaga gattttgaga cacaacgtgg ctttcccccg ccgctctaga actagtggat  1920
ccaaataaaa cgaaaggctc agtcgaaaga ctgggccttt cgttttatct gttgtttgtc  1980
gcattatacg agacgtccag gttgggatac ctgaaacaaa acccatcgta cggccaagga  2040
agtctccaat aactgtgatc caccacaagc gccagggttt tcccagtcac gacgttgtaa  2100
aacgacggcc agtcatgcat aatccgcacg catctggaat aaggaagtgc cattccgcct  2160
gacctttaat taagtcgact tgatgtttag agtgtccaga tccgcaagat cggctcgcac  2220
ttgtgttgtg ttgtttcaaa tcagcctgtc gttttgtgtc gtttgagatc attctgtctc  2280
actcttaggc tcgcttagaa ccgacaacgg agaatccggg ctcggttttt cggtcggcct  2340
tgatctgggc cttggacttg tactggtcgg ccatctccac gttgaccagc tccttgacct  2400
tgtagagctg accggcgata ccaggagaca ccttgtagta cttctgggag ccgaccttgc  2460
ccagaccgag ggtcttgagc acgtcacgtg ttctccacgg cattcgcagg atagatcgga  2520
cctgtgtgac tttgtagaac atggcgtttc aggtggttgc gtgagtgtgt aaaatcgtgt  2580
ctttcagaag ttacaaattt caccgcattt agagtttatg cagatgggcg gtgtgtggtt  2640
gggagttcga tttccgtgcg tgcatttgat cttgatgaat tggatttgta catggggaat  2700
agcacgtcaa gaaccgccta ctgcaaactc gtgaatattg agattattga ggaaattcaa  2760
ggaaaattca gatcagattt gagagcaaag tccaacaata ctacacaatc cctttcctgt  2820
attcttccac catcgtcatc gtcgtctgtc ttctcttcag ctttttaatt tcactcccca  2880
caaacccaaa tttagctgca tcattcatca acctccaatt ataactatac atcgcgacac  2940
gaacacgaaa cacgaaccac gaaccgccgc tttgtcgacg gagtgagacg ggagagagac  3000
catggtctct cgctcgtctc acgcttagcg gccgcgtcga cataacttcg tatagcatac  3060
attatacgaa gttattttct aatttggacc gatagccgta tagtccagtc tatctataag  3120
ttcaactaac tcgtaactat taccataaca tatacttcac tgccccagat aaggttccga  3180
taaaaagttg tgcagactaa atttatttca gtctcctctt caccaccaaa atgccctcct  3240
acgaagcgcg agctaacgtc cacaagtccg cctttgccgc ccgagtgctc aagctcgtgg  3300
cagccaagaa aaccaacctg tgtgcttctc tggatgttac caccaccaag gagctcattg  3360
agcttgccga taaggtcgga ccttatgtgt gcatgatcaa gacccatatc gacatcattg  3420
acgacttcac ctacgccgga actgtgctcc ccctcaagga acttgctctt aagcacggtt  3480
tcttcctgtt cgaggacaga aagttcgcag atattggcaa cactgtcaag caccagtaca  3540
agaacggtgt ctaccgaatc gccgagtggt ccgatatcac caacgcccac ggtgtacccg  3600
gaaccggaat cattgctggc ctgcgagctg gtgccgagga aactgtctct gaacagaaga  3660
aggaggatgt ctctgactac gagaactccc agtacaagga gttcctggtc ccctctccca  3720
acgagaagct ggccagaggt ctgctcatgc tggccgagct gtcttgcaag ggctctctgg  3780
ccactggcga gtactccaag cagaccattg agcttgcccg atccgacccc gagtttgtgg  3840
ttggcttcat tgcccagaac cgacctaagg gcgactctga ggactggctt attctgaccc  3900
ccggggtggg tcttgacgac aagggagatg ctctcggaca gcagtaccga actgttgagg  3960
atgtcatgtc taccggaacg gatatcataa ttgtcggccg aggtctgtac ggccagaacc  4020
gagatcctat tgaggaggcc aagcgatacc agaaggctgg ctgggaggct taccagaaga  4080
ttaactgtta gaggttagac tatggatatg tcatttaact gtgtatatag agagcgtgca  4140
agtatggagc gcttgttcag cttgtatgat ggtcagacga cctgtctgat cgagtatgta  4200
tgatactgca caacctgata acttcgtata gcatacatta tacgaagtta tctcgaggga  4260
tccctaggga ggcacatcta aacgaataac gaatattaat gataccatca tatctcagaa  4320
catgtatgac tgctgcttcc aaacgatatg aggatgagtc ctctttcaga ttaagataga  4380
gtacaaatat attatctata tactggtgtc tgtgcgatgt cgtatgagcg gtgaatcatg  4440
tgactgtcac gtggtttggc ccaagttaca ccgtagctac gcctttcttg accgactcca  4500
tggtcttctg ggcgggttga cagtttccac tggatgagcg tccgcctcct gttcctgtcg  4560
ttgtccctgc agctcagcct caatcttctg accgagctcg gagtccaggg aaatgccaac  4620
aggttgtcca agcaacatca tggtttggtg ggcagccgtg atctcatcgt cgttggatac  4680
cattcggtac ttggcctcaa tctgcacaaa gtagcggtac cactggtttc gagcaaaccg  4740
ctccaattga gcctctccgt cgagagagag agtaggtgat tgctccaact tgcggccaaa  4800
atgaagttct cgactcacct ttttgaagcg gttcttcttg cccatcttgg tggcgaaagt  4860
agtggctagt ggtggatgac tttgtataat gtaccgatga agagggttgt atttgctcag  4920
taagaagtag cgagtgaaat cagatcactt aacgagagca aagggcaatg gaatacctgc  4980
tgcctgatta acaacagctt ctgtgtcgtt tctctcttgt gaatgagtgt gttgctagag  5040
gtaggttggc actccaatgt tacttaatta a                                  5071
```

```
SEQ ID NO: 167          moltype = DNA  length = 5096
FEATURE                 Location/Qualifiers
misc_feature            1..5096
                        note = pLD101
source                  1..5096
                        mol_type = other DNA
                        organism = synthetic construct
SEQUENCE: 167
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc ccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaaggatct caagaagatc  840
ctttgatctt ttctacgggg tctgacgctc tattcaacaa agccgccgtc ccgtcaagtc  900
agcgtaaatg ggtagggggc ttcaaatcgt cctcgtgata ccaattcgga gcctgctttt  960
ttgtacaaac ttgttgataa tggcaattca aggatcttca cctagatcct tttaaattaa  1020
aaatgaagtt ttaaatcaat ctaaagtata tatgagtaaa cttggtctga cagttaccaa  1080
tgcttaatca gtgaggcacc tatctcagcg atctgtctat ttcgttcatc catagttgcc  1140
tgactccccg tcgtgtagat aactacgata cgggagggct taccatctgg ccccagtgct  1200
gcaatgatac cgcgagagcc acgctcaccg gctccagatt tatcagcaat aaaccagcca  1260
gccggaaggg ccgagcgcag aagtggtcct gcaactttat ccgcctccat ccagtctatt  1320
aattgttgcc gggaagctag agtaagtagt tcgccagtta atagtttgcg caacgttgtt  1380
gccattgcta caggcatcgt ggtgtcacgc tcgtcgtttg gtatggcttc attcagctcc  1440
ggttcccaac gatcaaggcg agttacatga tcccccatgt tgtgcaaaaa agcggttagc  1500
tccttcggtc ctccgatcgt tgtcagaagt aagttggccg cagtgttatc actcatggtt  1560
atggcagcac tgcataattc tcttactgtc atgccatccg taagatgctt ttctgtgact  1620
ggtgagtact caaccaagtc attctgagaa tagtgtatgc ggcgaccgag ttgctcttgc  1680
ccggcgtcaa tacgggataa taccgcgcca catagcagaa ctttaaaagt gctcatcatt  1740
ggaaaacgtt cttcggggcg aaaactctca aggatcttac cgctgttgag atccagttcg  1800
atgtaaccca ctcgtgcacc caactgatct tcagcatctt ttactttcac cagcgtttct  1860
gggtgagcaa aaacaggaag gcaaaatgcc gcaaaaaagg gaataagggc gacacggaaa  1920
tgttgaatac tcatactctt cctttttcaa tattattgaa gcatttatca gggttattgt  1980
ctcatgagcg gatacatatt tgaatgtatt tagaaaaata aacaaatagg ggttccgcgc  2040
acatttcccc gaaaagtgcc agatacctga aacaaaaccc atcgtacggc caaggaagtc  2100
tccaataact gtgatccacc acaagcgcca gggttttccc agtcacgacg ttgtaaaacg  2160
acggccagtc atgcataatc cgcacgcatc tggaataagg aagtgccatt ccgcctgacc  2220
tttaattaac gatccgcgta aattcagagc aatgccaaga tccttatttc cgataacagc  2280
gagatacaca tcagaagagg tggagactct ggccccgcac gaccaccacg tcgtcactca  2340
aagcaaagtc acgatgtaga aatcacaatc gtccccataa gcacgtggat tcccctggtt  2400
ttgtttcggc ctcggcagtg gcaattctgg ggtatataaa ccagcaaggt tatgacctga  2460
ttgacctgct tgtggcctga taaaccgcct gacttttgtg ataaggttgg gagcatgcgg  2520
ctcgggccat tgtgagcatt ttcgtcaagg actggccaag tccaactgga agagacatgg  2580
gcaaaatgtc gactttacag atgtacccga aattgcttca attgctctca gctgccggaa  2640
ccggatctat cggtgcaagt atcgtacagt agacatgtgc tattggtaac cctcggtatt  2700
ggctaggttt cgtatcaggg atacagttca acgctgatcg catatggcat gattccggct  2760
cgacacagcg accaagaacc aagcgtgtat gtcgtagact tgcaaatcat gtggggctta  2820
tccccggatt tccccaagtc acgttttcac aaaggctgtc tcccgaatgc atgagccgag  2880
gcaggctaaa ctggtttgtt catgtacccc acacaacgta aagatgcacc ccatgtgcag  2940
tgaaatacca caagtatata tataccgacc tacccgagat agcaaattga ttctacactt  3000
acactaccaa ttcttacatc aaaccaaacc gcttgagacc atccggtctc tgatcatcct  3060
cgagataact tcgtataatg tatgctatac gaagttatca ggttgtgcag tatcatacat  3120
actcgatcag acaggtcgtc tgaccatcat acaagctgaa caagcgctcc atacttgcac  3180
gctctctata tacacagtta aatgacatat ccatagtcta acctctaaca gttaatcttc  3240
tggtaagcct cccagccagc cttctggtat cgcttggcct cctcaatagg atctcggttc  3300
tggccgtaca gacctcggcc gacaattatg atatccgttc cggtagacat gacatcctca  3360
acagttcggt actgctgtcc gagagcatct cccttgtcgt caagacccac cccgggggtc  3420
agaataagcc agtcctcaga gtcgccctta ggtcggttct gggcaatgaa gccaaccaca  3480
aactcggggt cggatcgggc aagctcaatg gtctgcttgg agtactcgcc agtggccaga  3540
gagcccttgc aagacagctc ggccagcatg agcagacctc tggccagctt ctcgttggga  3600
gaggggacca ggaactcctt gtactgggag ttctcgtagt cagagacatc ctccttcttc  3660
tgttcagaga cagtttcctc ggcaccagct cgcaggccag caatgattcc ggttccgggt  3720
acaccgtggg cgttggtgat atcggaccac tcggcgattc ggtagacacc gttcttgtac  3780
tggtgcttga cagtgttgcc aatatctgcg aactttctgt cctcgaacag gaagaaaccg  3840
tgcttaagag caagttcctt gagggggagc acagttccgg cgtaggtgaa gtcgtcaatg  3900
atgtcgatat gggtcttgat catgcacaca taaggtccga ccttatcggc aagctcaatg  3960
agctccttgg tggtggtaac atccagagaa gcacacaggt tggttttctt ggctgccacg  4020
agcttgagca ctcgggcggc aaaggcggac ttgtggacgt tagctcgcgc ttcgtaggag  4080
ggcattttgg tggtgaagag gagactgaaa taaatttagt ctgcacaact ttttatcgga  4140
accttatctg ggcagtgaa gtatatgtta tggtaatagt tacgagttag ttgaacttat  4200
agatagactg gactatacgg ctatcggtcc aaattagaaa ataacttcgt ataatgtatg  4260
```

```
ctatacgaag ttatgtcgac gcggccgcac aagcactaca tggacgaggt caaggctgcc  4320
aacaaccctc gtaacaccca tgctccttac tacgagacaa agctgcgacc cttcctgttc  4380
cgacccgatg aggacgagga gatttgcgac ctggacgagt aggttgttgt aatactatga  4440
tttattgtgt ttatatgtta ttgatactat tgaaagagtt attgtgtaat tttagatgct  4500
gtatgttaac tagaagctca gattctacaa agagatcctc agatctgagg aatgatctac  4560
gttctgcaat agaagggaca actgcagctc tgaatgacca caaaaagaat acaccacaag  4620
cagttgtaac tgagctatta gccttgcttt cgcaccattc gcttttctgg atggtagccc  4680
tttactacaa gtagctaata tggaatgtac attaccgtct cattacaata tgtatatgca  4740
agttcatggc acttcatgca caccagcccc ttcgttaagt accttccaaa aagtgatcaa  4800
tgataagtga tatatctaat ttagagatct ggacacacga acaagtcggg aacacaaatc  4860
ccgagatgat tgcctgctca gaggagtcca attagtcttt acaccattcg tgctaatgaa  4920
gggcacagaa tattccactt tgaaagttta agattaagct cggctcgcaa ttatgcatga  4980
aaaatatgta gggagagaac gatcccacga gttctgtttg gttgcgagag tgttcgggtt  5040
ttctcctaaa aagaataggg gagggaaaaa ttatcgccta agtcaccatt aattaa      5096

SEQ ID NO: 168         moltype = DNA  length = 5096
FEATURE                Location/Qualifiers
misc_feature           1..5096
                       note = pLD102
source                 1..5096
                       mol_type = other DNA
                       organism = synthetic construct
SEQUENCE: 168
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc ccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaaggatct caagaagatc  840
ctttgatctt ttctacgggg tctgacgctc tattcaacaa agccgccgtc ccgtcaagtc  900
agcgtaaatg ggtagggggc ttcaaatcgt cctcgtgata ccaattcgga gcctgctttt  960
ttgtacaaac ttgttgataa tggcaattca aggatcttca cctagatcct tttaaattaa  1020
aaatgaagtt ttaaatcaat ctaaagtata tatgagtaaa cttggtctga cagttaccaa  1080
tgcttaatca gtgaggcacc tatctcagcg atctgtctat ttcgttcatc catagttgcc  1140
tgactccccg tcgtgtagat aactacgata cgggagggct taccatctgg ccccagtgct  1200
gcaatgatac cgcgagagcc acgctcaccg gctccagatt tatcagcaat aaaccagcca  1260
gccggaaggg ccgagcgcag aagtggtcct gcaactttat ccgcctccat ccagtctatt  1320
aattgttgcc gggaagctag agtaagtagt tcgccagtta atagtttgcg caacgttgtt  1380
gccattgcta caggcatcgt ggtgtcacgc tcgtcgtttg gtatggcttc attcagctcc  1440
ggttcccaac gatcaaggcg agttacatga tcccccatgt tgtgcaaaaa agcggttagc  1500
tccttcggtc ctccgatcgt tgtcagaagt aagttggccg cagtgttatc actcatggtt  1560
atggcagcac tgcataattc tcttactgtc atgccatccg taagatgctt ttctgtgact  1620
ggtgagtact caaccaagtc attctgagaa tagtgtatgc ggcgaccgag ttgctcttgc  1680
ccggcgtcaa tacgggataa taccgcgcca catagcagaa ctttaaaagt gctcatcatt  1740
ggaaaacgtt cttcggggcg aaaactctca aggatcttac cgctgttgag atccagttcg  1800
atgtaaccca ctcgtgcacc caactgatct tcagcatctt ttactttcac cagcgtttct  1860
gggtgagcaa aaacaggaag gcaaaatgcc gcaaaaaagg gaataagggc gacacggaaa  1920
tgttgaatac tcatactctt cctttttcaa tattattgaa gcatttatca gggttattgt  1980
ctcatgagcg gatacatatt tgaatgtatt tagaaaaata aacaaatagg ggttccgcgc  2040
acatttcccc gaaaagtgcc agatacctga aacaaaaccc atcgtacggc caaggaagtc  2100
tccaataact gtgatccacc acaagcgcca gggttttccc agtcacgacg ttgtaaaacg  2160
acggccagtc atgcataatc cgcacgcatc tggaataagg aagtgccatt ccgcctgacc  2220
tttaattaat tggcaaattt tactgtggcc ttcagaacgg taaaaataga ccaatcagaa  2280
ttctgaaaag cacatcttga tctcctcatt gcggggagtc caacggtggt cttattcccc  2340
cgaatttccc gctcaatctc gttccagacc gacccggaca cagtgcttaa cgccgttccg  2400
aaactctacc gcagatatgc tccaacggac tgggctgcat agatgtgatc ctcggcttgg  2460
agaaatggat aaaagccggc caaaaaaaaa gcggaaaaaa gcggaaaaaa agagaaaaaa  2520
aatcgcaaaa tttgaaaaat aggggggaaaa gacgcaaaaa cgcaaggagg ggggagtata  2580
tgacactgat aagcaagctc acaacggttc ctcttatttt tttcctcatc ttctgcctag  2640
gttcccaaaa tcccagatgc ttctctccag tgccaaaagt aagtacccca caggttttcg  2700
gccgaaaatt ccacgtgcag caacgtcgtg tggggtgtta aaatgtgggg gcggggaacc  2760
aggacaagag gctcttgtgg gagccgaatg agagcacaaa gcgggcgggt gtgataaggg  2820
catttttgcc cattttccct tctcctgtct ctccgacggt gatggcgttg tgcgtcctct  2880
atctatttct ttttatttct ttttgtttta tttctctgac taccgatttg gcttgatttc  2940
ctcaacccca cacaaataag ctcgggccga ggaatatata tatacacgga cacagtcgcc  3000
ctgtggacaa cacgtcacta cctctacgac gcttgagacc atccggtctc tgatcatcct  3060
cgagataact tcgtataatg tatgctatac gaagttatca ggttgtgcag tatcatacat  3120
actcgatcag acaggtcgtc tgaccatcat acaagctgaa caagcgctcc atacttgcac  3180
gctctctata tacacagtta aatgacatat ccatagtcta acctctaaca gttaatcttc  3240
tggtaagcct cccagccagc cttctggtat cgcttggcct cctcaatagg atctcggttc  3300
tggccgtaca gacctcggcc gacaattatg atatccgttc cggtagacat gacatcctca  3360
```

```
acagttcggt actgctgtcc gagagcatct cccttgtcgt caagacccac cccgggggtc  3420
agaataagcc agtcctcaga gtcgccctta ggtcggttct gggcaatgaa gccaaccaca  3480
aactcggggt cggatcgggc aagctcaatg gtctgcttgg agtactcgcc agtggccaga  3540
gagcccttgc aagacagctc ggccagcatg agcagacctc tggccagctt ctcgttggga  3600
gaggggacca ggaactcctt gtactgggag ttctcgtagt cagagacatc ctccttcttc  3660
tgttcagaga cagtttcctc ggcaccagct cgcaggccag caatgattcc ggttccgggt  3720
acaccgtggg cgttggtgat atcggaccac tcggcgattc ggtagacacc gttcttgtac  3780
tggtgcttga cagtgttgcc aatatctgcg aactttctgt cctcgaacag gaagaaaccg  3840
tgcttaagag caagttcctt gagggggagc acagttccgg cgtaggtgaa gtcgtcaatg  3900
atgtcgatat gggtcttgat catgcacaca taaggtccga ccttatcggc aagctcaatg  3960
agctccttgg tggtggtaac atccagagaa gcacacaggt tggttttctt ggctgccacg  4020
agcttgagca ctcgggcggc aaaggcggac ttgtggacgt tagctcgcgc ttcgtaggag  4080
ggcattttgg tggtgaagag gagactgaaa taaatttagt ctgcacaact ttttatcgga  4140
accttatctg gggcagtgaa gtatatgtta tggtaatagt tacgagttag ttgaacttat  4200
agatagactg gactatacgg ctatcggtcc aaattagaaa ataacttcgt ataatgtatg  4260
ctatacgaag ttatgtcgac gcggccgcat ggagcgtgtg ttctgagtcg atgttttcta  4320
tggagttgtg agtgttagta gacatgatgg gtttatatat gatgaatgaa tagatgtgat  4380
tttgatttgc acgatggaat tgagaacttt gtaaacgtac atgggaatgt atgaatgtgg  4440
gggttttgtg actggataac tgacggtcag tggacgccgt tgttcaaata tccaagagat  4500
gcgagaaact ttgggtcaag tgaacatgtc ctctctgttc aagtaaacca tcaactatgg  4560
gtagtatatt tagtaaggac aagagttgag attctttgga gtcctagaaa cgtattttcg  4620
cgttccaaga tcaaattagt agagtaatac gggcacggga atccattcat agtctcaatt  4680
ttcccatagg tgtgctacaa ggtgttgaga tgtggtacag taccaccatg attcgaggta  4740
aagagcccag aagtcattga tgaggtcaag aaatacacag atctacagct caatacaatg  4800
aatatcttct ttcatattct tcaggtgaca ccaagggtgt ctattttccc cagaaatgcg  4860
tgaaaaggcg cgtgtgtagc gtggagtatg ggttcggttg gcgtatcctt catatatcga  4920
cgaaatagta gggcaagaga tgacaaaaag tatctatatg tagacagcgt agaatatgga  4980
tttgattggt ataaattcat ttattgcgtg tctcacaaat actctcgata agttggggtt  5040
aaactggaga tggaacaatg tcgatatctc gacatatttt gatatttgtt aattaa      5096

SEQ ID NO: 169          moltype = DNA  length = 6044
FEATURE                 Location/Qualifiers
misc_feature            1..6044
                        note = pLD111
source                  1..6044
                        mol_type = other DNA
                        organism = synthetic construct
SEQUENCE: 169
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgcccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggcccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt atttgaata gttattcccc actaacattg ttcaaatctt  1560
cacgacataa tgaattgttc agcatttagt ttttggtttg tttgtaagat tatttcttc  1620
tttttgtcat ttaacattca aatttcaatt gcaaacccac aagaaaactt tttgaagtgt  1680
ttttcagaat acattccaaa caatccagct aacccaaagt ttatttacac acaacatgat  1740
caattgtaca tgtcagtttt gaactcaaca attcaaaact tgagatttac atcagatacc  1800
acaccaaagc cattggttat tgttacacca tcaaacgttt cccatattca agcatcaatc  1860
ttgtgttcaa agaaggttgg attgcaaatt agaaccagat caggaggaca cgatgcagaa  1920
ggaatgtcat acatttcaca agttccattc gttgttgttg atttgagaaa catgcactca  1980
attaagattg atgttcattc acaaacagca tgggttgaag caggagcaac attgggtgaa  2040
gtttactact ggattaacga aaagaacgaa aacttcagtt ttccaggagg ttactgtcca  2100
acagttggag ttggaggaca tttttcaggt ggaggatacg gagcattgat gagaaactac  2160
ggattggcag cagataacat tattgatgca cacttggtta acgttgatgg aaaggttttg  2220
gatagaaagt caatgggaga agatttgttt tgggcaatta gaggaggtgg tggagagaac  2280
tttggaatta ttgcagcatg gaagatcaag ttggttgcag ttccatcaaa gtcaacaatc  2340
ttttcagtta agaagaacat ggaaattcat ggtttggtta agttgtttaa caagtggcaa  2400
aacattgcat acaagtacga taaggatttg gttttgatga cacattttat tacaaagaac  2460
```

```
attacagata accatggaaa gaacaagaca acagttcacg gatacttttc atcaattttt  2520
cacggaggag ttgattcatt ggttgacttg atgaacaagt catttccaga attgggaatc  2580
aagaagacag attgtaagga attttcatgg attgatacaa caattttcta ctcaggagtt  2640
gttaacttta acacagcaaa ctttaagaag gaaattttgt tggacagatc agcaggaaag  2700
aagaccgcat tttccattaa gttggattac gttaagaaac caattccaga aacagcaatg  2760
gttaagattt tggaaaagtt gtacgaagaa gatgttggtg ttggaatgta cgttttgtac  2820
ccatacggag gaattatgga agaaatctca gaatcagcaa ttccatttcc acatagagca  2880
ggtattatgt acgaattgtg gtacacagca tcatgggaaa agcaagaaga taatgaaaag  2940
catattaact gggttagatc agtttacaac tttacaacac catacgtttc acaaaaccca  3000
agattggcat acttgaacta cagagatttg gatttgggaa agacaaaccc agaatcacca  3060
aacaactata cacaagctag aatttgggga gaaaagtact ttggtaagaa cttcaacaga  3120
ttggttaaag ttaagacaaa ggcagatcca aataacttct ttagaaacga acaatcaatt  3180
ccaccattgc caccacatca tcattaataa gagtgactct tttgataaga gtcgcaaatt  3240
tgatttcata agtatatatt cattatgtaa agtagtaaat ggaaaattca ttaaaaaaaa  3300
agcaaatttc cgttgtatgc atactccgaa cacaaaacta gccccggaaa aacccttagt  3360
tgatagttgc gaatttaggt cgaccatatg cgacgggtac aacgagaatt gtattgaatt  3420
gatcaagaac atgatcttgg tgttacagaa catcaagttc ttggaccaga ctgagaatgc  3480
acagatatac aaggcgtcat gtgataaaat ggatgagatt tatccacaat tgaagaaaga  3540
gtttatggaa agtggtcaac cagaagctaa acaggaagaa gcaaacgaag aggtgaaaca  3600
agaagaagaa ggtaaataag tattttgtat tatataacaa acaaagtaag gaatacagat  3660
ttatacaata aattgccata ctagtcacgt gagatatctc atccattccc caactcccaa  3720
gaaaataaaa aagtgaaaaa taaaatcaaa cccaaagatc aacctcccca tcatcatcgt  3780
catcaaaccc ccagctcaat tcgcaatggt tagcacaaaa acatacacag aaagggcatc  3840
agcacacccc tccaaggttg cccaacgttt attaattaaa ggctaggtgg aggctcagtg  3900
atgataagtc tgcgatggtg gatgcatgtg tcatggtcat agctgtttcc tgtgtgaaat  3960
tgttatccgc tcagagggca caatcctatt ccgcgctatc cgacaatctc caagacatta  4020
ggtggagttc agttcggcgt atggcatatg tcgctggaaa gaacatgtga gcaaaaggcc  4080
agcaaaaggc caggaaccgt aaaaaggccg cgttgctggc gtttttccat aggctccgcc  4140
cccctgacga gcatcacaaa aatcgacgct caagtcagag gtggcgaaac ccgacaggac  4200
tataaagata ccaggcgttt ccccctggaa gctccctcgt gcgctctcct gttccgaccc  4260
tgccgcttac cggatacctg tccgcctttc tcccttcggg aagcgtggcg ctttctcata  4320
gctcacgctg taggtatctc agttcggtgt aggtcgttcg ctccaagctg ggctgtgtgc  4380
acgaaccccc cgttcagccc gaccgctgcg ccttatccgg taactatcgt cttgagtcca  4440
acccggtaag acacgactta tcgccactgg cagcagccac tggtaacagg attagcagag  4500
cgaggtatgt aggcggtgct acagagttct tgaagtggtg gcctaactac ggctacacta  4560
gaagaacagt atttggtatc tgcgctctgc tgaagccagt taccttcgga aaaagagttg  4620
gtagctcttg atccggcaaa caaaccaccg ctggtagcgg tggttttttt gtttgcaagc  4680
agcagattac gcgcagaaaa aaaggatctc aagaagatcc tttgatcttt tctacggggt  4740
ctgacgctct attcaacaaa gccgccgtcc cgtcaagtca gcgtaaatgg gtagggggct  4800
tcaaatcgtc cgctctgcca gtgttacaac caattaacaa attctgatta gaaaaactca  4860
tcgagcatca aatgaaactg caatttattc atatcaggat tatcaatacc atatttttga  4920
aaaagccgtt tctgtaatga aggagaaaac tcaccgaggc agttccatag gatggcaaga  4980
tcctggtatc ggtctgcgat tccgactcgt ccaacatcaa tacaacctat taatttcccc  5040
tcgtcaaaaa taaggttatc aagtgagaaa tcaccatgag tgacgactga atccggtgag  5100
aatggcaaaa gcttatgcat ttctttccag acttgttcaa caggccagcc attacgctcg  5160
tcatcaaaat cactcgcatc aaccaaaccg ttattcattc gtgattgcgc ctgagcgaga  5220
cgaaatacgc gatcgctgtt aaaaggacaa ttacaaacag gaatcgaatg caaccggcgc  5280
aggaacactg ccagcgcatc aacaatattt tcacctgaat caggatattc ttctaatacc  5340
tggaatgctg ttttcccggg gatcgcagtg gtgagtaacc atgcatcatc aggagtacgg  5400
ataaaatgct tgatggtcgg aagaggcata aattccgtca gccagtttag tctgaccatc  5460
tcatctgtaa catcattggc aacgctacct ttgccatgtt tcagaaacaa ctctggcgca  5520
tcgggcttcc catacaatcg atagattgtc gcacctgatt gcccgacatt atcgcgagcc  5580
catttatacc catataaatc agcatccatg ttggaattta atcgcggcct cgagcaagac  5640
gtttcccgtt gaatatggct cataacaccc cttgtattac tgtttatgta agcagacagt  5700
tttattgttc atgatgatat atttttatct tgtgcaatgt aacatcagag attttgagac  5760
acaacgtggc tttccccccgc cgctctagaa ctagtggatc caaataaaac gaaaggctca  5820
gtcgaaagac tgggcctttc gttttatctg ttgtttgtcg cattatacga gacgtccagg  5880
ttgggatacc tgaaacaaaa cccatcgtac ggccaaggaa gtctccaata actgtgatcc  5940
accacaagcg ccagggtttt cccagtcacg acgttgtaaa acgacggcca gtcatgcata  6000
atccgcacgc atctggaata aggaagtgcc attccgcctg acct                    6044
```

```
SEQ ID NO: 170          moltype = DNA  length = 6044
FEATURE                 Location/Qualifiers
misc_feature            1..6044
                        note = pLD112
source                  1..6044
                        mol_type = other DNA
                        organism = synthetic construct
SEQUENCE: 170
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
```

```
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc ctttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgaattgtag cactttctca ttctggtttg tttgtaagat tattttcttt  1620
ttcttgtcat ttaacattca aatttcaatt gcaaacccac aagagaactt tttgaagtgt  1680
ttctcagaat acattccaaa caacccagct aacccaaagt ttatttacac ccaacacgat  1740
caattgtaca tgtcagtttt gaactcaaca attcaaaact tgagatttac atcagataca  1800
acaccaaagc cattggttat tgttacacca tcaaacgtta gtcatattca agcatcaatc  1860
ttgtgttcaa agaaggttgg attgcaaatt agaactagat caggaggaca tgatgcagaa  1920
ggattgtcat acatttcaca agttccattt gcaattgttg atttgagaaa catgcacaca  1980
gttaaggttg atattcattc acaaacagca tgggttgaag caggagcaac attgggtgaa  2040
gtttactact ggattaacga aatgaacgaa aacttctcat ttccaggagg atactgtcca  2100
acagttggtg ttggaggaca cttttcaggt ggtggatacg gagcattgat gagaaactac  2160
ggattggcag cagataacat tattgatgca catttggtta acgttgatgg aaaggttttg  2220
gatagaaagt caatgggaga agatttgttt tgggcaatta gaggaggtgg aggagaaaac  2280
tttggaatca ttgcagcatg taagatcaag ttggttgttg ttccatcaaa ggcaacaatc  2340
ttttcagtta agaagaacat ggaaatccat ggattggtta agttgtttaa caagtggcaa  2400
aacattgcat acaagtacga taaggatttg atgttgacaa cacattttag aacaagaaac  2460
attacagata accacggaaa gaataagaca acagttcatg gatacttttc atcaattttc  2520
ttgggaggag ttgattcatt ggttgacttg atgaacaaga gttttccaga attgggaatc  2580
aagaagacag attgtaagga attgtcatgg atcgatacaa ccatttcta ctcaggagtt  2640
gttaactaca acacagctaa ctttaagaag gaaattttgt tggacagatc agcaggtaaa  2700
aagacagcat tttcaattaa gttggattac gttaagaaat tgattccaga aacagcaatg  2760
gttaagattt tggaaaagtt gtacgaagaa gaagttggag ttggaatgta cgttttgtac  2820
ccatacggag gaattatgga tgaaatttca gaatcagcaa ttccatttcc acatagagca  2880
ggtattatgt acgaattgtg gtacacagca acatgggaaa agcaagaaga taacgaaaag  2940
catattaact gggttagatc agtttacaac tttacaaccc catacgtttc acaaaaccca  3000
agattggcat acttgaacta cagagatttg gatttgggaa agacaaaccc agaatcacca  3060
aataactaca cacaagctag aatttgggga gaaaagtact ttggtaagaa ctttaacaga  3120
ttggtgaagg ttaagacaaa ggcagaccca aacaatttct ttagaaacga acaatcaatt  3180
ccaccattgc caccaagaca tcattaataa gagtgactct tttgataaga gtcgcaaatt  3240
tgatttcata agtatatatt cattatgtaa agtagtaaat ggaaaattca ttaaaaaaaa  3300
agcaaatttc cgttgtatgc atactccgaa cacaaaacta gccccggaaa aacccttagt  3360
tgatagttgc gaatttaggt cgaccatatg cgacgggtac aacgagaatt gtattgaatt  3420
gatcaagaac atgatcttgg tgttacagaa catcaagttc ttggaccaga ctgagaatgc  3480
acagatatac aaggcgtcat gtgataaaat ggatgagatt tatccacaat tgaagaaaga  3540
gtttatggaa agtggtcaac cagaagctaa acaggaagaa gcaaacgaag aggtgaaaca  3600
agaagaagaa ggtaaataag tattttgtat tatataacaa acaaagtaag gaatacagat  3660
ttatacaata aattgccata ctagtcacgt gagatatctc atccattccc caactcccaa  3720
gaaaataaaa aagtgaaaaa taaaatcaaa cccaaagatc aacctcccca tcatcatcgt  3780
catcaaaccc ccagctcaat tcgcaatggt tagcacaaaa acatacacag aaagggcatc  3840
agcacacccc tccaaggttg cccaacgttt attaattaaa ggctaggtgg aggctcagtg  3900
atgataagtc tgcgatggtg gatgcatgtg tcatggtcat agctgtttcc tgtgtgaaat  3960
tgttatccgc tcagagggca caatcctatt ccgcgctatc cgacaatctc caagacatta  4020
ggtggagttc agttcggcgt atggcatatg tcgctggaaa gaacatgtga gcaaaaggcc  4080
agcaaaaggc caggaaccgt aaaaaggccg cgttgctggc gtttttccat aggctccgcc  4140
cccctgacga gcatcacaaa aatcgacgct caagtcagag gtggcgaaac ccgacaggac  4200
tataaagata ccaggcgttt ccccctggaa gctccctcgt gcgctctcct gttccgaccc  4260
tgccgcttac cggatacctg tccgcctttc tcccttcggg aagcgtggcg ctttctcata  4320
gctcacgctg taggtatctc agttcggtgt aggtcgttcg ctccaagctg ggctgtgtgc  4380
acgaaccccc cgttcagccc gaccgctgcg ccttatccgg taactatcgt cttgagtcca  4440
acccggtaag acacgactta tcgccactgg cagcagccac tggtaacagg attagcagag  4500
cgaggtatgt aggcggtgct acagagttct tgaagtggtg gcctaactac ggctacacta  4560
gaagaacagt atttggtatc tgcgctctgc tgaagccagt taccttcgga aaaagagttg  4620
gtagctcttg atccggcaaa caaaccaccg ctggtagcgg tggttttttt gtttgcaagc  4680
agcagattac gcgcagaaaa aaaggatctc aagaagatcc tttgatcttt tctacggggt  4740
ctgacgctct attcaacaaa gccgccgtcc cgtcaagtca gcgtaaatgg gtagggggct  4800
tcaaatcgtc cgctctgcca gtgttacaac caattaacaa attctgatta gaaaaactca  4860
tcgagcatca aatgaaactg caatttattc atatcaggat tatcaatacc atatttttga  4920
aaaagccgtt tctgtaatga aggagaaaac tcaccgaggc agttccatag gatggcaaga  4980
tcctggtatc ggtctgcgat tccgactcgt ccaacatcaa tacaacctat taatttcccc  5040
tcgtcaaaaa taaggttatc aagtgagaaa tcaccatgag tgacgactga atccggtgag  5100
aatggcaaaa gcttatgcat ttctttccag acttgttcaa caggccagcc attacgctcg  5160
tcatcaaaat cactcgcatc aaccaaaccg ttattcattc gtgattgcgc ctgagcgaga  5220
cgaaatacgc gatcgctgtt aaaaggacaa ttacaaacag gaatcgaatg caaccggcgc  5280
aggaacactg ccagcgcatc aacaatattt tcacctgaat caggatattc ttctaatacc  5340
```

```
tggaatgctg ttttcccggg gatcgcagtg gtgagtaacc atgcatcatc aggagtacgg  5400
ataaaatgct tgatggtcgg aagaggcata aattccgtca gccagtttag tctgaccatc  5460
tcatctgtaa catcattggc aacgctacct ttgccatgtt tcagaaacaa ctctggcgca  5520
tcgggcttcc catacaatcg atagattgtc gcacctgatt gcccgacatt atcgcgagcc  5580
catttatacc catataaatc agcatccatg ttggaattta atcgcggcct cgagcaagac  5640
gtttcccgtt gaatatggct cataacaccc cttgtattac tgtttatgta agcagacagt  5700
tttattgttc atgatgatat atttttatct tgtgcaatgt aacatcagag attttgagac  5760
acaacgtggc tttccccgc cgctctagaa ctagtggatc caaataaaac gaaaggctca  5820
gtcgaaagac tgggcctttc gttttatctg ttgtttgtcg cattatacga gacgtccagg  5880
ttgggatacc tgaaacaaaa cccatcgtac ggccaaggaa gtctccaata actgtgatcc  5940
accacaagcg ccagggtttt cccagtcacg acgttgtaaa acgacggcca gtcatgcata  6000
atccgcacgc atctggaata aggaagtgcc attccgcctg acct                    6044

SEQ ID NO: 171          moltype = DNA  length = 7167
FEATURE                 Location/Qualifiers
misc_feature            1..7167
                        note = pLD113
source                  1..7167
                        mol_type = other DNA
                        organism = synthetic construct
SEQUENCE: 171
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc ccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaaggatct caagaagatc  840
ctttgatctt ttctacgggg tctgacgctc tattcaacaa agccgccgtc ccgtcaagtc  900
agcgtaaatg ggtagggggc ttcaaatcgt ccgctctgcc agtgttacaa ccaattaaca  960
aattctgatt agaaaaactc atcgagcatc aaatgaaact gcaatttatt catatcagga  1020
ttatcaatac catatttttg aaaaagccgt ttctgtaatg aaggagaaaa ctcaccgagg  1080
cagttccata ggatggcaag atcctggtat cggtctgcga ttccgactcg tccaacatca  1140
atacaaccta ttaatttccc ctcgtcaaaa ataaggttat caagtgagaa atcaccatga  1200
gtgacgactg aatccggtga gaatggcaaa agcttatgca tttctttcca gacttgttca  1260
acaggccagc cattacgctc gtcatcaaaa tcactcgcat caaccaaacc gttattcatt  1320
cgtgattgcg cctgagcgag acgaaatacg cgatcgctgt taaaaggaca attacaaaca  1380
ggaatcgaat gcaaccggcg caggaacact gccagcgcat caacaatatt ttcacctgaa  1440
tcaggatatt cttctaatac ctggaatgct gttttcccgg ggatcgcagt ggtgagtaac  1500
catgcatcat caggagtacg gataaaatgc ttgatggtcg gaagaggcat aaattccgtc  1560
agccagttta gtctgaccat ctcatctgta acatcattgg caacgctacc tttgccatgt  1620
ttcagaaaca actctggcgc atcgggcttc ccatacaatc gatagattgt cgcacctgat  1680
tgcccgacat tatcgcgagc ccatttatac ccatataaat cagcatccat gttggaattt  1740
aatcgcggcc tcgagcaaga cgtttcccgt tgaatatggc tcataacacc ccttgtatta  1800
ctgtttatgt aagcagacag ttttattgtt catgatgata tatttttatc ttgtgcaatg  1860
taacatcaga gattttgaga cacaacgtgg ctttcccccg ccgctctaga actagtggat  1920
ccaaataaaa cgaaaggctc agtcgaaaga ctgggccttt cgttttatct gttgtttgtc  1980
gcattatacg agacgtccag gttgggatac ctgaaacaaa acccatcgta cggccaagga  2040
agtctccaat aactgtgatc caccacaagc gccagggttt tcccagtcac gacgttgtaa  2100
aacgacggcc agtcatgcat aatccgcacg catctggaat aaggaagtgc cattccgcct  2160
gacctgatcc caatattaca cccaagtagc atgcataagc taaaagtaac tcgcagcgca  2220
caccgtgcag attcataagt ctatgattaa ttgaacgcca ataacccggc ttactacaag  2280
tacaagtagg tatacatagc ggtaatgaat cattagaaaa ataaaaaaca aaaaaaaaca  2340
aaacaaactg ttgtggatgc atcaacagta gtacatagtt gtacgatgta cttgtacttg  2400
taaaagcaaa aatgtacaat atctcaggga gcgcaacttt tacgttcgaa gaacaatgta  2460
ccgcataccg cattctagat tctgcggaac gtctaacctg gaaatacgat tttttatttc  2520
tttcattttt tttgcttctt caaaagtatg gtaatttcct accattacag ttgacactga  2580
acgagggggg attgaattta agcaaaaaat taaatcaaaa tacctttatg tatccagccc  2640
atgtaataaa caaaaggatt atataacaag aaataaatat atacctttaa tggatcatta  2700
gaataaaaat aaatacgaga agcacaccag agaagctttt tgattgccac tataccgcta  2760
ctttggtata tcttattata attgttgaat ttgcaagata gaatgtcatt cattggagag  2820
aaatccaagg aatatgtggg atgaaatgac tagaagtatg aacaatgaga atagtacata  2880
cttgtacctg tatttctaga agagagaaag acagttgagt gtgtgattct cgtccaataa  2940
taatctcaat agtaacgtgt gaatagctgt tctttgatag ttgatatttc tcgatgacta  3000
tttatgttgt acaagggatt tttttcgttg ctgttgattt cgaattaggc aatgcagata  3060
tcatttatgc tatccatatt taagatttcc catacgcatt tataacattt attctacata  3120
aattgttaaa tgaacgaact gccattataa attgtttcct aaataggaag tgttttttcat  3180
aaagcaagta agttgtctaa taatactaag taataaaaat aagttcatac aatatatttt  3240
gagaacatca tttggaggcg gtagatggag tctgtttatt attaaacaat gcgagatgac  3300
cccttaaata ttgagaacat cagttggagg cggcagatgg agtctgtcta tttagcaatg  3360
ggacatgact gtcagtatca tcatatgtat atatataata catataatat tatataacac  3420
gattttttta aattattggc ccgaaaatta atcagtgtag actggatcct cgagaaccat  3480
```

```
ttaattaaca agtcgagaac gtaccactgt cctccactac aaacacaccc aatctgcttc  3540
ttctagtcaa ggttgctaca ccggtaaatt ataaatcatc atttcattag cagggctggg  3600
cccttttat agagtcttat acactagcgg accctgccgg tagaccaacc cgcaggcgcg  3660
tcagtttgct ccttccatca atgcgtcgta gaaacgactt actccttctt gagcagctcc  3720
ttgaccttgt tggcaacaaa gtctccgacc tcggaggtgg aggaggagcc tccgatatcg  3780
gcggtagtga taccagcctc gacggactcc ttgacggcag cctcaacagc gtcaccggcg  3840
ggcttcatgt taagagagaa cttgagcatc atggcggcag acagaatggt ggcaatgggg  3900
ttgaccttct gcttgccgag atcgggggca gatccgtgac agggctcgta cagaccgaac  3960
gcctcgttgg tgtcgggcag agaagccaga gaggcggagg gcagcagacc cagagaaccg  4020
gggatgacgg aggcctcgtc ggagatgata tcgccaaaca tgttggtggt gatgatgata  4080
ccattcatct tggagggctg cttgatgagg atcatggcgg ccgagtcgat cagctggtgg  4140
ttgagctcca gctgggggaa ttcgtccttg aggactcggg tgacggtctt tcgccaaagt  4200
cgagaggagg ccagcacgtt ggccttgtca agggaccaca cgggaagagg ggggttgtgc  4260
tgaagggcca ggaaggcggc cattcgggca attcgctcaa cctcaggaac ggagtaagtc  4320
tcagtgtcgg aagcgacgcc agatccgtca tcctcctttc gctctccaaa gtagatacct  4380
ccgacgagct ctcggacaat gatgaagtcg gtgccctcaa cgtttcggat gggggagaga  4440
tcggcgagct tgggcgacag cagctggcag ggtcgcaggt tggcgtacag gttcaggtcc  4500
tttcgcagct tgagaagacc ctgctcgggt cgcacgtcgg ttcgtccgtc gggagtggtc  4560
catacggtgt tggcagcgcc tccgacagca ccgagcataa tagagtcagc ctttcggcag  4620
atgtcgagag tagcgtcggt gatgggctcg ccctccttct caatggcagc tcctccaatg  4680
agtcggtcct caaacacaaa ctcggtgccg gaggcctcag caacagactt gagcaccttg  4740
acggcctcgg caatcacctc ggggccacag aagtcgccgc cgagaagaac aatcttcttg  4800
gagtcagtct tggtcttctt agtttcgggt tccattgtgg atgtgtgtgg ttgtatgtgt  4860
gatgtggtgt gtggagtgaa aatctgtggc tggcaaacgc tcttgtatat atacgcactt  4920
ttgcccgtgc tatgtggaag actaaacctc cgaagattgt gactcaggta gtgcggtatc  4980
ggctagggac ccaaaccttg tcgatgccga tagcgctatc gaacgtaccc cagccggccg  5040
ggagtatgtc ggaggggaca tacgagatcg tcaagggttt gtggccaact ggtaaataaa  5100
tgatgactca ggcgacgacg gaattcgaca gcaactactc ctttcaccaa ccatgtgcat  5160
tttagctcga ataacattca caggcttggt gatctacatc catggtgtct ggccgattac  5220
cgtggtgttt tggcagtaac gagaatattg agtgaactct tcccatcacc aataaagact  5280
catactacaa tcacgagcgc ttcagctgcc actatagtgt tggtgacaca atacccctcg  5340
atgctgggca ttactgtagc aagagatatt atttcatggc gcattttcca gtctacctga  5400
ctttttagtg tgatttcttc tccacatttt atgctcagtg tgaaaagttg gagtgcacac  5460
ttaattatcg ccggttttcg gaaagtacta tgtgctcaag gttgcacccc acgttacgta  5520
tgcagcacat tgagcagcct ttggaccgtg gagataacgg tgtggagata gcaacgggta  5580
gtcttcgtat taattcaatg cattgttagt tttatatgat atggtgtcga gcggccgcga  5640
ccgggttggc ggcgcatttg tgtcccaaaa aacagcccca attgccccaa ttgaccccaa  5700
attgacccag tagcgggccc aaccccggcg agagccccct tctccccaca tatcaaacct  5760
cccccggttc ccacacttgc cgttaagggc gtagggtact gcagtctgga atctacgctt  5820
gttcagactt tgtactagtt tctttgtctg gccatccggg taacccatgc cggacgcaaa  5880
atagactact gaaaattttt ttgctttgtg gttgggactt tagccaaggg tataaaagac  5940
caccgtcccc gaattacctt tcctcttctt ttctctctct ccttgtcaac tcacacccga  6000
aatcgttaag catttccttc tgagtataag aatcattcaa aatgtccaac ctcctcaccg  6060
tccaccagaa ccttcccgcc cttcccgtgg acgccacctc cgacgaggtc cgaaagaacc  6120
tcatggacat gttccgagat cgacaggcct tctccgagca cacttggaag atgctcctct  6180
ccgtctgccg atcctgggcc gcctggtgca agctcaacaa ccgaaagtgg ttccccgccg  6240
agcccgagga cgtccgagac tacctccttt acctccaggc ccgaggcctc gccgtcaaga  6300
ccatccagca gcacctcggc cagctcaaca tgctccaccg acgatccggc ctcccccgac  6360
cctccgactc caacgccgtg tccctcgtca tgcgacgaat ccgaaaggag aacgtggacg  6420
ccggcgagcg agccaagcag gcccttgcct tcgagcgaac cgacttcgac caggtccgat  6480
ccctcatgga gaactccgac cgatgccagg acatccgaaa cctcgccttc cttggcatcg  6540
cctacaacac cctccttcga atcgccgaga tcgcccgaat ccgagtcaag gacatctccc  6600
gaaccgacgg cggccgaatg ctcatccaca tcggccgaac caagaccctc gtgtccaccg  6660
ccggcgtcga gaaggccctc tccctcggcg tcaccaagct cgtcgagcga tggatctccg  6720
tgtccggcgt cgctgacgac cccaacaact acctcttctg ccgagtccga aagaacggcg  6780
tcgctgctcc ctccgccacc tcccagctct ccacccgagc ccttgagggc atcttcgagg  6840
ccacccaccg actcatctac ggcgccaagg acgactccgg ccagcgatac ctcgcctggt  6900
ccggccactc tgctcgagtc ggtgccgccc gagacatggc ccgagccggt gtctccatcc  6960
ccgagatcat gcaggccggc ggctggacca acgtcaacat cgtcatgaac tacatccgaa  7020
acctcgactc cgagactggc gccatggtcc gacttcttga ggacggcgac tgatgatcat  7080
atgattacat taatagctaa ttacgtgtat ccgatatata tactaattac aatagtacat  7140
attagaacat acaatagttt taattaa                                     7167
```

```
SEQ ID NO: 172          moltype = DNA  length = 6125
FEATURE                 Location/Qualifiers
misc_feature            1..6125
                        note = pLD125
source                  1..6125
                        mol_type = other DNA
                        organism = synthetic construct
SEQUENCE: 172
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
```

```
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc ctttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgttcttgaa acacattttt gttgctctcg cttttgcctt gttagctgac  1620
gctaccccag cccagaagag atctcccggc ttcgttgctt tagactttga catcgtcaag  1680
gttcaaaaga acgtgactgc caacgacgac gccgctgcca ttgttgccaa gagacagacc  1740
aacccaaggg aaaacttcct taagtgtttt ctgcagtaca tccctaacaa tgcaacaaac  1800
ctcaagttgg tgtacactca aaacaatcca ctctatatga gcgtgcttaa tagcacaatc  1860
cacaacttgc gcttcacgtc agatactacg cctaagccac tagtgatcgt tacaccatca  1920
cacgtcagcc atattcaagg aacgatccta tgtctgaaaa aggtcgggtt gcaaatcagg  1980
actcgatcag gagggcacga tagtgaggga atgagttaca tctcgcaagt acccttcgtg  2040
atagttgact tgcgaaatat gcggtctatt aaaattgacg tacatagcca gaccgcctgg  2100
gttgaagcag gggcaacctt gggtgaagtt tattactggg tcaatgaaaa aaacgaaaac  2160
ctaagtcttg ctgctggata ttgccccacc gtttgcgcgg gtggtcattt tggaggcggc  2220
ggatatggtc cgttgatgag aaattatgga cttgcagcag acaatattat agatgcccac  2280
ttggtgaacg ttcatggaaa ggtcttggac cgtaagtcca tgggtgaaga tcttttctgg  2340
gccttgagag gtggtggagc ggaatcgttt ggcatcatcg ttgcctggaa aattaggttg  2400
gttgcggtcc cgaagagtac aatgttctcc gtgaagaaga ttatggaaat acatgagctt  2460
gtcaagttag ttaacaagtg gcaaaatatc gcttataagt atgataaaga cttgcttttg  2520
atgactcatt ttattacgcg aaacataacc gataaccagg gcaagaacaa gactgctatt  2580
cacacgtact tctcctctgt atttcttgga ggagtagact ccttagttga cttgatgaac  2640
aagagtttcc cagaattggg gattaagaag acagattgca gacaattatc gtggatagat  2700
acaatcatat tctatagcgg tgtcgtcaat tacgatactg ataattttaa taaagaaatc  2760
ctcctagatc gttcagctgg gcaaaacggg gcattcaaaa ttaaattgga ttatgtgaag  2820
aaaccaattc cagagctggt gtttgttcag atattggaaa aactttacga agaagacatt  2880
ggcgcaggta tgtacgcttt gtatccatat ggaggcatta tggacgagat ctcagagctg  2940
gcgatcccct tcccgcacag agctgggata ctctacgagc tatggtacat ctgctcttgg  3000
gagaaacaag aagacaacga gaaacatctc aattggattc ggaacatata caactttatg  3060
accccatacg tatcaaaaaa cccgcgctta gcatacttga attacagaga cttagatatc  3120
ggtatcaatg atcctaagaa tcctaacaat tacacccaag cccgtatttg ggtgagaaa  3180
tatttcggca agaattttga cagattagtt aaggtcaaaa cactcgtgga ccccaacaac  3240
tttttccgaa acgagcagtc gattccacca ctacccaggc atagacactg agagtgactc  3300
ttttgataag agtcgcaaat ttgatttcat aagtatatat tcattatgta aagtagtaaa  3360
tggaaaattc attaaaaaaa aagcaaattt ccgttgtatg catactccga acacaaaact  3420
agccccggaa aaacccttag ttgatagttg cgaatttagg tcgaccatat gcgacgggta  3480
caacgagaat tgtattgaat tgatcaagaa catgatcttg gtgttacaga acatcaagtt  3540
cttggaccag actgagaatg cacagatata caaggcgtca tgtgataaaa tggatgagat  3600
ttatccacaa ttgaagaaag agtttatgga aagtggtcaa ccagaagcta aacaggaaga  3660
agcaaacgaa gaggtgaaac aagaagaaga aggtaaataa gtattttgta ttatataaca  3720
aacaaagtaa ggaatacaga tttatacaat aaattgccat actagtcacg tgagatatct  3780
catccattcc ccaactccca agaaaataaa aaagtgaaaa ataaaatcaa acccaaagat  3840
caacctcccc atcatcatcg tcatcaaacc cccagctcaa ttcgcaatgg ttagcacaaa  3900
aacatacaca gaaagggcat cagcacaccc ctccaaggtt gcccaacgtt tattaattaa  3960
aggctaggtg gaggctcagt gatgataagt ctgcgatggt ggatgcatgt gtcatggtca  4020
tagctgtttc ctgtgtgaaa ttgttatccg ctcagagggc acaatcctat tccgcgctat  4080
ccgacaatct ccaagacatt aggtggagtt cagttcggcg tatggcatat gtcgctggaa  4140
agaacatgtg agcaaaaggc cagcaaaagg ccaggaaccg taaaaaggcc gcgttgctgg  4200
cgtttttcca taggctccgc ccccctgacg agcatcacaa aaatcgacgc tcaagtcaga  4260
ggtggcgaaa cccgacagga ctataaagat accaggcgtt tccccctgga agctccctcg  4320
tgcgctctcc tgttccgacc ctgccgctta ccggatacct gtccgccttt ctcccttcgg  4380
gaagcgtggc gctttctcat agctcacgct gtaggtatct cagttcggtg taggtcgttc  4440
gctccaagct gggctgtgtg cacgaacccc ccgttcagcc cgaccgctgc gccttatccg  4500
gtaactatcg tcttgagtcc aacccggtaa gacacgactt atcgccactg gcagcagcca  4560
ctggtaacag gattagcaga gcgaggtatg taggcggtgc tacagagttc ttgaagtggt  4620
ggcctaacta cggctacact agaagaacag tatttggtat ctgcgctctg ctgaagccag  4680
ttaccttcgg aaaaagagtt ggtagctctt gatccggcaa acaaaccacc gctggtagcg  4740
gtggtttttt tgtttgcaag cagcagatta cgcgcagaaa aaaaggatct caagaagatc  4800
ctttgatctt ttctacgggg tctgacgctc tattcaacaa agccgccgtc ccgtcaagtc  4860
agcgtaaatg ggtagggggc ttcaaatcgt ccgctctgcc agtgttacaa ccaattaaca  4920
aattctgatt agaaaaactc atcgagcatc aaatgaaact gcaatttatt catatcagga  4980
ttatcaatac catatttttg aaaaagccgt ttctgtaatg aaggagaaaa ctcaccgagg  5040
cagttccata ggatggcaag atcctggtat cggtctgcga ttccgactcg tccaacatca  5100
atacaaccta ttaatttccc ctcgtcaaaa ataaggttat caagtgagaa atcaccatga  5160
gtgacgactg aatccggtga gaatggcaaa agcttatgca tttctttcca gacttgttca  5220
```

```
acaggccagc cattacgctc gtcatcaaaa tcactcgcat caaccaaacc gttattcatt  5280
cgtgattgcg cctgagcgag acgaaatacg cgatcgctgt taaaaggaca attacaaaca  5340
ggaatcgaat gcaaccggcg caggaacact gccagcgcat caacaatatt ttcacctgaa  5400
tcaggatatt cttctaatac ctggaatgct gttttcccgg ggatcgcagt ggtgagtaac  5460
catgcatcat caggagtacg gataaaatgc ttgatggtcg gaagaggcat aaattccgtc  5520
agccagttta gtctgaccat ctcatctgta acatcattgg caacgctacc tttgccatgt  5580
ttcagaaaca actctggcgc atcgggcttc ccatacaatc gatagattgt cgcacctgat  5640
tgcccgacat tatcgcgagc ccatttatac ccatataaat cagcatccat gttggaattt  5700
aatcgcggcc tcgagcaaga cgtttcccgt tgaatatggc tcataacacc ccttgtatta  5760
ctgtttatgt aagcagacag ttttattgtt catgatgata tatttttatc ttgtgcaatg  5820
taacatcaga gattttgaga cacaacgtgg ctttcccccg ccgctctaga actagtggat  5880
ccaaataaaa cgaaaggctc agtcgaaaga ctgggccttt cgttttatct gttgtttgtc  5940
gcattatacg agacgtccag gttgggatac ctgaaacaaa acccatcgta cggccaagga  6000
agtctccaat aactgtgatc caccacaagc gccagggttt tcccagtcac gacgttgtaa  6060
aacgacggcc agtcatgcat aatccgcacg catctggaat aaggaagtgc cattccgcct  6120
gacct                                                              6125
```

```
SEQ ID NO: 173          moltype = DNA  length = 6230
FEATURE                 Location/Qualifiers
misc_feature            1..6230
                        note = pLD127
source                  1..6230
                        mol_type = other DNA
                        organism = synthetic construct
SEQUENCE: 173
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc ctttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgcaattgtc cttgtcggtt ttatcaaccg ttgccacggc cttgttgtcc  1620
ctaaccaccg ccgtcgatgc taagtcccac aacatcaagt tgtccaagtt gtccaacgaa  1680
gaaacattgg acgcctccac attccaagaa tacacgagct ccttggccaa caagtacatg  1740
aacttgttca acgccgctca cggtaaccca accagctttg gcttgcaaca cgtcttgtcc  1800
aaccaagaag ctgaagtccc attcgttacc ccacaaaagg gtggcaaccc aagggaaaac  1860
ttccttaagt gttttctgca gtacatccct aacaatgcaa caaacctcaa gttggtgtac  1920
actcaaaaca atccactcta tatgagcgtg cttaatagca caatccacaa cttgcgcttc  1980
acgtcagata ctacgcctaa gccactagtg atcgttacac catcacacgt cagccatatt  2040
caaggaacga tcctatgtct gaaaaaggtc gggttgcaaa tcaggactcg atcaggaggg  2100
cacgatagtg agggaatgag ttacatctcg caagtaccct tcgtgatagt tgacttgcga  2160
aatatgcggt ctattaaaat tgacgtacat agccagaccg cctgggttga agcaggggca  2220
accttgggtg aagtttatta ctgggtcaat gaaaaaaacg aaaacctaag tcttgctgct  2280
ggatattgcc ccaccgtttg cgcgggtggt cattttggag gcggcggata tggtccgttg  2340
atgagaaatt atggacttgc agcagacaat attatagatg cccacttggt gaacgttcat  2400
ggaaaggtct tggaccgtaa gtccatgggt gaagatcttt tctgggcctt gagaggtggt  2460
ggagcggaat cgtttggcat catcgttgcc tggaaaatta ggttggttgc ggtcccgaag  2520
agtacaatgt tctccgtgaa gaagattatg gaaatacatg agcttgtcaa gttagttaac  2580
aagtggcaaa atatcgctta taagtatgat aaagacttgc ttttgatgac tcattttatt  2640
acgcgaaaca taaccgataa ccagggcaag aacaagactg ctattcacac gtacttctcc  2700
tctgtatttc ttggaggagt agactcctta gttgacttga tgaacaagag tttcccagaa  2760
ttggggatta agaagacaga ttgcagacaa ttatcgtgga tagatacaat catattctat  2820
agcggtgtcg tcaattacga tactgataat tttaataaag aaatcctcct agatcgttca  2880
gctgggcaaa acggggcatt caaaattaaa ttggattatg tgaagaaacc aattccagag  2940
ctggtgtttg ttcagatatt ggaaaaactt tacgaagaag acattggcgc aggtatgtac  3000
gctttgtatc catatggagg cattatggac gagatctcag agctggcgat ccccttcccg  3060
cacagagctg ggatactcta cgagctatgg tacatctgct cttgggagaa acaagaagac  3120
aacgagaaac atctcaattg gattcggaac atatacaact ttatgacccc atacgtatca  3180
aaaaacccgc gcttagcata cttgaattac agagacttag atatcggtat caatgatcct  3240
```

```
aagaatccta acaattacac ccaagcccgt atttggggtg agaaatattt cggcaagaat  3300
tttgacagat tagttaaggt caaaacactc gtggaccccca acaacttttt ccgaaacgag  3360
cagtcgattc caccactacc caggcataga cactgagagt gactcttttg ataagagtcg  3420
caaatttgat ttcataagta tatattcatt atgtaaagta gtaaatggaa aattcattaa  3480
aaaaaaagca aatttccgtt gtatgcatac tccgaacaca aaactagccc cggaaaaacc  3540
cttagttgat agttgcgaat ttaggtcgac catatgcgac gggtacaacg agaattgtat  3600
tgaattgatc aagaacatga tcttggtgtt acagaacatc aagttcttgg accagactga  3660
gaatgcacag atatacaagg cgtcatgtga taaaatggat gagatttatc cacaattgaa  3720
gaaagagttt atggaaagtg gtcaaccaga agctaaacag gaagaagcaa acgaagaggt  3780
gaaacaagaa gaagaaggta aataagtatt ttgtattata taacaaacaa agtaaggaat  3840
acagatttat acaataaatt gccatactag tcacgtgaga tatctcatcc attccccaac  3900
tcccaagaaa ataaaaaagt gaaaaataaa atcaaaccca aagatcaacc tccccatcat  3960
catcgtcatc aaaccccccag ctcaattcgc aatggttagc acaaaaacat acacagaaag  4020
ggcatcagca cacccctcca aggttgccca acgtttatta attaaaggct aggtggaggc  4080
tcagtgatga taagtctgcg atggtggatg catgtgtcat ggtcatagct gtttcctgtg  4140
tgaaattgtt atccgctcag agggcacaat cctattccgc gctatccgac aatctccaag  4200
acattaggtg gagttcagtt cggcgtatgg catatgtcgc tggaaagaac atgtgagcaa  4260
aaggccagca aaaggccagg aaccgtaaaa aggccgcgtt gctggcgttt ttccataggc  4320
tccgcccccc tgacgagcat cacaaaaatc gacgctcaag tcagaggtgg cgaaacccga  4380
caggactata aagataccag gcgtttcccc ctggaagctc cctcgtgcgc tctcctgttc  4440
cgaccctgcc gcttaccgga tacctgtccg cctttctccc ttcgggaagc gtggcgcttt  4500
ctcatagctc acgctgtagg tatctcagtt cggtgtaggt cgttcgctcc aagctgggct  4560
gtgtgcacga accccccgtt cagcccgacc gctgcgcctt atccggtaac tatcgtcttg  4620
agtccaaccc ggtaagacac gacttatcgc cactggcagc agccactggt aacaggatta  4680
gcagagcgag gtatgtaggc ggtgctacag agttcttgaa gtggtggcct aactacggct  4740
acactagaag aacagtattt ggtatctgcg ctctgctgaa gccagttacc ttcggaaaaa  4800
gagttggtag ctcttgatcc ggcaaacaaa ccaccgctgg tagcggtggt ttttttgttt  4860
gcaagcagca gattacgcgc agaaaaaaag gatctcaaga agatcctttg atcttttcta  4920
cggggtctga cgctctattc aacaaagccg ccgtcccgtc aagtcagcgt aaatgggtag  4980
ggggcttcaa atcgtccgct ctgccagtgt tacaaccaat taacaaattc tgattagaaa  5040
aactcatcga gcatcaaatg aaactgcaat ttattcatat caggattatc aataccatat  5100
ttttgaaaaa gccgtttctg taatgaagga gaaaactcac cgaggcagtt ccataggatg  5160
gcaagatcct ggtatcggtc tgcgattccg actcgtccaa catcaataca acctattaat  5220
ttcccctcgt caaaaataag gttatcaagt gagaaatcac catgagtgac gactgaatcc  5280
ggtgagaatg gcaaaagctt atgcatttct ttccagactt gttcaacagg ccagccatta  5340
cgctcgtcat caaaatcact cgcatcaacc aaaccgttat tcattcgtga ttgcgcctga  5400
gcgagacgaa atacgcgatc gctgttaaaa ggacaattac aaacaggaat cgaatgcaac  5460
cggcgcagga acactgccag cgcatcaaca atattttcac ctgaatcagg atattcttct  5520
aatacctgga atgctgtttt cccggggatc gcagtggtga gtaaccatgc atcatcagga  5580
gtacggataa aatgcttgat ggtcggaaga ggcataaatt ccgtcagcca gtttagtctg  5640
accatctcat ctgtaacatc attggcaacg ctacctttgc catgtttcag aaacaactct  5700
ggcgcatcgg gcttcccata caatcgatag attgtcgcac ctgattgccc gacattatcg  5760
cgagcccatt tatacccata taaatcagca tccatgttgg aatttaatcg cggcctcgag  5820
caagacgttt cccgttgaat atggctcata acaccccttg tattactgtt tatgtaagca  5880
gacagtttta ttgttcatga tgatatattt ttatcttgtg caatgtaaca tcagagattt  5940
tgagacacaa cgtggctttc cccgccgct ctagaactag tggatccaaa taaaacgaaa  6000
ggctcagtcg aaagactggg cctttcgttt tatctgttgt ttgtcgcatt atacgagacg  6060
tccaggttgg gatacctgaa acaaaaccca tcgtacggcc aaggaagtct ccaataactg  6120
tgatccacca caagcgccag ggttttccca gtcacgacgt tgtaaaacga cggccagtca  6180
tgcataatcc gcacgcatct ggaataagga agtgccattc cgcctgacct             6230
```

```
SEQ ID NO: 174          moltype = DNA  length = 8110
FEATURE                 Location/Qualifiers
misc_feature            1..8110
                        note = pLD131
source                  1..8110
                        mol_type = other DNA
                        organism = synthetic construct
SEQUENCE: 174
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc cccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaggatctc caagaagatc  840
ctttgatctt ttctacgggg tctgacgctc tattcaacaa agccgccgtc ccgtcaagtc  900
agcgtaaatg ggtagggggc ttcaaatcgt ccgctctgcc agtgttacaa ccaattaaca  960
aattctgatt agaaaaactc atcgagcatc aaatgaaact gcaatttatt catatcagga  1020
ttatcaatac catatttttg aaaaagccgt ttctgtaatg aaggagaaaa ctcaccgagg  1080
cagttccata ggatggcaag atcctggtat cggtctgcga ttccgactcg tccaacatca  1140
atacaaccta ttaatttccc ctcgtcaaaa ataaggttat caagtgagaa atcaccatga  1200
```

```
gtgacgactg aatccggtga gaatggcaaa agcttatgca tttctttcca gacttgttca  1260
acaggccagc cattacgctc gtcatcaaaa tcactcgcat caaccaaacc gttattcatt  1320
cgtgattgcg cctgagcgag acgaaatacg cgatcgctgt taaaaggaca attacaaaca  1380
ggaatcgaat gcaaccggcg caggaacact gccagcgcat caacaatatt ttcacctgaa  1440
tcaggatatt cttctaatac ctggaatgct gttttcccgg ggatcgcagt ggtgagtaac  1500
catgcatcat caggagtacg gataaaatgc ttgatggtcg gaagaggcat aaattccgtc  1560
agccagttta gtctgaccat ctcatctgta acatcattgg caacgctacc tttgccatgt  1620
ttcagaaaca actctggcgc atcgggcttc ccatacaatc gatagattgt cgcacctgat  1680
tgcccgacat tatcgcgagc ccatttatac ccatataaat cagcatccat gttggaattt  1740
aatcgcggcc tcgagcaaga cgtttcccgt tgaatatggc tcataacacc ccttgtatta  1800
ctgtttatgt aagcagacag ttttattgtt catgatgata tatttttatc ttgtgcaatg  1860
taacatcaga gattttgaga cacaacgtgg ctttcccccg ccgctctaga actagtggat  1920
ccaaataaaa cgaaaggctc agtcgaaaga ctgggccttt cgttttatct gttgtttgtc  1980
gcattatacg agacgtccag gttgggatac ctgaaacaaa acccatcgta cggccaagga  2040
agtctccaat aactgtgatc caccacaagc gccagggttt tcccagtcac gacgttgtaa  2100
aacgacggcc agtcatgcat aatccgcacg catctggaat aaggaagtgc cattccgcct  2160
gacctgatcc caatattaca cccaagtagc atgcataagc taaaagtaac tcgcagcgca  2220
caccgtgcag attcataagt ctatgattaa ttgaacgcca ataacccggc ttactacaag  2280
tacaagtagg tatacatagc ggtaatgaat cattagaaaa ataaaaaaca aaaaaaaaca  2340
aaacaaactg ttgtggatgc atcaacagta gtacatagtt gtacgatgta cttgtacttg  2400
taaaagcaaa aatgtacaat atctcaggga gcgcaacttt tacgttcgaa gaacaatgta  2460
ccgcataccg cattctagat tctgcggaac gtctaacctg gaaatacgat tttttatttc  2520
tttcattttt tttgcttctt caaaagtatg gtaatttcct accattacag ttgacactga  2580
acgagggggg attgaattta agcaaaaaat taaatcaaaa tacctttatg tatccagccc  2640
atgtaataaa caaaaggatt atataacaag aaataaatat atacctttaa tggatcatta  2700
gaataaaaat aaatacgaga agcacaccag agaagctttt tgattgccac tataccgcta  2760
ctttggtata tcttattata attgttgaat ttgcaagata gaatgtcatt cattggagag  2820
aaatccaagg aatatgtggg atgaaatgac tagaagtatg aacaatgaga atagtacata  2880
cttgtacctg tatttctaga agagagaaag acagttgagt gtgtgattct cgtccaataa  2940
taatctcaat agtaacgtgt gaatagctgt tctttgatag ttgatatttc tcgatgacta  3000
tttatgttgt acaagggatt tttttcgttg ctgttgattt cgaattaggc aatgcagata  3060
tcatttatgc tatccatatt taagatttcc catacgcatt tataacattt attctacata  3120
aattgttaaa tgaacgaact gccattataa attgtttcct aaataggaag tgtttttcat  3180
aaagcaagta agttgtctaa taatactaag taataaaaat aagttcatac aatatatttt  3240
gagaacatca tttggaggcg gtagatggag tctgtttatt attaaacaat gcgagatgac  3300
cccttaaata ttgagaacat cagttggagg cggcagatgg agtctgtcta tttagcaatg  3360
ggacatgact gtcagtatca tcatatgtat atatataata catataatat tatataacac  3420
gatttttta aattattggc ccgaaaatta atcagtgtag actggatcct cgagaaccat  3480
ttaattaaga tcgtcgacga ttccgccaag tgagactggc gatcgggaga agggttggtg  3540
gtcatggggg atagaatttg tacaagtgga aaaaccacta cgagtagcgg atttgatacc  3600
acaagtagca gagatataca gcaatggtgg gagtgcaagt atcggaatgt actgtacctc  3660
ctgtactcgt actcgtacgg cactcgtaga aacggggcaa tacgggggag aagcgatcgc  3720
ccgtctgttc aatcgccaca agtccgagta atgcttgagt atcgaagtct tgtacctccc  3780
tgtcaatcat ggcaccactg gtcttgactt gtctattcat actggacaag cgccagagtt  3840
aagcttgtag cgaatttcgc cctcggacat caccccatac gacggacaca catgcccgac  3900
aaacagcctc tcttattgta gctgaaagta tattgaatgt gaacgtgtac aatatcaggt  3960
accagcggga ggttacggcc aaggtgatac cggaataacc ctggcttgga gatggtcggt  4020
ccattgtact gaagtgtccg tgtcgtttcc gtcactgccc caattggaca tgtttgtttt  4080
tccgatcttt cgggcgccct ctccttgtct ccttgtctgt ctcctggact gttgctaccc  4140
catttctttg gcctccattg gttcctcccc gtctttcacg tcgtctatgg ttgcatggtt  4200
tcccttatac ttttccccac agtcacatgt tatggagggg tctagatgga ggcctaattt  4260
tgacgtgcaa ggggcgaatt ggggcgagaa acacgtcgtg gacatggtgc aaggcccgca  4320
gggttgattc gacgcttttc cgcgaaaaaa acaagtccaa atacccccgt ttattctccc  4380
tcggctctcg gtatttcaca tgaaaactat aacctagact acacgggcaa ccttaacccc  4440
agagtatact tatataccaa agggatgggt cctcaaaaat cacacaagca acgacgccat  4500
gggcctctct ctagtatgta ccttctcttt ccagaccaac tatcacactc tactgaaccc  4560
ccataacaag aaccctaaaa attctcttct cagttaccag caccccaaga cgcctatcat  4620
taagtcctcc tacgacaact ttccctctaa gtactgcctg accaaaaact tccatctcct  4680
gggactgaac tctcataaca gaattagtag ccagtcccga tctatccgag ctggctctga  4740
ccagattgag ggctcccctc accatgaatc cgacaacagc atcgctacca agattttgaa  4800
ttttggtcac acatgctgga agctccagcg accgtacgtc gtgaagggta tgatctcgat  4860
tgcctgtgga ctgttcggac gtgagctttt taataatcga cacttgtttt catggggcct  4920
catgtggaag gcttttttcg ccctcgtgcc cattctgtct ttcaacttct ttgccgctat  4980
tatgaaccaa atctacgacg ttgatattga taggatcaac aagcctgacc tgccgctcgt  5040
ctcgggggag atgtctatcg agacagcgtg gattctttcg attatcgtcg cgctgactgg  5100
ccttatcgtt accataaagt tgaagtctgc accctcttc gtgtttatct acattttcgg  5160
tatttttgct ggattcgcgt actccgttcc ccctatcaga tggaagcagt accccttac  5220
taactttctg attactatca gcagccacgt cggtttagcc tttacctcat attcggccac  5280
caccagtgca ctgggcctcc ccttcgtctg gcgacctgca ttttcattca tcatcgcctt  5340
catgactgtg atgggtatga ccatcgcttt cgctaaggac atctccgaca tcgagggtga  5400
tgctaaatat ggagtgtcca ccgtggccac taagctggga gcccggaaca tgacgttcgt  5460
cgtctctggt gttctgctcc ttaactactt ggtttcgatc tccattggca ttatctggcc  5520
acaagtcttc aagtccaaca ttatgattct gtcccacgcc attcttgcct tttgcctgat  5580
cttccagaca cgcgaactcg ctctcgctaa ctacgcctcc gccccatcgc gacagttctt  5640
cgagttcatc tggctgcttt actacgccga gtacttcgtt tacgtgttca tctaataaga  5700
gtaggcaatt aacagatagt ttgccggtga taattctctt aacctcccac actcctttga  5760
cataacgatt tatgtaacga aactgaaatt tgaccagata ttgttgtaaa tagaaaatct  5820
ggcttgtagg tggcaaaatg cggcgtcttt gttcatcaat tccctctgtg actactcgtc  5880
atccctttat gttcgactgt cgtatttctt attttccata catatgcaag tgagatgccc  5940
```

```
gtgtccgaat tcgctatgga tccatagcgt cgacaccata tcatataaaa ctaacaatgc  6000
attgaattaa tacgaagact acccgttgct atctccacac cgttatctcc acggtccaaa  6060
ggctgctcaa tgtgctgcat acgtaacgtg gggtgcaacc ttgagcacat agtactttcc  6120
gaaaaccggc gataattaag tgtgcactcc aacttttcac actgagcata aaatgtggag  6180
aagaaatcac actaaaaagt caggtagact ggaaaatgcg ccatgaaata atatctcttg  6240
ctacagtaat gcccagcatc gaggggtatt gtgtcaccaa cactatagtg gcagctgaag  6300
cgctcgtgat tgtagtatga gtctttattg gtgatgggaa gagttcactc aatattctcg  6360
ttactgccaa aacaccacgg taatcggcca gacaccatgg atgtagatca ccaagcctgt  6420
gaatgttatt cgagctaaaa tgcacatggt tggtgaaagg agtagttgct gtcgaattcc  6480
gtcgtcgcct gagtcatcat ttatttacca gttggccaca aacccttgac gatctcgtat  6540
gtcccctccg acatactccc ggccggctgg ggtacgttcg atagcgctat cggcatcgac  6600
aaggtttggg tccctagccg ataccgcact acctgagtca caatcttcgg aggtttagtc  6660
ttccacatag cacgggcaaa agtgcgtata tatacaagag cgtttgccag ccacagattt  6720
tcactccaca caccacatca cacatacaac cacacacatc cacaatggaa cccgaaacta  6780
agaagaccaa gactgactcc aagaagattg ttcttctcgg cggcgacttc tgtggccccg  6840
aggtgattgc cgaggccgtc aaggtgctca agtctgttgc tgaggcctcc ggcaccgagt  6900
ttgtgtttga ggaccgactc attggaggag ctgccattga gaaggagggc gagcccatca  6960
ccgacgctac tctcgacatc tgccgaaagg ctgactctat tatgctcggt gctgtcggag  7020
gcgctgccaa caccgtatgg accactcccg acggacgaac cgacgtgcga cccgagcagg  7080
gtcttctcaa gctgcgaaag gacctgaacc tgtacgccaa cctgcgaccc tgccagctgc  7140
tgtcgcccaa gctcgccgat ctctccccca tccgaaacgt tgagggcacc gacttcatca  7200
ttgtccgaga gctcgtcgga ggtatctact ttggagagcg aaaggaggat gacggatctg  7260
gcgtcgcttc cgacactgag acttactccg ttcctgaggt tgagcgaatt gcccgaatgg  7320
ccgccttcct ggcccttcag cacaaccccc ctcttcccgt gtggtccctt gacaaggcca  7380
acgtgctggc ctcctctcga ctttggcgaa agaccgtcac ccgagtcctc aaggacgaat  7440
tcccccagct ggagctcaac caccagctga tcgactcggc cgccatgatc ctcatcaagc  7500
agccctccaa gatgaatggt atcatcatca ccaccaacat gtttggcgat atcatctccg  7560
acgaggcctc cgtcatcccc ggttctctgg gtctgctgcc ctccgcctct ctggcttctc  7620
tgcccgacac caacgaggcg ttcggtctgt acgagccctg tcacggatct gcccccgatc  7680
tcggcaagca gaaggtcaac cccattgcca ccattctgtc tgccgccatg atgctcaagt  7740
tctctcttaa catgaagccc gccggtgacg ctgttgaggc tgccgtcaag gagtccgtcg  7800
aggctggtat cactaccgcc gatatcggag gctcctcctc cacctccgag gtcggagact  7860
ttgttgccaa caaggtcaag gagctgctca agaaggagta agtcgtttct acgacgcatt  7920
gatggaagga gcaaactgac gcgcctgcgg gttggtctac cggcagggtc cgctagtgta  7980
taagactcta taaaaagggc ccagccctgc taatgaaatg atgatttata atttaccggt  8040
gtagcaacct tgactagaag aagcagattg ggtgtgtttg tagtggagga cagtggtacg  8100
ttttaattaa                                                         8110

SEQ ID NO: 175          moltype = DNA  length = 7557
FEATURE                 Location/Qualifiers
misc_feature            1..7557
                        note = pLD132
source                  1..7557
                        mol_type = other DNA
                        organism = synthetic construct
SEQUENCE: 175
ttaattaaga tcgtcgacga ttccgccaag tgagactggc gatcgggaga agggttggtg  60
gtcatggggg atagaatttg tacaagtgga aaaaccacta cgagtagcgg atttgatacc  120
acaagtagca gagatataca gcaatggtgg gagtgcaagt atcggaatgt actgtacctc  180
ctgtactcgt actcgtacgg cactcgtaga aacggggcaa tacgggggag aagcgatcgc  240
ccgtctgttc aatcgccaca agtccgagta atgcttgagt atcgaagtct tgtacctccc  300
tgtcaatcat ggcaccactg gtcttgactt gtctattcat actggacaag cgccagagtt  360
aagcttgtag cgaatttcgc cctcggacat caccccatac gacggacaca catgcccgac  420
aaacagcctc tcttattgta gctgaaagta tattgaatgt gaacgtgtac aatatcaggt  480
accagcggga ggttacggcc aaggtgatac cggaataacc ctggcttgga gatggtcggt  540
ccattgtact gaagtgtccg tgtcgtttcc gtcactgccc caattggaca tgtttgtttt  600
tccgatcttt cgggcgccct ctccttgtct ccttgtctgt ctcctggact gttgctaccc  660
catttctttg gcctccattg gttcctcccc gtctttcacg tcgtctatgg ttgcatggtt  720
tcccttatac ttttccccac agtcacatgt tatggagggg tctagatgga ggcctaattt  780
tgacgtgcaa ggggcgaatt ggggcgagaa acacgtcgtg gacatggtgc aaggcccgca  840
gggttgattc gacgcttttc cgcgaaaaaa acaagtccaa atacccccgt ttattctccc  900
tcggctctcg gtatttcaca tgaaaactat aacctagact acacgggcaa ccttaacccc  960
agagtatact tatataccaa agggatgggt cctcaaaaat cacacaagca acgacgccat  1020
gaagtgttcg acgttttctt tttggtttgt ttgtaaaatc attttctttt tcttttcttt  1080
caacatccaa acgtcgatcg caaaccctag agagaacttt cttaagtgct tctcgcagta  1140
catccctaat aacgctacca accttaagct ggtgtacacc cagaacaacc ctctttacat  1200
gtctgttcta aacagcacca tccacaatct tagattcaca tcagacacca ctcccaagcc  1260
gctcgtcatc gtgaccccga gtcatgtgtc ccatatccaa ggcactatcc tgtgctctaa  1320
aaaggtcggt ctgcagattc ggactcgctc cggtggacat gattcggagg gcatgtccta  1380
cattagccag gtccccttttg tgatcgtgga cctgaggaac atgcggtcta ttaagattga  1440
tgtgcactca cagaccgctt gggtcgaggc tggtgcgaca ttgggtgagg tgtactactg  1500
ggtgaacgag aagaacgaga acctgagcct cgccgctggc tactgtccca ccgtttgtgc  1560
cggtggacac ttcggcggag gcggatacgg tccacttatg cgaaactacg ggctcgcagc  1620
tgataatatc atcgacgcac accttgttaa cgttcacggc aaggtgctgg accgaaaaag  1680
catgggtgag gacctatttt gggccttgcg aggcggtggt gccgaatcct tcggaattat  1740
cgtggcctgg aagatccgac tggtcgctgt gccaaagtcc actatgttct ccgtcaagaa  1800
aattatggag atccacgaac tcgtaaagct cgtcaataag tggcagaaca tcgcctacaa  1860
gtatgacaag gatctgctgc tcatgactca cttcatcacg cgaaacatta cagacaacca  1920
gggaaagaac aagaccgcta tccataccta cttctcctct gtcttccttg gggtgtcga  1980
```

```
ttccctcgtt gatctcatga acaaatcttt tccagagctc ggaatcaaga agaccgactg  2040
ccgacagctc tcttggatcg acaccattat tttctactca ggagtcgtaa actacgatac  2100
tgacaacttt aacaaggaga ttctgttaga tcgatcggcc ggccagaacg gtgccttcaa  2160
gatcaagctc gactatgtca aaaagcccat tcctgaatcc gtcttcgttc aaattcttga  2220
aaagttgtac gaggaggata tcggcgccgg aatgtacgcg ctgtacccct acggtggcat  2280
tatggacgag atttctgaaa gtgctattcc cttcccccac cgtgctggca ttctgtatga  2340
gctgtggtac atttgctcct gggaaaagca ggaggacaac gagaagcact tgaactggat  2400
acgaaacatt tacaatttca tgacccccta tgtttcgaag aaccctcgac tggcctacct  2460
gaattaccgc gacctcgaca tcggaattaa cgaccctaag aaccccaata actatactca  2520
ggccagaatc tggggcgaga agtacttcgg caagaacttt gaccgtctgg ttaaggtcaa  2580
gaccctcgtg gaccctaaca acttcttccg aaacgagcag tctatccccc ctctgccccg  2640
acaccggcat taataagagt aggcaattaa cagatagttt gccggtgata attctcttaa  2700
cctcccacac tcctttgaca taacgattta tgtaacgaaa ctgaaatttg accagatatt  2760
gttgtaaata gaaaatctgg cttgtaggtg gcaaaatgcg gcgtctttgt tcatcaattc  2820
cctctgtgac tactcgtcat ccctttatgt tcgactgtcg tatttcttat tttccataca  2880
tatgcaagtg agatgcccgt gtccgaattc gctatggatc catagcgcag gttgtgcagt  2940
atcatacata ctcgatcaga caggtcgtct gaccatcata caagctgaac aagcgctcca  3000
tacttgcacg ctctctatat acacagttaa atgacatatc catagtctaa cctctaacag  3060
ttaatcttct ggtaagcctc ccagccagcc ttctggtatc gcttggcctc ctcaatagga  3120
tctcggttct ggccgtacag acctcggccg acaattatga tatccgttcc ggtagacatg  3180
acatcctcaa cagttcggta ctgctgtccg agagcatctc ccttgtcgtc aagacccacc  3240
ccgggggtca gaataagcca gtcctcagag tcgcccttag gtcggttctg ggcaatgaag  3300
ccaaccacaa actcggggtc ggatcgggca agctcaatgg tctgcttgga gtactcgcca  3360
gtggccagag agcccttgca agacagctcg gccagcatga gcagacctct ggccagcttc  3420
tcgttgggag aggggaccag gaactccttg tactgggagt tctcgtagtc agagacatcc  3480
tccttcttct gttcagagac agtttcctcg gcaccagctc gcaggccagc aatgattccg  3540
gttccgggta caccgtgggc gttggtgata tcggaccact cggcgattcg gtagacaccg  3600
ttcttgtact ggtgcttgac agtgttgcca atatctgcga actttctgtc ctcgaacagg  3660
aagaaaccgt gcttaagagc aagttccttg agggggagca cagttccggc gtaggtgaag  3720
tcgtcaatga tgtcgatatg ggtcttgatc atgcacacat aaggtccgac cttatcggca  3780
agctcaatga gctccttggt ggtggtaaca tccagagaag cacacaggtt ggttttcttg  3840
gctgccacga gcttgagcac tcgggcggca aaggcggact tgtggacgtt agctcgcgct  3900
tcgtaggagg gcattttggt ggtgaagagg agactgaaat aaatttagtc tgcacaactt  3960
tttatcggaa ccttatctgg ggcagtgaag tatatgttat ggtaatagtt acgagttagt  4020
tgaacttata gatagactgg actatacggc tatcggtcca aattagaaat taattaaatg  4080
gttctcgagg atccagtcta cactgattaa ttttcgggcc aataatttaa aaaaatcgtg  4140
ttatataata ttatatgtat tatatatata catatgatga tactgacagt catgtcccat  4200
tgctaaatag acagactcca tctgccgcct ccaactgatg ttctcaatat ttaaggggtc  4260
atctcgcatt gtttaataat aaacagactc catctaccgc ctccaaatga tgttctcaaa  4320
atatattgta tgaacttatt tttattactt agtattatta gacaacttac ttgctttatg  4380
aaaaacactt cctatttagg aaacaattta taatggcagt tcgttcattt aacaatttat  4440
gtagaataaa tgttataaat gcgtatggga aatcttaaat atggatagca taaatgatat  4500
ctgcattgcc taattcgaaa tcaacagcaa cgaaaaaaat cccttgtaca acataaatag  4560
tcatcgagaa atatcaacta tcaaagaaca gctattcaca cgttactatt gagattatta  4620
ttggacgaga atcacacact caactgtctt tctctcttct agaaatacag gtacaagtat  4680
gtactattct cattgttcat acttctagtc atttcatccc acatattcct tggatttctc  4740
tccaatgaat gacattctat cttgcaaatt caacaattat aataagatat accaaagtag  4800
cggtatagtg gcaatcaaaa agcttctctg gtgtgcttct cgtatttatt tttattctaa  4860
tgatccatta aaggtatata tttatttctt gttatataat ccttttgttt attacatggg  4920
ctggatacat aaaggtattt tgatttaatt ttttgcttaa attcaatccc ccctcgttca  4980
gtgtcaactg taatggtagg aaattaccat acttttgaag aagcaaaaaa aatgaaagaa  5040
ataaaaaatc gtatttccag gttagacgtt ccgcagaatc tagaatgcgg tatgcggtac  5100
attgttcttc gaacgtaaaa gttgcgctcc ctgagatatt gtacattttt gcttttacaa  5160
gtacaagtac atcgtacaac tatgtactac tgttgatgca tccacaacag tttgttttgt  5220
tttttttgt tttttatttt tctaatgatt cattaccgct atgtatacct acttgtactt  5280
gtagtaagcc gggttattgg cgttcaatta atcatagact tatgaatctg cacggtgtgc  5340
gctgcgagtt acttttagct tatgcatgct acttgggtgt aatattggga tcaggtcagg  5400
cggaatggca cttccttatt ccagatgcgt gcggattatg catgactggc cgtcgtttta  5460
caacgtcgtg actgggaaaa ccctggcgct tgtggtggat cacagttatt ggagacttcc  5520
ttggccgtac gatgggtttt gtttcaggta tcccaacctg gacgtctcgt ataatgcgac  5580
aaacaacaga taaaacgaaa ggcccagtct ttcgactgag cctttcgttt tatttggatc  5640
cactagttct agagcggcgg gggaaagcca cgttgtgtct caaaatctct gatgttacat  5700
tgcacaagat aaaaatatat catcatgaac aataaaactg tctgcttaca taaacagtaa  5760
tacaaggggt gttatgagcc atattcaacg ggaaacgtct tgctcgaggc cgcgattaaa  5820
ttccaacatg gatgctgatt tatatgggta taaatgggct cgcgataatg tcgggcaatc  5880
aggtgcgaca atctatcgat tgtatgggaa gcccgatgcg ccagagttgt ttctgaaaca  5940
tggcaaaggt agcgttgcca atgatgttac agatgagatg gtcagactaa actggctgac  6000
ggaatttatg cctcttccga ccatcaagca ttttatccgt actcctgatg atgcatggtt  6060
actcaccact gcgatccccg ggaaaacagc attccaggta ttagaagaat atcctgattc  6120
aggtgaaaat attgttgatg cgctggcagt gttcctgcgc cggttgcatt cgattcctgt  6180
ttgtaattgt ccttttaaca gcgatcgcgt atttcgtctc gctcaggcgc aatcacgaat  6240
gaataacggt ttggttgatg cgagtgattt tgatgacgag cgtaatggct ggcctgttga  6300
acaagtctgg aaagaaatgc ataagctttt gccattctca ccggattcag tcgtcactca  6360
tggtgatttc tcacttgata accttatttt tgacgagggg aaattaatag gttgtattga  6420
tgttggacga gtcggaatcg cagaccgata ccaggatctt gccatcctat ggaactgcct  6480
cggtgagttt tctccttcat tacagaaacg gctttttcaa aaatatggta ttgataatcc  6540
tgatatgaat aaattgcagt ttcatttgat gctcgatgag tttttctaat cagaatttgt  6600
taattggttg taacactggc agagcggacg atttgaagcc ccctacccat ttacgctgac  6660
ttgacgggac ggcggctttg ttgaatagag cgtcagaccc cgtagaaaag atcaaaggat  6720
```

```
cttcttgaga tcctttttt ctgcgcgtaa tctgctgctt gcaaacaaaa aaaccaccgc 6780
taccagcggt ggtttgtttg ccggatcaag agctaccaac tctttttccg aaggtaactg 6840
gcttcagcag agcgcagata ccaaatactg ttcttctagt gtagccgtag ttaggccacc 6900
acttcaagaa ctctgtagca ccgcctacat acctcgctct gctaatcctg ttaccagtgg 6960
ctgctgccag tggcgataag tcgtgtctta ccgggttgga ctcaagacga tagttaccgg 7020
ataaggcgca gcggtcgggc tgaacggggg gttcgtgcac acagcccagc ttggagcgaa 7080
cgacctacac cgaactgaga tacctacagc gtgagctatg agaaagcgcc acgcttcccg 7140
aagggagaaa ggcggacagg tatccggtaa gcggcagggt cggaacagga gagcgcacga 7200
gggagcttcc agggggaaac gcctggtatc tttatagtcc tgtcgggttt cgccacctct 7260
gacttgagcg tcgatttttg tgatgctcgt caggggggcg gagcctatgg aaaaacgcca 7320
gcaacgcggc ctttttacgg ttcctggcct tttgctggcc ttttgctcac atgttctttc 7380
cagcgacata tgccatacgc cgaactgaac tccacctaat gtcttggaga ttgtcggata 7440
gcgcggaata ggattgtgcc ctctgagcgg ataacaattt cacacaggaa acagctatga 7500
ccatgacaca tgcatccacc atcgcagact tatcatcact gagcctccac ctagcct 7557

SEQ ID NO: 176          moltype = DNA  length = 8500
FEATURE                 Location/Qualifiers
misc_feature            1..8500
                        note = pLD135
source                  1..8500
                        mol_type = other DNA
                        organism = synthetic construct
SEQUENCE: 176
aggctaggtg gaggctcagt gatgataagt ctgcgatggt ggatgcatgt gtcatggtca 60
tagctgtttc ctgtgtgaaa ttgttatccg ctcagagggc acaatcctat tccgcgctat 120
ccgacaatct ccaagacatt aggtggagtt cagttcggcg tatggcatat gtcgctggaa 180
agaacatgtg agcaaaaggc cagcaaaagg ccaggaaccg taaaaaggcc gcgttgctgg 240
cgtttttcca taggctccgc ccccctgacg agcatcacaa aaatcgacgc tcaagtcaga 300
ggtggcgaaa cccgacagga ctataaagat accaggcgtt tccccctgga agctccctcg 360
tgcgctctcc tgttccgacc ctgccgctta ccggatacct gtccgccttt ctcccttcgg 420
gaagcgtggc gctttctcat agctcacgct gtaggtatct cagttcggtg taggtcgttc 480
gctccaagct gggctgtgtg cacgaacccc ccgttcagcc cgaccgctgc gccttatccg 540
gtaactatcg tcttgagtcc aacccggtaa gacacgactt atcgccactg gcagcagcca 600
ctggtaacag gattagcaga gcgaggtatg taggcggtgc tacagagttc ttgaagtggt 660
ggcctaacta cggctacact agaagaacag tatttggtat ctgcgctctg ctgaagccag 720
ttaccttcgg aaaaagagtt ggtagctctt gatccggcaa acaaaccacc gctggtagcg 780
gtggtttttt tgtttgcaag cagcagatta cgcgcagaaa aaaggatctc caagaagatc 840
ctttgatctt ttctacgggg tctgacgctc tattcaacaa agccgccgtc ccgtcaagtc 900
agcgtaaatg ggtagggggc ttcaaatcgt cctcgtgata ccaattcgga gcctgctttt 960
ttgtacaaac ttgttgataa tggcaattca aggatcttca cctagatcct tttaaattaa 1020
aaatgaagtt ttaaatcaat ctaaagtata tatgagtaaa cttggtctga cagttaccaa 1080
tgcttaatca gtgaggcacc tatctcagcg atctgtctat ttcgttcatc catagttgcc 1140
tgactccccg tcgtgtagat aactacgata cgggagggct taccatctgg ccccagtgct 1200
gcaatgatac cgcgagagcc acgctcaccg gctccagatt tatcagcaat aaaccagcca 1260
gccggaaggg ccgagcgcag aagtggtcct gcaactttat ccgcctccat ccagtctatt 1320
aattgttgcc gggaagctag agtaagtagt tcgccagtta atagtttgcg caacgttgtt 1380
gccattgcta caggcatcgt ggtgtcacgc tcgtcgtttg gtatggcttc attcagctcc 1440
ggttcccaac gatcaaggcg agttacatga tcccccatgt tgtgcaaaaa agcggttagc 1500
tccttcggtc ctccgatcgt tgtcagaagt aagttggccg cagtgttatc actcatggtt 1560
atggcagcac tgcataattc tcttactgtc atgccatccg taagatgctt ttctgtgact 1620
ggtgagtact caaccaagtc attctgagaa tagtgtatgc ggcgaccgag ttgctcttgc 1680
ccggcgtcaa tacgggataa taccgcgcca catagcagaa ctttaaaagt gctcatcatt 1740
ggaaaacgtt cttcggggcg aaaactctca aggatcttac cgctgttgag atccagttcg 1800
atgtaaccca ctcgtgcacc caactgatct tcagcatctt ttactttcac cagcgtttct 1860
gggtgagcaa aaacaggaag gcaaaatgcc gcaaaaaagg gaataagggc gacacggaaa 1920
tgttgaatac tcatactctt cctttttcaa tattattgaa gcatttatca gggttattgt 1980
ctcatgagcg gatacatatt tgaatgtatt tagaaaaata aacaaatagg ggttccgcgc 2040
acatttcccc gaaaagtgcc agatacctga aacaaaaccc atcgtacggc caaggaagtc 2100
tccaataact gtgatccacc acaagcgcca gggttttccc agtcacgacg ttgtaaaacg 2160
acggccagtc atgcataatc cgcacgcatc tggaataagg aagtgccatt ccgcctgacc 2220
tttaattaat tggcaaattt tactgtggcc ttcagaacgg taaaaataga ccaatcagaa 2280
ttctgaaaag cacatcttga tctcctcatt gcggggagtc caacggtggt cttattcccc 2340
cgaatttccc gctcaatctc gttccagacc gacccggaca cagtgcttaa cgccgttccg 2400
aaactctacc gcagatatgc tccaacggac tgggctgcat agatgtgatc ctcggcttgg 2460
agaaatggat aaaagccggc caaaaaaaaa gcggaaaaaa gcggaaaaaa agagaaaaaa 2520
aatcgcaaaa tttgaaaaat aggggggaaaa gacgcaaaaa cgcaaggagg ggggagtata 2580
tgacactgat aagcaagctc acaacggttc ctcttatttt tttcctcatc ttctgcctag 2640
gttcccaaaa tcccagatgc ttctctccag tgccaaaagt aagtacccca caggttttcg 2700
gccgaaaatt ccacgtgcag caacgtcgtg tggggtgtta aaatgtgggg gcggggaacc 2760
aggacaagag gctcttgtgg gagccgaatg agagcacaaa gcgggcgggt gtgataaggg 2820
catttttgcc cattttccct tctcctgtct ctccgacggt gatggcgttg tgcgtcctct 2880
atctatttct ttttatttct ttttgtttta tttctctgac taccgatttg gcttgatttc 2940
ctcaacccca cacaaataag ctcgggccga ggaatatata tatacacgga cacagtcgcc 3000
ctgtggacaa cacgtcacta cctctacgac gctatggatc catagcgaat tcggacacgg 3060
gcatctcact tgcatatgta tggaaaataa gaaatacgac agtcgaacat aaagggatga 3120
cgagtagtca cagagggaat tgatgaacaa agacgccgca ttttgccacc tacaagccag 3180
attttctatt tacaacaata tctggtcaaa tttcagtttc gttacataaa tcgttatgtc 3240
aaaggagtgt gggaggttaa gagaattatc accggcaaac tatctgttaa ttgcctactc 3300
ttattacagt ttggctcgtc gtccccgaga cttgccggcc ttgatagcga ggagtgtctt 3360
```

```
ctcgtcagca ggggcgctac cggaggctcg ttgctgtctg aagtaggttc gggcctcgtc  3420
ctgtcgggtg gcctcagcgc cggtggcgat agcggcccga aggtgctcgg ctccgtagcc  3480
gaaggcatca accagatcaa gtgcgtgtgg tcggatctta acgagaagac gattaatgta  3540
agtgccgacc gttcggcctc tctgcatcga gagcctaccg ttcatcagat accagctgag  3600
gtgcttctcg ataagggaca gaccaaaaag gtcacgcaat cgggtcaaca cttccttagt  3660
gccagcgtcg tccaccttgg ccaaagcctc agtaaaggcc tcccactgta aaagctcagc  3720
gtgggcctgg gcagcctcga tcagttcgtt ttgatgctga ttgaacagtg ctgccgcctg  3780
gtgctggggg agcttgcccg cgcctttgag agcagcgcca acctctgcaa ccatggactg  3840
gactctgtcg gtcagcagag ttcgctgacc ttcttcgtct cggagggcaa gagcagattt  3900
ctggacagat ccactgtcgg ccacgaactg agcgacctgt cgcagtccgg ttcggtgtag  3960
cgcgactccg gcagcctggt ccacgacgta ccgcgcgagc acgccgaagt tggcacctcg  4020
gaactcctta gcatagtcag cgagcagcct cttggccacc aactgaagaa gcacggtgtt  4080
gtctccttcg aaggtcacgt agacgtcgag atcggcccgg agagaagcga atcggttctc  4140
aatcagaaaa cctgcacccc cacacgcttc tcggcactct tgtagggtat cgagagcatg  4200
ccaggtagaa aggggcttca gagcagcagc cagtgtctca aggtcctgac ggtcggcgtc  4260
agtatcatga gcacccgaga acacgtcgtc gaatttctgc agcagttgct catgggcgaa  4320
cgatgcggcg taggtggtgg cgagtcgggt aaagaggcgc cgctggtgtc gctggtaatc  4380
caggagcacc tcctcctctg tgggcgaagt ggcgttgaac tgtcttcgct cagcggcgta  4440
gtggatggcg gattgcagag caaccttcga tgcagccact gcagcaccgt ccaggctgac  4500
tcggccctgg accagcgtac ctagcattgt aaagaatctt cgccccggag attcgatggt  4560
tgagctgtag gtgccatcga cggcaacatc gccgtaacgg ttaagcaggt tggttcgggg  4620
aatgcgaaca ttggtgaaat ggagacgtcc gttatcaatt ccgtttagtc ccccccttaat  4680
accgtcgtcc tctccaccaa taccagggag aaagtctccg gtggcgggat ctctcagatc  4740
gacgtagaag gcgtgcactc catggttaac ctttcgagta atcagttggg caaacacgac  4800
agcggccaaa ccgtcgttag cggcgtttcc aatgtagtcc ttccaggcgg ctcggaacgg  4860
ggtgtcaata acgaactcct gggtttcctc atcataggtg gccgttgtag caatggaagc  4920
gacatcggag ccatggccag tctcagtcat ggcaaagcaa ccagggattt ccagagacat  4980
gatgcctggg agccacttgt cgtggtgctc cctagttccc aagtgcataa cagcggagcc  5040
gaacagtccc cactggacgc cggccttgat ctggagggag gggtccgccg tgacaagctc  5100
ctcaaaacca gcgatgtttc cgccgtggtc gtcactacca cccagtcgag aaggaaaggc  5160
tcggtgaact gcgttgttat cgaccaagta cttgagctgg ccaaagacgc gagagcggtg  5220
ctctgtatga gtcagaccct ccaccttctg aactacctct cgtcccgcaa ggtcccgggc  5280
gtggagacgg atatcagccc atcggcccag cagctgctct cccagcgcag ccacatctac  5340
tcggggctcg acggccacct tagcaccgtc tgcggcggcc gtagttgagc caggggatgc  5400
gggggatgag gctctgtcaa ctacttcggt catggcgtcg ttgcttgtgt gatttttgag  5460
gacccatccc tttggtatat aagtatactc tggggttaag gttgcccgtg tagtctaggt  5520
tatagttttc atgtgaaata ccgagagccg agggagaata aacgggggta tttggacttg  5580
tttttttcgc ggaaaagcgt cgaatcaacc ctgcgggcct tgcaccatgt ccacgacgtg  5640
tttctcgccc caattcgccc cttgcacgtc aaaattaggc ctccatctag accccctccat  5700
aacatgtgac tgtggggaaa agtataaggg aaaccatgca accatagacg acgtgaaaga  5760
cggggaggaa ccaatggagg ccaaagaaat ggggtagcaa cagtccagga gacagacaag  5820
gagacaagga gagggcgccc gaaagatcgg aaaaacaaac atgtccaatt ggggcagtga  5880
cggaaacgac acggacactt cagtacaatg gaccgaccat ctccaagcca gggttattcc  5940
ggtatcacct tggccgtaac ctcccgctgg tacctgatat tgtacacgtt cacattcaat  6000
atactttcag ctacaataag agaggctgtt tgtcgggcat gtgtgtccgt cgtatggggt  6060
gatgtccgag ggcgaaattc gctacaagct taactctggc gcttgtccag tatgaataga  6120
caagtcaaga ccagtggtgc catgattgac agggaggtac aagacttcga tactcaagca  6180
ttactcggac ttgtggcgat tgaacagacg ggcgatcgct tctcccccgt attgccccgt  6240
ttctacgagt gccgtacgag tacgagtaca ggaggtacag tacattccga tacttgcact  6300
cccaccattg ctgtatatct ctgctacttg tggtatcaaa tccgctactc gtagtggttt  6360
ttccacttgt acaaattcta tcccccatga ccaccaaccc ttctcccgat cgccagtctc  6420
acttggcgga atcgtcgacg atcatcctcg agatgcggcc gcgtcgacat aacttcgtat  6480
agcatacatt atacgaagtt attttctaat ttggaccgat agccgtatag tccagtctat  6540
ctataagttc aactaactcg taactattac cataacatat acttcactgc cccagataag  6600
gttccgataa aaagttgtgc agactaaatt tatttcagtc tcctcttcac caccaaaatg  6660
ccctcctacg aagcgcgagc taacgtccac aagtccgcct ttgccgcccg agtgctcaag  6720
ctcgtggcag ccaagaaaac caacctgtgt gcttctctgg atgttaccac caccaaggag  6780
ctcattgagc ttgccgataa ggtcggacct tatgtgtgca tgatcaagac ccatatcgac  6840
atcattgacg acttcaccta cgccggaact gtgctccccc tcaaggaact tgctcttaag  6900
cacggtttct tcctgttcga ggacagaaag ttcgcagata ttggcaacac tgtcaagcac  6960
cagtacaaga acggtgtcta ccgaatcgcc gagtggtccg atatcaccaa cgcccacggt  7020
gtacccggaa ccggaatcat tgctggcctg cgagctggtg ccgaggaaac tgtctctgaa  7080
cagaagaagg aggatgtctc tgactacgag aactcccagt acaaggagtt cctggtcccc  7140
tctcccaacg agaagctggc cagaggtctg ctcatgctgg ccgagctgtc ttgcaagggc  7200
tctctggcca ctggcgagta ctccaagcag accattgagc ttgcccgatc cgaccccgag  7260
tttgtggttg gcttcattgc ccagaaccga cctaagggcg actctgagga ctggcttatt  7320
ctgacccccg gggtgggtct tgacgacaag ggagatgctc tcggacagca gtaccgaact  7380
gttgaggatg tcatgtctac cggaacggat atcataattg tcggccgagg tctgtacggc  7440
cagaaccgag atcctattga ggaggccaag cgataccaga aggctggctg ggaggcttac  7500
cagaagatta actgttagag gttagactat ggatatgtca tttaactgtg tatatagaga  7560
gcgtgcaagt atggagcgct tgttcagctt gtatgatggt cagacgacct gtctgatcga  7620
gtatgtatga tactgcacaa cctgataact tcgtatagca tacattatac gaagttatct  7680
cgaggcggcc gcatggagcg tgtgttctga gtcgatgttt tctatggagt tgtgagtgtt  7740
agtagacatg atgggtttat atatgatgaa tgaatagatg tgattttgat ttgcacgatg  7800
gaattgagaa ctttgtaaac gtacatggga atgtatgaat gtgggggttt tgtgactgga  7860
taactgacgg tcagtggacg ccgttgttca aatatccaag agatgcgaga aactttgggt  7920
caagtgaaca tgtcctctct gttcaagtaa accatcaact atgggtagta tatttagtaa  7980
ggacaagagt tgagattctt tggagtccta gaaacgtatt ttcgcgttcc aagatcaaat  8040
tagtagagta atacgggcac gggaatccat tcatagtctc aatttcccca taggtgtgct  8100
```

```
acaaggtgtt gagatgtggt acagtaccac catgattcga ggtaaagagc ccagaagtca  8160
ttgatgaggt caagaaatac acagatctac agctcaatac aatgaatatc ttctttcata  8220
ttcttcaggt gacaccaagg gtgtctattt tccccagaaa tgcgtgaaaa ggcgcgtgtg  8280
tagcgtggag tatgggttcg gttggcgtat ccttcatata tcgacgaaat agtagggcaa  8340
gagatgacaa aaagtatcta tatgtagaca gcgtagaata tggatttgat tggtataaat  8400
tcatttattg cgtgtctcac aaatactctc gataagttgg ggttaaactg gagatggaac  8460
aatgtcgata tctcgacata ttttgatatt tgttaattaa                        8500

SEQ ID NO: 177          moltype = DNA  length = 5655
FEATURE                 Location/Qualifiers
misc_feature            1..5655
                        note = pLD137
source                  1..5655
                        mol_type = other DNA
                        organism = synthetic construct
SEQUENCE: 177
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc ccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaaggatct caagaagatc  840
ctttgatctt ttctacgggg tctgacgctc tattcaacaa agccgccgtc ccgtcaagtc  900
agcgtaaatg ggtagggggc ttcaaatcgt ccgctctgcc agtgttacaa ccaattaaca  960
aattctgatt agaaaaactc atcgagcatc aaatgaaact gcaatttatt catatcagga  1020
ttatcaatac catatttttg aaaaagccgt ttctgtaatg aaggagaaaa ctcaccgagg  1080
cagttccata ggatggcaag atcctggtat cggtctgcga ttccgactcg tccaacatca  1140
atacaaccta ttaatttccc ctcgtcaaaa ataaggttat caagtgagaa atcaccatga  1200
gtgacgactg aatccggtga gaatggcaaa agcttatgca tttctttcca gacttgttca  1260
acaggccagc cattacgctc gtcatcaaaa tcactcgcat caaccaaacc gttattcatt  1320
cgtgattgcg cctgagcgag acgaaatacg cgatcgctgt taaaaggaca attacaaaca  1380
ggaatcgaat gcaaccggcg caggaacact gccagcgcat caacaatatt ttcacctgaa  1440
tcaggatatt cttctaatac ctggaatgct gttttcccgg ggatcgcagt ggtgagtaac  1500
catgcatcat caggagtacg gataaaatgc ttgatggtcg gaagaggcat aaattccgtc  1560
agccagttta gtctgaccat ctcatctgta acatcattgg caacgctacc tttgccatgt  1620
ttcagaaaca actctggcgc atcgggcttc ccatacaatc gatagattgt cgcacctgat  1680
tgcccgacat tatcgcgagc ccatttatac ccatataaat cagcatccat gttggaattt  1740
aatcgcggcc tcgagcaaga cgtttcccgt tgaatatggc tcataacacc ccttgtatta  1800
ctgtttatgt aagcagacag ttttattgtt catgatgata tatttttatc ttgtgcaatg  1860
taacatcaga gattttgaga cacaacgtgg ctttcccccg ccgctctaga actagtggat  1920
ccaaataaaa cgaaaggctc agtcgaaaga ctgggccttt cgttttatct gttgtttgtc  1980
gcattatacg agacgtccag gttgggatac ctgaaacaaa acccatcgta cggccaagga  2040
agtctccaat aactgtgatc caccacaagc gccagggttt tcccagtcac gacgttgtaa  2100
aacgacggcc agtcatgcat aatccgcacg catctggaat aaggaagtgc cattccgcct  2160
gacctgatcc caatattaca cccaagtagc atgcataagc taaaagtaac tcgcagcgca  2220
caccgtgcag attcataagt ctatgattaa ttgaacgcca ataacccggc ttactacaag  2280
tacaagtagg tatacatagc ggtaatgaat cattagaaaa ataaaaaaca aaaaaaaaca  2340
aaacaaactg ttgtggatgc atcaacagta gtacatagtt gtacgatgta cttgtacttg  2400
taaaagcaaa aatgtacaat atctcaggga gcgcaacttt tacgttcgaa gaacaatgta  2460
ccgcataccg cattctagat tctgcggaac gtctaacctg gaaatacgat tttttatttc  2520
tttcattttt tttgcttctt caaaagtatg gtaatttcct accattacag ttgacactga  2580
acgagggggg attgaattta agcaaaaaat taaatcaaaa tacctttatg tatccagccc  2640
atgtaataaa caaaaggatt atataacaag aaataaatat atacctttaa tggatcatta  2700
gaataaaaat aaatacgaga agcacaccag agaagctttt tgattgccac tataccgcta  2760
ctttggtata tcttattata attgttgaat ttgcaagata gaatgtcatt cattggagag  2820
aaatccaagg aatatgtggg atgaaatgac tagaagtatg aacaatgaga atagtacata  2880
cttgtacctg tatttctaga agagagaaag acagttgagt gtgtgattct cgtccaataa  2940
taatctcaat agtaacgtgt gaatagctgt tctttgatag ttgatatttc tcgatgacta  3000
tttatgttgt acaagggatt tttttcgttg ctgttgattt cgaattaggc aatgcagata  3060
tcatttatgc tatccatatt taagatttcc catacgcatt tataacattt attctacata  3120
aattgttaaa tgaacgaact gccattataa attgtttcct aaataggaag tgtttttcat  3180
aaagcaagta agttgtctaa taatactaag taataaaaat aagttcatac aatatatttt  3240
gagaacatca tttggaggcg gtagatggag tctgtttatt attaaacaat gcgagatgac  3300
cccttaaata ttgagaacat cagttggagg cggcagatgg agtctgtcta tttagcaatg  3360
ggacatgact gtcagtatca tcatatgtat atatataata catataatat tatataacac  3420
gatttttttta aattattggc ccgaaaatta atcagtgtag actggatcct cgagaaccat  3480
ttaattaaga tcagagaccg gatggtctca agcgtcgaca ccatatcata taaaactaac  3540
aatgcattga attaatacga agactacccg ttgctatctc cacaccgtta tctccacggt  3600
ccaaaggctg ctcaatgtgc tgcatacgta acgtggggtg caaccttgag cacatagtac  3660
tttccgaaaa ccggcgataa ttaagtgtgc actccaactt ttcacactga gcataaaatg  3720
tggagaagaa atcacactaa aaagtcaggt agactggaaa atgcgccatg aaataatatc  3780
```

```
tcttgctaca gtaatgccca gcatcgaggg gtattgtgtc accaacacta tagtggcagc  3840
tgaagcgctc gtgattgtag tatgagtctt tattggtgat gggaagagtt cactcaatat  3900
tctcgttact gccaaaacac cacggtaatc ggccagacac catggatgta gatcaccaag  3960
cctgtgaatg ttattcgagc taaaatgcac atggttggtg aaaggagtag ttgctgtcga  4020
attccgtcgt cgcctgagtc atcatttatt taccagttgg ccacaaaccc ttgacgatct  4080
cgtatgtccc ctccgacata ctcccggccg gctggggtac gttcgatagc gctatcggca  4140
tcgacaaggt ttgggtccct agccgatacc gcactacctg agtcacaatc ttcggaggtt  4200
tagtcttcca catagcacgg gcaaaagtgc gtatatatac aagagcgttt gccagccaca  4260
gattttcact ccacacacca catcacacat acaaccacac acatccacaa tggaacccga  4320
aactaagaag accaagactg actccaagaa gattgttctt ctcggcggcg acttctgtgg  4380
ccccgaggtg attgccgagg ccgtcaaggt gctcaagtct gttgctgagg cctccggcac  4440
cgagtttgtg tttgaggacc gactcattgg aggagctgcc attgagaagg agggcgagcc  4500
catcaccgac gctactctcg acatctgccg aaaggctgac tctattatgc tcggtgctgt  4560
cggaggcgct gccaacaccg tatggaccac tcccgacgga cgaaccgacg tgcgacccga  4620
gcagggtctt ctcaagctgc gaaaggacct gaacctgtac gccaacctgc gaccctgcca  4680
gctgctgtcg cccaagctcg ccgatctctc cccatccga aacgttgagg gcaccgactt  4740
catcattgtc cgagagctcg tcggaggtat ctactttgga gagcgaaagg aggatgacgg  4800
atctggcgtc gcttccgaca ctgagactta ctccgttcct gaggttgagc gaattgcccg  4860
aatggccgcc ttcctggccc ttcagcacaa ccccctctt cccgtgtggt cccttgacaa  4920
ggccaacgtg ctggcctcct ctcgactttg gcgaaagacc gtcacccgag tcctcaagga  4980
cgaattcccc cagctggagc tcaaccacca gctgatcgac tcggccgcca tgatcctcat  5040
caagcagccc tccaagatga atggtatcat catcaccacc aacatgtttg gcgatatcat  5100
ctccgacgag gcctccgtca tccccggttc tctgggtctg ctgccctccg cctctctggc  5160
ttctctgccc gacaccaacg aggcgttcgg tctgtacgag ccctgtcacg gatctgcccc  5220
cgatctcggc aagcagaagg tcaaccccat tgccaccatt ctgtctgccg ccatgatgct  5280
caagttctct cttaacatga agcccgccgg tgacgctgtt gaggctgccg tcaaggagtc  5340
cgtcgaggct ggtatcacta ccgccgatat cggaggctcc tcctccacct ccgaggtcgg  5400
agactttgtt gccaacaagg tcaaggagct gctcaagaag gagtaagtcg tttctacgac  5460
gcattgatgg aaggagcaaa ctgacgcgcc tgcgggttgg tctaccggca gggtccgcta  5520
gtgtataaga ctctataaaa agggcccagc cctgctaatg aaatgatgat ttataattta  5580
ccggtgtagc aaccttgact agaagaagca gattgggtgt gtttgtagtg gaggacagtg  5640
gtacgtttta attaa                                                   5655

SEQ ID NO: 178          moltype = DNA  length = 4664
FEATURE                 Location/Qualifiers
misc_feature            1..4664
                        note = pLD138
source                  1..4664
                        mol_type = other DNA
                        organism = synthetic construct
SEQUENCE: 178
aggctaggtg gaggctcagt gatgataagt ctgcgatggt ggatgcatgt gtcatggtca  60
tagctgtttc ctgtgtgaaa ttgttatccg ctcagagggc acaatcctat tccgcgctat  120
ccgacaatct ccaagacatt aggtggagtt cagttcggcg tatggcatat gtcgctggaa  180
agaacatgtg agcaaaaggc cagcaaaagg ccaggaaccg taaaaaggcc gcgttgctgg  240
cgtttttcca taggctccgc ccccctgacg agcatcacaa aaatcgacgc tcaagtcaga  300
ggtggcgaaa cccgacagga ctataaagat accaggcgtt tccccctgga agctccctcg  360
tgcgctctcc tgttccgacc ctgccgctta ccggatacct gtccgccttt ctcccttcgg  420
gaagcgtggc gctttctcat agctcacgct gtaggtatct cagttcggtg taggtcgttc  480
gctccaagct gggctgtgtg cacgaacccc ccgttcagcc cgaccgctgc gccttatccg  540
gtaactatcg tcttgagtcc aacccggtaa gacacgactt atcgccactg gcagcagcca  600
ctggtaacag gattagcaga gcgaggtatg taggcggtgc tacagagttc ttgaagtggt  660
ggcctaacta cggctacact agaagaacag tatttggtat ctgcgctctg ctgaagccag  720
ttaccttcgg aaaaagagtt ggtagctctt gatccggcaa acaaaccacc gctggtagcg  780
gtggtttttt tgtttgcaag cagcagatta cgcgcagaaa aaaaggatct caagaagatc  840
ctttgatctt ttctacgggg tctgacgctc tattcaacaa agccgccgtc ccgtcaagtc  900
agcgtaaatg ggtagggggc ttcaaatcgt ccgctctgcc agtgttacaa ccaattaaca  960
aattctgatt agaaaaactc atcgagcatc aaatgaaact gcaatttatt catatcagga  1020
ttatcaatac catatttttg aaaaagccgt ttctgtaatg aaggagaaaa ctcaccgagg  1080
cagttccata ggatggcaag atcctggtat cggtctgcga ttccgactcg tccaacatca  1140
atacaaccta ttaatttccc ctcgtcaaaa ataaggttat caagtgagaa atcaccatga  1200
gtgacgactg aatccggtga gaatggcaaa agcttatgca tttctttcca gacttgttca  1260
acaggccagc cattacgctc gtcatcaaaa tcactcgcat caaccaaacc gttattcatt  1320
cgtgattgcg cctgagcgag acgaaatacg cgatcgctgt taaaaggaca attacaaaca  1380
ggaatcgaat gcaaccggcg caggaacact gccagcgcat caacaatatt ttcacctgaa  1440
tcaggatatt cttctaatac ctggaatgct gttttcccgg ggatcgcagt ggtgagtaac  1500
catgcatcat caggagtacg gataaaatgc ttgatggtcg gaagaggcat aaattccgtc  1560
agccagttta gtctgaccat ctcatctgta acatcattgg caacgctacc tttgccatgt  1620
ttcagaaaca actctggcgc atcgggcttc ccatacaatc gatagattgt cgcacctgat  1680
tgcccgacat tatcgcgagc ccatttatac ccatataaat cagcatccat gttggaattt  1740
aatcgcggcc tcgagcaaga cgtttcccgt tgaatatggc tcataacacc ccttgtatta  1800
ctgtttatgt aagcagacag ttttattgtt catgatgata tatttttatc ttgtgcaatg  1860
taacatcaga gattttgaga cacaacgtgg ctttcccccg ccgctctaga actagtggat  1920
ccaaataaaa cgaaaggctc agtcgaaaga ctgggccttt cgttttatct gttgtttgtc  1980
gcattatacg agacgtccag gttgggatac ctgaaacaaa acccatcgta cggccaagga  2040
agtctccaat aactgtgatc caccacaagc gccagggttt tcccagtcac gacgttgtaa  2100
aacgacggcc agtcatgcat aatccgcacg catctggaat aaggaagtgc cattccgcct  2160
gacctgatcc caatattaca cccaagtagc atgcataagc taaaagtaac tcgcagcgca  2220
caccgtgcag attcataagt ctatgattaa ttgaacgcca ataacccggc ttactacaag  2280
```

```
tacaagtagg tatacatagc ggtaatgaat cattagaaaa ataaaaaaca aaaaaaaaca  2340
aaacaaactg ttgtggatgc atcaacagta gtacatagtt gtacgatgta cttgtacttg  2400
taaaagcaaa aatgtacaat atctcaggga gcgcaacttt tacgttcgaa gaacaatgta  2460
ccgcataccg cattctagat tctgcggaac gtctaacctg gaaatacgat tttttatttc  2520
tttcattttt tttgcttctt caaaagtatg gtaatttcct accattacag ttgacactga  2580
acgagggggg attgaattta agcaaaaaat taaatcaaaa tacctttatg tatccagccc  2640
atgtaataaa caaaaggatt atataacaag aaataaatat atacctttaa tggatcatta  2700
gaataaaaat aaatacgaga agcacaccag agaagctttt tgattgccac tataccgcta  2760
ctttggtata tcttattata attgttgaat ttgcaagata gaatgtcatt cattggagag  2820
aaatccaagg aatatgtggg atgaaatgac tagaagtatg aacaatgaga atagtacata  2880
cttgtacctg tatttctaga agagagaaag acagttgagt gtgtgattct cgtccaataa  2940
taatctcaat agtaacgtgt gaatagctgt tctttgatag ttgatatttc tcgatgacta  3000
tttatgttgt acaagggatt tttttcgttg ctgttgattt cgaattaggc aatgcagata  3060
tcatttatgc tatccatatt taagatttcc catacgcatt tataacattt attctacata  3120
aattgttaaa tgaacgaact gccattataa attgtttcct aaataggaag tgtttttcat  3180
aaagcaagta agttgtctaa taatactaag taataaaaat aagttcatac aatatatttt  3240
gagaacatca tttggaggcg gtagatggag tctgtttatt attaaacaat gcgagatgac  3300
cccttaaata ttgagaacat cagttggagg cggcagatgg agtctgtcta tttagcaatg  3360
ggacatgact gtcagtatca tcatatgtat atatataata catataatat tatataacac  3420
gatttttta aattattggc ccgaaaatta atcagtgtag actggatcct cgagaaccat  3480
ttaattaatt tctaatttgg accgatagcc gtatagtcca gtctatctat aagttcaact  3540
aactcgtaac tattaccata acatatactt cactgcccca gataaggttc cgataaaaag  3600
ttgtgcagac taaatttatt tcagtctcct cttcaccacc aaaatgccct cctacgaagc  3660
gcgagctaac gtccacaagt ccgcctttgc cgcccgagtg ctcaagctcg tggcagccaa  3720
gaaaaccaac ctgtgtgctt ctctggatgt taccaccacc aaggagctca ttgagcttgc  3780
cgataaggtc ggaccttatg tgtgcatgat caagacccat atcgacatca ttgacgactt  3840
cacctacgcc ggaactgtgc tccccctcaa ggaacttgct cttaagcacg gtttcttcct  3900
gttcgaggac agaaagttcg cagatattgg caacactgtc aagcaccagt acaagaacgg  3960
tgtctaccga atcgccgagt ggtccgatat caccaacgcc cacggtgtac ccggaaccgg  4020
aatcattgct ggcctgcgag ctggtgccga ggaaactgtc tctgaacaga agaaggagga  4080
tgtctctgac tacgagaact cccagtacaa ggagttcctg gtcccctctc ccaacgagaa  4140
gctggccaga ggtctgctca tgctggccga gctgtcttgc aagggctctc tggccactgg  4200
cgagtactcc aagcagacca ttgagcttgc ccgatccgac cccgagtttg tggttggctt  4260
cattgcccag aaccgaccta agggcgactc tgaggactgg cttattctga cccccggggt  4320
gggtcttgac gacaagggag atgctctcgg acagcagtac cgaactgttg aggatgtcat  4380
gtctaccgga acggatatca taattgtcgg ccgaggtctg tacggccaga accgagatcc  4440
tattgaggag gccaagcgat accagaaggc tggctgggag gcttaccaga agattaactg  4500
ttagaggtta gactatggat atgtcattta actgtgtata tagagagcgt gcaagtatgg  4560
agcgcttgtt cagcttgtat gatggtcaga cgacctgtct gatcgagtat gtatgatact  4620
gcacaacctg cgcttgagac catccggtct ctgatcttaa ttaa                  4664

SEQ ID NO: 179          moltype = DNA  length = 5975
FEATURE                 Location/Qualifiers
misc_feature            1..5975
                        note = pLD139
source                  1..5975
                        mol_type = other DNA
                        organism = synthetic construct
SEQUENCE: 179
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgaacccaag ggaaaacttc cttaagtgtt ttctgcagta catccctaac  1620
aatgcaacaa acctcaagtt ggtgtacact caaaacaatc cactctatat gagcgtgctt  1680
aatagcacaa tccacaactt gcgcttcacg tcagatacta cgcctaagcc actagtgatc  1740
gttacaccat cacacgtcag ccatattcaa ggaacgatcc tatgtctgaa aaaggtcggg  1800
```

```
ttgcaaatca ggactcgatc aggagggcac gatagtgagg gaatgagtta catctcgcaa  1860
gtacccttcg tgatagttga cttgcgaaat atgcggtcta ttaaaattga cgtacatagc  1920
cagaccgcct gggttgaagc aggggcaacc ttgggtgaag tttattactg ggtcaatgaa  1980
aaaaacgaaa acctaagtct tgctgctgga tattgcccca ccgtttgcgc gggtggtcat  2040
tttggaggcg gcggatatgg tccgttgatg agaaattatg gacttgcagc agacaatatt  2100
atagatgccc acttggtgaa cgttcatgga aaggtcttgg accgtaagtc catgggtgaa  2160
gatctttttct gggccttgag aggtggtgga gcggaatcgt ttggcatcat cgttgcctgg  2220
aaaattaggt tggttgcggt cccgaagagt acaatgttct ccgtgaagaa gattatggaa  2280
atacatgagc ttgtcaagtt agttaacaag tggcaaaata tcgcttataa gtatgataaa  2340
gacttgcttt tgatgactca ttttattacg cgaaacataa ccgataacca gggcaagaac  2400
aagactgcta ttcacacgta cttctcctct gtatttcttg gaggagtaga ctccttagtt  2460
gacttgatga acaagagttt cccagaattg gggattaaga agacagattg cagacaatta  2520
tcgtggatag atacaatcat attctatagc ggtgtcgtca attacgatac tgataatttt  2580
aataaagaaa tcctcctaga tcgttcagct gggcaaaacg gggcattcaa aattaaattg  2640
gattatgtga agaaaccaat tccagagctg gtgtttgttc agatattgga aaaactttac  2700
gaagaagaca ttggcgcagg tatgtacgct ttgtatccat atggaggcat tatggacgag  2760
atctcagagc tggcgatccc cttcccgcac agagctggga tactctacga gctatggtac  2820
atctgctctt gggagaaaca agaagacaac gagaaacatc tcaattggat tcggaacata  2880
tacaacttta tgaccccata cgtatcaaaa aacccgcgct tagcatactt gaattacaga  2940
gacttagata tcggtatcaa tgatcctaag aatcctaaca attacaccca agcccgtatt  3000
tggggtgaga aatatttcgg caagaatttt gacagattag ttaaggtcaa aacactcgtg  3060
gaccccaaca actttttccg aaacgagcag tcgattccac cactacccag gcatagacac  3120
ggaagaaggg caaagttgta agagtgactc ttttgataag agtcgcaaat ttgatttcat  3180
aagtatatat tcattatgta aagtagtaaa tggaaaattc attaaaaaaa aagcaaattt  3240
ccgttgtatg catactccga acacaaaact agccccggaa aaacccttag ttgatagttg  3300
cgaatttagg tcgaccatat gcgacgggta caacgagaat tgtattgaat tgatcaagaa  3360
catgatcttg gtgttacaga acatcaagtt cttggaccag actgagaatg cacagatata  3420
caaggcgtca tgtgataaaa tggatgagat ttatccacaa ttgaagaaag agtttatgga  3480
aagtggtcaa ccagaagcta aacaggaaga agcaaacgaa gaggtgaaac aagaagaaga  3540
aggtaaataa gtattttgta ttatataaca aacaaagtaa ggaatacaga tttatacaat  3600
aaattgccat actagtcacg tgagatatct catccattcc ccaactccca agaaaataaa  3660
aaagtgaaaa ataaaatcaa acccaaagat caacctcccc atcatcatcg tcatcaaacc  3720
cccagctcaa ttcgcaatgg ttagcacaaa aacatacaca gaaagggcat cagcacaccc  3780
ctccaaggtt gcccaacgtt tattaattaa aggctaggtg gaggctcagt gatgataagt  3840
ctgcgatggt ggatgcatgt gtcatggtca tagctgtttc ctgtgtgaaa ttgttatccg  3900
ctcagagggc acaatcctat tccgcgctat ccgacaatct ccaagacatt aggtggagtt  3960
cagttcggcg tatggcatat gtcgctggaa agaacatgtg agcaaaaggc cagcaaaagg  4020
ccaggaaccg taaaaaggcc gcgttgctgg cgtttttcca taggctccgc ccccctgacg  4080
agcatcacaa aaatcgacgc tcaagtcaga ggtggcgaaa cccgacagga ctataaagat  4140
accaggcgtt tccccctgga agctccctcg tgcgctctcc tgttccgacc ctgccgctta  4200
ccggatacct gtccgccttt ctcccttcgg gaagcgtggc gctttctcat agctcacgct  4260
gtaggtatct cagttcggtg taggtcgttc gctccaagct gggctgtgtg cacgaacccc  4320
ccgttcagcc cgaccgctgc gccttatccg gtaactatcg tcttgagtcc aacccggtaa  4380
gacacgactt atcgccactg gcagcagcca ctggtaacag gattagcaga gcgaggtatg  4440
taggcggtgc tacagagttc ttgaagtggt ggcctaacta cggctacact agaagaacag  4500
tatttggtat ctgcgctctg ctgaagccag ttaccttcgg aaaaagagtt ggtagctctt  4560
gatccggcaa acaaaccacc gctggtagcg gtggtttttt tgtttgcaag cagcagatta  4620
cgcgcagaaa aaaaggatct caagaagatc ctttgatctt ttctacgggg tctgacgctc  4680
tattcaacaa agccgccgtc ccgtcaagtc agcgtaaatg ggtagggggc ttcaaatcgt  4740
ccgctctgcc agtgttacaa ccaattaaca aattctgatt agaaaaactc atcgagcatc  4800
aaatgaaact gcaatttatt catatcagga ttatcaatac catatttttg aaaaagccgt  4860
ttctgtaatg aaggagaaaa ctcaccgagg cagttccata ggatggcaag atcctggtat  4920
cggtctgcga ttccgactcg tccaacatca atacaaccta ttaatttccc ctcgtcaaaa  4980
ataaggttat caagtgagaa atcaccatga gtgacgactg aatccggtga gaatggcaaa  5040
agcttatgca tttctttcca gacttgttca acaggccagc cattacgctc gtcatcaaaa  5100
tcactcgcat caaccaaacc gttattcatt cgtgattgcg cctgagcgag acgaaatacg  5160
cgatcgctgt taaaaggaca attacaaaca ggaatcgaat gcaaccggcg caggaacact  5220
gccagcgcat caacaatatt ttcacctgaa tcaggatatt cttctaatac ctggaatgct  5280
gttttcccgg ggatcgcagt ggtgagtaac catgcatcat caggagtacg gataaaatgc  5340
ttgatggtcg gaagaggcat aaattccgtc agccagttta gtctgaccat ctcatctgta  5400
acatcattgg caacgctacc tttgccatgt ttcagaaaca actctggcgc atcgggcttc  5460
ccatacaatc gatagattgt cgcacctgat tgcccgacat tatcgcgagc ccatttatac  5520
ccatataaat cagcatccat gttggaattt aatcgcggcc tcgagcaaga cgtttcccgt  5580
tgaatatggc tcataacacc ccttgtatta ctgtttatgt aagcagacag ttttattgtt  5640
catgatgata tatttttatc ttgtgcaatg taacatcaga gattttgaga cacaacgtgg  5700
ctttcccccg ccgctctaga actagtggat ccaaataaaa cgaaaggctc agtcgaaaga  5760
ctgggccttt cgttttatct gttgtttgtc gcattatacg agacgtccag gttgggatac  5820
ctgaaacaaa acccatcgta cggccaagga agtctccaat aactgtgatc caccacaagc  5880
gccagggttt tcccagtcac gacgttgtaa aacgacggcc agtcatgcat aatccgcacg  5940
catctggaat aaggaagtgc cattccgcct gacct                             5975
```

```
SEQ ID NO: 180          moltype = DNA  length = 5594
FEATURE                 Location/Qualifiers
misc_feature            1..5594
                        note = pLD19
source                  1..5594
                        mol_type = other DNA
                        organism = synthetic construct
SEQUENCE: 180
```

```
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga attttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tgggtttatc gtcagtgtgc actttttctt ttcaaacaaa ctaccacacc  1620
ctcctaaacc ctcacaataa taacccaaaa acctccttgc tatgttacag acatccaaag  1680
acaccgatca agtattcata caacaatttt cccagtaaac attgctcaac gaagtccttc  1740
cacttgcaaa acaaatgcag cgaatcattg tcgatagcta aaaactcgat acgtgcggca  1800
accactaacc aaactgagcc accagagagc gataatcatt cagtcgccac caagattttg  1860
aactttggaa aagcctgttg gaaacttcaa aggccttaca ccattatcgc atttaccagt  1920
tgcgcatgtg gtttgttcgg gaaggaatta ttacacaaca caaatttgat cagctggagc  1980
ctaatgttta aggcattttt cttcttagtt gcaattttgt gtatagcttc gtttacaacg  2040
accattaatc agatttacga ccttcacatc gatcggatca ataaaccaga cttgcccctt  2100
gcctctgggg aaatctctgt aaatactgca tggatcatgc tgataatcgt ggctttgttt  2160
ggattgatta ttacaattaa gatgaagggg ggtccattat atatattcgg gtactgcttc  2220
ggcattttcg gtggtatcgt ttactccgtc ccacccttta gatggaaaca gaaccccagt  2280
acggcctttc tactcaattt cttggctcat atcatcacaa acttcacatt ctattatgca  2340
agccgagcgg cgcttggttt gccgttcgaa ctcagaccga gttttacatt tctccttgcc  2400
ttcatgaaac tgatgggact ggcccttgca ttgatcaagg atgcgtcaga tgtcgaaggc  2460
gacactaagt tcggcattct gacgcttgct tccaagtatg gaagtagaaa tctaacgctt  2520
ttttgttcag gaatagtgct acttagttat gttgctgcta tactcgctgg cattatttgg  2580
cctcaggcct tcaactctaa cgtaatgttg ttatcccatg ctattttggc gttctggttg  2640
atcttgcaaa cgcgagattt tgcactcact aactacgacc cagaggcagg aaggcgcttt  2700
tacgagttta tgtggaagtt gtattatgcc gaatacttgg tttatgtttt catttgataa  2760
gagtgactct tttgataaga gtcgcaaatt tgatttcata agtatatatt cattatgtaa  2820
agtagtaaat ggaaaattca ttaaaaaaaa agcaaatttc cgttgtatgc atactccgaa  2880
cacaaaacta gccccggaaa aacccttagt tgatagttgc gaatttaggt cgaccatatg  2940
cgacgggtac aacgagaatt gtattgaatt gatcaagaac atgatcttgg tgttacagaa  3000
catcaagttc ttggaccaga ctgagaatgc acagatatac aaggcgtcat gtgataaaat  3060
ggatgagatt tatccacaat tgaagaaaga gtttatggaa agtggtcaac cagaagctaa  3120
acaggaagaa gcaaacgaag aggtgaaaca agaagaagaa ggtaaataag tattttgtat  3180
tatataacaa acaaagtaag gaatacagat ttatacaata aattgccata ctagtcacgt  3240
gagatatctc atccattccc caactcccaa gaaaataaaa aagtgaaaaa taaaatcaaa  3300
cccaaagatc aacctcccca tcatcatcgt catcaaaccc ccagctcaat tcgcaatggt  3360
tagcacaaaa acatacacag aaagggcatc agcacacccc tccaaggttg cccaacgttt  3420
attaattaaa ggctaggtgg aggctcagtg atgataagtc tgcgatggtg gatgcatgtg  3480
tcatggtcat agctgtttcc tgtgtgaaat tgttatccgc tcagagggca caatcctatt  3540
ccgcgctatc cgacaatctc caagacatta ggtggagttc agttcggcgt atggcatatg  3600
tcgctggaaa gaacatgtga gcaaaaggcc agcaaaaggc caggaaccgt aaaaaggccg  3660
cgttgctggc gtttttccat aggctccgcc cccctgacga gcatcacaaa aatcgacgct  3720
caagtcagag gtggcgaaac ccgacaggac tataaagata ccaggcgttt ccccctggaa  3780
gctccctcgt gcgctctcct gttccgaccc tgccgcttac cggatacctg tccgcctttc  3840
tcccttcggg aagcgtggcg ctttctcata gctcacgctg taggtatctc agttcggtgt  3900
aggtcgttcg ctccaagctg ggctgtgtgc acgaaccccc cgttcagccc gaccgctgcg  3960
ccttatccgg taactatcgt cttgagtcca acccggtaag acacgactta tcgccactgg  4020
cagcagccac tggtaacagg attagcagag cgaggtatgt aggcggtgct acagagttct  4080
tgaagtggtg gcctaactac ggctacacta gaagaacagt atttggtatc tgcgctctgc  4140
tgaagccagt taccttcgga aaaagagttg gtagctcttg atccggcaaa caaaccaccg  4200
ctggtagcgg tggttttttt gtttgcaagc agcagattac gcgcagaaaa aaaggatctc  4260
aagaagatcc tttgatcttt tctacggggt ctgacgctct attcaacaaa gccgccgtcc  4320
cgtcaagtca gcgtaaatgg gtagggggct tcaaatcgtc cgctctgcca gtgttacaac  4380
caattaacaa attctgatta gaaaaactca tcgagcatca aatgaaactg caatttattc  4440
atatcaggat tatcaatacc atatttttga aaaagccgtt tctgtaatga aggagaaaac  4500
tcaccgaggc agttccatag gatggcaaga tcctggtatc ggtctgcgat tccgactcgt  4560
ccaacatcaa tacaacctat taatttcccc tcgtcaaaaa taaggttatc aagtgagaaa  4620
tcaccatgag tgacgactga atccggtgag aatggcaaaa gcttatgcat ttctttccag  4680
acttgttcaa caggccagcc attacgctcg tcatcaaaat cactcgcatc aaccaaaccg  4740
```

```
ttattcattc gtgattgcgc ctgagcgaga cgaaatacgc gatcgctgtt aaaaggacaa  4800
ttacaaacag gaatcgaatg caaccggcgc aggaacactg ccagcgcatc aacaatattt  4860
tcacctgaat caggatattc ttctaatacc tggaatgctg ttttcccggg gatcgcagtg  4920
gtgagtaacc atgcatcatc aggagtacgg ataaaatgct tgatggtcgg aagaggcata  4980
aattccgtca gccagtttag tctgaccatc tcatctgtaa catcattggc aacgctacct  5040
ttgccatgtt tcagaaacaa ctctggcgca tcgggcttcc catacaatcg atagattgtc  5100
gcacctgatt gcccgacatt atcgcgagcc catttatacc catataaatc agcatccatg  5160
ttggaattta atcgcggcct cgagcaagac gtttcccgtt gaatatggct cataacaccc  5220
cttgtattac tgtttatgta agcagacagt tttattgttc atgatgatat atttttatct  5280
tgtgcaatgt aacatcagag attttgagac acaacgtggc tttccccccgc cgctctagaa  5340
ctagtggatc caaataaaac gaaaggctca gtcgaaagac tgggcctttc gttttatctg  5400
ttgtttgtcg cattatacga gacgtccagg ttgggatacc tgaaacaaaa cccatcgtac  5460
ggccaaggaa gtctccaata actgtgatcc accacaagcg ccagggtttt cccagtcacg  5520
acgttgtaaa acgacggcca gtcatgcata atccgcacgc atctggaata aggaagtgcc  5580
attccgcctg acct                                                    5594

SEQ ID NO: 181          moltype = DNA  length = 5372
FEATURE                 Location/Qualifiers
misc_feature            1..5372
                        note = pLD26
source                  1..5372
                        mol_type = other DNA
                        organism = synthetic construct
SEQUENCE: 181
ttaattaatt ccgcttaatg gagtccaaaa agaccaacct ctgcgcctcg atcgacgtga  60
ccacaaccgc cgagttcctt tcgctcatcg acaagctcgg tccccacatc tgtctcgtga  120
agacgcacat cgatatcatc tcagacttca gctacgaggg cacgattgag ccgttgcttg  180
tgcttgcaga gcgccacggg ttcttgatat tcgaggacag gaagtttgct gatatcggaa  240
acaccgtgat gttgcagtac acctcggggg tataccggat cgcggcgtgg agtgacatca  300
cgaacgcgca cggagtgact gggaagggcg tcgttgaagg gttgaaacgc ggtgcggagg  360
gggtagaaaa ggaaaggggc gtgttgatgt tggcggagtt gtcgagtaaa ggctcgttgg  420
cgcatggtga atatacccgt gagacgatcg agattgcgaa gagtgatcgg gagttcgtga  480
ttgggttcat cgcgcagcgg gacatggggg gtagagaaga agggtttgat tggatcatca  540
tgacgcctgg tgtggggttg gatgataaag gcgatgcgtt gggccagcag tataggactg  600
ttgatgaggt ggttctgact ggtaccgatg tgattattgt cgggagaggg ttgtttggaa  660
aaggaagaga ccctgaggtg gagggaaaga gatacaggga tgctggatgg aaggcatact  720
tgaagagaac tggtcagtta gaataaatat tgtaataaat aggtctatat acatacacta  780
agcttctagg acgtcattgt agtcttcgaa gttgtctgct agtttagttc tcatgatttc  840
gaaaaccaat aacgcaatgg atgtagcagg gatggtggtt agtgcgttcc tgacaaaccc  900
agagtacgcc gcctcaaacc acgtcacatt cgccctttgc ttcatccgca tcacttgctt  960
gaaggtatcc acgtacgagt tgtaatacac cttgaagaac ggcttcgtct agttcggcat  1020
ggcagatcat catgcctgca ggagctccaa ttgtaatatt tcgggagaaa tatcgttggg  1080
gtaaaacaac agagagagag agggagagat ggttctggta gaattataat ctggttgttg  1140
caaatgctac tgatcgactc tggcaatgtc tgtagctcgc tagttgtatg caacttaggt  1200
gttatgcata cacacggtta ttcggttgaa ttgtggagta aaaattgtct gagttgtgtc  1260
ttagctactg gctggccccc cgcgaaagat aatcaaaatt acacttgtga atttttgcac  1320
acacaccgat taacatttcc cttttttgtc caccgataca cgcttgcctc ttcttatttt  1380
ctctgtgctt ccccctcctg tgactttttc caccattgat ataaaatcaa ctccatttcc  1440
ctaaaatctc cccagattct aaaaacaact tcttctcttc tgcttttcct tatttttgtt  1500
atatttattt accatccctt attttgaata gttattcccc actaacattg ttcaaatctt  1560
cacgacataa tggcggcaac cactaaccaa actgagccac cagagagcga taatcattca  1620
gtcgccacca agattttgaa ctttggaaaa gcctgttgga aacttcaaag gccttacacc  1680
attatcgcat ttaccagttg cgcatgtggt ttgttcggga aggaattatt acacaacaca  1740
aatttgatca gctggagcct aatgtttaag gcatttttct tcttagttgc aattttgtgt  1800
atagcttcgt ttacaacgac cattaatcag atttacgacc ttcacatcga tcggatcaat  1860
aaaccagact tgccccttgc ctctggggaa atctctgtaa atactgcatg gatcatgctg  1920
ataatcgtgg ctttgtttgg attgattatt acaattaaga tgaagggggg tccattatat  1980
atattcgggt actgcttcgg catttcggt ggtatcgttt actccgtccc accctttaga  2040
tggaaacaga accccagtac ggcctttcta ctcaatttct tggctcatat catcacaaac  2100
ttcacattct attatgcaag ccgagcggcg cttggtttgc cgttcgaact cagaccgagt  2160
tttacatttc tccttgcctt catgaaactg atggactgg ccttgcatt gatcaaggat  2220
gcgtcagatg tcgaaggcga cactaagttc ggcattctga cgcttgcttc caagtatgga  2280
agtagaaatc taacgctttt ttgttcagga atagtgctac ttagttatgt tgctgctata  2340
ctcgctggca ttatttggcc tcaggccttc aactctaacg taatgttgtt atcccatgct  2400
attttggcgt tctggttgat cttgcaaacg cgagattttg cactcactaa ctacgaccca  2460
gaggcaggaa ggcgctttta cgagtttatg tggaagttgt attatgccga atacttggtt  2520
tatgttttca tttgataaga gtgactcttt tgataagagt cgcaaatttg atttcataag  2580
tatatattca ttatgtaaag tagtaaatgg aaaattcatt aaaaaaaaag caaatttccg  2640
ttgtatgcat actccgaaca caaaactagc cccggaaaaa cccttagttg atagttgcga  2700
atttaggtcg accatatgcg acgggtacaa cgagaattgt attgaattga tcaagaacat  2760
gatcttggtg ttacagaaca tcaagttctt ggaccagact gagaatgcac agatatacaa  2820
ggcgtcatgt gataaaatgg atgagattta tccacaattg aagaaagagt ttatggaaag  2880
tggtcaacca gaagctaaac aggaagaagc aaacgaagag gtgaaacaag aagaagaagg  2940
taaataagta ttttgtatta tataacaaac aaagtaagga atacagattt atacaataaa  3000
ttgccatact agtcacgtga gatatctcat ccattcccca actcccaaga aaataaaaaa  3060
gtgaaaaata aaatcaaacc caaagatcaa cctccccatc atcatcgtca tcaaaccccc  3120
agctcaattc gcaatggtta gcacaaaaac atacacagaa agggcatcag cacacccctc  3180
caaggttgcc caacgtttat taattaaagg ctaggtggag gctcagtgat gataagtctg  3240
cgatggtgga tgcatgtgtc atggtcatag ctgtttcctg tgtgaaattg ttatccgctc  3300
```

-continued

```
agagggcaca atcctattcc gcgctatccg acaatctcca agacattagg tggagttcag  3360
ttcggcgtat ggcatatgtc gctggaaaga acatgtgagc aaaaggccag caaaaggcca  3420
ggaaccgtaa aaaggccgcg ttgctggcgt ttttccatag gctccgcccc cctgacgagc  3480
atcacaaaaa tcgacgctca agtcagaggt ggcgaaaccc gacaggacta taaagatacc  3540
aggcgtttcc ccctggaagc tccctcgtgc gctctcctgt tccgaccctg ccgcttaccg  3600
gatacctgtc cgcctttctc ccttcgggaa gcgtggcgct ttctcatagc tcacgctgta  3660
ggtatctcag ttcggtgtag gtcgttcgct ccaagctggg ctgtgtgcac gaaccccccg  3720
ttcagcccga ccgctgcgcc ttatccggta actatcgtct tgagtccaac ccggtaagac  3780
acgacttatc gccactggca gcagccactg gtaacaggat tagcagagcg aggtatgtag  3840
gcggtgctac agagttcttg aagtggtggc ctaactacgg ctacactaga agaacagtat  3900
ttggtatctg cgctctgctg aagccagtta ccttcggaaa aagagttggt agctcttgat  3960
ccggcaaaca aaccaccgct ggtagcggtg gtttttttgt ttgcaagcag cagattacgc  4020
gcagaaaaaa aggatctcaa gaagatcctt tgatcttttc tacggggtct gacgctctat  4080
tcaacaaagc cgccgtcccg tcaagtcagc gtaaatgggt agggggcttc aaatcgtccg  4140
ctctgccagt gttacaacca attaacaaat tctgattaga aaaactcatc gagcatcaaa  4200
tgaaactgca atttattcat atcaggatta tcaataccat atttttgaaa aagccgtttc  4260
tgtaatgaag gagaaaactc accgaggcag ttccatagga tggcaagatc ctggtatcgg  4320
tctgcgattc cgactcgtcc aacatcaata caacctatta atttcccctc gtcaaaaata  4380
aggttatcaa gtgagaaatc accatgagtg acgactgaat ccggtgagaa tggcaaaagc  4440
ttatgcattt ctttccagac ttgttcaaca ggccagccat tacgctcgtc atcaaaatca  4500
ctcgcatcaa ccaaaccgtt attcattcgt gattgcgcct gagcgagacg aaatacgcga  4560
tcgctgttaa aaggacaatt acaaacagga atcgaatgca accggcgcag gaacactgcc  4620
agcgcatcaa caatattttc acctgaatca ggatattctt ctaatacctg gaatgctgtt  4680
ttcccgggga tcgcagtggt gagtaaccat gcatcatcag gagtacggat aaaatgcttg  4740
atggtcggaa gaggcataaa ttccgtcagc cagtttagtc tgaccatctc atctgtaaca  4800
tcattggcaa cgctaccttt gccatgtttc agaaacaact ctggcgcatc gggcttccca  4860
tacaatcgat agattgtcgc acctgattgc ccgacattat cgcgagccca tttataccca  4920
tataaatcag catccatgtt ggaatttaat cgcggcctcg agcaagacgt ttcccgttga  4980
atatggctca taacacccct tgtattactg tttatgtaag cagacagttt tattgttcat  5040
gatgatatat ttttatcttg tgcaatgtaa catcagagat tttgagacac aacgtggctt  5100
tcccccgccg ctctagaact agtggatcca aataaaacga aaggctcagt cgaaagactg  5160
ggcctttcgt tttatctgtt gtttgtcgca ttatacgaga cgtccaggtt gggatacctg  5220
aaacaaaacc catcgtacgg ccaaggaagt ctccaataac tgtgatccac cacaagcgcc  5280
agggttttcc cagtcacgac gttgtaaaac gacggccagt catgcataat ccgcacgcat  5340
ctggaataag gaagtgccat tccgcctgac ct                                5372

SEQ ID NO: 182          moltype = AA  length = 11
FEATURE                 Location/Qualifiers
REGION                  1..11
                        note = VSV-G
source                  1..11
                        mol_type = protein
                        organism = synthetic construct
SEQUENCE: 182
YTDIEMNRLG K                                                       11
```